United States Patent
Altenbach et al.

(10) Patent No.: US 9,840,513 B2
(45) Date of Patent: Dec. 12, 2017

(54) SUBSTITUTED TRICYCLICS AND METHOD OF USE

(71) Applicants: AbbVie S.à.r.l., Luxembourg (LU); Galapagos NV, Mechelen (BE)

(72) Inventors: Robert J. Altenbach, Chicago, IL (US); Andrew Bogdan, Evanston, IL (US); Marlon D. Cowart, Round Lake Beach, IL (US); William Ramesh Esmieu, Saffron Walden (GB); Gregory A. Gfesser, Lindenhurst, IL (US); Stephen N. Greszler, Vernon Hills, IL (US); John R. Koenig, Chicago, IL (US); Philip R. Kym, Libertyville, IL (US); Bo Liu, Waukegan, IL (US); Karine Fabienne Malagu, Saffron Walden (GB); Sachin V. Patel, Round Lake, IL (US); Marc J. Scanio, Libertyville, IL (US); Xenia B. Searle, Grayslake, IL (US); Eric Voight, Pleasant Prairie, WI (US); Xeuquing Wang, Northbrook, IL (US); Ming C. Yeung, Grayslake, IL (US)

(73) Assignees: AbbVie S.á.r.l., Luxembourg (LU); Galapagos NV, Mechelen (BE)

( * ) Notice: Subject to any disclaimer, the term of this patent is extended or adjusted under 35 U.S.C. 154(b) by 0 days.

(21) Appl. No.: 15/205,512

(22) Filed: Jul. 8, 2016

(65) Prior Publication Data
US 2017/0015675 A1 Jan. 19, 2017

Related U.S. Application Data

(60) Provisional application No. 62/193,391, filed on Jul. 16, 2015, provisional application No. 62/299,633, filed on Feb. 25, 2016.

(51) Int. Cl.
| | | |
|---|---|---|
| C07D 493/04 | (2006.01) |
| C07D 317/70 | (2006.01) |
| C07D 405/12 | (2006.01) |
| C07D 407/12 | (2006.01) |
| C07D 519/00 | (2006.01) |
| A61K 31/357 | (2006.01) |
| A61K 31/397 | (2006.01) |
| A61K 31/433 | (2006.01) |
| A61K 31/443 | (2006.01) |
| A61K 31/4439 | (2006.01) |
| A61K 31/4709 | (2006.01) |
| A61K 31/501 | (2006.01) |
| A61K 31/5377 | (2006.01) |
| A61K 45/06 | (2006.01) |

(52) U.S. Cl.
CPC ........ *C07D 493/04* (2013.01); *A61K 31/357* (2013.01); *A61K 31/397* (2013.01); *A61K 31/433* (2013.01); *A61K 31/443* (2013.01); *A61K 31/4439* (2013.01); *A61K 31/4709* (2013.01); *A61K 31/501* (2013.01); *A61K 31/5377* (2013.01); *A61K 45/06* (2013.01); *C07D 317/70* (2013.01); *C07D 405/12* (2013.01); *C07D 407/12* (2013.01); *C07D 519/00* (2013.01)

(58) Field of Classification Search
CPC .. C07D 493/04; C07D 407/12; A61K 31/443; A61K 45/06
See application file for complete search history.

(56) References Cited

U.S. PATENT DOCUMENTS

| | | | |
|---|---|---|---|
| 8,999,976 B2 | 4/2015 | Binch et al. | |
| 2015/0005275 A1 | 1/2015 | Plas et al. | |
| 2015/0045327 A1 | 2/2015 | Van Der Plas et al. | |
| 2016/0120841 A1 | 5/2016 | Kym et al. | |
| 2016/0122331 A1* | 5/2016 | Kym ................. | C07D 407/12 514/459 |

FOREIGN PATENT DOCUMENTS

| | | |
|---|---|---|
| WO | 2005120497 A2 | 12/2005 |
| WO | 2006002421 A3 | 1/2006 |

(Continued)

OTHER PUBLICATIONS

Quinton, P.M. et al., "Cystic Fibrosis: a disease in electrolyte transport," FASEB J, 1990.4(10): 2709-2717.
Kerem, B. et al., "Identification of the cystic fibrosis gene: genetic analysis." Science, 1989. 245(4922): 1073-1080.
Bobadilla, J.L. et al., "Cystic fibrosis: a worldwide analysis of CFTR mutations—correlation with incidence data and application to screening," Human Mutation, 2002 19, 575-606. doi:10.1002/humu.10041.
Pasyk, E.A. et al., "Mutant (ΔF508) Cystic Fibrosis Transmembrane Conductance Regulator Cl—Channel Is Functional When Retained in Endoplasmic Reticulum of Mammalian Cells." J. Biol. Chem, 1995. 270: 12347-12350.
Morello, J.-P. et al., "Pharmacological chaperones: a new twist on receptor folding." Trends Pharmacol. Sci., 2000. 21 (12): 466-469. doi:10.1016/S0165-6147(00)01575-3;.

(Continued)

*Primary Examiner* — Yong L Chu
(74) *Attorney, Agent, or Firm* — Quarles & Brady LLP

(57) ABSTRACT

The present invention provides for compounds of formula (I)

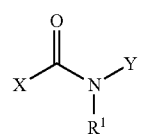

wherein X, Y, and $R^1$ have any of the values defined in the specification, and pharmaceutically acceptable salts thereof, that are useful as agents in the treatment of diseases and conditions mediated and modulated by CFTR, including cystic fibrosis, Sjögren's syndrome, pancreatic insufficiency, chronic obstructive lung disease, and chronic obstructive airway disease. Also provided are pharmaceutical compositions comprised of one or more compounds of formula (I).

68 Claims, No Drawings

(56) References Cited

FOREIGN PATENT DOCUMENTS

| | | |
|---|---|---|
| WO | 2008147952 A1 | 4/2008 |
| WO | 2009076593 A1 | 6/2009 |
| WO | 2009074575 A3 | 8/2009 |
| WO | 2010048573 A1 | 4/2010 |
| WO | 2011113894 A1 | 9/2011 |
| WO | 2011072241 A9 | 6/2012 |
| WO | 2012048181 A4 | 6/2012 |
| WO | 2013038373 A1 | 3/2013 |
| WO | 2013038378 A1 | 3/2013 |
| WO | 2013038381 A1 | 3/2013 |
| WO | 2013038386 A1 | 3/2013 |
| WO | 2013038390 A1 | 3/2013 |
| WO | 2013043720 A1 | 3/2013 |
| WO | 2014180562 A1 | 11/2014 |
| WO | 2015018823 A1 | 2/2015 |
| WO | 2015138909 A1 | 9/2015 |
| WO | 2015138934 A1 | 9/2015 |

OTHER PUBLICATIONS

Shastry, B.S., "Neurodegenerative disorders of protein aggregation." Neurochem. Int., 2003. 43(1): 1-7. doi:10.1016/S0197-0186(02)00196-1.

Zhang, W. et al., "Recent advances and new perspectives in targeting CFTR for therapy of cystic fibrosis and enterotoxin-induced secretory diarrheas." Future Med. Chem., 2012. 4(3), 329-345. doi:10.4155/fmc.12.1.

* cited by examiner

SUBSTITUTED TRICYCLICS AND METHOD OF USE

CROSS REFERENCE TO RELATED APPLICATIONS

This application claims priority to U.S. Provisional Application No. 62/193,391, filed Jul. 16, 2015 and U.S. Provisional Application No. 62/299,633, filed Feb. 25, 2016, both of which are incorporated herein by reference for all purposes.

BACKGROUND OF THE INVENTION

Technical Field

The invention relates to substituted tricyclic compounds that are modulators of the Cystic Fibrosis Transmembrane Conductance Regulator (CFTR) protein, useful in treating diseases and conditions mediated and modulated by CFTR. Additionally, the invention relates to compositions containing compounds of the invention and processes for their preparation.

Description of Related Technology

ABC transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cells types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue (Quinton, P. M., 1990. Cystic fibrosis: a disease in electrolyte transport. FASEB J. 4, 2709-2717).

The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis (CF) is caused by a defect in this gene which induces mutations in CFTR. Cystic fibrosis is the most common fatal genetic disease in humans, and affects ~0.04% of white individuals (Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi:10.1002/humu.10041), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations has been identified through sequence analysis of the CFTR gene of CF chromosomes (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). ΔF508-CFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if ΔF508-CFTR is allowed to reach the cell plasma membrane by low-temperature (27° C.) rescue where it can function as a cAMP-activated chloride channel, its activity is decreased significantly compared with WT-CFTR (Pasyk, E. A., Foskett, J. K., 1995. Mutant (δF508) Cystic Fibrosis Transmembrane Conductance Regulator Cl—Channel Is Functional When Retained in Endoplasmic Reticulum of Mammalian Cells. J. Biol. Chem. 270, 12347-12350).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, and G1349D. Mutations affecting chloride conductance have a CFTR protein that is correctly trafficked to the cell membrane but that generates reduced chloride flow (e.g. missense mutations located within the membrane-spanning domain), examples of these mutations are R117H and R334W.

In addition to cystic fibrosis, CFTR activity modulation may be beneficial for other diseases not directly caused by mutations in CFTR, such as, for example, chronic obstructive pulmonary disease (COPD), dry eye disease, and Sjogren's syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjogrens's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjogrens's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjogrens's syndrome is also associated with rheumatoid arthritis, systemic lupus, systemic sclerosis, and polymypositis/dermatomyositis. The cause of the disease is believed to lie in defective protein trafficking, for which treatment options are limited. As a consequence, modulation of CFTR activity may help hydrating the various organs and help to elevate the associated symptoms.

In addition to CF, the defective protein trafficking induced by the ΔF508-CFTR has been shown to be the underlying basis for a wide range of other diseases, in particular diseases where the defective functioning of the endoplasmic reticulum (ER) may either prevent the CFTR protein to exit the ER, and/or the misfolded protein is degraded (Morello, J.-P., Bouvier, M., Petaja-Repo, U. E., Bichet, D. G., 2000. Pharmacological chaperones: a new twist on receptor folding. Trends Pharmacol. Sci. 21, 466-469. doi:10.1016/S0165-6147(00)01575-3; Shastry, B. S., 2003. Neurodegenerative disorders of protein aggregation. Neurochem. Int. 43, 1-7. doi:10.1016/S0197-0186(02)00196-1; Zhang, W., Fujii, N., Naren, A. P., 2012. Recent advances and new perspectives in targeting CFTR for therapy of cystic fibrosis and enterotoxin-induced secretory diarrheas. Future Med. Chem. 4, 329-345. doi:10.4155/fmc.12.1).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurophyseal DI (vasopvessin hormoneN2-receptor), neprogenic DI (aquaporin II), Charcot-Marie Tooth syndrome (peripheral myelin protein 22), Perlizaeus-Merzbacher disease, neurodegenerative diseases such as Alzheimer's disease (APP and presenilins), Parkinson's disease, amyotrophic lateral sclerosis, progressive supranuclear palsy, Pick's disease, several polyglutamine neurological disorders such as Huntington's disease, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (prion protein processing defect), Fabry disease (lysosomal α-galactosidase A), Straussler-Scheinker syndrome, chronic obstructive pulmonary disease (COPD), dry eye disease, and Sjogren's Syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrhoeas, and results in dehydration, acidosis, impaired growth and death. Acute and chronic diarrhoeas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhoea is a dangerous condition.

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect the present invention provides for compounds of formula (I)

or a pharmaceutically acceptable salt thereof, wherein
$R^1$ is H or $C_1$-$C_3$ alkyl;
X is formula (a) or formula (b)

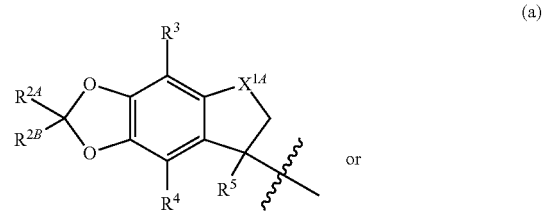

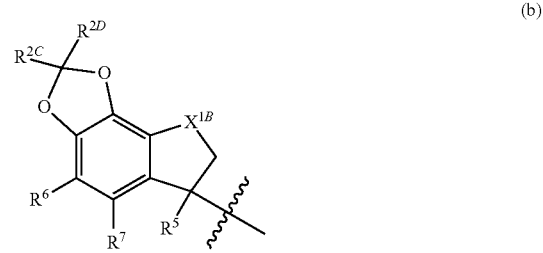

wherein $R^{2A}$, $R^{2B}$, $R^{2C}$, and $R^{2D}$, are each independently hydrogen or halogen;

$R^3$, $R^4$, $R^6$, and $R^7$, are each independently hydrogen, $C_1$-$C_3$ alkyl, or halogen;

$R^5$, at each occurrence, is independently hydrogen, $C_1$-$C_3$ alkyl, $C_2$-$C_4$ alkenyl, or $C_1$-$C_3$ haloalkyl;

$X^{1A}$ is O or $CH_2$;

$X^{1B}$ is O or $CH_2$;

Y is $-G^1$, or Y is formula (c), (d), (e), (f), or (g);

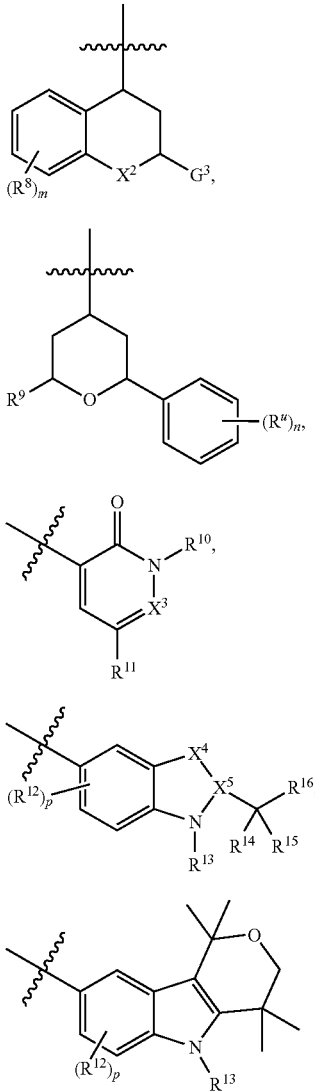

wherein $G^1$ is phenyl or monocyclic heteroaryl, each of which is optionally substituted with 1, 2, or 3 independently selected $R^p$ groups; wherein each $R^p$ is independently $C_1$-$C_6$ alkyl, halogen, $C_1$-$C_6$ haloalkyl, $G^2$, $C_1$-$C_3$ alkoxy, $C_1$-$C_3$ haloalkoxy, $-C(O)$-$G^A$, $-C(O)NR^AR^B$, or $-NR^AR^B$; wherein $R^A$, at each occurrence, is independently hydrogen, $C_1$-$C_6$ alkyl, or $C_1$-$C_6$ haloalkyl;

$R^B$, at each occurrence, is independently hydrogen, $C_1$-$C_6$ haloalkyl, or $C_1$-$C_6$ alkyl which is optionally substituted with 1 or 2 $-$OH;

$G^A$ is a $C_3$-$C_6$ cycloalkyl or a 4-6 membered monocyclic heterocycle; each of which is optionally substituted with 1, 2, or 3 substituents independently selected from the group consisting of halogen, $C_1$-$C_6$ alkyl, $C_1$-$C_6$ haloalkyl, $-$OH, $C_1$-$C_3$ alkoxy, and $C_1$-$C_3$ haloalkoxy; and $G^2$ is phenyl, heterocycle, or monocyclic heteroaryl; each of which is optionally substituted with 1, 2, or 3 independently selected $R^q$ groups;

$X^2$ is O or $N(R^{2x})$ wherein $R^{2x}$ is hydrogen, $C_1$-$C_3$ alkyl, or $C_1$-$C_3$ haloalkyl;

$X^3$ is N or CH;

$X^4$-$X^5$ is N=C, $C(R^{4x})$=C, or $C(R^{4x})_2$—$C(R^{5x})$, wherein $R^{4x}$ and $R^{5x}$, at each occurrence, are each independently hydrogen, halogen, $C_1$-$C_3$ alkyl, or $C_1$-$C_3$ haloalkyl;

$R^8$ groups are optional substituents on the benzo ring, and are each independently halogen, $C_1$-$C_3$ alkyl, $C_1$-$C_3$ haloalkyl, $C_1$-$C_3$ alkoxy, or $C_1$-$C_3$ haloalkoxy;

m is 0, 1, 2, 3, or 4;

$G^3$ is $-(C_1$-$C_3$ alkylenyl)-$OR^g$, $-(C_1$-$C_3$ alkylenyl)-$G^B$, phenyl, cycloalkyl, 4-6 membered monocyclic heterocycle, or monocyclic heteroaryl; wherein the phenyl, the cycloalkyl, the 4-6 membered monocyclic heterocycle, and the monocyclic heteroaryl are each optionally substituted with 1, 2, or 3 independently selected $R^s$ groups;

$G^B$ is phenyl, cycloalkyl, 4-6 membered monocyclic heterocycle, or monocyclic heteroaryl; each of which is optionally substituted with 1, 2, or 3 independently selected $R^s$ groups;

$R^g$ is $C_1$-$C_3$ alkyl, $C_3$-$C_6$ cycloalkyl, or phenyl; wherein the $C_3$-$C_6$ cycloalkyl and the phenyl are each optionally substituted with 1, 2, or 3 substituents independently selected from the group consisting of halogen, $-$OH, $C_1$-$C_3$ alkyl, $C_1$-$C_3$ haloalkyl, $C_1$-$C_3$ alkoxy, and $C_1$-$C_3$ haloalkoxy;

n is 0, 1, 2, or 3;

$R^{10}$ is $C_1$-$C_6$ alkyl substituted with 1, 2, or 3 substituents independently selected from the group consisting of halogen, OH, $C_1$-$C_3$ alkoxy, $C_1$-$C_3$ haloalkoxy, and 2,2-dimethyl-1,3-dioxolan-4-yl; or $R^{10}$ is phenyl, $C_3$-$C_6$ cycloalkyl, or monocyclic heteroaryl, wherein the phenyl, $C_3$-$C_6$ cycloalkyl, and monocyclic heteroaryl are each optionally substituted with 1, 2, or 3 independently selected $R^w$ groups;

$R^{11}$ is halogen, $C_1$-$C_3$ alkyl, or $G^4$ wherein $G^4$ is $C_3$-$C_6$ cycloalkyl, 4-6 membered monocyclic heterocycle, monocyclic heteroaryl, or phenyl; each $G^4$ is optionally substituted with 1, 2, or 3 independently selected $R^w$ groups;

$R^{12}$ are optional substituents of the benzo ring, and are each independently halogen, $C_1$-$C_3$ alkyl, or $C_1$-$C_3$ haloalkyl;

p is 0, 1, 2, or 3;

$R^{13}$ is hydrogen or $C_1$-$C_6$ alkyl which is substituted with 1, 2, or 3 substituents independently selected from the group consisting of $-$CN, 2,2-dimethyl-1,3-dioxolan-4-yl, $OR^{13a}$, $-$O-benzyl, $-N(R^{13})_2$, $-N(R^{13a})S(O)_2R^{13b}$, and $-N(R^{13b})C(O)R^{13b}$, wherein $R^{13a}$, at each occurrence, is independently hydrogen, $C_1$-$C_6$ alkyl, or $C_1$-$C_6$ haloalkyl, and $R^{13b}$, at each occurrence, is independently $C_1$-$C_6$ alkyl or $C_1$-$C_6$ haloalkyl;

$R^{14}$ and $R^{15}$ are each independently $C_1$-$C_3$ alkyl, or $R^{14}$ and $R^{15}$, together with the carbon atom to which they are attached, form a $C_3$-$C_6$ cycloalkyl or a 4-6 membered monocyclic heterocycle containing one heteroatom selected from the group consisting of oxygen and nitrogen; wherein the $C_3$-$C_6$ cycloalkyl and the 4-6 membered monocyclic heterocycle are each optionally substituted with 1 or 2 substituents independently selected from the group consisting of $C_1$-$C_3$ alkyl, halogen, $C_1$-$C_3$ haloalkyl, $-$OH, $C_1$-$C_3$ alkoxy, and $C_1$-$C_3$ haloalkoxy;

$R^{16}$ is OH or $C_1$-$C_6$ alkyl optionally substituted with 1 or 2 substituents independently selected from the group consisting of —CN, —$OR^j$, —O-benzyl, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, and —$N(R^j)C(O)N(R^j)_2$;

$R^q$ is $C_2$-$C_6$ alkenyl, $C_2$-$C_6$ alkynyl, halogen, $C_1$-$C_6$ haloalkyl, —CN, oxo, $NO_2$, —$OR^x$, —$OC(O)R^y$, —$OC(O)N(R^x)_2$, —$SR^x$, —$S(O)_2R^x$, —$S(O)_2N(R^x)_2$, —$C(O)R^x$, —$C(O)OR^x$, —$C(O)N(R^x)_2$, —$C(O)N(R^x)S(O)_2R^y$, —$N(R^x)_2$, —$N(R^x)C(O)R^y$, —$N(R^x)S(O)_2R^y$, —$N(R^x)C(O)O(R^y)$, —$N(R^x)C(O)N(R^x)_2$, $G^{2A}$, or $C_1$-$C_6$ alkyl which is optionally substituted with 1 or 2 substituents independently selected from the group consisting of —CN, $NO_2$, —$OR^x$, —$OC(O)R^y$, —$OC(O)N(R^x)_2$, —$SR^x$, —$S(O)_2R^x$, —$S(O)_2N(R^x)_2$, —$C(O)R^x$, —$C(O)OR^x$, —$C(O)N(R^x)_2$, —$C(O)N(R^x)S(O)_2R^y$, —$N(R^x)_2$, —$N(R^x)C(O)R^y$, —$N(R^x)S(O)_2R^y$, —$N(R^x)C(O)O(R^y)$, —$N(R^x)C(O)N(R^x)_2$, and $G^{2A}$;

$R^x$, at each occurrence, is independently hydrogen, $C_1$-$C_6$ alkyl, $G^{2A}$, $C_1$-$C_6$ haloalkyl, or —($C_1$-$C_6$ alkylenyl)-$G^{2A}$;

$R^y$, at each occurrence, is independently $C_1$-$C_6$ alkyl, $G^{2A}$, $C_1$-$C_6$ haloalkyl, or —($C_1$-$C_6$ alkylenyl)-$G^{2A}$;

$G^{2A}$, at each occurrence, is independently phenyl or $C_3$-$C_6$ cycloalkyl; each of which is optionally substituted with 1, 2, or 3 $R^z$ groups;

$R^s$, at each occurrence, is independently $C_2$-$C_6$ alkenyl, $C_2$-$C_6$ alkynyl, halogen, $C_1$-$C_6$ haloalkyl, —CN, oxo, $NO_2$, —$OR^j$, —$OR^h$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)O(benzyl)$, —$C(O)N(R^j)_2$, —$C(O)N(R^m)(R^n)$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, $G^{3A}$, —$N(R^j)C(O)N(R^j)_2$, or $C_1$-$C_6$ alkyl which is optionally substituted with 1 or 2 substituents independently selected from the group consisting of —CN, $NO_2$, —$OR^j$, —O-benzyl, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, and $G^{3A}$;

$G^{3A}$, at each occurrence, is independently phenyl or 4-6 membered monocyclic heterocycle; each $G^{3A}$ is optionally substituted with 1, 2, 3, or 4 $R^e$ groups;

$R^g$ is hydrogen or benzyl, or $R^g$ is $C_2$-$C_6$ alkyl which is substituted with 1 or 2 —$OR^j$;

$R^h$ is benzyl or $R^h$ is $C_2$-$C_6$ alkyl which is substituted with 1 or 2 —$OR^j$;

$R^m$ is $G^{3B}$ or $C_1$-$C_6$ alkyl which is substituted with 1 or 2 substituents independently selected from the group consisting of —$OR^j$, —$S(O)_2R^j$, —$C(O)N(R^j)_2$, and $G^{3B}$;

$R^n$ is hydrogen, $C_1$-$C_6$ alkyl, $C_1$-$C_6$ haloalkyl, benzyl, or —($C_2$-$C_6$ alkylenyl)-$OR^j$; or $R^m$ and $R^n$, together with the nitrogen atom to which they are attached, form a 4-7 membered monocyclic heterocycle, wherein the 4-7 membered monocyclic heterocycle is optionally substituted with 1, 2, 3, or 4 independently selected $R^e$ groups;

$G^{3B}$, at each occurrence, is independently a phenyl, a 4-7 membered monocyclic heterocycle, or a 3-10 membered cycloalkyl, each of which is optionally substituted with 1, 2, 3, or 4 independently selected $R^e$ groups;

$R^e$, $R^u$, $R^v$, $R^w$, and $R^z$, at each occurrence, are each independently $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, or $C_1$-$C_6$ alkyl which is optionally substituted with 1 or 2 substituents independently selected from the group consisting of —CN, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^3)S(O)_2R^k$, —$N(R^j)_2$, —$N(R^j)C(O)R^k$, —$N(R^j)S(O)_2R^k$, —$N(R^j)C(O)O(R^k)$, and —$N(R^j)C(O)N(R^j)_2$;

$R^j$, at each occurrence, is independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl.

Another aspect of the invention relates to pharmaceutical compositions comprising a compound of the invention, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

Yet another aspect of the invention relates to a method for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of cystic fibrosis. In a particular aspect, the compounds of the invention are provided for use in the treatment of cystic fibrosis caused by class I, II, III, IV, V, and/or VI mutations.

The present invention also provides pharmaceutical compositions comprising a compound of the invention, and a suitable pharmaceutical carrier for use in medicine. In a particular aspect, the pharmaceutical composition is for use in the treatment of cystic fibrosis.

These and other objects of the invention are described in the following paragraphs. These objects should not be deemed to narrow the scope of the invention.

DETAILED DESCRIPTION OF THE INVENTION

Described herein are compounds of formula (I)

(I)

wherein $R^1$, X, and Y are defined above in the Summary of the Invention and below in the Detailed Description. Further, compositions comprising such compounds and methods for treating conditions and disorders using such compounds and compositions are also described.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. The term "$C_2$-$C_4$ alkenyl" means an alkenyl group containing 2-4 carbon atoms. Non-limiting examples of alkenyl include buta-1,3-dienyl, ethenyl, 2-propenyl, 2-methyl-2-propenyl, 3-butenyl, 4-pentenyl, and 5-hexenyl.

The term "$C_1$-$C_3$ alkoxy" as used herein, means a $C_1$-$C_3$ alkyl group, as defined herein, appended to the parent molecular moiety through an oxygen atom. Examples of $C_1$-$C_3$ alkoxy include, but are not limited to, methoxy, ethoxy, propoxy, and 2-propoxy.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl. The terms "alkyl," "$C_1$-$C_6$ alkyl," "$C_2$-$C_6$ alkyl," and "$C_1$-$C_3$ alkyl" are unsubstituted unless otherwise indicated.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms ($C_1$-$C_4$ alkylenyl) or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —CH$_2$—, —CH$_2$CH$_2$—, —C((CH$_3$)$_2$)—CH$_2$CH$_2$CH$_2$—, —C((CH$_3$)$_2$)—CH$_2$CH$_2$, —CH$_2$CH$_2$CH$_2$CH$_2$—, and —CH$_2$CH(CH$_3$)CH$_2$—.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited, to acetylenyl, 1-propynyl, 2-propynyl, 3-butynyl, 2-pentynyl, and 1-butynyl.

The term "cycloalkyl" as used herein, means a $C_3$-$C_6$ cycloalkyl as defined herein, wherein the $C_3$-$C_6$ cycloalkyl may further contain one or two alkylene bridges of 1, 2, 3, or 4 carbon atoms, and each links two non-adjacent carbon atoms of the ring. Examples of such bridged ring system include, but are not limited to, bicyclo[1.1.1]pentyl, bicyclo[2.2.1]heptyl, bicyclo[2.1.1]hexyl, and bicyclo[3.1.1]heptyl. The cycloalkyl ring systems (including the exemplary rings) are optionally substituted unless otherwise indicated.

The term "$C_3$-$C_6$ cycloalkyl" as used herein, means cyclopropyl, cyclobutyl, cyclopentyl, and cyclohexyl, each of which is optionally substituted unless otherwise indicated.

The term "3-10 membered cycloalkyl" as used herein, means a hydrocarbon ring radical containing 3-10 carbon atoms and zero heteroatom. The 3-10 membered cycloalkyl may be a monocyclic cycloalkyl, a spiro cycloalkyl, or a bicyclic cycloalkyl. The monocyclic cycloalkyl typically is a carbocyclic ring system containing three to eight carbon ring atoms, zero heteroatoms and zero double bonds. More typically the monocyclic cycloalkyl is $C_3$-$C_6$ cycloalkyl, as defined herein above. The bicyclic cycloalkyl is a monocyclic cycloalkyl fused to a monocyclic cycloalkyl ring or a monocyclic cycloalkyl fused to a phenyl ring. The monocyclic and the bicyclic cycloalkyl groups may further contain one or two alkylene bridges, each consisting of one, two, three, or four carbon atoms in length, and each bridge links two non-adjacent carbon atoms of the ring system. Non-limiting examples of bicyclic ring systems include 2,3-dihydro-1H-indenyl, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). A spiro cycloalkyl is a monocyclic cycloalkyl wherein two substituents on the same carbon atom of the monocyclic cycloalkyl ring together with said carbon atom form a $C_3$-$C_6$ cycloalkyl ring. The monocyclic, the bicyclic, and the spiro cycloalkyl groups are attached to the parent molecular moiety through any substitutable atom contained within the ring system. The 3-10 membered cycloalkyls, including the exemplary rings, are optionally substituted unless indicated otherwise.

The term "$C_4$-$C_6$ cycloalkenyl" as used herein, means cyclobutenyl, cyclopentenyl, and cyclohexenyl, each of which is optionally substituted unless otherwise indicated.

The term "halo" or "halogen" as used herein, means Cl, Br, I, and F.

The term "$C_1$-$C_3$ haloalkoxy" as used herein, means a $C_1$-$C_3$ haloalkyl group, as defined herein, appended to the parent molecular moiety through an oxygen atom. Examples of $C_1$-$C_3$ haloalkoxy include, but are not limited to, trifluoromethoxy, difluoromethoxy, and 2-fluoroethoxy.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "heterocycle" or "heterocyclic" as used herein, means a radical of a monocyclic heterocycle, a bicyclic heterocycle, or a spiro heterocycle. A monocyclic heterocycle is a three-, four-, five-, six-, seven-, or eight-membered monocyclic carbocyclic ring wherein at least one carbon atom is replaced by heteroatom independently selected from the group consisting of O, N, and S. A three- or four-membered ring contains zero or one double bond, and one heteroatom selected from the group consisting of O, N, and S. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Non limiting examples of 5-membered heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of 6-membered heterocyclic groups include tetrahydropyranyl, dihydropyranyl, dioxanyl, 1,4-dithianyl, hexahydropyrimidine, morpholinyl, piperazinyl, piperidinyl, 1,2,3,6-tetrahydropyridinyl, tetrahydrothiopyranyl, thiomorpholinyl, thioxanyl, and trithianyl Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a $C_3$-$C_6$ cycloalkyl, or a monocyclic heterocycle fused to a $C_4$-$C_6$ cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl, hexahydropyrrolo[3,4-c]pyrrol-2(1H)-yl, and hexahydrocyclopenta[c]pyrrol-3a(1H)-yl. The monocyclic heterocycle and the bicyclic heterocycle may further contain one or two alkylene bridges, each consisting of 1, 2, 3, or 4 carbon atoms and each linking two non-adjacent atoms of the ring system. Examples of such bridged heterocycles include, but are not limited to, azabicyclo[2.2.1]heptyl (including 2-azabicyclo[2.2.1]hept-2-yl), 8-azabicyclo[3.2.1]oct-8-yl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The term "spiro heterocycle" as used herein, means a monocyclic heterocycle as defined herein wherein two substituents on the same carbon atom of the monocyclic heterocycle ring together with said carbon atom form a second monocyclic heterocycle or a $C_3$-$C_6$ cycloalkyl ring. Non limiting examples of the spiro heterocycle include 6-azaspiro[3.4]octane, 2-oxa-6-azaspiro[3.4]octan-6-yl, and 2,7-diazaspiro[4.4]nonane. The monocyclic, the bicyclic, and the Spiro heterocycles, including exemplary rings, are optionally substituted unless otherwise indicated. The monocyclic, the bicyclic, and the spiro heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl) and the nitrogen atoms may optionally be quaternized.

The term "4-6 membered monocyclic heterocycle" or "4-6 membered monocyclic heterocyclic" as used herein, means a 4-, 5-, or 6-membered monocyclic heterocycle as defined herein above. Examples of 4-6 membered monocyclic heterocycle include azetidinyl, dihydropyranyl, pyrrolidinyl, tetrahydrofuranyl, 1,3-dioxolanyl, tetrahydropyranyl, hexahydrothiopyranyl, piperazinyl, piperidinyl, thiomorpholinyl, and morpholinyl. The 4-6 membered monocyclic heterocycles, including exemplary rings, are optionally substituted unless indicated otherwise.

The term "4-7 membered monocyclic heterocycle" or "4-7 membered monocyclic heterocyclic" as used herein, means a 4-, 5-, 6-, or 7-membered monocyclic heterocycle as defined herein above. Examples of 4-7 membered monocyclic heterocycle include azetidinyl, dihydropyranyl, pyrrolidinyl, tetrahydrofuranyl, tetrahydropyranyl, piperazinyl, piperidinyl, thiomorpholinyl, morpholinyl, hexahydrothiopyranyl, and 1,4-oxazepanyl. The 4-7 membered monocyclic heterocycles, including exemplary rings, are optionally substituted unless indicated otherwise.

The term "monocyclic heteroaryl" as used herein, means a 5- or 6-membered monocyclic aromatic ring. The five-membered ring contains two double bonds. The five membered ring may contain one heteroatom selected from the group consisting of O and S; or one, two, three, or four nitrogen atoms and optionally one oxygen or one sulfur atom. The six-membered ring contains three double bonds and one, two, three, or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The monocyclic heteroaryls, including exemplary rings, are optionally substituted unless otherwise indicated. The monocyclic heteroaryls are connected to the parent molecular moiety through any substitutable carbon atom or any substitutable nitrogen atom contained within the ring systems. The nitrogen atom in the heteroaryl rings may optionally be oxidized and may optionally be quaternized.

The term "heteroatom" as used herein, means a nitrogen, oxygen, and sulfur.

The term "oxo" as used herein, means a =O group.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

The term 'one or more' refers to one to four. In another embodiment it refers to one to three. In a further embodiment it refers to one to two. In yet other embodiment it refers to two. In yet other further embodiment it refers to one.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p. Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G; G1349D; S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326dellTC, or 4279insA mutations. More particularly, Class VI mutation(s) refers to Rescued F508del mutations.

Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments of formula (I), X is formula (a).

In certain embodiments of formula (I), X is formula (b).

The carbon atom bearing $R^5$ in formula (a) and (b) is an asymmetrically substituted atom, and thus may exist as individual stereoisomers. For example, certain embodiments are directed to compounds wherein X is formula (a-i)

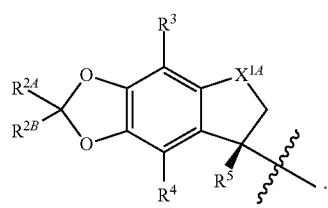
(a-i)

Certain embodiments are directed to compounds wherein X is formula (a-ii)

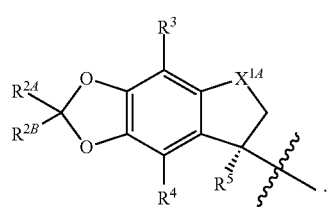
(a-ii)

Certain embodiments are directed to compounds wherein X is formula (b-i)

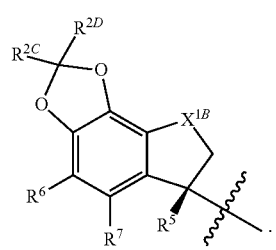
(b-i)

Certain embodiments are directed to compounds wherein X is formula (b-ii)

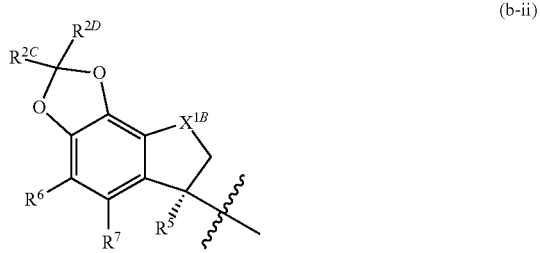
(b-ii)

Certain embodiments are directed to compounds wherein Y is $-G^1$.

Certain embodiments are directed to compounds wherein Y is formula (c)

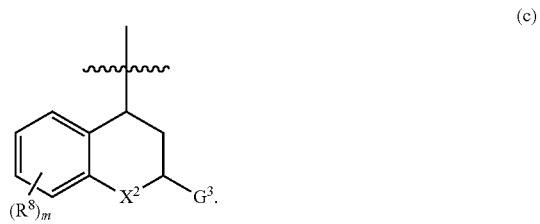
(c)

Certain embodiments are directed to compounds wherein Y is formula (c-i)

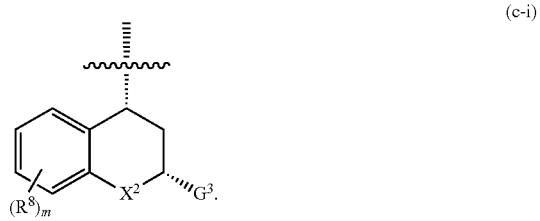
(c-i)

Certain embodiments are directed to compounds wherein Y is formula (d)

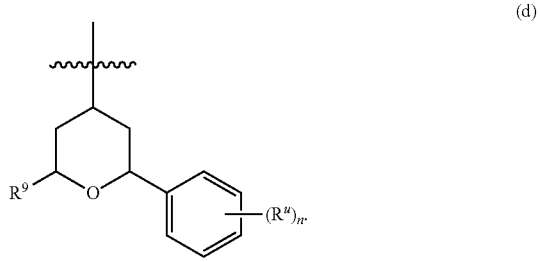
(d)

Certain embodiments are directed to compounds wherein Y is formula (d-i)

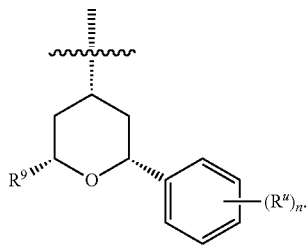

(d-i)

Certain embodiments are directed to compounds wherein Y is formula (d-ii)

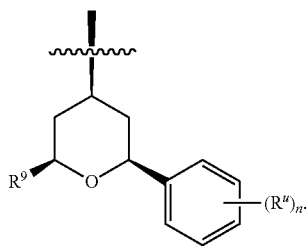

(d-ii)

Certain embodiments are directed to compounds wherein Y is formula (e)

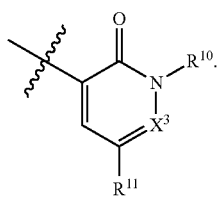

(e)

Certain embodiments are directed to compounds wherein Y is formula (f)

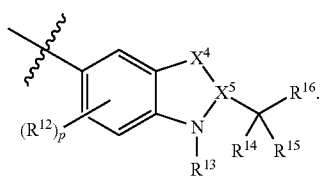

(f)

Certain embodiments are directed to compounds wherein Y is formula (g)

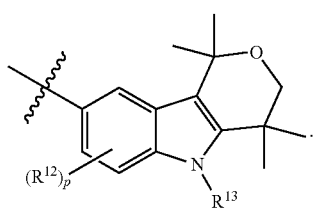

(g)

Certain embodiments are directed to compounds of formula (I-a-i)

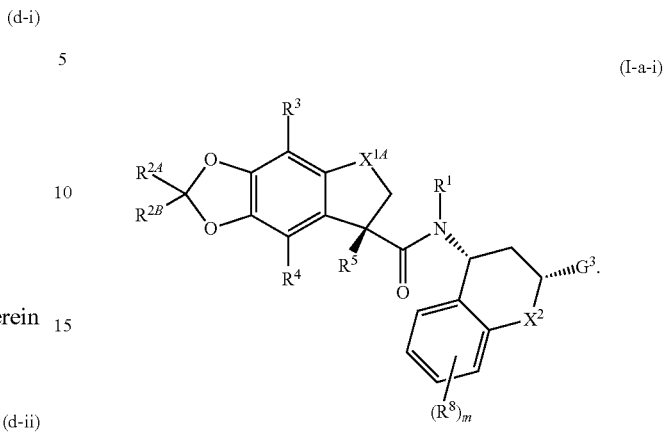

(I-a-i)

In certain embodiments $R^1$ is H.

In certain embodiments $R^1$ is $C_1$-$C_3$ alkyl. In some such embodiments, $R^1$ is $CH_3$.

In certain embodiments $R^{2A}$, $R^{2B}$, $R^{2C}$ and $R^{2D}$ are hydrogen or $R^{2A}$, $R^{2B}$, $R^{2C}$ and $R^{2D}$ are halogen. In some such embodiments, the halogen is F.

In certain embodiments $R^{2A}$ and $R^{2B}$ are F; and $R^{2C}$ and $R^{2D}$ are hydrogen, or $R^{2C}$ and $R^{2D}$ are F.

In certain embodiments $R^{2A}$ and $R^{2B}$ are hydrogen.

In certain embodiments $R^{2A}$ and $R^{2B}$ are halogen.

In certain embodiments $R^{2A}$ and $R^{2B}$ are F.

In certain embodiments $R^{2C}$ and $R^{2D}$ are hydrogen.

In certain embodiments $R^{2C}$ and $R^{2D}$ are halogen.

In certain embodiments $R^{2C}$ and $R^{2D}$ are F.

In certain embodiments $R^3$, $R^4$, $R^6$, and $R^7$ are hydrogen.

In certain embodiments $R^5$ is $C_1$-$C_3$ alkyl.

In certain embodiments $R^5$ is $CH_3$.

In certain embodiments $X^{1A}$ is O.

In certain embodiments $X^{1A}$ is $CH_2$.

In certain embodiments $X^{1B}$ is O.

In certain embodiments $X^{1B}$ is $CH_2$.

In certain embodiments, Y is -$G^1$.

In certain embodiments, $G^1$ is phenyl, pyridinyl, pyrazinyl, 1,3-thiazolyl, or 1,3,4-thiadiazolyl; each of which is optionally substituted with 1, 2, or 3 independently selected $R^p$ groups. In some such embodiments $G^1$ is substituted.

In certain embodiments, $G^1$ is phenyl or pyridinyl; each of which is optionally substituted with 1, 2, or 3 independently selected $R^p$ groups. In some such embodiments $G^1$ is substituted.

In certain embodiments, $G^1$ is phenyl which is optionally substituted with 1, 2, or 3 independently selected $R^p$ groups. In some such embodiments $G^1$ is substituted.

In certain embodiments, $G^1$ is monocyclic heteroaryl which is optionally substituted with 1, 2, or 3 independently selected $R^p$ groups. In some such embodiments $G^1$ is substituted.

In certain embodiments, $G^1$ is pyridinyl which is optionally substituted with 1, 2, or 3 independently selected $R^p$ groups. In some such embodiments, $G^1$ is substituted.

In certain embodiments, each $R^p$, when present, is independently $C_1$-$C_6$ alkyl, halogen, $G^2$, —C(O)NR$^A$R$^B$, or —NR$^A$R$^B$.

In certain embodiments, $G^1$ is substituted with 1, 2, or 3 independently selected $R^p$ groups wherein one $R^p$ group is $G^2$, and the 1 or 2 optional $R^p$ groups are independently $C_1$-$C_6$ alkyl, halogen, $C_1$-$C_6$ haloalkyl, $G^2$, $C_1$-$C_3$ alkoxy, or $C_1$-$C_3$ haloalkoxy.

In certain embodiments, $G^1$ is substituted with 1, 2, or 3 independently selected $R^p$ groups wherein one $R^p$ groups is $G^2$, and the 1 or 2 optional $R^p$ groups are independently $C_1$-$C_6$ alkyl, halogen, or $C_1$-$C_6$ haloalkyl.

In certain embodiments, $G^2$, when present, is independently phenyl, azetidinyl, pyrrolidinyl, piperidinyl, morpholinyl, hexahydropyrrolo[3,4-c]pyrrol-2(1H)-yl, hexahydrocyclopenta[c]pyrrol-3a(1H)-yl, 2-oxa-6-azaspiro[3.4]octan-6-yl, imidazolyl, or thienyl, each of which is optionally substituted. In some such embodiments, $G^2$ is substituted.

In certain embodiments, $G^2$ is optionally substituted phenyl. In some such embodiments, $G^2$ is substituted.

In certain embodiments, $G^2$ is an optionally substituted 4-6 membered monocyclic heterocycle. In some such embodiments, $G^2$ is substituted.

In certain embodiments, $G^2$ is azetidinyl, pyrrolidinyl, piperidinyl, or morpholinyl; each of which is optionally substituted. In some such embodiments, $G^2$ is substituted.

In certain embodiments, $G^2$ is optionally substituted pyrrolidinyl. In some such embodiments, $G^2$ is substituted.

In certain embodiments, $G^2$ is optionally substituted monocyclic heteroaryl. In some such embodiments, $G^2$ is substituted.

In certain embodiments, $G^2$ is optionally substituted thienyl. In some such embodiments, $G^2$ is substituted.

In certain embodiments, each $G^2$ (including exemplary rings) is optionally substituted with 1, 2, or 3 independently selected $R^q$ groups. In some such embodiments, $G^2$ is substituted.

In certain embodiments, each $R^q$, when present, is independently —CN, halogen, $C_1$-$C_3$ haloalkyl, —OR$^x$, —S(O)$_2$R$^x$, —S(O)$_2$N(R$^x$)$_2$, —C(O)OR$^x$, —C(O)N(R$^x$)$_2$, —C(O)N(R$^x$)S(O)$_2$R$^y$, $G^{2A}$, or $C_1$-$C_6$ alkyl which is optionally substituted with 1 or 2 substituents independently selected from the group consisting of —OR$^x$ and $G^{2A}$.

In certain embodiments, each $G^2$ (including specific examples) is unsubstituted.

In certain embodiments, each $G^2$ (including specific examples) is substituted with 1, 2, or 3 $R^q$ groups, wherein one $R^q$ group is —C(O)OR$^x$ or —OR$^x$, and the 1 or 2 optional $R^q$ groups are independently $C_1$-$C_6$ alkyl, halogen, or $C_1$-$C_3$ haloalkyl. In some such embodiments, R$^x$ is hydrogen or $C_1$-$C_6$ alkyl.

In certain embodiments, each $G^2$ (including specific examples) is substituted with 1, 2, or 3 $R^q$ groups, wherein one $R^q$ group is —C(O)OR$^x$, and the 1 or 2 optional $R^q$ groups are independently $C_1$-$C_6$ alkyl, halogen, or $C_1$-$C_3$ haloalkyl. In some such embodiments, le is hydrogen or $C_1$-$C_6$ alkyl.

In certain embodiments, each $G^2$ (including specific examples) is substituted with one $R^q$ group wherein $R^q$ is —C(O)OR$^x$ or R$^x$; and R$^x$ is hydrogen or $C_1$-$C_6$ alkyl.

In certain embodiments, each $G^2$ (including specific examples) is substituted with one $R^q$ group wherein $R^q$ is —C(O)OR$^x$; and R$^x$ is hydrogen or $C_1$-$C_6$ alkyl.

In certain embodiments, $G^2$ is phenyl substituted with one —C(O)OR$^x$ wherein R$^x$ is hydrogen or $C_1$-$C_6$ alkyl. In some such embodiments, R$^x$ is hydrogen. In some such embodiments, R$^x$ is $C_1$-$C_6$ alkyl.

In certain embodiments, $G^2$ is pyrrolidinyl substituted with one $R^q$ group, and $R^q$ is —C(O)OR$^x$ wherein R$^x$ is hydrogen or $C_1$-$C_6$ alkyl, or $R^q$ is —OR$^x$ wherein R$^x$ is hydrogen or $C_1$-$C_6$ alkyl. In some such embodiments, $R^q$ is —C(O)OR$^x$ wherein R$^x$ is hydrogen. In some such embodiments, $R^q$ is —C(O)OR$^x$ wherein R$^x$ is $C_1$-$C_6$ alkyl. In some such embodiments, $R^q$ is —OR$^x$ wherein R$^x$ is hydrogen.

In certain embodiments, Y is formula (c).
In certain embodiments, m is 0, 1, or 2.
In certain embodiments, m is 0 or 1.
In certain embodiments, m is 0.
In certain embodiments, m is 1.
In certain embodiments, $R^8$ is F, CH$_3$, CF$_3$, —OCH$_3$, —OCHF$_2$, —OCF$_3$, or OCH$_2$CH$_2$F.
In certain embodiments, $R^8$ is F, CH$_3$, CF$_3$, —OCH$_3$, —OCHF$_2$, or OCH$_2$CH$_2$F.
In certain embodiments, $R^8$ is $C_1$-$C_3$ alkoxy or $C_1$-$C_3$ haloalkoxy.
In certain embodiments, $R^8$ is —OCH$_3$, —OCF$_3$, or —OCHF$_2$.
In certain embodiments, $R^8$ is —OCH$_3$ or —OCHF$_2$.
In certain embodiments, $X^2$ is O.
In certain embodiments, $X^2$ is N(R$^{2x}$).
In certain embodiments, $X^2$ is N(R$^{2x}$) wherein R$^{2x}$ is hydrogen.
In certain embodiments, $G^3$ is —($C_1$-$C_3$ alkylenyl)-OR$^g$.
In certain embodiments, $G^3$ is —($C_1$-$C_3$ alkylenyl)-OR$^g$, wherein R$^g$ is hydrogen, benzyl, or

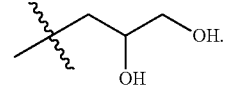 [SMILES: *CC(O)CO]

In certain embodiments, $G^3$ is —($C_1$-$C_3$ alkylenyl)-$G^B$. In certain embodiments, $G^B$ is substituted with 1, 2, or 3 R$^s$ groups; and R$^s$ is as defined in the Summary and embodiments herein below.

In certain embodiments $G^3$ is phenyl, cyclopropyl, cyclohexyl, azetidinyl, tetrahydrofuranyl, 1,6-dihydropyridazinyl, piperidinyl, tetrazolyl, pyrazinyl, pyridazinyl, or pyridinyl; each of which is optionally substituted.

In certain embodiments $G^3$ is phenyl, cyclopropyl, cyclohexyl, azetidinyl, tetrahydrofuranyl, or pyridinyl; each of which is optionally substituted.

In certain embodiments $G^3$ is phenyl, cyclohexyl, or pyridinyl; each of which is optionally substituted.

In certain embodiments, $G^3$ is phenyl or monocyclic heteroaryl; each of which is optionally substituted.

In certain embodiments, $G^3$ is phenyl or pyridinyl; each of which is optionally substituted.

In certain embodiments, $G^3$ is optionally substituted phenyl.

In certain embodiments, $G^3$ is optionally substituted cycloalkyl.

In certain embodiments, $G^3$ is optionally substituted $C_3$-$C_6$ cycloalkyl. In some such embodiments, $G^3$ is cyclopropyl, cyclobutyl, or cyclohexyl, each of which is optionally substituted. In some such embodiments, $G^3$ is cyclopropyl or cyclohexyl, each of which is optionally substituted. In some such embodiments, $G^3$ is optionally substituted cyclohexyl.

In certain embodiments, $G^3$ is optionally substituted cyclohexyl.

In certain embodiments, $G^3$ is an optionally substituted 4-6 membered monocyclic heterocycle.

In certain embodiments, $G^3$ is azetidinyl, tetrahydrofuranyl, 1,6-dihydropyridazinyl, or piperidinyl; each of which is optionally substituted.

In certain embodiments, $G^3$ is optionally substituted monocyclic heteroaryl.

In certain embodiments, $G^3$ is tetrazolyl, pyrazinyl, pyridazinyl, or pyridinyl; each of which is optionally substituted.

In certain embodiments, $G^3$ is optionally substituted pyridinyl.

In certain embodiments, each $G^3$ (including specific examples) is optionally substituted with 1, 2, or 3 independently selected $R^s$ groups.

In certain embodiments, $G^3$ (including specific examples) is unsubstituted.

In certain embodiments, $G^3$ (including specific examples) is substituted with 1, 2, or 3 $R^s$ groups.

In certain embodiments, $G^3$ (including specific examples) is substituted with one $R^s$ group.

In certain embodiments, $R^s$, when present, is $C_2$-$C_6$ alkenyl, oxo, —C(O)$R^j$, —N($R^j$)C(O)O($R^k$), halogen, $C_1$-$C_6$ haloalkyl, —O$R^j$, —O$R^h$, —C(O)O$R^j$, —C(O)O(benzyl), —C(O)N($R^m$)($R^n$), —SO$_2R^j$, $G^{3A}$, or $C_1$-$C_6$ alkyl which is optionally substituted with 1 or 2 substituents independently selected from the group consisting of —O$R^j$, —O-benzyl, —C(O)O$R^j$, —N($R^j$)$_2$, and $G^{3A}$.

In certain embodiments, $R^s$, when present, is $C_2$-$C_6$ alkenyl, oxo, —C(O)$R^j$, —N($R^j$)C(O)O($R^k$), halogen, $C_1$-$C_6$ haloalkyl, —O$R^j$, —C(O)O$R^j$, —SO$_2R^j$, or $C_1$-$C_6$ alkyl which is optionally substituted with 1 or 2 substituents independently selected from the group consisting of —O$R^j$ and —C(O)O$R^j$.

In certain embodiments, $R^s$, when present, is $C_1$-$C_6$ alkyl, halogen, $C_1$-$C_6$ haloalkyl, —O$R^j$, —C(O)O$R^j$, or —SO$_2R^j$.

In certain embodiments, $R^s$, when present, is —O$R^j$ or —C(O)O$R^j$; and $R^j$ is hydrogen or $C_1$-$C_6$ alkyl.

In certain embodiments, $G^3$ (including specific examples) is substituted with 1, 2, or 3 independently selected $R^s$ groups wherein one $R^s$ group is —C(O)O$R^j$ wherein $R^j$ is hydrogen or $C_1$-$C_6$ alkyl; and the optional $R^s$ groups are independently $C_1$-$C_3$ alkyl, halogen, or $C_1$-$C_3$ haloalkyl.

In certain embodiments, $G^3$ (including specific examples) is substituted with one $R^s$ group, and $R^s$ is —C(O)O$R^j$ wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $G^3$ is

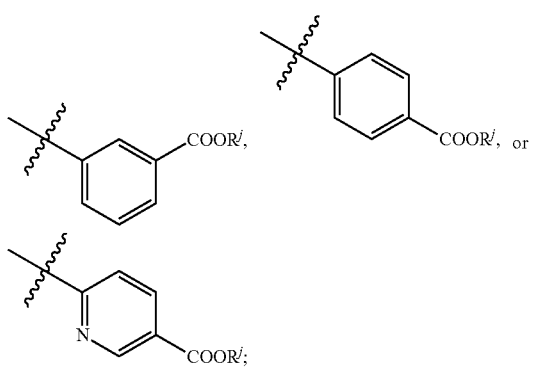

wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $G^3$ is

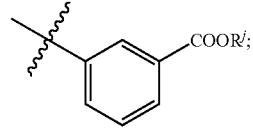

wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $G^3$ is

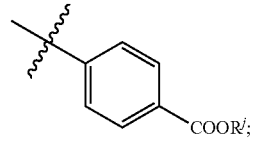

wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $G^3$ is

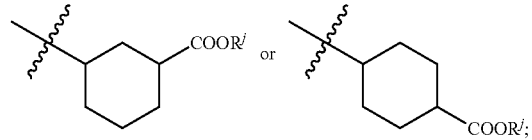

wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $G^3$ is

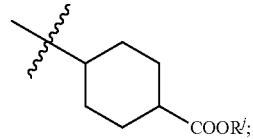

wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $R^s$ is —C(O)N($R^m$)($R^n$).

In certain embodiments, $R^s$ is —C(O)N($R^m$)($R^n$) wherein $R^m$ is $G^{3B}$ or $C_1$-$C_6$ alkyl which is substituted with 1 or 2 substituents independently selected from the group consisting of —O$R^j$, —S(O)$_2R^j$, —C(O)N($R^j$)$_2$, and $G^{3B}$; and $R^n$ is hydrogen, $C_1$-$C_6$ alkyl, $C_1$-$C_6$ haloalkyl, benzyl, or —($C_2$-$C_6$ alkylenyl)-O$R^j$.

In certain embodiments, $R^s$ is —C(O)N($R^m$)($R^n$) wherein $R^m$ is $C_1$-$C_6$ alkyl which is substituted with 1 or 2 substituents independently selected from the group consisting of —O$^j$ and optionally substituted phenyl; and $R^e$ is hydrogen, $C_1$-$C_6$ alkyl, $C_1$-$C_6$ haloalkyl, or —($C_2$-$C_6$ alkylenyl)-O$R^j$.

In certain embodiments, $R^s$ is —C(O)N($R^m$)($R^n$) wherein $R^m$ and $R^n$, together with the nitrogen atom to which they are attached, form a 4-7 membered monocyclic heterocycle, wherein the 4-7 membered monocyclic heterocycle is optionally substituted with 1, 2, 3, or 4 independently selected $R^c$ groups. In some such embodiments, the 4-7 membered monocyclic heterocycle is azetidinyl, pyrrolidinyl, piperidinyl, piperazinyl, morpholinyl, or 1,4-oxazepanyl; each of which is optionally substituted with 1, 2, or 3 independently selected $R^e$ groups. In some such embodiments, each $R^c$ is independently halogen, $C_1$-$C_6$ haloalkyl, —$OR^j$, or $C_1$-$C_6$ alkyl which is optionally substituted with one —$OR^j$. In some such embodiments, each $R^c$ is independently F, $CH_3$, —OH, or $CH_2OH$.

In certain embodiments, $R^s$ is $G^{3A}$ wherein $G^{3A}$ is a 4-7 membered monocyclic heterocycle; each $G^{3A}$ is optionally substituted with 1, 2, 3, or 4 $R^c$ groups. In some such embodiments, $G^{3A}$ is pyrrolidinyl substituted with 1, 2, 3, or 4 $R^c$ groups. In some such embodiments, $G^{3A}$ is pyrrolidinyl substituted with two —OH.

In certain embodiments, $R^s$ is —$OR^h$.

In certain embodiments, Y is formula (d).

In certain embodiments, $R^9$ is optionally substituted $C_3$-$C_6$ cycloalkyl.

In certain embodiments, $R^9$ is unsubstituted cyclopropyl.

In certain embodiments, $R^9$ is $C_1$-$C_3$ alkyl or optionally substituted phenyl.

In certain embodiments, $R^9$ is $C_1$-$C_3$ alkyl.

In certain embodiments, $R^9$ is methyl.

In certain embodiments, $R^9$ is optionally substituted phenyl.

In certain embodiments, $R^9$ is unsubstituted phenyl.

In certain embodiments, n is 0, 1, 2, or 3, and each $R^e$ is independently $C_1$-$C_3$ alkyl, halogen, $C_1$-$C_3$ haloalkyl, —C(O)$OR^j$, or —$OR^j$.

In certain embodiments, n is 0.

In certain embodiments, n is 1, 2, or 3.

In certain embodiments, each $R^u$ is independently $C_1$-$C_3$ alkyl, halogen, $C_1$-$C_3$ haloalkyl, —C(O)$OR^j$, or —$OR^j$.

In certain embodiments, n is 1, 2, or 3, one $R^u$ is —C(O)$OR^j$ wherein $R^j$ is hydrogen or $C_1$-$C_6$ alkyl, and the 1 or 2 optional $R^u$ groups are each independently $C_1$-$C_3$ alkyl, halogen, or $C_1$-$C_3$ haloalkyl.

In certain embodiments, n is 1, and $R^u$ is —C(O)$OR^j$ wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, Y is formula (e).

In certain embodiments, $X^3$ is N.

In certain embodiments, $X^3$ is CH.

In certain embodiments, $R^{10}$ is $C_1$-$C_6$ alkyl substituted with 1, 2, or 3 substituents independently selected from the group consisting of OH and 2,2-dimethyl-1,3-dioxolan-4-yl; or $R^{10}$ is optionally substituted phenyl.

In certain embodiments, $R^{10}$ is $C_2$-$C_6$ alkyl substituted with 1 or 2 OH groups or $R^{10}$ is (2,2-dimethyl-1,3-dioxolan-4-yl)methyl.

In certain embodiments, $R^{10}$ is n-propyl substituted with 2 OH groups.

In certain embodiments, $R^{10}$ is

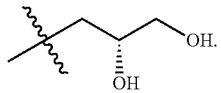 [SMILES: *C[C@@H](O)CO]

In certain embodiments, $R^{10}$ is phenyl, $C_3$-$C_6$ cycloalkyl, or monocyclic heteroaryl, each of which is optionally substituted with 1, 2, or 3 independently selected $R^v$ groups.

In certain embodiments, $R^{10}$ is phenyl optionally substituted with 1, 2, or 3 independently selected $R^v$ groups.

In certain embodiments, $R^{10}$ is phenyl substituted with 1, 2, or 3 independently selected $R^v$ groups; wherein one $R^v$ group is —C(O)$OR^j$ wherein $R^j$ is hydrogen or $C_1$-$C_6$ alkyl; and the 1 or 2 optional $R^v$ groups are each independently $C_1$-$C_3$ alkyl, halogen, or $C_1$-$C_3$ haloalkyl.

In certain embodiments, $R^{10}$ is

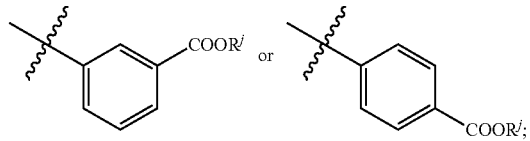

wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $R^{10}$ is

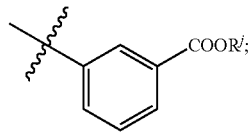

wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $R^{10}$ is

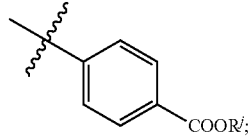

wherein $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $R^{10}$ is $C_3$-$C_6$ cycloalkyl optionally substituted with 1, 2, or 3 independently selected $R^v$ groups. In some such embodiments, $R^{10}$ is cyclopentyl or cyclohexyl, each of which is optionally substituted with 1, 2, or 3 independently selected $R^v$ groups.

In certain embodiments, $R^{10}$ is monocyclic heteroaryl optionally substituted with 1, 2, or 3 independently selected $R^v$ groups. In some such embodiments, $R^{10}$ is pyridinyl substituted with 1, 2, or 3 independently selected $R^v$ groups.

In certain embodiments, each $R^v$ is independently $C_1$-$C_3$ alkyl, halogen, $C_1$-$C_3$ haloalkyl, —C(O)$OR^j$, or —$OR^j$.

In certain embodiments, $R^{10}$ is $C_3$-$C_6$ cycloalkyl or monocyclic heteroaryl; each of which is substituted with one $R^v$ group, wherein $R^v$ is —C(O)$OR^j$, and $R^j$ is hydrogen or $C_1$-$C_6$ alkyl. In some such embodiments, $R^j$ is hydrogen. In some such embodiments, $R^j$ is $C_1$-$C_6$ alkyl.

In certain embodiments, $R^{11}$ is halogen or $G^4$ wherein $G^4$ is $C_3$-$C_6$ cycloalkyl or phenyl; each of which is optionally substituted.

In certain embodiments, $R^{11}$ is $G^4$; and $G^4$ is $C_3$-$C_6$ cycloalkyl or phenyl; each of which is optionally substituted.

In certain embodiments, $R^{11}$ is $G^4$, and $G^4$ is optionally substituted $C_3$-$C_6$ cycloalkyl.

In certain embodiments, $R^{11}$ is $G^4$, and $G^4$ is cyclopropyl or cyclopentyl; each of which is optionally substituted.

In certain embodiments, $R^{11}$ is $G^4$, and $G^4$ is optionally substituted cyclopropyl.

In certain embodiments, $R^{11}$ is $G^4$, and $G^4$ is an optionally substituted 4-6 membered monocyclic heterocycle.

In certain embodiments, $R^{11}$ is $G^4$, and $G^4$ is azetidinyl, morpholinyl, pyrrolidinyl, or dihydropyranyl, each of which is optionally substituted.

In certain embodiments, $R^{11}$ is $G^4$, and $G^4$ is optionally substituted monocyclic heteroaryl.

In certain embodiments, $R^{11}$ is $G^4$, and $G^4$ is pyridinyl, pyrimidinyl, or pyrazolyl; each of which is optionally substituted.

In certain embodiments, $R^{11}$ is $G^4$, and $G^4$ is optionally substituted phenyl.

Each $G^4$ (including specific examples) is optionally substituted with 1, 2, or 3 independently selected $R^w$ groups.

In certain embodiments, $G^4$ (including specific examples) is unsubstituted.

In certain embodiments, $G^4$ (including specific examples) is substituted with 1, 2, or 3 independently selected $R^w$ groups.

In certain embodiments, when present, is independently $C_1$-$C_3$ alkyl, halogen, $C_1$-$C_3$ haloalkyl, or —$OR^j$.

In certain embodiments, Y is formula (f).

In certain embodiments, p is 0 or 1 and $R^{12}$ is halogen. In some such embodiments, $R^{12}$ is F.

In certain embodiments, $X^4$-$X^5$ is N=C, $C(R^{4x})$=C, or $C(R^{4x})_2$—$C(R^{5x})$, wherein $R^{4x}$ and $R^{5x}$ are hydrogen.

In certain embodiments, $X^4$-$X^5$ is N=C or $C(R^{4x})_2$—$C(R^{5x})$, wherein $R^{4x}$ and $R^{5x}$ are hydrogen.

In certain embodiments, $X^4$-$X^5$ is N=C.

In certain embodiments, $X^4$-$X^5$ is $C(R^{4x})$=C. In some such embodiments, $R^{4x}$ is hydrogen.

In certain embodiments, $R^{13}$ is hydrogen or $C_1$-$C_6$ alkyl substituted with 1, 2, or 3 substituents independently selected from the group consisting of 2,2-dimethyl-1,3-dioxolan-4-yl, —$OR^{13a}$, and —O-benzyl. In some such embodiments, $R^{13a}$ is hydrogen.

In certain embodiments, $R^{13}$ is hydrogen.

In certain embodiments, $R^{13}$ is $C_1$-$C_6$ alkyl substituted with 1, 2, or 3 substituents independently selected from the group consisting of 2,2-dimethyl-1,3-dioxolan-4-yl and —$OR^{13a}$. In some such embodiments, $R^{13a}$ is hydrogen.

In certain embodiments, $R^{13}$ is $C_2$-$C_6$ alkyl substituted with 1, 2, or 3 —$OR^{13a}$. In some such embodiments, $R^{13a}$ is hydrogen.

In certain embodiments, $R^{13}$ is n-propyl substituted with 2 —OH.

In certain embodiments, $R^{13}$ is

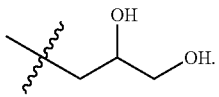 [SMILES: *CC(O)CO]

In certain embodiments, $R^{13}$ is

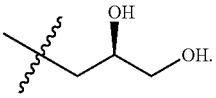 [SMILES: *C[C@@H](O)CO]

In certain embodiments, $R^{14}$ and $R^{15}$ are each independently $C_1$-$C_3$ alkyl. In some such embodiments, $R^{14}$ and $R^{15}$ are methyl.

In certain embodiments, $R^{14}$ and $R^{15}$, together with the carbon atom to which they are attached, form a $C_3$-$C_6$ cycloalkyl or a 4-6 membered monocyclic heterocycle containing one heteroatom selected from the group consisting of oxygen and nitrogen; each of which is optionally substituted.

In certain embodiments, $R^{14}$ and $R^{15}$, together with the carbon atom to which they are attached, form a $C_3$-$C_6$ cycloalkyl or a 4-6 membered monocyclic heterocycle containing one oxygen atom; each of which is optionally substituted.

In certain embodiments, $R^{14}$ and $R^{15}$, together with the carbon atom to which they are attached, is cyclopropyl or cyclobutyl; each of which is optionally substituted. In some such embodiments, the cyclopropyl and the cyclobutyl are unsubstituted.

In certain embodiments, $R^{14}$ and $R^{15}$, together with the carbon atom to which they are attached, is optionally substituted oxetanyl or optionally substituted tetrahydropyranyl. In some such embodiment, $R^{14}$ and $R^{15}$, together with the carbon atom to which they are attached, is unsubstituted oxetanyl.

In certain embodiments, $R^{16}$ is $C_1$-$C_6$ alkyl optionally substituted with an OH group. In some such embodiments, $R^{16}$ is $CH_3$ or —$CH_2OH$.

In certain embodiments, $R^{16}$ is $C_1$-$C_6$ alkyl. In some such embodiments, $R^{16}$ is methyl.

In certain embodiments, $R^{16}$ is $C_1$-$C_6$ alkyl substituted with an OH group. In some such embodiments, $R^{16}$ is —$CH_2OH$.

In certain embodiments, $R^{16}$ is $C_1$-$C_6$ alkyl substituted with an O-benzyl group.

Various embodiments of substituents X, $X^{1A}$, $X^{1B}$, $X^2$, $X^4$, $X^5$, Y, $G^1$, $G^3$, $G^4$, $R^1$, $R^{2A}$, $R^{2B}$, $R^{2C}$, $R^{2D}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^p$, $R^q$, $R^s$, $R^u$, $R^v$, $R^w$, $R^z$, m, n, and p have been discussed above. These substituents embodiments can be combined to form various embodiments of the invention. All embodiments of present compounds, formed by combining the substituent embodiments discussed above are within the scope of Applicant's invention, and some illustrative embodiments of present compounds are provided below.

In one embodiment, the invention is directed to compounds of formula (I) wherein $R^{2A}$, $R^{2B}$, $R^{2C}$, and $R^{2D}$ are H or $R^{2A}$, $R^{2B}$, $R^{2C}$, an $R^{2D}$ are halogen; $R^1$, $R^3$, $R^4$, $R^6$, and $R^7$ are hydrogen; and $R^5$ is $C_1$-$C_3$ alkyl. In some such embodiment, the halogen is F. In some such embodiments, $R^5$ is methyl.

In one embodiment, the invention is directed to compounds of formula (I) wherein X is formula (a), wherein $R^{2A}$ and $R^{2B}$ are F; and $R^1$, $R^3$, $R^4$, are hydrogen.

In one embodiment, the invention is directed to compounds of formula (I) wherein X is formula (b), wherein $R^{2C}$ and $R^{2d}$ are H, or $R^{2C}$ and $R^{2d}$ are F; and $R^1$, $R^6$, and $R^7$ are hydrogen.

In one embodiment, the invention is directed to compounds of formula (I) wherein Y is -$G^1$; $G^1$ is phenyl, pyridinyl, pyrazinyl, 1,3-thiazolyl, or 1,3,4-thiadiazolyl; each of which is optionally substituted with 1, 2, or 3 independently selected $R^p$ groups, wherein each $R^p$ is independently $C_1$-$C_6$ alkyl, halogen, $G^2$, —C(O)$NR^AR^B$, or —$NR^AR^B$.

In one embodiment, the invention is directed to compounds of formula (I) wherein Y is -$G^1$; $G^1$ is phenyl, pyridinyl, pyrazinyl, 1,3-thiazolyl, or 1,3,4-thiadiazolyl; each of which is optionally substituted with 1, 2, or 3 independently selected $R^p$ groups, wherein each $R^p$ is independently $C_1$-$C_6$ alkyl, halogen, $G^2$, —C(O)$NR^AR^B$, or —$NR^AR^B$;
$G^2$ is phenyl, azetidinyl, pyrrolidinyl, piperidinyl, morpholinyl, hexahydropyrrolo[3,4-c]pyrrol-2(1H)-yl, hexahydrocyclopenta[c]pyrrol-3a(1H)-yl, 2-oxa-6-azaspiro[3.4]octan-6-yl, imidazolyl, or thienyl, each of which is optionally substituted with 1, 2, or 3 independently selected $R^q$ groups; and
$R^q$ is —CN, halogen, $C_1$-$C_3$ haloalkyl, —$OR^x$, —S(O)$_2R^x$, —S(O)$_2$N($R^x$)$_2$, —C(O)$OR^x$, —C(O)N($R^x$)$_2$, —C(O)N($R^x$)S(O)$_2R^y$, $G^{2A}$, or $C_1$-$C_6$ alkyl which is optionally substituted with 1 or 2 substituents independently selected from the group consisting of —$OR^x$ and $G^{2A}$.

In one embodiment, the invention is directed to compounds of formula (I) wherein Y is formula (c), $X^2$ is O or N($R^{2x}$) wherein $R^{2x}$ is hydrogen; m is 0, 1, or 2; and $G^3$ is $C_3$-$C_6$ cycloalkyl which is optionally substituted with 1, 2, or 3 independently selected $R^s$ groups.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is phenyl or monocyclic heteroaryl; each of which is optionally substituted with 1, 2, or 3 independently selected $R^s$ groups.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is $C_3$-$C_6$ cycloalkyl which is substituted with 1, 2, or 3 independently selected $R^s$ groups; and $R^s$ is $C_1$-$C_6$ alkyl, halogen, $C_1$-$C_6$ haloalkyl, —$OR^j$, —C(O)$OR^j$, or —$SO_2R^j$. In some such embodiments, the $C_3$-$C_6$ cycloalkyl of $G^3$ is cyclopropyl or cyclohexyl. In some such embodiments, the $C_3$-$C_6$ cycloalkyl of $G^3$ is cyclopropyl. In some such embodiments, the $C_3$-$C_6$ cycloalkyl of $G^3$ is cyclohexyl.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is phenyl or monocyclic heteroaryl; each of which is substituted with 1, 2, or 3 independently selected $R^s$ groups; and $R^s$ is $C_1$-$C_6$ alkyl, halogen, $C_1$-$C_6$ haloalkyl, —$OR^j$, —C(O)$OR^j$, or —$SO_2R^j$. In some such embodiments, the monocyclic heteroaryl of $G^3$ is pyridinyl.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is cyclopropyl or cyclohexyl; each of which is substituted with 1, 2, or 3 independently selected $R^s$ groups; wherein one $R^s$ group is —C(O)$OR^j$ wherein $R^j$ is hydrogen or $C_1$-$C_6$ alkyl; and the optional $R^s$ groups are independently $C_1$-$C_3$ alkyl, halogen, or $C_1$-$C_3$ haloalkyl.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is phenyl or pyridinyl; each of which is substituted with 1, 2, or 3 independently selected $R^s$ groups wherein one $R^s$ group is —C(O)$OR^j$ wherein $R^j$ is hydrogen or $C_1$-$C_6$ alkyl; and the optional $R^s$ groups are independently $C_1$-$C_3$ alkyl, halogen, or $C_1$-$C_3$ haloalkyl.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is cyclohexyl which is substituted with one $R^s$ group, and $R^s$ is —C(O)$OR^j$ wherein $R^j$ is hydrogen or $C_1$-$C_6$ alkyl.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is phenyl or pyridinyl; each of which is substituted with one $R^s$ group, and $R^s$ is —C(O)$OR^j$ wherein $R^j$ is hydrogen or $C_1$-$C_6$ alkyl.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is

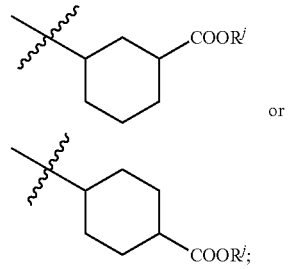

wherein $R^j$ is hydrogen or $C_1$-$C_6$ alkyl. In some such embodiments, $R^j$ is hydrogen. In some such embodiments, $R^j$ is $C_1$-$C_6$ alkyl.

In one embodiment, the invention is directed to compounds of formula (I) wherein Y is formula (c), $X^2$ is O or N($R^{2x}$) wherein $R^{2x}$ is hydrogen; m is 0 or 1; and $G^3$ is

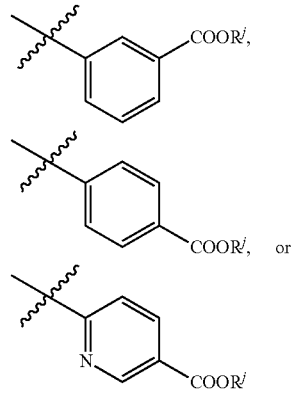

wherein $R^j$ is hydrogen or $C_1$-$C_6$ alkyl.

In one embodiment, the invention is directed to compounds of formula (I) wherein Y is formula (d), $R^9$ is $C_1$-$C_3$ alkyl or optionally substituted phenyl, and each $R^u$ is independently $C_1$-$C_3$ alkyl, halogen, $C_1$-$C_3$ haloalkyl, —C(O)$OR^j$, or —$OR^j$. In some such embodiments, $R^9$ is methyl or unsubstituted phenyl.

In one embodiment, the invention is directed to compounds of formula (I) wherein Y is formula (e), $R^{11}$ is halogen or $G^4$ wherein $G^4$ is $C_3$-$C_6$ cycloalkyl or phenyl, each of which is optionally substituted with 1, 2, or 3 independently selected $R^w$ groups; and $R^{10}$ is $C_1$-$C_6$ alkyl substituted with 1, 2, or 3 substituents independently selected from the group consisting of OH and 2,2-dimethyl-1,3-dioxolan-4-yl; or $R^{10}$ is phenyl optionally substituted with 1, 2, or 3 independently selected $R^v$ groups.

In one embodiment, the invention is directed to compounds of formula (I) wherein Y is formula (f), p is 0 or 1; and $R^{13}$ is hydrogen or $C_1$-$C_6$ alkyl substituted with 1, 2, or 3 substituents independently selected from the group consisting of 2,2-dimethyl-1,3-dioxolan-4-yl, —$OR^{13a}$, and —O-benzyl.

In one embodiment, the invention is directed to compounds of formula (I) wherein Y is formula (f), p is 0 or 1; $R^{12}$ is halogen; and $R^{13}$ is $C_2$-$C_6$ alkyl substituted with 1, 2, or 3 substituents independently selected from the group consisting of —$OR^{13a}$ and —O-benzyl. In some such embodiments, $R^{12}$ is F.

In one embodiment, the invention is directed to compounds of formula (I) wherein Y is formula (f), p is 0 or 1; $R^{12}$ is halogen; and $R^{13}$ is $C_2$-$C_6$ alkyl substituted with 1, 2, or 3 —$OR^{13a}$.

In some such embodiments, $R^{12}$ is F. In some such embodiments, $R^{13a}$ is hydrogen.

In one embodiment, the invention is directed to compounds of formula (I) wherein Y is formula (f), p is 0 or 1; $R^{12}$ is F; and $R^{13}$ is n-propyl substituted with 2 —OH.

In one embodiment, the invention is directed to compounds of formula (I) wherein Y is formula (f), p is 0 or 1; $R^{12}$ is F; and $R^{13}$ is

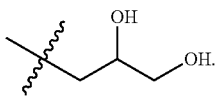 [SMILES: *CC(O)CO]

In one embodiment, the invention is directed to compounds of formula (I) wherein Y is formula (f), p is 0 or 1; $R^{12}$ is F; $R^{4x}$ is hydrogen; and $R^{13}$ is

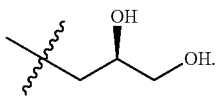

In one embodiment, the invention is directed to compounds of formula (I) wherein
$R^{2A}$, $R^{2B}$, $R^{2C}$, and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is -$G^1$; and
$G^1$ is phenyl, pyridinyl, pyrazinyl, 1,3-thiazolyl, or 1,3,4-thiadiazolyl; each of which is optionally substituted with 1, 2, or 3 independently selected $R^p$ groups, wherein each $R^p$ is independently $C_1$-$C_6$ alkyl, halogen, $G^2$, —C(O)$NR^AR^B$, or —$NR^AR^B$.

In one embodiment, the invention is directed to compounds of formula (I) wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is -$G^1$;
$G^1$ is phenyl, pyridinyl, pyrazinyl, 1,3-thiazolyl, or 1,3,4-thiadiazolyl; each of which is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl.

In one embodiment, the invention is directed to compounds of formula (I) wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is -$G^1$;
$G^1$ is phenyl, pyridinyl, pyrazinyl, 1, 3-thiazolyl, or 1,3,4-thiadiazolyl; each of which is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl;
$G^2$ is phenyl, azetidinyl, pyrrolidinyl, piperidinyl, morpholinyl, hexahydropyrrolo[3,4-c]pyrrol-2(1H)-yl, hexahydrocyclopenta[c]pyrrol-3a(1H)-yl, 2-oxa-6-azaspiro[3.4]octan-6-yl, imidazolyl, or thienyl, each of which is optionally substituted with 1, 2, or 3 independently selected $R^q$ groups; and
$R^q$ is CN, halogen, $C_1$-$C_3$ haloalkyl, —$OR^x$, —$S(O)_2R^x$, —$S(O)_2N(R^x)_2$, —C(O)$OR^x$, —C(O)N($R^x)_2$, —C(O)N($R^x$)S(O)$R^y$, $G^{2A}$, or $C_1$-$C_6$ alkyl which is optionally substituted with 1 or 2 substituents independently selected from the group consisting of —$OR^x$ and $G^{2A}$.

In one embodiment, the invention is directed to compounds of formula (I) wherein
X is formula (a);
$R^{2A}$ and $R^{2B}$ are F;
$R^1$, $R^3$, and $R^4$ are hydrogen;
$R^5$ is methyl;
Y is -$G^1$;
$G^1$ is phenyl or pyridinyl; each of which is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl; and
$G^2$ is phenyl, pyrrolidinyl, or thienyl, each of which is substituted with 1, 2, or 3 independently selected $R^q$ groups; wherein one $R^q$ group is —C(O)$OR^x$ or —$OR^x$, and the 1 or 2 optional $R^q$ groups are independently $C_1$-$C_6$ alkyl, halogen, or $C_1$-$C_3$ haloalkyl.

In some such embodiments, $X^{1A}$ is O. In some such embodiments, $X^{1A}$ is $CH_2$.

In one embodiment, the invention is directed to compounds of formula (I) wherein
X is formula (a);
$X^{1A}$ is O;
$R^{2A}$ and $R^{2B}$ are F;
$R^1$, $R^3$, and $R^4$ are hydrogen;
$R^5$ is methyl;
Y is -$G^1$;
$G^1$ is phenyl or pyridinyl; each of which is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl;
$G^2$ is phenyl, pyrrolidinyl, or thienyl, each of which is substituted with 1, 2, or 3 independently selected $R^q$ groups; wherein one $R^q$ group is —C(O)$OR^x$, and the 1 or 2 optional $R^p$ groups are independently $C_1$-$C_6$ alkyl, halogen, or $C_1$-$C_3$ haloalkyl; and
$R^x$ is hydrogen or $C_1$-$C_6$ alkyl.

In one embodiment, the invention is directed to compounds of formula (I) wherein X is formula (a-i);

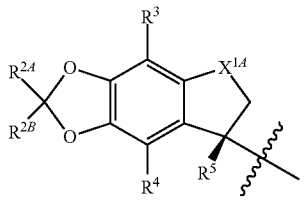

$X^{1A}$ is O;
$R^{2A}$ and $R^{2B}$ are F;
$R^1$, $R^3$, and $R^4$ are hydrogen;
$R^5$ is $C_1$-$C_3$ alkyl;
Y is -$G^1$;
$G^1$ is phenyl or pyridinyl; each of which is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl;
$G^2$ is phenyl, pyrrolidinyl, or thienyl, each of which is substituted with one —C(O)O$R^x$, and
$R^x$ is hydrogen or $C_1$-$C_6$ alkyl.

In some such embodiments, $R^5$ is methyl.

In one embodiment, the invention is directed to compounds of formula (I) wherein X is formula (a-i);

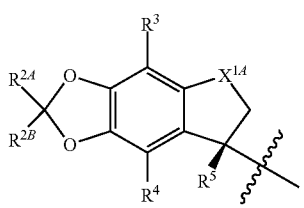

$X^{1A}$ is O;
$R^{2A}$ and $R^{2B}$ are F;
$R^1$, $R^3$, and $R^4$ are hydrogen;
$R^5$ is methyl;
Y is -$G^1$;
$G^1$ is pyridinyl which is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl;
$G^2$ is phenyl, pyrrolidinyl, or thienyl, each of which is substituted with one —C(O)O$R^x$, and
$R^x$ is hydrogen or $C_1$-$C_6$ alkyl.

In some such embodiments, $R^x$ is hydrogen. In some such embodiments, $R^x$ is $C_1$-$C_6$ alkyl.

In one embodiment, the invention is directed to compounds of formula (I) wherein $R^{2A}$, $R^{2B}$, $R^{2C}$, and $R^{2D}$ are hydrogen or $R^{2A}$, $R^{2B}$, $R^{2C}$, and $R^{2D}$ are F;

$R^1$, $R^3$, $R^4$, $R^6$, and $R^7$ are hydrogen;
$R^5$ is $C_1$-$C_3$ alkyl;
Y is formula (c);
$X^2$ is O or N($R^{2x}$) wherein $R^{2x}$ is hydrogen;
m is 0 or 1; and
$G^3$ is $C_3$-$C_6$ cycloalkyl which is optionally substituted with 1, 2, or 3 independently selected $R^s$ groups.

In one embodiment, the invention is directed to compounds of formula (I) wherein
$R^{2A}$, $R^{2B}$, $R^{2C}$, and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (c);
$X^2$ is O or N($R^{2x}$) wherein $R^{2x}$ is hydrogen;
m is 0 or 1; and
$G^3$ is phenyl or monocyclic heteroaryl; each of which is optionally substituted with 1, 2, or 3 independently selected $R^s$ groups.

In one embodiment, the invention is directed to compounds of formula (I) wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is formula (c);
$X^2$ is O or N($R^{2x}$) wherein $R^{2x}$ is hydrogen;
m is 0 or 1;
$G^3$ is $C_3$-$C_6$ cycloalkyl which is substituted with 1, 2, or 3 independently selected $R^s$ groups; and
each $R^s$ is independently $C_1$-$C_6$ alkyl, halogen, $C_1$-$C_6$ haloalkyl, —C(O)O$R^j$, or —SO$_2R^j$.

In one embodiment, the invention is directed to compounds of formula (I) wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is formula (c);
$X^2$ is O or N($R^{2x}$) wherein $R^{2x}$ is hydrogen;
m is 0 or 1;
$G^3$ is phenyl or monocyclic heteroaryl; each of which is substituted with 1, 2, or 3 independently selected $R^s$ groups; and
each $R^s$ is independently $C_1$-$C_6$ alkyl, halogen, $C_1$-$C_6$ haloalkyl, —O$R^j$, —C(O)O$R^j$, or —SO$_2R^j$.

In one embodiment, the invention is directed to compounds of formula (I) wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^2$ are hydrogen;
$R^5$ is methyl;
Y is formula (c);
$X^2$ is O or N($R^{2x}$) wherein $R^{2x}$ is hydrogen;
m is 0 or 1;
$G^3$ is $C_3$-$C_6$ cycloalkyl which is substituted with 1, 2, or 3 independently selected $R^s$ groups wherein one $R^s$ group is —C(O)O$R^j$ wherein $R^j$ is hydrogen or $C_1$-$C_6$ alkyl; and the optional $R^s$ groups are independently $C_1$-$C_3$ alkyl, halogen, or $C_1$-$C_3$ haloalkyl.

In some such embodiments, $R^j$ is hydrogen. In some such embodiments, $R^k$ is $C_1$-$C_6$ alkyl.

In one embodiment, the invention is directed to compounds of formula (I) wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is formula (c);
$X^2$ is O or $N(R^{2x})$ wherein $R^{2x}$ is hydrogen;
m is 0 or 1;
$G^3$ is phenyl or monocyclic heteroaryl; each of which is substituted with 1, 2, or 3 independently selected $R^s$ groups wherein one $R^s$ group is —C(O)O$R^j$ wherein $R^j$ is hydrogen or $C_1$-$C_6$ alkyl; and the optional $R^s$ groups are independently $C_1$-$C_3$ alkyl, halogen, or $C_1$-$C_3$ haloalkyl.

In some such embodiments, $R^j$ is hydrogen. In some such embodiments, $R^j$ is $C_1$-$C_6$ alkyl.

In one embodiment, the invention is directed to compounds of formula (I) wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is formula (c);
$X^2$ is O or $N(R^{2x})$ wherein $R^{2x}$ is hydrogen;
m is 0 or 1;
$G^3$ is $C_3$-$C_6$ cycloalkyl which is substituted with one $R^s$ group, and
$R^s$ is —C(O)O$R^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I) wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is formula (c);
$X^2$ is O or $N(R^{2x})$ wherein $R^{2x}$ is hydrogen;
m is 0 or 1;
$G^3$ is phenyl or pyridinyl; each of which is substituted with one $R^s$ group, and
$R^s$ is —C(O)O$R^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I) wherein
X is formula (a);
$X^{1A}$ is O;
$R^{2A}$ and $R^{2B}$ are F;
$R^1$, $R^3$, and $R^4$ are hydrogen;
$R^5$ is methyl;
Y is formula (c);
$X^2$ is O or $N(R^{2x})$ wherein $R^{2x}$ is hydrogen;
m is 0 or 1;
$G^3$ is $C_3$-$C_6$ cycloalkyl which is substituted with one $R^s$ group, and
$R^s$ is —C(O)O$R^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I) wherein
X is formula (a);
$X^{1A}$ is O;
$R^{2A}$ and $R^{2B}$ are F;
$R^1$, $R^3$, and $R^4$ are hydrogen;
$R^5$ is methyl;
Y is formula (c);
$X^2$ is O or $N(R^{2x})$ wherein $R^{2x}$ is hydrogen;
m is 0 or 1;
$G^3$ is phenyl or pyridinyl; each of which is substituted with one $R^s$ group, and
$R^s$ is —C(O)O$R^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I) wherein
X is formula (a);
$X^{1A}$ is $CH_2$;
$R^{2A}$ and $R^{2B}$ are F;
$R^1$, $R^3$, and $R^4$ are hydrogen;
$R^5$ is methyl;
Y is formula (c);
$X^2$ is O or $N(R^{2x})$ wherein $R^{2x}$ is hydrogen;
m is 0 or 1;
$G^3$ is $C_3$-$C_6$ cycloalkyl which is substituted with one $R^s$ group, and
$R^s$ is —C(O)O$R^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I) wherein
X is formula (a);
$X^{1A}$ is $CH_2$;
$R^{2A}$ and $R^{2B}$ are F;
$R^1$, $R^3$, and $R^4$ are hydrogen;
$R^5$ is methyl;
Y is formula (c);
$X^2$ is O or $N(R^{2x})$ wherein $R^{2x}$ is hydrogen;
m is 0 or 1;
$G^3$ is phenyl or pyridinyl; each of which is substituted with one $R^s$ group, and
$R^s$ is —C(O)O$R^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I) wherein
X is formula (a-i)

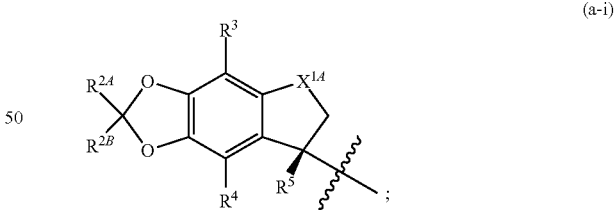

(a-i)

$X^{1A}$ is O or $CH_2$;
$R^{2A}$ and $R^{2B}$ are F;
$R^1$, $R^3$, and $R^4$ are hydrogen;
$R^5$ is $C_1$-$C_3$ alkyl;
Y is formula (c);
$X^2$ is O or $N(R^{2x})$ wherein $R^{2x}$ is hydrogen;
m is 0 or 1;
$R^8$ is an optional substituent on the benzo ring, and is halogen, $C_1$-$C_3$ alkyl, $C_1$-$C_3$ haloalkyl, $C_1$-$C_3$ alkoxy, or $C_1$-$C_3$ haloalkoxy; and
$G^3$ is $C_3$-$C_6$ cycloalkyl which is substituted with 1, 2, or 3 independently selected $R^s$ groups wherein one $R^s$ group is —C(O)OR$^j$ wherein R$^j$ is hydrogen or C$_1$-C$_6$ alkyl; and the optional R$^s$ groups are independently C$_1$-C$_3$ alkyl, halogen, or C$_1$-C$_3$ haloalkyl.

In some such embodiments, R$^j$ is hydrogen. In some such embodiments, R$^j$ is C$_1$-C$_6$ alkyl.

In some such embodiments, R$^5$ is methyl.

In some such embodiments, X$^{1A}$ is O.

In some such embodiments, X$^{1A}$ is CH$_2$.

In some such embodiments, X$^2$ is O. In some such embodiments, X$^2$ is N(R$^{2x}$) wherein R$^{2x}$ is hydrogen.

In some such embodiments, the C$_3$-C$_6$ cycloalkyl of G$^3$ is cyclopropyl or cyclohexyl, each of which is substituted as described. In some such embodiments, the C$_3$-C$_6$ cycloalkyl of G$^3$ is cyclohexyl which is substituted as described.

In one embodiment, the invention is directed to compounds of formula (I) wherein
X is formula (a-i)

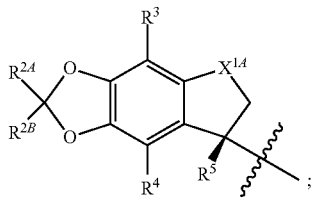

X$^{1A}$ is O;
R$^{2A}$ and R$^{2B}$ are F;
R$^1$, R$^3$, and R$^4$ are hydrogen;
R$^5$ is C$_1$-C$_3$ alkyl;
Y is formula (c);
X$^2$ is O or N(R$^{2x}$) wherein R$^{2x}$ is hydrogen;
m is 0 or 1;
R$^8$ is an optional substituent on the benzo ring, and is halogen, C$_1$-C$_3$ alkyl, C$_1$-C$_3$ haloalkyl, C$_1$-C$_3$ alkoxy, or C$_1$-C$_3$ haloalkoxy;
G$^3$ is phenyl or monocyclic heteroaryl; each of which is substituted with one R$^s$ group, and R$^s$ is —C(O)OR$^j$ wherein R$^j$ is hydrogen or C$_1$-C$_6$ alkyl.

In some such embodiments, R$^j$ is hydrogen. In some such embodiments, R$^j$ is C$_1$-C$_6$ alkyl.

In some such embodiments, R$^5$ is methyl.

In some such embodiments, the monocyclic heteroaryl of G$^3$ is pyridinyl which is substituted with one R$^s$ group.

In some such embodiments, X$^2$ is O. In some such embodiments, X$^2$ is N(R$^{2x}$) wherein R$^{2x}$ is hydrogen.

In one embodiment, the invention is directed to compounds of formula (I-a-i)

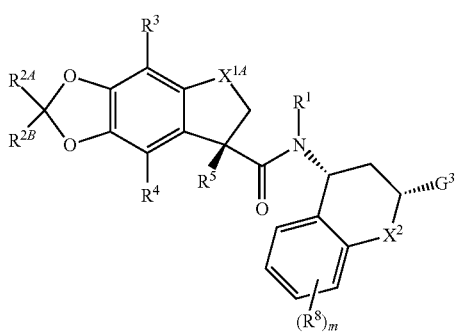

wherein
R$^{2A}$ and R$^{2B}$ are F;
R$^1$, R$^3$, and R$^4$ are hydrogen;
R$^5$ is C$_1$-C$_3$ alkyl;
X$^{1A}$ is O or CH$_2$;
X$^2$ is O or N(R$^{2x}$) wherein R$^{2x}$ is hydrogen;
m is 0 or 1;
R$^8$ is an optional substituent on the benzo ring, and is halogen, C$_1$-C$_3$ alkyl, C$_1$-C$_3$ haloalkyl, C$_1$-C$_3$ alkoxy, or C$_1$-C$_3$ haloalkoxy;
G$^3$ is C$_3$-C$_6$ cycloalkyl which is substituted with one R$^s$ group, and
R$^s$ is —C(O)O$^j$ wherein R$^j$ is hydrogen or C$_1$-C$_6$ alkyl.

In some such embodiments, X$^{1A}$ is O. In some such embodiments, X$^{1A}$ is CH$_2$.

In some such embodiments, R$^j$ is hydrogen. In some such embodiments, R$^j$ is C$_1$-C$_6$ alkyl.

In some such embodiments, the C$_3$-C$_6$ cycloalkyl of G$^3$ is cyclopropyl or cyclohexyl, each of which is substituted with one R$^s$ group. In some such embodiments, the C$_3$-C$_6$ cycloalkyl of G$^3$ is cyclohexyl which is substituted with one R$^s$ group.

In one embodiment, the invention is directed to compounds of formula (I-a-i)

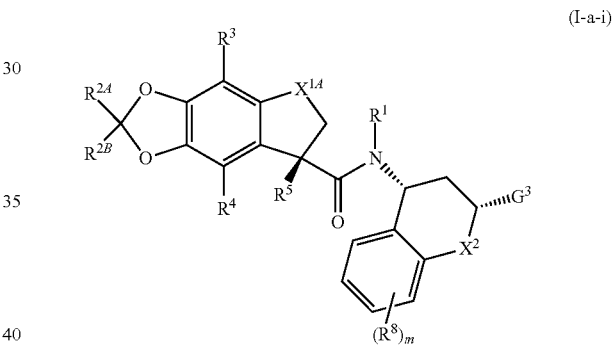

wherein
R$^{2A}$ and R$^{2B}$ are F;
R$^1$, R$^3$, and R$^4$ are hydrogen;
R$^5$ is C$_1$-C$_3$ alkyl;
X$^{1A}$ is O;
X$^2$ is O or N(R$^{2x}$) wherein R$^{2x}$ is hydrogen;
m is 0 or 1;
R$^8$ is an optional substituent on the benzo ring, and is halogen, C$_1$-C$_3$ alkyl, C$_1$-C$_3$ haloalkyl, C$_1$-C$_3$ alkoxy, or C$_1$-C$_3$ haloalkoxy;
G$^3$ is phenyl or monocyclic heteroaryl; each of which is substituted with one R$^s$ group, and R$^s$ is —C(O)OR$^j$ wherein R$^j$ is hydrogen or C$_1$-C$_6$ alkyl.

In some such embodiments, R$^j$ is hydrogen. In some such embodiments, R$^j$ is C$_1$-C$_6$ alkyl.

In some such embodiments, the monocyclic heteroaryl of G$^3$ is pyridinyl which is substituted with one R$^s$ group.

In one embodiment, the invention is directed to compounds of formula (I-a-i) wherein
R$^{2A}$ and R$^{2B}$ are F;
R$^1$, R$^3$, and R$^4$ are hydrogen;
R$^5$ is methyl;
X$^{1A}$ is O;
X$^2$ is O or N(R$^{2x}$) wherein R$^{2x}$ is hydrogen;
m is 0 or 1;

$R^8$ is an optional substituent on the benzo ring, and is $C_1$-$C_3$ alkoxy or $C_1$-$C_3$ haloalkoxy;

$G^3$ is cyclopropyl or cyclohexyl; each of which is substituted with one $R^s$ group, and $R^s$ is —C(O)O$^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In some such embodiments, $X^2$ is O. In some such embodiments, $X^2$ is N($R^{2x}$) wherein $R^{2x}$ is hydrogen.

In one embodiment, the invention is directed to compounds of formula (I-a-i) wherein $R^{2A}$ and $R^{2B}$ are F;

$R^1$, $R^3$, and $R^4$ are hydrogen;

$R^5$ is methyl;

$X^{1A}$ is O;

$X^2$ is O or N($R^{2x}$) wherein $R^{2x}$ is hydrogen;

m is 0 or 1;

$R^8$ is an optional substituent on the benzo ring, and is $C_1$-$C_3$ alkoxy or $C_1$-$C_3$ haloalkoxy;

$G^3$ is phenyl or pyridinyl; each of which is substituted with one $R^s$ group, and $R^s$ is —C(O)O$^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In some such embodiments, $X^2$ is O. In some such embodiments, $X^2$ is N($R^{2x}$) wherein $R^{2x}$ is hydrogen.

In one embodiment, the invention is directed to compounds of formula (I-a-i) wherein $R^{2A}$ and $R^{2B}$ are F;

$R^1$, $R^3$, and $R^4$ are hydrogen;

$R^5$ is methyl;

$X^{1A}$ is O;

$X^2$ is O;

m is 0 or 1;

$R^8$ is an optional substituent on the benzo ring, and is $C_1$-$C_3$ alkoxy or $C_1$-$C_3$ haloalkoxy;

$G^3$ is cyclohexyl which is substituted with one $R^s$ group; and $R^s$ is —C(O)OR$^j$ wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I-a-i) wherein $R^{2A}$ and $R^{2B}$ are F;

$R^1$, $R^3$, and $R^4$ are hydrogen;

$R^5$ is methyl;

$X^{1A}$ is O;

$X^2$ is O;

m is 0 or 1;

$R^8$ is an optional substituent on the benzo ring, and is $C_1$-$C_3$ alkoxy or $C_1$-$C_3$ haloalkoxy; and $G^3$ is

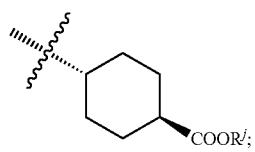

wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I-a-i) wherein $R^{2A}$ and $R^{2B}$ are F;

$R^1$, $R^3$, and $R^4$ are hydrogen;

$R^5$ is methyl;

$X^{1A}$ is O;

$X^2$ is O;

m is 0 or 1;

$R^8$ is an optional substituent on the benzo ring, and is $C_1$-$C_3$ alkoxy or $C_1$-$C_3$ haloalkoxy; and $G^3$ is

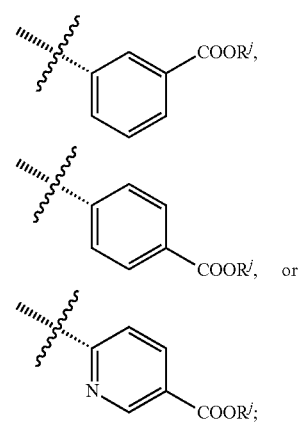

wherein $R^j$ is hydrogen or $C_1$-$C_6$ alkyl.

In some such embodiments, $R^j$ is hydrogen. In some such embodiments, $R^j$ is $C_1$-$C_6$ alkyl.

In one embodiment, the invention is directed to compounds of formula (I) wherein $R^{2A}$, $R^{2B}$, $R^{2C}$, and $R^{2D}$ are hydrogen or $R^{2A}$, $R^{2B}$, $R^{2C}$, and $R^{2D}$ are F;

$R^1$, $R^3$, $R^4$, $R^6$, and $R^7$ are hydrogen $R^5$ is $C_1$-$C_3$ alkyl;

Y is formula (d);

n is 1, 2, or 3;

each $R^u$ is independently $C_1$-$C_3$ alkyl, halogen, $C_1$-$C_3$ haloalkyl, —C(O)OR$^j$, or —O$^j$; and $R^9$ is $C_1$-$C_3$ alkyl or optionally substituted phenyl.

In some such embodiments, $R^5$ is methyl.

In one embodiment, the invention is directed to compounds of formula (I) wherein X is formula (a);

$R^{2A}$ and $R^{2B}$ are F;

$R^1$, $R^3$, and $R^4$ are hydrogen;

$X^{1A}$ is O;

$R^5$ is methyl;

Y is formula (d);

n is 1, 2, or 3;

each $R^u$ is independently $C_1$-$C_3$ alkyl, halogen, $C_1$-$C_3$ haloalkyl, —C(O)OR$^j$, or —O$^j$; and $R^9$ is $C_1$-$C_3$ alkyl or unsubstituted phenyl.

In one embodiment, the invention is directed to compounds of formula (I) wherein
X is formula (a);
$R^{2A}$ and $R^{2B}$ are F;
$R^1$, $R^3$, and $R^4$ are hydrogen;
$X^{1A}$ is O;
$R^5$ is methyl;
Y is formula (d);
n is 1, 2, or 3;
one $R^u$ is —C(O)O$R^j$ wherein $R^j$ is hydrogen or $C_1$-$C_6$ alkyl; and the 1 or 2 optional $R^u$ groups are each independently $C_1$-$C_3$ alkyl, halogen, or $C_1$-$C_3$ haloalkyl; and
$R^9$ is unsubstituted phenyl.

In one embodiment, the invention is directed to compounds of formula (I) wherein
$R^{2A}$, $R^{2B}$, $R^{2C}$, and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (e);
$R^{10}$ is $C_1$-$C_6$ alkyl substituted with 1, 2, or 3 substituents independently selected from the group consisting of OH and 2,2-dimethyl-1,3-dioxolan-4-yl; or $R^{10}$ is phenyl optionally substituted with 1, 2, or 3 independently selected $R^v$ groups; and
$R^{11}$ is halogen or $G^4$ wherein $G^4$ is $C_3$-$C_6$ cycloalkyl or phenyl; each of which is optionally substituted with 1, 2, or 3 independently selected $R^w$ groups.

In one embodiment, the invention is directed to compounds of formula (I) wherein
X is formula (a)
$R^{2A}$ and $R^{2B}$ are F;
$R^1$, $R^3$, and $R^4$ are hydrogen;
$X^{1A}$ is O;
$R^5$ is methyl;
Y is formula (e);
$R^{10}$ is $C_1$-$C_6$ alkyl substituted with 1, 2, or 3 substituents independently selected from the group consisting of OH and 2,2-dimethyl-1,3-dioxolan-4-yl; or $R^{10}$ is phenyl optionally substituted with 1, 2, or 3 independently selected $R^v$ groups; and
$R^{11}$ is halogen or $G^4$ wherein $G^4$ is $C_3$-$C_6$ cycloalkyl or phenyl; each of which is optionally substituted with 1, 2, or 3 independently selected $R^w$ groups.

In one embodiment, the invention is directed to compounds of formula (I) wherein
X is formula (a)
$R^{2A}$ and $R^{2B}$ are F;
$R^1$, $R^3$, and $R^4$ are hydrogen;
$X^{1A}$ is O;
$R^5$ is methyl;
Y is formula (e);
$R^{10}$ is $C_1$-$C_6$ alkyl substituted with 1, 2, or 3 substituents independently selected from the group consisting of OH and 2,2-dimethyl-1,3-dioxolan-4-yl; or
$R^{10}$ is phenyl substituted with 1, 2, or 3 independently selected $R^v$ groups wherein one $R^v$ group is —C(O)O$R^j$ wherein $R^j$ is hydrogen or $C_1$-$C_6$ alkyl; and the 1 or 2 optional $R^v$ groups are each independently $C_1$-$C_3$ alkyl, halogen, or $C_1$-$C_3$ haloalkyl; and
$R^{11}$ is $G^4$ wherein $G^4$ is $C_3$-$C_6$ cycloalkyl or phenyl; each of which is optionally substituted with 1, 2, or 3 independently selected $R^w$ groups.

In one embodiment, the invention is directed to compounds of formula (I) wherein
$R^{2A}$, $R^{2B}$, $R^{2C}$ and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (f); and
$R^{16}$ is $C_1$-$C_6$ alkyl optionally substituted with one —OH group.

In one embodiment, the invention is directed to compounds of formula (I) wherein
$R^{2A}$, $R^{2B}$, $R^{2C}$ and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (f); and
$R^{13}$ is hydrogen or $C_1$-$C_6$ alkyl substituted with 1, 2, or 3 substituents independently selected from the group consisting of 2,2-dimethyl-1,3-dioxolan-4-yl, —O$R^{13a}$, and —O-benzyl.

In one embodiment, the invention is directed to compounds of formula (I) wherein
$R^{2A}$, $R^{2B}$, $R^{2C}$ and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (f);
$R^{13}$ is $C_2$-$C_6$ alkyl substituted with 1, 2, or 3 substituents independently selected from the group consisting of —O$R^{13a}$ and —O-benzyl, and
$R^{16}$ is $C_1$-$C_6$ alkyl optionally substituted with one —OH group.

In one embodiment, the invention is directed to compounds of formula (I) wherein
X is formula (a);
$R^{2A}$ and $R^{2B}$ are F;
$R^1$, $R^3$, and $R^4$ are hydrogen;
$R^5$ is $C_1$-$C_3$ alkyl;
Y is formula (f);
$R^{13}$ is $C_2$-$C_6$ alkyl substituted with 1, 2, or 3 —O$R^{13a}$; and
$R^{16}$ is $C_1$-$C_6$ alkyl optionally substituted with one OH group.

In one embodiment, the invention is directed to compounds of formula (I) wherein
X is formula (a);
$R^{2A}$ and $R^{2B}$ are F;
$R^1$, $R^3$, and $R^4$ are hydrogen;
$R^5$ is $C_1$-$C_3$ alkyl;
Y is formula (0;
p is 0 or 1;
$R^{12}$ is halogen;
$R^{13}$ is $C_2$-$C_6$ alkyl substituted with 1, 2, or 3 —O$R^{13a}$;
$R^{14}$ and $R^{15}$ are each independently $C_1$-$C_3$ alkyl; and
$R^{16}$ is $C_1$-$C_6$ alkyl optionally substituted with one OH group.

In one embodiment, the invention is directed to compounds of formula (I) wherein
X is formula (a);
$R^{2A}$ and $R^{2B}$ are F;
$R^1$, $R^3$, and $R^4$ are hydrogen;
$R^5$ is $C_1$-$C_3$ alkyl;
Y is formula (0;
p is 0 or 1;
$R^{12}$ is halogen;
$R^{13}$ is $C_2$-$C_6$ alkyl substituted with 1, 2, or 3 —O$R^{13a}$;
$R^{14}$ and $R^{15}$, together with the carbon atom to which they are attached, is $C_3$-$C_6$ cycloalkyl, or a 4-6 membered monocyclic heterocycle containing one oxygen atom; each of which is optionally substituted; and
$R^{16}$ is $C_1$-$C_6$ alkyl optionally substituted with one OH group.

In one embodiment, the invention is directed to compounds of formula (I) wherein
X is formula (a);
$R^{2A}$ and $R^{2B}$ are F;
$R^1$, $R^3$, and $R^4$ are hydrogen;
$R^5$ is $C_1$-$C_3$ alkyl;
Y is formula (f);
$X^4$-$X^5$ is $C(R^{4x})$=C; wherein $R^{4x}$ is hydrogen;
p is 0 or 1;
$R^{12}$ is halogen;
$R^{13}$ is $C_2$-$C_6$ alkyl substituted with 1, 2, or 3 —$OR^{13a}$;
$R^{14}$ and $R^{15}$, together with the carbon atom to which they are attached, is unsubstituted cyclopropyl, unsubstituted cyclobutyl, or unsubstituted oxetanyl; and
$R^{16}$ is $C_1$-$C_6$ alkyl optionally substituted with one OH group.

In one embodiment, the invention is directed to compounds of formula (I) wherein
$R^1$ is H;
X is formula (a-i)

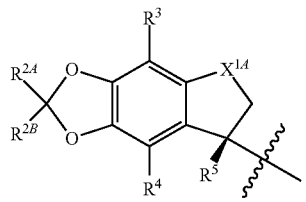

wherein
$R^{2A}$ and $R^{2B}$ are F;
$R^3$ and $R^4$ are hydrogen;
$R^5$ is $C_1$-$C_3$ alkyl;
$X^{1A}$ is O;
Y is formula (f);

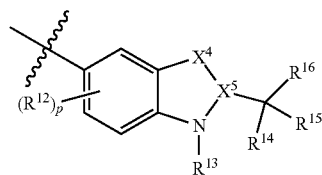

wherein
$X^4$-$X^5$ is N=C, $C(R^{4x})$=C, or $C(R^{4x})_2$—$C(R^{5x})$; wherein $R^{4x}$ and $R^{5x}$ are hydrogen;
p is 0 or 1;
$R^{12}$ is halogen;
$R^{14}$ and $R^{15}$ are each independently $C_1$-$C_3$ alkyl; or $R^{14}$ and $R^{15}$, together with the carbon atom to which they are attached, is cyclopropyl, cyclobutyl, or oxetanyl; each of which is optionally substituted with 1 or 2 substituents independently selected from the group consisting of $C_1$-$C_3$ alkyl, halogen, $C_1$-$C_3$ haloalkyl, —OH, $C_1$-$C_3$ alkoxy, and $C_1$-$C_3$ haloalkoxy; $R^{13}$ is $C_2$-$C_6$ alkyl substituted with 1, 2, or 3 —$OR^{13a}$;
$R^{13a}$ is hydrogen; and
$R^{16}$ is $CH_3$ or —$CH_2OH$.

In one embodiment, the invention is directed to compounds of formula (I) wherein
$R^1$ is H;
X is formula (a-i)

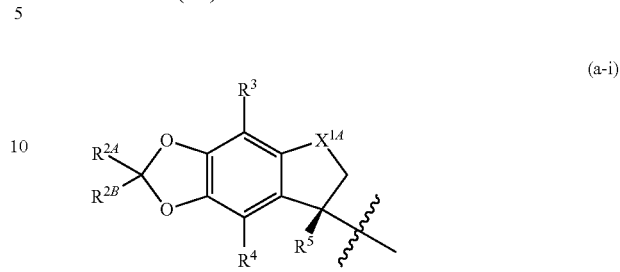

wherein
$R^{2A}$ and $R^{2B}$ are F;
$R^3$ and $R^4$ are hydrogen;
$R^5$ is $C_1$-$C_3$ alkyl;
$X^{1A}$ is O;
Y is formula (f);

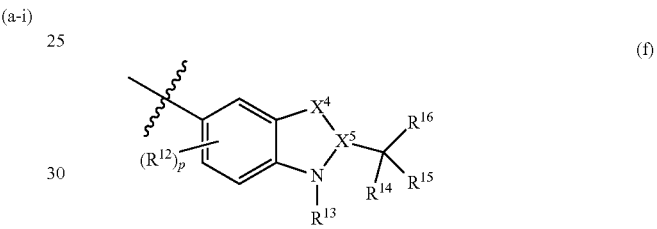

wherein
$X^4$-$X^5$ is N=C, $C(R^{4x})$=C, or $C(R^{4x})_2$—$C(R^{5x})$; wherein $R^{4x}$ and $R^{5x}$ are hydrogen;
p is 0 or 1;
$R^{12}$ is halogen;
$R^{14}$ and $R^{15}$ are each independently $C_1$-$C_3$ alkyl; or $R^{14}$ and $R^{15}$, together with the carbon atom to which they are attached, is cyclopropyl, cyclobutyl, or oxetanyl; each of which is optionally substituted with 1 or 2 substituents independently selected from the group consisting of $C_1$-$C_3$ alkyl, halogen, $C_1$-$C_3$ haloalkyl, —OH, $C_1$-$C_3$ alkoxy, and $C_1$-$C_3$ haloalkoxy;
$R^{13}$ is n-propyl substituted with 2 —OH groups; and
$R^{16}$ is $CH_3$ or —$CH_2OH$.

In one embodiment, the invention is directed to compounds of formula (I) wherein
$R^1$ is H;
X is formula (a-i)

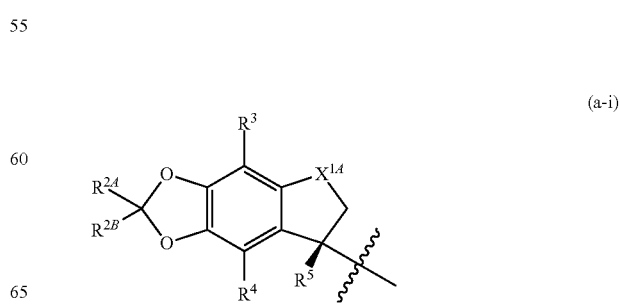

wherein
R$^{2A}$ and R$^{2B}$ are F;
R$^3$ and R$^4$ are hydrogen;
R$^5$ is C$_1$-C$_3$ alkyl;
X$^{1A}$ is O;
Y is formula (f);

(f)
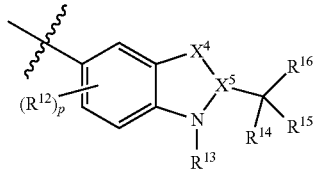

wherein

X$^4$-X$^5$ is N=C, C(R$^{4x}$)=C, or C(R$^{4x}$)$_2$—C(R$^{5x}$); wherein R$^{4x}$ and R$^{5x}$ are hydrogen;
p is 0 or 1;
R$^{12}$ is halogen;
R$^{14}$ and R$^{15}$ are each independently C$_1$-C$_3$ alkyl; or R$^{14}$ and R$^{15}$, together with the carbon atom to which they are attached, is cyclopropyl, cyclobutyl, or oxetanyl; each of which is optionally substituted with 1 or 2 substituents independently selected from the group consisting of C$_1$-C$_3$ alkyl, halogen, C$_1$-C$_3$ haloalkyl, —OH, C$_1$-C$_3$ alkoxy, and C$_1$-C$_3$ haloalkoxy;
R$^{13}$ is

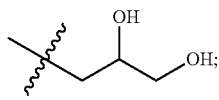

and
R$^{16}$ is CH$_3$ or —CH$_2$OH.

In one embodiment, the invention is directed to compounds of formula (I) wherein
R$^1$ is H;
X is formula (a-i)

(a-i)
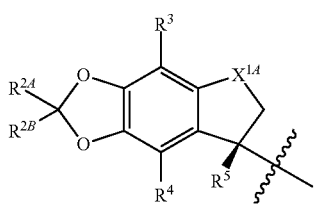

wherein
R$^{2A}$ and R$^{2B}$ are F;
R$^3$ and R$^4$ are hydrogen;
R$^5$ is C$_1$-C$_3$ alkyl;
X$^{1A}$ is O;
Y is formula (f);

(f)
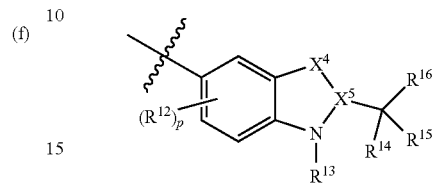

wherein
X$^4$-X$^5$ is N=C, C(R$^{4x}$)=C, or C(R$^{4x}$)$_2$—C(R$^{5x}$); wherein R$^{4x}$ and R$^{5x}$ are hydrogen;
p is 0 or 1;
R$^{12}$ is halogen;
R$^{14}$ and R$^{15}$ are each independently C$_1$-C$_3$ alkyl; or R$^{14}$ and R$^{15}$, together with the carbon atom to which they are attached, is cyclopropyl, cyclobutyl, or oxetanyl; each of which is optionally substituted with 1 or 2 substituents independently selected from the group consisting of C$_1$-C$_3$ alkyl, halogen, C$_1$-C$_3$ haloalkyl, —OH, C$_1$-C$_3$ alkoxy, and C$_1$-C$_3$ haloalkoxy;
R$^{13}$ is

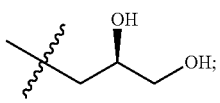 [SMILES: *C[C@@H](O)CO]

and
R$^{16}$ is CH$_3$ or —CH$_2$OH.

In one embodiment, the invention is directed to compounds of formula (I)

(I)
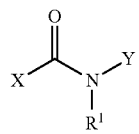

wherein
R$^1$ is H or C$_1$-C$_3$ alkyl;
X is formula (a) or formula (b)

(a)
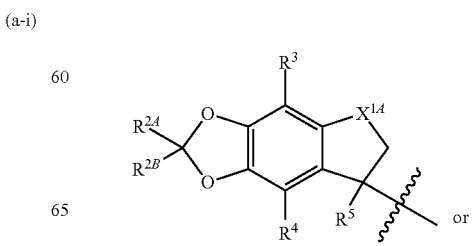

or

-continued (b)
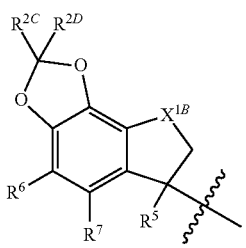

wherein
$R^{2A}$, $R^{2B}$, $R^{2C}$, and $R^{2D}$, are each independently hydrogen or halogen;
$R^3$, $R^4$, $R^6$, and $R^7$, are each independently hydrogen, $C_1$-$C_3$ alkyl, or halogen;
$R^5$, at each occurrence, is independently hydrogen, $C_1$-$C_3$ alkyl, $C_2$-$C_4$ alkenyl, or $C_1$-$C_3$ haloalkyl;
$X^{1A}$ is O or $CH_2$;
$X^{1B}$ is O or $CH_2$;
Y is -$G^1$, or Y is formula (c), (d), (e), or (f)

(c)
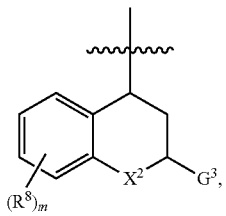

(d)
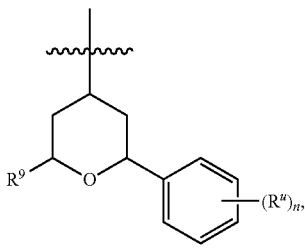

(e)
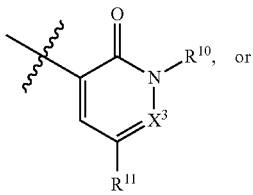

or (f)
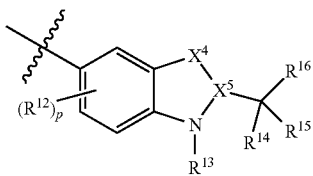

wherein
$G^1$ is phenyl or monocyclic heteroaryl, each of which is optionally substituted with 1, 2, or 3 independently selected $R^p$ groups; wherein each $R^p$ is independently $C_1$-$C_6$ alkyl, halogen, $C_1$-$C_6$ haloalkyl, $G^2$, $C_1$-$C_3$ alkoxy, $C_1$-$C_3$ haloalkoxy, —C(O)-$G^A$, —C(O)N$R^A R^B$, or —N$R^A R^B$;
wherein $R^A$, at each occurrence, is independently hydrogen, $C_1$-$C_6$ alkyl, or $C_1$-$C_6$ haloalkyl;
$R^B$, at each occurrence, is independently hydrogen, $C_1$-$C_6$ haloalkyl, or $C_1$-$C_6$ alkyl which is optionally substituted with 1 or 2 —OH;
$G^A$ is a $C_3$-$C_6$ cycloalkyl or a 4-6 membered monocyclic heterocycle; each of which is optionally substituted with 1, 2, or 3 substituents independently selected from the group consisting of halogen, $C_1$-$C_6$ alkyl, $C_1$-$C_6$ haloalkyl, —OH, $C_1$-$C_3$ alkoxy, and $C_1$-$C_3$ haloalkoxy; and
$G^2$ is phenyl, heterocycle, or monocyclic heteroaryl; each of which is optionally substituted with 1, 2, or 3 independently selected $R^q$ groups;
$X^2$ is O or N($R^{2x}$) wherein $R^{2x}$ is hydrogen, $C_1$-$C_3$ alkyl, or $C_1$-$C_3$ haloalkyl;
$X^3$ is N or CH;
$X^4$-$X^5$ is N=C, C($R^{4x}$)=C, or C($R^{4c}$)$_2$—C($R^{5x}$), wherein $R^{4x}$ and $R^{5x}$, at each occurrence, are each independently hydrogen, halogen, $C_1$-$C_3$ alkyl, or $C_1$-$C_3$ haloalkyl;
$R^8$ groups are optional substituents on the benzo ring, and are each independently halogen, $C_1$-$C_3$ alkyl, $C_1$-$C_3$ haloalkyl, $C_1$-$C_3$ alkoxy, or $C_1$-$C_3$ haloalkoxy;
m is 0, 1, 2, 3, or 4;
$G^3$ is phenyl, cycloalkyl, 4-6 membered monocyclic heterocycle, or monocyclic heteroaryl; each of which is optionally substituted with 1, 2, or 3 independently selected $R^s$ groups;
$R^9$ is $C_1$-$C_3$ alkyl, $C_3$-$C_6$ cycloalkyl, or phenyl; wherein the $C_3$-$C_6$ cycloalkyl and the phenyl are each optionally substituted with 1, 2, or 3 substituents independently selected from the group consisting of halogen, —OH, $C_1$-$C_3$ alkyl, $C_1$-$C_3$ haloalkyl, $C_1$-$C_3$ alkoxy, and $C_1$-$C_3$ haloalkoxy;
n is 0, 1, 2, or 3;
$R^{10}$ is $C_1$-$C_6$ alkyl substituted with 1, 2, or 3 substituents independently selected from the group consisting of halogen, OH, $C_1$-$C_3$ alkoxy, $C_1$-$C_3$ haloalkoxy, and 2,2-dimethyl-1,3-dioxolan-4-yl; or $R^{10}$ is phenyl, $C_3$-$C_6$ cycloalkyl, or monocyclic heteroaryl, wherein the phenyl, $C_3$-$C_6$ cycloalkyl, and monocyclic heteroaryl are each optionally substituted with 1, 2, or 3 independently selected $R^v$ groups;
$R^{11}$ is halogen, $C_1$-$C_3$ alkyl, or $G^4$ wherein $G^4$ is $C_3$-$C_6$ cycloalkyl, 4-6 membered monocyclic heterocycle, monocyclic heteroaryl, or phenyl; each $G^4$ is optionally substituted with 1, 2, or 3 independently selected $R^w$ groups;
$R^{12}$ are optional substituents of the benzo ring, and are each independently halogen, $C_1$-$C_3$ alkyl, or $C_1$-$C_3$ haloalkyl;
p is 0, 1, 2, or 3;
$R^{13}$ is hydrogen or $C_1$-$C_6$ alkyl substituted with 1, 2, or 3 substituents independently selected from the group consisting of —CON, 2,2-dimethyl-1,3-dioxolan-4-yl, —O$R^{13a}$, —O-benzyl, —N($R^{13}$)$_2$, —N($R^{13a}$)S(O)$_2 R^{13b}$, and —N($R^{13b}$)C(O)$R^{13b}$, wherein $R^{13a}$, at each occurrence, is independently hydrogen, $C_1$-$C_6$ alkyl, or $C_1$-$C_6$ haloalkyl, and $R^{13b}$, at each occurrence, is independently $C_1$-$C_6$ alkyl or $C_1$-$C_6$ haloalkyl;
$R^{14}$ and $R^{15}$ are each independently $C_1$-$C_3$ alkyl, or
$R^{14}$ and $R^{15}$, together with the carbon atom to which they are attached, form a $C_3$-$C_6$ cycloalkyl or a 4-6 membered monocyclic heterocycle containing one heteroatom selected from the group consisting of oxygen and nitrogen; wherein the $C_3$-$C_6$ cycloalkyl and the 4-6 membered monocyclic heterocycle are each optionally substituted with 1 or 2 substituents independently selected from the group consisting of $C_1$-$C_3$ alkyl, halogen, $C_1$-$C_3$ haloalkyl, —OH, $C_1$-$C_3$ alkoxy, and $C_1$-$C_3$ haloalkoxy;

$R^{16}$ is OH or $C_1$-$C_6$ alkyl optionally substituted with 1 or 2 substituents independently selected from the group consisting of —CN, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, and —$N(R^j)C(O)N(R^j)_2$;

$R^q$ is $C_2$-$C_6$ alkenyl, $C_2$-$C_6$ alkynyl, halogen, $C_1$-$C_6$ haloalkyl, —CN, oxo, $NO_2$, —$OR^x$, —$OC(O)R^{3x}$, —$OC(O)N(R^x)_2$, —$SR^x$, —$S(O)_2R^x$, —$S(O)_2N(R^x)_2$, —$C(O)R^x$, —$C(O)OR^x$, —$C(O)N(R^x)_2$, —$C(O)N(R^x)S(O)_2R^y$, —$N(R^x)_2$, —$N(R^x)C(O)R^{3x}$, —$N(R^x)S(O)_2R^{3x}$, —$N(R^x)C(O)O(R^y)$, —$N(R^x)C(O)N(R^x)_2$, $G^{2A}$, or $C_1$-$C_6$ alkyl which is optionally substituted with 1 or 2 substituents independently selected from the group consisting of —CN, $NO_2$, —$OR^x$, —$OC(O)R^{3x}$, —$OC(O)N(R^x)_2$, —$SR^x$, —$S(O)_2R^x$, —$S(O)_2N(R^x)_2$, —$C(O)R^x$, —$C(O)OR^x$, —$C(O)N(R^x)_2$, —$C(O)N(R^x)S(O)_2R^y$, —$N(R^x)_2$, —$N(R^x)C(O)R^y$, —$N(R^x)S(O)_2R^y$, —$N(R^x)C(O)O(R^3)$, —$N(R^x)C(O)N(R^x)_2$, and $G^{2A}$;

$R^x$, at each occurrence, is independently hydrogen, $C_1$-$C_6$ alkyl, $G^{2A}$, $C_1$-$C_6$ haloalkyl, or —($C_1$-$C_6$ alkylenyl)-$G^{2A}$;

$R^y$, at each occurrence, is independently $C_1$-$C_6$ alkyl, $G^{2A}$, $C_1$-$C_6$ haloalkyl, or —($C_1$-$C_6$ alkylenyl)-$G^{2A}$;

$G^{2A}$ is phenyl or $C_3$-$C_6$ cycloalkyl; each of which is optionally substituted with 1, 2, or 3 $R^z$ groups;

$R^s$, $R^u$, $R^v$, $R^w$, and $R^z$, at each occurrence, are each independently $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, or $C_1$-$C_6$ alkyl which is optionally substituted with 1 or 2 substituents independently selected from the group consisting of —CN, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$C(O)N(R^j)S(O)_2R^k$, —$N(R^j)_2$, —$N(R^j)C(O)R^k$, —$N(R^j)S(O)_2R^k$, —$N(R^j)C(O)O(R^k)$, and —$N(R^j)C(O)N(R^j)_2$;

$R^j$, at each occurrence, is independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl.

Exemplary compounds include, but are not limited to:

tert-butyl 3-{6-[(2,2-difluoro-7-methyl-6,7-dihydro-2H-furo[2,3-f][1,3]benzodioxole-7-carbonyl)amino]-3-methylpyridin-2-yl}benzoate;

3-{6-[(2,2-difluoro-7-methyl-6,7-dihydro-2H-furo[2,3-f][1,3]benzodioxole-7-carbonyl)amino]-3-methylpyridin-2-yl}benzoic acid;

tert-butyl 3-(6-{[(7S)-2,2-difluoro-7-methyl-6,7-dihydro-2H-furo[2,3-f][1,3]benzodioxole-7-carbonyl]amino}-3-methylpyridin-2-yl)benzoate;

3-(6-{[(7S)-2,2-difluoro-7-methyl-6,7-dihydro-2H-furo[2,3-f][1,3]benzodioxole-7-carbonyl]amino}-3-methylpyridin-2-yl)benzoic acid;

tert-butyl 3-(6-{[(7R)-2,2-difluoro-7-methyl-6,7-dihydro-2H-furo[2,3-f][1,3]benzodioxole-7-carbonyl]amino}-3-methylpyridin-2-yl)benzoate;

3-(6-{[(7R)-2,2-difluoro-7-methyl-6,7-dihydro-2H-furo[2,3-f][1,3]benzodioxole-7-carbonyl]amino}-3-methylpyridin-2-yl)benzoic acid;

methyl (3R)-1-{6-[(2,2-difluoro-7-methyl-6,7-dihydro-2H-furo[2,3-f][1,3]benzodioxole-7-carbonyl)amino]pyridin-2-yl}pyrrolidine-3-carboxylate;

(3R)-1-{6-[(2,2-difluoro-7-methyl-6,7-dihydro-2H-furo[2,3-f][1,3]benzodioxole-7-carbonyl)amino]pyridin-2-yl}pyrrolidine-3-carboxylic acid;

(3R)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylic acid;

methyl 3-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoate;

3-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoic acid;

methyl 3-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate;

3-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid;

3-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid;

methyl 4-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoate;

4-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoic acid;

methyl 4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate;

4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid;

methyl 4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate;

4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid;

3-{(2R,4R)-4-[(2,2-difluoro-7-methyl-6,7-dihydro-2H-furo[2,3-f][1,3]benzodioxole-7-carbonyl)amino]-3,4-dihydro-2H-1-benzopyran-2-yl}benzoic acid;

3-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid;

4-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid;

N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

N-{2-[(2R)-2,3-dihydroxypropyl]-3-oxo-6-phenyl-2,3-dihydropyridazin-4-yl}-2,2-difluoro-7-methyl-6,7-dihydro-2H-furo[2,3-f][1,3]benzodioxole-7-carboxamide;

(7R)—N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

(7R)—N-{2-[(2R)-2,3-dihydroxypropyl]-3-oxo-6-phenyl-2,3-dihydropyridazin-4-yl}-2,2-difluoro-7-methyl-6,7-dihydro-2H-furo[2,3-f][1,3]benzodioxole-7-carboxamide;

methyl 3-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoate;

3-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoic acid;

4-{3-cyclopropyl-5-[(2,2-difluoro-7-methyl-6,7-dihydro-2H-furo[2,3-f][1,3]benzodioxole-7-carbonyl)amino]-6-oxopyridazin-1(6H)-yl}benzoic acid;

4-[3-cyclopropyl-5-{[(7S)-2,2-difluoro-7-methyl-6,7-dihydro-2H-furo[2,3-f][1,3]benzodioxole-7-carbonyl]amino}-6-oxopyridazin-1(6H)-yl]benzoic acid;

4-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoic acid;

methyl 4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoate and methyl 4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoate;

4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid and 4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid;

3-{(2R,4R)-4-[(2,2-difluoro-5-methyl-6,7-dihydro-2H,5H-indeno[5,6-d][1,3]dioxole-5-carbonyl)amino]-3,4-dihydro-2H-1-benzopyran-2-yl}benzoic acid;

2'-methyl-5'-[(6-methyl-7,8-dihydro-2H,6H-indeno[4,5-d][1,3]dioxole-6-carbonyl)amino][1,1'-biphenyl]-3-carboxylic acid;

2'-methyl-5'-{[(6R)-6-methyl-7,8-dihydro-2H,6H-indeno[4,5-d][1,3]dioxole-6-carbonyl]amino}[1,1'-biphenyl]-3-carboxylic acid;

2'-methyl-5'-{[(6S)-6-methyl-7,8-dihydro-2H,6H-indeno[4,5-d][1,3]dioxole-6-carbonyl]amino}[1,1'-biphenyl]-3-carboxylic acid;

4-{(2R,4R)-4-[(2,2-difluoro-6-methyl-6,7-dihydro-2H-furo[2,3-e][1,3]benzodioxole-6-carbonyl)amino]-7-methoxy-3,4-dihydro-2H-1-benzopyran-2-yl}benzoic acid;

methyl 3-{3-cyclopropyl-5-[(2,2-difluoro-7-methyl-6,7-dihydro-2H-furo[2,3-f][1,3]benzodioxole-7-carbonyl)amino]-6-oxopyridazin-1(6H)-yl}benzoate;

(7S)—N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

4-[(2R,4R)-7-methoxy-4-{[(6S)-6-methyl-7,8-dihydro-2H,6H-indeno[4,5-d][1,3]dioxole-6-carbonyl]amino}-3,4-dihydro-2H-1-benzopyran-2-yl]benzoic acid;

4-[(2R,4S,6R)-4-{[(7R)-2,2-difluoro-7-methyl-6,7-dihydro-2H-furo[2,3-f][1,3]benzodioxole-7-carbonyl]amino}-6-methyloxan-2-yl]benzoic acid and 4-[(2S,4R,6S)-4-{[(7R)-2,2-difluoro-7-methyl-6,7-dihydro-2H-furo[2,3-f][1,3]benzodioxole-7-carbonyl]amino}-6-methyloxan-2-yl]benzoic acid;

4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid;

4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid;

4-[(2R,4R)-7-methoxy-4-{[(6R)-6-methyl-7,8-dihydro-2H,6H-indeno[4,5-d][1,3]dioxole-6-carbonyl]amino}-3,4-dihydro-2H-1-benzopyran-2-yl]benzoic acid;

4-[(2R,4R)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoic acid;

4-[(2S,4S)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoic acid;

4-[(2R,4R)-4-{[(5R)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid;

4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid;

3-{6-[(2,2-difluoro-5-methyl-6,7-dihydro-2H,5H-indeno[5,6-d][1,3]dioxole-5-carbonyl)amino]-3-methylpyridin-2-yl}benzoic acid;

methyl 3-{(2R,4R)-4-[(2,2-difluoro-5-methyl-6,7-dihydro-2H,5H-indeno[5,6-d][1,3]dioxole-5-carbonyl)amino]-7-methoxy-3,4-dihydro-2H-1-benzopyran-2-yl}benzoate;

4-{5-[(2,2-difluoro-7-methyl-6,7-dihydro-2H-furo[2,3-f][1,3]benzodioxole-7-carbonyl)amino]-1,3,4-thiadiazol-2-yl}benzoic acid;

N-([1,1'-biphenyl]-3-yl)-2,2-difluoro-7-methyl-6,7-dihydro-2H-furo[2,3-f][1,3]benzodioxole-7-carboxamide;

2,2-difluoro-7-methyl-N-(6-phenylpyridin-2-yl)-6,7-dihydro-2H-furo[2,3-f][1,3]benzodioxole-7-carboxamide;

3-[(2R,4R)-4-{[(5R)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid;

3-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid;

4-[(2R,4R)-4-{[(5R)-2,2-difluoro-5-methyl-6,7-dihydro-2H,5H-indeno[5,6-d][1,3]dioxole-5-carbonyl]amino}-3,4-dihydro-2H-1-benzopyran-2-yl]benzoic acid;

4-[(2R,4R)-4-{[(5S)-2,2-difluoro-5-methyl-6,7-dihydro-2H,5H-indeno[5,6-d][1,3]dioxole-5-carbonyl]amino}-3,4-dihydro-2H-1-benzopyran-2-yl]benzoic acid;

5'-[(2,2-difluoro-7-methyl-6,7-dihydro-2H-furo[2,3-f][1,3]benzodioxole-7-carbonyl)amino]-2'-methyl[1,1'-biphenyl]-3-carboxylic acid;

1-{4-[(2,2-difluoro-7-methyl-6,7-dihydro-2H-furo[2,3-f][1,3]benzodioxole-7-carbonyl)amino]phenyl}azetidine-3-carboxylic acid;

1-{2-[(2,2-difluoro-7-methyl-6,7-dihydro-2H-furo[2,3-f][1,3]benzodioxole-7-carbonyl)amino]-4-(trifluoromethyl)phenyl}-5-methyl-1H-imidazole-4-carboxylic acid;

N-[4-(4-cyanophenyl)-1,3-thiazol-2-yl]-2,2-difluoro-7-methyl-6,7-dihydro-2H-furo[2,3-f][1,3]benzodioxole-7-carboxamide;

methyl 4-{2-[(2,2-difluoro-7-methyl-6,7-dihydro-2H-furo[2,3-f][1,3]benzodioxole-7-carbonyl)amino]-1,3-thiazol-4-yl}benzoate;

6-[(2,2-difluoro-7-methyl-6,7-dihydro-2H-furo[2,3-f][1,3]benzodioxole-7-carbonyl)amino]-N-[(2R)-2,3-dihydroxypropyl]pyridine-2-carboxamide;

methyl 3'-[(2,2-difluoro-7-methyl-6,7-dihydro-2H-furo[2,3-f][1,3]benzodioxole-7-carbonyl)amino][1,1'-biphenyl]-4-carboxylate;

2,2-difluoro-N-(6-fluoropyridin-2-yl)-7-methyl-6,7-dihydro-2H-furo[2,3-f][1,3]benzodioxole-7-carboxamide;

4-{2-[(2,2-difluoro-7-methyl-6,7-dihydro-2H-furo[2,3-f][1,3]benzodioxole-7-carbonyl)amino]-1,3-thiazol-4-yl}benzoic acid;

3'-[(2,2-difluoro-7-methyl-6,7-dihydro-2H-furo[2,3-f][1,3]benzodioxole-7-carbonyl)amino][1,1'-biphenyl]-4-carboxylic acid;

methyl 1-{6-[(2,2-difluoro-7-methyl-6,7-dihydro-2H-furo[2,3-f][1,3]benzodioxole-7-carbonyl)amino]pyridin-2-yl}piperidine-4-carboxylate;

1-{6-[(2,2-difluoro-7-methyl-6,7-dihydro-2H-furo[2,3-f][1,3]benzodioxole-7-carbonyl)amino]pyridin-2-yl}piperidine-4-carboxylic acid;

(7R)-2,2-difluoro-N-[6-(3-hydroxypyrrolidin-1-yl)pyridin-3-yl]-7-methyl-6,7-dihydro-2H-furo[2,3-f][1,3]benzodioxole-7-carboxamide;

3-(6-{[(7R)-2,2-difluoro-7-methyl-6,7-dihydro-2H-furo[2,3-f][1,3]benzodioxole-7-carbonyl]amino}pyridin-2-yl)benzoic acid;

N-[6-(3-carbamoylphenyl)-5-methylpyridin-2-yl]-2,2-difluoro-7-methyl-6,7-dihydro-2H-furo[2,3-f][1,3]benzodioxole-7-carboxamide;

N-{6-[3-(dimethylcarbamoyl)phenyl]-5-methylpyridin-2-yl}-2,2-difluoro-7-methyl-6,7-dihydro-2H-furo[2,3-f][1,3]benzodioxole-7-carboxamide;

2,2-difluoro-7-methyl-N-{5-methyl-6-[3-(methylcarbamoyl)phenyl]pyridin-2-yl}-6,7-dihydro-2H-furo[2,3-f][1,3]benzodioxole-7-carboxamide;

(7R)—N-(6-chloro-5-methylpyridin-2-yl)-2,2-difluoro-7-methyl-6,7-dihydro-2H-furo[2,3-f][1,3]benzodioxole-7-carboxamide;

(7R)—N-[6-(3-cyanophenyl)-5-methylpyridin-2-yl]-2,2-difluoro-7-methyl-6,7-dihydro-2H-furo[2,3-f][1,3]benzodioxole-7-carboxamide;

methyl 4-(6-{[(7R)-2,2-difluoro-7-methyl-6,7-dihydro-2H-furo[2,3-f][1,3]benzodioxole-7-carbonyl]amino}pyridin-2-yl)benzoate;

(7R)-2,2-difluoro-7-methyl-N-[5-(pyrrolidin-1-yl)pyridin-2-yl]-6,7-dihydro-2H-furo[2,3-f][1,3]benzodioxole-7-carboxamide;

4-(6-{[(7R)-2,2-difluoro-7-methyl-6,7-dihydro-2H-furo[2,3-f][1,3]benzodioxole-7-carbonyl]amino}pyridin-2-yl)benzoic acid;

ethyl 5-(6-{[(7R)-2,2-difluoro-7-methyl-6,7-dihydro-2H-furo[2,3-f][1,3]benzodioxole-7-carbonyl]amino}pyridin-2-yl)thiophene-3-carboxylate;

4-(6-{[(7R)-2,2-difluoro-7-methyl-6,7-dihydro-2H-furo[2,3-f][1,3]benzodioxole-7-carbonyl]amino}-3-methylpyridin-2-yl)benzoic acid;

3-(6-{[(7R)-2,2-difluoro-7-methyl-6,7-dihydro-2H-furo[2,3-f][1,3]benzodioxole-7-carbonyl]amino}-5-methylpyridin-2-yl)benzoic acid;

(7R)-2,2-difluoro-N-(6-fluoropyridin-2-yl)-7-methyl-6,7-dihydro-2H-furo[2,3-f][1,3]benzodioxole-7-carboxamide;

5-(6-{[(7R)-2,2-difluoro-7-methyl-6,7-dihydro-2H-furo[2,3-f][1,3]benzodioxole-7-carbonyl]amino}pyridin-2-yl)thiophene-3-carboxylic acid;

(7R)-2,2-difluoro-N-{6-[2-(hydroxymethyl)morpholin-4-yl]pyridin-2-yl}-7-methyl-6,7-dihydro-2H-furo[2,3-f][1,3]benzodioxole-7-carboxamide;

(7R)-2,2-difluoro-N-{6-[(3S)-3-hydroxypyrrolidin-1-yl]pyridin-2-yl}-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxylic acid;

(3S)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylic acid;

(7R)-2,2-difluoro-N-{6-[(3R)-3-hydroxypyrrolidin-1-yl]pyridin-2-yl}-7-methyl-6,7-dihydro-2H-furo[2,3-f][1,3]benzodioxole-7-carboxamide;

(7R)—N-(6-{[(2R)-2,3-dihydroxypropyl]amino}pyridin-2-yl)-2,2-difluoro-7-methyl-6,7-dihydro-2H-furo[2,3-f][1,3]benzodioxole-7-carboxamide;

(7R)—N-(6-{[(2S)-2,3-dihydroxypropyl]amino}pyridin-2-yl)-2,2-difluoro-7-methyl-6,7-dihydro-2H-furo[2,3-f][1,3]benzodioxole-7-carboxamide;

1-(5-{[(7R)-2,2-difluoro-7-methyl-6,7-dihydro-2H-furo[2,3-f][1,3]benzodioxole-7-carbonyl]amino}pyrazin-2-yl)pyrrolidine-3-carboxylic acid;

3-(3-chloro-6-{[(7R)-2,2-difluoro-7-methyl-6,7-dihydro-2H-furo[2,3-f][1,3]benzodioxole-7-carbonyl]amino}pyridin-2-yl)benzoic acid;

1-(6-{[(7R)-2,2-difluoro-7-methyl-6,7-dihydro-2H-furo[2,3-f][1,3]benzodioxole-7-carbonyl]amino}pyridin-2-yl)-3-methylazetidine-3-carboxylic acid;

4-[5-bromo-3-{[(7R)-2,2-difluoro-7-methyl-6,7-dihydro-2H-furo[2,3-f][1,3]benzodioxole-7-carbonyl]amino}-2-oxopyridin-1(2H)-yl]benzoic acid;

(7R)—N-{5-bromo-1-[(2R)-2,3-dihydroxypropyl]-2-oxo-1,2-dihydropyridin-3-yl}-2,2-difluoro-7-methyl-6,7-dihydro-2H-furo[2,3-f][1,3]benzodioxole-7-carboxamide;

4-[3-{[(7R)-2,2-difluoro-7-methyl-6,7-dihydro-2H-furo[2,3-f][1,3]benzodioxole-7-carbonyl]amino}-2-oxo-5-phenylpyridin-1(2H)-yl]benzoic acid;

(7R)—N-{1-[(2R)-2,3-dihydroxypropyl]-2-oxo-5-phenyl-1,2-dihydropyridin-3-yl}-2,2-difluoro-7-methyl-6,7-dihydro-2H-furo[2,3-f][1,3]benzodioxole-7-carboxamide;

(7R)—N-[6-(3,3-dimethylpyrrolidin-1-yl)pyridin-2-yl]-2,2-difluoro-7-methyl-6,7-dihydro-2H-furo[2,3-f][1,3]benzodioxole-7-carboxamide;

1-(5-{[(7R)-2,2-difluoro-7-methyl-6,7-dihydro-2H-furo[2,3-f][1,3]benzodioxole-7-carbonyl]amino}pyrazin-2-yl)proline;

3-(6-{[(7R)-2,2-difluoro-7-methyl-6,7-dihydro-2H-furo[2,3-f][1,3]benzodioxole-7-carbonyl]amino}-4-methylpyridin-2-yl)benzoic acid;

(7R)—N-(2-{(2S)-2-[(4R)-2,2-dimethyl-1,3-dioxolan-4-yl]-2-hydroxyethyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

(7R)-2,2-difluoro-7-methyl-N-{3-oxo-6-phenyl-2-[(2S,3R)-2,3,4-trihydroxybutyl]-2,3-dihydropyridazin-4-yl}-6,7-dihydro-2H-furo[2,3-f][1,3]benzodioxole-7-carboxamide;

(7R)—N-(2-{(2R)-2-[(4R)-2,2-dimethyl-1,3-dioxolan-4-yl]-2-hydroxyethyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

2,2-difluoro-7-methyl-N-[6-(5-methylhexahydropyrrolo[3,4-c]pyrrol-2(1H)-yl)pyridin-2-yl]-6,7-dihydro-2H-furo[2,3-f][1,3]benzodioxole-7-carboxamide;

2,2-difluoro-7-methyl-N-{6-[5-(2-methylpropyl)hexahydropyrrolo[3,4-c]pyrrol-2(1H)-yl]pyridin-2-yl}-6,7-dihydro-2H-furo[2,3-f][1,3]benzodioxole-7-carboxamide;

(7R)-2,2-difluoro-N-{6-[3-(methanesulfonyl)pyrrolidin-1-yl]pyridin-2-yl}-7-methyl-6,7-dihydro-2H-furo[2,3-f][1,3]benzodioxole-7-carboxamide;

(7R)—N-{6-[3-(chloromethyl)-3-(hydroxymethyl)pyrrolidin-1-yl]pyridin-2-yl}-2,2-difluoro-7-methyl-6,7-dihydro-2H-furo[2,3-f][1,3]benzodioxole-7-carboxamide;

(7R)-2,2-difluoro-N-{6-[(3R)-3-(methanesulfonyl)pyrrolidin-1-yl]pyridin-2-yl}-7-methyl-6,7-dihydro-2H-furo[2,3-f][1,3]benzodioxole-7-carboxamide;
methyl (3R,4S)-1-(6-{[(7R)-2,2-difluoro-7-methyl-6,7-dihydro-2H-furo[2,3-f][1,3]benzodioxole-7-carbonyl]amino}pyridin-2-yl)-4-phenylpyrrolidine-3-carboxylate;
(7R)—N-[6-(3-benzylpyrrolidin-1-yl)pyridin-2-yl]-2,2-difluoro-7-methyl-6,7-dihydro-2H-furo[2,3-f][1,3]benzodioxole-7-carboxamide;
(7R)-2,2-difluoro-N-{6-[3-(4-fluorophenyl)pyrrolidin-1-yl]pyridin-2-yl}-7-methyl-6,7-dihydro-2H-furo[2,3-f][1,3]benzodioxole-7-carboxamide;
1-(6-{[(7R)-2,2-difluoro-7-methyl-6,7-dihydro-2H-furo[2,3-f][1,3]benzodioxole-7-carbonyl]amino}pyridin-2-yl)-4,4-dimethylpyrrolidine-3-carboxylic acid;
1-(6-{[(7R)-2,2-difluoro-7-methyl-6,7-dihydro-2H-furo[2,3-f][1,3]benzodioxole-7-carbonyl]amino}pyridin-2-yl)-4-methylpyrrolidine-3-carboxylic acid;
2-(6-{[(7R)-2,2-difluoro-7-methyl-6,7-dihydro-2H-furo[2,3-f][1,3]benzodioxole-7-carbonyl]amino}pyridin-2-yl)hexahydrocyclopenta[c]pyrrole-3a(1H)-carboxylic acid;
(7R)-2,2-difluoro-7-methyl-N-[6-(pyrrolidin-1-yl)pyridin-2-yl]-6,7-dihydro-2H-furo[2,3-f][1,3]benzodioxole-7-carboxamide;
(7R)-2,2-difluoro-7-methyl-N-[6-(piperidin-1-yl)pyridin-2-yl]-6,7-dihydro-2H-furo[2,3-f][1,3]benzodioxole-7-carboxamide;
4-(6-{[(7R)-2,2-difluoro-7-methyl-6,7-dihydro-2H-furo[2,3-f][1,3]benzodioxole-7-carbonyl]amino}pyridin-2-yl)-3-methylbenzoic acid;
(7R)—N-[5-(3R,4R)-dihydroxypyrrolidin-1-yl)pyrazin-2-yl]-2,2-difluoro-7-methyl-6,7-dihydro-2H-furo[2,3-f][1,3]benzodioxole-7-carboxamide and (7R)—N-[5-(3S,4S)-dihydroxypyrrolidin-1-yl)pyrazin-2-yl]-2,2-difluoro-7-methyl-6,7-dihydro-2H-furo[2,3-f][1,3]benzodioxole-7-carboxamide;
3-(6-{[(7R)-2,2-difluoro-7-methyl-6,7-dihydro-2H-furo[2,3-f][1,3]benzodioxole-7-carbonyl]amino}pyridin-2-yl)-2-methylbenzoic acid;
4-(6-{[(7R)-2,2-difluoro-7-methyl-6,7-dihydro-2H-furo[2,3-f][1,3]benzodioxole-7-carbonyl]amino}pyridin-2-yl)-3-fluorobenzoic acid;
(7R)—N-{6-[3-(cyclopropylsulfamoyl)phenyl]-5-methylpyridin-2-yl}-2,2-difluoro-7-methyl-6,7-dihydro-2H-furo[2,3-f][1,3]benzodioxole-7-carboxamide;
3-(6-{[(7R)-2,2-difluoro-7-methyl-6,7-dihydro-2H-furo[2,3-f][1,3]benzodioxole-7-carbonyl]amino}pyridin-2-yl)-2-fluorobenzoic acid;
(7R)—N-{6-[3-(1,2-dihydroxyethyl)phenyl]-5-methylpyridin-2-yl}-2,2-difluoro-7-methyl-6,7-dihydro-2H-furo[2,3-f][1,3]benzodioxole-7-carboxamide;
5-(6-{[(7R)-2,2-difluoro-7-methyl-6,7-dihydro-2H-furo[2,3-f][1,3]benzodioxole-7-carbonyl]amino}-3-methylpyridin-2-yl)thiophene-3-carboxylic acid;
3-(6-{[(7R)-2,2-difluoro-7-methyl-6,7-dihydro-2H-furo[2,3-f][1,3]benzodioxole-7-carbonyl]amino}pyridin-2-yl)-4-fluorobenzoic acid;
3-(6-{[(7R)-2,2-difluoro-7-methyl-6,7-dihydro-2H-furo[2,3-f][1,3]benzodioxole-7-carbonyl]amino}pyridin-2-yl)-4-methylbenzoic acid;
(7R)—N-{1-[(2R)-2,3-dihydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide;
(7R)—N-(2-tert-butyl-1H-indol-5-yl)-2,2-difluoro-7-methyl-6,7-dihydro-2H-furo[2,3-f][1,3]benzodioxole-7-carboxamide;
(7R)—N-{1-[(2R)-3-(benzyloxy)-2-hydroxypropyl]-2-tert-butyl-6-fluoro-1H-indol-5-yl}-2,2-difluoro-7-methyl-6,7-dihydro-2H-furo[2,3-f][1,3]benzodioxole-7-carboxamide;
(7R)—N-{2-tert-butyl-1-[(2R)-2,3-dihydroxypropyl]-6-fluoro-1H-indol-5-yl}-2,2-difluoro-7-methyl-6,7-dihydro-2H-furo[2,3-f][1,3]benzodioxole-7-carboxamide;
(7R)—N-{1-[(2R)-2,3-dihydroxypropyl]-6-fluoro-2-[1-(hydroxymethyl)cyclobutyl]-1H-indol-5-yl}-2,2-difluoro-7-methyl-6,7-dihydro-2H-furo[2,3-f][1,3]benzodioxole-7-carboxamide;
(7R)—N-{1-[(2R)-2,3-dihydroxypropyl]-6-fluoro-2-[3-(hydroxymethyl)oxetan-3-yl]-1H-indol-5-yl}-2,2-difluoro-7-methyl-6,7-dihydro-2H-furo[2,3-f][1,3]benzodioxole-7-carboxamide;
(7R)—N-{1-[(2R)-2,3-dihydroxypropyl]-6-fluoro-2-[1-(hydroxymethyl)cyclopropyl]-1H-indol-5-yl}-2,2-difluoro-7-methyl-6,7-dihydro-2H-furo[2,3-f][1,3]benzodioxole-7-carboxamide;
(7R)—N-{1-[(2R)-2,3-dihydroxypropyl]-6-fluoro-2-(1-hydroxy-2-methylpropan-2-yl)-1H-benzimidazol-5-yl}-2,2-difluoro-7-methyl-6,7-dihydro-2H-furo[2,3-f][1,3]benzodioxole-7-carboxamide;
(7S)—N-{1-[(2R)-2,3-dihydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide;
4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid;
(7R)—N-[(2R)-1-[(2R)-2,3-dihydroxypropyl]-6-fluoro-2-(1-hydroxy-2-methylpropan-2-yl)-2,3-dihydro-1H-indol-5-yl]-2,2-difluoro-7-methyl-6,7-dihydro-2H-furo[2,3-f][1,3]benzodioxole-7-carboxamide;
(7R)—N-[(2S)-1-[(2R)-2,3-dihydroxypropyl]-6-fluoro-2-(1-hydroxy-2-methylpropan-2-yl)-2,3-dihydro-1H-indol-5-yl]-2,2-difluoro-7-methyl-6,7-dihydro-2H-furo[2,3-f][1,3]benzodioxole-7-carboxamide;
(7R)-2,2-difluoro-N-(6-{4-[(methanesulfonyl)carbamoyl]phenyl}-5-methylpyridin-2-yl)-7-methyl-6,7-dihydro-2H-furo[2,3-f][1,3]benzodioxole-7-carboxamide;
(7R)-2,2-difluoro-N-[6-fluoro-2-(1-hydroxy-2-methylpropan-2-yl)-1H-indol-5-yl]-7-methyl-6,7-dihydro-2H-furo[2,3-f][1,3]benzodioxole-7-carboxamide;
methyl 6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxylate;
5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;
6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylic acid;
5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-2-carboxylic acid;
ethyl trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;
ethyl trans-4-[(2R,4R)-4-{[(7R)-2,2-difluoro-7-methyl-6,7-dihydro-2H-furo[2,3-f][1,3]benzodioxole-7-carbonyl]

amino}-7-(trifluoromethoxy)-3,4-dihydro-2H-1-benzopyran-2-yl]cyclohexane-1-carboxylate;
trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;
trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;
6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid;
ethyl trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylate;
ethyl trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylate;
trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;
trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;
ethyl trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;
ethyl cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;
ethyl cis-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;
ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;
trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;
cis-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;
cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;
trans-4-[(2S,4S)-7-(difluoromethoxy)-4-{[(7R)-2,2-difluoro-7-methyl-6,7-dihydro-2H-furo[2,3-][1,3]benzodioxole-7-carbonyl]amino}-3,4-dihydro-2H-1-benzopyran-2-yl]cyclohexane-1-carboxylic acid;
ethyl 1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylate;
ethyl 1-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylate;
1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;
trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;
trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid;
trans-4-[(2R,4R)-4-{[(5R)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;
(7R)—N-{1-[(2R)-2,3-dihydroxypropyl]-6-fluoro-2-[4-(hydroxymethyl)oxan-4-yl]-1H-indol-5-yl}-2,2-difluoro-7-methyl-6,7-dihydro-2H-furo[2,3-f][1,3]benzodioxole-7-carboxamide;
(7R)—N-{1-[(2R)-2,3-dihydroxypropyl]-6-fluoro-2-(3-methyloxetan-3-yl)-1H-indol-5-yl}-2,2-difluoro-7-methyl-6,7-dihydro-2H-furo[2,3-f][1,3]benzodioxole-7-carboxamide;
(7R)-2,2-difluoro-N-{6-fluoro-2-[1-(hydroxymethyl)cyclobutyl]-1H-indol-5-yl}-7-methyl-6,7-dihydro-2H-furo[2,3-f][1,3]benzodioxole-7-carboxamide;
(7R)-2,2-difluoro-N-{(2R,4R)-2-[5-(hydroxymethyl)pyrazin-2-yl]-7-methoxy-3,4-dihydro-2H-1-benzopyran-4-yl}-7-methyl-6,7-dihydro-2H-furo[2,3-f][1,3]benzodioxole-7-carboxamide;
(7R)-2,2-difluoro-N-{(2R,4R)-2-[5-(hydroxymethyl)pyridin-2-yl]-7-methoxy-3,4-dihydro-2H-1-benzopyran-4-yl}-7-methyl-6,7-dihydro-2H-furo[2,3-f][1,3]benzodioxole-7-carboxamide;
(7R)—N-{(2R,4R)-2-[5-(1,2-dihydroxyethyl)pyrazin-2-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;
(7R)—N-[(2R,4R)-2-(6-bromopyridin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;
(7R)-2,2-difluoro-N-[(2R,4R)-2-[5-(hydroxymethyl)pyridin-2-yl]-7-(trifluoromethoxy)-3,4-dihydro-2H-1-benzopyran-4-yl]-7-methyl-6,7-dihydro-2H-furo[2,3-f][1,3]benzodioxole-7-carboxamide;
(7R)-2,2-difluoro-N-{(2R,4R)-2-[6-(hydroxymethyl)pyridin-3-yl]-7-methoxy-3,4-dihydro-2H-1-benzopyran-4-yl}-7-methyl-6,7-dihydro-2H-furo[2,3-f][1,3]benzodioxole-7-carboxamide;
(7R)—N-{1-[(2S)-3-cyano-2-hydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide;
(7R)—N-[(2R,4R)-2-(5-acetylpyridin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;
(7R)-2,2-difluoro-N-{(2R,4R)-2-[5-(2-hydroxypropan-2-yl)pyridin-2-yl]-7-methoxy-3,4-dihydro-2H-1-benzopyran-4-yl}-7-methyl-6,7-dihydro-2H-furo[2,3-f][1,3]benzodioxole-7-carboxamide;

(7R)-2,2-difluoro-7-methyl-N-[(2R,4R)-2-(piperidin-4-yl)-7-(trifluoromethoxy)-3,4-dihydro-2H-1-benzopyran-4-yl]-6,7-dihydro-2H-furo[2,3-f][1,3]benzodioxole-7-carboxamide;

tert-butyl {4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetate;

{4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetic acid;

(7R)-2,2-difluoro-7-methyl-N-[(2S,4S)-2-(piperidin-4-yl)-7-(trifluoromethoxy)-3,4-dihydro-2H-1-benzopyran-4-yl]-6,7-dihydro-2H-furo[2,3-f][1,3]benzodioxole-7-carboxamide;

tert-butyl {4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetate;

{4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetic acid;

(7R)—N-[(2S,4S)-2-{1-[(2S)-2,3-dihydroxypropyl]piperidin-4-yl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{1-[(2S)-2,3-dihydroxypropyl]piperidin-4-yl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-(5-ethenylpyrazin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(1R)-1,2-dihydroxyethyl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(1S)-1,2-dihydroxyethyl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-(5-chloropyrazin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

propan-2-yl trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;

(7R)—N-[(2R,4R)-2-(6-chloropyridazin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(4R)-2-{1-[(2R)-2,3-dihydroxypropyl]-6-oxo-1,6-dihydropyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-7-methoxy-2-(6-oxo-1,6-dihydropyridazin-3-yl)-3,4-dihydro-2H-1-benzopyran-4-yl]-7-methyl-6,7-dihydro-2H-furo[2,3-f][1,3]benzodioxole-7-carboxamide;

tert-butyl {trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexyl}carbamate;

tert-butyl {trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexyl}carbamate;

(7R)-2,2-difluoro-N-[(2S,4R)-7-methoxy-2-(6-oxo-1,6-dihydropyridazin-3-yl)-3,4-dihydro-2H-1-benzopyran-4-yl]-7-methyl-6,7-dihydro-2H-furo[2,3-f][1,3]benzodioxole-7-carboxamide;

1-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

(7R)-2,2-difluoro-N-[(2R,4R)-7-methoxy-2-(1H-tetrazol-5-yl)-3,4-dihydro-2H-1-benzopyran-4-yl]-7-methyl-6,7-dihydro-2H-furo[2,3-f][1,3]benzodioxole-7-carboxamide;

(7R)—N-(2-{1-[(benzyloxy)methyl]cyclopropyl}-1-[(2R)-2,3-dihydroxypropyl]-6-fluoro-1H-indol-5-yl)-2,2-difluoro-7-methyl-6,7-dihydro-2H-furo[2,3-f][1,3]benzodioxole-7-carboxamide;

(7R)—N-{2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide;

(7S)—N-{1-[(2R)-3-(benzyloxy)-2-hydroxypropyl]-2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide;

(7R)—N-{5-[(2R)-2,3-dihydroxypropyl]-7-fluoro-1, 1,4,4-tetramethyl-1,3,4,5-tetrahydropyrano[4,3-b]indol-8-yl}-2,2-difluoro-7-methyl-6,7-dihydro-2H-furo[2,3-f][1,3]benzodioxole-7-carboxamide;

(7R)—N-(5-{[(4R)-2,2-dimethyl-1,3-dioxolan-4-yl]methyl}-7-fluoro-1, 1,4,4-tetramethyl-1,3,4,5-tetrahydropyrano[4,3-b]indol-8-yl)-2,2-difluoro-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyphenyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)-N-propylpyridine-3-carboxamide;

N-benzyl-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-2-phenylethyl)-N-methylpyridine-3-carboxamide;

(7R)-2,2-difluoro-N-{(2R,4R)-2-[5-(4-hydroxypiperidine-1-carbonyl)pyridin-2-yl]-7-methoxy-3,4-dihydro-2H-1-benzopyran-4-yl}-7-methyl-6,7-dihydro-2H-furo[2,3-f][1,3]benzodioxole-7-carboxamide;

(7R)-2,2-difluoro-N-[(2R,4R)-2-{5-[4-(2-hydroxyethyl)piperazine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-2-methylpropyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7- methoxy-3,4-dihydro-2H-1-benzopyran-2-yl]-N-(1-hydroxy-2-methylpropan-2-yl)pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-1-phenylethyl)pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1,1-dioxo-1~lambda-6~-thian-4-yl)pyridine-3-carboxamide;
(7R)—N-{(2R,4R)-2-[5-(4,4-difluoropiperidine-1-carbonyl)pyridin-2-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;
(7R)-2,2-difluoro-N-{(2R,4R)-7-methoxy-2-[5-(1,4-oxazepane-4-carbonyl)pyridin-2-yl]-3,4-dihydro-2H-1-benzopyran-4-yl}-7-methyl-6,7-dihydro-2H-furo[2,3-f][1,3]benzodioxole-7-carboxamide;
(7R)-2,2-difluoro-N-{(2R,4R)-7-methoxy-2-[5-(morpholine-4-carbonyl)pyridin-2-yl]-3,4-dihydro-2H-1-benzopyran-4-yl}-7-methyl-6,7-dihydro-2H-furo[2,3-f][1,3]benzodioxole-7-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-2,3-dihydro-1H-inden-1-yl)pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[2-hydroxy-1-(2-methoxyphenyl)ethyl]pyridine-3-carboxamide;
(7R)—N-{(2R,4R)-2-[4-(4,4-difluoropiperidine-1-carbonyl)phenyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;
benzyl 4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidine-1-carboxylate;
benzyl 4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidine-1-carboxylate;
(7R)—N-[(2S,4S)-2-(1-{[(4S)-2,2-dimethyl-1,3-dioxolan-4-yl]methyl}piperidin-4-yl)-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;
N-(2-amino-2-oxoethyl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide;
N-(4-amino-4-oxobutyl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide;
N-(4-amino-4-oxobutan-2-yl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[2-(methanesulfonyl)ethyl]pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[(5-oxopyrrolidin-3-yl)methyl]pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-oxopiperidin-4-yl)pyridine-3-carboxamide;
(7R)-2,2-difluoro-N-{(2R,4R)-7-methoxy-2-[5-(4-sulfamoylpiperazine-1-carbonyl)pyridin-2-yl]-3,4-dihydro-2H-1-benzopyran-4-yl}-7-methyl-6,7-dihydro-2H-furo[2,3-f][1,3]benzodioxole-7-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)-N-methylpyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-ethyl-N-(2-hydroxyethyl)pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N,N-bis(2-hydroxyethyl)pyridine-3-carboxamide;
(7R)-2,2-difluoro-N-[(2R,4R)-2-{5-[2-(hydroxymethyl)morpholine-4-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;
(7R)-2,2-difluoro-N-[(2R,4R)-2-{5-[3-hydroxy-3-(2-hydroxyethyl)pyrrolidine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;
(7R)-2,2-difluoro-N-[(2R,4R)-2-{5-[3-hydroxy-3-(2-hydroxyethyl)azetidine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;
(7R)-2,2-difluoro-N-[(2R,4R)-2-{5-[3-(hydroxymethyl)morpholine-4-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxypropyl)pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1-hydroxypropan-2-yl)pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2,3-dihydroxypropyl)pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[(trans-3-hydroxycyclobutyl)methyl]pyridine-3-carboxamide;
6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1-hydroxy-3-methoxypropan-2-yl)pyridine-3-carboxamide;
(7R)—N-[(2R,4R)-2-(1-{[(4S)-2,2-dimethyl-1,3-dioxolan-4-yl]methyl}piperidin-4-yl)-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(3R,4R)-3,4-dihydroxypyrrolidine-1-carbonyl]pyridin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(3S,4S)-3,4-dihydroxypyrrolidine-1-carbonyl]pyridin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(3R,4R)-3,4-dihydroxypyrrolidin-1-yl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{6-[(3R,4R)-3,4-dihydroxypyrrolidin-1-yl]pyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(4R)-2-{6-[(2S)-2,3-dihydroxypropoxy]pyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[ethyl(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[bis(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[(3R,4R)-3,4-dihydroxypyrrolidine-1-carbonyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[(3S,4S)-3,4-dihydroxypyrrolidine-1-carbonyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-2-{trans-4-[3-(hydroxymethyl)morpholine-4-carbonyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(2-hydroxypropyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(1-hydroxypropan-2-yl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)—N-[(2R,4R)-2-{trans-4-[(2,3-dihydroxypropyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-2-{trans-4-[(2-hydroxyethyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(2-hydroxyphenyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(2-hydroxyethyl)(propyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)—N-[(2R,4R)-2-{trans-4-[benzyl(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-2-[trans-4-(4-hydroxypiperidine-1-carbonyl)cyclohexyl]-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[4-(2-hydroxyethyl)piperazine-1-carbonyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(2-hydroxy-2-methylpropyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(1-hydroxy-2-methylpropan-2-yl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(2-hydroxy-1-phenylethyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)—N-[(2R,4R)-2-[trans-4-(4,4-difluoropiperidine-1-carbonyl)cyclohexyl]-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-7-methyl-N-[(2R,4R)-2-[trans-4-(morpholine-4-carbonyl)cyclohexyl]-7-(trifluoromethoxy)-3,4-dihydro-2H-1-benzopyran-4-yl]-6,7-dihydro-2H-furo[2,3-f][1,3]benzodioxole-7-carboxamide;

(7R)—N-{(2S,4R)-2-[6-(benzyloxy)pyridazin-3-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)—N-{(2R,4R)-2-[6-(benzyloxy)pyridazin-3-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)—N-[(2R,4R)-2-{[(2R)-2,3-dihydroxypropoxy]methyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2S,4S)-2-{[(2R)-2,3-dihydroxypropoxy]methyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-{(2R,4R)-2-[(benzyloxy)methyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)-2,2-difluoro-N-[(2R,4R)-2-(hydroxymethyl)-7-methoxy-3,4-dihydro-2H-1-benzopyran-4-yl]-7-methyl-6,7-dihydro-2H-furo[2,3-f][1,3]benzodioxole-7-carboxamide;

(7R)—N-{(2S,4S)-2-[(benzyloxy)methyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)—N-[(2R,4R)-2-{1-[bis(2-hydroxyethyl)carbamoyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2S,4S)-2-{1-[bis(2-hydroxyethyl)carbamoyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[(3S,4S)-3,4-dihydroxypyrrolidine-1-carbonyl]cyclohexyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{1-[(3S,4S)-3,4-dihydroxypyrrolidine-1-carbonyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-(1-benzyl-1H-tetrazol-5-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-{(2S,4S)-7-methoxy-2-[(6-oxopyridazin-1(6H)-yl)methyl]-3,4-dihydro-2H-1-benzopyran-4-yl}-7-methyl-6,7-dihydro-2H-furo[2,3-f][1,3]benzodioxole-7-carboxamide;

(7R)-2,2-difluoro-N-{(2R,4R)-7-methoxy-2-[(6-oxopyridazin-1(6H)-yl)methyl]-3,4-dihydro-2H-1-benzopyran-4-yl}-7-methyl-6,7-dihydro-2H-furo[2,3-f][1,3]benzodioxole-7-carboxamide;

(7R)—N-(1-[(2R)-3-(benzyloxy)-2-hydroxypropyl]-2-{1-[(benzyloxy)methyl]cyclopropyl}-6-fluoro-1H-indol-5-yl)-2,2-difluoro-7-methyl-6,7-dihydro-2H-furo[2,3-f][1,3]benzodioxole-7-carboxamide;

ethyl 1-(aminomethyl)-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;

4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]-1-(hydroxymethyl)cyclohexane-1-carboxylic acid;

1-(aminomethyl)-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2R,4R)-6-bromo-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-4-iodo-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid; and 4-[(2S,4S)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid.

Compound of the invention are named by using Name 2015 naming algorithm by Advanced Chemical Development or Struct-Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I) and (I-a-i) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^{2}H$ and $^{3}H$, carbon, such as $^{11}C$, $^{13}C$ and $^{14}C$, chlorine, such as $^{36}O$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula (I) and (I-a-i), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) and (I-a-i) may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of formula (I) and (I-a-i) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) and (I-a-i) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid, and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, refers to derivatives of the compounds of the invention which have cleavable groups. Such derivatives become, by solvolysis or under physiological conditions, the compounds of the invention which are pharmaceutically active in vivo. Prodrugs of the compounds of the invention are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of formula (I) and (I-a-i) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds of the invention can be better understood in connection with the following synthetic schemes and methods which illustrate a means by which the compounds may be prepared.

The compounds of this invention can be prepared by a variety of synthetic procedures. Representative procedures are shown in, but are not limited to, Schemes 1-15. In Schemes 1-15, the variables $R^1$, $R^{2A}$, $R^{2B}$, $R^{2C}$, $R^{2D}$, $R^3$, $R^4$, $R^5$, $R^6$, $R^7$, $R^8$, $R^9$, $R^{12}$, $R^{13}$, $R^{14}$, $R^{15}$, $R^{16}$, $R^p$, $R^q$, $R^u$, $R^v$, $R^w$, $G^3$, $G^4$, $X^{1A}$, $X^{1B}$, Y, m, n, and p are as described in the Summary.

Abbreviations used in the descriptions of the schemes and the specific examples have the following meanings: APCI for atmospheric pressure chemical ionization; $BE_3.OEt_2$ for boron trifluoride diethyl etherate; n-BuLi for n-butyllithium; DIBAL for diisobutylaluminum hydride; DIEA for diisopropylethylamine, DMA for N,N-dimethylacetamide, DMF for N,N-dimethylformamide, DMSO for dimethylsulfoxide, dppb for 1,4-bis(diphenylphosphino)butane, EDAC or EDCI or EDC for 1-ethyl-3-[3-(dimethylamino)propyl]-carbodiimide hydrochloride, Et for ethyl; EtOAc for ethyl acetate, HATU for N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N',N'-tetramethyluronium hexafluorophosphate or 1-[bis(dimethylamino)methylene]-1H-1,2,3-triazolo[4,5-b]pyridinium 3-oxid hexafluorophosphate, HPLC for high performance liquid chromatography, HOAc for acetic acid; LC/MS for liquid chromatography/mass spectrometry, MS for mass spectrometry, NMR for nuclear magnetic resonance, Me for methyl; MeOH for methanol, NaOAc for sodium acetate, NBS for N-bromosuccinimide, NIS for N-iodosuccinimide, psi for pounds per square inch, PdCl$_2$(dppf) for [1,1'-bis(diphenylphosphino)ferrocene]dichloropalladium(II), Pd(OAc)$_2$ for palladium(II) acetate, Ra—Ni for Raney® nickel, TLC for TFA for trifluoroacetic acid, THF for tetrahydrofuran, and TLC for thin layer chromatography.

and ethyl acetate. The reactions may be carried out at ambient temperature or heated. The heating can be accomplished either conventionally or with microwave irradiation.

Alternatively, carboxylic acids of formula (1-1) can be converted to the corresponding acid chlorides of formula (1-4) by reaction with thionyl chloride, PCl$_3$, PCl$_5$, cyanuric

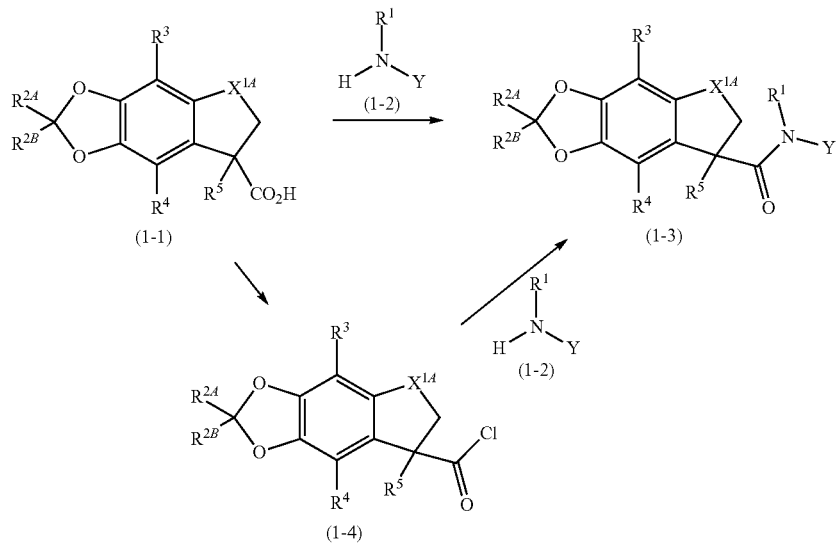

Scheme 1

As shown in Scheme 1, compounds of formula (1-3) can be prepared from compounds of formula (1-1). Carboxylic acids of formula (1-1) can be coupled with amines of formula (1-2) under amide bond forming conditions to give compounds of formula (1-3). Examples of conditions known to generate amides from a mixture of a carboxylic acid and an amine include but are not limited to adding a coupling reagent such as but not limited to N-(3-dimethylaminopropyl)-N-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (TBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine, N,N-diisopropylethylamine or pyridine. The coupling reaction may be carried out in solvents such as but not limited to tetrahydrofuran, N,N-dimethylformamide, N,N-dimethylacetamide, dimethyl sulfoxide, dichloromethane, chloride, or oxalyl chloride. The reactions with thionyl chloride and oxalyl chloride can be catalyzed with N,N-dimethylformamide at ambient temperature in a solvent such as dichloromethane. The resultant acid chlorides of formula (1-4) can then reacted with amines of formula (1-2) optionally in the presence of a base such as a tertiary amine base such as but not limited to triethylamine or N,N-diisopropylethylamine or an aromatic base such as pyridine, at room temperature or heated in a solvent such as dichloromethane to give amides of formula (1-3).

Compounds of formula (1-3) are representative of compounds of formula (I).

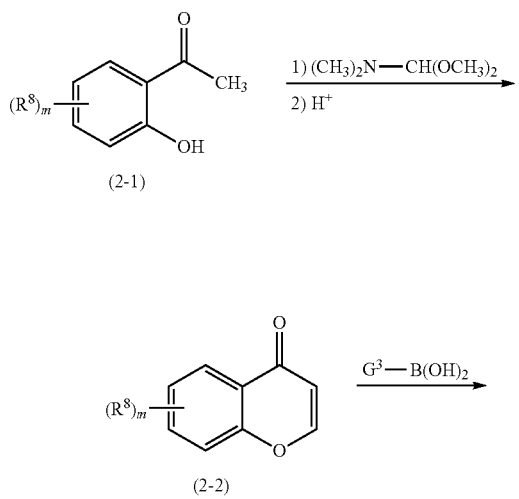

Scheme 2

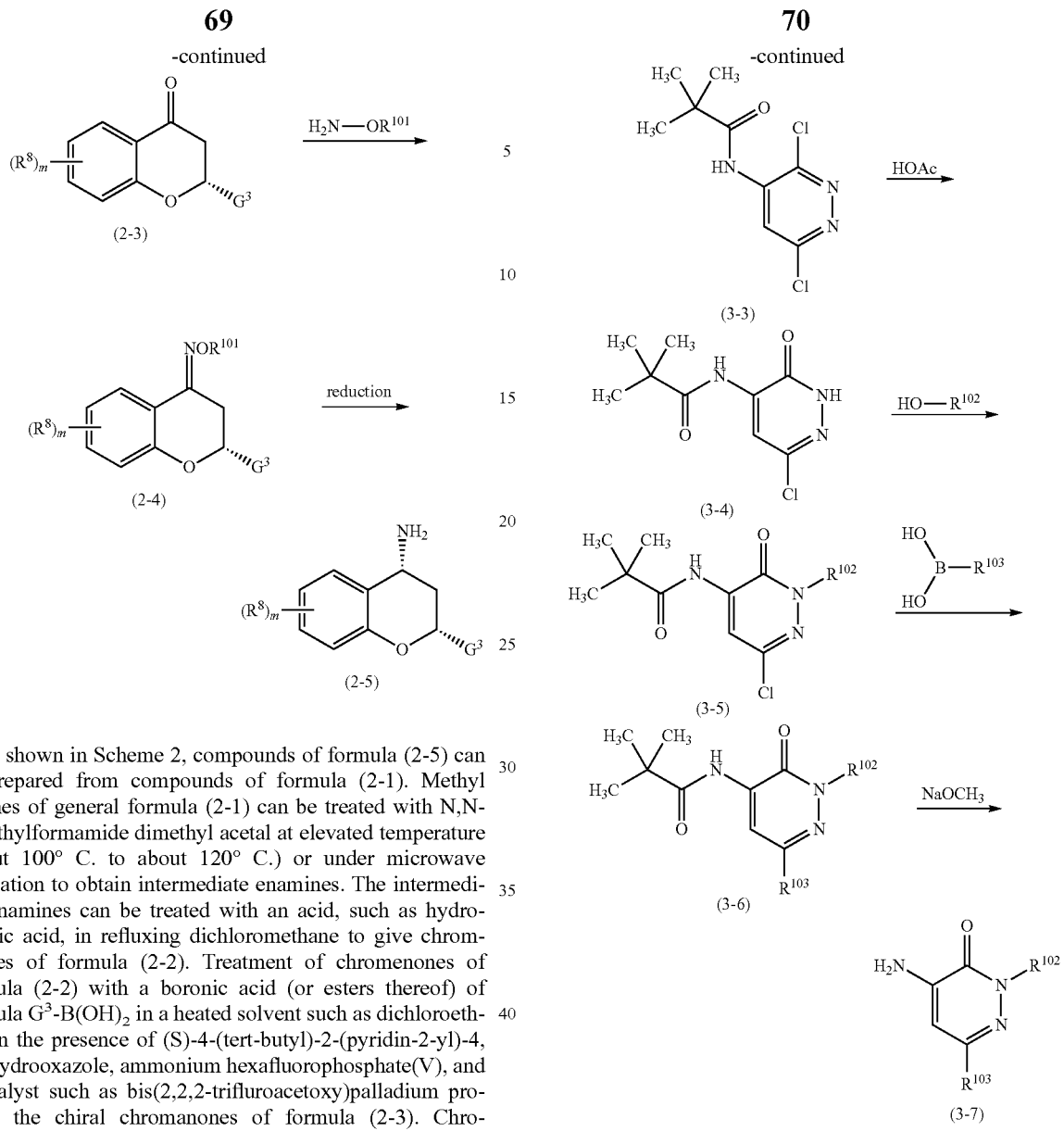

As shown in Scheme 2, compounds of formula (2-5) can be prepared from compounds of formula (2-1). Methyl ketones of general formula (2-1) can be treated with N,N-dimethylformamide dimethyl acetal at elevated temperature (about 100° C. to about 120° C.) or under microwave irradiation to obtain intermediate enamines. The intermediate enamines can be treated with an acid, such as hydrochloric acid, in refluxing dichloromethane to give chromenones of formula (2-2). Treatment of chromenones of formula (2-2) with a boronic acid (or esters thereof) of formula $G^3$-$B(OH)_2$ in a heated solvent such as dichloroethane in the presence of (S)-4-(tert-butyl)-2-(pyridin-2-yl)-4,5-dihydrooxazole, ammonium hexafluorophosphate(V), and a catalyst such as bis(2,2,2-trifluroacetoxy)palladium provides the chiral chromanones of formula (2-3). Chromanones of formula (2-3) can be reacted with hydroxylamines or alkoxyamines; $H_2N$—$OR^{101}$ wherein, $R^{101}$ is hydrogen, $C_1$-$C_6$alkyl, or benzyl; in heated pyridine to give oximes of formula (2-4). Stereoselective hydrogenolysis of oximes of formula (2-4) can be achieved in the presence of a catalyst such as platinum on carbon or platinum(IV) oxide/acetic acid. The reduction provides selectively a single enantiomer of formula (2-5) Amines of formula (2-5) are representative of amines of formula (1-2) in Scheme 1 and Scheme 12.

Scheme 3

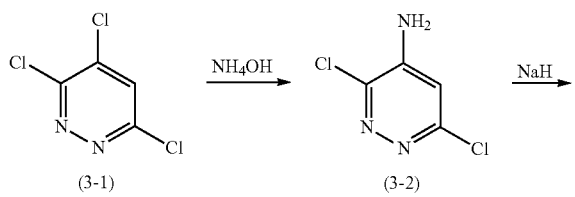

As shown in Scheme 3, compounds of formula (3-7) can be prepared form 3,4,6-trichloropyridazine. Accordingly, 3,4,6-trichloropyridazine, (3-1), can be reacted with ammonium hydroxide in a heated pressure reactor to give 3,6-dichloropyridazine-4-amine, (3-2). 3,6-Dichloropyridazine-4-amine, (3-2), can be reacted with a base, such as sodium hydride, in the presence of pivaloyl chloride to give compound (3-3). Treatment of compound (3-3) with heated acetic acid provides compound (3-4). Compound (3-4) can be reacted with alcohol, HO—$R^{102}$, under Mitsunobu reaction conditions to obtain compounds of formula (3-5). $R^{102}$ is $C_1$-$C_6$ alkyl substituted with 1 or 2 substituents independently selected from the group consisting of halogen, (4R)-2,2-dimethyl-1,3-dioxolan-4-yl, $C_1$-$C_3$ alkoxy, and $C_1$-$C_3$ haloalkoxy; or $R^{102}$ is $C_3$-$C_6$ cycloalkyl which is optionally substituted with 1, 2, or 3 $R^v$ groups that do not interfere with a Mitsunobu reaction. Compounds of formula (3-5) can be reacted with a boronic acid (or the corresponding boronate), $R^{103}$—$B(OH)_2$, under cross-coupling reaction conditions to give compounds of formula (3-6). $R^{103}$ is $C_1$-$C_3$ alkyl or $G^4$. Compounds of formula (3-6) can be reacted with sodium methoxide in heated methanol to give compounds of formula (3-7). Compounds of formula (3-7) are representative of amines of formula (1-2) in Scheme 1 and Scheme 12.

heated methanol to give compounds of formula (4-3). Compounds of formula (4-3) are representative of amines of formula (1-2) in Scheme 1 and Scheme 12.

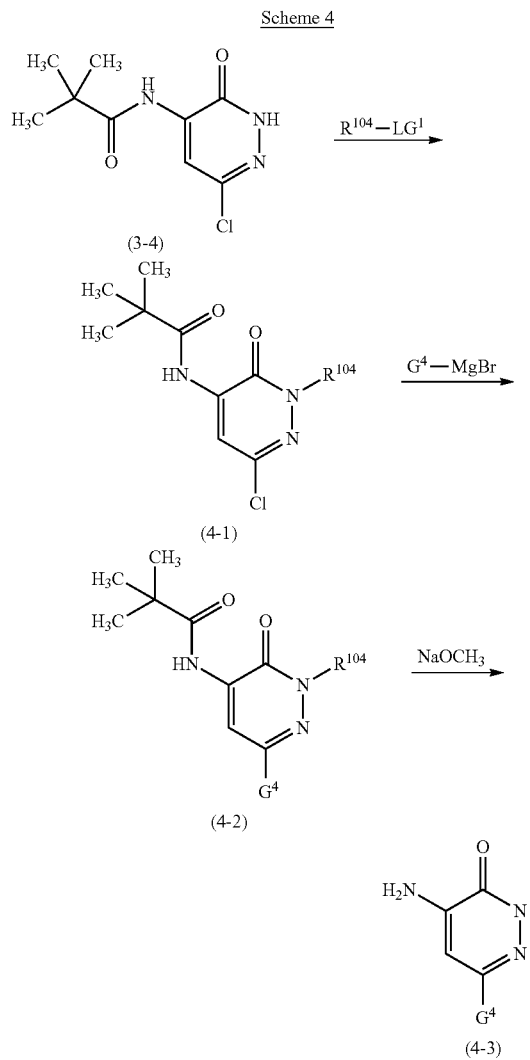

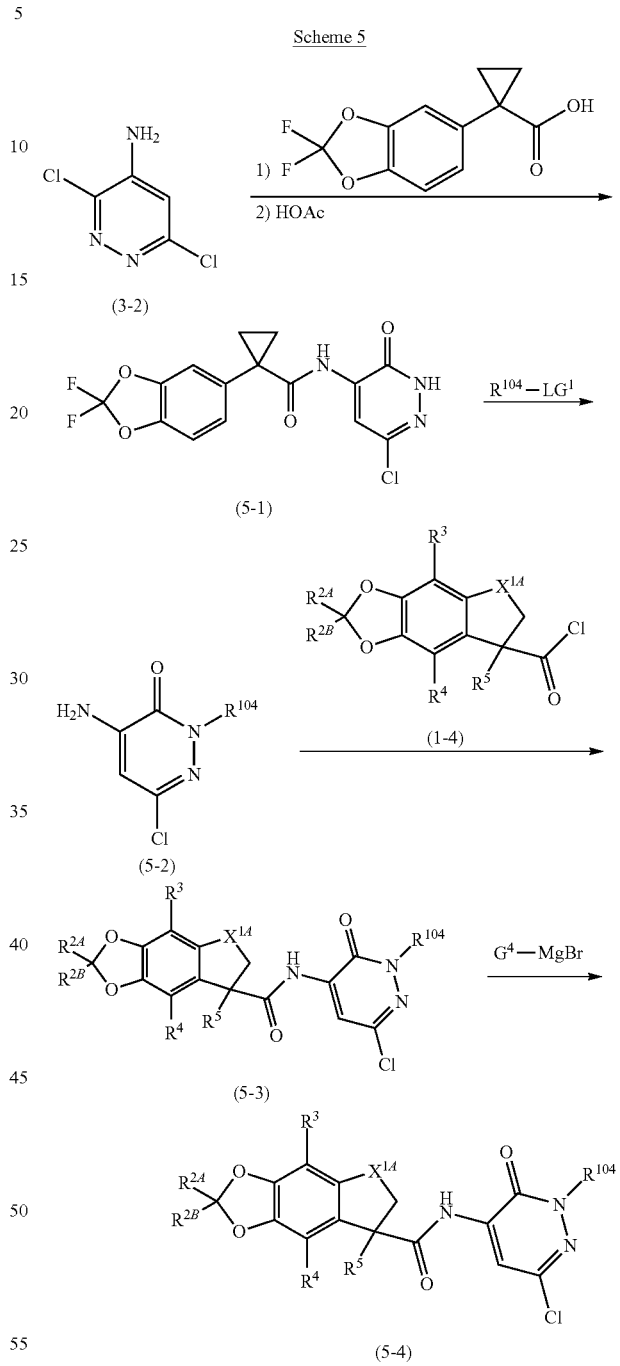

As shown in Scheme 4, compounds of formula (4-3) can be prepared from compound (3-4). Compound (3-4) can be reacted with $R^{104}$-$LG^1$ under cross-coupling conditions to give compounds of formula (4-1). $R^{104}$ is phenyl or monocyclic heteroaryl, each of which is optionally substituted with 1, 2, or 3 $R^v$ groups, wherein the $R^v$ groups are selected to not interfere with the cross-coupling reaction. $LG^1$ is a leaving group such as chlorine, bromine, iodine or a sulfonate. The cross-coupling reaction between compound (3-4) and $R^{104}$-$LG^1$ can be carried out in a solvent such as heated N,N-dimethylformamide in the presence of a catalyst such as bis(quinolin-8-yloxy)copper and a base such as potassium carbonate. Compounds of formula (4-1) can then be reacted with a Grignard, $G^4$-MgBr, in the presence of tris(((Z)-4-oxopent-2-en-2-yl)oxy)iron and N-methyl-2-pyrrolidinone in a solvent such as cooled tetrahydrofuran to give compounds of formula (4-2). $G^4$ is as described in the Summary, and the $R^w$ groups are selected so as not to interfere with the cross-coupling reaction. Compounds of formula (4-2) can be reacted with sodium methoxide in As shown in Scheme 5, compounds of formula (5-4) can be prepared from compound (3-2). Compound (3-2) can be coupled with 1-(2,2-difluorobenzo[d][1,3]dioxol-5-yl)cyclopropanecarboxylic acid under amide bond forming reaction conditions described in Scheme 1. Subsequently, the intermediate can be treated with heated acetic acid to give the compound of formula (5-1). Using the conditions described in Scheme 4 for the conversion of compound (3-4) to compounds of formula (4-1), compound (5-1) can be converted to compounds of formula (5-2). Compounds of formula (5-2) can be reacted with carboxylic acid chlorides of formula (1-4) under the reaction conditions described in Scheme 1 to give compounds of formula (5-3). Compounds of formula (5-3) can be transformed to compounds of formula (5-4) by reaction with $G^4$-MgBr under the conditions described in Scheme 4 for the conversion of compounds of formula (4-1) to compounds of formula (4-2). Compounds of formula (5-4) are representative of compounds of formula (I).

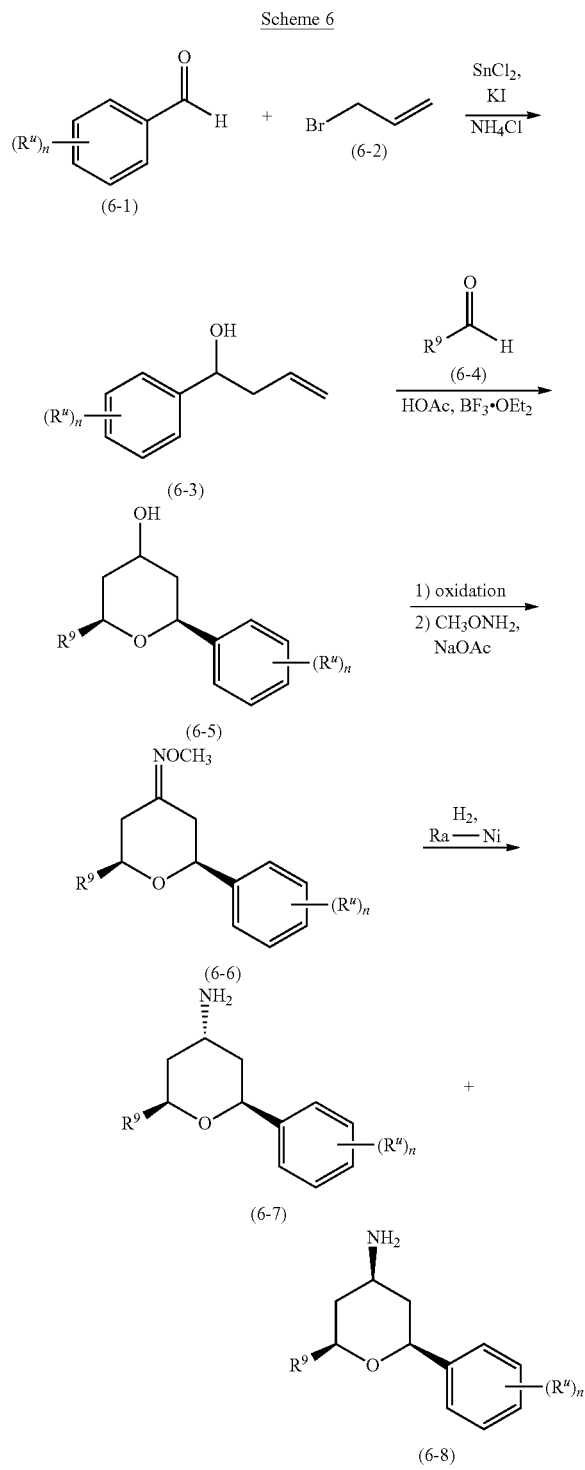

As shown in Scheme 6, compounds of formula (6-7) and formula (6-8) can be prepared from aldehydes of formula (6-1) and 3-bromoprop-1-ene of formula (6-2). Aldehydes of formula (6-1) and 3-bromoprop-1-ene of formula (6-2) can be reacted in the presence of stannous chloride, potassium iodide, and saturated ammonium chloride in water at ambient temperature for 1 to 8 hours to give compounds of formula (6-3). Compounds of formula (6-3) can be reacted with aldehydes of formula (6-4) in the presence of acetic acid and boron trifluoride diethyl etherate in a solvent such as benzene at or near 0° C. for 1 to 8 hours to give compounds of formula (6-5). Compounds of formula (6-5) can be oxidized with an oxidant such as pyridinium chlorochromate. The intermediate ketone can be reacted with O-methylhydroxylamine hydrochloride in the presence of sodium acetate in heated (40-64° C.) methanol to give compounds of formula (6-6). Compounds of formula (6-6) can be reduced with hydrogen (15-45 psi) in the presence of Raney® nickel in a solvent such as methanol at ambient temperature from 4 to 24 hours to give diastereomeric compounds of formula (6-7) and formula (6-8) which can be chromatographically separated. Compounds of formula (6-7) and formula (6-8) are representative of amines of formula (1-2) in Scheme 1 and Scheme 12.

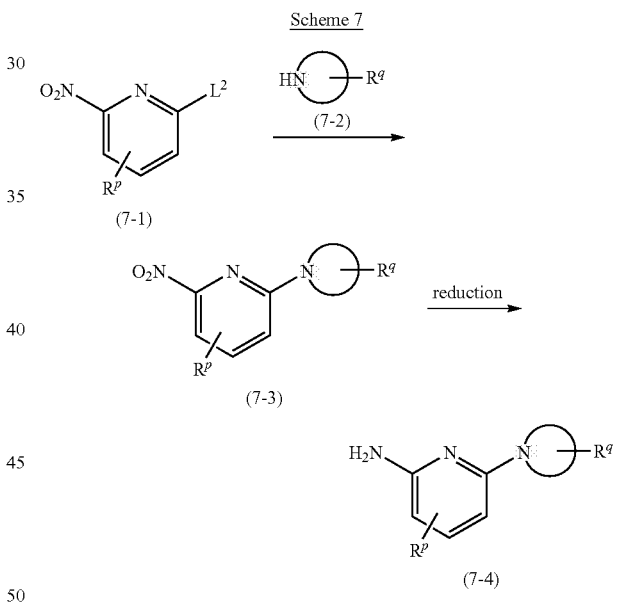

As illustrated in Scheme 7, compounds of formula (7-4) can be prepared from compounds of formula (7-1). Compounds of formula (7-1), wherein $L^2$ is a leaving group selected from chlorine or bromine, can be reacted with heterocycles of formula (7-2) in a solvent such as tetrahydrofuran optionally spiked with water in the presence of a base such as triethylamine or N,N-diisopropylethylamine at ambient or elevated temperature over 24 to 96 hours to give compounds of formula (7-3). Compounds of formula (7-3) can be reduced with hydrogen in the presence of a catalyst such as 5% palladium on carbon in a solvent such as methanol at ambient temperature or heated over 0.5 to 6 hours to obtain compounds of formula (7-4). Compounds of formula (7-4) are representative of amines of formula (1-2) in Scheme 1 and Scheme 12.

Scheme 8

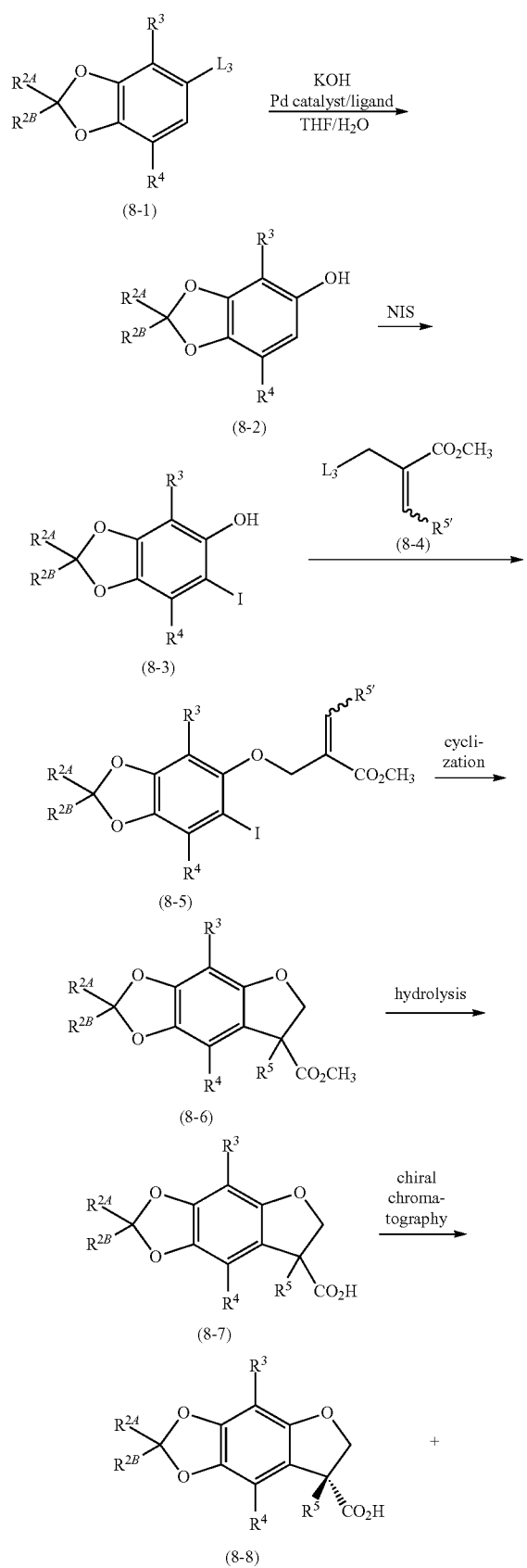

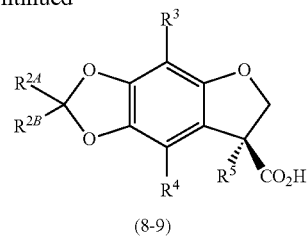

As shown in Scheme 8, compounds of formula (8-7), formula (8-8), and formula (8-9) can be prepared form compounds of formula (8-1). Compounds of formula (8-1), wherein $L^3$ is a leaving group such as chlorine, bromine, or iodine, can be reacted in a mixture of water and tetrahydrofuran in the presence of potassium hydroxide, a catalyst such as tris(dibenzylideneacetone)dipalladium(0), and a ligand such as 2-di-tert-butylphosphino-3,4,5,6-tetramethyl-2',4', 6'-triisopropyl-1,1'-biphenyl heated in a sealed vessel for 8-24 hours to give compounds of (8-2). Compounds of formula (8-2) can be reacted with N-iodosuccinimide in 1-butyl-3-methylimidazolium hexafluorophosphate to give compounds of formula (8-3). Compounds of formula (8-3) can be reacted with acrylates of formula (8-4), wherein $L^3$ is as previously described and $R^{5'}$ is hydrogen, $C_1$-$C_2$ alkyl, $C_2$-$C_3$ alkenyl or $C_1$-$C_2$ haloalkyl, in the presence of a base such as cesium carbonate in a solvent such as acetonitrile at or near ambient temperature over 0.25-4 hours to give compounds of formula (8-5). Compounds of formula (8-5) can be cyclized to compounds of formula (8-6) in the presence of palladium(II) acetate, formic acid, and an amine such as tributylamine in a solvent such as heated acetonitrile in a sealed reaction vessel over 8-24 hours. Compounds of formula (8-6) can be hydrolyzed in the presence of a base such as potassium trimethylsilanoate in heated tetrahydrofuran over 0.5 to 4 hours to give compounds of formula (8-7). The enantiomers of compounds of formula (8-7) can be separated by chiral chromatography to give compounds of formula (8-8) and formula (8-9). Compounds of formula (8-7), formula (8-8), and formula (8-9) are representative of compounds of formula (1-1) in Scheme 1.

Scheme 9

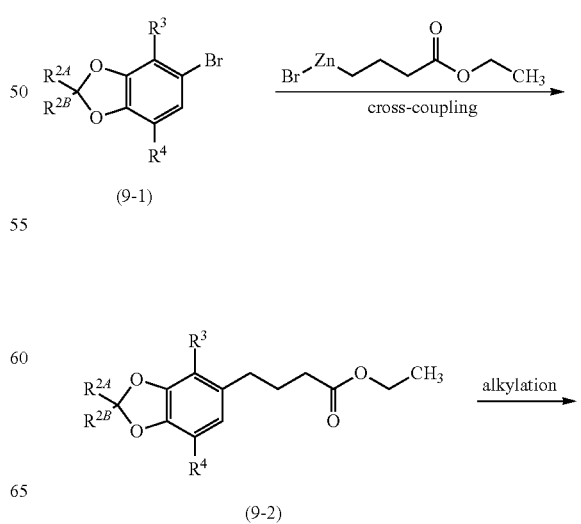

-continued

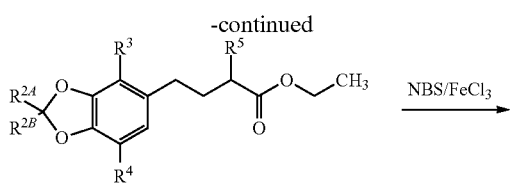

(9-3)

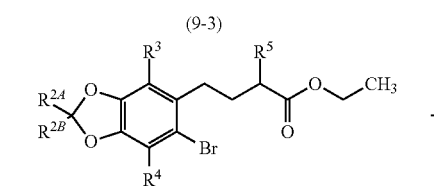

(9-4)

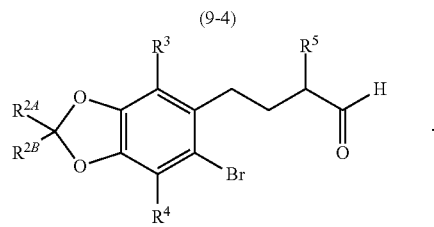

(9-5)

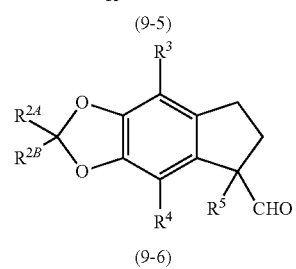

(9-6)

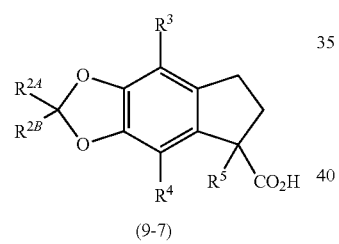

(9-7)

As shown in Scheme 9, compounds of formula (9-1) can be converted to compounds of formula (9-7). Compounds of formula (9-1) can be reacted with of 4-ethoxy-4-oxobutyl-zinc bromide in a solvent such as tetrahydrofuran in the presence of a ligand such as 2-dicyclohexylphosphino-2',6'-dimethoxybiphenyl (SPhos) and a catalyst such as palladium (II) acetate at or near ambient temperature over 0.5 to 6 hours to give compounds of formula (9-2). Compounds of formula (9-2) can be alkylated with an alkylating agent such as an alkyl halide in the presence of a strong base such as lithium diisopropyl amide in a solvent such as tetrahydrofuran over 6 to 24 hours to give compounds of formula (9-3). Compounds of formula (9-3) can be brominated by treatment with N-bromosuccinimide and iron(III) chloride in a solvent such as acetonitrile over 8 to 24 hours to give compounds of formula (9-4). Esters of formula (9-4) can be reduced to aldehydes of formula (9-5) with a reductant such as diisobutylaluminum hydride in a solvent such as hexanes. Compounds of formula (9-5) can be cyclized to give compounds of formula (9-6) in the presence of palladium(II) acetate, a ligand such as (R)-(+)-2-[2-(diphenylphosphino)phenyl]-4-isopropyl-2-oxazoline, and a base such as cesium carbonate in heated N,N-dimethylformamide in a sealed vessel over 24 to 72 hours. Compounds of formula (9-6) can be converted to the corresponding carboxylic acids, (9-7), by treatment with sodium chlorite, sodium dihydrogen phosphate, and 2-methyl-2-butene in tetrahydrofuran over 1 to 4 hours. Compounds of formula (9-7) are representative of compounds of formula (1-1) in Scheme 1.

Scheme 10

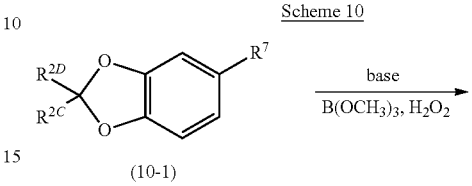

(10-1)

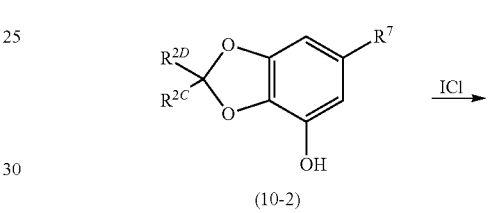

(10-2)

(10-3)

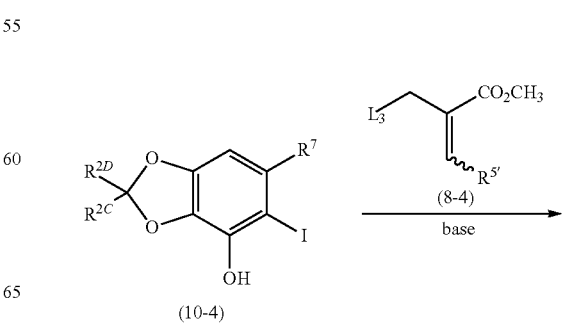

(10-4)

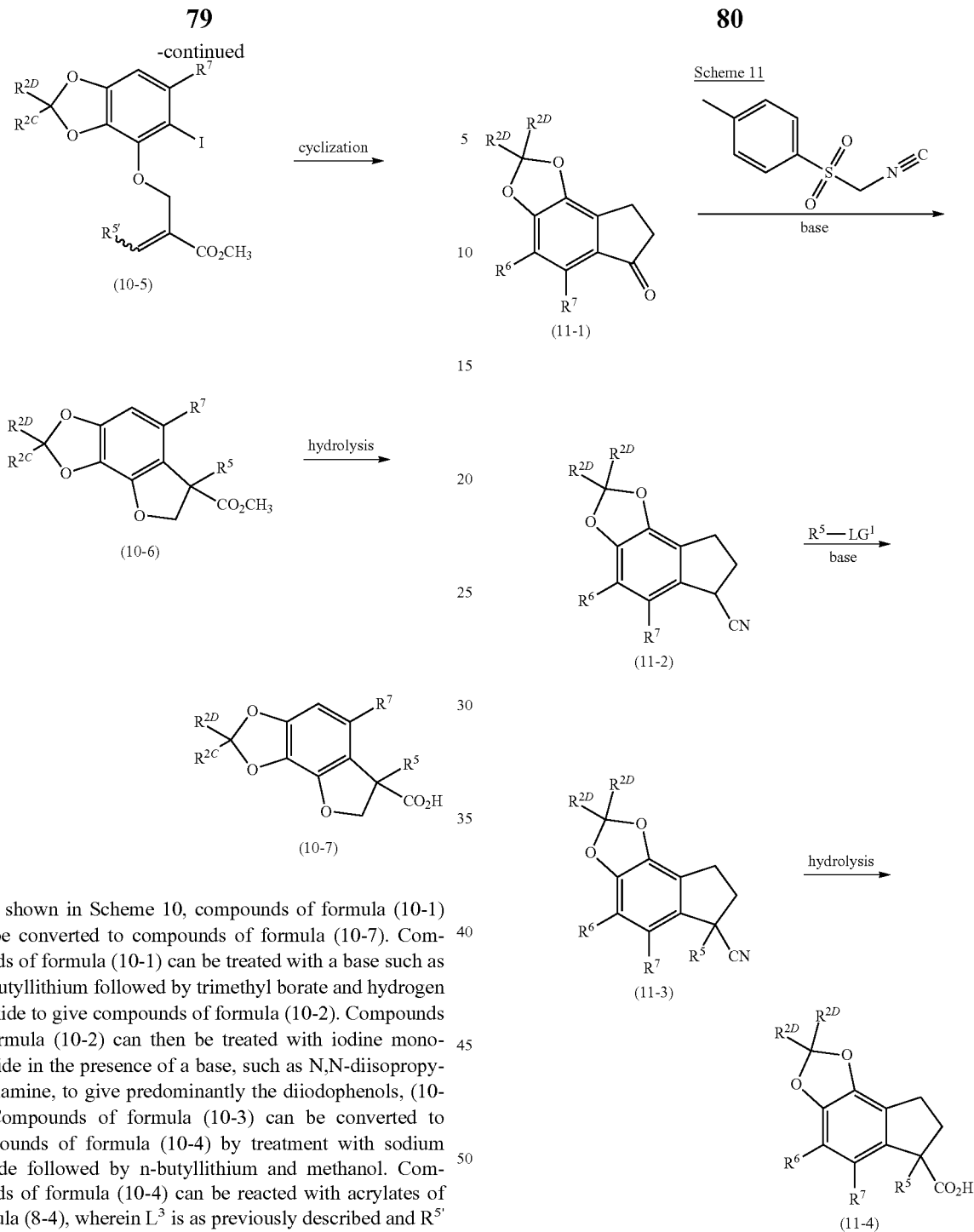

As shown in Scheme 10, compounds of formula (10-1) can be converted to compounds of formula (10-7). Compounds of formula (10-1) can be treated with a base such as sec-butyllithium followed by trimethyl borate and hydrogen peroxide to give compounds of formula (10-2). Compounds of formula (10-2) can then be treated with iodine monochloride in the presence of a base, such as N,N-diisopropylethylamine, to give predominantly the diiodophenols, (10-3). Compounds of formula (10-3) can be converted to compounds of formula (10-4) by treatment with sodium hydride followed by n-butyllithium and methanol. Compounds of formula (10-4) can be reacted with acrylates of formula (8-4), wherein $L^3$ is as previously described and $R^{5'}$ is hydrogen, $C_1$-$C_2$ alkyl, $C_2$-$C_3$ alkenyl or $C_1$-$C_2$ haloalkyl, in the presence of a base such as cesium carbonate in a solvent such as acetonitrile at or near ambient temperature to give compounds of formula (10-5). Compounds of formula (10-5) can be cyclized to compounds of formula (10-6) in the presence of palladium(II) acetate, formic acid, and an amine such as tributylamine in a solvent such as heated acetonitrile. Compounds of formula (10-6) can be hydrolyzed in the presence of a base such as potassium trimethylsilanoate in heated tetrahydrofuran over 0.5 to 4 hours to give compounds of formula (10-7). Compounds of formula (10-7) are representative of compounds of formula (12-1) in Scheme 12.

As illustrated in Scheme 11, compounds of formula (11-4) can be prepared from compounds of formula (11-1). Compounds of formula (11-1) can be reacted with 1-((isocyanomethyl)sulfonyl)-4-methylbenzene in the presence of a base such as but not limited to potassium tert-butoxide to give compounds of formula (11-2). Compounds of formula (11-2) can be alkylated with $R^5$-$LG^1$ in the presence of a base such as but not limited to n-butyllithium, wherein $LG^A$ is a leaving group selected from chlorine, bromine, iodine or a sulfonate, to give compounds of formula (11-3). Nitriles of formula (11-3) can be hydrolyzed in a heated hydroxide solution to give compounds of formula (11-4). Compounds of formula (11-4) are representative of compounds of formula (12-1) in Scheme 12.

Scheme 12

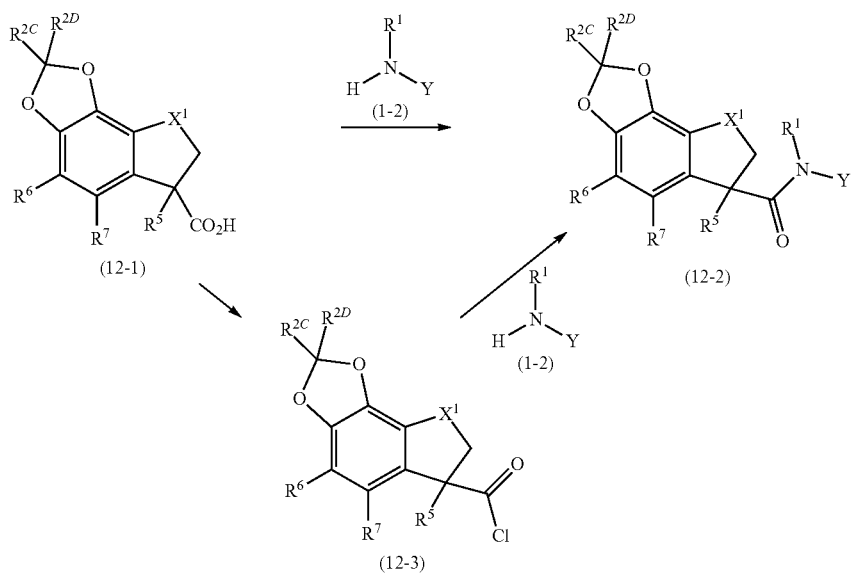

As shown in Scheme 12, compounds of formula (12-2) can be prepared from compounds of formula (12-1). Carboxylic acids of formula (12-1) can be coupled with amines of formula (1-2) under amide bond forming conditions to give compounds of formula (12-2). Examples of conditions known to generate amides from a mixture of a carboxylic acid and an amine include but are not limited to adding a coupling reagent such as but not limited to N-(3-dimethylaminopropyl)-N-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine, N,N-diisopropylethylamine or pyridine. The coupling reaction may be carried out in solvents such as but not limited to tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation.

Alternatively, carboxylic acids of formula (12-1) can be converted to the corresponding acid chlorides of formula (12-3) by reaction with thionyl chloride, $PCl_3$, $PCl_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides of formula (12-3) can then reacted with amines of formula (1-2) optionally in the presence of a base such as a tertiary amine base such as but not limited to triethylamine or N,N-diisopropylethylamine or an aromatic base such as pyridine, at room temperature or heated in a solvent such as dichloromethane to give amides of formula (12-2).

Compounds of formula (12-2) are representative of compounds of formula (I).

Scheme 13

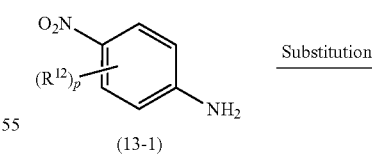

(13-1)

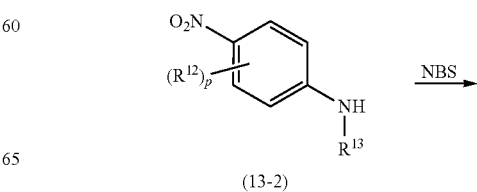

(13-2)

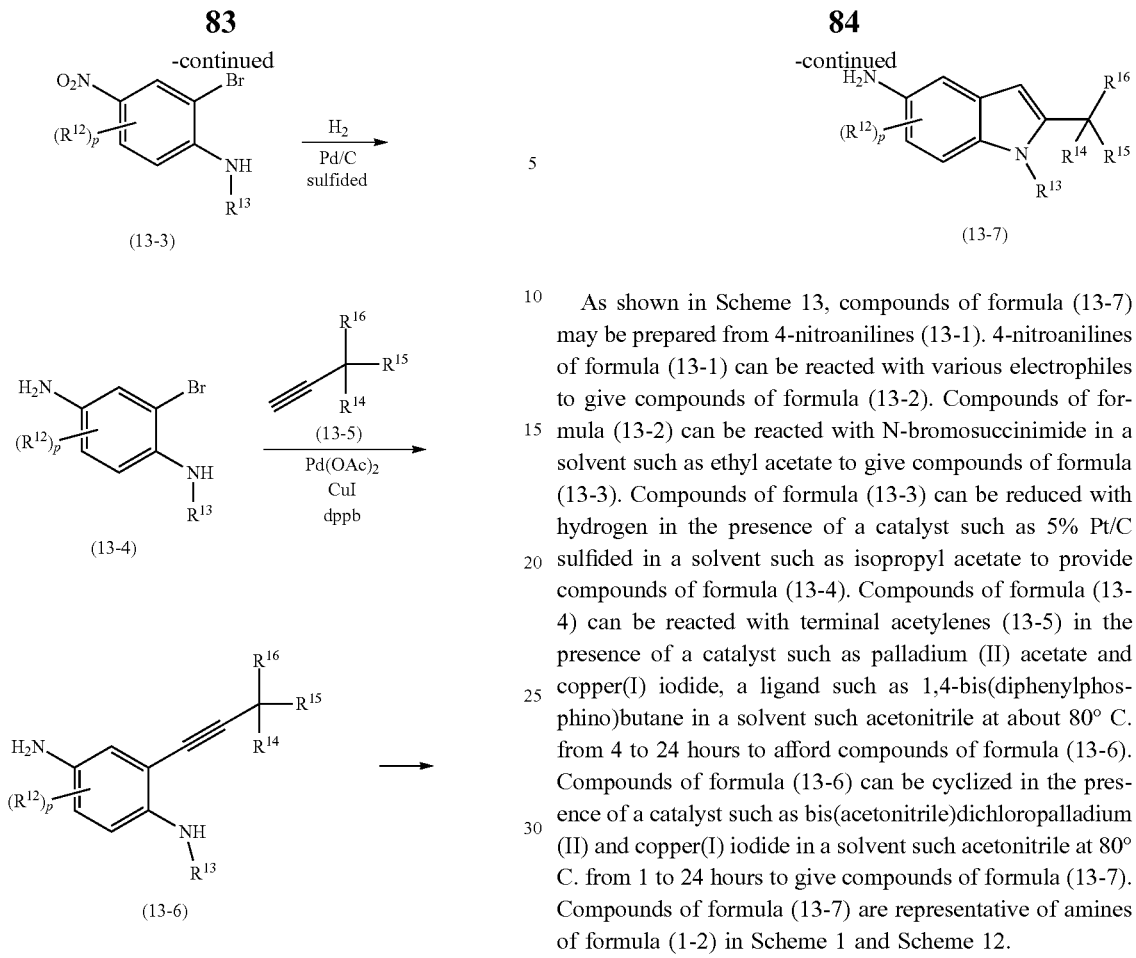

As shown in Scheme 13, compounds of formula (13-7) may be prepared from 4-nitroanilines (13-1). 4-nitroanilines of formula (13-1) can be reacted with various electrophiles to give compounds of formula (13-2). Compounds of formula (13-2) can be reacted with N-bromosuccinimide in a solvent such as ethyl acetate to give compounds of formula (13-3). Compounds of formula (13-3) can be reduced with hydrogen in the presence of a catalyst such as 5% Pt/C sulfided in a solvent such as isopropyl acetate to provide compounds of formula (13-4). Compounds of formula (13-4) can be reacted with terminal acetylenes (13-5) in the presence of a catalyst such as palladium (II) acetate and copper(I) iodide, a ligand such as 1,4-bis(diphenylphosphino)butane in a solvent such acetonitrile at about 80° C. from 4 to 24 hours to afford compounds of formula (13-6). Compounds of formula (13-6) can be cyclized in the presence of a catalyst such as bis(acetonitrile)dichloropalladium (II) and copper(I) iodide in a solvent such acetonitrile at 80° C. from 1 to 24 hours to give compounds of formula (13-7). Compounds of formula (13-7) are representative of amines of formula (1-2) in Scheme 1 and Scheme 12.

Scheme 14

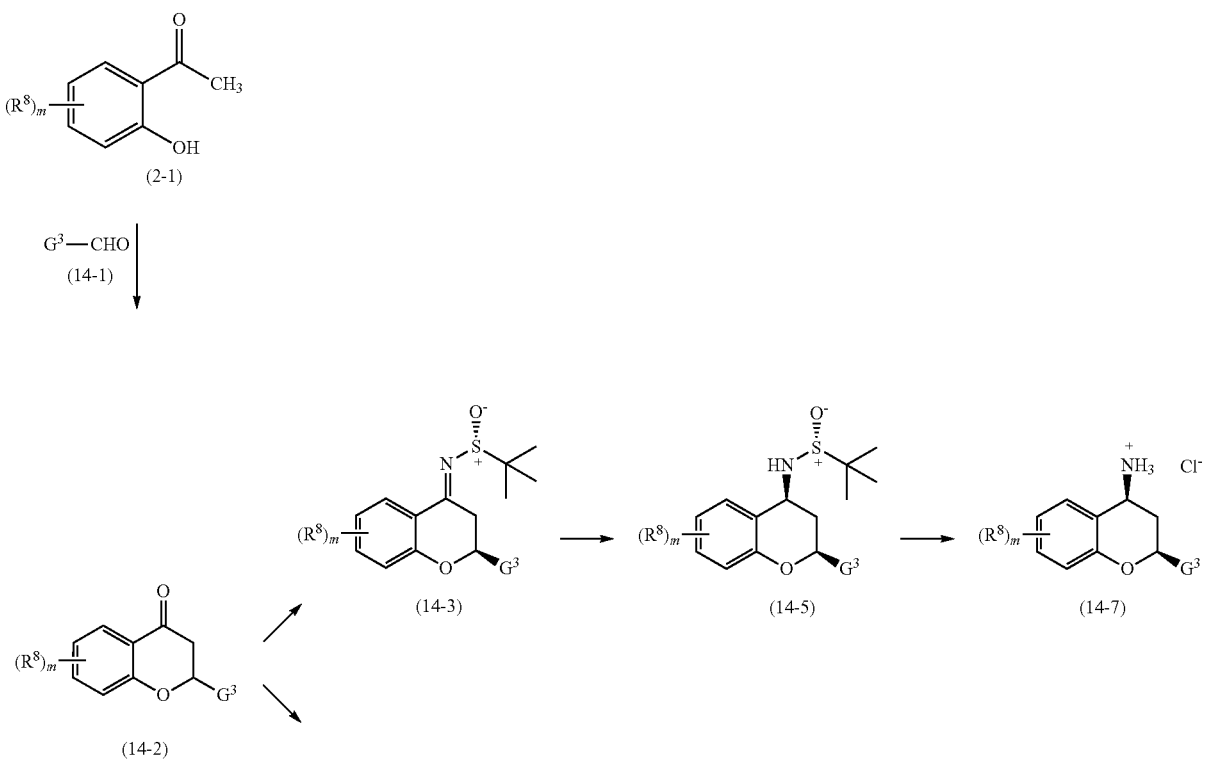

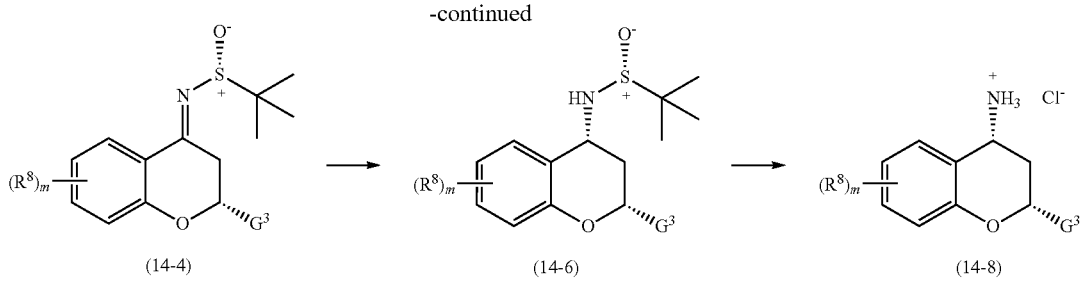

As shown in Scheme 14, compounds of formula (14-7) and formula (14-8) may be prepared from compounds of formula (2-1). Compounds of formula (2-1) may be reacted with aldehydes of formula (14-1) in the presence of pyrrolidine and optionally, acetic acid, to provide compounds of formula (14-2). The reaction is typically performed at an elevated temperature, for example, at about 70° C., and in a solvent, such as, but not limited to, toluene.

The hydrochloride salts of the chiral amines (14-7) and (14-8) may be prepared from ketones of formula (14-2) according to the general procedure described by Ellman and co-workers (Tanuwidjaja, J.; Ellman, J. A. et al. *J. Org. Chem.* 2007, 72, 626) as illustrated in Scheme 14. Chromanones (14-2) may be condensed with a chiral sulfinamide such as (R)-(+)-tert-butanesulfinamide in the presence of a Lewis acid such as titanium(IV) ethoxide to provide N-sulfinyl imine intermediates (14-3) and (14-4). The diastereomeric mixture of (14-3) and (14-4) may be separated via chromatography. The respective N-sulfinyl imine intermediates (14-3) and (14-4) may undergo a subsequent reduction with reagents such as sodium borohydride to provide sulfinamides of general formula (14-5) and (14-6). Treatment of the sulfinamides (14-5) and (14-6) with HCl or acetyl chloride/methanol provides the hydrochloride salts of amines (14-7) and (14-8) Amines of formula (14-7) and (14-8) are salts of representative of amines of formula (1-2) in Scheme 1.

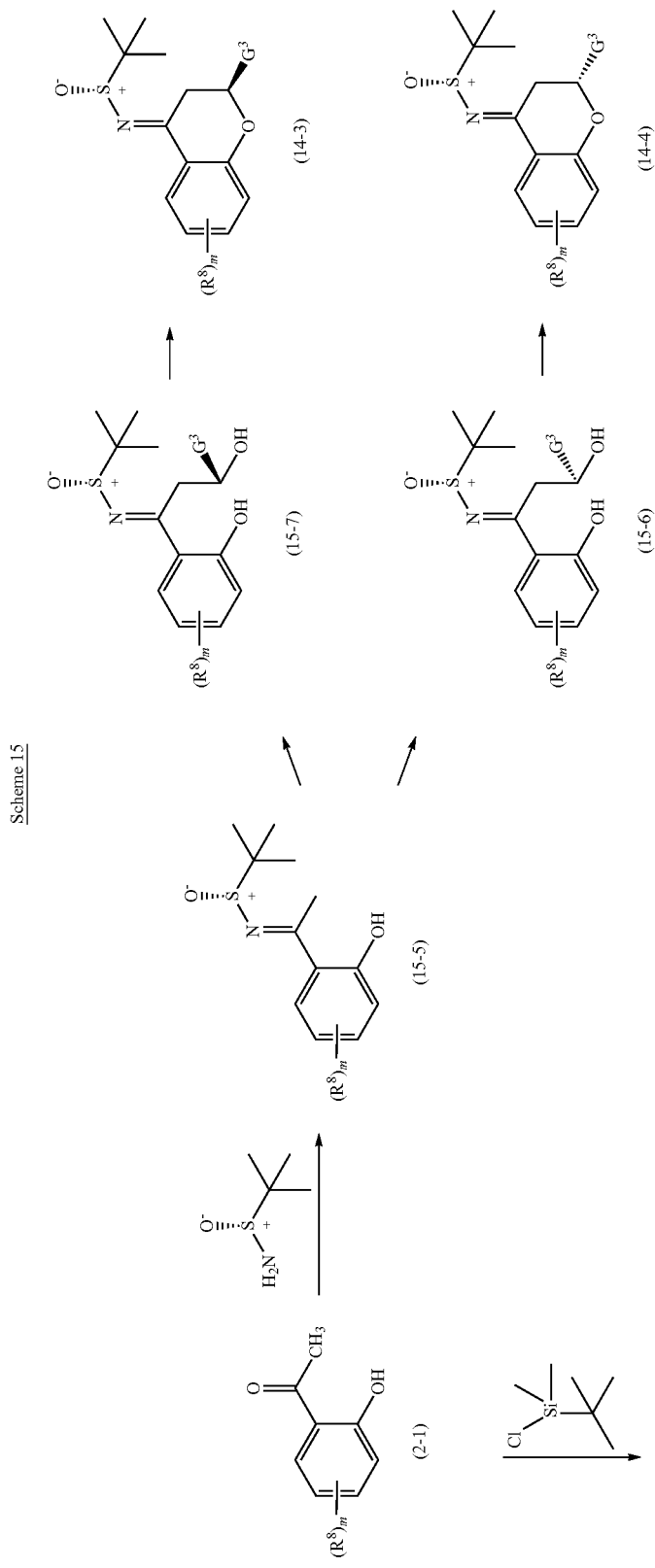

-continued
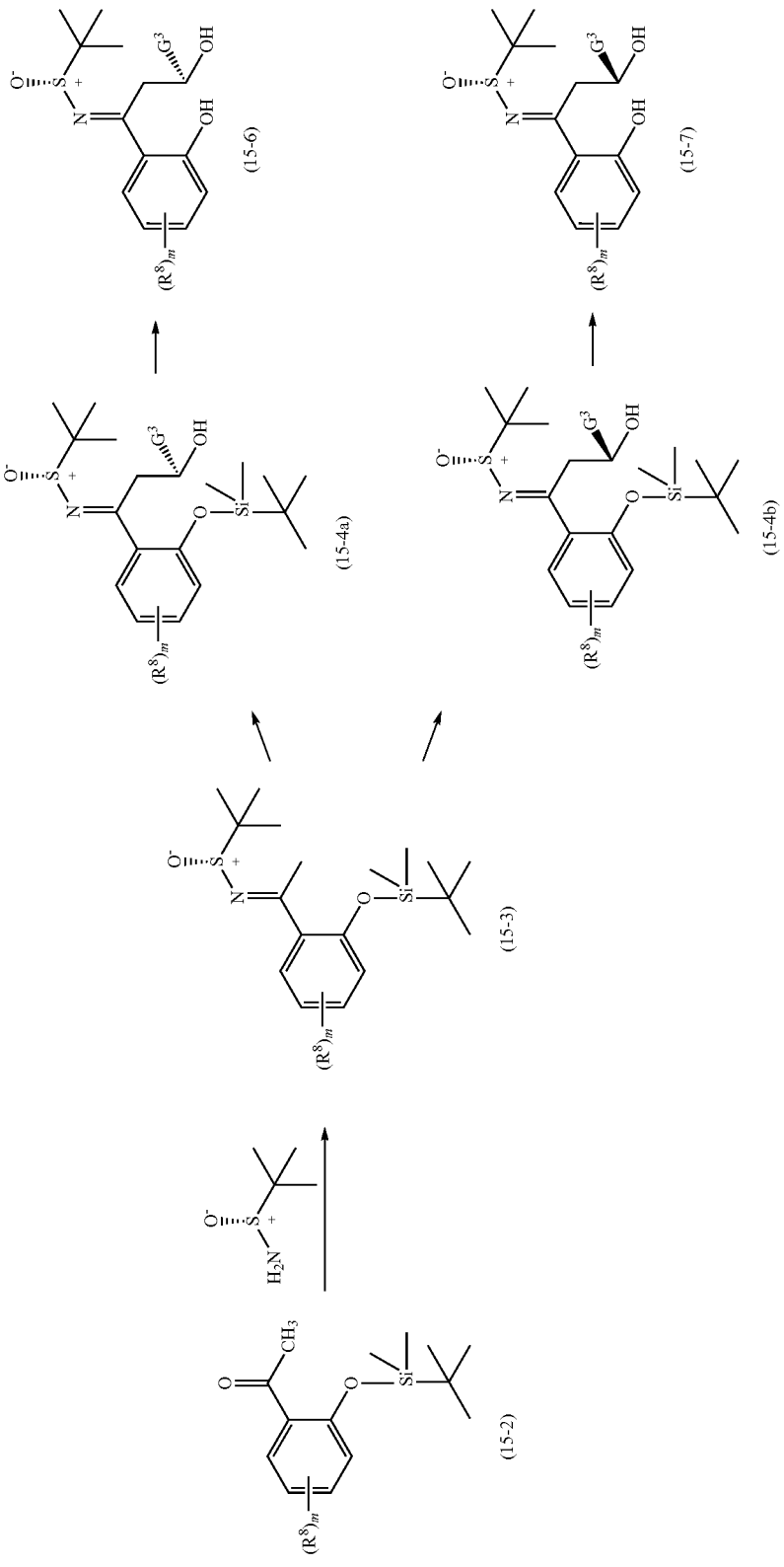

Scheme 15 illustrates an alternative route for the preparation of representative of the N-sulfinyl imine intermediates of formula (14-3) and (14-4).

Compounds of formula (2-1) may be treated with a chiral sulfinamide such as (R)-(+)-tert-butanesulfinamide in the presence of a Lewis acid such as titanium(IV) ethoxide to provide N-sulfinyl imine intermediates (15-5). Compounds of formula (15-5) may be treated with aldehydes of formula $G^3CHO$ in the presence of lithium diisopropanamide (prepared in situ from n-butyl lithium and N,N-diisopropylamine) to provide compounds of formula (15-6) and (15-7). The diastereomeric mixture of (15-6) and (15-7) may be separated via chromatography. Treatment of (15-6) and (15-7) with diethyl azodicarboxylate in the presence of triphenyl phosphine provides N-sulfinyl imine intermediates of formula (14-4) and (14-3) respectively.

Alternatively, the hydroxyl functionality of compounds of formula (2-1) may be protected before treatment with the chiral sulfinamide. For example, compounds of formula (2-1) may be treated with tert-butyldimethylsilyl chloride in the presence of an organic base such as, but not limited to, triethylamine to provide compounds of formula (15-2). Treatment of (15-2) with a chiral sulfinamide such as tert-butanesulfinamide in the presence of a Lewis acid such as titanium(IV) ethoxide provides the intermediates (15-3). Reaction of (15-3) with aldehydes of formula $G^3CHO$ in the presence of lithium diisopropanamide (prepared in situ from n-butyl lithium and N,N-diisopropylamine) provides compounds of formula (15-4a) and (15-4b). The diastereomeric mixture of (15-4a) and (15-4b) may be separated via chromatography. Subsequent removal of the silyl protecting group provides compounds of formula (15-6) and (15-7) respectively.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

When employed as a pharmaceutical, a compound of the invention is typically administered in the form of a pharmaceutical composition. Such compositions can be prepared in a manner well known in the pharmaceutical art and comprise a therapeutically effective amount of a compound of formula (I) or (I-a-i), or a pharmaceutically acceptable salt thereof together with a pharmaceutically acceptable carrier. The phrase "pharmaceutical composition" refers to a composition suitable for administration in medical or veterinary use.

The pharmaceutical compositions that comprise a compound of formula (I) or (I-a-i), alone or in combination with further therapeutically active ingredient, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous diluents, solvents, or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it may be desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In certain embodiments, solid dosage forms may contain from 1% to 95% (w/w) of a compound of formula (I) or (I-a-i). In certain embodiments, the compound of formula (I) or (I-a-i), or pharmaceutically acceptable salts thereof, may be present in the solid dosage form in a range of from 5% to 70% (w/w). In such solid dosage forms, the active compound may be mixed with at least one inert, pharmaceutically acceptable carrier, such as sodium citrate or dicalcium phosphate and/or a), fillers or extenders such as starches, lactose, sucrose, glucose, mannitol, and silicic acid; b) binders such as carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; 0 absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

A compound of the invention may also be administered in sustained release forms or from sustained release drug delivery systems.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's Syndrome (SS), chronic obstructive lung disease (COLD), or chronic obstructive airway disease (COAD) in a subject, wherein the method comprises the step of administering to said subject a therapeutically effective amount of a compound of formula (I) or (I-a-i), or a pharmaceutically acceptable salt thereof, or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

One embodiment is directed to a compound of the invention or a pharmaceutically acceptable salt thereof, or pharmaceutical compositions comprising a compound of the invention for use in medicine. One embodiment is directed to a compound of the invention or a pharmaceutically acceptable salt thereof, or pharmaceutical compositions thereof, for use in the treatment of cystic fibrosis, pancreatic insufficiency, Sjögren's Syndrome (SS), chronic obstructive lung disease (COLD) or chronic obstructive airway disease (COAD). In a more particular embodiment, the present invention provides compounds of the invention or pharmaceutically acceptable salts thereof, or pharmaceutical compositions comprising thereof, for use in the treatment of cystic fibrosis. In a more particular embodiment, the cystic fibrosis is caused by a Class I, II, III, IV, V, and/or VI mutation.

One embodiment is directed to the use of a compound according to formula (I) or (I-a-i) or a pharmaceutically acceptable salt thereof in the preparation of a medicament. The medicament optionally can comprise one or more additional therapeutic agents. In some embodiments, the medicament is for use in the treatment of cystic fibrosis, pancreatic insufficiency, Sjögren's Syndrome (SS), chronic obstructive lung disease (COLD) or chronic obstructive airway disease (COAD). In a particular embodiment, the medicament is for use in the treatment of cystic fibrosis. In a more particular embodiment, the cystic fibrosis is caused by a Class I, II, III, IV, V, and/or VI mutation.

This invention also is directed to the use of a compound according to formula (I) or (I-a-i) or a pharmaceutically acceptable salt thereof in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of a compound according to formula (I) or (I-a-i) or a pharmaceutically acceptable salt thereof in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention or a pharmaceutically acceptable salt thereof, and one or more additional therapeutic agents. In a particular embodiment, the other therapeutic agent is a cystic fibrosis treatment agent. In a particular embodiment, the additional therapeutic agents are selected from the group consisting of CFTR modulators and CFTR amplifiers. In a further embodiment, the pharmaceutical composition may further comprises of one potentiator and one or more additional correctors. In a more particular embodiment, the pharmaceutical composition may further comprises of one potentiator and one additional corrector. In a more particular embodiment, the pharmaceutical composition may further comprises of one potentiator. In a more particular embodiment, the cystic fibrosis is caused by a Class I, II, III, IV, V, and/or VI mutation.

The present compounds or pharmaceutically acceptable salts thereof may be administered as the sole active agent or it may be co-administered with other therapeutic agents, including other compounds or a pharmaceutically acceptable salt thereof that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis, chronic obstructive pulmonary disease (COPD), dry eye disease, pancreatic insufficiency, or Sjogren's Syndrome. In one embodiment, the CFTR mediated disease is cystic fibrosis. In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and one corrector. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, GLPG2451, GLPG1837, and N-(3-carbamoyl-5,5,7,7-tetramethyl-5,7-dihydro-4H-thieno[2,3-c]pyran-2-yl)-1H-pyrazole-5-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, and U.S. patent application Ser. Nos. 14/271,080, 14/451,619 and 15/164,317.

In one embodiment, the potentiator can be selected from the group consisting of
Ivacaftor (VX-770, N-(2,4-di-tert-butyl-5-hydroxyphenyl)-4-oxo-1,4-dihydroquinoline-3-carboxamide);
CTP-656;
NVS-QBW251;
FD1860293;
GLPG1837;
GLPG2451;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;

N-(3-carbamoyl-5,5,7,7-tetramethyl-5,7-dihydro-4H-thieno[2,3-c]pyran-2-yl)-5-methyl-1H-pyrazole-3-carboxamide;

N-(3-carbamoyl-5,5,7,7-tetramethyl-5,7-dihydro-4H-thieno[2,3-c]pyran-2-yl)-5-cyclopropyl-1H-pyrazole-3-carboxamide;

N-(3-carbamoyl-5,5,7,7-tetramethyl-5,7-dihydro-4H-thieno[2,3-c]pyran-2-yl)-5-isopropyl-1H-pyrazole-3-carboxamide;

N-(3-carbamoyl-5,5,7,7-tetramethyl-5,7-dihydro-4H-thieno[2,3-c]pyran-2-yl)-5-(trifluoromethyl)-1H-pyrazole-3-carboxamide;

5-tert-butyl-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-5-ethyl-1H-pyrazole-3-carboxamide;

N-(3-carbamoyl-5,5,7,7-tetramethyl-5,7-dihydro-4H-thieno[2,3-c]pyran-2-yl)-3-ethyl-4-methyl-1H-pyrazole-5-carboxamide;

2-(2-hydroxypropanamido)-5,5,7,7-tetramethyl-5,7-dihydro-4H-thieno[2,3-c]pyran-3-carboxamide;

N-(3-carbamoyl-5,5,7,7-tetramethyl-5,7-dihydro-4H-thieno[2,3-c]pyran-2-yl)-4-chloro-1H-pyrazole-3-carboxamide;

N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;

4-bromo-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-4-chloro-5-methyl-1H-pyrazole-3-carboxamide;

N-(3-carbamoyl-5,5,7,7-tetramethyl-5,7-dihydro-4H-thieno[2,3-c]pyran-2-yl)-4-methyl-1H-pyrazole-3-carboxamide;

2-(2-hydroxy-3,3-dimethylbutanamido)-5,5,7,7-tetramethyl-5,7-dihydro-4H-thieno[2,3-c]pyran-3-carboxamide;

2-[(2-hydroxy-4-methyl-pentanoyl)amino]-5,5,7,7-tetramethyl-4H-thieno[2,3-c]pyran-3-carboxamide;

5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;

N-(3-carbamoyl-5,5,7,7-tetramethyl-4H-thieno[2,3-c]pyran-2-yl)-4-(3-methoxypropyl)-1H-pyrazole-3-carboxamide;

N-(3-carbamoyl-5,5,7,7-tetramethyl-4H-thieno[2,3-c]pyran-2-yl)-4-(2-ethoxyethyl)-1H-pyrazole-3-carboxamide;

2-[[(2S)-2-hydroxy-3,3-dimethyl-butanoyl]amino]-5,5,7,7-tetramethyl-4H-thieno[2,3-c]pyran-3-carboxamide;

2-[[(2R)-2-hydroxy-3,3-dimethyl-butanoyl]amino]-5,5,7,7-tetramethyl-4H-thieno[2,3-c]pyran-3-carboxamide;

2-[(2-hydroxy-2,3,3-dimethyl-butanoyl)amino]-5,5,7,7-tetramethyl-4H-thieno[2,3-c]pyran-3-carboxamide;

[5-[(3-carbamoyl-5,5,7,7-tetramethyl-4H-thieno[2,3-c]pyran-2-yl)carbamoyl]pyrazol-1-yl]methyl dihydrogen phosphate;

[3-[(3-carbamoyl-5,5,7,7-tetramethyl-4H-thieno[2,3-c]pyran-2-yl)carbamoyl]pyrazol-1-yl]methyl dihydrogen phosphate;

N-(3-carbamoyl-5,5,7,7-tetramethyl-4H-thieno[2,3-c]pyran-2-yl)-4-(1,4-dioxan-2-yl)-1H-pyrazole-3-carboxamide;

5,5,7,7-tetramethyl-2-[[(2S)-3,3,3-trifluoro-2-hydroxy-2-methyl-propanoyl]amino]-4H-thieno[2,3-c]pyran-3-carboxamide;

2-[[(2S)-2-hydroxypropanoyl]amino]-5,5,7,7-tetramethyl-4H-thieno[2,3-c]pyran-3-carboxamide;

3-amino-N-(2-hydroxy-2-methylpropyl)-5-{[4-(trifluoromethoxy)phenyl]sulfonyl}pyridine-2-carboxamide;

3-amino-N-[(4-hydroxy-1-methylpiperidin-4-yl)methyl]-5-{[4-(trifluoromethoxy)phenyl]sulfonyl}pyridine-2-carboxamide;

3-amino-N-(3-hydroxy-2,2-dimethylpropyl)-5-{[4-(trifluoromethoxy)phenyl]sulfonyl}pyridine-2-carboxamide;

3-amino-5-[(4-fluorophenyl)sulfonyl]-N-[(1-hydroxycyclopropyl)methyl]pyridine-2-carboxamide;

3-amino-5-[(4-fluorophenyl)sulfonyl]-N-[(2R)-3,3,3-trifluoro-2-hydroxypropyl]pyridine-2-carboxamide;

3-amino-5-[(3-fluorophenyl)sulfonyl]-N-(2-hydroxy-2-methylpropyl)pyridine-2-carboxamide;

3-amino-N-[2-(cyclopropylamino)-2-oxoethyl]-5-{[4-(trifluoromethoxy)phenyl]sulfonyl}pyridine-2-carboxamide;

(3-amino-5-{[4-(trifluoromethoxy)phenyl]sulfonyl}pyridin-2-yl)(azetidin-1-yl)methanone;

(3-amino-5-{[4-(trifluoromethoxy)phenyl]sulfonyl}pyridin-2-yl)[3-(hydroxymethyl)azetidin-1-yl]methanone;

(3-amino-5-{[4-(trifluoromethoxy)phenyl]sulfonyl}pyridin-2-yl)(3-fluoroazetidin-1-yl)methanone;

3-amino-N-[(2R)-2-hydroxy-3-methoxypropyl]-5-{[4-(trifluoromethyl)phenyl]sulfonyl}pyridine-2-carboxamide;

(3-amino-5-{[2-fluoro-4-(trifluoromethoxy)phenyl]sulfonyl}pyridin-2-yl)(3-hydroxyazetidin-1-yl)methanone;

(3-amino-5-{[2-(trifluoromethoxy)phenyl]sulfonyl}pyridin-2-yl)(3,3-difluoroazetidin-1-yl)methanone;

rac-3-amino-N-[(3R,4S)-4-hydroxytetrahydro-2H-pyran-3-yl]-5-{[2-(trifluoromethoxy)phenyl]sulfonyl}pyridine-2-carboxamide;

3-amino-5-[(4,4-difluoropiperidin-1-yl)sulfonyl]-N-(3,3,3-trifluoro-2-hydroxypropyl)pyridine-2-carboxamide;

(3-amino-5-{[2-(trifluoromethoxy)phenyl]sulfonyl}pyridin-2-yl)[3-hydroxy-3-(trifluoromethyl)azetidin-1-yl]methanone;

3-amino-N-(2-hydroxy-4-methylpentyl)-5-{[4-(trifluoromethoxy)phenyl]sulfonyl}pyridine-2-carboxamide;

(3-amino-5-{[4-(trifluoromethyl)phenyl]sulfonyl}pyridin-2-yl)(3-hydroxy-3-methylazetidin-1-yl)methanone;

3-amino-N-(3,3,3-trifluoro-2-hydroxypropyl)-5-{[4-(trifluoromethyl)piperidin-1-yl]sulfonyl}pyridine-2-carboxamide;

3-amino-N-[2-hydroxy-1-(4-methoxyphenyl)ethyl]-5-{[4-(trifluoromethoxy)phenyl]sulfonyl}pyridine-2-carboxamide;

3-amino-5-[(3,3-difluoroazetidin-1-yl)sulfonyl]-N-(3,3,3-trifluoro-2-hydroxypropyl)pyridine-2-carboxamide;

3-amino-5-{[2-fluoro-4-(trifluoromethyl)phenyl]sulfonyl}-N-[(2S)-2-hydroxypropyl]pyridine-2-carboxamide;

3-amino-5-{[2-fluoro-4-(trifluoromethyl)phenyl]sulfonyl}-N-[(2R)-2-hydroxy-3-methoxypropyl]pyridine-2-carboxamide;

3-amino-N-[2-oxo-2-(propan-2-ylamino)ethyl]-5-{[4-(trifluoromethyl)phenyl]sulfonyl}pyridine-2-carboxamide;

(3-amino-5-{[4-(trifluoromethyl)phenyl]sulfonyl}pyridin-2-yl)[3-hydroxy-3-(trifluoromethyl)azetidin-1-yl]methanone;

3-amino-5-{[2-fluoro-4-(trifluoromethyl)phenyl]sulfonyl}-N-[(3R)-tetrahydrofuran-3-ylmethyl]pyridine-2-carboxamide;

(3-amino-5-{[2-fluoro-4-(trifluoromethyl)phenyl]
sulfonyl}pyridin-2-yl)[3-hydroxy-3-(trifluoromethyl)
azetidin-1-yl]methanone;
3-amino-5-{[2-fluoro-4-(trifluoromethyl)phenyl]sulfonyl}-
N-[(3S)-tetrahydrofuran-3-ylmethyl]pyridine-2-carbox-
amide;
3-amino-5-{[2-fluoro-4-(trifluoromethoxy)phenyl]sulfo-
nyl}-N-[(3S)-tetrahydrofuran-3-ylmethyl]pyridine-2-car-
boxamide;
3-amino-N-[2-hydroxy-3-(2,2,2-trifluoroethoxy)propyl]-5-
{[4-(trifluoromethyl)phenyl]sulfonyl}pyridine-2-carbox-
amide;
3-amino-N-(3-tert-butoxy-2-hydroxypropyl)-5-{[2-fluoro-
4-(trifluoromethyl)phenyl]sulfonyl}pyridine-2-carbox-
amide;
[3-amino-5-(phenylsulfonyl)pyridin-2-yl][3-hydroxy-3-(tri-
fluoromethyl)azetidin-1-yl]methanone;
{3-amino-5-[(3-fluorophenyl)sulfonyl]pyridin-2-yl}[3-hy-
droxy-3-(trifluoromethyl)azetidin-1-yl]methanone; and
3-amino-N-[(2S)-2-hydroxypropyl]-5-{[4-(trifluo-
romethoxy)phenyl]sulfonyl}pyridine-2-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2222, GLPG2665, GLPG2737, VX-152, VX-440, FDL169, FDL304, FD2052160, and FD2035659. Examples of correctors are also disclosed in US20160095858A1, and U.S. application Ser. Nos. 14/925,649 and 14/926,727.

In one embodiment, the corrector(s) can be selected from the group consisting of
Lumacaftor (VX-809);
1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);
VX-983;
VX-152;
VX-440;
FDL169
FDL304;
FD2052160;
FD2035659;
GLPG2665,
GLPG2737,
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;
3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;
3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;
3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;
4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;
4-[(2R,4R)-4-({[1-(2,2-difluoro-1,3-benzodioxol-5-yl)cyclopropyl]carbonyl}amino)-3,4-dihydro-2H-chromen-2-yl]benzoic acid;
4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
rac-3-[(2R,4S)-4-({[1-(2,2-difluoro-1,3-benzodioxol-5-yl)cyclopropyl]carbonyl}amino)tetrahydro-2H-pyran-2-yl]benzoic acid;
rac-4-[(2R,4S)-4-({[1-(2,2-difluoro-1,3-benzodioxol-5-yl)cyclopropyl]carbonyl}amino)tetrahydro-2H-pyran-2-yl]benzoic acid;
3-[(2S,4R)-4-({[1-(2,2-difluoro-1,3-benzodioxol-5-yl)cyclopropyl]carbonyl}amino)tetrahydro-2H-pyran-2-yl]benzoic acid;
3-[(2R,4S)-4-({[1-(2,2-difluoro-1,3-benzodioxol-5-yl)cyclopropyl]carbonyl}amino)tetrahydro-2H-pyran-2-yl]benzoic acid;
rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;
3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;
3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid; and
4-[(2R,4S)-4-({[1-(2,2-difluoro-1,3-benzodioxol-5-yl)cyclopropyl]carbonyl}amino)tetrahydro-2H-pyran-2-yl]benzoic acid.

In one embodiment, the additional therapeutic agent is a CFTR amplifier. CFTR amplifiers enhance the effect of known CFTR modulators, such as potentiators and correctors. Examples of CFTR amplifier include PTI130 and PTI-428. Examples of amplifiers are also disclosed in publications: WO2015138909 and WO2015138934.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in PCT Publication No. WO2009074575 and WO2013043720; and U.S. Pat. No. 8,999,976.

In one embodiment, the ENaC inhibitor is VX-371.

In one embodiment, the ENaC inhibitor is SPX-101 (S18).

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

Further benefits of Applicants' invention will be apparent to one skilled in the art from reading this patent application.

The following Examples may be used for illustrative purposes and should not be deemed to narrow the scope of the invention.

EXAMPLES

All reagents were of commercial grade and were used as received without further purification, unless otherwise stated. Commercially available anhydrous solvents were used for reactions conducted under inert atmosphere. Reagent grade solvents were used in all other cases, unless otherwise specified. Chemical shifts ($\delta$) for $^1$H NMR spectra were reported in parts per million (ppm) relative to tetramethylsilane ($\delta$ 0.00) or the appropriate residual solvent peak, i.e. CHCl$_3$ ($\delta$ 7.27), as internal reference. Multiplicities were given as singlet (s), doublet (d), triplet (t), quartet (q), quintuplet (quin), multiplet (m) and broad (br). Microwave heating was performed with a Biotage® Initiator.

Enantiomeric purity was determined on an Agilent HP1100 system with UV detection. Column used: Chiralpak IA (4.6×250 mm, 5 µm). Solvents used: isopropanol and tert-butyl methyl ether.

Prep LC/MS Method TFA6

Samples were purified by reverse phase preparative HPLC on a Phenomenex Luna C8(2) 5 µm 100 Å a AXIA column (50 mm×21.2 mm). A gradient of acetonitrile (A) and 0.1% trifluoroacetic acid in water (B) was used, at a flow rate of 30 mL/min (0-0.5 min 15% A, 0.5-8.0 min linear gradient 15-100% A, 8.0-9.0 min 100% A, 7.0-8.9 min 100% A, 9.0-9.1 min linear gradient 100-15% A, 9.1-10 minutes 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA7

Samples were purified by reverse phase preparative HPLC on a Phenomenex Luna C8(2) 5 µm 100 Å a AXIA column (50 mm×21.2 mm). A gradient of acetonitrile (A) and 0.1% trifluoroacetic acid in water (B) was used, at a flow rate of 30 mL/min (0-0.5 min 25% A, 0.5-8.0 min linear gradient 25-100% A, 8.0-9.0 min 100% A, 7.0-8.9 min 100% A, 9.0-9.1 min linear gradient 100-25% A, 9.1-10 min 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA7

Samples were purified by reverse phase preparative HPLC on a Phenomenex Luna C8(2) 5 µm 100 Å a AXIA column (50 mm×21.2 mm). A gradient of acetonitrile (A) and 0.1% ammonium acetate in water (B) was used, at a flow rate of 30 mL/min (0-0.5 min 25% A, 0.5-8.0 min linear gradient 25-100% A, 8.0-9.0 min 100% A, 7.0-8.9 min 100% A, 9.0-9.1 min linear gradient 100-25% A, 9.1-10 min 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Chiral Analytical Supercritical Fluid Chromatography (SFC)

Analytical SFC was performed on an Aurora A5 SFC Fusion and Agilent 1100 system running under Agilent Chemstation software control. The SFC system included a 10-way column switcher, CO$_2$ pump, modifier pump, oven, and backpressure regulator. The mobile phase comprised of supercritical CO$_2$ supplied by a beverage-grade CO$_2$ cylinder with a modifier mixture of methanol at a flow rate of 3 mL/min. Oven temperature was at 35° C. and the outlet pressure at 150 bar. The mobile phase gradient started with 5% modifier and held it for 0.1 minutes at a flow rate of 1 mL/min, then the flow rate was ramped up to 3 mL/min and held for 0.4 minute. The modifier was ramped from 5% to 50% over the next 8 minutes at 3 mL/min then held for 1 minute at 50% modifier (3 mL/min). The gradient was ramped down from 50% to 5% modifier over 0.5 min (3 mL/min). The instrument was fitted with a Chiralpak IC column with dimensions of 4.6 mm i.d.×150 mm length with 5 fun particles.

Example 1 tert-butyl 3-{6-[(2,2-difluoro-7-methyl-6,7-dihydro-2H-furo[2,3-f][1,3]benzodioxole-7-carbonyl)amino]-3-methylpyridin-2-yl}benzoate

Example 1A 2,2-difluoro-2H-1,3-benzodioxol-5-ol

To a mixture of 5-bromo-2,2-difluorobenzo[d][1,3]dioxole (10 g, 42.2 mmol), 2-di-tert-butylphosphino-3,4,5,6-tetramethyl-2',4',6'-triisopropyl-1,1'-biphenyl (2.028 g, 4.22 mmol) and potassium hydroxide (4.74 g, 84 mmol) was added degassed water (10 mL). The reaction mixture was sparged with a nitrogen stream for 5 minutes. To the reaction mixture was added a degassed solution of tris(dibenzylideneacetone)dipalladium(0) (0.773 g, 0.844 mmol) in dioxane (10 mL). The combined reaction mixture was sparged with nitrogen for 5-7 minutes. The reaction vial was capped and stirred at 100° C. overnight (16 hours). The reaction mixture was cooled to ambient temperature, and partitioned between ethyl acetate and 1 N HCl solution. The organic fractions were combined and washed with brine, dried over anhydrous sodium sulfate, filtered, and concentrated in vacuo, maintaining a bath temp at or below 25° C. The residue was purified by flash chromatography using a 220 g silica gel cartridge, eluting with 25-75% dichloromethane/heptanes to afford 6.02 g of the title compound (82% yield). $^1$H NMR (400 MHz, CDCl$_3$) δ ppm 5.51 (s, 1H), 6.50 (dd, J=8.6, 2.5 Hz, 1H), 6.63 (d, J=2.4 Hz, 1H), 6.90 (dd, J=8.7, 1.4 Hz, 1H); MS (ESI−) m/z 173.1 (M−H)$^−$.

Example 1B 2,2-difluoro-6-iodo-2H-1,3-benzodioxol-5-ol

To a cold (−10° C.) solution of Example 1A (6.0215 g, 34.6 mmol) in 1-butyl-3-methylimidazolium hexafluorophosphate (14.00 mL, 67.6 mmol) was added N-iodosuccinimide (7.78 g, 34.6 mmol) in two portions over 5 minutes. The reaction was stirred for an additional 5 minutes at the same temperature, the ice bath was removed, and the reaction mixture was stirred at ambient temperature for 15 minutes. Then the reaction mixture was extracted twice with tert-butyl methyl ether. The combined extracts were washed with saturated Na$_2$S$_2$O$_3$ solution, dried over anhydrous sodium sulfate, and concentrated in vacuo. The resulting crude residue was purified by flash chromatography using a 220 g silica gel cartridge, eluting with 25-75% dichloromethane/hexanes to afford 4.68 g of the title compound (45% yield). $^1$H NMR (501 MHz, CDCl$_3$) δ ppm 5.27 (s, 1H), 6.84 (s, 1H), 7.34 (s, 1H); MS (ESI−) m/z 299.0 (M−H)$^−$.

Example 1C ethyl 2-{[(2,2-difluoro-6-iodo-2H-1,3-benzodioxol-5-yl)oxy]methyl}prop-2-enoate To a stirred solution of Example 1B (4.6625 g, 15.54 mmol) in acetonitrile (42 mL) was added cesium carbonate (7.60 g, 23.31 mmol) at room temperature, and the resulting suspension was stirred for 5 minutes. Ethyl 2-(bromomethyl)acrylate (2.5 mL, 18.11 mmol) was added to the reaction mixture in one portion. The reaction mixture was stirred at ambient temperature for 30 minutes, then diluted with water. The resulting precipitate was collected by filtration and washed with water. The solid was dried in a vacuum oven at 70° C. for 3 hours to afford 6.23 g (97% crude yield) of the title compound, which was used directly in the next step without purification. $^1$H NMR (501 MHz, CDCl$_3$) δ ppm 1.37 (t, J=7.1 Hz, 3H), 4.31 (q, J=7.1 Hz, 2H), 4.78 (t, J=1.8 Hz, 2H), 6.23 (td, J=1.9, 1.1 Hz, 1H), 6.50 (q, J=1.5 Hz, 1H), 6.76 (s, 1H), 7.49 (s, 1H); LC/MS (ESI+) m/z 412.0 (M+H)$^+$.

Example 1D ethyl 2,2-difluoro-7-methyl-6,7-dihydro-2H-furo[2,3-f][1,3]benzodioxole-7-carboxylate To a solution of tributylamine (7.92 mL, 33.2 mmol) in acetonitrile (84 mL) was added formic acid (0.643 mL, 16.62 mmol) dropwise over 2 minutes, and the reaction mixture was stirred at ambient temperature for 10 minutes. Example 1C (6.2263 g, 15.11 mmol) was added to the reaction mixture, and the mixture was sparged with nitrogen for 5 minutes. Palladium(II) acetate (0.339 g, 1.511 mmol) was added to the reaction mixture, sparging was continued for 2-3 minutes more, and then the reaction flask was capped. The reaction mixture was stirred at 60° C. for 17 hours. The reaction mixture was filtered, and the collected solids were washed with tert-butyl methyl ether. Then the solids were partitioned between tert-butyl methyl ether and brine. The combined organic extracts were dried over anhydrous sodium sulfate, filtered, and concentrated in vacuo. Then the residue was purified via flash chromatography using a 120 g silica gel cartridge, eluted with 0-10% tert-butyl methyl ether/heptanes to afford 2.69 g of the title compound (62% yield). $^1$H NMR (501 MHz, CDCl$_3$) δ ppm 1.31 (t, J=7.1 Hz, 3H), 1.62 (s, 3H), 4.23 (q, J=7.1 Hz, 2H), 4.31 (d, J=9.1 Hz, 1H), 5.11 (d, J=9.1 Hz, 1H), 6.59 (s, 1H), 7.05 (s, 1H); LC/MS (ESI+) m/z 286.3 (M+H)$^+$.

Example 1E 2,2-difluoro-7-methyl-6,7-dihydro-2H-furo[2,3-f][1,3]benzodioxole-7-carboxylic acid To a solution of Example 1D (2.6849 g, 9.38 mmol) in tetrahydrofuran (36 mL) was added potassium trimethylsilanoate (1.444 g, 11.26 mmol), and the resultant mixture was stirred at 50° C. for 70 minutes. The reaction mixture was diluted with water and washed with tert-butyl methyl ether. The aqueous layer was acidified with concentrated HCl solution, and the mixture was extracted with dichloromethane. The organic extracts were washed with brine, dried over anhydrous sodium sulfate, and then concentrated in vacuo to afford 2.23 g of the title compound (92% yield). $^1$H NMR (501 MHz, CDCl$_3$) δ ppm 1.67 (s, 3H), 4.32 (d, J=9.2 Hz, 1H), 5.11 (d, J=9.2 Hz, 1H), 6.60 (s, 1H), 7.07 (s, 1H); MS (ESI−) m/z 256.9 (M−H)$^−$.

Example 1F tert-butyl 3-{6-[(2,2-difluoro-7-methyl-6,7-dihydro-2H-furo[2,3-f][1,3]benzodioxole-7-carbonyl)amino]-3-methylpyridin-2-yl}benzoate Example 1E (55.6 mg, 0.215 mmol) was dissolved in dichloromethane (1 mL). Oxalyl chloride (80 μL) and N,N-dimethylformamide (25 μL) were added which resulted in bubbling of the reaction mixture. The reaction mixture was stirred at ambient temperature for 1 hour. The reaction mixture was concentrated; the residue was dissolved in dichloromethane (1 mL) and concentrated two times. The residue was dissolved in dichloromethane (1 mL) and pyridine (0.5 mL), tert-butyl 3-(6-amino-3-methylpyridin-2-yl) benzoate (CAS [1083057-14-0], 54.8 mg, 0.193 mmol) was added, and the reaction mixture was stirred at 60° C. for 16 hours. The reaction mixture was concentrated, and the residue was purified by reverse-phase preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield 71.0 mg (70%) of the title compound. $^1$H NMR (400 MHz, DMSO-$d_6$) δ ppm 10.14 (s, 1H), 8.02 (t, J=1.7 Hz, 1H), 7.98-7.90 (m, 2H), 7.81-7.73 (m, 2H), 7.65 (s, 1H), 7.60 (t, J=7.7 Hz, 1H), 7.03 (s, 1H), 5.10 (d, J=9.3 Hz, 1H), 4.41 (d, J=9.3 Hz, 1H), 2.25 (s, 3H), 1.71 (s, 3H), 1.56 (s, 9H); MS (ESI+) m/z 525.0 (M+H)$^+$.

Example 2

3-{6-[(2,2-difluoro-7-methyl-6,7-dihydro-2H-furo[2,3-f][1,3]benzodioxole-7-carbonyl)amino]-3-methylpyridin-2-yl}benzoic acid The product of Example 1F (53.7 mg, 0.102 mmol) was dissolved in dichloromethane (1 mL). Trifluoroacetic acid (0.5 mL, 6.49 mmol) was added, and the reaction mixture was stirred at ambient temperature for 15 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield 33.5 mg (70%) of the title compound. $^1$H NMR (400 MHz, DMSO-$d_6$) δ ppm 13.08 (s, 1H), 10.15 (s, 1H), 8.08 (t, J=1.7 Hz, 1H), 8.00 (dt, J=7.7, 1.4 Hz, 1H), 7.92 (d, J=8.4 Hz, 1H), 7.79 (dt, J=7.7, 1.5 Hz, 1H), 7.75 (d, J=8.5 Hz, 1H), 7.66-7.56 (m, 2H), 7.02 (s, 1H), 5.10 (d, J=9.3 Hz, 1H), 4.41 (d, J=9.4 Hz, 1H), 2.26 (s, 3H), 1.71 (s, 3H); MS (ESI+) m/z 469.1 (M+H)$^-$.

Example 3 tert-butyl 3-(6-{[(7S)-2,2-difluoro-7-methyl-6,7-dihydro-2H-furo[2,3-f][1,3]benzodioxole-7-carbonyl]amino}-3-methylpyridin-2-yl)benzoate Example 3A (7S)-2,2-difluoro-7-methyl-6,7-dihydro-2H-furo[2,3-f][1,3]benzodioxole-7-carboxylic acid Example 1E (2.18 g) was chromatographed by preparative supercritical fluid chromatography using a CHIRALPAK® AD-H column, 21×250 mm, 5 micron, with the sample at a concentration of 100 mg/mL in methanol, and with a co-solvent of methanol to provide the title compound (803 mg). $[α]_D^{23.5}$+1.64° (c=1, CH$_3$OH), % ee=99.2%; retention time=1.158 minutes; stereochemistry confirmed by X-ray analysis.

Example 3B (7R)-2,2-difluoro-7-methyl-6,7-dihydro-2H-furo[2,3-f][1,3]benzodioxole-7-carboxylic acid Example 1E (2.18 g) was chromatographed by preparative supercritical fluid chromatography using a CHIRALPAK® AD-H column, 21×250 mm, 5 micron, with the sample at a concentration of 100 mg/mL in methanol, and with a co-solvent of methanol to provide the title compound (835 mg). $[α]_D^{23.7}$−2.43° (c=1, CH$_3$OH), % ee=94.7%; retention time=2.720 minutes, stereochemistry confirmed by X-ray analysis.

Example 3C tert-butyl 3-(6-{[(7S)-2,2-difluoro-7-methyl-6,7-dihydro-2H-furo[2,3-f][1,3]benzodioxole-7-carbonyl]amino}-3-methylpyridin-2-yl)benzoate A solution of the product from Example 3A (0.052 g, 0.2 mmol) in 0.5 mL dichloromethane was treated with N,N-dimethylformamide (0.025 mL, 0.320 mmol) and then dropwise with oxalyl chloride (0.077 mL, 0.880 mmol). The mixture was stirred at ambient temperature for 1 hour and then concentrated (rotary evaporator). An additional 0.5 mL dichloromethane was added, and the mixture was concentrated again. The addition/concentration procedure was repeated twice more. Then the residue was taken up in 0.5 mL dichloromethane and treated with pyridine (0.485 mL, 6.00 mmol) and tert-butyl 3-(6-amino-3-methylpyridin-2-yl) benzoate) (CAS [1083057-14-0], 0.057 g, 0.200 mmol). The reaction stirred at 60° C. overnight. The reaction mixture then was concentrated (rotary evaporator), and the residue was purified by reverse-phase preparative HPLC on a Waters Nova-Pak® HR C18 6 µm 60 Å Prep-Pak® cartridge column (40 mm×100 mm) and eluting with a gradient of 10% to 100% acetonitrile in 10 mM aqueous ammonium acetate over 12 minutes, at a flow rate of 70 mL/minute to yield the title compound (11 mg, 11%). $^1$H NMR (400 MHz, DMSO-$d_6$) δ ppm 10.14 (s, 1H), 8.06-7.87 (m, 3H), 7.84-7.70 (m, 2H), 7.69-7.54 (m, 2H), 7.03 (s, 1H), 5.10 (d, J=9.3 Hz, 1H), 4.40 (d, J=9.3 Hz, 1H), 2.24 (s, 3H), 1.70 (s, 3H), 1.56 (s, 9H); MS (ESI$^+$) m/z 525.1 (M+H)$^+$.

Example 4

3-(6-{[(7S)-2,2-difluoro-7-methyl-6,7-dihydro-2H-furo[2,3-f][1,3]benzodioxole-7-carbonyl]amino}-3-methylpyridin-2-yl)benzoic acid A solution of the compound from Example 3C (8 mg, 0.015 mmol) in dichloromethane (0.2 mL) was treated with trifluoroacetic acid (0.1 mL, 1.296 mmol), and the mixture was stirred at ambient temperature for 1.5 hours. The reaction mixture was concentrated (rotary evaporator), and then the residue was concentrated twice from acetonitrile. The residue was dried under vacuum (70° C.) to afford the title compound (6.3 mg, 88%). $^1$H NMR (500 MHz, DMSO-$d_6$) δ ppm 13.03 (br s, 1H), 10.14 (s, 1H), 8.11-7.88 (m, 3H), 7.81-7.71 (m, 2H), 7.68-7.53 (m, 2H), 7.02 (s, 1H), 5.09 (d, J=9.2 Hz, 1H), 4.41 (d, J=9.3 Hz, 1H), 2.26 (s, 3H), 1.70 (s, 3H).

Example 5 tert-butyl 3-(6-{[(7R)-2,2-difluoro-7-methyl-6,7-dihydro-2H-furo[2,3-f][1,3]benzodioxole-7-carbonyl]amino}-3-methylpyridin-2-yl)benzoate The product from Example 3B (54.5 mg, 0.211 mmol) was dissolved in dichloromethane (1 mL). Oxalyl chloride (80 µL) and N,N-dimethylformamide (25 µL) were added.

The reaction mixture was stirred at ambient temperature for 1 hour. The reaction mixture was concentrated. The resulting residue was dissolved in dichloromethane (1 mL) and concentrated two times. The residue was dissolved in dichloromethane (1 mL) and pyridine (0.5 mL). tert-Butyl 3-(6-amino-3-methylpyridin-2-yl)benzoate (CAS [1083057-14-0], 53.8, 0.189 mmol) was added, and the reaction mixture was stirred at 60° C. for 16 hours. The reaction mixture was concentrated and purified by reverse-phase preparative HPLC on a Waters Nova-Pak® HR C18 6 μm 60 Å Prep-Pak® cartridge column (40 mm×100 mm), eluting with a gradient of 10% to 100% acetonitrile in 10 mM aqueous ammonium acetate over 12 minutes, at a flow rate of 70 mL/minute to yield the title compound (50.8 mg, 51%). $^1$H NMR (400 MHz, DMSO-$d_6$) δ ppm 10.14 (s, 1H), 8.02 (t, J=1.7 Hz, 1H), 7.98-7.90 (m, 2H), 7.78 (dt, J=7.7, 1.5 Hz, 1H), 7.75 (d, J=8.5 Hz, 1H), 7.65 (s, 1H), 7.60 (t, J=7.7 Hz, 1H), 7.03 (s, 1H), 5.10 (d, J=9.3 Hz, 1H), 4.41 (d, J=9.3 Hz, 1H), 2.25 (s, 3H), 1.71 (s, 3H), 1.56 (s, 9H); MS (ESI+) m/z 525.0 (M+H)$^+$.

Example 6

3-(6-{[(7R)-2,2-difluoro-7-methyl-6,7-dihydro-2H-furo[2,3-f][1,3]benzodioxole-7-carbonyl]amino}-3-methylpyridin-2-yl)benzoic acid The product from Example 5 (40.7 mg, 0.078 mmol) was dissolved in dichloromethane (1 mL). Trifluoroacetic acid (0.5 mL, 6.49 mmol) was added, and the reaction mixture was stirred at ambient temperature for 5 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (45.2 mg, 100%) as the trifluoroacetate salt. $^1$H NMR (501 MHz, DMSO-$d_6$) δ ppm 10.15 (s, 1H), 8.07 (t, J=1.7 Hz, 1H), 8.00 (dt, J=7.8, 1.5 Hz, 1H), 7.92 (d, J=8.4 Hz, 1H), 7.79 (dt, J=7.7, 1.5 Hz, 1H), 7.75 (d, J=8.5 Hz, 1H), 7.65-7.57 (m, 2H), 7.02 (s, 1H), 5.10 (d, J=9.3 Hz, 1H), 4.41 (d, J=9.3 Hz, 1H), 2.26 (s, 3H), 1.71 (s, 3H); MS (ESI+) m/z 469.1 (M+H)$^+$.

Example 7 methyl (3R)-1-{6-[(2,2-difluoro-7-methyl-6,7-dihydro-2H-furo[2,3-f][1,3]benzodioxole-7-carbonyl)amino]pyridin-2-yl}pyrrolidine-3-carboxylate Example 7A methyl (3R)-1-(6-nitropyridin-2-yl)pyrrolidine-3-carboxylate A mixture of (R)-methyl pyrrolidine-3-carboxylate, hydrochloric acid (204 mg, 1.232 mmol), 2-bromo-6-nitropyridine (250 mg, 1.232 mmol) and triethylamine (0.687 mL, 4.93 mmol) in tetrahydrofuran (2 mL) was treated with 2 drops water and stirred at ambient temperature for 72 hours. The mixture was concentrated, and the resulting oil was partitioned between water and dichloromethane. The organic fraction was concentrated, and the crude residue was purified using a 24 g silica gel cartridge with a gradient of 0-70% ethyl acetate/heptanes over a period of 20 minutes to give the title compound (145 mg, 0.577 mmol, 46.9% yield). $^1$H NMR (501 MHz, DMSO-$d_6$) δ ppm 7.87-7.81 (m, 1H), 7.41 (d, J=7.5 Hz, 1H), 6.93 (d, J=8.4 Hz, 1H), 3.72 (dd, J=10.8, 7.9 Hz, 1H), 3.66 (s, 3H), 3.63 (dd, J=10.8, 6.3 Hz, 1H), 3.58-3.44 (m, 2H), 3.37-3.33 (m, 1H), 2.27 (dtd, J=12.8, 7.3, 5.4 Hz, 1H), 2.18 (dq, J=12.5, 7.4 Hz, 1H); MS (ESI+) m/z 252 (M+H)$^+$.

Example 7B methyl (3R)-1-(6-aminopyridin-2-yl)pyrrolidine-3-carboxylate

Example 7A (141.3 mg, 0.562 mmol) in methanol (1.8 mL) was added to 5% palladium on carbon (wet JM#9) (29.1 mg, 0.273 mmol) in a 4 mL pressure bottle. The mixture was stirred under 30 psi of hydrogen at 40° C. for 1 hour. The mixture was filtered through a polypropylene membrane, and the filtrate was concentrated. The residue was azeotroped with toluene (2×5 mL) to give the title compound (103 mg, 0.466 mmol, 81% yield). $^1$H NMR (400 MHz, DMSO-$d_6$) δ ppm 7.11 (t, J=7.8 Hz, 1H), 5.69 (d, J=7.8 Hz, 1H), 5.57 (d, J=7.8 Hz, 1H), 5.43 (s, 2H), 3.64 (s, 3H), 3.56 (dd, J=10.4, 8.0 Hz, 1H), 3.47 (dd, J=10.5, 6.3 Hz, 1H), 3.37 (ddd, J=9.9, 7.8, 5.3 Hz, 1H), 3.30-3.26 (m, 1H), 3.21 (qd, J=7.6, 6.3 Hz, 1H), 2.22-2.04 (m, 2H); MS (ESI+) m/z 222 (M+H)$^+$.

Example 7C methyl (3R)-1-{6-[(2,2-difluoro-7-methyl-6,7-dihydro-2H-furo[2,3-f][1,3]benzodioxole-7-carbonyl)amino]pyridin-2-yl}pyrrolidine-3-carboxylate The product from Example 1E (59.2, 0.229 mmol) was dissolved in dichloromethane (1 mL). Oxalyl chloride (80 μL) and N,N-dimethylformamide (25 μL) were added. The reaction mixture was stirred at ambient temperature for 1 hour, and concentrated. The resulting residue was dissolved in dichloromethane (1 mL) and concentrated two times. The residue was dissolved in dichloromethane (1 mL) and pyridine (0.5 mL). The product of Example 7B (48.7 mg, 0.220 mmol) was added, and the reaction mixture was stirred at 60° C. for 17 hours, and concentrated. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (79.6 mg, 78%). $^1$H NMR (400 MHz, DMSO-$d_6$) δ ppm 9.39 (s, 1H), 7.61 (d, J=1.9 Hz, 1H), 7.49 (t, J=8.0 Hz, 1H), 7.20 (d, J=7.8 Hz, 1H), 7.04 (s, 1H), 6.23 (d, J=8.2 Hz, 1H), 5.06 (dd, J=9.4, 2.0 Hz, 1H), 4.42 (dd, J=9.4, 1.1 Hz, 1H), 3.73-3.62 (m, 4H), 3.57 (ddd, J=10.7, 6.4, 2.2 Hz, 1H), 3.47 (dddd, J=10.2, 7.7, 5.2, 2.2 Hz, 1H), 3.39 (dtd, J=10.1, 7.2, 2.8 Hz, 1H), 3.33-3.21 (m, 1H), 2.30-2.08 (m, 2H), 1.69 (s, 3H); MS (ESI+) m/z 462.2 (M+H)$^+$.

Example 8

(3R)-1-{6-[(2,2-difluoro-7-methyl-6,7-dihydro-2H-furo[2,3-f][1,3]benzodioxole-7-carbonyl)amino]pyridin-2-yl}pyrrolidine-3-carboxylic acid The product of example 7C (72.2 mg, 0.156 mmol) and potassium trimethylsilanolate (49.0 mg, 90% purity, 0.344 mmol) were dissolved in tetrahydrofuran (1 mL) and stirred at ambient temperature for 2 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield 58.7 mg (67%) of the title compound as the trifluoroacetate salt. $^1$H NMR (400 MHz, DMSO-d$_6$) δ ppm 9.48 (s, 1H), 7.60 (d, J=1.6 Hz, 1H), 7.52 (t, J=8.0 Hz, 1H), 7.17 (d, J=7.8 Hz, 1H), 7.05 (s, 1H), 6.27 (d, J=8.3 Hz, 1H), 5.06 (d, J=9.4 Hz, 1H), 4.42 (d, J=9.4 Hz, 1H), 3.62 (m 2H), 3.53-3.29 (m, 2H), 3.21-3.14 (m, 1H) 2.28-2.07 (m, 2H), 1.68 (s, 3H). MS (ESI+) m/z 448 (M+H)$^+$.

Example 9

(3R)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylic acid Example 9A methyl (3R)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylate The product from Example 3B (28.4 mg, 0.110 mmol) was dissolved in dichloromethane (1 mL). Oxalyl chloride (40 μL) and N,N-dimethylformamide (25 μL) were added. The reaction was stirred at ambient temperature for 1 hour. The reaction mixture was concentrated, and the residue was dissolved in dichloromethane (1 mL) and concentrated two times. The residue was then dissolved in dichloromethane (1 mL) and pyridine (0.5 mL). The product of Example 7B (35.7 mg, 0.161 mmol) was added, and the reaction mixture was stirred at 60° C. for 15 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (20.7 mg, 41%). $^1$H NMR (501 MHz, DMSO-d$_6$) δ ppm 9.43 (s, 1H), 7.61 (s, 1H), 7.50 (t, J=8.0 Hz, 1H), 7.19 (d, J=7.7 Hz, 1H), 7.05 (s, 1H), 6.25 (d, J=8.2 Hz, 1H), 5.06 (d, J=9.3 Hz, 1H), 4.42 (d, J=9.4 Hz, 1H), 3.72-3.64 (m, 4H), 3.57 (dd, J=10.6, 6.5 Hz, 1H), 3.48 (ddd, J=9.8, 7.9, 5.2 Hz, 1H), 3.39 (dt, J=9.9, 7.2 Hz, 1H), 3.32-3.24 (m, 1H), 2.30-2.07 (m, 2H), 1.69 (s, 3H); MS (ESI+) m/z 462.2 (M+H)$^+$.

Example 9B (3R)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylic acid The product of Example 9A (19.1 mg, 0.041 mmol) and potassium trimethylsilanolate (20.2 mg, 90% purity, 0.142 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield 18.9 mg (81%) of the title compound as the trifluoroacetate salt. $^1$H NMR (400 MHz, DMSO-d$_6$) δ ppm 9.41 (s, 1H), 7.61 (s, 1H), 7.50 (t, J=8.0 Hz, 1H), 7.18 (d, J=7.7 Hz, 1H), 7.05 (s, 1H), 6.24 (d, J=8.2 Hz, 1H), 5.06 (d, J=9.3 Hz, 1H), 4.42 (d, J=9.3 Hz, 1H), 3.70-3.53 (m, 2H), 3.53-3.31 (m, 2H), 3.23-3.09 (m, 1H), 2.27-2.06 (m, 2H), 1.68 (s, 3H); MS (ESI+) m/z 448 (M+H)$^+$.

Example 10 methyl 3-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoate Example 10A 7-methoxy-4H-1-benzopyran-4-one 1-(2-Hydroxy-4-methoxyphenyl)ethanone (47 g, 283 mmol) was dissolved in N,N-dimethylformamide dimethyl acetal (47 mL, 351 mmol), and the solution was heated to >100° C. in a sand bath for 10 minutes, at which point a solid mass had formed. The flask was cooled to ambient temperature, and 200 mL of heptanes were added. The solids were broken up with a spatula and collected by filtration with a frilled funnel. The solid material was crushed with a pestle and then washed with heptanes. The solid was then dried on the filter to give about 60 g of the crude intermediate. This intermediate was dissolved in dichloromethane (1 L) and stirred with 150 mL of concentrated HCl at 40° C. for 30 minutes. The flask was cooled to ambient temperature, and about 100 mL of water was added. The layers were separated, and the aqueous layer was extracted with dichloromethane (2×100 mL). The combined organic extracts were washed with saturated sodium bicarbonate (100 mL) and brine (100 mL) and dried over sodium sulfate. The mixture was filtered, and the filtrate was concentrated in vacuo to give a solid. The solid was then precipitated from 500 mL of 1:1 cyclopentyl methyl ether:heptanes to give the title compound (35 g, 70% yield). $^1$H NMR (400 MHz, CDCl$_3$) δ ppm 8.11 (d, J=8.9 Hz, 1H), 7.77 (d, J=6.0 Hz, 1H), 6.97 (dd, J=8.9, 2.4 Hz, 1H), 6.84 (d, J=2.4 Hz, 1H), 6.28 (d, J=6.0 Hz, 1H), 3.90 (s, 3H); MS(ESI+) m/z 176.9 (M+H)$^+$.

Example 10B methyl 3-[(2R)-7-methoxy-4-oxo-3,4-dihydro-2H-1-benzopyran-2-yl]benzoate A 4 mL vial was charged with bis(2,2,2-trifluoroacetoxy)palladium (9.44 mg, 0.028 mmol), (S)-4-(tert-butyl)-2-(pyridin-2-yl)-4,5-dihydrooxazole (6.96 mg, 0.034 mmol), ammonium hexafluorophosphate(V) (27.8 mg, 0.170 mmol), and 3-methoxycarbonylphenylboronic acid (204 mg, 1.135 mmol), and the mixture was stirred in dichloroethane (1.0 mL) for 5 minutes. To this suspension was added Example 10A (100 mg, 0.568 mmol) and water (0.051 mL, 2.84 mmol), and the sides of the vial were washed with more dichloroethane (1.0 mL). The vial was capped and the mixture stirred at 60° C. overnight. The mixture was filtered through a plug of silica gel eluted with dichloromethane and then ethyl acetate. The filtrate was concentrated, and the crude material was chromatographed using a 12 g silica gel cartridge with a gradient of 5-50% ethyl acetate/heptanes over 20 minutes to give the title compound (133 mg, 0.426 mmol, 75% yield). $^1$H NMR (400 MHz, DMSO-$d_6$) δ ppm 8.15 (t, J=1.8 Hz, 1H), 7.98 (dt, J=7.8, 1.4 Hz, 1H), 7.84 (dt, J=7.9, 1.5 Hz, 1H), 7.74 (d, J=8.5 Hz, 1H), 7.61 (t, J=7.8 Hz, 1H), 6.69 (d, J=8.6 Hz, 2H), 5.77 (dd, J=12.9, 2.9 Hz, 1H), 3.88 (s, 3H), 3.83 (s, 3H), 3.17 (dd, J=16.8, 13.0 Hz, 1H), 2.80 (dd, J=16.8, 3.0 Hz, 1H); MS (ESI+) m/z 313 (M+H)$^+$.

Example 10C methyl 3-[(2R)-7-methoxy-4-(methoxyimino)-3,4-dihydro-2H-1-benzopyran-2-yl]benzoate Example 10B (100 mg, 0.320 mmol) and O-methylhydroxylamine hydrochloride (29.4 mg, 0.352 mmol) were stirred in pyridine (640 μL) at 60° C. overnight. An additional 0.3 equivalents (7 mg) of O-methylhydroxylamine hydrochloride was added with continued heating at 60° C. for 12 hours. The mixture was concentrated, and the residue was diluted with ethyl acetate. The ethyl acetate mixture was washed sequentially with saturated aqueous sodium bicarbonate and saturated aqueous ammonium chloride. The organic fraction was concentrated, and the crude material was purified using a 12 g silica gel cartridge eluting with 5-20% ethyl acetate/heptanes over 20 minutes to give the title compound (107 mg, 0.313 mmol). $^1$H NMR (400 MHz, CDCl$_3$) δ ppm 8.15 (t, J=1.9 Hz, 1H), 8.03 (dt, J=7.7, 1.5 Hz, 1H), 7.84 (d, J=8.8 Hz, 1H), 7.77-7.63 (m, 1H), 7.49 (t, J=7.7 Hz, 1H), 6.59 (dd, J=8.8, 2.6 Hz, 1H), 6.50 (d, J=2.5 Hz, 1H), 5.12 (dd, J=12.5, 3.1 Hz, 1H), 3.96 (s, 3H), 3.94 (s, 3H), 3.80 (s, 3H), 3.48 (dd, J=17.2, 3.1 Hz, 1H), 2.65 (dd, J=17.1, 12.5 Hz, 1H); MS (ESI+) m/z 342.0 (M+H)$^+$.

Example 10D methyl 3-[(2R,4R)-4-amino-7-methoxy-3,4-dihydro-2H-1-benzopyran-2-yl]benzoate hydrochloride A 250-mL round bottom flask was charged with Example 10C (3.74 g, 10.96 mmol) and platinum (IV) oxide (0.343 g, 1.510 mmol) which were suspended in acetic acid (27.4 mL). The flask was purged with a balloon of H$_2$ and then was stirred under 1 atmosphere of H$_2$ for 7 hours. The reaction seemed to stall after 6 hours. An additional 5 mol % platinum (IV) oxide was added, and the reaction was run for an additional 1 hour at ambient temperature. Then the mixture was diluted with ethyl acetate, filtered, and concentrated. The residue was dissolved in tert-butyl methyl ether (35 mL) and treated with HCl (4 M in dioxane, 5.48 mL, 21.91 mmol) dropwise at ambient temperature. The resulting suspension was stirred vigorously at ambient temperature for 1 hour, and the resultant solid was collected by filtration and washed with tert-butyl methyl ether (2×5 mL). The solid was then heated at 50° C. for 1 hour in a mixture of 30 mL of tert-butyl methyl ether and 4 mL of dioxane. The solid was collected by filtration and dried in a vacuum oven at 40° C. to afford the title compound (2.27 g, 59%). $^1$H NMR (501 MHz, DMSO-$d_6$) δ ppm 8.69 (s, 3H), 8.05 (t, J=1.7 Hz, 1H), 7.98 (d, J=7.9 Hz, 1H), 7.74 (dt, J=7.7, 1.4 Hz, 1H), 7.62 (t, J=7.7 Hz, 1H), 7.58 (d, J=8.7 Hz, 1H), 6.65 (dd, J=8.7, 2.6 Hz, 1H), 6.53 (d, J=2.5 Hz, 1H), 5.35 (dd, J=11.8, 1.6 Hz, 1H), 4.73 (dd, J=11.1, 6.3 Hz, 1H), 3.87 (s, 3H), 3.73 (s, 3H), 2.55 (ddd, J=13.0, 6.4, 1.8 Hz, 1H), 2.01 (dt, J=13.0, 11.5 Hz, 1H); MS (ESI+) m/z 297 (M−NH$_3$+H)$^+$.

Example 10E methyl 3-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoate The products from Example 1E (51.7 mg, 0.200 mmol), Example 10D (58.6 mg, 0.168 mmol) and N-(3-dimethylaminopropyl)-N'-ethylcarbodiimide hydrochloride (72.3 mg, 0.377 mmol) were dissolved in N,N-dimethylformamide (0.5 mL) and pyridine (0.5 mL). The reaction mixture was stirred at 60° C. for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (90.4 mg, 97%). $^1$H NMR (400 MHz, DMSO-$d_6$) δ ppm 8.06 (dt, J=4.0, 1.7 Hz, 1H), 8.01-7.91 (m, 2H), 7.73 (ddt, J=6.7, 5.3, 1.5 Hz, 1H), 7.58 (td, J=7.7, 4.3 Hz, 1H), 7.44 (d, J=14.2 Hz, 1H), 7.01 (d, J=11.6 Hz, 1H), 6.77 (d, J=9.3 Hz, 1H), 6.58-6.42 (m, 2H), 5.46-5.29 (m, 2H), 5.02 (dd, J=11.5, 9.0 Hz, 1H), 4.33 (dd, J=9.0, 2.9 Hz, 1H), 3.88 (d, J=1.9 Hz, 3H), 3.71 (d, J=5.5 Hz, 3H), 2.27-2.09 (m, 2H), 1.57 (d, J=5.1 Hz, 3H); MS (ESI+) m/z 554 (M+H)$^+$.

Example 11

3-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoic acid The product of Example 10E (80.2 mg, 0.149 mmol) and potassium trimethylsilanolate (48.8 mg, 90% purity, 0.312 mmol) were dissolved in tetrahydrofuran (1 mL), and the mixture was stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (69.0 mg, 86%). $^1$H NMR (500 MHz, DMSO-$d_6$) δ ppm 13.05 (s, 1H), 8.05 (dt, J=5.3, 1.7 Hz, 1H), 8.01-7.90 (m, 2H), 7.73-7.66 (m, 1H), 7.55 (td, J=7.7, 5.3 Hz, 1H), 7.44 (d, J=17.1 Hz, 1H), 7.06-6.98 (m, 1H), 6.80-6.73 (m, 1H), 6.57-6.42 (m, 2H), 5.38 (dddd, J=17.7, 15.2, 7.1, 3.9 Hz, 2H), 5.02 (dd, J=13.3, 9.0 Hz, 1H), 4.33 (dd, J=9.0, 3.8 Hz, 1H), 3.71 (d, J=6.7 Hz, 3H), 2.29-1.99 (m, 2H), 1.57 (d, J=5.9 Hz, 3H); MS (ESI−) m/z 538.1 (M−H)$^-$.

Example 12 methyl 3-[(2R,4R)-4-{[7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate A mixture of the product of Example 10D (0.070 g, 0.2 mmol) and the product of Example 3A (0.052 g, 0.2 mmol)

in N,N-dimethylformamide (0.5 mL) and pyridine (0.5 mL) was treated with N-(3-dimethylaminopropyl)-N'-ethylcarbodiimide hydrochloride (0.077 g, 0.400 mmol), and the reaction mixture was stirred at ambient temperature overnight. The reaction mixture was concentrated (rotary evaporated), and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to give the title compound (34 mg, 31%). $^1$H NMR (400 MHz, DMSO-d$_6$) δ ppm 8.11-8.02 (m, 1H), 7.95 (ddd, J=8.8, 4.0, 2.5 Hz, 2H), 7.74 (dt, J=7.9, 1.5 Hz, 1H), 7.58 (t, J=7.7 Hz, 1H), 7.41 (s, 1H), 7.02 (s, 1H), 6.82-6.71 (m, 1H), 6.51-6.39 (m, 2H), 5.47-5.28 (m, 2H), 5.00 (d, J=8.9 Hz, 1H), 4.33 (d, J=9.0 Hz, 1H), 3.88 (s, 3H), 3.70 (s, 3H), 2.20 (m, 1H), 2.11 (m, 1H), 1.56 (s, 3H); MS (ESI$^-$) m/z 552.1 (M−H)$^-$.

Example 13

3-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid A solution of the compound from Example 12 (0.030 g, 0.054 mmol) in tetrahydrofuran (0.6 mL) was treated with potassium trimethylsilanoate (0.015 g, 0.119 mmol), and the mixture was stirred overnight at ambient temperature. After this time, the reaction mixture was diluted with 2 mL dichloromethane and treated with 1 mL of 1 N HCl. The mixture was stirred vigorously for 30 minutes and was then diluted with 10 mL ethyl acetate. The phases were separated, and the organic layer was washed with water (5 mL) and brine (5 mL), dried over sodium sulfate, filtered, and concentrated (rotary evaporator). The crude material was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to afford the title compound (17 mg, 58%). $^1$H NMR (400 MHz, CDCl$_3$) δ ppm 8.19 (d, J=1.7 Hz, 1H), 8.15-8.00 (m, 1H), 7.68 (d, J=7.6 Hz, 1H), 7.51 (t, J=7.7 Hz, 1H), 6.91 (d, J=8.5 Hz, 1H), 6.78 (s, 1H), 6.68-6.41 (m, 3H), 5.65-5.38 (m, 2H), 5.28 (dd, J=11.1, 1.8 Hz, 1H), 4.95 (d, J=9.2 Hz, 1H), 4.35 (d, J=9.2 Hz, 1H), 3.76 (s, 3H), 2.57 (ddd, J=13.1, 5.9, 2.0 Hz, 1H), 1.85 (m, 1H), 1.60 (s, 3H); MS (ESI$^-$) m/z 538.1 (M−H)$^-$.

Example 14

3-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid Example 14A methyl 3-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate The product from Example 3B (26.9, 0.104 mmol), the product from Example 10D (37.5 mg, 0.107 mmol) and N-(3-dimethylaminopropyl)-N'-ethylcarbodiimide hydrochloride (48.1 mg, 0.251 mmol) were dissolved in N,N-dimethylformamide (0.5 mL) and pyridine (0.5 mL). The reaction mixture was stirred at 60° C. for 7 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (40.1 mg, 70%). $^1$H NMR (400 MHz, DMSO-d$_6$) δ ppm 8.06 (t, J=1.7 Hz, 1H), 8.01-7.90 (m, 2H), 7.73 (dt, J=7.8, 1.5 Hz, 1H), 7.57 (t, J=7.7 Hz, 1H), 7.45 (s, 1H), 7.03 (dd, J=8.5, 1.0 Hz, 1H), 6.99 (s, 1H), 6.55 (dd, J=8.6, 2.6 Hz, 1H), 6.47 (d, J=2.5 Hz, 1H), 5.47-5.28 (m, 2H), 5.03 (d, J=9.0 Hz, 1H), 4.33 (d, J=9.0 Hz, 1H), 3.87 (s, 3H), 3.72 (s, 3H), 2.22-2.01 (m, 2H), 1.58 (s, 3H).); MS (ESI−) m/z 552 (M−H)$^-$.

Example 14B

3-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid The product of example 14A (37.0 mg, 0.067 mmol) and potassium trimethylsilanolate (24.4 mg, 90% purity, 0.171 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (23.7 mg, 66%). $^1$H NMR (400 MHz, DMSO-d$_6$) δ ppm 13.02 (s, 1H), 8.05 (t, J=1.8 Hz, 1H), 7.98 (d, J=8.7 Hz, 1H), 7.92 (dt, J=7.7, 1.4 Hz, 1H), 7.69 (dt, J=7.8, 1.5 Hz, 1H), 7.54 (t, J=7.7 Hz, 1H), 7.45 (s, 1H), 7.03 (d, J=8.4 Hz, 1H), 6.99 (s, 1H), 6.54 (dd, J=8.6, 2.6 Hz, 1H), 6.47 (d, J=2.5 Hz, 1H), 5.45-5.24 (m, 2H), 5.03 (d, J=9.0 Hz, 1H), 4.34 (d, J=9.0 Hz, 1H), 3.72 (s, 3H), 2.21-2.07 (m, 2H), 1.58 (s, 3H); MS (ESI−) m/z 538.1 (M−H)$^-$.

Example 15 methyl 4-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoate Example 15A methyl 4-[(2R)-7-methoxy-4-oxo-3,4-dihydro-2H-1-benzopyran-2-yl]benzoate A 250-mL round-bottomed flask was charged with (4-(methoxycarbonyl)phenyl)boronic acid (30.6 g, 170 mmol), ammonium hexafluorophosphate(V) (4.16 g, 25.5 mmol), bis(2,2,2-trifluoroacetoxy)palladium (2.123 g, 6.39 mmol), and (S)-4-(tert-butyl)-2-(pyridin-2-yl)-4,5-dihydrooxazole (1.565 g, 7.66 mmol), and then 1,2-dichloroethane (85 mL)

was added. The resulting suspension was stirred at ambient temperature for 10 minutes, at which point Example 10A (15 g, 85.0 mmol) was added, followed by water (7.67 g, 426 mmol) and an additional 85 mL of 1,2-dichloroethane to rinse the sides of the flask. The reaction was heated at 60° C. in a sand bath (internal temperature) for 36 hours. The flask was cooled to room temperature, and the suspension was filtered through a 1-inch pad of silica, eluted with dichloromethane. The filtrates were concentrated to give a crude solid. tert-Butyl methyl ether (100 mL) and heptanes (100 mL) were added, and the solids were broken up with a spatula. The resulting suspension was heated at 60° C. for 1 hour while stirring vigorously. The mixture was then cooled to ambient temperature, and the resulting solid was collected via filtration through a fitted funnel to give 10.54 g of the title compound (39% yield). $^1$H NMR (400 MHz, CDCl$_3$) δ ppm 8.10 (d, J=8.3 Hz, 2H), 7.87 (d, J=8.9 Hz, 1H), 7.56 (d, J=8.3 Hz, 2H), 6.64 (dd, J=8.8, 2.3 Hz, 1H), 6.52 (d, J=2.4 Hz, 1H), 5.53 (dd, J=13.0, 3.2 Hz, 1H), 3.94 (s, 3H), 3.85 (s, 3H), 2.99 (dd, J=16.9, 13.0 Hz, 1H), 2.86 (dd, J=16.8, 3.2 Hz, 1H); MS (ESI+) m/z 312.8 (M+H)$^+$.

Example 15B methyl 4-{(2R)-4-[(benzyloxy)imino]-7-methoxy-3,4-dihydro-2H-1-benzopyran-2-yl}benzoate Example 15A (2 g, 6.40 mmol) was dissolved in 15 mL of dry pyridine. O-Benzylhydroxylamine hydrochloride (1.073 g, 6.72 mmol) was added, and the solution was heated at 50° C. for 16 hours. The reaction was cooled to ambient temperature and concentrated. The residue was partitioned between tert-butyl methyl ether and saturated aqueous ammonium chloride. The organic extracts were concentrated in vacuo and purified via flash chromatography, eluting with 10-40% ethyl acetate/heptanes over 20 minutes on an 80 g silica gel column to give the title compound (10:1 mixture of E and Z oximes, 2.57 g, 96% yield). Analytical data for the major isomer: $^1$H NMR (501 MHz, CDCl$_3$) δ ppm 8.06 (d, J=8.3 Hz, 2H), 7.84 (d, J=8.8 Hz, 1H), 7.54-7.46 (m, 2H), 7.40-7.28 (m, 5H), 6.57 (dd, J=8.8, 2.5 Hz, 1H), 6.48 (d, J=2.5 Hz, 1H), 5.19 (d, J=2.0 Hz, 2H), 5.11 (dd, J=12.3, 3.2 Hz, 1H), 3.92 (s, 3H), 3.78 (s, 3H), 3.48 (dd, J=17.2, 3.2 Hz, 1H), 2.67 (dd, J=17.2, 12.2 Hz, 1H); MS (ESI+) m/z 418.1 (M+H)$^+$.

Example 15C methyl 4-[(2R,4R)-4-amino-7-methoxy-3,4-dihydro-2H-1-benzopyran-2-yl]benzoate Acetic acid (300 mL) was added to Example 15B (20 g 47.9 mmol) and 5% Pt/C wet (1.5 g wet weight, 58.9% water, 0.884 g or 4.42% dry basis) in a 300-mL stainless steel reactor. The headspace was inerted with argon and then pressurized to 30 psig with hydrogen. The mixture was shaken at ambient temperature under 30 psig of hydrogen for 18 hours. The reactor was vented and the reaction mixture was filtered through 0.45 μm GHP Acrodisc® membrane. The filtrate was concentrated in vacuo to give 60 g of crude material. The crude material was heated at 70° C. in 250 mL of 4:1 tert-butyl methyl ether:heptanes until a clear solution resulted. HCl (3 M in cyclopentyl methyl ether, 47.9 mL, 144 mmol) was added dropwise at the same temperature, and a solid precipitated from the reaction mixture. The flask was allowed to cool to ambient temperature over 1 hour, and the resulting precipitate was collected by filtration. The solid was washed with tert-butyl methyl ether (2×100 mL) and dried in the funnel. The resulting solid was further heated at 70° C. in toluene (20 mL) for 30 minutes to remove additional impurities. After cooling to ambient temperature, the resulting solid was collected by filtration, washed with 75 mL of toluene and 100 mL of heptanes, and then dried to constant weight to give 19.8 g of the title compound (79% yield) as the hydrochloride salt. $^1$H NMR (400 MHz, DMSO-d$_6$) δ ppm 8.67 (s, 3H), 8.08-7.95 (m, 2H), 7.58 (dd, J=8.4, 6.1 Hz, 3H), 6.62 (dd, J=8.7, 2.6 Hz, 1H), 6.50 (d, J=2.5 Hz, 1H), 5.33 (dd, J=11.8, 1.6 Hz, 1H), 4.70 (dd, J=11.1, 6.2 Hz, 1H), 3.84 (s, 3H), 3.70 (s, 3H), 2.60-2.50 (m, 1H), 1.96 (q, J=11.8 Hz, 1H); MS (ESI+) m/z 297.1 (M−NH$_3$+H)$^+$.

Example 15D methyl 4-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoate The product from Example 1E (50.8, 0.197 mmol), the product from Example 15C (69.2 mg, 0.198 mmol) and N-(3-dimethylaminopropyl)-N'-ethylcarbodiimide hydrochloride (73.3 mg, 0.382 mmol) were dissolved in N,N-dimethylformamide (0.5 mL) and pyridine (0.5 mL). The reaction was stirred at 60° C. for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (73.4 mg, 67%). $^1$H NMR (400 MHz, DMSO-d$_6$) δ ppm 8.05-7.93 (m, 3H), 7.65-7.57 (m, 2H), 7.44 (d, J=14.5 Hz, 1H), 7.00 (d, J=11.3 Hz, 1H), 6.80-6.72 (m, 1H), 6.58-6.42 (m, 2H), 5.46-5.28 (m, 2H), 5.02 (dd, J=15.2, 9.0 Hz, 1H), 4.33 (dd, J=9.0, 2.6 Hz, 1H), 3.87 (d, J=1.5 Hz, 3H), 3.71 (d, J=5.5 Hz, 3H), 2.20 (dddd, J=23.6, 13.1, 6.2, 2.0 Hz, 1H), 2.11-1.98 (m, 1H), 1.57 (d, J=5.6 Hz, 3H); MS (ESI−) m/z 552 (M−H)$^−$.

Example 16

4-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoic acid The product of Example 15D (65.8 mg, 0.119 mmol) and potassium trimethylsilanolate (34.5 mg, 90% purity, 0.242 mmol) were dissolved in tetrahydrofuran (1 mL) and stirred at ambient temperature for 2 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (43.6 mg, 68%). $^1$H NMR (400 MHz, DMSO-d$_6$) δ ppm 12.96 (s, 1H), 8.04-7.93 (m, 3H), 7.61-7.55 (m, 2H), 7.44 (d, J=14.5 Hz, 1H), 7.00 (d, J=11.1 Hz, 1H), 6.80-6.73 (m, 1H), 6.57-6.42 (m, 2H), 5.38 (tdd, J=15.0, 6.4, 4.0 Hz, 2H), 5.02 (dd, J=15.0, 9.0 Hz, 1H), 4.33 (dd, J=9.1, 2.6 Hz, 1H), 3.71 (d, J=5.4 Hz, 3H), 2.20 (dddd, J=24.0, 13.0, 6.0, 2.0 Hz, 1H), 2.07 (s, 1H), 1.57 (d, J=5.6 Hz, 3H); MS (ESI–) m/z 538.1 (M–H)⁻.

Example 17 methyl 4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate To a solution of the product from Example 15C (0.070 g, 0.2 mmol) and the product of Example 3A (0.052 g, 0.200 mmol) in 0.5 mL N,N-dimethylformamide and 0.5 mL pyridine was added N-(3-dimethylaminopropyl)-N'-ethylcarbodiimide hydrochloride (0.077 g, 0.400 mmol), and the reaction mixture was stirred at 60° C. overnight. The reaction mixture was concentrated (rotary evaporator), and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to give the title compound (62 mg, 56%). ¹H NMR (500 MHz, DMSO-d₆) δ ppm 8.06-7.92 (m, 3H), 7.66-7.57 (m, 2H), 7.42 (s, 1H), 7.02 (s, 1H), 6.81-6.72 (m, 1H), 6.46 (d, J=7.1 Hz, 2H), 5.46-5.30 (m, 2H), 5.00 (d, J=8.9 Hz, 1H), 4.32 (d, J=8.9 Hz, 1H), 3.87 (s, 31), 3.70 (s, 3H), 2.23 (ddd, J=13.1, 6.3, 1.9 Hz, 1H), 2.06 (m, 1H), 1.56 (s, 3H); MS (ESI⁻) m/z 552.1 (M–H)⁻.

Example 18

4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid The product from Example 17 (0.050 g, 0.09 mmol) in tetrahydrofuran (0.9 mL) was treated with potassium trimethylsilanoate (0.025 g, 0.199 mmol), and the reaction was stirred at ambient temperature overnight. The mixture was diluted with 2 mL of dichloromethane and 1 mL of 1 N HCl, and stirred vigorously at ambient temperature for 30 minutes. It was then diluted with 10 mL of ethyl acetate and washed with 5 mL of water and 5 mL of brine. The organic layer was dried over sodium sulfate, filtered, and concentrated (rotary evaporator). The crude material was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to afford the title compound (31 mg, 64% yield). ¹H NMR (400 MHz, DMSO-d₆) δ ppm 12.97 (s, 1H), 7.98 (m, 3H), 7.67-7.53 (m, 2H), 7.42 (s, 1H), 7.02 (s, 1H), 6.82-6.71 (m, 1H), 6.50-6.39 (m, 2H), 5.38 (m, 2H), 5.00 (d, J=9.0 Hz, 1H), 4.32 (d, J=9.2 Hz, 1H), 3.70 (s, 3H), 2.29-2.16 (m, 1H), 2.06 (q, J=11.9 Hz, 1H), 1.56 (s, 3H); MS (ESI⁻) m/z 538.1 (M–H)⁻.

Example 19 methyl 4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate The product from Example 3B (50.4, 0.195 mmol), the product from Example 15C (74.1 mg, 0.212 mmol) and N-(3-dimethylaminopropyl)-N'-ethylcarbodiimide hydrochloride (77.1 mg, 0.402 mmol) were dissolved in N,N-dimethylformamide (0.5 mL) and pyridine (0.5 mL). The reaction mixture was stirred at 60° C. for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A, to yield the title compound (91.3 mg, 84%). ¹H NMR (400 MHz, DMSO-d₆) δ ppm 8.05-7.97 (m, 3H), 7.64-7.55 (m, 2H), 7.46 (s, 1H), 7.03 (d, J=8.6 Hz, 1H), 6.99 (s, 1H), 6.55 (dd, J=8.6, 2.6 Hz, 1H), 6.48 (d, J=2.5 Hz, 1H), 5.44-5.31 (m, 2H), 5.04 (d, J=8.9 Hz, 1H), 4.33 (d, J=8.9 Hz, 1H), 3.87 (s, 3H), 3.72 (s, 3H), 2.18 (ddd, J=12.9, 6.2, 2.1 Hz, 1H), 2.09-1.97 (m, 1H), 1.58 (s, 3H); MS (ESI–) m/z 552 (M–H)⁻.

Example 20

4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid The product of Example 19 (83.5 mg, 0.151 mmol) and potassium trimethylsilanolate (48.8 mg, 90% purity, 0.342 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (53.3 mg, 66%). ¹H NMR (400 MHz, DMSO-d₆) δ ppm 12.97 (s, 1H), 8.04-7.94 (m, 3H), 7.57 (d, J=8.3 Hz, 2H), 7.46 (s, 1H), 7.03 (d, J=8.6 Hz, 1H), 6.99 (s, 1H), 6.55 (dd, J=8.5, 2.5 Hz, 1H), 6.47 (d, J=2.5 Hz, 1H), 5.37 (ddt, J=15.3, 11.2, 4.0 Hz, 2H), 5.04 (d, J=9.0 Hz, 1H), 4.33 (d, J=9.0 Hz, 1H), 3.72 (s, 3H), 2.17 (ddd, J=13.0, 6.3, 2.1 Hz, 1H), 2.04 (q, J=12.0 Hz, 1H), 1.58 (s, 3H); MS (ESI–) m/z 538.1 (M–H)⁻.

Example 21

3-{(2R,4R)-4-[(2,2-difluoro-7-methyl-6,7-dihydro-2H-furo[2,3-f][1,3]benzodioxole-7-carbonyl)amino]-3,4-dihydro-2H-1-benzopyran-2-yl}benzoic acid Example 21A methyl 3-[(2R)-4-oxo-3,4-dihydro-2H-1-benzopyran-2-yl]benzoate A 20 mL vial was charged with bis(2,2,2-trifluoroacetoxy)palladium (56.9 mg, 0.171 mmol), (S)-4-(tert-butyl)-2-(pyridin-2-yl)-4,5-dihydrooxazole (41.9 mg, 0.205 mmol), ammonium hexafluorophosphate(V) (167 mg, 1.026 mmol), and 3-methoxycarbonylphenylboronic acid (1231 mg, 6.84 mmol). The mixture was stirred in dichloroethane (5 mL) for 5 minutes. To this suspension was added 4H-chromen-4-one (CAS 11013-97-1) (500 mg, 3.42 mmol) and water (0.308 mL, 17.11 mmol), and the sides of the vial were washed with more dichloroethane (5 mL). The vial was capped, and the mixture stirred at 60° C. for 16 hours. The mixture was filtered through a plug of silica gel and diatomaceous earth eluted with ethyl acetate. The filtrate was concentrated, and the crude material was chromatographed using a 40 g silica gel cartridge with a gradient of 5-50% ethyl acetate/heptanes over 40 minutes to give the title compound (329 mg, 1.165 mmol, 34.1% yield). $^1$H NMR (400 MHz, DMSO-$d_6$) δ ppm 8.16 (t, J=1.8 Hz, 1H), 7.98 (dt, J=7.7, 1.5 Hz, 1H), 7.84 (dt, J=7.9, 1.4 Hz, 1H), 7.81 (dd, J=7.8, 1.8 Hz, 1H), 7.65-7.58 (m, 2H), 7.17-7.10 (m, 2H), 5.80 (dd, J=13.1, 2.8 Hz, 1H), 3.88 (s, 3H), 3.28 (dd, J=16.8, 13.1 Hz, 1H), 2.88 (dd, J=16.8, 3.0 Hz, 1H); MS (ESI+) m/z 300 (M+NH$_4$)$^+$.

Example 21B methyl 3-[(2R)-4-(methoxyimino)-3,4-dihydro-2H-1-benzopyran-2-yl]benzoate Example 21A (13.35 g, 47.3 mmol) was treated with methoxylamine hydrochloride (11.85 g, 142 mmol) in pyridine (125 mL). The resulting suspension was heated to 60° C. for 30 minutes. The reaction mixture was concentrated in vacuo and partitioned between tert-butyl methyl ether and saturated ammonium chloride. The combined organic layers were washed with 1 M HCl, water, and brine sequentially, dried over sodium sulfate, filtered, and concentrated. Heptanes (100 mL) were added to the residue, and the mixture was heated to give a solution and then cooled. The precipitate was collected by filtration and washed with heptanes. The filtrate was concentrated, and the residue was purified via flash chromatography (40 g silica gel, 10-30% ethyl acetate/heptanes over 20 minutes) to provide additional material (2.4 g). Total yield of title compound was 13.9 g. $^1$H NMR (400 MHz, CDCl$_3$) δ ppm 8.15 (t, J=1.8 Hz, 1H), 8.03 (dt, J=7.7, 1.4 Hz, 1H), 7.94 (dd, J=8.2, 1.7 Hz, 1H), 7.68 (dt, J=7.9, 1.5 Hz, 1H), 7.49 (t, J=7.8 Hz, 1H), 7.29 (ddd, J=8.5, 7.3, 1.7 Hz, 1H), 7.02-6.95 (m, 2H), 5.12 (dd, J=12.5, 3.1 Hz, 1H), 3.99 (s, 3H), 3.94 (s, 3H), 3.50 (dd, J=17.2, 3.1 Hz, 1H), 2.68 (dd, J=17.2, 12.5 Hz, 1H); MS (ESI+) m/z 312 (M+H)$^+$.

Example 21C methyl 3-[(2R,4R)-4-amino-3,4-dihydro-2H-1-benzopyran-2-yl]benzoate

Methyl 3-[(2R)-4-(methoxyimino)-3,4-dihydro-2H-chromen-2-yl]benzoate (13.9 g, 44.6 mmol) was dissolved in 110 mL of glacial acetic acid in a 1 L round-bottomed flask, and platinum (IV) oxide (0.507 g, 2.232 mmol, 0.075 equivalent) was added. The flask was purged with a balloon of H$_2$, and then the mixture was stirred under 1 atmosphere of H$_2$ for 16 hours. Additional platinum (IV) oxide (0.507 g, 2.232 mmol, 0.05 equivalent) was added, and the reaction was continued (total 22 hours). The mixture was filtered through a fitted funnel, and the filtrate was concentrated at 50° C. in vacuo. The resulting crude material was dissolved in tert-butyl methyl ether (140 mL), and the mixture was stirred vigorously during the dropwise addition of a premixed solution of acetyl chloride (6.35 mL, 89 mmol) in methanol (18.06 mL, 446 mmol). The mixture was stirred at ambient temperature for 1 hour, and the solid was collected by filtration using a fitted funnel. The solid was washed with tert-butyl methyl ether (30 mL) and dried to constant weight to afford 8.6 g of the title compound (60% yield) as the hydrochloride salt. $^1$H NMR (400 MHz, DMSO-$d_6$) δ ppm 8.90 (s, 3H), 8.07 (s, 1H), 7.99 (d, J=7.8 Hz, 1H), 7.82-7.70 (m, 2H), 7.63 (t, J=7.7 Hz, 1H), 7.37-7.19 (m, 1H), 7.06 (td, J=7.5, 1.2 Hz, 1H), 7.01-6.87 (m, 1H), 5.54-5.35 (m, 1H), 4.83 (dd, J=11.3, 6.2 Hz, 1H), 3.89 (s, 3H), 2.62 (ddd, J=13.0, 6.3, 1.8 Hz, 1H), 2.07 (q, J=12.0 Hz, 1H); MS (ESI+) m/z 267 (M−NH$_3$+H)$^+$.

Example 21D methyl 3-{(2R,4R)-4-[(2,2-difluoro-7-methyl-6,7-dihydro-2H-furo[2,3-f][1,3]benzodioxole-7-carbonyl)amino]-3,4-dihydro-2H-1-benzopyran-2-yl}benzoate To a solution of Example 1E (0.0783 g, 0.303 mmol) in N,N-dimethylformamide (1.00 mL) was added N-[(dimethylamino)-1H-1,2,3-triazolo-[4,5-b]pyridin-1-ylmethylene]-N-methylmethanaminium hexafluorophosphate N-oxide (HATU, 0.173 g, 0.455 mmol), and the mixture was stirred at ambient temperature for 15 minutes. The product of Example 21C (0.097 g, 0.303 mmol) was added to the reaction mixture followed by addition of N,N-diisopropylethylamine (0.212 mL, 1.213 mmol). The mixture was stirred at ambient temperature for 1 hour. The reaction mixture was partitioned between ethyl acetate and water. The organic fraction was dried over anhydrous sodium sulfate, filtered, and concentrated in vacuo. The residue was purified by flash chromatography using a 24 g silica gel cartridge eluted with 0-75% tert-butyl methyl ether/heptanes to supply the title compound (0.121 gm, 76%). $^1$H NMR (501 MHz, CDCl$_3$) δ ppm 1.66 (d, J=25.2 Hz, 3H), 1.92 (dtd, J=13.3, 11.1, 7.8 Hz, 1H), 2.57 (dddd, J=13.3, 6.1, 3.0, 2.1 Hz, 1H), 3.96 (d, J=3.6 Hz, 3H), 4.37 (dd, J=21.2, 9.2 Hz, 1H), 4.91 (dd, J=74.1, 9.2 Hz, 1H), 5.22-5.36 (m, 1H), 5.44-5.57 (m, 1H), 5.67 (t, J=9.4 Hz, 1H), 6.65 (d, J=19.0 Hz, 1H), 6.86 (d, J=50.5 Hz, 1H), 6.94-7.06 (m, 2H), 7.24 (ddddd, J=8.1, 7.0, 6.1, 1.8, 0.8 Hz, 1H), 7.49 (dt, J=15.4, 7.8 Hz, 1H), 7.64 (dddd, J=12.3, 7.9, 2.3, 1.3 Hz, 1H), 8.03 (ddt, J=15.1, 7.8, 1.4 Hz, 1H), 8.12 (dt, J=11.2, 1.8 Hz, 1H); MS (ESI−) m/z 522 (M−H)$^-$.

Example 21E

3-{(2R,4R)-4-[(2,2-difluoro-7-methyl-6,7-dihydro-2H-furo[2,3-f][1,3]benzodioxole-7-carbonyl)amino]-3,4-dihydro-2H-1-benzopyran-2-yl}benzoic acid The product of Example 21D (0.118 g, 0.225 mmol) and potassium trimethylsilanolate (0.035 g, 0.270 mmol) were dissolved in tetrahydrofuran (3 mL) and stirred at 50° C. for 1 hour 15 minutes. The reaction mixture was partitioned between tert-butyl methyl ether and 1 N HCl. The organic fraction was separated, dried over anhydrous sodium sulfate, filtered, and concentrated in vacuo. The residue was purified by flash chromatography using a 24 g silica gel cartridge, eluted with 0-10% CH$_3$OH/CH$_2$Cl$_2$ to give the title compound (0.097 gm, 84%). $^1$H NMR (400 MHz, CDCl$_3$) δ ppm 1.68 (dd, J=19.8, 1.4 Hz, 2H), 1.92 (qd, J=11.3, 7.1 Hz, 1H), 2.61 (d, J=12.9 Hz, 1H), 3.53 (d, J=1.3 Hz, 0H), 4.38 (dd, J=17.0, 9.3 Hz, 1H), 4.92 (dd, J=60.6, 9.3 Hz, 1H), 5.33 (d, J=10.9 Hz, 1H), 5.56 (p, J=8.6, 8.1 Hz, 1H), 5.72 (t, J=8.4 Hz, 1H), 6.58-6.85 (m, 1H), 6.88-7.09 (m, 3H), 7.24 (d, J=7.0 Hz, 1H), 7.53 (dt, J=11.6, 7.6 Hz, 1H), 7.63-7.74 (m, 1H), 8.03-8.14 (m, 1H), 8.22 (d, J=9.4 Hz, 1H); MS (ESI−) m/z 508 (M−H)⁻.

Example 22

3-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid

Example 22A methyl 3-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoate The product from Example 3B (27.9, 0.108 mmol), the product from Example 21C (35.2 mg, 0.110 mmol) and N-(3-dimethylaminopropyl)-N'-ethylcarbodiimide hydrochloride (41.4 mg, 0.216 mmol) were dissolved in N,N-dimethylformamide (0.5 mL) and pyridine (0.5 mL). The reaction mixture was stirred at 60° C. for 6 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (37.3 mg, 66%). ¹H NMR (400 MHz, DMSO-d₆) δ ppm 8.09-8.01 (m, 2H), 7.95 (dt, J=7.8, 1.4 Hz, 1H), 7.73 (dt, J=7.7, 1.4 Hz, 1H), 7.58 (t, J=7.7 Hz, 1H), 7.46 (s, 1H), 7.24-7.11 (m, 2H), 7.00 (s, 1H), 6.95 (td, J=7.5, 1.2 Hz, 1H), 6.89 (dd, J=8.1, 1.2 Hz, 1H), 5.43 (qd, J=9.0, 7.7, 5.2 Hz, 2H), 5.04 (d, J=9.0 Hz, 1H), 4.35 (d, J=9.0 Hz, 1H), 3.87 (s, 3H), 2.24-2.04 (m, 2H), 1.59 (s, 3H).); MS (ESI−) m/z 522 (M−H)⁻.

Example 22B

3-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid The product of Example 22A (34.7 mg, 0.066 mmol) and potassium trimethylsilanolate (23.3 mg, 90% purity, 0.163 mmol) were dissolved in tetrahydrofuran (1 mL) and stirred at ambient temperature for 16 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (21.9 mg, 65%). ¹H NMR (400 MHz, DMSO-d₆) δ ppm 13.02 (s, 1H), 8.08-8.02 (m, 2H), 7.93 (dt, J=7.8, 1.5 Hz, 1H), 7.69 (dt, J=7.9, 1.5 Hz, 1H), 7.55 (t, J=7.7 Hz, 1H), 7.46 (s, 1H), 7.23-7.11 (m, 2H), 7.00 (s, 1H), 6.94 (t, J=7.5 Hz, 1H), 6.88 (d, J=8.2 Hz, 1H), 5.49-5.36 (m, 2H), 5.03 (d, J=9.0 Hz, 1H), 4.35 (d, J=9.1 Hz, 1H), 2.23-2.08 (m, 2H), 1.59 (s, 3H); MS (ESI−) m/z 508.1 (M−H)⁻.

Example 23

4-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid

Example 23A methyl 4-[(2R)-4-oxo-3,4-dihydro-2H-1-benzopyran-2-yl]benzoate

A mixture of bis(2,2,2-trifluoroacetoxy)palladium (0.341 g, 1.026 mmol), (S)-4-(tert-butyl)-2-(pyridin-2-yl)-4,5-dihydrooxazole (0.252 g, 1.232 mmol), ammonium hexafluorophosphate(V) (1.004 g, 6.16 mmol), methyl 4-(4,4,5,5-tetramethyl-1,3,2-dioxaborolan-2-yl)benzoate (4.04 g, 15.40 mmol) and dichloroethane (8 mL) in a 20 mL vial was stirred at room temperature for 5 minutes, followed by the addition of 4H-chromen-4-one (CAS 11013-97-1, 1.5 g, 10.26 mmol) and water (0.256 mL, 14.19 mmol). The vial was capped, and the mixture was stirred at 60° C. overnight. The mixture was filtered through a plug of diatomaceous earth eluted with ethyl acetate. The filtrate was washed with water, dried over MgSO₄, filtered, and concentrated in vacuo. The crude material was chromatographed using a 100 g silica gel cartridge eluted with a gradient of 5-40% ethyl acetate in heptane to yield the title compound (1.66 g, 57.3% yield). ¹H NMR (400 MHz, CDCl₃) δ ppm 8.16-8.06 (m, 2H), 7.94 (dd, J=8.0, 1.7 Hz, 1H), 7.62-7.47 (m, 3H), 7.14-7.02 (m, 2H), 5.56 (dd, J=13.1, 3.1 Hz, 1H), 3.94 (s, 3H), 3.13-2.86 (m, 2H); LC/MS (ESI+) 283 (M+1)⁺.

Example 23B methyl 4-[(2R)-4-(methoxyimino)-3,4-dihydro-2H-1-benzopyran-2-yl]benzoate A mixture of Example 23A (1.65 g, 5.85 mmol), sodium acetate (0.959 g, 11.69 mmol) and O-methylhydroxylamine, hydrochloric acid (0.976 g, 11.69 mmol) in methanol (20 mL) was stirred at 60° C. overnight. Volatiles were removed under reduced pressure, and the residue was dissolved in ethyl acetate and washed with water. The organic layer was dried over MgSO₄, filtered, and concentrated. The residue was washed with ether to provide the title compound (1.758 g, 97% yield). ¹H NMR (400 MHz, CDCl₃) δ ppm 8.16-8.04 (m, 2H), 7.93 (dd, J=8.2, 1.7 Hz, 1H), 7.62-7.47 (m, 2H), 7.32-7.26 (m, 1H), 7.01-6.95 (m, 2H), 5.13 (dd, J=12.4, 3.2 Hz, 1H), 3.99 (s, 3H), 3.93 (s, 3H), 3.48 (dd, J=17.2, 3.2 Hz, 1H), 2.66 (dd, J=17.2, 12.3 Hz, 1H); MS (ESI+) m/z=312 (M+H)⁺.

Example 23C methyl 4-[(2R,4R)-4-amino-3,4-dihydro-2H-1-benzopyran-2-yl]benzoate The product from Example 23B (1.75 g, 5.62 mmol) was treated with 5% platinum (0.05 equivalent) on carbon in acetic acid (10 mL). The reaction mixture was stirred for 24 hours at room temperature under hydrogen (1 atmosphere).

The reaction mixture was filtered through a pad of diatomaceous earth, and the filtrate was concentrated under reduced pressure. tert-Butyl methyl ether was added to the residue, followed by drop wise addition of 4 M HCl in tetrahydrofuran solution (2 mL). The mixture was stirred for 1 hour at room temperature. The precipitated solid was collected by filtration, washed with ether, and dried to provide the hydrochloride salt of the title compound (1.2 g, 66.8% yield). $^1$H NMR (400 MHz, CDCl$_3$) δ ppm 8.08 (d, J=7.9 Hz, 2H), 7.50 (dd, J=23.2, 7.8 Hz, 3H), 7.20 (t, J=7.8 Hz, 1H), 7.07-6.84 (m, 2H), 5.22 (d, J=11.4 Hz, 1H), 4.36 (dd, J=10.8, 5.8 Hz, 1H), 3.93 (s, 3H), 2.46 (dd, J=13.2, 5.8 Hz, 1H), 2.00-1.85 (m, 1H); MS (ESI+) m/z 267 (M−NH$_3$+H)$^+$.

Example 23D methyl 4-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoate The product from Example 3B (48.0 mg, 0.186 mmol), the product from Example 23C (62.5 mg, 0.195 mmol) and N-(3-dimethylaminopropyl)-N'-ethylcarbodiimide hydrochloride (77.8 mg, 0.406 mmol) were dissolved in N,N-dimethylformamide (0.5 mL) and pyridine (0.5 mL). The reaction mixture was stirred at 60° C. for 6 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (50.0 mg, 51.4%). $^1$H NMR (400 MHz, DMSO-d$_6$) δ ppm 8.08 (d, J=8.8 Hz, 1H), 8.04-7.96 (m, 2H), 7.64-7.58 (m, 2H), 7.46 (s, 1H), 7.20 (td, J=7.7, 1.7 Hz, 1H), 7.14 (dt, J=7.8, 1.4 Hz, 1H), 6.99 (s, 1H), 6.95 (td, J=7.5, 1.2 Hz, 1H), 6.89 (dd, J=8.2, 1.2 Hz, 1H), 5.50-5.38 (m, 2H), 5.05 (d, J=9.0 Hz, 1H), 4.34 (d, J=9.0 Hz, 1H), 3.87 (s, 3H), 2.20 (ddd, J=13.0, 6.2, 2.1 Hz, 1H), 2.07 (s, 1H), 1.59 (s, 3H); MS (ESI−) m/z 522 (M−H)$^−$.

Example 23E

4-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid The product of Example 23D (50.0 mg, 0.096 mmol) and potassium trimethylsilanolate (39.4 mg, 90% purity, 0.276 mmol) were dissolved in tetrahydrofuran (1 mL), and the mixture was stirred at ambient temperature for 2 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (28.0 mg, 58%). $^1$H NMR (400 MHz, DMSO-d$_6$) δ ppm 12.93 (s, 1H), 8.08 (d, J=8.8 Hz, 1H), 8.02-7.95 (m, 2H), 7.61-7.55 (m, 2H), 7.47 (s, 1H), 7.24-7.16 (m, 1H), 7.14 (d, J=7.7 Hz, 1H), 7.00 (s, 1H), 6.98-6.91 (m, 1H), 6.89 (d, J=8.2 Hz, 1H), 5.52-5.36 (m, 2H), 5.05 (d, J=9.0 Hz, 1H), 4.34 (d, J=8.9 Hz, 1H), 2.25-2.01 (m, 2H), 1.59 (s, 3H); MS (ESI−) m/z 508.1 (M−H)$^−$.

Example 24

N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide

Example 24A 3,6-dichloropyridazin-4-amine 3,4,6-Trichloropyridazine (25 g, 136 mmol) was added to 14.8 N ammonium hydroxide (200 mL) in a 500 mL stainless steel pressure bottle. The mixture was stirred for 16 hours at 75° C. The mixture was cooled to ambient temperature, and 17 g (76%) of the title compound was collected by filtration as a solid. $^1$H NMR (400 MHz, DMSO-d$_6$) δ ppm 7.16 (s, 2H), 6.82 (s, 1H); MS (ESI+) m/z 164 (M+H)$^+$.

Example 24B

N-(3,6-dichloropyridazin-4-yl)-2,2-dimethylpropanamide

Example 24A (10 g, 61.0 mmol, 1.0 equivalent) was suspended in 200 mL of dry tetrahydrofuran in a 1 L round bottomed flask, and the flask was cooled to an internal temperature of <5° C. in an ice-water bath. Sodium hydride (5.37 g, 134 mmol, 2.2 equivalents, 60% dispersion in mineral oil) was added in portions over 2 minutes, maintaining a temperature of <10° C. during the addition. Once all the NaH had been added, pivaloyl chloride (7.88 mL, 64.0 mmol, 1.05 equivalents) was added dropwise over 5 minutes, during which point the internal temperature was kept below 20° C. Once the addition was complete, the flask was warmed to ambient temperature for 15 minutes. The flask was cooled to <5° C., and the mixture was quenched with saturated ammonium chloride (100 mL). The mixture was diluted with ethyl acetate (100 mL), and the layers were separated. The organic layer was washed with water and brine, dried over sodium sulfate, filtered, and concentrated to give 15 g of crude title compound which was used without additional purification. $^1$H NMR (400 MHz, CDCl$_3$) δ ppm 8.64 (s, 1H), 8.15 (s, 1H), 1.37 (s, 9H); MS (ESI+): m/z 248.0 (M+H)$^+$.

Example 24C

N-(6-chloro-3-oxo-2,3-dihydropyridazin-4-yl)-2,2-dimethylpropanamide

Crude N-(3,6-dichloropyridazin-4-yl)-2,2-dimethylpropanamide (15 g) from Example 24B was dissolved in 200 mL of glacial acetic acid and heated to 110° C. for 3 hours. The solvent was removed in vacuo, and then the residue was loaded directly onto a 220 g silica gel column with dichloromethane and eluted with 0-50% ethyl acetate/heptanes over 20 minutes to give 10.06 g of the title compound (73% yield over 2 steps). $^1$H NMR (400 MHz, CDCl$_3$) δ ppm 11.13 (br s, 1H), 8.76 (br s, 1H), 8.18 (s, 1H), 1.33 (s, 9H); MS (ESI−) m/z 228.0 (M−H)$^−$.

Example 24D

N-(6-chloro-2-{[(4R)-2,2-dimethyl-1,3-dioxolan-4-yl]methyl}-3-oxo-2,3-dihydropyridazin-4-yl)-2,2-dimethylpropanamide Example 24C (5.9 g, 25.7 mmol), (R)-(2,2-dimethyl-1,3-dioxolan-4-yl)methanol (4.07 g, 30.8 mmol), and triphenylphosphine (7.75 g, 29.5 mmol) were suspended in tetrahydrofuran (64.2 mL). Diisopropyl azodicarboxylate (DIAD, 5.74 mL, 29.5 mmol) was added neat and dropwise at ambient temperature while stirring vigorously, and all solids dissolved once the addition was complete. During the addition of DIAD, the internal temperature rose to 30° C. The mixture was concentrated to approximately 20 mL and loaded directly onto a 330 g silica gel column eluted with 0-25% ethyl acetate/heptanes over 30 minutes to give 8.69 g of the title compound (98% yield). $^1$H NMR (400 MHz, CDCl$_3$) δ ppm 8.89 (br s, 1H), 8.15 (s, 1H), 4.63-4.54 (m, 1H), 4.45 (dd, J=13.1, 6.5 Hz, 1H), 4.18-4.07 (m, 2H), 3.90 (dd, J=8.7, 5.2 Hz, 1H), 1.47 (s, 3H), 1.36 (s, 3H), 1.34 (s, 9H); MS (ESI−): m/z 342.2 (M−H)$^-$.

Example 24E

N-(2-{[(4R)-2,2-dimethyl-1,3-dioxolan-4-yl]methyl}-3-oxo-6-phenyl-2,3-dihydropyridazin-4-yl)-2,2-dimethylpropanamide Example 24D (8.43 g, 24.52 mmol) from Example 15D was dissolved in a mixture of toluene (131 mL) and aqueous sodium carbonate (2 M, 32.7 mL), and the resulting biphasic mixture was sparged with N$_2$ for 20 minutes. Tetrakis(triphenylphosphine)palladium(0) (1.417 g, 1.226 mmol, 0.05 equivalent) and phenylboronic acid (4.48 g, 36.8 mmol) were added, and the reaction mixture was heated at 90° C. for 1.5 hours. The mixture was cooled to ambient temperature and diluted with ethyl acetate (100 mL). The organic fraction was separated, washed with brine, dried over sodium sulfate, filtered, and concentrated. The residue was purified via silica gel chromatography, eluting with 0-20% ethyl acetate/heptanes on a 120 g silica gel column over 20 minutes to give 9.36 g of the title compound. $^1$H NMR (400 MHz, CDCl$_3$) δ ppm 8.94 (br s, 1H), 8.67 (s, 1H), 7.91-7.74 (m, 2H), 7.51-7.36 (m, 3H), 4.73-4.49 (m, 2H), 4.27 (dd, J=12.9, 6.3 Hz, 1H), 4.12 (dd, J=8.7, 5.9 Hz, 1H), 3.99 (dd, J=8.6, 5.2 Hz, 1H), 1.48 (s, 3H), 1.36 (s, 3H), 1.35 (s, 9H); MS (ESI−) m/z 384.3 (M−H)$^-$.

Example 24F 4-amino-2-{[(4R)-2,2-dimethyl-1,3-dioxolan-4-yl]methyl}-6-phenylpyridazin-3(2H)-one Example 24E (9.35 g, 24.26 mmol, 1.0 equivalent) was dissolved in 100 mL of methanol, and sodium methanolate (11.09 mL, 48.5 mmol, 2.0 equivalents) was added. The reaction mixture was heated at 50° C. for 30 minutes, and then cooled to ambient temperature. The mixture was then concentrated in vacuo, and the resulting residue was partitioned between tert-butyl methyl ether and brine. The organic fraction was dried over sodium sulfate, filtered, and concentrated. The residue was purified on an 80 g silica gel cartridge, eluting with 25-100% tert-butyl methyl ether/heptanes over 10 minutes then 100% tert-butyl methyl ether for 10 minutes to give 6.02 g of the title compound (6.02 g, 82%). $^1$H NMR (400 MHz, CDCl$_3$) δ ppm 7.78-7.68 (m, 2H), 7.46-7.33 (m, 3H), 6.71 (s, 1H), 5.01 (s, 2H), 4.70-4.53 (m, 2H), 4.21 (dd, J=12.7, 6.6 Hz, 1H), 4.12 (dd, J=8.6, 5.9 Hz, 1H), 4.00 (dd, J=8.6, 5.4 Hz, 1H), 1.48 (s, 3H), 1.36 (s, 3H); MS (ESI−) m/z 300.2 (M−H)$^-$.

Example 24G

N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide The product of Example 1E (59.3 mg, 0.230 mmol) was dissolved in dichloromethane (1 mL). Oxalyl chloride (80 µL) and N,N-dimethylformamide (25 µL) were added. The reaction mixture was stirred at ambient temperature for 1 hour and then concentrated. The residue was dissolved in dichloromethane (1 mL) and concentrated two times. The residue was dissolved in dichloromethane (1 mL) and pyridine (0.5 mL). The product of Example 24F (61.1 mg, 0.203 mmol) was added, and the reaction mixture was stirred at 60° C. for 16 hours. The reaction mixture was concentrated, and the residue as purified by reverse-phase preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (65.5 mg, 60%). $^1$H NMR (400 MHz, DMSO-d$_6$) δ ppm 9.04 (d, J=3.5 Hz, 1H), 8.48 (s, 1H), 7.84-7.77 (m, 2H), 7.67 (d, J=4.5 Hz, 1H), 7.56-7.44 (m, 3H), 7.18 (d, J=1.2 Hz, 1H), 5.02 (dd, J=9.5, 1.4 Hz, 1H), 4.53 (q, J=5.9 Hz, 1H), 4.47 (dd, J=9.6, 1.6 Hz, 1H), 4.38 (dt, J=13.3, 6.8 Hz, 1H), 4.15 (dt, J=12.5, 6.0 Hz, 1H), 4.05 (dd, J=8.6, 6.2 Hz, 1H), 3.87 (dd, J=8.6, 4.9 Hz, 1H), 1.69 (s, 3H), 1.34 (s, 3H), 1.24 (s, 3H); MS (ESI−) m/z 540.1 (M−H)$^-$.

Example 25

N-{2-[(2R)-2,3-dihydroxypropyl]-3-oxo-6-phenyl-2,3-dihydropyridazin-4-yl}-2,2-difluoro-7-methyl-6,7-dihydro-2H-furo[2,3-f][1,3]benzodioxole-7-carboxamide To the product of Example 24G (59.1 mg, 0.109 mmol) in methanol (1 mL) was added hydrochloric acid (3 M, 50 µL). The reaction mixture was stirred at ambient temperature for 17 hours, and concentrated. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (51.0 mg, 93%). $^1$H NMR (400 MHz, DMSO-d$_6$) δ ppm 9.01 (d, J=1.9 Hz, 1H), 8.47 (s, 1H), 7.83-7.76 (m, 2H), 7.68 (d, J=0.9 Hz, 1H), 7.55-7.43 (m, 3H), 7.19 (d, J=1.2 Hz, 1H), 5.02 (dd, J=9.6, 1.1 Hz, 1H), 4.47 (dd, J=9.6, 1.1 Hz, 1H), 4.24 (ddd, J=13.2, 8.5, 4.9 Hz, 1H), 4.12 (dt, J=12.9, 4.2 Hz, 1H), 4.02 (dq, J=9.5, 5.1 Hz, 1H), 3.47-3.38 (m, 2H), 1.69 (s, 3H); MS (ESI+) m/z 502.1 (M+H)$^+$.

Example 26

(7R)—N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide The product of Example 3B (51.8 mg, 0.201 mmol) was dissolved in dichloromethane (1 mL). Oxalyl chloride (80

μL) and N,N-dimethylformamide (25 μL) were added which resulted in bubbling of the reaction mixture. The reaction mixture was stirred at ambient temperature for 1 hour, and then it was concentrated. The residue was dissolved in dichloromethane (1 mL) and concentrated two times. The residue was then dissolved in dichloromethane (1 mL) and pyridine (0.5 mL). The product of Example 24F (66.1 mg, 0.219 mmol) was added, and the reaction mixture was stirred at 60° C. for 16 hours. The reaction mixture was then concentrated, and the residue was purified by reverse-phase preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (48.7 mg, 41%). $^1$H NMR (501 MHz, DMSO-$d_6$) δ ppm 9.04 (s, 1H), 8.48 (s, 1H), 7.82-7.77 (m, 2H), 7.66 (s, 1H), 7.55-7.44 (m, 3H), 7.18 (s, 1H), 5.02 (d, J=9.5 Hz, 1H), 4.57-4.50 (m, 1H), 4.47 (d, J=9.6 Hz, 1H), 4.38 (dd, J=13.1, 6.7 Hz, 1H), 4.16 (dd, J=13.1, 5.9 Hz, 1H), 4.05 (dd, J=8.7, 6.1 Hz, 1H), 3.88 (dd, J=8.6, 4.9 Hz, 1H), 1.69 (s, 3H), 1.34 (s, 3H), 1.24 (s, 3H); MS (ESI-) m/z 540.1 (M-H)$^-$.

Example 27

(7R)—N-{2-[(2R)-2,3-dihydroxypropyl]-3-oxo-6-phenyl-2,3-dihydropyridazin-4-yl}-2,2-difluoro-7-methyl-6,7-dihydro-2H-furo[2,3-f][1,3]benzodioxole-7-carboxamide To the solution of Example 26 (43.7 mg, 0.081 mmol) in methanol (1 mL) was added hydrochloric acid (3M, 50 μL). The reaction mixture was stirred at ambient temperature for 16 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (35.7 mg, 88%). $^1$H NMR (400 MHz, DMSO-$d_6$) δ ppm 9.01 (s, 1H), 8.47 (s, 1H), 7.81-7.78 (m, 2H), 7.67 (d, J=1.9 Hz, 1H), 7.56-7.41 (m, 3H), 7.18 (d, J=1.7 Hz, 1H), 5.02 (d, J=9.6 Hz, 1H), 4.47 (d, J=9.5 Hz, 1H), 4.41-3.98 (m, 5H), 3.43 (h, J=5.4 Hz, 2H), 1.69 (s, 3H); MS (ESI-) m/z 500.0 (M-H)$^-$.

Example 28 methyl 3-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl] benzoate Example 28A tert-butyl 3-[3-chloro-5-(2,2-dimethylpropanamido)-6-oxopyridazin-1(6H)-yl]benzoate To Example 24C (1.2 g, 5.23 mmol) in N,N-dimethylformamide (8.71 mL) was added bis(quinolin-8-yloxy)copper (0.092 g, 0.261 mmol) and potassium carbonate (0.722 g, 5.23 mmol), followed by tert-butyl 3-iodobenzoate (2.066 g, 6.79 mmol). The reaction vessel was sealed, and the mixture was heated at 115° C. for 15 hours. The reaction mixture was cooled to ambient temperature, diluted with ethyl acetate, and filtered through a 25 mL syringe plugged with cotton. The filtrate was washed with 50% brine (3×) and 100% brine and then concentrated. The residue was purified using a 40 g silica gel column eluted with 0-50% ethyl acetate/heptanes over 30 minutes to give 1.10 g of the title compound. $^1$H NMR (400 MHz, CDCl$_3$) δ ppm 9.00 (br. s., 1H), 8.23 (s, 1H), 8.21 (s, 1H), 8.06 (d, J=7.9 Hz, 1H), 7.77 (d, J=8.2 Hz, 1H), 7.55 (t, J=7.9 Hz, 1H), 1.61 (s, 9H), 1.34 (s, 9H).

Example 28B tert-butyl 3-[3-cyclopropyl-5-(2,2-dimethylpropanamido)-6-oxopyridazin-1(6H)-yl]benzoate Example 28A (1.08 g, 2.66 mmol) and tris(((Z)-4-oxopent-2-en-2-yl)oxy)iron (0.094 g, 0.266 mmol) were dissolved in tetrahydrofuran (24.19 mL) and N-methyl-2-pyrrolidinone (2.419 mL) was added. The resulting bright red solution was cooled to <5° C. (ice bath), and 1.0 M cyclopropylmagnesium bromide in tetrahydrofuran (6.65 mL, 6.65 mmol) was added dropwise until the red color had dissipated at such a rate that the temperature did not exceed 5° C. Subsequent dropwise addition of the remaining cyclopropylmagnesium bromide solution was performed at such a rate that the resulting dark black color dissipated in between the addition of each drop. An additional 0.2 equivalents of cyclopropylmagnesium bromide solution was added, and then saturated ammonium chloride (0.5 mL) was added to quench the reaction. The mixture was then loaded directly onto a 40 g silica gel column eluted with 0-30% ethyl acetate/heptanes over 30 minutes to give 780 mg (71%) of the title compound. $^1$H NMR (400 MHz, CDCl$_3$) δ ppm 9.00 (br. s., 1H), 8.22 (s, 1H), 8.02 (d, J=7.7 Hz, 1H), 7.99 (s, 1H), 7.79 (d, J=8.2 Hz, 1H), 7.52 (t, J=7.8 Hz, 1H), 2.00-1.91 (m, 1H), 1.61 (s, 9H), 1.33 (s, 9H), 1.02-0.90 (m, 4H).

Example 28C methyl 3-(5-amino-3-cyclopropyl-6-oxopyridazin-1 (614)-yl)benzoate

Example 28B (760 mg, 1.847 mmol) was dissolved in methanol (20 mL) and sodium methoxide (1.267 mL, 5.54 mmol) was added. The resulting solution was heated at 60° C. under nitrogen. After 4 hours, the reaction mixture was acidified with acetyl chloride (0.657 mL, 9.23 mmol) in methanol (3 mL) and heating was continued for 15 minutes. The mixture was then concentrated in vacuo, and the residue was then loaded directly onto a 25 g silica column and eluted with 20-70% ethyl acetate/heptanes over 20 minutes to give 410 mg (78%) of the title compound. $^1$H NMR (400 MHz, CD$_3$OD) δ ppm 8.22 (s, 1H), 8.08 (d, J=7.9 Hz, 1H), 7.84 (d, J=7.9 Hz, 1H), 7.63 (t, J=7.9 Hz, 1H), 6.24 (s, 1H), 3.94 (s, 3H), 1.92-1.84 (m, 1H), 1.04-0.96 (m, 2H), 0.92-0.85 (m, 2H).

Example 28D methyl 3-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl] benzoate The product of Example 3B (35.4 mg, 0.137 mmol) was dissolved in dichloromethane (1 mL). Oxalyl chloride (80 μL) and N,N-dimethylformamide (25 μL) were added which resulted in bubbling of the reaction mixture. The reaction mixture was stirred at ambient temperature for 1 hour and then concentrated. The residue was dissolved in dichloromethane (1 mL) and concentrated two times. The residue was dissolved in dichloromethane (1 mL) and pyridine (0.5 mL). The product of Example 28C (42.2 mg, 0.148 mmol) was added, and the reaction mixture was stirred at 60° C. for 18 hours. The reaction mixture was concentrated, and the residue was purified by reverse-phase preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (25.9 mg, 36%). $^1$H NMR (400 MHz, DMSO-$d_6$) δ ppm 8.98 (s, 1H), 8.14 (t, J=1.9 Hz, 1H), 7.99 (dt, J=7.8, 1.3 Hz, 1H), 7.87 (s, 1H), 7.84 (ddd, J=8.1, 2.2, 1.1 Hz, 1H), 7.70-7.61 (m, 2H), 7.16 (s, 1H), 5.00 (d, J=9.6 Hz, 1H), 4.45 (d, J=9.6 Hz, 1H), 3.88 (s, 3H), 2.04 (tt, J=8.3, 4.9 Hz, 1H), 1.67 (s, 3H), 1.03-0.91 (m, 2H), 0.80 (ddd, J=6.6, 5.1, 3.7 Hz, 2H); MS (ESI+) m/z 526.1 (M+H)$^+$.

Example 29

3-[3-cyclopropyl-5-{[(7R)-2,2-difluoro-7-methyl-6, 7-dihydro-2H-furo[2,3-f][1,3]benzodioxole-7-carbonyl]amino}-6-oxopyridazin-1(6H)-yl]benzoic acid The product of Example 28D (22.9 mg, 0.044 mmol) and potassium trimethylsilanolate (9.0 mg, 90% purity, 0.063 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (14.8 mg, 66%). $^1$H NMR (400 MHz, DMSO-$d_6$) δ ppm 13.17 (s, 1H), 8.98 (s, 1H), 8.11 (t, J=2.0 Hz, 1H), 7.97 (d, J=7.7 Hz, 1H), 7.88 (s, 1H), 7.84-7.77 (m, 1H), 7.66-7.56 (m, 2H), 7.16 (s, 1H), 5.00 (d, J=9.5 Hz, 1H), 4.45 (d, J=9.5 Hz, 1H), 2.06-2.00 (m, 1H), 1.67 (s, 3H), 0.96 (dt, J=8.6, 3.2 Hz, 2H), 0.85-0.70 (m, 2H); MS (ESI+) m/z 512.1 (M+H)$^+$.

Example 30

4-{3-cyclopropyl-5-[(2,2-difluoro-7-methyl-6,7-dihydro-2H-furo[2,3-f][1,3]benzodioxole-7-carbonyl)amino]-6-oxopyridazin-1(614)-yl}benzoic acid Example 30A N-(3,6-dichloropyridazin-4-yl)-1-(2,2-difluoro-2H-1, 3-benzodioxol-5-yl)cyclopropane-1-carboxamide To 1-(2,2-difluorobenzo[d][1,3]dioxol-5-yl)cyclopropanecarboxylic acid (2.0453 g, 8.45 mmol) in N,N-dimethylformamide (10.56 mL) was added N-[(dimethylamino)-1H-1,2,3-triazolo-[4,5-b]pyridin-1-ylmethylene]-N-methylmethanaminium hexafluorophosphate N-oxide (HATU, 3.700 g, 9.73 mmol). The mixture was stirred for 5 minutes, and then Example 24A (1.429 g, 8.71 mmol) was added, followed by dropwise addition of triethylamine (4.71 mL, 33.8 mmol). The reaction mixture was stirred overnight at room temperature. The reaction mixture was quenched with saturated aqueous sodium bicarbonate (50 mL) and diluted with 400 mL of tert-butyl methyl ether. The aqueous layer was removed, and the organic fraction was washed with water (50 mL) and brine (50 mL), and dried over sodium sulfate. The reaction solution was adsorbed onto silica gel (5 g) and purified using a 150 g silica gel cartridge eluted with a gradient of 5-100% ethyl acetate/heptanes to give the title compound (0.752 g, 1.937 mmol, 22.94% yield). $^1$H NMR (400 MHz, DMSO-$d_6$) δ ppm 8.34 (s, 1H), 8.29 (s, 1H), 7.65 (d, J=1.7 Hz, 1H), 7.53 (d, J=8.4 Hz, 1H), 7.45 (dd, J=8.4, 1.8 Hz, 1H), 1.60 (q, J=4.1 Hz, 2H), 1.36 (q, J=4.1 Hz, 2H); MS (ESI+) m/z 389 (M+H)$^+$.

Example 30B

N-(6-chloro-3-oxo-2,3-dihydropyridazin-4-yl)-1-(2, 2-difluoro-2H-1,3-benzodioxol-5-yl)cyclopropane-1-carboxamide A solution of Example 30A (0.742 g, 1.912 mmol) in acetic acid (4.0 mL) was stirred at 120° C. for 4 hours. The volume was reduced to half in vacuo, and the reaction mixture was cooled to room temperature, and a precipitate formed. tert-Butyl methyl ether (10 mL) was added, and the mixture was stirred vigorously for 90 minutes. The mixture was filtered, and the solid was washed with more tert-butyl methyl ether (10 mL). The filtrate and wash were collected and concentrated to give the title compound (0.569 g, 1.539 mmol, 81% yield), the major isomer. $^1$H NMR (400 MHz, DMSO-$d_6$) δ ppm 13.40 (s, 1H), 8.42 (s, 1H), 7.85 (s, 1H), 7.67 (d, J=1.7 Hz, 1H), 7.52 (d, J=8.3 Hz, 1H), 7.42 (dd, J=8.3, 1.7 Hz, 1H), 1.57 (q, J=4.1 Hz, 2H), 1.31 (q, J=4.1 Hz, 2H); MS (ESI−) m/z 368 (M−H)$^−$. Regiochemistry confirmed by small molecule X-ray crystallography.

Example 30C tert-butyl 4-(5-amino-3-chloro-6-oxopyridazin-1 (6H)-yl)benzoate

A mixture of Example 30B (0.507 g, 1.371 mmol), bis(quinolin-8-yloxy)copper (0.034 g, 0.096 mmol), potassium carbonate (0.227 g, 1.646 mmol), and tert-butyl 4-iodobenzoate (0.443 mL, 1.646 mmol) were suspended in N,N-dimethylformamide (2.74 mL) in a sealed 20 mL scintillation vial. The vial contents were heated at 120° C. in a heating block for 72 hours. The reaction mixture was diluted with 4 mL of ammonium chloride and then filtered. The filtrate was chromatographed using a 40 g silica gel cartridge eluted with a gradient of 5-100% ethyl acetate/heptanes over 30 minutes to give the title compound (88 mg, 0.273 mmol, 19.94% yield). $^1$H NMR (501 MHz, DMSO-$d_6$) δ ppm 8.02-7.97 (m, 2H), 7.77-7.69 (m, 2H), 7.14 (s, 2H), 6.29 (s, 1H), 1.57 (s, 9H); MS (ESI+) m/z 322 (M+H)$^+$.

Example 30D tert-butyl 4-{3-chloro-5-[(2,2-difluoro-7-methyl-6,7-dihydro-2H-furo[2,3-f][1,3]benzodioxole-7-carbonyl)amino]-6-oxopyridazin-1(6H)-yl}benzoate To a solution of Example 1E (59.3 mg, 0.230 mmol) in dichloromethane (1 mL) was added one drop of N,N-dimethylformamide followed by dropwise addition of oxalyl chloride (80 μL, 0.914 mmol) in 0.3 mL of dichloromethane. The reaction mixture was stirred at ambient temperature for 30 minutes and then concentrated. The residue was dissolved in dichloromethane (0.5 mL) and concentrated two times. The residue was dissolved in dichloromethane (0.5 mL), and this solution was added dropwise to a solution of Example 30C (88 mg, 0.273 mmol) and pyridine (177 µL, 2.188 mmol). The reaction was stirred at 50° C. for 6 hours. The solvent was removed under a stream of nitrogen, and the crude material was chromatographed using a 12 g silica gel cartridge eluted with a gradient of 5-100% ethyl acetate/heptanes over 20 minutes to give the title compound. $^1$H NMR (400 MHz, DMSO-d$_6$) δ ppm 9.11 (s, 1H), 8.06-7.96 (m, 3H), 7.71 (d, J=8.6 Hz, 2H), 7.65 (s, 1H), 7.18 (s, 1H), 5.01 (d, J=9.6 Hz, 1H), 4.46 (d, J=9.6 Hz, 1H), 1.68 (s, 3H), 1.57 (s, 9H); MS (ESI+) m/z 562 (M+H)$^+$.

Example 30E tert-butyl 4-{3-cyclopropyl-5-[(2,2-difluoro-7-methyl-6,7-dihydro-2H-furo[2,3-f][1,3]benzodioxole-7-carbonyl)amino]-6-oxopyridazin-1(6H)-yl}benzoate A mixture of Example 30D (49 mg, 0.087 mmol) from and tris(((Z)-4-oxopent-2-en-2-yl)oxy)iron (1.540 mg, 4.36 µmol) in tetrahydrofuran (800 µL) and N-methyl-2-pyrrolidinone (80 µL) was cooled to 0° C. in an ice bath and 1.0 M cyclopropylmagnesium bromide in tetrahydrofuran (218 µL, 0.218 mmol) was added dropwise. The reaction turned black and then faded to light yellowish brown. An additional 40 µL of the cyclopropylmagnesium bromide solution was added, and the reaction mixture was stirred for more 10 minutes in the ice bath. Saturated ammonium chloride (3 drops) was added to quench the reaction. The reaction mixture then combined with silica gel (1 g) and concentrated. The crude material absorbed on silica gel (1 g) and was chromatographed using a 12 g silica gel cartridge eluted with a gradient of 5-40% tert-butyl methyl ether/heptanes over 30 minutes to give the title compound (30 mg, 0.053 mmol, 60.6% yield). $^1$H NMR (400 MHz, DMSO-d$_6$) δ ppm 8.99 (s, 1H), 8.02-7.97 (m, 2H), 7.88 (s, 1H), 7.73-7.68 (m, 2H), 7.64 (s, 1H), 7.17 (s, 1H), 5.00 (d, J=9.5 Hz, 1H), 4.45 (d, J=9.6 Hz, 1H), 2.03 (d, J=4.3 Hz, 1H), 1.67 (s, 3H), 1.56 (s, 9H), 0.97 (dd, J=8.2, 2.9 Hz, 2H), 0.88-0.82 (m, 2H); MS (ESI+) m/z 568 (M+H)$^+$.

Example 30F

4-{3-cyclopropyl-5-[(2,2-difluoro-7-methyl-6,7-dihydro-2H-furo[2,3-f][1,3]benzodioxole-7-carbonyl)amino]-6-oxopyridazin-1(6H)-yl}benzoic acid To a suspension of Example 30E (28 mg, 0.049 mmol) in acetonitrile (216 µL) was added hydrochloric acid (6 M, 108 µL). The resulting solution was heated at 50° C. for 3 hours. The mixture was concentrated under a stream of nitrogen, and the residue was purified using a 4 g silica gel cartridge, eluting with a 3:1:4 ethyl acetate:ethanol:heptanes solvent system to give the title compound (21 mg, 0.041 mmol, 83% yield). $^1$H NMR (400 MHz, DMSO-d$_6$) δ ppm 13.09 (s, 1H), 8.98 (s, 1H), 8.07-8.00 (m, 2H), 7.88 (s, 1H), 7.72-7.67 (m, 2H), 7.64 (s, 1H), 7.17 (s, 1H), 5.00 (d, J=9.5 Hz, 1H), 4.45 (d, J=9.6 Hz, 1H), 2.04 (ddd, J=13.2, 8.6, 4.9 Hz, 1H), 1.66 (s, 3H), 0.96 (dt, J=8.5, 3.2 Hz, 2H), 0.85 (dd, J=8.3, 2.4 Hz, 2H); MS (ESI+) m/z 512 (M+H)$^+$.

Example 31

4-[3-cyclopropyl-5-{[(7S)-2,2-difluoro-7-methyl-6,7-dihydro-2H-furo[2,3-f][1,3]benzodioxole-7-carbonyl]amino}-6-oxopyridazin-1(6H)-yl]benzoic acid Example 31A tert-butyl 4-[3-chloro-5-{[(7S)-2,2-difluoro-7-methyl-6,7-dihydro-2H-furo[2,3-f][1,3]benzodioxole-7-carbonyl]amino}-6-oxopyridazin-1(6H)-yl]benzoate To a solution of Example 3A (50.6 mg, 0.196 mmol) in dichloromethane (1 mL) was added one drop of N,N-dimethylformamide followed by dropwise addition of oxalyl chloride (0.280 mL, 0.559 mmol) in dichloromethane. The reaction mixture was stirred at ambient temperature for 30 minutes and then concentrated. The residue was dissolved in dichloromethane (0.5 mL) and concentrated two times. The residue was then dissolved in dichloromethane (0.5 mL), and this solution was added dropwise to a solution Example 30C (60 mg, 0.186 mmol) and pyridine (0.121 mL, 1.492 mmol). The mixture was warmed to 50° C. After 7 hours, the mixture was concentrated under a stream of nitrogen, and the crude material was chromatographed using a 12 g silica gel cartridge eluted with a gradient of 5-100% ethyl acetate/heptanes over 20 minutes to give the title compound (48 mg, 0.085 mmol, 45.8% yield). $^1$H NMR (400 MHz, DMSO-d$_6$) δ ppm 9.11 (s, 1H), 8.06-7.96 (m, 3H), 7.71 (d, J=8.6 Hz, 2H), 7.65 (s, 1H), 7.18 (s, 1H), 5.01 (d, J=9.5 Hz, 1H), 4.46 (d, J=9.7 Hz, 1H), 1.68 (s, 3H), 1.57 (s, 9H); MS (ESI+) m/z 562 (M+H)$^+$.

Example 31B tert-butyl 4-[3-cyclopropyl-5-{[(7S)-2,2-difluoro-7-methyl-6,7-dihydro-2H-furo[2,3-f][1,3]benzodioxole-7-carbonyl]amino}-6-oxopyridazin-1(6H)-yl]benzoate A mixture of Example 31A (49 mg, 0.087 mmol) and tris(((Z)-4-oxopent-2-en-2-yl)oxy)iron (1.540 mg, 4.36 µmol) in tetrahydrofuran (800 µL) and N-methyl-2-pyrrolidinone (80 µL) was cooled to 0° C. in an ice bath and 1.0 M cyclopropylmagnesium bromide in tetrahydrofuran (218 µL, 0.218 mmol) was added dropwise. The reaction turned black, then faded to light yellowish brown. An additional 40 µL of the cyclopropylmagnesium bromide solution was added, and the reaction mixture was stirred for 10 minutes more in the ice bath. Saturated ammonium chloride (3 drops) was added to quench the reaction. The reaction mixture was adsorbed onto silica gel (1 g). The crude material absorbed onto silica gel was chromatographed using a 12 g silica gel cartridge eluted with a gradient of 5-40% tert-butyl methyl ether/heptanes over 30 minutes to give the title compound (14 mg, 0.025 mmol, 28.3% yield). $^1$H NMR (400 MHz, DMSO-d$_6$) δ ppm 8.99 (s, 1H), 8.02-7.97 (m, 2H), 7.88 (s, 1H), 7.74-7.67 (m, 2H), 7.64 (s, 1H), 7.16 (s, 1H), 5.00 (d, J=9.5 Hz, 1H), 4.45 (d, J=9.6 Hz, 1H), 2.03 (tt, J=8.3, 4.9 Hz, 1H), 1.67 (s, 3H), 1.56 (s, 9H), 1.00-0.93 (m, 2H), 0.83-0.79 (m, 2H); MS (ESI+) m/z 568 (M+H)$^+$.

Example 31C

4-[3-cyclopropyl-5-{[(7S)-2,2-difluoro-7-methyl-6,7-dihydro-2H-furo[2,3-f][1,3]benzodioxole-7-carbonyl]amino}-6-oxopyridazin-1(6H)-yl]benzoic acid To a suspension of Example 31B (14 mg, 0.025 mmol) in acetonitrile (108 µL) was added 6 M hydrochloric acid (54.1

μL). The resulting solution was heated at 50° C. for 7 hours, and then the solution was concentrated under a stream of nitrogen. The residue was purified using a 4 g silica gel cartridge eluted with tert-butyl methyl ether then ethyl acetate to give the title compound (7.5 mg, 0.015 mmol, 59.4% yield). $^1$H NMR (501 MHz, DMSO-$d_6$) δ ppm 13.13 (s, 1H), 8.98 (s, 1H), 8.08-7.98 (m, 2H), 7.88 (s, 1H), 7.75-7.67 (m, 2H), 7.64 (s, 1H), 7.17 (s, 1H), 5.00 (d, J=9.5 Hz, 1H), 4.45 (d, J=9.5 Hz, 1H), 2.04 (tt, J=8.3, 4.9 Hz, 1H), 1.67 (s, 3H), 0.96 (dt, J=8.7, 3.2 Hz, 2H), 0.84-0.79 (m, 2H); MS (ESI+) m/z 512 (M+H)$^+$.

Example 32

4-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoic acid Example 32A tert-butyl 4-[3-chloro-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoate To a solution of Example 3B (50.6 mg, 0.196 mmol) in dichloromethane (1 mL) was added one drop of N,N-dimethylformamide followed by dropwise addition of oxalyl chloride (0.280 mL, 0.559 mmol) in dichloromethane. The reaction mixture was stirred at ambient temperature for 30 minutes and then concentrated. The residue was dissolved in dichloromethane (0.5 mL) and concentrated two times. The residue was then dissolved in dichloromethane (0.5 mL), and this solution was added dropwise to a solution of Example 30C (60 mg, 0.186 mmol) and pyridine (0.121 mL, 1.492 mmol). The mixture was warmed to 50° C. After 5 hours, the volatiles were removed under a stream of nitrogen, and the crude material was chromatographed using a 12 g silica gel cartridge eluted with a gradient of 5-100% ethyl acetate/heptanes over 20 minutes to give the title compound (45 mg, 0.080 mmol, 42.9% yield). $^1$H NMR (400 MHz, DMSO-$d_6$) δ ppm 9.11 (s, 1H), 8.02 (d, J=8.6 Hz, 2H), 7.99 (s, 1H), 7.71 (d, J=8.6 Hz, 2H), 7.65 (s, 1H), 7.18 (s, 1H), 5.01 (d, J=9.6 Hz, 1H), 4.46 (d, J=9.7 Hz, 1H), 1.68 (s, 3H), 1.57 (s, 9H); MS (ESI+) m/z 562 (M+H)$^+$.

Example 32B tert-butyl 4-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoate A mixture of Example 32A (43 mg, 0.077 mmol) and tris(((Z)-4-oxopent-2-en-2-yl)oxy)iron (2.2 mg, 6.23 μmol) in tetrahydrofuran (800 μL) and N-methyl-2-pyrrolidinone (80 μL) was cooled to 0° C. in an ice bath and 1.0 M cyclopropylmagnesium bromide in tetrahydrofuran (191 μL, 0.191 mmol) was added dropwise. The reaction turned black, then faded to light yellowish brown. An additional 40 μL of the cyclopropylmagnesium bromide solution was added, and the reaction mixture was stirred for an additional 10 minutes in the ice bath. Saturated ammonium chloride (3 drops) was added to quench the reaction. The reaction mixture was then adsorbed onto silica gel with solvent removal. The crude material adsorbed on silica gel was chromatographed using a 12 g silica gel cartridge eluted with a gradient of 5-40% tert-butyl methyl ether/heptanes over 30 minutes to give the title compound (18 mg, 0.032 mmol, 41.4% yield). $^1$H NMR (400 MHz, DMSO-$d_6$) δ ppm 8.99 (s, 1H), 8.03-7.96 (m, 2H), 7.88 (s, 1H), 7.74-7.68 (m, 2H), 7.64 (s, 1H), 7.16 (s, 1H), 5.00 (d, J=9.5 Hz, 1H), 4.45 (d, J=9.6 Hz, 1H), 2.03 (tt, J=8.2, 4.9 Hz, 1H), 1.67 (s, 3H), 1.56 (s, 9H), 1.01-0.93 (m, 2H), 0.83-0.78 (m, 2H); MS (ESI+) m/z 568 (M+H)$^+$.

Example 32C

4-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoic acid To a suspension of Example 32B (15 mg, 0.026 mmol) in acetonitrile (116 μL) was added 6 M hydrochloric acid (58.0 μL). The resulting solution was heated at 50° C. for 7 hours. The volatiles were removed under a stream of nitrogen, and the resulting residue was purified using a 4 g silica gel cartridge eluted first with tert-butyl methyl ether and then with ethyl acetate to give the title compound (8.8 mg, 0.017 mmol, 65.1% yield). $^1$H NMR (501 MHz, DMSO-$d_6$) δ ppm 13.13 (s, 1H), 8.96 (s, 1H), 8.05-7.97 (m, 2H), 7.86 (s, 1H), 7.73-7.65 (m, 2H), 7.62 (s, 1H), 7.15 (s, 1H), 4.98 (d, J=9.5 Hz, 1H), 4.43 (d, J=9.5 Hz, 1H), 2.02 (tt, J=8.3, 4.9 Hz, 1H), 1.65 (s, 3H), 0.98-0.92 (m, 2H), 0.79 (ddd, J=6.4, 4.8, 3.4 Hz, 2H); MS (ESI+) m/z 512 (M+H)$^+$.

Example 33 methyl 4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoate and methyl 4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoate Example 33A methyl 3-(1-hydroxybut-3-en-1-yl)benzoate Methyl 3-formylbenzoate (2.64 g, 16.08 mmol) was added to $H_2O$ (40 mL) containing potassium iodide (8.01 g, 48.2 mmol), stannous chloride (4.57 g, 24.12 mmol) and 3-bromoprop-1-ene (2.087 mL, 24.12 mmol). Saturated ammonium chloride (20 mL) was added. The reaction mixture was stirred at ambient temperature for 2 hours and then extracted with $CH_2Cl_2$ (2×50 mL). The organic layer was washed with water, dried over sodium sulfate, filtered, and concentrated. Purification by flash chromatography on a 50 g silica gel cartridge, eluted with ethyl acetate in heptane at 5-30% gradient gave the title compound (3.0 g, 90% yield). $^1$H NMR (400 MHz, CDCl$_3$) δ ppm 8.02 (d, J=1.8 Hz, 1H), 7.96-7.92 (m, 1H), 7.59-7.54 (m, 1H), 7.42 (t, J=7.7 Hz, 1H), 5.86-5.73 (m, 1H), 5.20-5.16 (m, 1H), 5.14 (s, 1H), 4.80 (dd, J=7.8, 5.0 Hz, 1H), 3.92 (s, 3H), 2.59-2.45 (m, 2H), 2.23 (d, J=2.5 Hz, 1H).

Example 33B methyl rac-3-[(2R,4S,6S)-4-hydroxy-6-phenyloxan-2-yl]benzoate

To methyl 3-(1-hydroxybut-3-en-1-yl)benzoate (1.856 g, 9.0 mmol) from Example 33A in benzene (15 mL) was added benzaldehyde (1.9 mL, 18.00 mmol) and acetic acid (1.65 mL, 28.8 mmol) followed by addition of boron trifluoride diethyl etherate (2.25 mL, 20 mmol) at 0° C. The mixture was stirred at 0° C. for 3 hours and extracted with $CH_2Cl_2$. Saturated $NaHCO_3$ (10 mL) was added to the reaction media followed by extraction with ethyl acetate (2×20 mL). The combined organic layers were washed with brine, dried over $Na_2SO_4$, filtered and concentrated under reduced pressure. The acetylated intermediate, methyl 3-[4-(acetyloxy)-6-phenyltetrahydro-2H-pyran-2-yl]benzoate, obtained in this reaction was dissolved in $CH_3OH$ (10 mL) and $K_2CO_3$ (500 mg) was added. The mixture was stirred for 0.5 hour at ambient temperature, and then filtered and concentrated. Purification by flash chromatography on silica gel (50 g), eluted with ethyl acetate in heptane (5-30%) gave the title compound (865 mg, 30.7% yield). MS (APCI+) m/z 313 (M+H)$^+$.

Example 33C methyl rac-3-[(2R,6S)-4-oxo-6-phenyloxan-2-yl]benzoate

To Example 33B (860 mg, 2.75 mmol) in $CH_2Cl_2$ (10 mL) was added pyridinium chlorochromate (593 mg, 2.75 mmol) portionwise at room temperature. The mixture was stirred at room temperature for 3 hours. The reaction mixture was filtered through a pad of diatomaceous earth and extracted with $CH_2Cl_2$. The organic layer was washed with water, dried over $NaSO_4$, filtered, and concentrated. Purification by flash chromatography on a 25 g silica gel cartridge, eluted with ethyl acetate in heptane (5-20%) yielded the title compound (820 mg, 96% yield). $^1$H NMR (400 MHz, $CDCl_3$) δ ppm 8.12 (t, J=1.7 Hz, 1H), 8.00 (dt, J=7.8, 1.4 Hz, 1H), 7.67 (dt, J=7.8, 1.5 Hz, 1H), 7.50-7.44 (m, 3H), 7.43-7.37 (m, 2H), 7.36-7.30 (m, 1H), 4.88 (ddd, J=14.9, 10.6, 3.8 Hz, 2H), 3.93 (s, 3H), 2.82-2.64 (m, 4H).

Example 33D methyl rac-3-[(2R,6S)-4-(methoxyimino)-6-phenyloxan-2-yl]benzoate A mixture of Example 33C (800 mg, 2.58 mmol), sodium acetate (423 mg, 5.16 mmol) and O-methylhydroxylamine hydrochloride (431 mg, 5.16 mmol) in methanol (10 mL) was stirred at 60° C. overnight. The reaction mixture was concentrated under reduced pressure, and the residue was dissolved in ethyl acetate which was washed with brine. The organic layers was dried over $MgSO_4$, filtered, and concentrated to give the title compound (625 mg, 71.4% yield). $^1$H NMR (400 MHz, $CDCl_3$) δ ppm 8.12 (q, J=1.7 Hz, 1H), 7.98 (dt, J=7.9, 1.5 Hz, 1H), 7.68 (ddt, J=12.3, 7.7, 1.5 Hz, 1H), 7.46 (tt, J=7.5, 4.2 Hz, 3H), 7.38 (t, J=7.5 Hz, 2H), 7.33-7.28 (m, 1H), 4.69 (dddd, J=32.8, 14.9, 11.6, 2.7 Hz, 2H), 3.93 (d, J=2.3 Hz, 3H), 3.90 (d, J=1.7 Hz, 3H), 3.57 (ddt, J=14.5, 8.6, 2.2 Hz, 1H), 2.72 (ddt, J=14.1, 4.1, 2.0 Hz, 1H), 2.43 (ddd, J=14.0, 11.6, 8.0 Hz, 1H), 2.08 (dt, J=14.6, 11.2 Hz, 1H); MS (ESI+) m/z 399.9 (M+H)$^+$.

Example 33E methyl rac-3-[(2R,4R,6S)-4-amino-6-phenyloxan-2-yl]benzoate and

Example 33F methyl rac-3-[(2R,4S,6S)-4-amino-6-phenyloxan-2-yl]benzoate

To a solution of Example 33D (500 mg, 1.473 mmol) in $CH_3OH$ (10 mL) was added Raneye®-nickel 2800, water slurry (1.5 g) in a 100 mL pressure bottle. The mixture was charged with 30 psi of hydrogen and stirred at ambient temperature for 16 hours, filtered through a pad of diatomaceous earth, and concentrated under reduced pressure. Purification by chromatography on 100 g silica gel, eluted with $CH_3OH$ in ethyl acetate, with gradient from 0-15% yielded the first eluting fraction (125 mg, 0.401 mmol, 27.2% yield) which contained methyl rac-3-[(2R,4R,6S)-4-amino-6-phenyloxan-2-yl]benzoate (Example 33E). $^1$H NMR (500 MHz, $CDCl_3$) δ ppm 8.08 (t, J=1.7 Hz, 1H), 7.93 (dt, J=7.7, 1.5 Hz, 1H), 7.66 (dt, J=7.7, 1.5 Hz, 1H), 7.47-7.38 (m, 3H), 7.34 (dd, J=8.4, 6.9 Hz, 2H), 7.28-7.22 (m, 1H), 5.19-5.03 (m, 2H), 3.91 (s, 3H), 3.74 (q, J=4.7, 3.3 Hz, 1H), 1.95 (qt, J=7.0, 3.1 Hz, 4H); MS (ESI+) m/z=311.9 (M+H)$^+$. The second eluting fraction (242 mg, 0.777 mmol, 52.8% yield) contained methyl rac-3-[(2R,4S,6S)-4-amino-6-phenyloxan-2-yl]benzoate (Example 33F). $^1$H NMR (400 MHz, $CDCl_3$) δ ppm 8.07 (t, J=1.8 Hz, 1H), 7.94 (dt, J=7.7, 1.5 Hz, 1H), 7.65 (dt, J=7.9, 1.5 Hz, 1H), 7.47-7.38 (m, 3H), 7.38-7.32 (m, 2H), 7.30-7.24 (m, 1H), 4.60 (ddd, J=16.3, 11.4, 2.0 Hz, 2H), 3.91 (s, 3H), 3.28 (tt, J=11.3, 4.2 Hz, 1H), 2.20 (dtt, J=12.7, 4.1, 2.0 Hz, 2H), 1.46 (dtd, J=13.0, 11.3, 7.9 Hz, 2H); MS(ESI+) m/z=312 (M+H)$^+$.

Example 33G methyl 4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoate and methyl 4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoate To Example 3B (99 mg, 0.385 mmol) in N,N-dimethylformamide (2 mL) was added N-[(dimethylamino)-1H-1,2,3-triazolo-[4,5-b]pyridin-1-ylmethylene]-N-methylmethanaminium hexafluorophosphate N-oxide (HATU, 220 mg, 0.578 mmol). The mixture was stirred for 10 minutes, and then Example 33F (120 mg, 0.385 mmol) was added followed by N-ethyl-N-isopropylpropan-2-amine (0.269 mL, 1.542 mmol). The mixture was stirred at 35° C. for 2 hours. The mixture was loaded on 24 g silica gel cartridge directly without work-up and purified by chromatography, eluted with 5-40% ethyl acetate/heptane to yield the title compounds (165 mg, 0.299 mmol, 78% yield); MS (ESI−) m/z 550 (M−H)$^-$.

Example 34

4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid and 4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid To Example 33G (140 mg, 0.254 mmol) in methanol (4 mL) was added aqueous 2 N lithium hydroxide (1 mL). The mixture was stirred at ambient temperature overnight. The reaction mixture was concentrated. Water (2 mL) was added to the residue and the pH was adjusted to 1-2 with 2 N HCl. The precipitate was collected by filtration and dried in a vacuum oven at 50° C. to yield the mixture of title compounds (112 mg, 0.208 mmol, 82% yield). $^1$H NMR (400 MHz, CDCl$_3$) δ ppm 8.08 (dd, J=8.2, 5.2 Hz, 2H), 7.50 (dd, J=8.3, 5.3 Hz, 2H), 7.44-7.31 (m, 4H), 7.29 (ddd, J=7.3, 4.3, 2.1 Hz, 1H), 6.82 (d, J=2.3 Hz, 1H), 6.61 (s, 1H), 5.40 (dd, J=7.8, 1.9 Hz, 1H), 4.81 (dd, J=9.2, 2.2 Hz, 1H), 4.72 (d, J=11.2 Hz, 1H), 4.66 (dt, J=11.3, 2.3 Hz, 1H), 4.37 (dtt, J=12.0, 7.7, 4.0 Hz, 1H), 4.29 (dd, J=9.2, 1.5 Hz, 1H), 2.33-2.11 (m, 2H), 1.58 (s, 3H), 1.36 (dqd, J=18.3, 11.9, 6.2 Hz, 2H); MS (ESI-) m/z 536 (M-H)$^-$.

Example 35

3-{(2R,4R)-4-[(2,2-difluoro-5-methyl-6,7-dihydro-2H,5H-indeno[5,6-d][1,3]dioxole-5-carbonyl)amino]-3,4-dihydro-2H-1-benzopyran-2-yl}benzoic acid Example 35A ethyl 4-(2,2-difluoro-2H-1,3-benzodioxol-5-yl)butanoate
To a solution of 5-bromo-2,2-difluorobenzo[d][1,3]dioxole (9.9 g, 41.8 mmol) in tetrahydrofuran (40 mL) was added 2-dicyclohexylphosphino-2',6'-dimethoxybiphenyl (SPhos, 0.343 g, 0.835 mmol) and palladium(II) acetate (0.094 g, 0.418 mmol). A 0.5 M solution of 4-ethoxy-4-oxobutylzinc bromide in tetrahydrofuran (100 mL, 50.1 mmol) was added to the reaction mixture at ambient temperature under nitrogen over 15 minutes. A slight exotherm from 22° C. to 42° C. was noted. The reaction mixture was stirred at ambient temperature for 1 hour. The reaction mixture was partitioned between ethyl acetate and 1 N HCl solution. The organic fraction was separated, washed by brine, dried over anhydrous sodium sulfate, filtered, and concentrated in vacuo. The residue was purified by flash chromatography using a 220 g silica gel cartridge eluted with 0-10% tert-butyl methyl ether/heptanes to give the title compound (8.96 g, 79% yield). $^1$H NMR (400 MHz, CDCl$_3$) δ ppm 1.28 (t, J=7.1 Hz, 3H), 1.95 (p, J=7.5 Hz, 2H), 2.33 (t, J=7.4 Hz, 2H), 2.67 (t, J=7.6 Hz, 2H), 4.16 (q, J=7.1 Hz, 2H), 6.84-6.95 (m, 2H), 6.98 (d, J=8.1 Hz, 1H).

Example 35B ethyl 4-(2,2-difluoro-2H-1,3-benzodioxol-5-yl)-2-methylbutanoate

To a cold (-78° C.) solution of diisopropylamine (5.85 mL, 41.0 mmol) in tetrahydrofuran (50 mL) was added a 2.5 M solution of N-butyllithium in hexane (15.11 mL, 37.8 mmol) dropwise, and the reaction mixture was stirred at that temperature for 20 minutes. A solution of Example 35A (8.94 g, 32.8 mmol) in tetrahydrofuran (30 mL) was added dropwise to the reaction mixture at -78° C., and the solution was stirred at the same temperature for 30 minutes. Iodomethane (6.16 mL, 99 mmol) was then added to the reaction mixture in one portion, and the flask was allowed to warm to ambient temperature over 14 hours. The reaction mixture was partitioned between tert-butyl methyl ether and a saturated aqueous solution of NH$_4$Cl. The organic fraction was washed with brine, dried over sodium sulfate, filtered, and concentrated in vacuo. The resulting crude material was purified by flash chromatography using a 220 g silica gel cartridge eluted with 0-25% dichloromethane/heptane to afford the title compound (7.78 g, 83% yield). $^1$H NMR (501 MHz, CDCl$_3$) δ ppm 1.19-1.24 (m, 3H), 1.30 (t, J=7.1 Hz, 3H), 1.65-1.78 (m, 1H), 1.95-2.07 (m, 1H), 2.47 (dqd, J=8.1, 7.0, 5.9 Hz, 1H), 2.64 (ddd, J=9.1, 6.8, 2.6 Hz, 2H), 4.17 (q, J=7.1 Hz, 2H), 6.87-6.91 (m, 1H), 6.92 (d, J=1.7 Hz, 1H), 6.98 (d, J=8.1 Hz, 1H).

Example 35C ethyl 4-(6-bromo-2,2-difluoro-2H-1,3-benzodioxol-5-yl)-2-methylbutanoate To a solution of Example 35B (7.76 g, 27.1 mmol) in acetonitrile (60 mL) was added N-bromosuccinimide (5.31 g, 29.8 mmol) and iron(III) chloride (1.319 g, 8.13 mmol), and the resulting suspension was stirred at ambient temperature for 16 hours. The reaction mixture was diluted with dichloromethane and washed with a saturated aqueous solution of sodium bicarbonate. The organic fraction was dried over anhydrous sodium sulfate, filtered, and concentrated in vacuo. The residue was then purified by flash chromatography using a 220 g silica gel cartridge eluted with 0-20% dichloromethane/heptanes to afford the title compound (9.33 g, 94% yield). $^1$H NMR (501 MHz, CDCl$_3$) δ ppm 1.25 (d, J=7.0 Hz, 3H), 1.31 (t, J=7.1 Hz, 3H), 1.67-1.77 (m, 1H), 1.91-2.02 (m, 1H), 2.52 (dqd, J=8.0, 7.0, 5.8 Hz, 1H), 2.75 (dd, J=8.8, 7.4 Hz, 2H), 4.19 (q, J=7.1 Hz, 2H), 6.99 (s, 1H), 7.27 (s, 1H).

Example 35D 4-(6-bromo-2,2-difluoro-2H-1,3-benzodioxol-5-yl)-2-methylbutanal

To a cold (-78° C.) solution of Example 35C (2.5 g, 6.85 mmol) in hexanes (25 mL) was added a 1.0 M solution of diisobutylaluminum hydride in hexanes (7.19 mL, 7.19 mmol) dropwise over 1 hour, maintaining the temperature <-70° C. The reaction mixture was then stirred at the same temperature for an additional 2.5 hours. Methanol (2.5 mL) was added to the reaction mixture dropwise, maintaining the temperature <-70° C. The mixture was then allowed to warm to ambient temperature over 16 hours. The reaction mixture was filtered through diatomaceous earth and washed with hexanes. The combined filtrate was concentrated in vacuo, and the residue was purified by flash chromatography using an 80 g silica gel cartridge eluted with 0-10% tert-butyl methyl ether/heptanes to afford the title compound (0.863 g, 39% yield). $^1$H NMR (501 MHz, CDCl$_3$) δ ppm 1.23 (d, J=7.1 Hz, 3H), 1.62-1.73 (m, 1H), 1.97-2.10 (m, 1H), 2.45 (qd, J=6.9, 1.8 Hz, 1H), 2.76-2.80 (m, 2H), 7.00 (s, 1H), 7.29 (s, 1H), 9.70 (d, J=1.7 Hz, 1H).

Example 35E 2,2-difluoro-5-methyl-6,7-dihydro-2H,5H-indeno[5,6-d][1,3]dioxole-5-carbaldehyde A microwave tube with magnetic stir bar was charged with palladium (II) acetate (0.030 g, 0.133 mmol), (R)-(+)-2-[2-(diphenylphosphino)phenyl]-4-isopropyl-2-oxazoline (0.099 g, 0.266 mmol) and cesium carbonate (1.040 g, 3.19 mmol) under nitrogen. A solution of Example 35D (0.8538 g, 2.66 mmol) in N,N-dimethylformamide (5.00 mL) was added to the reaction mixture and sparged with a stream of nitrogen for 10 minutes. The reaction vial was capped, and the mixture was stirred at 80° C. for 43 hours. The reaction mixture was diluted with tert-butyl methyl ether and washed with water. The organic extracts were dried over anhydrous sodium sulfate, filtered, and concentrated in vacuo. The residue was purified by flash chromatography using a 40 g silica gel cartridge eluted with 0-25% tert-butyl methyl ether/heptanes to afford the title compound (0.489 g, 77% yield). $^1$H NMR (400 MHz, CDCl$_3$) δ ppm 1.43 (s, 3H), 2.01 (dt, J=13.1, 8.0 Hz, 1H), 2.59-2.71 (m, 1H), 3.01 (dd, J=8.3, 6.4 Hz, 2H), 6.85 (s, 1H), 6.98 (d, J=1.1 Hz, 1H), 9.56 (s, 1H).

Example 35F 2,2-difluoro-5-methyl-6,7-dihydro-2H,5H-indeno[5,6-d][1,3]dioxole-5-carboxylic acid To a solution of Example 35E (0.4814 g, 2.004 mmol) in tetrahydrofuran (10 mL) was added a 2.0 M solution of 2-methyl-2-butene in tetrahydrofuran (30.1 mL, 60.1 mmol) under nitrogen, and then a solution of sodium dihydrogen phosphate (1.683 g, 14.03 mmol) in water (5 mL) was added, followed by the addition of a solution of sodium chlorite (1.813 g, 20.04 mmol) in water (5 mL). The vial containing sodium chlorite was washed with water (3 mL), and the wash solution was added to the reaction mixture, resulting in a light yellow solution. The reaction mixture was stirred at ambient temperature for 100 minutes. The color of the reaction mixture changed from light yellow to almost colorless during this period. The reaction mixture was partitioned between tert-butyl methyl ether and 1 N NaOH solution. The aqueous layer was acidified with concentrated hydrochloric acid and then extracted with dichloromethane. The organic extracts were separated, washed with brine, dried over anhydrous sodium sulfate, filtered, and then concentrated in vacuo to give the title compound (0.412 g, 80% yield). $^1$H NMR (400 MHz, CDCl$_3$) δ ppm 1.56 (s, 3H), 1.95-2.09 (m, 1H), 2.76 (dddd, J=13.0, 8.4, 4.5, 1.1 Hz, 1H), 2.91 (ddd, J=15.8, 8.6, 4.5 Hz, 1H), 3.05 (dt, J=15.9, 7.9 Hz, 1H), 6.90 (s, 1H), 7.04 (s, 1H); MS (ESI-) m/z 255 (M-H)$^-$.

Example 35G methyl 3-{(2R,4R)-4-[(2,2-difluoro-5-methyl-6,7-dihydro-2H,5H-indeno[5,6-d][1,3]dioxole-5-carbonyl)amino]-3,4-dihydro-2H-1-benzopyran-2-yl}benzoate To a solution of the product of Example 35F (0.055 g, 0.216 mmol) in N,N-dimethylformamide (1.00 mL) was added N-[(dimethylamino)-1H-1,2,3-triazolo-[4,5-b]pyridin-1-ylmethylene]-N-methylmethanaminium hexafluorophosphate N-oxide (HATU, 0.123 g, 0.324 mmol), and the mixture was stirred at ambient temperature for 15 minutes. The product of Example 21C (0.069 g, 0.216 mmol) was added to the reaction mixture followed by addition of N,N-diisopropylethylamine (0.151 mL, 0.863 mmol), and the mixture was stirred at ambient temperature for 2 hours. The reaction mixture was then partitioned between tert-butyl methyl ether and water. The organic fraction was separated, dried over anhydrous sodium sulfate, filtered, and concentrated in vacuo. The residue was purified by flash chromatography using a 12 g silica gel cartridge eluted with 15-70% tert-butyl methyl ether/heptanes to give the title compound (0.0448 g, 40% yield). $^1$H NMR (400 MHz, CDCl$_3$) δ ppm 1.56 (s, 3H), 1.86 (dt, J=13.2, 11.2 Hz, 1H), 2.04-2.20 (m, 1H), 2.49-2.63 (m, 1H), 2.68 (ddd, J=12.7, 7.8, 4.6 Hz, 1H), 2.84-3.08 (m, 2H), 3.94 (d, J=0.9 Hz, 3H), 5.26 (dd, J=11.4, 1.8 Hz, 1H), 5.43 (d, J=8.8 Hz, 1H), 5.53 (td, J=10.4, 9.8, 6.2 Hz, 1H), 6.88 (s, 1H), 6.90-7.00 (m, 3H), 7.00-7.10 (m, 1H), 7.20 (dddd, J=8.1, 7.2, 1.8, 0.8 Hz, 1H), 7.48 (t, J=7.8 Hz, 1H), 7.58-7.66 (m, 1H), 8.01 (tt, J=9.1, 1.5 Hz, 1H), 8.10 (dt, J=6.9, 1.8 Hz, 1H); MS (ESI-) m/z 520 (M-H)$^-$.

Example 35H

3-{(2R,4R)-4-[(2,2-difluoro-5-methyl-6,7-dihydro-2H,5H-indeno[5,6-d][1,3]dioxole-5-carbonyl)amino]-3,4-dihydro-2H-1-benzopyran-2-yl}benzoic acid The product of Example 35G (0.042 g, 0.081 mmol) and potassium trimethylsilanolate (0.012 g, 0.097 mmol) were dissolved in tetrahydrofuran (2 mL) and stirred at 50° C. for 1.5 hours. The reaction mixture was partitioned between tert-butyl methyl ether and water. The aqueous layer was separated and then acidified with concentrated hydrochloric acid solution. The acidic aqueous layer was extracted with dichloromethane. The organic phase was separated, washed with brine, dried over anhydrous sodium sulfate, filtered, and concentrated in vacuo to supply the title compound (0.0298 g, 73% yield). $^1$H NMR (400 MHz, CDCl$_3$) δ ppm 1.19-1.37 (m, 2H), 1.61 (d, J=16.4 Hz, 3H), 1.87 (dt, J=13.2, 11.1 Hz, 1H), 2.05-2.26 (m, 1H), 2.54-2.79 (m, 2H), 2.84-3.13 (m, 2H), 5.34 (dd, J=11.4, 1.8 Hz, 1H), 5.51 (dd, J=8.9, 4.1 Hz, 1H), 5.60 (tt, J=13.9, 6.9 Hz, 1H), 6.88-7.12 (m, 5H), 7.17-7.27 (m, 1H), 7.53 (t, J=7.7 Hz, 1H), 7.72 (dt, J=7.8, 1.5 Hz, 1H), 8.10 (tt, J=9.0, 1.4 Hz, 1H), 8.20-8.32 (m, 1H); MS (ESI-) m/z 506 (M-H)$^-$.

Example 36

2'-methyl-5'-[(6-methyl-7,8-dihydro-2H,6H-indeno[4,5-d][1,3]dioxole-6-carbonyl)amino][1,1'-biphenyl]-3-carboxylic acid Example 36A 7,8-dihydro-2H,6H-indeno[4,5-d][1,3]dioxol-6-one To a solution of 4,5-dihydroxy-2,3-dihydro-1H-inden-1-one (964 mg, 5.9 mmol) in anhydrous N,N-dimethylformamide (19 mL) was added cesium carbonate (2.04 g, 6.25 mmol) and bromochloromethane (0.39 mL, 6 mmol), and the reaction mixture was stirred at 145° C. for 1.5 hours. The reaction mixture was diluted with dichloromethane and was washed with a 4% aqueous lithium chloride solution. The aqueous fraction was further extracted with dichloromethane, and the combined organic layers were passed through a hydrophobic frit. The filtrate was concentrated under reduced pressure to provide the title compound. $^1$H NMR (400 MHz, CDCl$_3$) δ ppm 7.40 (d, J=8.0 Hz, 1H), 6.88 (d, J=8.0 Hz, 1H), 6.10 (s, 2H), 3.08-3.04 (m, 2H), 2.72-2.68 (m, 2H).

Example 36B 7,8-dihydro-2H,6H-indeno[4,5-d][1,3]dioxole-6-carbonitrile

To a stirred suspension of Example 36A (988 mg, 5.61 mmol) and 1-((isocyanomethyl)sulfonyl)-4-methylbenzene (1.2 g, 6.2 mmol) in 1,2-dimethoxyethane (19 mL) cooled to 0° C. with an ice bath was added a warm solution of potassium tert-butoxide (1.26 g, 11.2 mmol) in tert-butanol (7.5 mL) dropwise over approximately 10 minutes. The stirring was continued with cooling for another 15 minutes, after which the ice bath was removed. After a further 95 minutes, aqueous ammonium chloride was added, and the mixture was extracted with ethyl acetate (2×). The combined organic layers were dried (MgSO$_4$), filtered, and concentrated under reduced pressure. The residue was purified by flash chromatography using a Biotage® SNAP 50 g silica column, eluted with 10-13% ethyl acetate in iso-hexane, to provide the title compound. $^1$H NMR (400 MHz, CDCl$_3$) δ ppm 6.90 (d, J=7.9 Hz, 1H), 6.74 (d, J=7.9 Hz, 1H), 5.97 (s, 2H), 4.04 (dd, J=8.0, 8.0 Hz, 1H), 3.06 (ddd, J=4.5, 8.6, 16.1 Hz, 1H), 2.92-2.83 (m, 1H), 2.63-2.54 (m, 1H), 2.40 (ddd, J=7.9, 12.8, 16.3 Hz, 1H).

Example 36C 6-methyl-7,8-dihydro-2H,6H-indeno[4,5-d][1,3]dioxole-6-carbonitrile

To a stirred solution of Example 36B in anhydrous tetrahydrofuran (5 mL) cooled to −60° C. with an acetone-dry ice bath, was added a solution of n-butyllithium in hexanes (1.2 mL, 3.1 mmol, 2.5 M). The solution was stirred for a further 5 minutes at −60° C., after which the acetone-dry ice bath was swapped for an ice bath at 0° C., and methyl iodide (0.196 mL, 3.1 mmol) was added. The resulting solution was left to warm to room temperature over 17 hours. Aqueous 1 N hydrochloric acid was added, and the mixture was extracted with diethyl ether (2×). The combined organic layers were dried (MgSO$_4$), filtered, and concentrated under reduced pressure to provide the title compound. $^1$H NMR (400 MHz, CDCl$_3$) δ ppm 6.85 (d, J=7.9 Hz, 1H), 6.75 (d, J=7.9 Hz, 1H), 5.97 (s, 2H), 3.06-2.88 (m, 2H), 2.72-2.64 (m, 1H), 2.21-2.14 (m, 1H), 1.63 (s, 3H).

Example 36D 6-methyl-7,8-dihydro-2H,6H-indeno[4,5-d][1,3]dioxole-6-carboxylic acid A suspension of Example 36C and 4 N sodium hydroxide solution (3 mL, 12 mmol) in methanol (3 mL) was stirred at 80° C. for 19 hours. Water and dichloromethane were added to the reaction mixture, and the phases were separated. The aqueous phase was acidified to pH 1-2 and extracted with dichloromethane (2×). The combined organic layers were passed through a hydrophobic frit, and the filtrate was concentrated under reduced pressure to provide the title compound. $^1$H NMR (400 MHz, CDCl$_3$) δ ppm 6.79 (d, J=8.0 Hz, 1H), 6.69 (d, J=8.0 Hz, 1H), 5.94 (dd, J=1.4, 6.6 Hz, 2H), 3.05-2.84 (m, 2H), 2.78-2.71 (m, 1H), 2.02-1.94 (m, 1H), 1.55 (s, 3H).

Example 36E tert-butyl 5'-amino-2'-methyl[1,1'-biphenyl]-3-carboxylate

A mixture of 4-methyl-3-(4,4,5,5-tetramethyl-1,3,2-dioxaborolan-2-yl)aniline (5.00 g, 19.8 mmol) and tert-butyl 3-bromobenzoate (5.08 g, 19.8 mmol) in 1,4-dioxane (110 mL) and water (30 mL) was degassed under a N$_2$ flow for 40 minutes. Potassium carbonate (13.7 g, 99 mmol) and 1,1'-bis(diphenylphosphino)ferrocene-palladium(II)dichloride dichloromethane complex (816 mg, 1.00 mmol) were added, and the mixture stirred at 80° C. for 7 hours. Water was then added to the reaction mixture, and it was extracted with ethyl acetate (2×). The combined organic layers were dried (MgSO$_4$), filtered, and concentrated under reduced pressure. The residue was purified by flash chromatography using a Biotage® SNAP 340 g silica column, eluted with 10-25% ethyl acetate in iso-hexane, to provide the title compound. $^1$H NMR (400 MHz, CDCl$_3$) δ ppm 7.97-7.93 (m, 2H), 7.49-7.41 (m, 2H), 7.06 (d, J=8.0 Hz, 1H), 6.64 (dd, J=2.4, 8.0 Hz, 1H), 6.60 (d, J=2.4 Hz, 1H), 3.60 (broad s, 2H), 2.14 (s, 3H), 1.60 (s, 9H).

Example 36F

2'-methyl-5'-[(6-methyl-7,8-dihydro-2H,6H-indeno[4,5-d][1,3]dioxole-6-carbonyl)amino][1,1'-biphenyl]-3-carboxylic acid To a solution of Example 36D (72 mg, 0.33 mmol) and Example 36E (93 mg, 0.33 mmol) in dichloromethane (2.2 mL) was added N,N-diisopropylethylamine (0.174 mL, 1 mmol) and N-[(dimethylamino)-1H-1,2,3-triazolo-[4,5-b]pyridin-1-ylmethylene]-N-methylmethanaminium hexafluorophosphate N-oxide (188 mg, 0.5 mmol), and the mixture was stirred at 40° C. for 17 hours. Dichloromethane and saturated sodium bicarbonate aqueous solution were added and the phases were separated. The aqueous phase was extracted with dichloromethane (2×). The combined organic layers were passed through a hydrophobic frit, and the filtrate was concentrated under reduced pressure. The resulting residue was dissolved in dichloromethane (1.5 mL) and trifluoroacetic acid (1.5 mL), and the resulting mixture was stirred for 2 hours before the mixture was concentrated. The resulting residue was purified by reversed-phase HPLC using a Waters Sunfire™ C18 column (150×19 mm id, 10 µm) eluted using a gradient of about 20 80% acetonitrile in 0.1% aqueous formic acid at a flow rate of 20 mL/minute with total run time was 28 minutes to provide the title compound. $^1$H NMR (400 MHz, DMSO-d$_6$) δ ppm 13.10 (broad s, 1H), 9.11 (s, 1H), 7.96-7.92 (m, 1H), 7.84 (s, 1H), 7.60-7.56 (m, 3H), 7.49 (d, J=2.4 Hz, 1H), 7.22 (d, J=8.4 Hz, 1H), 6.86 (d, J=7.9 Hz, 1H), 6.76 (d, J=7.9 Hz, 1H), 5.98 (d, J=2.3 Hz, 2H), 2.94-2.79 (m, 2H), 2.77-2.70 (m, 1H), 2.17 (s, 3H), 1.98 (ddd, J=6.4, 8.0, 12.5 Hz, 1H), 1.51 (s, 3H); MS (ESI+) m/z 430 (M+H)$^+$.

Example 37

2'-methyl-5'-{[(6R)-6-methyl-7,8-dihydro-2H,6H-indeno[4,5-d][1,3]dioxole-6-carbonyl]amino}[1,1'-biphenyl]-3-carboxylic acid Example 36F (70 mg, 0.163 mmol) was dissolved in ethanol (12 mL) and was chromatographed by supercritical fluid chromatography using a stacker 5 mL loop. 47 Injections were carried out using a YMC chiral amylose-C column (21×250 mm, 5 micron), eluted with 15% ethanol (0.1% diethylamine) in CO$_2$, at a 100 mL/minute flow rate, 120 bar, and 40° C. to yield the first eluting fraction which contained the title compound as the partial diethylamine salt. The chirality was arbitrarily assigned. $^1$H NMR (400 MHz, DMSO-d$_6$) δ ppm 9.10 (broad s, 1H), 7.91-7.89 (m, 1H), 7.82 (s, 1H), 7.56 (dd, J=2.3, 8.3 Hz, 1H), 7.48-7.45 (m, 3H), 7.20 (d, J=8.4 Hz, 1H), 6.87 (d, J=7.9 Hz, 1H), 6.76 (d, J=7.9 Hz, 1H), 5.98 (d, J=2.4 Hz, 2H), 2.89-2.82 (m, 3.5H), 2.80-2.67 (m, 2H), 2.17 (s, 3H), 1.98 (ddd, J=6.3, 8.1, 12.6 Hz, 1H), 1.51 (s, 3H), 1.15 (t, J=7.3 Hz, 4.5H); MS (ESI) m/z 430 (M+H)$^+$.

Example 38

2'-methyl-5'-{[(6S)-6-methyl-7,8-dihydro-2H,6H-indeno[4,5-d][1,3]dioxole-6-carbonyl]amino}[1,1'-biphenyl]-3-carboxylic acid Example 36F (70 mg, 0.163 mmol) was dissolved in ethanol (12 mL) and was purified by supercritical fluid chromatography using a stacker 5 mL loop. 47 Injections were carried out using a YMC chiral amylose-C column (21×250 mm, 5 micron), eluted with 15% ethanol (0.1% diethylamine) in $CO_2$, at a 100 mL/minute flow rate, 120 bar, and 40° C. to yield the second eluting fraction which contained the title compound as the partial diethylamine salt. The chirality was arbitrarily assigned. $^1$H NMR (400 MHz, DMSO-$d_6$) δ ppm 9.10 (broad s, 1H), 7.91-7.89 (m, 1H), 7.82 (s, 1H), 7.56 (dd, J=2.3, 8.3 Hz, 1H), 7.48-7.45 (m, 3H), 7.20 (d, J=8.4 Hz, 1H), 6.87 (d, J=7.9 Hz, 1H), 6.76 (d, J=7.9 Hz, 1H), 5.98 (d, J=2.4 Hz, 2H), 2.89-2.82 (m, 3.5H), 2.80-2.67 (m, 2H), 2.17 (s, 3H), 1.98 (ddd, J=6.3, 8.1, 12.6 Hz, 1H), 1.51 (s, 3H), 1.15 (t, J=7.3 Hz, 4.5H); MS (ESI) m/z 430 (M+H)$^+$.

Example 39

4-{(2R,4R)-4-[(2,2-difluoro-6-methyl-6,7-dihydro-2H-furo[2,3-e][1,3]benzodioxole-6-carbonyl)amino]-7-methoxy-3,4-dihydro-2H-1-benzopyran-2-yl}benzoic acid

Example 39A 2,2-difluoro-2H-1,3-benzodioxol-4-ol

A solution of 2,2-difluoro-1,3-benzodioxole (0.230 mL, 2.53 mmol) in tetrahydrofuran (4 mL) was cooled to <−70° C. and sec-butyllithium (1.988 mL, 2.78 mmol) was added dropwise at <−68° C. After 2 hours, trimethyl borate (0.339 mL, 3.04 mmol) was added at <−65° C. (exothermic, dropwise addition), and the mixture was then warmed to ambient temperature. Hydrogen peroxide (0.503 mL, 5.06 mmol) and sodium hydroxide (101 mg, 2.53 mmol) were added and after 20 minutes, the reaction temperature was raised to 50° C. for an additional 25 minutes. Water (2 mL) was added to give a homogeneous biphasic mixture. The mixture was extracted with tert-butyl methyl ether (3×20 mL) and ethyl acetate (2×20 mL). The combined organic fractions were extracted with 2 N NaOH (3×10 mL). The combined aqueous fractions were acidified with 2 N HCl (40 mL) and extracted with tert-butyl methyl ether (150 mL). This organic phase was combined with the previous organic fractions, and the combined fractions were dried ($Na_2SO_4$) and concentrated. The residue was purified by flash chromatography on silica gel, eluted with 0-50% tert-butyl methyl ether/heptanes to obtain the title compound (364 mg, 2.091 mmol, 83% yield). $^1$H NMR (400 MHz, CDCl$_3$) δ ppm 6.93 (t, J=8.3 Hz, 1H), 6.67 (m, 2H), 5.84 (br s, 1H).

Example 39B 2,2-difluoro-5,7-diiodo-2H-1,3-benzodioxol-4-ol

A solution of Example 39A (359 mg, 2.062 mmol) in methanol (3.6 mL) was cooled to <5° C. and N,N diisopropylethylamine (0.396 mL, 2.268 mmol) and iodine monochloride (0.103 mL, 2.062 mmol) were added (dropwise at <5° C.). After 30 minutes the reaction was quenched with saturated aqueous $Na_2S_2O_3$ (10 mL), and the mixture was partitioned between water (10 mL) and tert-butyl methyl ether (30 mL). The organic layer was washed with brine (5 mL), dried over $Na_2SO_4$, filtered, and concentrated. The residue was purified by silica gel column chromatography, eluting with 0-20% tert-butyl methyl ether/heptanes to give the title compound (355 mg, 0.834 mmol, 40% yield). $^1$H NMR (501 MHz, DMSO-$d_6$) δ ppm 11.55 (s, 1H), 7.81 (s, 1H).

Example 39C 2,2-difluoro-5-iodo-2H-1,3-benzodioxol-4-ol

A solution of Example 39B (342 mg, 0.803 mmol) in tetrahydrofuran (3.4 mL) was cooled to 10° C. and sodium hydride (32.1 mg, 60 weight %, 0.803 mmol) was added at <20° C. After 5 minutes, the reaction mixture was cooled further to <−75° C. and n-butyllithium (0.321 mL, 2.5 M, 0.803 mmol) was added. Methanol (1 mL) was added after 10 minutes at <−65° C., and then saturated aqueous $NH_4Cl$ (10 mL) was added. The mixture was extracted with tert-butyl methyl ether (20 mL). The organic layer was washed with brine (5 mL), dried ($Na_2SO_4$), filtered, and concentrated. The residue was purified by silica gel chromatography, eluting with 0-20% tert-butyl methyl ether/heptanes to give the title compound (178 mg, 0.593 mmol, 74% yield). $^1$H NMR (501 MHz, DMSO-$d_6$) δ ppm 11.33 (s, 1H), 7.54 (d, J=8.5 Hz, 1H), 6.75 (d, J=8.4 Hz, 1H).

Example 39D ethyl 2-{[(2,2-difluoro-5-iodo-2H-1,3-benzodioxol-4-yl)oxy]methyl}prop-2-enoate A solution of Example 39C (404 mg, 1.597 mmol) in acetonitrile (4 mL) was stirred at ambient temperature and cesium carbonate (780 mg, 2.395 mmol) and ethyl-2-(bromomethyl)acrylate (0.265 mL, 1.916 mmol) were added (exotherm to 26° C.). After 20 minutes, the mixture was partitioned between tert-butyl methyl ether (30 mL) and water (10 mL). The organic fraction was washed with brine (5 mL), dried ($Na_2SO_4$), filtered, and concentrated. The residue was purified by flash chromatography on silica gel, eluting with 0-10% tert-butyl methyl ether/heptanes) to obtain the title compound (468 mg, 1.282 mmol, 80% yield). $^1$H NMR (400 MHz, CDCl$_3$) δ ppm 7.26 (d, J=8.6 Hz, 1H), 6.66 (d, J=8.6 Hz, 1H), 6.43 (d, J=1.2 Hz, 1H), 6.08 (q, J=1.5 Hz, 1H), 5.05 (t, J=1.4 Hz, 2H), 4.27 (q, J=7.1 Hz, 2H), 1.31 (t, J=7.1 Hz, 3H).

Example 39E ethyl 2,2-difluoro-6-methyl-6,7-dihydro-2H-furo[2,3-e][1,3]benzodioxole-6-carboxylate A solution of ethyl 2-(((2,2-difluoro-5-iodobenzo[d][1,3]dioxol-4-yl)oxy)methyl)acrylate (181 mg, 0.439 mmol), acetonitrile (4.6 mL), tributylamine (0.230 mL, 0.966 mmol), and formic acid (0.019 mL, 0.483 mmol) was stirred at room temperature with a nitrogen sparge for 10 minutes. Palladium(II) acetate (9.86 mg, 0.044 mmol) was added, and the reaction mixture was heated at 70° C. for 24 hours and then cooled to room temperature for 60 hours. The reaction mixture was concentrated and purified by silica gel chromatography (0-10% tert-butyl methyl ether/heptanes to give the title compound (42.2 mg, 0.147 mmol, 34% yield). $^1$H NMR (400 MHz, CDCl$_3$) δ ppm 7.02 (d, J=8.0 Hz, 1H), 6.62 (dd, J=8.2, 1.1 Hz, 1H), 5.21 (d, J=9.2 Hz, 1H), 4.39 (dd, J=9.1, 1.1 Hz, 1H), 4.20 (q, J=7.1 Hz, 2H), 1.62 (s, 3H), 1.31-1.18 (m, 3H).

Example 39F 2,2-difluoro-6-methyl-6,7-dihydro-2H-furo[2,3-e][1,3]benzodioxole-6-carboxylic acid The product of Example 39E (40.3 mg, 0.141 mmol) and potassium trimethylsilanolate (41.2 mg, 90% purity, 0.289 mmol) were dissolved in tetrahydrofuran (1 mL), and the mixture was stirred at ambient temperature for 2 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (28.0 mg, 58%). $^1$H NMR (500 MHz, DMSO-d$_6$) δ ppm 13.08 (s, 1H), 7.15 (d, J=8.2 Hz, 1H), 6.93 (d, J=8.2 Hz, 1H), 5.12 (d, J=9.1 Hz, 1H), 4.48 (d, J=9.1 Hz, 1H), 1.55 (s, 3H); MS (ESI-) m/z 257 (M-H)$^-$.

Example 39G methyl 4-{(2R,4R)-4-[(2,2-difluoro-6-methyl-6,7-dihydro-2H-furo[2,3-e][1,3]benzodioxole-6-carbonyl)amino]-7-methoxy-3,4-dihydro-2H-1-benzopyran-2-yl}benzoate The product from Example 39F (21.4 mg, 0.083 mmol), the product from Example 15C (36.0 mg, 0.103 mmol) and N-(3-dimethylaminopropyl)-N'-ethylcarbodiimide hydrochloride (32.8 mg, 0.171 mmol) were dissolved in N,N-dimethylformamide (0.5 mL) and pyridine (0.5 mL). The reaction mixture was stirred at 60° C. for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (26.2 mg, 57%). $^1$H NMR (400 MHz, DMSO-d$_6$) δ ppm 8.10-7.95 (m, 3H), 7.60 (dd, J=8.1, 5.7 Hz, 2H), 7.21 (dd, J=15.0, 8.2 Hz, 1H), 7.01 (d, J=8.5 Hz, 0.5H), 6.92 (dd, J=15.2, 8.2 Hz, 1H), 6.79 (d, J=8.5 Hz, 0.5H), 6.58-6.43 (m, 2H), 5.47-5.28 (m, 2H), 5.19 (dd, J=8.9, 4.0 Hz, 1H), 4.48 (dd, J=8.9, 2.1 Hz, 1H), 3.87 (d, J=1.2 Hz, 3H), 3.71 (d, J=2.2 Hz, 3H), 2.26-1.97 (m, 2H), 1.59 (d, J=7.9 Hz, 3H); MS (ESI-) m/z 552.1 (M-H)$^-$.

Example 39H

4-{(2R,4R)-4-[(2,2-difluoro-6-methyl-6,7-dihydro-2H-furo[2,3-e][1,3]benzodioxole-6-carbonyl)amino]-7-methoxy-3,4-dihydro-2H-1-benzopyran-2-yl}benzoic acid The product of Example 39G (22.9 mg, 0.041 mmol) and potassium trimethylsilanolate (34.5 mg, 90% purity, 0.242 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (16.1 mg, 72%). $^1$H NMR (400 MHz, DMSO-d$_6$) δ ppm 12.96 (s, 1H), 8.06 (dd, J=8.8, 5.1 Hz, 1H), 7.99 (dd, J=8.3, 3.5 Hz, 2H), 7.57 (dd, J=8.1, 5.5 Hz, 2H), 7.22 (dd, J=15.3, 8.2 Hz, 1H), 7.04-6.76 (m, 2H), 6.57-6.43 (m, 2H), 5.46-5.28 (m, 2H), 5.19 (dd, J=9.0, 4.9 Hz, 1H), 4.48 (dd, J=9.0, 2.0 Hz, 1H), 3.71 (d, J=2.3 Hz, 3H), 2.27-1.93 (m, 2H), 1.60 (d, J=8.0 Hz, 3H); MS (ESI-) m/z 538.1 (M-H)$^-$.

Example 40 methyl 3-{3-cyclopropyl-5-[(2,2-difluoro-7-methyl-6,7-dihydro-2H-furo[2,3-f][1,3]benzodioxole-7-carbonyl)amino]-6-oxopyridazin-1(6H)-yl}benzoate The product of Example 1E (50.9 mg, 0.197 mmol) was dissolved in dichloromethane (1 mL). Oxalyl chloride (80 μL) and N,N-dimethylformamide (25 μL) were added which resulted in bubbling of the reaction mixture. The reaction mixture was stirred at ambient temperature for 1 hour and then concentrated. The residue was dissolved in dichloromethane (1 mL) and concentrated two times. The residue was dissolved in dichloromethane (1 mL) and pyridine (0.5 mL). The product of Example 28C (54.9 mg, 0.192 mmol) was added, and the reaction mixture was stirred at 60° C. for 16 hours. The reaction mixture was concentrated, and the residue was purified by reverse-phase preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (73.7 mg, 73%). $^1$H NMR (501 MHz, DMSO-d$_6$) δ 8.98 (s, 1H), 8.14 (t, J=1.9 Hz, 1H), 7.99 (dt, J=7.8, 1.4 Hz, 1H), 7.87 (s, 1H), 7.84 (ddd, J=8.6, 2.2, 1.1 Hz, 1H), 7.68-7.62 (m, 2H), 7.16 (s, 1H), 5.00 (d, J=9.5 Hz, 1H), 4.45 (d, J=9.5 Hz, 1H), 3.88 (s, 3H), 2.04 (tt, J=8.3, 4.9 Hz, 1H), 1.67 (s, 3H), 1.01-0.89 (m, 2H), 0.80 (ddd, J=6.4, 5.0, 3.5 Hz, 2H); MS (ESI+) m/z 526 (M+H)$^+$.

Example 41

(7S)—N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide The product from Example 3A (0.052 g, 0.2 mmol) in 0.5 mL CH$_2$Cl$_2$ was treated with DMF (0.025 mL, 0.320 mmol) and then in a very slow dropwise fashion with oxalyl chloride (0.077 mL, 0.880 mmol). After the addition was complete, the reaction stirred at room temperature for 1 hour and was then concentrated in vacuo. Excess oxalyl chloride was chased with CH$_2$Cl$_2$ (3×0.5 mL), then the residue was taken up in 0.5 mL CH$_2$Cl$_2$ and treated with pyridine (0.485 ml, 6.00 mmol) and the product from Example 24F (0.060 g, 0.200 mmol). The reaction mixture was then heated at 60° C. overnight. After this time, the reaction mixture was concentrated in vacuo, and the residue was purified by reverse-phase preparative HPLC on a Waters Nova-Pak®

HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (0.002, g, 2% yield). $^1$H NMR (500 MHz, DMSO-d$_6$) δ 9.05 (s, 1H), 8.48 (s, 1H), 7.86-7.75 (m, 2H), 7.67 (s, 1H), 7.59-7.41 (m, 3H), 7.18 (s, 1H), 5.02 (d, J=9.5 Hz, 1H), 4.58-4.34 (m, 3H), 4.14 (dd, J=13.2, 5.8 Hz, 1H), 4.05 (dd, J=8.6, 6.1 Hz, 1H), 3.87 (dd, J=8.6, 5.1 Hz, 1H), 1.70 (s, 3H), 1.34 (s, 3H), 1.24 (s, 3H). MS (ESI$^-$) m/z 540.1 (M−H)$^-$.

Example 42

4-[(2R,4R)-7-methoxy-4-{[(6S)-6-methyl-7,8-di-hydro-2H,6H-indeno[4,5-d][1,3]dioxole-6-carbonyl]amino}-3,4-dihydro-2H-1-benzopyran-2-yl]benzoic acid Example 42A (6S)-6-methyl-7,8-dihydro-2H,6H-indeno[4,5-d][1,3]dioxole-6-carboxylic acid Example 36D (235 mg, 1.06 mmol) was dissolved in methanol (3 mL) and chromatographed by Supercritical Fluid Chromatography. 12 Injections were carried out using an YMC amylose-C column (21×250 mm, 5 micron), 15% methanol in CO$_2$, at a 100 mL/minute flow rate, at 120 bar, and at 40° C. to yield the second eluting fractions which contained the title compound. The stereochemistry of the compound was confirmed by X-ray analysis. $^1$H NMR (400 MHz, CDCl$_3$) δ ppm 6.79 (d, J=7.9 Hz, 1H), 6.69 (d, J=8.0 Hz, 1H), 5.94 (dd, J=1.5, 6.5 Hz, 2H), 3.05-2.84 (m, 2H), 2.78-2.70 (m, 1H), 2.02-1.94 (m, 1H), 1.53 (s, 3H); 89.2% purity, 100% ee.

Example 42B methyl 4-[(2R,4R)-7-methoxy-4-{[(6S)-6-methyl-7,8-dihydro-2H,6H-indeno[4,5-d][1,3]dioxole-6-carbonyl]amino}-3,4-dihydro-2H-1-benzopyran-2-yl]benzoate The product from Example 42A (13.8 mg, 0.063 mmol), the product from Example 15C (27.7 mg, 0.079 mmol) and N-(3-dimethylaminopropyl)-N'-ethylcarbodiimide hydrochloride (37.1 mg, 0.194 mmol) were dissolved in N,N-dimethylformamide (0.5 mL) and pyridine (0.5 mL). The reaction mixture was stirred at 60° C. for 17 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (26.2 mg, 57%). $^1$H NMR (501 MHz, DMSO-d$_6$) δ 8.04-7.96 (m, 2H), 7.61-7.57 (m, 2H), 7.53 (d, J=8.9 Hz, 1H), 6.96 (dd, J=8.5, 1.1 Hz, 1H), 6.80 (d, J=7.9 Hz, 1H), 6.73 (d, J=7.9 Hz, 1H), 6.52 (dd, J=8.6, 2.5 Hz, 1H), 6.45 (d, J=2.5 Hz, 1H), 5.95 (q, J=1.1 Hz, 2H), 5.44-5.27 (m, 2H), 3.87 (s, 3H), 3.70 (s, 3H), 2.90-2.73 (m, 2H), 2.69-2.58 (m, 1H), 2.12-2.00 (m, 2H), 1.96-1.86 (m, 1H), 1.44 (s, 3H). MS (ESI+) m/z 516 (M+H)$^+$.

Example 42C

4-[(2R,4R)-7-methoxy-4-{[(6S)-6-methyl-7,8-dihydro-2H,6H-indeno[4,5-d][1,3]dioxole-6-carbonyl]amino}-3,4-dihydro-2H-1-benzopyran-2-yl]benzoic acid The product of Example 42B (18.3 mg, 0.035 mmol) and potassium trimethylsilanolate (17.5 mg, 90% purity, 0.123 mmol) were dissolved in tetrahydrofuran (1 mL) and stirred at ambient temperature for 16 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (16.1 mg, 72%). $^1$H NMR (400 MHz, DMSO-d$_6$) δ 12.95 (s, 1H), 8.00-7.93 (m, 2H), 7.59-7.50 (m, 3H), 6.96 (d, J=8.6 Hz, 1H), 6.81 (d, J=7.9 Hz, 1H), 6.73 (d, J=7.9 Hz, 1H), 6.52 (dd, J=8.6, 2.6 Hz, 1H), 6.44 (d, J=2.5 Hz, 1H), 5.95 (s, 2H), 5.41-5.26 (m, 2H), 3.70 (s, 3H), 2.92-2.73 (m, 2H), 2.65 (ddd, J=13.3, 8.3, 5.3 Hz, 1H), 2.13-1.99 (m, 2H), 1.91 (ddd, J=12.6, 8.2, 6.6 Hz, 1H), 1.44 (s, 3H).); MS (ESI−) m/z 501 (M−H)$^-$.

Example 43

4-[(2R,4S,6R)-4-{[(7R)-2,2-difluoro-7-methyl-6,7-dihydro-2H-furo[2,3-f][1,3]benzodioxole-7-carbonyl]amino}-6-methyloxan-2-yl]benzoic acid and 4-[(2S,4R,6S)-4-{[(7R)-2,2-difluoro-7-methyl-6,7-dihydro-2H-furo[2,3-f][1,3]benzodioxole-7-carbonyl]amino}-6-methyloxan-2-yl]benzoic acid Example 43A rac-methyl 4-[(2R,6R)-6-methyl-4-oxooxan-2-yl]benzoate To a solution of methyl 4-formylbenzoate (7.27 g, 44.3 mmol) in toluene (100 mL) at −72° C. (internal) was added boron trifluoride diethyl etherate (1.112 mL, 8.85 mmol). After 15 minutes, (E)-trimethyl(penta-1,3-dien-2-yloxy)silane (6.92 g, 44.3 mmol) was added dropwise in less than 5 minutes. Stirring continued at −65° C. (internal). The reaction was allowed to warm to room temperature slowly and stirred overnight. To this mixture was added 1 M HCl (20 mL) and vigorously stirred for 36 hours. The layers were partitioned in ethyl acetate and water. The organic phase was washed with brine and dried over MgSO$_4$, filtered, and concentrated. The residue was then taken up in tetrahydrofuran (50 mL) and treated with tetrabutyl ammonium fluoride in THF (1M, 20 mL, 20 mmol). After 2 hours the reaction was complete. The reaction mixture was partitioned between ether and 1 M HCl. The organic phase was washed with saturated NaHCO$_3$ and brine sequentially, dried over MgSO$_4$, filtered, and concentrated. The residue was purified by chromatography, eluting with ether/CH$_2$Cl$_2$ to yield the product (10.99 g, 90%). $^1$H NMR (501 MHz, C$_6$D$_6$) δ 8.16-8.10 (m, 2H), 7.13-7.08 (m, 2H), 4.11 (dd, J=11.8, 2.7 Hz, 1H), 3.50 (s, 3H), 3.28 (ddd, J=11.7, 6.0, 2.5 Hz, 1H), 2.32 (ddd, J=14.3, 2.7, 2.0 Hz, 1H), 2.09 (dt, J=14.3, 2.2 Hz, 1H), 1.97 (ddd, J=14.3, 11.8, 0.9 Hz, 1H), 1.85-1.71 (m, 1H), 1.00 (d, J=6.1 Hz, 3H). MS(ESI+) m/z=266 (M+NH$_4$)$^+$.

Example 43B rac-methyl 4-[(2R,4S,6R)-4-amino-6-methyloxan-2-yl]benzoate

To the product of Example 43A (6.0 g, 19.33 mmol) and O-methylhydroxylamine hydrochloride (4.84 g, 58.0 mmol) in CH$_2$Cl$_2$ (50 mL) and methanol (50 mL) at room temperature was added acetic acid (3.41 mL, 58.0 mmol) and stirred overnight. The reaction mixture was concentrated and the residue partitioned between saturated NaHCO$_3$ and CH$_2$Cl$_2$. The organic phase was dried (Na$_2$SO$_4$), filtered, and concentrated. The residue was dissolved in acetic acid (55 mL), to which was added 5% Pt/C wet (0.80 g, 1.685 mmol) in a 250 mL stainless steel pressure bottle and shaken for 16 hours at 30 psi hydrogen at room temperature. Added more 5% Pt/C wet (0.8 g, 1.685 mmol) and continue hydrogenation for 16 hours. Added more 5% Pt/C wet, (0.8 g, 1.685 mmol) and hydrogenated for another 32 hours. Solvent was removed under reduced pressure. The crude product (4 g). was dissolved in tert-butyl methyl ether (10 mL) and 4M HCl in dioxane (8 mL) was added slowly. The white solid precipitated was collected by filtration, and dried to yield the title compound as the HCl salt (1.6 g, 29%). MS(ESI+) m/z=250 (M+H)$^+$.

Example 43C methyl 4-[(2R,4S,6R)-4-{[(7R)-2,2-difluoro-7-methyl-6,7-dihydro-2H-furo[2,3-f][1,3]benzodioxole-7-carbonyl]amino}-6-methyloxan-2-yl]benzoate and methyl 4-[(2S,4R,6S)-4-{[(7R)-2,2-difluoro-7-methyl-6,7-dihydro-2H-furo[2,3-f][1,3]benzodioxole-7-carbonyl]amino}-6-methyloxan-2-yl]benzoate To Example 3B (50 mg, 0.194 mmol) in N,N-dimethylformamide (2 mL) was added HATU (110 mg, 0.291 mmol). The mixture was stirred for 10 minutes, and then the product of Example 43B (55.3 mg, 0.194 mmol) was added, following by the addition of N-ethyl-N-isopropylpropan-2-amine (0.135 mL, 0.775 mmol). The mixture was stirred at 35° C. for 2 hours. The mixture was loaded on a 24 g silica gel cartridge directly without work-up and purified by chromatography, eluting with ethyl acetate in heptane at 5-40% gradient to yield the title compound (70 mg, 0.143 mmol, 73.8% yield). $^1$H NMR (400 MHz, CDCl$_3$) δ 8.03-7.93 (m, 2H), 7.46-7.34 (m, 2H), 6.83 (d, J=14.8 Hz, 1H), 6.62 (d, J=6.2 Hz, 1H), 5.34 (d, J=8.0 Hz, 1H), 4.81 (dd, J=15.9, 9.2 Hz, 1H), 4.50 (dt, J=11.3, 2.5 Hz, 1H), 4.29 (dd, J=9.2, 5.5 Hz, 1H), 4.15 (tdt, J=12.2, 8.4, 4.4 Hz, 1H), 3.90 (d, J=2.4 Hz, 3H), 3.71 (tdd, J=10.1, 5.4, 3.1 Hz, 1H), 2.12 (dddd, J=13.8, 12.0, 5.8, 3.8 Hz, 1H), 1.95 (dtd, J=11.9, 4.2, 1.9 Hz, 1H), 1.58 (d, J=5.5 Hz, 3H), 1.33-1.24 (m, 3H), 1.22-0.98 (m, 2H). MS(ESI–): m/z=488 (M–H)$^-$.

Example 43D

4-[(2R,4S,6R)-4-{[(7R)-2,2-difluoro-7-methyl-6,7-dihydro-2H-furo[2,3-f][1,3]benzodioxole-7-carbonyl]amino}-6-methyloxan-2-yl]benzoic acid and 4-[(2S,4R,6S)-4-{[(7R)-2,2-difluoro-7-methyl-6,7-dihydro-2H-furo[2,3-f][1,3]benzodioxole-7-carbonyl]amino}-6-methyloxan-2-yl]benzoic acid Example 43C (55 mg, 0.112 mmol) in methanol (1 mL) was added lithium hydroxide (16.15 mg, 0.674 mmol) in water (0.3 mL). The mixture was stirred at room temperature overnight. Solvent was removed in vacuo and water was added (2 mL). The pH was adjusted to 1-2 with the addition of 2N HCl. The precipitated white solid was collected by filtration and dried in oven to the title compound (41 mg, 0.086 mmol, 77% yield). $^1$H NMR (400 MHz, CDCl$_3$) δ 8.16-7.99 (m, 2H), 7.52-7.33 (m, 2H), 6.84 (d, J=14.1 Hz, 1H), 6.63 (d, J=6.0 Hz, 1H), 5.37 (d, J=7.9 Hz, 1H), 4.82 (dd, J=16.1, 9.2 Hz, 1H), 4.52 (dt, J=11.3, 2.4 Hz, 1H), 4.30 (dd, J=9.3, 5.3 Hz, 1H), 4.17 (tdt, J=12.0, 8.3, 4.4 Hz, 1H), 3.72 (ddt, J=11.0, 6.4, 2.4 Hz, 1H), 2.15 (dtd, J=12.5, 4.3, 1.9 Hz, 1H), 1.95 (ddq, J=11.2, 4.9, 2.4 Hz, 1H), 1.58 (d, J=5.2 Hz, 3H), 1.29 (dd, J=6.2, 5.1 Hz, 3H), 1.23-1.03 (m, 2H); MS(ESI–): m/z=474 (M–H)$^-$.

Example 44

4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid The diastereomeric mixture of the product from Example 34 (104 mg, 193 mmol) was separated by Supercritical Fluid Chromatography using a Whelk-O1 (S,S) 21×250 mm, 5 micron column eluted with 5-30% methanol/CO$_2$, at 3 mL/minute flow rate over 10 minutes, and at 150 bar, to yield the first eluting diastereomer which contained the title compound (24 mg, 0.045 mmol, 17.59% yield). Chirality was arbitrarily assigned. $^1$H NMR (400 MHz, CDCl$_3$) δ 8.02 (s, 2H), 7.44 (d, J=7.6 Hz, 2H), 7.35 (dd, J=14.0, 6.5 Hz, 4H), 7.28 (d, J=6.7 Hz, 1H), 6.80 (s, 1H), 6.60 (s, 1H), 5.41 (d, J=7.8 Hz, 1H), 4.80 (d, J=9.3 Hz, 1H), 4.64 (t, J=13.9 Hz, 2H), 4.40-4.25 (m, 2H), 2.18 (d, J=12.0 Hz, 2H), 1.57 (s, 3H), 1.33 (td, J=22.8, 21.5, 10.5 Hz, 2H), (ESI–): m/z=536 (M–H)$^-$.

Example 45

4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid The diastereomeric mixture of the product from Example 34 (104 mg, 193 mmol) was separated by Supercritical Fluid Chromatography using a Whelk-O1 (S,S) 21×250 mm, 5 micron column eluted with 5-30% methanol/CO$_2$, at 3 mL/minute flow rate over 10 minutes, and at 150 bar, to yield the second eluting diastereomer which contained the title compound (25 mg, 0.047 mmol, 18.32% yield). Chirality was arbitrarily assigned. $^1$H NMR (400 MHz, Chloroform-d) δ 8.03 (s, 2H), 7.44 (s, 2H), 7.39-7.26 (m, 5H), 6.81 (s, 1H), 6.60 (s, 1H), 5.42 (d, J=7.7 Hz, 1H), 4.81 (d, J=9.2 Hz, 1H), 4.62 (t, J=15.0 Hz, 2H), 4.27 (d, J=9.2 Hz, 3H), 2.32-2.04 (m, 2H), 1.57 (s, 1H), 1.32 (p, J=14.0, 13.2 Hz, 3H); (ESI–): m/z=536 (M–H)$^-$.

Example 46

4-[(2R,4R)-7-methoxy-4-{[(6R)-6-methyl-7,8-dihydro-2H,6H-indeno[4,5-d][1,3]dioxole-6-carbonyl]amino}-3,4-dihydro-2H-1-benzopyran-2-yl]benzoic acid

Example 46A (6R)-6-methyl-7,8-dihydro-2H,6H-indeno[4,5-d][1,3]dioxole-6-carboxylic acid Example 36D (235 mg, 1.06 mmol) was dissolved in methanol (3 mL) and purified by Supercritical Fluid Chromatography. 12 Injections were carried out using a YMC amylose-C (21×250 mm, 5 micron) column, 15% methanol in CO$_2$, at a 100 mL/minute flow rate, at 120 bar and at 40° C. to yield the first eluted enantiomer which contained the title compound. $^1$H NMR (400 MHz, CDCl$_3$) δ ppm 6.79 (d, J=7.9 Hz, 1H), 6.69 (d, J=7.9 Hz, 1H), 5.94 (dd, J=1.4, 6.7 Hz, 2H), 3.05-2.84 (m, 2H), 2.78-2.70 (m, 1H), 2.02-1.93 (m, 1H), 1.53 (s, 3H); 95.9% purity, 100% ee.

Example 46B methyl 4-[(2R,4R)-7-methoxy-4-{[(6R)-6-methyl-7,8-dihydro-2H,6H-indeno[4,5-d][1,3]dioxole-6-carbonyl]amino}-3,4-dihydro-2H-1-benzopyran-2-yl]benzoate The product from Example 46A (17.8 mg, 0.079 mmol), the product from Example 15C (29.7 mg, 0.085 mmol) and N-(3-dimethylaminopropyl)-N'-ethylcarbodiimide hydrochloride (28.4 mg, 0.148 mmol) were dissolved in N,N-dimethylformamide (0.5 mL) and pyridine (0.5 mL). The reaction mixture was stirred at 60° C. for 18 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (20.7 mg, 51%). $^1$H NMR (400 MHz, DMSO-d$_6$) δ 8.05-7.95 (m, 2H), 7.64-7.56 (m, 2H), 7.54 (d, J=8.9 Hz, 1H), 6.83-6.68 (m, 3H), 6.50-6.39 (m, 2H), 6.00-5.92 (m, 2H), 5.35 (ddt, J=26.4, 10.1, 4.3 Hz, 2H), 3.86 (d, J=4.0 Hz, 3H), 3.69 (d, J=4.0 Hz, 3H), 2.93-2.73 (m, 2H), 2.66 (ddd, J=12.9, 8.2, 4.8 Hz, 1H), 2.20-1.99 (m, 2H), 1.91 (dt, J=12.7, 7.9 Hz, 1H), 1.44 (s, 3H). MS (ESI−) m/z 514 (M−H)$^-$.

Example 46C

4-[(2R,4R)-7-methoxy-4-{[(6R)-6-methyl-7,8-dihydro-2H,6H-indeno[4,5-d][1,3]dioxole-6-carbonyl]amino}-3,4-dihydro-2H-1-benzopyran-2-yl]benzoic acid The product of Example 46B (20.7 mg, 0.040 mmol) and potassium trimethylsilanolate (17.5 mg, 90% purity, 0.123 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (12.1 mg, 60%). $^1$H NMR (501 MHz, DMSO-d$_6$) δ 12.97 (s, 1H), 8.02-7.92 (m, 2H), 7.59-7.56 (m, 2H), 7.54 (d, J=8.9 Hz, 1H), 6.80-6.71 (m, 3H), 6.46 (dd, J=8.5, 2.5 Hz, 1H), 6.43 (d, J=2.5 Hz, 1H), 5.97 (dd, J=6.9, 1.1 Hz, 2H), 5.38 (dd, J=11.3, 2.0 Hz, 1H), 5.35-5.27 (m, 1H), 3.70 (s, 3H), 2.90-2.74 (m, 2H), 2.66 (ddd, J=12.8, 8.2, 4.8 Hz, 1H), 2.15 (ddd, J=12.9, 6.2, 2.2 Hz, 1H), 2.07 (s, 1H), 1.91 (ddd, J=12.5, 8.3, 7.2 Hz, 1H), 1.44 (s, 3H); MS (ESI−) m/z 501 (M−H)$^-$.

Example 47

4-[(2R,4R)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoic acid Example 47A (2S)-2-amino-N-(2,4,6-trimethylbenzene-1-sulfonyl)propanamide Under a dry nitrogen atmosphere, to a stirred solution of 2,4,6-trimethylbenzenesulfonamide (16.4 g, 82 mmol) in dichloromethane (200 ml) were added (S)-2-((tert-butoxycarbonyl)amino)propanoic acid (17.13 g, 91 mmol), dimethylaminopyridine (11.06 g, 91 mmol) and N-(3-dimethylaminopropyl)-N'-ethylcarbodiimide (31.6 g, 165 mmol). The resulting mixture was stirred at room temperature for 16 hours before partitioning between ethyl acetate (500 mL) and aqueous HCl (1 M, 200 mL). The organic layer was washed with half-saturated brine, dried over Na$_2$SO$_4$, filtered, and concentrated in vacuo to give the intermediate (S)-tert-butyl (1-oxo-1-(2,4,6-trimethylphenylsulfonamido)propan-2-yl)carbamate (26.5 g, 71.5 mmol, 87% yield). Under a dry nitrogen atmosphere, to a stirred solution (S)-tert-butyl (1-oxo-1-(2,4,6-trimethylphenylsulfonamido)propan-2-yl)carbamate (6.14 g, 16.57 mmol) in dichloromethane (10 mL) were added trifluoroacetic acid (10 mL, 130 mmol) dropwise. The resulting mixture was stirred at room temperature for 2 hours. The solvent and excess of trifluoroacetic acid were removed in vacuo. The residue was dissolved in dichloromethane (10 mL), and neutralized with NH$_4$OH. The aqueous layer was extracted with dichloromethane (3×50 mL). The combined organic layers were dried with Na$_2$SO$_4$, filtered, and concentrated to yield the title compound (4.2 g, 94%): $^1$H NMR: (400 MHz, DMSO-d$_6$) δ 7.06 (s, 2H), 3.96 (q, J=7.2 1H), 2.69 (s, 6H), 2.31 (s, 3H), 1.50 (d, J=7.2 3H); LC-MS: MS (M+1)=271.

Example 47B methyl 4-(4-oxo-1,2,3,4-tetrahydroquinolin-2-yl)benzoate

Under a dry nitrogen atmosphere, to a stirred solution of 1-(2-aminophenyl)ethanone (15 g, 111 mmol) in methanol (200 ml) were added methyl 4-formylbenzoate (18.22 g, 111 mmol) and the product of Example 47A (6.00 g, 22.20 mmol). The resulting mixture was stirred at 60° C. for 72 hours before partitioning between ethyl acetate (500 mL) and aqueous HCl (1 M, 200 mL). The organic layer was washed with half-saturated brine, dried over Na$_2$SO$_4$, filtered, and concentrated in vacuo to give crude product which was purified by column chromatography (on silica gel, eluted with ethyl acetate/petroleum ether=1/5) to yield the title compound (16 g, 51.3%): LC-MS: (M+1)=282.

Example 47C methyl 4-[(4Z)-4-(hydroxyimino)-1,2,3,4-tetrahydroquinolin-2-yl]benzoate To a solution of the product from Example 47B (5 g, 17.77 mmol) was added hydroxylamine hydrochloride (3.71 g, 53.3 mmol) and sodium acetate (4.37 g, 53.3 mmol) in methanol (50 mL). The reaction was stirred at 40° C. overnight. The suspension was concentrated to dryness. The residue was dissolved in dichloromethane (100 mL) and washed with saturated NaCl (3×100 mL). The organic layer was dried over $Na_2SO_4$, filtered through Buchner funnel and concentrated to give the title compound (5.2 g, 99%). LC/MS (M+1)=297.

Example 47D methyl rel 4-((2R,4R)-4-amino-1,2,3,4-tetrahydroquinolin-2-yl)benzoate To a solution of the product from Example 47C (5.27 g, 17.78 mmol) in $NH_3$-methanol (50 mL) was treated with Raney nickel (1.044 g, 17.78 mmol). The mixture was stirred at room temperature under 5 atmosphere of 112 for 8 hours. The mixture was filtrated and concentrated to dryness to give the racemic mixture of the title compound (4.0 g, 80%). LC-MS: MS (M+1-$NH_2$)=265. The racemic mixture was purified by supercritical fluid chromatography on a CHIRALPAK OD-H column (21×250 mm, 5 micron), with the sample at a concentration of 25 mg/mL in methanol with co-solvent of methanol yield the first eluting isomer which contained the title compound (220 mg, 3.96%). The stereochemistry was arbitrarily assigned. $^1$H NMR: (400 MHz, $CD_3OD$): δ 8.11 (d, J=8.4, 2H), 7.73 (d, J=8.4 2H), 7.49 (d, J=7.6 1H), 7.31 (t, J=7.6, 1H), 7.09 (t, J=8.4 1H), 7.01 (t, J=8.4, 1H), 4.94~4.92 (m, 1H), 4.79 (dd, J1=12, J2=2.0, 1H), 3.94 (s, 3H), 2.66~2.60 (m, 1H), 2.32 (q, J=12, 1H). LC/MS: MS (M+1-17)=266.

Example 47E methyl rel 4-[(2S,4S)-4-amino-1,2,3,4-tetrahydroquinolin-2-yl]benzoate The racemic compound in Example 47D was purified by was purified by supercritical fluid chromatography on a CHIRALPAK OD-H column (21×250 mm, 5 micron), with the sample at a concentration of 25 mg/mL in methanol with co-solvent of methanol yield the second eluting isomer which contained the title compound (300 mg, 5.41% yield). The stereochemistry was arbitrarily assigned. $^1$H NMR: (400 MHz, $CD_3OD$): δ 8.05 (d, J=8.4, 2H), 7.68 (d, J=8.4, 2H), 7.37 (d, J=7.6 1H), 7.23 (t, J=7.6, 1H), 6.94~6.87 (m, 2H), 4.90~4.85 (m, 1H), 4.71 (dd, J1=12, J2=2.0, 1H), 3.94 (s, 3H), 2.75~2.52 (m, 1H), 2.17 (q, J=12, 1H). LC/MS: MS (M+1-17)=266.

Example 47F methyl 4-[(2R,4R)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoate To a solution of the product from Example 3B (20 mg, 0.077 mmol) in N,N-dimethylformamide (1.00 mL) was added N-[(dimethylamino)-1H-1,2,3-triazolo-[4,5-b]pyridin-1-ylmethylene]-N-methylmethanaminium hexafluorophosphate N-oxide (HATU, 41.2 mg, 0.108 mmol), and the solution was stirred at ambient temperature for 15 minutes. The product of Example 47D (30.3 mg, 0.077 mmol) was added to the reaction mixture followed by addition of triethylamine (0.065 mL, 0.465 mmol). The mixture was stirred at ambient temperature for 4 hours, followed by the addition of water (3 mL). The white precipitate was collected by filtration and was purified by flash chromatography using a 12 g silica gel cartridge eluted with a gradient 0-40% ethyl acetate/heptanes over 20 minutes to supply the title compound (38 mg, 94%). 1H NMR (400 MHz, DMSO-$d_6$) δ 7.96 (dd, J=8.4, 3.3 Hz, 3H), 7.61-7.54 (m, 2H), 7.44 (s, 1H), 6.97 (d, J=1.7 Hz, 2H), 6.92 (d, J=7.6 Hz, 1H), 6.64 (dd, J=8.0, 1.2 Hz, 1H), 6.57 (td, J=7.3, 1.2 Hz, 1H), 6.16 (s, 1H), 5.28 (q, J=8.8 Hz, 1H), 5.03 (d, J=9.0 Hz, 1H), 4.63 (dd, J=10.1, 4.0 Hz, 1H), 4.32 (d, J=9.0 Hz, 1H), 3.86 (s, 3H), 1.94 (dd, J=22.7, 12.5 Hz, 2H), 1.57 (s, 3H); MS (ESI+) m/z 523 (M+H)$^+$.

Example 47G

4-[(2R,4R)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoic acid To a solution of the product from Example 47F (52 mg, 0.103 mmol) in ethanol (0.4 mL)/tetrahydrofuran (0.3 mL) was added 2 N sodium hydroxide (0.113 mL, 0.226 mmol). The reaction was stirred at ambient temperature for 16 hours and sonicated at ambient temperature for 2 hours. The reaction was quenched with 0.36 mL of 1 N HCl, followed by the addition of 15 mL water, extracted with 25 mL dichloromethane, and concentrated. The crude material was purified with a 4 g silica gel cartridge using a gradient of 0-10% methanol/dichloromethane over 20 minutes to supply the title compound (36 mg, 71.2%): 1H NMR (400 MHz, DMSO-$d_6$) δ 12.85 (s, 1H), 7.91-7.85 (m, 2H), 7.49-7.43 (m, 2H), 7.34 (d, J=1.7 Hz, 1H), 7.26 (d, J=8.3 Hz, 1H), 7.15 (dd, J=8.3, 1.7 Hz, 1H), 7.06 (d, J=8.9 Hz, 1H), 6.91-6.85 (m, 1H), 6.80 (dt, J=7.6, 1.2 Hz, 1H), 6.54 (dd, J=8.1, 1.2 Hz, 1H), 6.49 (td, J=7.4, 1.2 Hz, 1H), 6.03 (s, 1H), 5.22 (ddt, J=10.8, 7.1, 3.6 Hz, 1H), 4.55 (dd, J=11.1, 3.2 Hz, 1H), 1.94-1.79 (m, 2H), 1.47-1.40 (m, 1H), 1.34-1.29 (m, 1H), 1.04-0.94 (m, 2H); MS (ESI−) m/z 507 (M−H)$^-$.

Example 48

4-[(2S,4S)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoic acid Example 48A methyl 4-[(2S,4S)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoate To a solution of the product from Example 3B (30.9 mg, 0.125 mmol) in N,N-dimethylformamide (1.00 mL) was added N-[(dimethylamino)-1H-1,2,3-triazolo-[4,5-b]pyridin-1-ylmethylene]-N-methylmethanaminium hexafluorophosphate N-oxide (HATU, 67.9 mg, 0.179 mmol), and the solution was stirred at ambient temperature for 15 minutes. The product of Example 47E (50 mg, 0.128 mmol) was added to the reaction mixture followed by addition of triethylamine (0.107 mL, 0.766 mmol). The mixture was stirred at ambient temperature for 4 hour, followed by the addition of water (3 mL), The white precipitate was collected by filtration and was purified by flash chromatography using a 12 g silica gel cartridge eluted with a gradient 0-40% ethyl acetate/heptanes over 20 minutes to supply the title compound (54 mg, 84%). $^1$H NMR (400 MHz, DMSO-$d_6$) δ 7.95 (d, J=8.3 Hz, 2H), 7.53 (d, J=8.4 Hz, 2H), 7.37 (d, J=1.7 Hz, 1H), 7.30 (d, J=8.3 Hz, 1H), 7.19 (dd, J=8.3, 1.7 Hz, 1H), 7.08 (d, J=9.0 Hz, 1H), 6.92 (t, J=7.4 Hz, 1H), 6.84

(d, J=7.6 Hz, 1H), 6.58 (dd, J=8.2, 1.2 Hz, 1H), 6.53 (td, J=7.4, 1.2 Hz, 1H), 6.08 (s, 1H), 5.32-5.17 (m, 1H), 4.60 (dd, J=10.8, 3.4 Hz, 1H), 3.85 (s, 3H), 1.99-1.82 (m, 2H), 1.51-1.44 (m, 1H), 1.39-1.31 (m, 1H), 1.09-0.96 (m, 2H); MS (ESI+) m/z 507 (M+H)+.

Example 48B

4-[(2S,4S)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoic acid To a solution of the product from Example 48A (48 mg, 0.095 mmol) in ethanol (0.4 mL)/tetrahydrofuran (0.3 mL) was added 2 N sodium hydroxide (0.095 mL, 0.190 mmol). The reaction was stirred at ambient temperature for 16 hour and sonicated at ambient temperature for 2 hours. The reaction was quenched with 0.3 mL of 1 N HCl, followed by the addition of water (15 mL). The mixture was extracted with 25 mL dichloromethane. The organic phase was concentrated and the crude material was purified with a 4 g silica gel cartridge using a gradient of 0-10% methanol/dichloromethane over 20 minutes to provide the title compound (38 mg, 81%): $^1$H NMR (400 MHz, DMSO-d$_6$) δ 12.88 (s, 1H), 7.91 (d, J=8.2 Hz, 2H), 7.48 (d, J=8.2 Hz, 2H), 7.36 (d, J=1.7 Hz, 1H), 7.28 (d, J=8.3 Hz, 1H), 7.17 (dd, J=8.3, 1.7 Hz, 1H), 7.08 (d, J=9.0 Hz, 1H), 6.93-6.87 (m, 1H), 6.84-6.79 (m, 1H), 6.56 (dd, J=8.1, 1.2 Hz, 1H), 6.51 (td, J=7.4, 1.2 Hz, 1H), 6.04 (s, 1H), 5.24 (td, J=10.3, 6.2 Hz, 1H), 4.57 (dd, J=11.1, 3.2 Hz, 1H), 1.96-1.81 (m, 2H), 1.49-1.41 (m, 1H), 1.36-1.29 (m, 1H), 1.06-0.96 (m, 2H); MS (ESI−) m/z 491 (M−H)−.

Example 49

4-[(2R,4R)-4-{[(5R)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid Example 49A methyl 4-{(2R,4R)-4-[(2,2-difluoro-5-methyl-6,7-dihydro-2H,5H-indeno[5,6-d][1,3]dioxole-5-carbonyl)amino]-7-methoxy-3,4-dihydro-2H-1-benzopyran-2-yl}benzoate The product from Example 35F (57.6 mg, 0.225 mmol), the product from Example 15C (90.5 mg, 0.259 mmol) and N-(3-dimethylaminopropyl)-N'-ethylcarbodiimide hydrochloride (86.4 mg, 0.451 mmol) were dissolved in N,N-dimethylformamide (0.5 mL) and pyridine (0.5 mL). The reaction mixture was stirred at 60° C. for 18 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (52.6 mg, 42%). $^1$H NMR (400 MHz, DMSO-d$_6$) δ 8.05-7.93 (m, 2H), 7.71-7.55 (m, 2H), 7.35 (d, J=10.8 Hz, 1H), 7.25 (d, J=7.1 Hz, 1H), 6.98 (d, J=8.5 Hz, 0H), 6.77 (dt, J=7.8, 1.3 Hz, 1H), 6.53 (dd, J=8.6, 2.5 Hz, 0H), 6.49-6.40 (m, 2H), 5.46-5.27 (m, 2H), 3.87 (s, 3H), 3.70 (d, J=4.2 Hz, 3H), 2.98-2.80 (m, 2H), 2.60 (ddd, J=12.8, 8.0, 5.1 Hz, 1H), 2.23-1.90 (m, 3H), 1.48 (d, J=3.1 Hz, 3H). MS (ESI−) m/z 550 (M−H)−.

Example 49B

4-[(2R,4R)-4-{[(5R)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid The product of Example 49A (48.1 mg, 0.087 mmol) and potassium trimethylsilanolate (27.0 mg, 90% purity, 0.189 mmol) were dissolved in tetrahydrofuran (1 mL) and stirred at ambient temperature for 3 hours. The reaction mixture was concentrated, and the residue was purified by preparative supercritical fluid chromatography using a WHELK-O S. S, 21×250 mm column, with the sample at a concentration of 10 mg/mL in methanol with co-solvent of methanol to give the first eluting diastereomer which contained the title compound (10 mg, 21%). Peak A: Retention time=7.154 min, 88.7% de. Chirality was arbitrarily assigned. $^1$H NMR (400 MHz, DMSO-d$_6$) δ 7.93-7.81 (m, 2H), 7.67 (d, J=8.8 Hz, 1H), 7.40-7.30 (m, 3H), 7.24 (s, 1H), 6.96 (d, J=8.6 Hz, 1H), 6.50 (dd, J=8.5, 2.6 Hz, 1H), 6.42 (d, J=2.6 Hz, 1H), 5.36-5.20 (m, 2H), 3.70 (s, 3H), 3.08-2.83 (m, 2H), 2.71-2.54 (m, 1H), 2.21-1.88 (m, 3H), 1.47 (s, 3H). MS (ESI−) m/z 536 (M−H)−.

Example 50

4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid The product of Example 49A (48.1 mg, 0.087 mmol) and potassium trimethylsilanolate (27.0 mg, 90% purity, 0.189 mmol) were dissolved in tetrahydrofuran (1 mL) and stirred at ambient temperature for 3 hours. The reaction mixture was concentrated, and the residue was purified by preparative supercritical fluid chromatography using a WHELK-O S.S, 21×250 mm column, with the sample at a concentration of 10 mg/mL in methanol with co-solvent of methanol to give the second eluting diastereomer which contain the title compound (24 mg, 51%). Peak B: Retention time=7.507 mM, 99.2% de. Chirality was arbitrarily assigned. $^1$H NMR (400 MHz, DMSO-d$_6$) δ 8.00-7.93 (m, 2H), 7.66 (d, J=8.9 Hz, 1H), 7.55-7.48 (m, 2H), 7.34 (s, 1H), 7.26 (s, 1H), 6.80-6.73 (m, 1H), 6.47-6.41 (m, 2H), 5.39-5.30 (m, 2H), 3.70 (s, 3H), 2.98-2.79 (m, 2H), 2.65-2.55 (m, 1H), 2.20-1.92 (m, 3H), 1.48 (s, 3H). 1.47 (s, 3H). MS (ESI−) m/z 536 (M−H)−.

Example 51

3-{6-[(2,2-difluoro-5-methyl-6,7-dihydro-2H,5H-indeno[5,6-d][1,3]dioxole-5-carbonyl)amino]-3-methylpyridin-2-yl}benzoic acid Example 51A tert-butyl 3-{6-[(2,2-difluoro-5-methyl-6,7-dihydro-2H,5H-indeno[5,6-d][1,3]dioxole-5-carbonyl)amino]-3-methylpyridin-2-yl}benzoate The product from Example 35F (0.055 g, 0.215 mmol), tert-butyl 3-(6-amino-3-methylpyridin-2-yl)benzoate (CAS

[1083057-14-0], 0.070 g, 0.247 mmol), and EDCI (0.082 g, 0.429 mmol) were stirred in DMF (0.5 mL) and pyridine (0.500 mL) at 60° C. overnight. After this time, the reaction mixture was concentrated in vacuo, and the residue was purified by reverse-phase preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (0.011, g, 10% yield). $^1$H NMR (400 MHz, DMSO-d$_6$) δ 9.69 (s, 1H), 8.04-7.88 (m, 3H), 7.75 (dd, J=14.2, 8.1 Hz, 2H), 7.65-7.50 (m, 2H), 7.28 (s, 1H), 2.92 (q, J=6.8, 5.8 Hz, 2H), 2.70 (ddd, J=13.1, 8.0, 5.4 Hz, 1H), 2.23 (s, 3H), 2.18-2.02 (m, 1H), 1.60 (s, 3H), 1.55 (s, 9H). MS (ESI$^+$) m/z 523.1 (M+H).

Example 51B

3-{6-[(2,2-difluoro-5-methyl-6,7-dihydro-2H,5H-indeno[5,6-d][1,3]dioxole-5-carbonyl)amino]-3-methylpyridin-2-yl}benzoic acid The product from Example 51A (0.011 g, 0.021 mmol) in CH$_2$Cl$_2$ (0.3 mL) was treated with trifluoroacetic acid (0.14 mL, 1.817 mmol), and the mixture stirred overnight at room temperature. After this time, the mixture was concentrated in vacuo. The residue was dried azeotropically with acetonitrile. Further drying under vacuum (75°) afforded the title compound as a colorless residue (0.0088 g, 90% yield). $^1$H NMR (400 MHz, DMSO-d$_6$) δ 9.71 (s, 1H), 8.09-7.87 (m, 3H), 7.83-7.68 (m, 2H), 7.64-7.49 (m, 2H), 7.28 (s, 1H), 2.92 (m, 2H), 2.71 (m, 1H), 2.24 (s, 3H), 2.11 (dt, J=12.7, 7.5 Hz, 1H), 1.60 (s, 3H). MS (ESI$^+$) m/z 467.2 (M+H).

Example 52 methyl 3-{(2R,4R)-4-[(2,2-difluoro-5-methyl-6,7-dihydro-2H,5H-indeno[5,6-d][1,3]dioxole-5-carbonyl)amino]-7-methoxy-3,4-dihydro-2H-1-benzopyran-2-yl}benzoate The product of Example 35F (0.055 g, 0.215 mmol), the product from Example 10D (0.086 g, 0.247 mmol), and EDCI (0.082 g, 0.429 mmol) were stirred in DMF (0.5 mL) and pyridine (0.500 mL) at 60° C. overnight. After this time, the reaction mixture was concentrated in vacuo, and the residue was purified by reverse-phase preparative HPLC on a Waters Nova-Pak® HR C18 6 µm 60 Å Prep-Pak® cartridge column (40 mm×100 mm), using a gradient of 10% to 100% acetonitrile in 10 mM aqueous ammonium acetate over 12 minutes at a flow rate of 70 mL/minute to yield the title compound (0.073, g, 62% yield). $^1$H NMR (400 MHz, DMSO-d$_6$) δ 8.06 (t, J=1.8 Hz, 1H), 7.95 (dt, J=7.9, 1.5 Hz, 1H), 7.78-7.51 (m, 3H), 7.40-7.20 (m, 2H), 6.77 (d, J=8.1 Hz, 1H), 6.52-6.39 (m, 2H), 5.45-5.28 (m, 2H), 3.87 (s, 3H), 3.70 (s, 3H), 2.90 (m, 2H), 2.60 (m, 1H), 2.19-2.04 (m, 2H), 1.98 (m, 1H), 1.48 (s, 3H). MS (ESI$^+$) m/z 551.6 (M+H).

Example 53

4-{5-[(2,2-difluoro-7-methyl-6,7-dihydro-2H-furo[2,3-f][1,3]benzodioxole-7-carbonyl)amino]-1,3,4-thiadiazol-2-yl}benzoic acid Example 53A methyl 4-{5-[(2,2-difluoro-7-methyl-6,7-dihydro-2H-furo[2,3-f][1,3]benzodioxole-7-carbonyl)amino]-1,3,4-thiadiazol-2-yl}benzoate The product from Example 1E (54.5, 0.211 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). Methyl 4-(5-amino-1,3,4-thiadiazol-2-yl)benzoate (CAS [51542-42-8], 50.0 mg, 0.213 mmol) was added, and the reaction mixture was stirred at 60° C. for 17 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (20.7 mg, 21%). $^1$H NMR (400 MHz, DMSO-d$_6$) δ 12.85 (s, 1H), 8.12-8.06 (m, 4H), 7.60 (s, 1H), 7.06 (s, 1H), 5.12 (d, J=9.5 Hz, 1H), 4.46 (d, J=9.5 Hz, 1H), 3.89 (s, 3H), 1.74 (s, 3H); MS (ESI–) m/z 474 (M–H)$^-$.

Example 53B

4-{5-[(2,2-difluoro-7-methyl-6,7-dihydro-2H-furo[2,3-f][1,3]benzodioxole-7-carbonyl)amino]-1,3,4-thiadiazol-2-yl}benzoic acid The product of Example 53A (18.1 mg, 0.038 mmol) and potassium trimethylsilanolate (22.8 mg, 90% purity, 0.160 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (12.8 mg, 73%). $^1$H NMR (400 MHz, DMSO-d$_6$) δ 13.52-12.66 (m, 2H), 8.19-8.12 (m, 4H), 7.69 (s, 1H), 7.15 (s, 1H), 5.21 (d, J=9.5 Hz, 1H), 4.55 (d, J=9.5 Hz, 1H), 1.83 (s, 3H); MS (ESI–) m/z 460 (M–H)$^-$.

Example 54

N-([1,1'-biphenyl]-3-yl)-2,2-difluoro-7-methyl-6,7-dihydro-2H-furo[2,3-f][1,3]benzodioxole-7-carboxamide The product from Example 1E (54.4 mg, 0.211 mmol), [1,1'-biphenyl]-3-amine (39.8 mg, 0.235 mmol) and N-(3-dimethylaminopropyl)-N'-ethylcarbodiimide hydrochloride (80.1 mg, 0.418 mmol) were dissolved in N,N-dimethylformamide (0.5 mL) and pyridine (0.5 mL). The reaction mixture was stirred at 60° C. for 18 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (56.2 mg, 65%). $^1$H NMR (501 MHz, DMSO-d$_6$) δ 9.57 (s, 1H), 7.92 (t, J=1.9 Hz, 1H), 7.65-7.60 (m, 3H), 7.58 (s, 1H), 7.50-7.44 (m, 2H), 7.43-7.35 (m, 3H), 7.05 (s, 1H), 5.11 (d, J=9.2 Hz, 1H), 4.43 (d, J=9.2 Hz, 1H), 1.69 (s, 3H). MS (ESI+) m/z 410 (M+H)+.

Example 55

2,2-difluoro-7-methyl-N-(6-phenylpyridin-2-yl)-6,7-dihydro-2H-furo[2,3-f][1,3]benzodioxole-7-carboxamide The product from Example 1E (45.9 mg, 0.178 mmol), 6-phenylpyridin-2-amine (45.6 mg, 0.268 mmol) and N-(3-dimethylaminopropyl)-N'-ethylcarbodiimide hydrochloride (80.8 mg, 0.421 mmol) were dissolved in N,N-dimethylformamide (0.5 mL) and pyridine (0.5 mL). The reaction mixture was stirred at 60° C. for 16 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound as the TFA salt (20.0 mg, 21%). $^1$H NMR (400 MHz, DMSO-d$_6$) δ 10.05 (s, 1H), 8.13-8.05 (m, 2H), 7.95 (d, J=8.0 Hz, 1H), 7.88 (t, J=7.9 Hz, 1H), 7.73-7.68 (m, 1H), 7.66 (s, 1H), 7.55-7.41 (m, 3H), 7.05 (s, 1H), 5.13 (d, J=9.4 Hz, 1H), 4.46 (d, J=9.3 Hz, 1H), 1.74 (s, 3H).). MS (ESI+) m/z 411 (M+H)+.

Example 56

3-[(2R,4R)-4-{[(5R)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid The product of Example 52 (71 mg, 0.129 mmol) and potassium trimethylsilanolate (36 mg, purity, 0.283 mmol) were dissolved in tetrahydrofuran (1 mL) and stirred at ambient temperature for 16 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide a mixture of Examples 56 and 57 (14 mg). The epimeric mixture was separated by preparative supercritical fluid chromatography using a Whelk-O1 (S,S) column, 21×250 mm, 5 micron, with the sample at a concentration of 28 mg/mL in methanol with co-solvent of methanol, to provide the title compound (0.0024 g, 3.5% yield) as the first eluting isomer. Chirality was arbitrarily assigned. $^1$H NMR (500 MHz, DMSO-d$_6$) δ 8.01-7.79 (m, 2H), 7.66 (d, J=8.8 Hz, 1H), 7.36 (m, 3H), 7.24 (s, 1H), 6.97 (d, J=8.4 Hz, 1H), 6.55-6.39 (m, 2H), 5.38-5.24 (m, 2H), 3.70 (s, 3H), 2.90 (m, 2H), 2.67-2.55 (m, 1H), 2.18-1.91 (m, 3H), 1.47 (s, 3H). MS (ESI−) m/z 536.3 (M−H)−.

Example 57

3-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid The epimeric mixture in Example 56 was separated by preparative supercritical fluid chromatography using a Whelk-O1 (S,S) column, 21×250 mm, 5 micron, with the sample at a concentration of 28 mg/mL in methanol with co-solvent of methanol, to provide the title compound (0.009 g, 13% yield) as the second eluting isomer. Chirality was arbitrarily assigned. $^1$H NMR (500 MHz, DMSO-d$_6$) δ 8.03 (s, 1H), 7.90 (d, J=7.6 Hz, 1H), 7.64 (m, 2H), 7.50 (m, 1H), 7.34 (s, 1H), 7.26 (s, 1H), 6.77 (d, J=8.1 Hz, 1H), 6.49-6.40 (m, 2H), 5.40-5.27 (m, 2H), 3.69 (s, 3H), 2.89 (m, 2H), 2.68-2.55 (m, 1H), 2.20-1.92 (m, 3H), 1.48 (s, 3H). MS (ESI−) m/z 536.2 (M−H)−.

Example 58

4-[(2R,4R)-4-{[(5R)-2,2-difluoro-5-methyl-6,7-dihydro-2H,5H-indeno[5,6-d][1,3]dioxole-5-carbonyl]amino}-3,4-dihydro-2H-1-benzopyran-2-yl]benzoic acid Example 58A methyl 4-{(2R,4R)-4-[(2,2-difluoro-5-methyl-6,7-dihydro-2H,5H-indeno[5,6-d][1,3]dioxole-5-carbonyl)amino]-3,4-dihydro-2H-1-benzopyran-2-yl}benzoate The product from Example 35F (0.055 g, 0.215 mmol), the product from Example 23C (0.079 g, 0.247 mmol), and EDCI (0.082 g, 0.429 mmol) were stirred in DMF (0.5 mL) and pyridine (0.500 mL) at 60° C. overnight. After this time, the reaction mixture was concentrated in vacuo, and the residue was purified by reverse-phase preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (0.018 g, 16%). $^1$H NMR (400 MHz, DMSO-d$_6$) δ 8.01 (m, 2H), 7.73 (d, J=8.8 Hz, 1H), 7.60 (m, 2H), 7.42-7.08 (m, 3H), 6.94-6.81 (m, 2H), 5.43 (m, 2H), 3.87 (s, 3H), 2.91 (m, 2H), 2.61 (m, 1H), 2.23-1.93 (m, 3H), 1.49 (s, 3H). MS (ESI+) m/z 522.0 (M+H)+.

Example 58B

4-[(2R,4R)-4-{[(5R)-2,2-difluoro-5-methyl-6,7-dihydro-2H,5H-indeno[5,6-d][1,3]dioxole-5-carbonyl]amino}-3,4-dihydro-2H-1-benzopyran-2-yl]benzoic acid The product from Example 58A in THF (0.5 ml) was treated with potassium trimethylsilanolate (10 mg, 0.078 mmol), and the mixture stirred overnight at room temperature. After this time, 0.5 mL CH$_2$Cl$_2$ and 0.25 mL 1N HCl were added, and the mixture stirred vigorously for 30 minutes. The reaction mixture was then diluted with ethyl acetate (5 mL), and the phases were separated. The organic layer was washed with water (2×2 mL) and with brine (2 mL), dried over Na$_2$SO$_4$, filtered, and concentrated in vacuo. The epimeric mixture thus obtained was purified by preparative supercritical fluid chromatography by using a Whelk-01 (S,S) column, 21×250 mm, 5 micron, with the sample at a concentration of 28 mg/mL in methanol with co-solvent of methanol, to afford the title compound (0.0025 g, 14% yield) as the first eluting isomer. Chirality was arbitrarily assigned. $^1$H NMR (500 MHz, DMSO-d$_6$) δ 7.84 (d, J=7.9 Hz, 2H), 7.74 (d, J=8.9 Hz, 1H), 7.41-7.28 (m, 3H), 7.28-7.03 (m, 3H), 6.95-6.73 (m, 2H), 5.38 (m, 1H), 5.27 (d, J=10.9 Hz, 1H), 2.91 (m, 2H), 2.67-2.56 (m, 1H), 2.18-1.92 (m, 3H), 1.48 (s, 3H). MS (ESI+) m/z 506.4 (M−H)−.

Example 59

4-[(2R,4R)-4-{[(5S)-2,2-difluoro-5-methyl-6,7-dihydro-2H,5H-indeno[5,6-d][1,3]dioxole-5-carbonyl]amino}-3,4-dihydro-2H-1-benzopyran-2-yl]benzoic acid The epimeric mixture obtained in Example 58B was purified by preparative supercritical fluid chromatography by using a Whelk-O1 (S,S) column, 21×250 mm, 5 micron, with the sample at a concentration of 28 mg/mL in methanol with co-solvent of methanol, to afford the title compound (0.0072 g, 41%) as the second eluting isomer. Chirality was arbitrarily assigned. $^1$H NMR (400 MHz, DMSO-d$_6$) δ 7.94 (d, J=8.0 Hz, 2H), 7.74 (d, J=8.9 Hz, 1H), 7.48 (m, 2H), 7.35 (s, 1H), 7.31-7.09 (m, 2H), 6.86 (m, 3H), 5.38 (m, 2H), 3.01-2.79 (m, 2H), 2.62 (m, 1H), 2.24-1.91 (m, 3H), 1.49 (s, 3H). MS (ESI+) m/z 506.2 (M+H).

Example 60

5'-[(2,2-difluoro-7-methyl-6,7-dihydro-2H-furo[2,3-f][1,3]benzodioxole-7-carbonyl)amino]-2'-methyl[1,1'-biphenyl]-3-carboxylic acid Example 60A tert-butyl 5'-[(2,2-difluoro-7-methyl-6,7-dihydro-2H-furo[2,3-f][1,3]benzodioxole-7-carbonyl)amino]-2'-methyl[1,1'-biphenyl]-3-carboxylate The product from Example 1E (51.4 mg, 0.188 mmol), the product of Example 36E (76.3 mg, 0.269 mmol) and N-(3-dimethylaminopropyl)-N'-ethylcarbodiimide hydrochloride (80.1 mg, 0.418 mmol) were dissolved in N,N-dimethylformamide (0.5 mL) and pyridine (0.5 mL). The reaction mixture was stirred at 60° C. for 16 hours. The reaction mixture was concentrated, and the residue was purified by reverse-phase preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield 74.6 mg (72%) of the title compound. $^1$H NMR (400 MHz, DMSO-d$_6$) δ 9.48 (s, 1H), 7.91 (ddd, J=6.2, 2.7, 1.7 Hz, 1H), 7.80-7.78 (m, 1H), 7.61-7.56 (m, 3H), 7.54 (s, 1H), 7.48 (d, J=2.3 Hz, 1H), 7.26 (d, J=8.4 Hz, 1H), 7.03 (s, 1H), 5.08 (d, J=9.2 Hz, 1H), 4.39 (d, J=9.2 Hz, 1H), 2.16 (s, 3H), 1.66 (s, 3H), 1.55 (s, 9H). MS (ESI−) m/z 522 (M−H)−.

Example 60B

5'-[(2,2-difluoro-7-methyl-6,7-dihydro-2H-furo[2,3-f][1,3]benzodioxole-7-carbonyl)amino]-2'-methyl[1,1'-biphenyl]-3-carboxylic acid The product of Example 60A (61.8 mg, 0.118 mmol) was dissolved in dichloromethane (1 mL). Trifluoroacetic acid (0.5 mL, 6.49 mmol) was added, and the reaction mixture was stirred at ambient temperature for 17 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield 45.8 mg (83%) of the title compound. $^1$H NMR (400 MHz, HMSO-d$_6$) δ 13.04 (s, 1H), 9.47 (s, 1H), 7.94 (dt, J=7.0, 1.8 Hz, 1H), 7.84 (d, J=1.8 Hz, 1H), 7.63-7.51 (m, 4H), 7.49 (d, J=2.3 Hz, 1H), 7.24 (d, J=8.3 Hz, 1H), 7.02 (s, 1H), 5.06 (d, J=9.2 Hz, 1H), 4.38 (d, J=9.2 Hz, 1H), 2.17 (s, 3H), 1.64 (s, 3H); MS (ESI+) m/z 468 (M+1)−.

Example 61

1-{4-[(2,2-difluoro-7-methyl-6,7-dihydro-2H-furo[2,3-f][1,3]benzodioxole-7-carbonyl)amino]phenyl}azetidine-3-carboxylic acid The product of Example 1E (20 mg, 0.077 mmol) and N,N-diisopropylethylamine (41 μL, 0.23 mmol, 3.0 equivalents) in dimethylacetamide (400 uL) was mixed with HATU (35.4 mg, 0.093 mmol, 1.2 equivalents) in dimethylacetamide (400 μL). Methyl 1-(4-aminophenyl)azetidine-3-carboxylate (CAS [887595-92-8], 24.0 mg, 0.12 mmol, 1.5 equivalents) in dimethylacetamide (200 μL) was added at room temperature and the mixture was stirred for 30 minutes. The vial was loaded directly into a Gilson GX-271 autosampler. A gradient of acetonitrile (A) and 0.1% trifluoroacetic acid in water (B) was used, at a flow rate of 30 mL/min (0-0.5 min 35% A, 0.5-8.0 min linear gradient 35-100% A, 8.0-9.0 min 100% A, 9.0-9.1 min linear gradient 100-35% A, 9.1-10 min 35% A). Fractions were collected based upon MS signal threshold and selected fractions subsequently analyzed by flow injection analysis mass spectrometry using positive APCI ionization on Thermo Scientific MSQ Plus using 0.1% formic acid in 3:1 MeOH:water at a flow rate of 1.0 mL/min to yield the methyl ester of Example 61. The methyl ester was dissolved in THF (500 μL). Potassium trimethylsilanolate (29.8 mg, 0.23 mmol, 3.0 equivalents) in THF (500 μL) was added and the reaction was stirred at 35° C. for 1 hour. Aqueous HCl (1 M, 500 μL) and acetonitrile (300 μL) were added and the reaction was stirred for 10 minutes at room temperature. The vial was loaded directly into a Gilson GX-271 autosampler. A gradient of acetonitrile (A) and 0.1% trifluoroacetic acid in water (B) was used, at a flow rate of 30 mL/min (0-0.5 min 5% A, 0.5-4.5 min linear gradient 5-100% A, 4.5-5.0 min 100% A). Fractions were collected based upon MS signal threshold and selected fractions subsequently analyzed by flow injection analysis mass spectrometry using positive APCI ionization on Thermo Scientific MSQ Plus using 0.1% formic acid in 3:1 MeOH:water at a flow rate of 1.0 mL/min to yield the title compound. $^1$H NMR (400 MHz, DMSO-d$_6$) δ 7.50 (s, 1H), 7.33 (dd, J=8.8, 3.6 Hz, 2H), 6.99 (s, 1H), 6.50-6.37 (m, 2H), 5.06 (d, J=9.2 Hz, 1H), 4.37 (d, J=9.2 Hz, 1H), 3.98 (dd, J=8.5, 7.2 Hz, 2H), 3.81 (dd, J=7.3, 5.9 Hz, 2H), 3.51 (tt, J=8.5, 5.9 Hz, 1H), 1.64 (s, 3H). MS (APCI+) 433.

Example 62

1-{2-[(2,2-difluoro-7-methyl-6,7-dihydro-2H-furo[2,3-f][1,3]benzodioxole-7-carbonyl)amino]-4-(trifluoromethyl)phenyl}-5-methyl-1H-imidazole-4-carboxylic acid To a colorless solution of the product of Example 1E (180 mg, 0.697 mmol) in dichloromethane (2 mL) in a 4 mL vial was added oxalyl dichloride (0.122 mL, 1.394 mmol), and the mixture was stirred for 10 minutes at room temperature. N,N-dimethylformamide (5.40 µL, 0.070 mmol) was added, and the reaction was stirred at ambient temperature for 30 minutes. Solvent was removed under a stream of nitrogen. The acid chloride core (21 mg, 0.076 mmol) and trimethylamine (32 µL, 0.23 mmol, 3 equivalents) were dissolved in 1 mL dichloromethane. Ethyl 1-(2-amino-4-(trifluoromethyl)phenyl)-5-methyl-1H-imidazole-4-carboxylate (CAS [164330-67-0], 35.7 mg, 0.11 mmol, 1.5 equivalents) in dichloromethane (300 µL) was added at room temperature and the reaction was stirred overnight at room temperature. The vial was loaded directly into a Gilson GX-271 autosampler. A gradient of acetonitrile (A) and 0.1% trifluoroacetic acid in water (B) was used, at a flow rate of 30 mL/min (0-0.5 min 35% A, 0.5-8.0 min linear gradient 35-100% A, 8.0-9.0 min 100% A, 9.0-9.1 min linear gradient 100-35% A, 9.1-10 min 35% A). Fractions were collected based upon MS signal threshold and selected fractions subsequently analyzed by flow injection analysis mass spectrometry using positive APCI ionization on Thermo Scientific MSQ Plus using 0.1% formic acid in 3:1 MeOH:water at a flow rate of 1.0 mL/min to yield the ethyl ester of Example 62. The ethyl ester was dissolved in THF (1 mL). Potassium trimethylsilanolate (38.8 mg, 0.30 mmol, 4.0 equivalents) in THF (500 µL) was added and the reaction was stirred at 40 C for 2 hour. Aqueous HCl (1 M, 400 µL) and acetonitrile (300 µL) were added and the reaction was stirred for 10 minutes at room temperature. The vial was loaded directly into a Gilson GX-271 autosampler. A gradient of acetonitrile (A) and 0.1% trifluoroacetic acid in water (B) was used, at a flow rate of 30 mL/min (0-0.5 min 5% A, 0.5-4.5 min linear gradient 5-100% A, 4.5-5.0 min 100% A). Fractions were collected based upon MS signal threshold and selected fractions subsequently analyzed by flow injection analysis mass spectrometry using positive APCI ionization on Thermo Scientific MSQ Plus using 0.1% formic acid in 3:1 methanol: water at a flow rate of 1.0 mL/min to yield the title compound. $^1$H NMR (400 MHz, DMSO-$d_6$) δ 7.93 (s, 2H), 7.88 (dd, J=8.3, 2.1 Hz, 1H), 7.74 (d, J=8.3 Hz, 1H), 7.17 (s, 1H), 6.94 (s, 1H), 4.73 (d, J=9.4 Hz, 1H), 4.26 (d, J=9.3 Hz, 1H), 2.14 (s, 3H), 1.47 (s, 3H). MS (APCI+) 526.

Example 63

N-[4-(4-cyanophenyl)-1,3-thiazol-2-yl]-2,2-difluoro-7-methyl-6,7-dihydro-2H-furo[2,3-f][1,3]benzodioxole-7-carboxamide The product from Example 1E (54.0, 0.209 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). 4-(2-Aminothiazol-4-yl)benzonitrile (CAS 436151-85-8, 99.1 mg, 0.492 mmol) was added, and the reaction mixture was stirred at 60° C. for 17 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (59.8 mg, 65%). $^1$H NMR (400 MHz, DMSO-$d_6$) δ 12.37 (s, 1H), 8.14-8.06 (m, 2H), 7.96 (s, 1H), 7.93-7.87 (m, 2H), 7.63 (s, 1H), 7.06 (s, 1H), 5.12 (d, J=9.4 Hz, 1H), 4.44 (d, J=9.4 Hz, 1H), 1.74 (s, 3H); MS (ESI+) m/z 422 (M+H)$^+$.

Example 64 methyl 4-{2-[(2,2-difluoro-7-methyl-6,7-dihydro-2H-furo[2,3-f][1,3]benzodioxole-7-carbonyl)amino]-1,3-thiazol-4-yl}benzoate The product from Example 1E (54.0, 0.209 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). Methyl 4-(2-aminothiazol-4-yl)benzoate (CAS [206555-77-3], 68.0 mg, 0.290 mmol) was added, and the reaction mixture was stirred at 60° C. for 18 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (69.5 mg, 70%). $^1$H NMR (400 MHz, DMSO-$d_6$) δ 12.37 (s, 1H), 8.10-8.00 (m, 4H), 7.88 (s, 1H), 7.64 (s, 1H), 7.05 (s, 1H), 5.13 (d, J=9.4 Hz, 1H), 4.44 (d, J=9.4 Hz, 1H), 3.87 (s, 3H), 1.74 (s, 3H); MS (ESI+) m/z 475 (M+H)$^+$.

Example 65

6-[(2,2-difluoro-7-methyl-6,7-dihydro-2H-furo[2,3-f][1,3]benzodioxole-7-carbonyl)amino]-N-[(2R)-2,3-dihydroxypropyl]pyridine-2-carboxamide Example 65A methyl 6-[(2,2-difluoro-7-methyl-6,7-dihydro-2H-furo[2,3-f][1,3]benzodioxole-7-carbonyl)amino] pyridine-2-carboxylate The product from Example 1E (108.7, 0.421 mmol) was dissolved in dichloromethane (1 mL). Oxalyl chloride (150 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). Methyl 6-aminopicolinate (96.1 mg, 0.632 mmol) was added, and the reaction mixture was stirred at 60° C. for 18 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (67.0 mg, 41%). $^1$H NMR (400 MHz, DMSO-$d_6$) δ

10.52 (s, 1H), 8.21 (dd, J=8.4, 0.8 Hz, 1H), 7.99 (dd, J=8.4, 7.5 Hz, 1H), 7.81 (dd, J=7.6, 0.9 Hz, 1H), 7.65 (s, 1H), 7.03 (s, 1H), 5.10 (d, J=9.4 Hz, 1H), 4.44 (d, J=9.4 Hz, 1H), 3.89 (s, 3H), 1.73 (s, 3H); MS (ESI+) m/z 393 (M+H)$^+$.

Example 65B

6-[(2,2-difluoro-7-methyl-6,7-dihydro-2H-furo[2,3-f][1,3]benzodioxole-7-carbonyl)amino]pyridine-2-carboxylic acid The product of Example 65A (59.6 mg, 0.152 mmol) and potassium trimethylsilanolate (44.2 mg, 90% purity, 0.310 mmol) were dissolved in tetrahydrofuran (1 mL) and stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (31.9 mg, 56%). $^1$H NMR (400 MHz, DMSO-d$_6$) δ 13.25 (s, 1H), 10.38 (s, 1H), 8.17 (d, J=8.2 Hz, 1H), 7.96 (t, J=8.0 Hz, 1H), 7.82-7.75 (m, 1H), 7.65 (s, 1H), 7.04 (s, 1H), 5.09 (d, J=9.4 Hz, 1H), 4.44 (d, J=9.4 Hz, 1H), 1.72 (s, 3H); MS (ESI+) m/z 379 (M+H)$^+$.

Example 65C

6-[(2,2-difluoro-7-methyl-6,7-dihydro-2H-furo[2,3-f][1,3]benzodioxole-7-carbonyl)amino]-N-[(2R)-2,3-dihydroxypropyl]pyridine-2-carboxamide The products from Example 65B (23.3, 0.062 mmol), (R)-3-aminopropane-1,2-diol (31.7 mg, 0.348 mmol) and N-(3-dimethylaminopropyl)-N'-ethylcarbodiimide hydrochloride (29.7 mg, 0.348 mmol) were dissolved in N,N-dimethylformamide (0.5 mL) and pyridine (0.5 mL). The reaction mixture was stirred at 60° C. for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (6.1 mg, 22%). $^1$H NMR (400 MHz, DMSO-d$_6$) δ 10.23 (s, 1H), 8.33 (t, J=6.2 Hz, 1H), 8.14 (d, J=8.3 Hz, 1H), 7.97 (t, J=7.9 Hz, 1H), 7.76 (d, J=7.4 Hz, 1H), 7.60 (s, 1H), 7.04 (s, 1H), 5.09 (d, J=9.4 Hz, 1H), 4.96 (d, J=11.0 Hz, 1H), 4.64 (s, 1H), 4.44 (d, J=9.4 Hz, 1H), 3.67-3.51 (m, 2H), 3.41-3.34 (m, 1H), 3.17 (d, J=12.0 Hz, 2H), 1.71 (s, 3H); MS (ESI+) m/z 452 (M+H)$^+$.

Example 66 methyl 3'-[(2,2-difluoro-7-methyl-6,7-dihydro-2H-furo[2,3-f][1,3]benzodioxole-7-carbonyl)amino][1,1'-biphenyl]-4-carboxylate The product from Example 1E (52.0 mg, 0.201 mmol), methyl 3'-amino-[1,1'-biphenyl]-4-carboxylate (CAS [159503-24-9], 82.1 mg, 0.361 mmol) and N-(3-dimethylaminopropyl)-N'-ethylcarbodiimide hydrochloride (57.9 mg, 0.302 mmol) were dissolved in N,N-dimethylformamide (0.5 mL) and pyridine (0.5 mL). The reaction mixture was stirred at 60° C. for 17 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (63.2 mg, 67%). $^1$H NMR (400 MHz, DMSO-d$_6$) δ 9.61 (s, 1H), 8.06-8.02 (m, 2H), 8.01-7.97 (m, 1H), 7.80-7.74 (m, 2H), 7.68 (dt, J=6.7, 2.2 Hz, 1H), 7.56 (s, 1H), 7.48-7.39 (m, 2H), 7.04 (s, 1H), 5.10 (d, J=9.2 Hz, 1H), 4.41 (d, J=9.2 Hz, 1H), 3.87 (s, 3H), 1.68 (s, 3H). MS (ESI+) m/z 468 (M+H)$^+$.

Example 67

2,2-difluoro-N-(6-fluoropyridin-2-yl)-7-methyl-6,7-dihydro-2H-furo[2,3-f][1,3]benzodioxole-7-carboxamide The product from Example 1E (112.1, 0.434 mmol) was dissolved in dichloromethane (1 mL). Oxalyl chloride (100 μL) and N,N-dimethylformamide (25 μL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). 6-Fluoropyridin-2-amine (93.1 mg, 0.830 mmol) was added, and the reaction mixture was stirred at 60° C. for 17 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (47.0 mg, 31%). $^1$H NMR (400 MHz, DMSO-d$_6$) δ 10.37 (s, 1H), 8.01-7.87 (m, 2H), 7.62 (s, 1H), 7.01 (s, 1H), 6.92-6.83 (m, 1H), 5.07 (d, J=9.3 Hz, 1H), 4.39 (d, J=9.3 Hz, 1H), 1.68 (s, 31). MS (ESI+) m/z 353 (M+H)$^+$.

Example 68

4-{2-[(2,2-difluoro-7-methyl-6,7-dihydro-2H-furo[2,3-f][1,3]benzodioxole-7-carbonyl)amino]-1,3-thiazol-4-yl}benzoic acid The product of Example 64 (60.8 mg, 0.128 mmol) and potassium trimethylsilanolate (40.0 mg, 90% purity, 0.281 mmol) were dissolved in tetrahydrofuran (1 mL) and stirred at ambient temperature for 18 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (44.5 mg, 75%). $^1$H NMR (400 MHz, DMSO-d$_6$) δ 12.93 (s, 1H), 12.36 (s, 1H), 8.07-7.97 (m, 4H), 7.85 (s, 1H), 7.64 (s, 1H), 7.06 (s, 1H), 5.13 (d, J=9.4 Hz, 1H), 4.44 (d, J=9.4 Hz, 1H), 1.74 (s, 3H); MS (ESI+) m/z 461 (M+H)$^+$.

Example 69

3'-[(2,2-difluoro-7-methyl-6,7-dihydro-2H-furo[2,3-f][1,3]benzodioxole-7-carbonyl)amino][1,1'-biphenyl]-4-carboxylic acid The product of Example 66 (55.3 mg, 0.118 mmol) and potassium trimethylsilanolate (40.0 mg, 90% purity, 0.281 mmol) were dissolved in tetrahydrofuran (1 mL) and stirred at ambient temperature for 16 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (39.4 mg, 74%). $^1$H NMR (400 MHz, DMSO-$d_6$) δ 12.98 (s, 1H), 9.62 (s, 1H), 8.08-7.97 (m, 3H), 7.80-7.73 (m, 2H), 7.69 (dt, J=6.5, 2.3 Hz, 1H), 7.58 (s, 1H), 7.50-7.40 (m, 2H), 7.06 (s, 1H), 5.11 (d, J=9.2 Hz, 1H), 4.43 (d, J=9.2 Hz, 1H), 1.69 (s, 3H); MS (ESI+) m/z 454 (M+H)$^+$.

Example 70 methyl 1-{6-[(2,2-difluoro-7-methyl-6,7-dihydro-2H-furo[2,3-f][1,3]benzodioxole-7-carbonyl)amino]pyridin-2-yl}piperidine-4-carboxylate The product from Example 67 (39.6 mg, 0.112 mmol) was dissolved in dimethylsulfoxide (1 mL). Methyl 4-piperidinecarboxylate (101.9 mg, 0.712 mmol) was added and the reaction was stirred at 80° C. for 18 hours. The reaction mixture was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (24.6 mg, 46%). $^1$H NMR (400 MHz, DMSO-$d_6$) δ 9.39 (s, 1H), 7.61 (s, 1H), 7.49 (t, J=8.1 Hz, 1H), 7.24 (d, J=7.8 Hz, 1H), 7.03 (s, 1H), 6.54 (d, J=8.3 Hz, 1H), 5.06 (d, J=9.3 Hz, 1H), 4.41 (d, J=9.4 Hz, 1H), 4.25-4.14 (m, 2H), 3.62 (s, 3H), 2.89 (ddd, J=13.5, 11.6, 2.7 Hz, 2H), 2.60 (tt, J=11.2, 3.9 Hz, 1H), 1.96-1.83 (m, 2H), 1.69 (s, 3H), 1.61-1.45 (m, 2H); MS (ESI+) m/z 476 (M+H)$^+$.

Example 71

1-{6-[(2,2-difluoro-7-methyl-6,7-dihydro-2H-furo[2,3-f][1,3]benzodioxole-7-carbonyl)amino]pyridin-2-yl}piperidine-4-carboxylic acid The product of Example 70 (17.3 mg, 0.036 mmol) and potassium trimethylsilanolate (15.2 mg, 90% purity, 0.107 mmol) were dissolved in tetrahydrofuran (1 mL) and stirred at ambient temperature for 19 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (15.2 mg, 91%). $^1$H NMR (400 MHz, DMSO-$d_6$) δ 9.41 (s, 1H), 7.61 (s, 1H), 7.49 (t, J=8.1 Hz, 1H), 7.23 (d, J=7.8 Hz, 1H), 7.04 (s, 1H), 6.54 (d, J=8.4 Hz, 1H), 5.06 (d, J=9.4 Hz, 1H), 4.41 (d, J=9.3 Hz, 1H), 4.25-4.14 (m, 2H), 2.89 (td, J=13.1, 12.5, 2.8 Hz, 2H), 2.46 (dt, J=11.2, 4.0 Hz, 1H), 1.94-1.80 (m, 2H), 1.69 (s, 3H), 1.52 (qd, J=11.5, 4.0 Hz, 2H); MS (ESI+) m/z 462 (M+H)$^+$.

Example 72

(7R)-2,2-difluoro-N-[6-(3-hydroxypyrrolidin-1-yl)pyridin-3-yl]-7-methyl-6,7-dihydro-2H-furo[2,3-f][1,3]benzodioxole-7-carboxamide The product from Example 3B (56.2 mg, 0.218 mmol), 1-(5-aminopyridin-2-yl)pyrrolidin-3-ol, hydrochloric acid (70.6 mg, 0.280 mmol) and N-(3-dimethylaminopropyl)-N'-ethylcarbodiimide hydrochloride (93.3 mg, 0.489 mmol) were dissolved in N,N-dimethylformamide (0.5 mL) and pyridine (0.5 mL). The reaction mixture was stirred at 60° C. for 16 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to yield the title compound (86.5 mg, 75%) as the trifluoroacetic acid salt. $^1$H NMR (400 MHz, DMSO-$d_6$) δ 9.73 (s, 1H), 8.30 (d, J=2.5 Hz, 1H), 8.02 (dd, J=9.6, 2.6 Hz, 1H), 7.52 (s, 1H), 7.11-6.99 (m, 2H), 5.06 (d, J=9.1 Hz, 1H), 4.47 (s, 1H), 4.41 (d, J=9.2 Hz, 1H), 3.59 (tt, J=8.2, 4.7 Hz, 3H), 3.39 (d, J=11.1 Hz, 1H), 2.17-2.03 (m, 1H), 2.03-1.89 (m, 1H), 1.65 (s, 3H); MS (ESI+) m/z 420 (M+H)$^+$.

Example 73

3-(6-{[(7R)-2,2-difluoro-7-methyl-6,7-dihydro-2H-furo[2,3-f][1,3]benzodioxole-7-carbonyl]amino}pyridin-2-yl)benzoic acid

Example 73A tert-butyl 3-(6-aminopyridin-2-yl)benzoate

A mixture of 6-chloropyrid-2-amine (259.6 mg, 2.019 mmol) and (3-(tert-butoxycarbonyl)phenyl)boronic acid (491.8 mg, 2.215 mmol) in dimethoxyethane (5 mL) and water (2.5 mL) was degassed under a N$_2$ flow for 15 minutes. Potassium carbonate (621.0 mg, 4.49 mmol) and 1,1'-bis(diphenylphosphino)ferrocene-palladium(II)dichloride (88.5 mg, 0.125 mmol) were added, and the mixture stirred at 80° C. for 18 hours. Water was then added to the reaction mixture (35 mL), and it was extracted with ethyl acetate (3×35 mL). The combined organic layers were dried (MgSO$_4$), filtered, and concentrated under reduced pressure. The residue was purified by flash chromatography, eluted with 5% ethyl acetate in dichloromethane (R$_f$=0.43), to provide the title compound (340.5 mg, 62%). $^1$H NMR (400 MHz, DMSO-$d_6$) δ 8.50 (t, J=1.7 Hz, 1H), 8.16 (dt, J=7.9, 1.4 Hz, 1H), 7.88 (dt, J=7.8, 1.3 Hz, 1H), 7.54 (t, J=7.7 Hz, 1H), 7.47 (t, J=7.8 Hz, 1H), 7.07 (d, J=7.4 Hz, 1H), 6.45 (d, J=8.2 Hz, 1H), 6.05 (s, 2H), 1.56 (s, 9H): MS (ESI+) m/z 271 (M+H)$^+$.

Example 73B tert-butyl 3-(6-{[(7R)-2,2-difluoro-7-methyl-6,7-dihydro-2H-furo[2,3-f][1,3]benzodioxole-7-carbonyl]amino}pyridin-2-yl)benzoate The product from Example 3B (55.1, 0.213 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product from Example 73A (60.1 mg, 0.222 mmol) was added, and the reaction mixture was stirred at 60° C. for 18 hours. The reaction mixture was concentrated, and the residue was purified by reverse-phase preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield 24.3 mg (22%) of the title compound. $^1$H NMR (400 MHz, DMSO-$d_6$) δ 10.11 (s, 1H), 8.59 (t, J=1.8 Hz, 1H), 8.30 (dt, J=7.7, 1.4 Hz, 1H), 8.01-7.95 (m, 2H), 7.92 (t, J=7.9 Hz, 1H), 7.75 (d, J=7.5 Hz, 1H), 7.68 (s, 1H), 7.63 (t, J=7.8 Hz, 1H), 7.05 (s, 1H), 5.14 (d, J=9.4 Hz, 1H), 4.45 (d, J=9.4 Hz, 1H), 1.75 (s, 3H), 1.59 (s, 9H); MS (ESI+) m/z 511 (M+H)$^+$.

Example 73C 3-(6-{[(7R)-2,2-difluoro-7-methyl-6,7-dihydro-2H-furo[2,3-f][1,3]benzodioxole-7-carbonyl]amino}pyridin-2-yl)benzoic acid The product from Example 73B (20.3 mg, 0.040 mmol) was dissolved in dichloromethane (1 mL). Trifluoroacetic acid (0.5 mL, 6.49 mmol) was added, and the reaction mixture was stirred at ambient temperature for 5 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (22.4 mg, 99%) as the trifluoroacetate salt. $^1$H NMR (400 MHz, DMSO-$d_6$) δ 10.20 (s, 1H), 8.67 (t, J=1.8 Hz, 1H), 8.30 (dt, J=7.8, 1.5 Hz, 1H), 8.05-7.96 (m, 2H), 7.91 (t, J=7.9 Hz, 1H), 7.76 (d, J=7.8 Hz, 1H), 7.68-7.59 (m, 2H), 7.05 (s, 1H), 5.13 (d, J=9.4 Hz, 1H), 4.47 (d, J=9.4 Hz, 1H), 1.75 (s, 3H); MS (ESI+) m/z 455 (M+H)$^+$.

Example 74

N-[6-(3-carbamoylphenyl)-5-methylpyridin-2-yl]-2,2-difluoro-7-methyl-6,7-dihydro-2H-furo[2,3-f][1,3]benzodioxole-7-carboxamide

Example 74A tert-butyl 3-{6-[(2,2-difluoro-7-methyl-6,7-dihydro-2H-furo[2,3-f][1,3]benzodioxole-7-carbonyl)amino]-3-methylpyridin-2-yl}benzoate A solution of the product from Example 1E (0.052 g, 0.2 mmol) in 0.5 mL dichloromethane was treated with N,N-dimethylformamide (0.025 mL, 0.320 mmol) and then dropwise with oxalyl chloride (0.077 mL, 0.880 mmol). The mixture was stirred at ambient temperature for 1 hour and then concentrated (rotary evaporator). An additional 0.5 mL dichloromethane was added, and the mixture was concentrated again. The addition/concentration procedure was repeated twice more. Then the residue was taken up in 0.5 mL dichloromethane and treated with pyridine (0.485 mL, 6.00 mmol) and tert-butyl 3-(6-amino-3-methylpyridin-2-yl)benzoate (CAS [1083057-14-0], 0.057 g, 0.200 mmol). The reaction was stirred at 60° C. overnight. The reaction mixture then was concentrated (rotary evaporator), and the residue was purified by reverse-phase preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (11 mg, 11%). $^1$H NMR (400 MHz, DMSO-$d_6$) δ ppm 10.14 (s, 1H), 8.06-7.87 (m, 3H), 7.84-7.70 (m, 2H), 7.69-7.54 (m, 2H), 7.03 (s, 1H), 5.10 (d, J=9.3 Hz, 1H), 4.40 (d, J=9.3 Hz, 1H), 2.24 (s, 3H), 1.70 (s, 3H), 1.56 (s, 9H); MS (ESI$^+$) m/z 525.1 (M+H)$^+$.

Example 74B

3-{6-[(2,2-difluoro-7-methyl-6,7-dihydro-2H-furo[2,3-f][1,3]benzodioxole-7-carbonyl)amino]-3-methylpyridin-2-yl}benzoic acid The product from Example 74A (0.253 g, 0.482 mmol) in $CH_2Cl_2$ (6.4 mL) was treated with trifluoroacetic acid (3.2 mL, 41.5 mmol). The reaction stirred at room temperature for 70 minutes, and concentrated in vacuo. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a foamy white solid (0.110 g, 49% yield). $^1$H NMR (400 MHz, DMSO-$d_6$) δ 13.05 (s, 1H), 10.15 (s, 1H), 8.10-7.89 (m, 3H), 7.89-7.68 (m, 2H), 7.68-7.54 (m, 2H), 7.02 (s, 1H), 5.10 (d, J=9.3 Hz, 1H), 4.41 (d, J=9.3 Hz, 1H), 2.26 (s, 3H), 1.71 (s, 3H). MS (ESI$^+$) m/z 469.1 (M+H).

Example 74C

N-[6-(3-carbamoylphenyl)-5-methylpyridin-2-yl]-2,2-difluoro-7-methyl-6,7-dihydro-2H-furo[2,3-f][1,3]benzodioxole-7-carboxamide A solution of the product of Example 74B in $CH_2Cl_2$ (2 mL) was treated with DMF (6.13 µl, 0.079 mmol) and then cooled to 0° C. Oxalyl chloride (0.013 mL, 0.149 mmol) was then added dropwise. After completion of the addition, the mixture was brought to room temperature and stirred for 90 minutes. It was then concentrated in vacuo, and the residue was taken up in 1.5 mL THF and cooled to 0° C. Concentrated aqueous NH$_4$OH (0.75 mL) was added. After completion of the addition, the mixture was brought to room temperature and stirred overnight. After this time, the mixture was concentrated in vacuo, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a white solid (0.023 g, 66%). $^1$H NMR (400 MHz, HMSO-d$_6$) δ 10.14 (s, 1H), 8.10-7.97 (m, 2H), 7.99-7.91 (m, 2H), 7.74 (d, J=8.5 Hz, 1H), 7.71-7.64 (m, 2H), 7.55 (t, J=7.7 Hz, 1H), 7.40 (s, 1H), 7.02 (br, 1H), 5.09 (d, J=9.4 Hz, 1H), 4.41 (d, J=9.4 Hz, 1H), 2.25 (s, 3H), 1.70 (s, 3H). MS (ESI$^+$) m/z 468.1 (M+H).

Example 75

N-{6-[3-(dimethylcarbamoyl)phenyl]-5-methylpyridin-2-yl}-2,2-difluoro-7-methyl-6,7-dihydro-2H-furo[2,3-f][1,3]benzodioxole-7-carboxamide The product from Example 74B (0.035 g, 0.075 mmol) in CH$_2$Cl$_2$ (2 ml) was treated with DMF (6.13 μL, 0.079 mmol), and the mixture was cooled to 0° C. Oxalyl chloride (0.013 mL, 0.149 mmol) was added dropwise. After completion of the addition, the mixture was brought to room temperature and stirred for 90 minutes, and concentrated in vacuo. The residue was taken up in 1.5 mL THF and cooled to 0° C., followed by the addition of 0.7 mL of 40% aqueous dimethylamine solution. The mixture was brought to room temperature and stirred overnight. The mixture was concentrated in vacuo, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), yielding the title compound as a white solid (0.020 g, 54% yield). $^1$H NMR (400 MHz, DMSO-d$_6$) δ 10.12 (s, 1H), 7.91 (d, J=8.4 Hz, 1H), 7.79-7.39 (m, 6H), 7.02 (s, 1H), 5.09 (d, J=9.4 Hz, 1H), 4.40 (d, J=9.4 Hz, 1H), 3.00 (s, 3H), 2.94 (s, 3H), 2.27 (s, 3H), 1.70 (s, 3H). MS (ESI$^+$) m/z 496.1 (M+H).

Example 76

2,2-difluoro-7-methyl-N-{5-methyl-6-[3-(methylcarbamoyl)phenyl]pyridin-2-yl}-6,7-dihydro-2H-furo[2,3-f][1,3]benzodioxole-7-carboxamide The product from Example 74B (0.035 g, 0.075 mmol) in DMF (0.2 mL) and pyridine (0.2 mL) was treated with methylamine hydrochloride (6 mg, 0.089 mmol) and N-(3-dimethylaminopropyl)-N'-ethylcarbodiimide hydrochloride (26 mg, 0.136 mmol), and the reaction stirred overnight at room temperature. After this time, the mixture was concentrated in vacuo, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a white solid (0.022 g, 61%). $^1$H NMR (400 MHz, DMSO-d$_6$) δ 10.14 (s, 1H), 8.48 (m, 1H), 7.97-7.83 (m, 3H), 7.78-7.49 (m, 4H), 7.02 (s, 1H), 5.09 (d, J=9.3 Hz, 1H), 4.41 (d, J=9.4 Hz, 1H), 2.79 (d, J=4.4 Hz, 3H), 2.24 (s, 3H), 1.70 (s, 3H). MS (ESI$^+$) m/z 482.1 (M+H).

Example 77

(7R)—N-(6-chloro-5-methylpyridin-2-yl)-2,2-difluoro-7-methyl-6,7-dihydro-2H-furo[2,3-f][1,3]benzodioxole-7-carboxamide The product from Example 3B (0.129 g, 0.5 mmol) in 1.2 mL CH$_2$Cl$_2$ was treated with DMF (0.06 mL, 0.775 mmol) and then dropwise with oxalyl chloride (0.18 mL, 2.056 mmol). The mixture was stirred at room temperature for 1 hour and was then concentrated in vacuo. An additional 1.2 mL CH$_2$Cl$_2$ was added, and the mixture was concentrated again. The procedure was repeated twice more, then the residue was treated with 1.2 mL CH$_2$Cl$_2$, triethylamine (0.21 mL, 1.507 mmol), and 6-chloro-5-methylpyridin-2-amine (0.071 g, 0.500 mmol). An additional 3 mL CH$_2$Cl$_2$ was added to facilitate stirring of the thick mixture, then it was stirred overnight. The mixture was diluted with additional CH$_2$Cl$_2$ (20 mL) and was washed three times with water (5 mL each). The organic layer was dried over Na$_2$SO$_4$ and concentrated in vacuo, and the crude material was purified by silica gel chromatography, eluting with 0 to 30% ethyl acetate-heptanes, to afford the title compound (0.147 g, 77% yield). $^1$H NMR (400 MHz, DMSO-d$_6$) δ 10.40 (s, 1H), 7.90 (d, J=8.2 Hz, 1H), 7.79 (d, J=8.3 Hz, 1H), 7.63 (s, 1H), 7.02 (d, J=3.9 Hz, 1H), 5.07 (d, J=9.3 Hz, 1H), 4.39 (d, J=9.3 Hz, 1H), 2.28 (s, 3H), 1.69 (s, 3H). MS (ESI$^+$) m/z 383.1 (M+H).

Example 78

(7R)—N-[6-(3-cyanophenyl)-5-methylpyridin-2-yl]-2,2-difluoro-7-methyl-6,7-dihydro-2H-furo[2,3-f][1,3]benzodioxole-7-carboxamide Example 78A 3-(3-methylpyridin-2-yl)benzonitrile 2-Bromo-3-methylpyridine (0.688 g, 4 mmol), (3-cyanophenyl) boronic acid (0.588 g, 4 mmol), potassium carbonate (1.16 g, 8.4 mmol), and PdCl$_2$dppf (0.146 g, 0.2 mmol) were mixed in dimethoxyethane (8.5 mL) and water (4.7 mL), and the mixture was heated overnight at 80° C. After this time, the mixture was diluted with ether (50 mL), washed with a solution of 0.25 mL CH$_3$SO$_3$H in 12 mL water, followed by washing with brine (10 mL). The organic layer was dried over Na$_2$SO$_4$, filtered, and concentrated in vacuo. The residue was purified by silica gel chromatography, eluting with 0 to 50% ethyl acetate-heptanes, to afford the title compound as a yellow oil (0.355 g, 46% yield). $^1$H NMR (500 MHz, CDCl$_3$) δ 8.55 (dd, J=4.6, 1.6 Hz, 1H), 7.89-7.75 (m, 2H), 7.74-7.52 (m, 3H), 7.25 (dd, J=7.7, 4.7 Hz, 1H), 2.36 (s, 3H). MS (DCI$^+$) m/z 195.0 (M+H).

Example 78B 2-(3-cyanophenyl)-3-methylpyridine 1-oxide

The product from Example 78A (0.355 g, 1.828 mmol) in ethyl acetate (17 mL) and water (1.2 mL) was treated in one portion with urea-hydrogen peroxide (0.516 g, 5.48 mmol), then in four portions over about 10 minutes with phthalic anhydride (0.812 g, 5.48 mmol). After the completion of the additions, the reaction mixture was stirred at 45° C. for 5 hours, and cooled to room temperature. The mixture was then treated with a solution of 1 g Na$_2$SO$_3$ in 10 mL water, and the mixture was stirred vigorously for 1 hour. The phases were separated, and the organic layer was washed with 1M Na$_2$CO$_3$ solution (5 mL) and brine (5 mL). The organic layer was then dried over Na$_2$SO$_4$, filtered, and concentrated in vacuo, then further dried azeotropically with toluene. The title compound was obtained as a yellow syrup (0.251 g, 65% yield). $^1$H NMR (400 MHz, CDCl$_3$) δ 8.24 (m, 1H), 7.79-7.61 (m, 4H), 7.28 (m, 2H), 2.16 (s, 3H). MS (DCI$^+$) m/z 210.9 (M+H).

Example 78C 3-(6-amino-3-methylpyridin-2-yl)benzonitrile

The product from Example 78B (0.251 g, 1.194 mmol) in dry acetonitrile (9.2 ml) was treated with pyridine (0.386 mL, 4.78 mmol), and the mixture was heated up to 65° C. It was then treated with a solution of methanesulfonic anhydride (0.312 g, 1.791 mmol) in 3 mL dry CH$_3$CN over an hour. After completion of the addition, the mixture was stirred another 30 minutes at 65° C. and then cooled to room temperature. Ethanolamine (0.722 mL, 11.94 mmol) was added dropwise, and the mixture was allowed to stir overnight at room temperature. The mixture was then poured into water (50 mL) and extracted with ethyl acetate (4×50 mL). The combined organic extracts were washed with water (20 mL) and brine (20 mL), dried over Na$_2$SO$_4$, filtered, and concentrated in vacuo. The residue was purified by silica gel chromatography, eluting with 40 to 80% ethyl acetate-heptanes, to afford the title compound as a thick colorless oil that slowly solidified upon standing (0.125 g, 50% yield). $^1$H NMR (500 MHz, CDCl$_3$) δ 7.85-7.70 (m, 2H), 7.69-7.60 (m, 1H), 7.53 (t, J=7.8 Hz, 1H), 7.37 (d, J=8.2 Hz, 1H), 6.49 (d, J=8.4 Hz, 1H), 4.41-4.35 (m, 2H), 2.19 (s, 3H). MS (DCI$^+$) m/z 210.0 (M+H).

Example 78D (7R)—N-[6-(3-cyanophenyl)-5-methylpyridin-2-yl]-2,2-difluoro-7-methyl-6,7-dihydro-2H-furo[2,3-f][1,3]benzodioxole-7-carboxamide The product from Example 3B (0.154 g, 0.597 mmol) in 1.4 mL CH$_2$Cl$_2$ was treated with DMF (0.07 mL, 0.904 mmol) and then dropwise with oxalyl chloride (0.21 mL, 2.399 mmol). The mixture was stirred at room temperature for 1 hour, and concentrated in vacuo. An additional 1.4 mL CH$_2$Cl$_2$ was added, and the mixture was again concentrated in vacuo. The procedure was repeated twice more, then the residue was treated with a solution of the product from Example 78C (0.125 g, 0.597 mmol) in 3 mL CH$_2$Cl$_2$, followed by triethylamine (0.250 mL, 1.792 mmol). The reaction was then stirred overnight at room temperature. After this time, the reaction mixture was diluted with additional CH$_2$Cl$_2$ (20 mL) and washed with water (3×5 mL) and with brine (5 mL). The organic layer was dried over Na$_2$SO$_4$, filtered, and concentrated in vacuo. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a colorless solid (0.007 g, 3% yield). $^1$H NMR (400 MHz, DMSO-d$_6$) δ 10.14 (s, 1H), 8.06-7.84 (m, 4H), 7.82-7.59 (m, 3H), 7.03 (s, 1H), 5.09 (d, J=9.4 Hz, 1H), 4.41 (d, J=9.4 Hz, 1H), 2.26 (s, 3H), 1.70 (s, 3H). MS (ESI$^+$) m/z 450.1 (M+H).

Example 79 methyl 4-(6-{[(7R)-2,2-difluoro-7-methyl-6,7-dihydro-2H-furo[2,3-f][1,3]benzodioxole-7-carbonyl]amino}pyridin-2-yl)benzoate Example 79A methyl 4-(6-aminopyridin-2-yl)benzoate A mixture of 6-chloropyrid-2-amine (255.1 mg, 1.984 mmol) and methyl 4-(4,4,5,5-tetramethyl-1,3,2-dioxaborolan-2-yl)benzoate (611.2 mg, 2.332 mmol) in dimethoxyethane (5 mL) and water (2.5 mL) was degassed under a N$_2$ flow for 15 minutes. Potassium carbonate (581.9 mg, 4.21 mmol) and 1,1'-bis(diphenylphosphino)ferrocene-palladium (II)dichloride (87.5 mg, 0.120 mmol) were added, and the mixture stirred at 80° C. for 18 hours. Water was then added to the reaction mixture (35 mL), and it was extracted with ethyl acetate (3×35 mL). The combined organic layers were dried (MgSO$_4$), filtered, and concentrated under reduced pressure. The residue was purified by flash chromatography, eluted with 5% ethyl acetate in dichloromethane (R$_f$=0.28), to provide the title compound (344.5 mg, 76%). $^1$H NMR (400 MHZ), DMSO-d$_6$) δ 8.16-8.09 (m, 2H), 8.05-7.96 (m, 2H), 7.50 (dd, J=8.2, 7.5 Hz, 1H), 7.18-7.11 (m, 1H), 6.49 (d, J=8.3 Hz, 1H), 6.08 (s, 2H), 3.87 (s, 3H): MS (ESI+) m/z 229 (M+H)$^+$.

Example 79B methyl 4-(6-{[(7R)-2,2-difluoro-7-methyl-6,7-dihydro-2H-furo[2,3-f][1,3]benzodioxole-7-carbonyl]amino}pyridin-2-yl)benzoate The product from Example 3B (54.4, 0.211 mmol) was dissolved in dichloromethane (1 mL). Oxalyl chloride (80 μL) and N,N-dimethylformamide (25 μL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product from Example 79A (61.4 mg, 0.269 mmol) was added, and the reaction mixture was stirred at 60° C. for 17 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (91.5 mg, 93%) as the trifluoroacetic acid salt. $^1$H NMR (501 MHz, DMSO-d$_6$) δ 10.18 (s, 1H), 8.27-8.21 (m, 2H), 8.10-8.05 (m, 2H), 8.01 (d, J=8.2 Hz, 1H), 7.93 (t, J=7.9 Hz, 1H), 7.80 (d, J=7.6 Hz, 1H), 7.65 (s, 1H), 7.05 (s, 1H), 5.13 (d, J=9.4 Hz, 1H), 4.46 (d, J=9.4 Hz, 1H), 3.89 (s, 3H), 1.75 (s, 3H); MS (ESI+) m/z 469 (M+H)$^+$.

Example 80

(7R)-2,2-difluoro-7-methyl-N-[5-(pyrrolidin-1-yl)pyridin-2-yl]-6,7-dihydro-2H-furo[2,3-f][1,3]benzodioxole-7-carboxamide The product from Example 3B (54.4, 0.211 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). 5-(pyrrolidin-1-yl)pyridin-2-amine (CAS [937623-38-6], 71.4 mg, 0.437 mmol) was added, and the reaction mixture was stirred at 60° C. for 20 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (37.3 mg, 34%) as the trifluoroacetic acid salt. $^1$H NMR (400 MHz, DMSO-d$_6$) δ 9.96 (s, 1H), 7.75-7.59 (m, 3H), 7.18 (dd, J=9.1, 3.0 Hz, 1H), 7.04 (s, 1H), 5.09 (d, J=9.2 Hz, 1H), 4.39 (d, J=9.2 Hz, 1H), 3.29-3.18 (m, 4H), 2.00-1.89 (m, 4H), 1.68 (s, 3H); MS (ESI+) m/z 404 (M+H)$^+$.

Example 81

4-(6-{[(7R)-2,2-difluoro-7-methyl-6,7-dihydro-2H-furo[2,3-f][1,3]benzodioxole-7-carbonyl]amino}pyridin-2-yl)benzoic acid The product of Example 79B (86.5 mg, 0.185 mmol) and potassium trimethylsilanolate (54.3 mg, 90% purity, 0.381 mmol) were dissolved in tetrahydrofuran (1 mL) and stirred at ambient temperature for 18 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (25.1 mg, 24%) as the trifluoroacetic acid salt. $^1$H NMR (400 MHz, DMSO-d$_6$) δ 10.16 (s, 1H), 8.26-8.19 (m, 2H), 8.09-8.03 (m, 2H), 8.01 (d, J=8.1 Hz, 1H), 7.92 (t, J=7.9 Hz, 1H), 7.79 (d, J=7.5 Hz, 1H), 7.65 (s, 1H), 7.05 (s, 1H), 5.13 (d, J=9.4 Hz, 1H), 4.46 (d, J=9.4 Hz, 1H), 1.75 (s, 3H); MS (ESI+) m/z 455 (M+H)$^+$.

Example 82 ethyl 5-(6-{[(7R)-2,2-difluoro-7-methyl-6,7-dihydro-2H-furo[2,3-f][1,3]benzodioxole-7-carbonyl]amino}pyridin-2-yl)thiophene-3-carboxylate

Example 82A ethyl 5-(6-aminopyridin-2-yl)thiophene-3-carboxylate

A mixture of 6-chloropyrid-2-amine (257.2 mg, 2.001 mmol) and ethyl 5-(4,4,5,5-tetramethyl-1,3,2-dioxaborolan-2-yl)thiophene-3-carboxylate (528.1 mg, 1.872 mmol) in dimethoxyethane (5 mL) and water (2.5 mL) was degassed under a N$_2$ flow for 15 minutes. Potassium carbonate (599.5 mg, 4.34 mmol) and 1,1'-bis(diphenylphosphino)ferrocene-palladium(II)dichloride (95.2 mg, 0.130 mmol) were added, and the mixture stirred at 80° C. for 18 hours. Water was then added to the reaction mixture (35 mL), and it was extracted with ethyl acetate (3×35 mL). The combined organic layers were dried (MgSO$_4$), filtered, and concentrated under reduced pressure. The residue was purified by flash chromatography, eluted with 5% ethyl acetate in dichloromethane (R$_f$=0.46), to provide the title compound (193.8 mg, 42%). $^1$H NMR (501 MHz, DMSO-d$_6$) δ 8.27 (d, J=1.3 Hz, 1H), 7.90 (d, J=1.4 Hz, 1H), 7.42 (dd, J=8.2, 7.4 Hz, 1H), 7.10 (dd, J=7.4, 0.7 Hz, 1H), 6.39 (dd, J=8.2, 0.7 Hz, 1H), 6.07 (s, 2H), 4.28 (q, J=7.1 Hz, 2H), 1.31 (t, J=7.1 Hz, 3H): MS (ESI+) m/z 249 (M+H)$^+$.

Example 82B ethyl 5-(6-{[(7R)-2,2-difluoro-7-methyl-6,7-dihydro-2H-furo[2,3-f][1,3]benzodioxole-7-carbonyl]amino}pyridin-2-yl)thiophene-3-carboxylate The product from Example 3B (58.4, 0.226 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product from Example 82A (67.0 mg, 0.270 mmol) was added, and the reaction mixture was stirred at 60° C. for 18 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (78.0 mg, 71%) as the trifluoroacetic acid salt. $^1$H NMR (400 MHz, DMSO-d$_6$) δ 10.04 (s, 1H), 8.39 (d, J=1.3 Hz, 1H), 8.11 (d, J=1.4 Hz, 1H), 7.93-7.81 (m, 2H), 7.77 (dd, J=7.5, 1.2 Hz, 1H), 7.64 (s, 1H), 7.05 (s, 1H), 5.11 (d, J=9.4 Hz, 1H), 4.45 (d, J=9.4 Hz, 1H), 4.30 (q, J=7.1 Hz, 2H), 1.73 (s, 3H), 1.32 (t, J=7.1 Hz, 3H); MS (ESI+) m/z 489 (M+H)$^+$.

Example 83

4-(6-{[(7R)-2,2-difluoro-7-methyl-6,7-dihydro-2H-furo[2,3-f][1,3]benzodioxole-7-carbonyl]amino}-3-methylpyridin-2-yl)benzoic acid

Example 83A tert-butyl 4-(3-methylpyridin-2-yl)benzoate

A mixture of 2-bromo-3-methylpyridine (0.688 g, 4 mmol), (4-(tert-butoxycarbonyl)phenyl)boronic acid (0.888 g, 4 mmol), potassium carbonate (1.16 g, 8.40 mmol), and PdCl$_2$dppf (0.146 g, 0.2 mmol) in dimethoxyethane (8.5 mL) and water (4.7 mL) was heated at 80° C. overnight. The mixture was diluted with 50 mL of ether and was then washed with a solution of methanesulfonic acid (0.25 mL) in water (12 mL) and with brine sequentially. The organic layer was dried over Na₂SO₄, filtered, and concentrated in vacuo. The crude material was purified by silica gel chromatography (0 to 50% EtOAc-heptanes, eluent) to afford the title compound as a yellow oil (0.560 g, 52%). ¹H NMR (400 MHz, CDCl₃) δ 8.55 (m, 1H), 8.07 (d, J=8.3 Hz, 2H), 7.65-7.52 (m, 3H), 7.21 (dd, J=7.8, 4.8 Hz, 1H), 2.34 (s, 3H), 1.58 (s, 9H). MS (DCI⁺) m/z 270.0 (M+H).

Example 83B 2-(4-(tert-butoxycarbonyl)phenyl)-3-methylpyridine 1-oxide

The product from Example 83A (0.560 g, 2.079 mmol) in ethyl acetate (20 ml) and water (1.4 ml) was treated in one portion with urea-hydrogen peroxide (0.587 g, 6.24 mmol), then in four portions with phthalic anhydride (0.924 g, 6.24 mmol). After the completion of the additions, the reaction mixture was stirred at 45° C. for 5 hours before cooling to room temperature. A solution of 1.2 g Na₂SO₃ in 12 mL water was then added, and the mixture was stirred vigorously for 1 hour. The phases were separated, and the organic layer was washed with 1M aqueous sodium carbonate solution and then with brine, dried over Na₂SO₄, filtered, and concentrated in vacuo to afford the title compound as a pale tan solid (0.454 g, 77%). ¹H NMR (400 MHz, CDCl₃) δ 8.28-8.02 (m, 3H), 7.47-7.36 (m, 2H), 7.20-7.11 (m, 2H), 2.10 (s, 3H), 1.61 (s, 9H). MS (DCI⁺) m/z 286.0 (M+H).

Example 83C tert-butyl 4-(6-amino-3-methylpyridin-2-yl)benzoate

The product from Example 83B (0.454 g, 1.591 mmol) was dried azeotropically from toluene three times and then taken up in dry acetonitrile (12 mL) and treated with pyridine (0.515 mL, 6.36 mmol). The mixture was heated to 65° C., and then methanesulfonic anhydride (0.416 g, 2.387 mmol) in 4 mL dry acetonitrile was added over 1 hour. After completion of the addition, the mixture was stirred for another 30 minutes at 65° C. and was then cooled to room temperature and treated dropwise with ethanolamine (0.962 ml, 15.91 mmol). The mixture was allowed to stir overnight at room temperature. It was then poured into 100 mL water and extracted with ethyl acetate (3×50 mL). The combined organic extracts were washed with brine, dried over Na₂SO₄, filtered, and concentrated in vacuo. The crude orange oil was purified by silica gel chromatography (0 to 50% ethyl acetate-heptanes, eluent) to afford the title compound as a pale yellow oil, which slowly solidified upon standing (0.308 g, 68%). ¹H NMR (400 MHz, CDCl₃) δ 8.09-7.98 (m, 2H), 7.59-7.48 (m, 2H), 7.34 (m, 1H), 6.46 (d, J=8.2 Hz, 1H), 4.39 (s, 2H), 2.18 (s, 3H), 1.61 (s, 9H). MS (DCI⁺) m/z 285.0 (M+H).

Example 83D tert-butyl 4-(6-{[(7R)-2,2-difluoro-7-methyl-6,7-dihydro-2H-furo[2,3-f][1,3]benzodioxole-7-carbonyl]amino}-3-methylpyridin-2-yl)benzoate A mixture of the product from Example 3B (0.091 g, 0.35 mmol), the product from Example 83C (0.100 g, 0.35 mmol), HATU (0.140 g, 0.6 mmol), and DIEA (0.24 ml, 1.4 mmol) in CH₂Cl₂ (7.2 mL) was stirred at room temperature overnight. After this time, the mixture was washed with water (3×5 mL), was dried over Na₂SO₄, filtered, and concentrated in vacuo. The crude material was purified by silica gel chromatography (0 to 25% ethyl acetate-heptanes, eluent) over 10 minutes to afford the title compound as foamy white solid (0.097 g, 53%). ¹H NMR (400 MHz, DMSO-d₆) δ 10.16 (s, 1H), 8.05-7.87 (m, 3H), 7.75 (d, J=9.0 Hz, 1H), 7.64 (dd, J=6.3, 2.1 Hz, 3H), 7.03 (s, 1H), 5.09 (d, J=9.3 Hz, 1H), 4.41 (d, J=9.3 Hz, 1H), 2.22 (s, 3H), 1.70 (s, 3H), 1.58 (s, 9H). MS (ESI⁺) m/z 525.0 (M+H).

Example 83E 4-(6-{[(7R)-2,2-difluoro-7-methyl-6,7-dihydro-2H-furo[2,3-f][1,3]benzodioxole-7-carbonyl]amino}-3-methylpyridin-2-yl)benzoic acid A solution of the product from Example 83D (0.097 g, 0.185 mmol) in CH₂Cl₂ (2.4 mL) was treated with trifluoroacetic acid (1.2 mL, 15.58 mmol), and the mixture stirred at room temperature for 1 hour. The reaction mixture was concentrated in vacuo, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a white solid (0.048 g, 55%). ¹H NMR (400 MHz, DMSO-d₄) δ 13.04 (br, 1H), 10.15 (s, 1H), 8.03 (d, J=8.3 Hz, 2H), 7.92 (d, J=8.5 Hz, 1H), 7.80-7.59 (m, 4H), 7.03 (s, 1H), 5.09 (d, J=9.5 Hz, 1H), 4.41 (d, J=9.4 Hz, 1H), 2.25 (s, 3H), 1.70 (s, 3H). MS (ESI⁺) m/z 469.1 (M+H).

Example 84

3-(6-{[(7R)-2,2-difluoro-7-methyl-6,7-dihydro-2H-furo[2,3-f][1,3]benzodioxole-7-carbonyl]amino}-5-methylpyridin-2-yl)benzoic acid Example 84A tert-butyl 3-(5-methylpyridin-2-yl)benzoate 2-Bromo-5-methylpyridine (0.688 g, 4 mmol), (3-(tert-butoxycarbonyl)phenyl)boronic acid (0.888, 4 mmol), potassium carbonate (1.16 g, 8.4 mmol), and PdCl₂dppf (0.146 g, 0.2 mmol) were mixed in dimethoxyethane (8.5 mL) and water (4.7 mL), and the mixture was heated overnight at 80° C. After this time, the mixture was diluted with ether (75 mL), washed with a solution of 0.25 mL CH₃SO₃H in 12 mL water, followed by washing with brine (20 mL). The organic layer was dried over Na₂SO₄, filtered, and concentrated in vacuo. The crude oil was purified by silica gel chromatography (0 to 25% ethyl acetate-heptanes, eluent) to afford the title compound as a yellow oil (0.445 g, 41% yield). ¹H NMR (400 MHz, CDCl₃) δ 8.61-8.49 (m, 2H), 8.20 (dt, J=7.8, 1.4 Hz, 1H), 8.02 (dt, J=7.7, 1.5 Hz, 1H), 7.65-7.46 (m, 2H), 7.14-7.04 (m, 1H), 2.43 (s, 3H), 1.63 (s, 9H). MS (DCI⁺) m/z 270.0 (M+H).

Example 84B 2-(3-(tert-butoxycarbonyl)phenyl)-5-methylpyridine 1-oxide

The product from Example 84A (0.703 g, 2.61 mmol) in ethyl acetate (24 mL) and water (1.7 mL) was treated in one portion with urea-hydrogen peroxide (0.737 g, 7.83 mmol), then in four portions with phthalic anhydride (1.160 g, 7.83 mmol). After the completion of the additions, the reaction mixture was stirred at 45° C. for 5 hours before cooling to room temperature. The mixture was then treated with 1.5 g $Na_2SO_3$ in 15 mL water, and the mixture stirred vigorously at room temperature for 1 hour. The phases were separated, and the organic layer was washed with 1M $Na_2CO_3$ (30 mL) and brine (30 mL) sequentially. The organic layer was dried over $Na_2SO_4$, filtered, and concentrated in vacuo to afford the title compound as a thick colorless oil. The crude product was taken into the next reaction without further purification. $^1$H NMR (400 MHz, $CDCl_3$) δ 8.28 (m, 1H), 8.23 (m, 1H), 8.07 (m, 2H), 7.52 (m, 1H), 7.36 (m, 1H), 7.17 (m, 1H), 2.37 (s, 3H), 1.60 (s, 9H). MS ($DCI^+$) m/z 286.0 (M+H).

Example 84C tert-butyl 3-(6-amino-5-methylpyridin-2-yl)benzoate

The product from Example 84B (0.745 g, 2.61 mmol) was dried azeotropically with toluene, then was taken up in dry acetonitrile (20 mL) and treated with pyridine (0.85 mL, 10.51 mmol). The mixture was heated to 65° C., and treated with a solution of methanesulfonic anhydride (0.682 g, 3.92 mmol) in 6.6 mL dry acetonitrile over 1 hour. After the addition was complete, the reaction mixture was continued to stir at 65° C. for 30 minutes and was then cooled to room temperature. It was then treated dropwise with ethanolamine (1.6 mL, 26.5 mmol), and the reaction stirred overnight at room temperature. The reaction mixture was poured into water (120 mL) and extracted three times with ethyl acetate (3×50 mL). The combined organic extracts were washed with water (25 mL) and brine (25 mL) sequentially, dried over $Na_2SO_4$, filtered, and concentrated in vacuo. The crude oil was purified by silica gel chromatography, eluting with 0 to 30% ethyl acetate-heptanes, to afford the title compound (0.267 g, 36% yield). $^1$H NMR (500 MHz, $CDCl_3$) δ 8.52 (t, J=1.8 Hz, 1H), 8.11 (dt, J=7.8, 1.5 Hz, 1H), 7.97 (dt, J=7.7, 1.5 Hz, 1H), 7.47 (t, J=7.8 Hz, 1H), 7.36 (dd, J=7.4, 1.0 Hz, 1H), 7.11 (d, J=7.5 Hz, 1H), 4.48 (s, 2H), 2.18 (s, 3H), 1.62 (s, 9H). MS ($DCI^+$) m/z 285.0 (M+H).

Example 84D tert-butyl 3-(6-{[(7R)-2,2-difluoro-7-methyl-6,7-dihydro-2H-furo[2,3-f][1,3]benzodioxole-7-carbonyl]amino}-5-methylpyridin-2-yl)benzoate The product from Example 3B (0.091 g, 0.352 mmol), the product from Example 84C (0.100 g, 0.352 mmol), HATU (0.140 g, 0.369 mmol), and DIEA (0.240 mL, 1.372 mmol) were stirred in $CH_2Cl_2$ (7 mL) overnight at room temperature. The mixture was diluted with $CH_2Cl_2$ (10 mL) and washed with water (3×5 mL). The organic layer was dried over $Na_2SO_4$, filtered, and concentrated in vacuo. The crude oil was purified by silica gel chromatography, eluting with 0 to 35% ethyl acetate-heptanes, to afford the crude title compound, which was taken into the next reaction without further purification. $^1$H NMR (400 MHz, DMSO-$d_6$) δ 9.97 (s, 1H), 8.60 (t, J=1.8 Hz, 1H), 8.27 (dt, J=7.9, 1.5 Hz, 1H), 7.94-7.80 (m, 3H), 7.62 (m, 2H), 7.07 (d, J=7.6 Hz, 1H), 5.15 (d, J=9.1 Hz, 1H), 4.42 (d, J=9.1 Hz, 1H), 2.09 (s, 3H), 1.74 (s, 3H), 1.58 (s, 9H). MS ($ESI^+$) m/z 525.0 (M+H).

Example 84E 3-(6-{[(7R)-2,2-difluoro-7-methyl-6,7-dihydro-2H-furo[2,3-f][1,3]benzodioxole-7-carbonyl]amino}-5-methylpyridin-2-yl)benzoic acid The product from Example 84D (0.108 g, 0.206 mmol) in $CH_2Cl_2$ (2.6 mL) was treated with trifluoroacetic acid (1.3 mL, 16.87 mmol), and the reaction mixture stirred at room temperature for 90 minutes. The mixture was concentrated in vacuo. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a white solid (0.041 g, 43% yield). $^1$H NMR (400 MHz, DMSO-$d_6$) δ 13.10 (br, 1H), 9.99 (s, 1H), 8.63 (t, J=1.8 Hz, 1H), 8.27 (d, J=7.9 Hz, 1H), 8.04-7.74 (m, 3H), 7.68-7.55 (m, 2H), 7.06 (s, 1H), 5.14 (d, J=9.1 Hz, 1H), 4.42 (d, J=9.1 Hz, 1H), 2.07 (s, 3H), 1.74 (s, 3H). MS ($ESI^+$) m/z 469.1 (M+H).

Example 85

(7R)-2,2-difluoro-N-(6-fluoropyridin-2-yl)-7-methyl-6,7-dihydro-2H-furo[2,3-f][1,3]benzodioxole-7-carboxamide The product from Example 3B (1.02 g, 3.95 mmol) was dissolved in dichloromethane (5 mL). Oxalyl chloride (500 μL) and N,N-dimethylformamide (50 μL) were added which resulted in bubbling of the reaction mixture. The reaction was stirred at ambient temperature for 1 hour. The reaction was concentrated, and the residue was dissolved in dichloromethane (2 mL) and concentrated two times. The residue was dissolved in dichloromethane (5 mL) and pyridine (2.5 mL). 6-Fluoropyridin-2-amine (559.1 mg, 4.99 mmol) was added, and the reaction mixture was stirred at 60° C. for 17 hours. The reaction mixture was concentrated, and the residue was purified by flash chromatography, eluted with dichloromethane ($R_f$=0.36), to provide the title compound (1.09 g, 78%). $^1$H NMR (400 MHz, DMSO-$d_6$) δ 10.37 (s, 1H), 8.01-7.87 (m, 2H), 7.62 (s, 1H), 7.01 (s, 1H), 6.92-6.83 (m, 1H), 5.07 (d, J=9.3 Hz, 1H), 4.39 (d, J=9.3 Hz, 1H), 1.68 (s, 3H). MS (ESI+) m/z 353 (M+H)$^+$.

Example 86

5-(6-{[(7R)-2,2-difluoro-7-methyl-6,7-dihydro-2H-furo[2,3-f][1,3]benzodioxole-7-carbonyl]amino}pyridin-2-yl)thiophene-3-carboxylic acid The product of Example 82B (69.6 mg, 0.142 mmol) and potassium trimethylsilanolate (52.8 mg, 90% purity, 0.370 mmol) were dissolved in tetrahydrofuran (1 mL) and stirred at ambient temperature for 19 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B)

was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (44.0 mg, 67%). $^1$H NMR (400 MHz, DMSO-d$_6$) δ 12.84 (s, 1H), 10.03 (s, 1H), 8.32 (d, J=1.4 Hz, 1H), 8.08 (d, J=1.4 Hz, 1H), 7.93-7.80 (m, 2H), 7.75 (dd, J=7.4, 1.2 Hz, 1H), 7.64 (s, 1H), 7.05 (s, 1H), 5.11 (d, J=9.4 Hz, 1H), 4.45 (d, J=9.4 Hz, 1H), 1.74 (s, 3H); MS (ESI+) m/z 461 (M+H)$^+$.

Example 87

(7R)-2,2-difluoro-N-{6-[2-(hydroxymethyl)morpholin-4-yl]pyridin-2-yl}-7-methyl-6,7-dihydro-2H-furo[2,3-f][1,3]benzodioxole-7-carboxamide The product from Example 85 (36.9 mg, 0.105 mmol) was dissolved in dimethylsulfoxide (1 mL). Morpholin-2-yl-methanol (65.2 mg, 0.559 mmol) and sodium carbonate (81.0 mg, 0.764 mmol) were added. The reaction was stirred at 150° C. for 16 hours. The reaction mixture was diluted with methanol (1 mL), filtered, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (11.2 mg, 24%). $^1$H NMR (501 MHz, DMSO-d$_6$) δ 9.45 (dd, J=14.2, 2.7 Hz, 1H), 7.62-7.59 (m, 1H), 7.55 (dt, J=14.1, 8.1 Hz, 1H), 7.30 (dd, J=12.3, 7.8 Hz, 1H), 7.04 (d, J=1.2 Hz, 1H), 6.55 (dd, J=17.7, 8.3 Hz, 1H), 5.06 (dd, J=9.4, 2.7 Hz, 1H), 4.58-4.44 (m, 0H), 4.44-4.37 (m, 1H), 4.21-4.11 (m, 1H), 3.99 (dd, J=47.3, 11.4 Hz, 2H), 1.68 (s, 3H). MS (ESI+) m/z 450 (M+H)$^+$.

Example 88

(7R)-2,2-difluoro-N-{6-[(3S)-3-hydroxypyrrolidin-1-yl]pyridin-2-yl}-7-methyl-6,7-dihydro-2H-furo[2,3-f][1,3]benzodioxole-7-carboxamide The product from Example 85 (36.4 mg, 0.103 mmol) and (S)-3-hydroxypyrrolidine (71.3 mg, 0.818 mmol) were dissolved in dimethylsulfoxide (1 mL). The reaction was stirred at 100° C. for 17 hours. The reaction mixture was diluted with methanol (1 mL), filtered, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (44.0 mg, 80%) as the trifluoroacetic acid salt. $^1$H NMR (501 MHz, DMSO-d$_6$) δ 9.56 (s, 1H), 7.60 (s, 1H), 7.54 (t, J=8.1 Hz, 1H), 7.13 (d, J=7.8 Hz, 1H), 7.06 (s, 1H), 6.28 (d, J=8.4 Hz, 1H), 5.06 (d, J=9.4 Hz, 1H), 4.43 (d, J=9.4 Hz, 1H), 4.41-4.37 (m, 1H), 3.54-3.41 (m, 3H), 3.33 (d, J=11.1 Hz, 1H), 2.08-1.95 (m, 1H), 1.95-1.85 (m, 1H), 1.69 (s, 3H). MS (ESI+) m/z 420 (M+H)$^+$.

Example 89

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxylic acid Example 89A (S)—N-[(1E)-1-(2-hydroxy-4-methoxyphenyl)ethylidene]-2-methylpropane-2-sulfinamide A solution of 2'-hydroxy-4'-methoxyacetophenone (1 g, 6.02 mmol) and (S)-(−)-2-methyl-2-propanesulfinamide (0.802 g, 6.62 mmol) in 2-methyl-tetrahydrofuran (10 mL) was treated with titanium(IV) ethoxide (5.15 g, 22.57 mmol), heated at 90° C. under N$_2$ for 2 hours, cooled and partitioned between ethyl acetate and water. The mixture was filtered through diatomaceous earth to remove the solids. The ethyl acetate layer was washed with brine, dried (MgSO$_4$), filtered, and concentrated. The residue was chromatographed on silica gel, eluting with a gradient of 30% to 100% ethyl acetate in heptane provided the title compound (377 mg, 1.400 mmol, 23.26% yield). $^1$H NMR (400 MHz, CDCl$_3$) δ 13.62 (s, 1H), 7.55 (d, J=8.9 Hz, 1H), 6.48-6.43 (m, 2H), 3.84 (s, 3H), 2.76 (s, 3H), 1.32 (s, 9H); MS (ESI+) m/z 435 (M+H)$^+$; MS (ESI−) m/z 433 (M−H)$^-$.

Example 89B methyl 6-[(1S,3E)-1-hydroxy-3-(2-hydroxy-4-methoxyphenyl)-3-{[(S)-2-methylpropane-2-sulfinyl]imino}propyl]pyridine-3-carboxylate A solution of diisopropylamine (163 μL, 1.143 mmol) in tetrahydrofuran (2 mL) under N$_2$ at −20° C. was treated with n-BuLi in hexanes (2.5 M, 437 μL, 1.091 mmol) and stirred for 15 minutes. This solution was added over 1 minute to a solution of the product from Example 89A (140 mg, 0.520 mmol) in tetrahydrofuran (2 mL) under N$_2$ at −20° C. The resulting mixture was stirred at −20° C. for 1 hour, cooled to −78° C., treated with a solution of methyl 6-formylnicotinate (86 mg, 0.520 mmol) in tetrahydrofuran (1.5 mL), warmed to 0° C., cooled to −30° C., treated with a solution of 10% acetic acid in tetrahydrofuran (about 1.5 mL) and allowed to warm to room temperature. The mixture was partitioned between ethyl acetate and saturated NaHCO$_3$ solution. The ethyl acetate layer was washed with brine, dried (MgSO$_4$), filtered, and concentrated. The residue was chromatographed on silica gel (50% ethyl acetate/heptanes) to provide the minor undesired isomer as the first to elute from the column: $^1$H NMR (400 MHz, CDCl$_3$) δ 13.12 (s, 1H), 9.19-9.18 (m, 1H), 8.34 (dd, J=8.2, 2.0 Hz, 1H), 8.00 (d, J=9.0 Hz, 1H), 7.83 (d, J=8.2 Hz, 1H), 6.58 (d, J=9.1 Hz, 1H), 5.73 (d, J=8.5 Hz, 1H), 5.18-5.11 (m, 1H), 4.06-3.98 (m, 1H), 3.97 (s, 3H), 3.86 (s, 3H), 3.46 (dd, J=13.5, 11.0 Hz, 1H), 1.40 (s, 9H); followed by the title compound (52 mg, 23% yield), which was the second isomer to elute from the column. $^1$H NMR (400 MHz, CDCl$_3$) δ 13.25 (s, 1H), 9.19 (d, J=1.9 Hz, 1H), 8.22 (dd, J=8.2, 2.1 Hz, 1H), 7.57 (d, J=8.2 Hz, 1H), 7.38 (d, J=9.1 Hz, 1H), 6.40 (d, J=2.6 Hz, 1H), 6.28 (dd, J=9.1, 2.6 Hz, 1H), 5.34 (q, J=5.1 Hz, 1H), 4.92 (d, J=5.2 Hz, 1H), 3.96 (s, 3H), 3.80 (s, 3H), 3.82-3.71 (m, 2H), 1.39 (s, 9H); MS (ESI+) m/z 435 (M+H)$^+$.

Example 89C methyl 6-[(2R,4E)-7-methoxy-4-{[(S)-2-methylpropane-2-sulfinyl]imino}-3,4-dihydro-2H-1-benzopyran-2-yl]pyridine-3-carboxylate A solution of the product from Example 89B (52 mg, 0.120 mmol) and triphenylphosphine (31.4 mg, 0.120 mmol) in $CH_2Cl_2$ (1 mL) at 0° C. was treated dropwise with a 40 weight % solution of diethyl azodicarboxylate in toluene (54.5 µL, 0.120 mmol) over 3 minutes, stirred at 0° C. for 10 minutes, allowed to stir at ambient temperature for 1 hour, concentrated, and directly chromatographed on silica gel eluting with 50% ethyl acetate in heptanes to provide the title compound (18 mg, 0.043 mmol, 36.1% yield). $^1$H NMR (400 MHz, $CDCl_3$) δ 9.20-9.18 (m, 1H), 8.37 (dd, J=8.2, 2.1 Hz, 1H), 7.98 (d, J=8.9 Hz, 1H), 7.70 (d, J=8.2 Hz, 1H), 6.62 (dd, J=8.9, 2.5 Hz, 1H), 6.53 (d, J=2.5 Hz, 1H), 5.40 (dd, J=12.5, 3.0 Hz, 1H), 3.97 (s, 3H), 3.92 (dd, J=17.5, 3.1 Hz, 1H), 3.85 (s, 3H), 3.28 (dd, J=17.5, 12.5 Hz, 1H), 1.30 (s, 9H); MS (ESI+) m/z 417 (M+H)$^+$.

Example 89D methyl 6-[(2R,4R)-4-amino-7-methoxy-3,4-dihydro-2H-1-benzopyran-2-yl]pyridine-3-carboxylate A solution of the product from Example 89C (17.4 mg, 0.042 mmol) in methanol (1 mL) was cooled to 0° C., treated with $NaBH_4$ (4.74 mg, 0.125 mmol), stirred at 0° C. for 30 minutes, treated with 4 M HCl in dioxane (209 µL, 0.836 mmol), stirred at 0° C. for 5 minutes and then stirred at ambient temperature for 30 minutes. The mixture was partitioned between methyl tert-butyl ether (30 mL) and water (15 mL). The aqueous layer was basified to pH 8 with solid $NaHCO_3$ and extracted with ethyl acetate. The ethyl acetate layer was washed with brine, dried ($MgSO_4$), filtered, and concentrated to provide the title compound (12 mg, 0.038 mmol, 91% yield). $^1$H NMR (501 MHz, $CDCl_3$) δ 9.18 (d, J=1.5 Hz, 1H), 8.36 (dd, J=8.2, 2.1 Hz, 1H), 7.72 (d, J=8.2 Hz, 1H), 7.42 (d, J=8.6 Hz, 1H), 6.59 (d, J=8.5 Hz, 1H), 6.50 (d, J=2.5 Hz, 1H), 5.32 (d, J=10.8 Hz, 1H), 4.29 (s, 1H), 3.97 (s, 3H), 3.80 (s, 3H), 2.68 (dd, J=12.5, 4.0 Hz, 1H), 1.83 (q, J=11.5 Hz, 1H).

Example 89E methyl 6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxylate A solution of the product from Example 3B (4.93 mg, 0.019 mmol) and 1-[bis(dimethylamino) methylene]-1H-1,2,3-triazolo[4,5-b]pyridinium 3-oxid hexafluorophosphate (10.89 mg, 0.029 mmol) in tetrahydrofuran (1 mL) was treated with triethylamine (7.98 µL, 0.057 mmol) and stirred at ambient temperature for 1 hour. This solution was transferred to a flask containing the product from Example 89D (6 mg, 0.019 mmol). The mixture was stirred at ambient temperature for 1 hour, treated with 37% ammonium hydroxide solution (about 0.5 mL), stirred for 5 minutes, and partitioned between ethyl acetate (30 mL) and $NaHCO_3$ solution (15 mL). The ethyl acetate layer was washed with brine, dried ($MgSO_4$), filtered, and concentrated. The residue was chromatographed on silica gel, eluting with a gradient of 30%-100% ethyl acetate in heptanes to provide the title compound (7.4 mg, 0.013 mmol, 69.9% yield). $^1$H NMR (400 MHz, $CDCl_3$) δ 9.11 (d, J=1.5 Hz, 1H), 8.28 (dd, J=8.2, 2.1 Hz, 1H), 7.59 (d, J=8.2 Hz, 1H), 6.90 (d, J=8.5 Hz, 1H), 6.82 (s, 1H), 6.57 (s, 1H), 6.52 (dd, J=8.5, 2.6 Hz, 1H), 6.50 (d, J=2.5 Hz, 1H), 5.65 (d, J=8.6 Hz, 1H), 5.44-5.31 (m, 2H), 4.75 (d, J=9.3 Hz, 1H), 4.30 (d, J=9.3 Hz, 1H), 3.97 (s, 3H), 3.78 (s, 3H), 2.75 (ddd, J=13.5, 6.2, 2.8 Hz, 1H), 2.01 (dt, J=13.5, 9.3 Hz, 1H), 1.62 (s, 3H); MS (ESI−) m/z 553 (M−H)$^-$.

Example 89F

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxylic acid A solution of the product from Example 89E (7.4 mg, 0.013 mmol) in tetrahydrofuran (1 mL) was diluted with methanol (1 mL), treated with 1 M NaOH (0.25 mL), stirred at ambient temperature for 15 minutes, treated with 1 M HCl (3 mL) and extracted with ethyl acetate (25 mL). The ethyl acetate layer was washed with brine, dried ($MgSO_4$), filtered, and concentrated. The residue was chromatographed on silica gel, eluting with a gradient of 50%-100% [200:1:1 ethyl acetate:$HCOOH$:$H_2O$] in heptanes. The fractions containing the product were combined, washed with 0.1 M HCl (15 mL), washed with brine, dried ($MgSO_4$), filtered, and concentrated to provide the title compound (6 mg, 0.011 mmol, 83% yield). $^1$H NMR (400 MHz, $CDCl_3$) δ 9.20 (s, 1H), 8.35 (dd, J=8.2, 1.9 Hz, 1H), 7.64 (d, J=8.2 Hz, 1H), 6.89 (d, J=8.4 Hz, 1H), 6.84 (s, 1H), 6.58 (s, 1H), 6.54-6.49 (m, 2H), 5.67 (d, J=8.6 Hz, 1H), 5.45-5.35 (m, 2H), 4.76 (d, J=9.3 Hz, 1H), 4.31 (d, J=9.3 Hz, 1H), 3.78 (s, 3H), 2.77 (ddd, J=13.4, 6.1, 2.7 Hz, 1H), 2.01 (dt, J=13.4, 9.5 Hz, 1H), 1.63 (s, 3H); MS (ESI−) m/z 539 (M−H)$^-$.

Example 90

(3S)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylic acid

Example 90A methyl (3S)-1-(6-nitropyridin-2-yl)pyrrolidine-3-carboxylate

A mixture of (S)-methyl pyrrolidine-3-carboxylate, hydrochloric acid (204 mg, 1.232 mmol), 2-bromo-6-nitropyridine (250 mg, 1.232 mmol) and triethylamine (0.687 mL, 4.93 mmol) in tetrahydrofuran (2 mL) was treated with 2 drops of water. The mixture was stirred at ambient temperature for 72 hours and concentrated. The resulting oil was partitioned between water and dichloromethane. The organic fraction was concentrated, and the crude residue was purified using a 24 g silica gel cartridge, eluting with a gradient of 0-70% ethyl acetate/heptanes over a period of 20 minutes to give the title compound (145 mg, 0.577 mmol, 47% yield). $^1$H NMR (501 MHz, DMSO-$d_6$) δ ppm 7.87-7.81 (m, 1H), 7.41 (d, J=7.5 Hz, 1H), 6.93 (d, J=8.4 Hz, 1H), 3.72 (dd, J=10.8, 7.9 Hz, 1H), 3.66 (s, 3H), 3.63 (dd, J=10.8, 6.3 Hz, 1H), 3.58-3.44 (m, 2H), 3.37-3.33 (m, 1H), 2.27 (dtd, J=12.8, 7.3, 5.4 Hz, 1H), 2.18 (dq, J=12.5, 7.4 Hz, 1H); MS (ESI+) m/z 252 (M+H)$^+$.

Example 90B methyl (3S)-1-(6-aminopyridin-2-yl)pyrrolidine-3-carboxylate

The product of Example 90A (141.3 mg, 0.562 mmol) in methanol (1.8 mL) was added to 5% palladium on carbon (wet JM#9) (29.1 mg, 0.273 mmol) in a 4 mL pressure bottle. The mixture was stirred under 30 psi of hydrogen at 40° C. for 1 hour. The mixture was filtered through a polypropylene membrane, and the filtrate was concentrated. The residue was azeotroped with toluene (2×5 mL) to give the title compound (103 mg, 0.466 mmol, 81% yield). 1H NMR (400 MHz, DMSO-$d_6$) δ ppm 7.11 (t, J=7.8 Hz, 1H), 5.69 (d, J=7.8 Hz, 1H), 5.57 (d, J=7.8 Hz, 1H), 5.43 (s, 2H), 3.64 (s, 3H), 3.56 (dd, J=10.4, 8.0 Hz, 1H), 3.47 (dd, J=10.5, 6.3 Hz, 1H), 3.37 (ddd, J=9.9, 7.8, 5.3 Hz, 1H), 3.30-3.26 (m, 1H), 3.21 (qd, J=7.6, 6.3 Hz, 1H), 2.22-2.04 (m, 2H); MS (ESI+) m/z 222 (M+H)$^+$.

Example 90C methyl (3S)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylate The product from Example 3B (51.4, 0.199 mmol) was dissolved in dichloromethane (1 mL). Oxalyl chloride (80 μL) and N,N-dimethylformamide (25 μL) were added which resulted in bubbling of the reaction mixture. The reaction was stirred at ambient temperature for 1 hour, and concentrated. The residue was dissolved in dichloromethane (1 mL) and concentrated two times. The residue was dissolved in dichloromethane (1 mL) and pyridine (0.5 mL). The product of Example 90B (47.0 mg, 0.212 mmol) was added, and the reaction mixture was stirred at 60° C. for 18 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (66.4 mg, 72%). $^1$H NMR (501 MHz, DMSO-$d_6$) δ 9.35 (s, 1H), 7.61 (s, 1H), 7.48 (t, J=8.0 Hz, 1H), 7.20 (d, J=7.8 Hz, 1H), 7.04 (s, 1H), 6.22 (d, J=8.2 Hz, 1H), 5.05 (d, J=9.3 Hz, 1H), 4.42 (d, J=9.4 Hz, 1H), 3.70-3.66 (m, 1H), 3.65 (s, 3H), 3.57 (dd, J=10.7, 6.3 Hz, 1H), 3.46 (ddd, J=10.1, 7.8, 5.3 Hz, 1H), 3.42-3.36 (m, 1H), 3.31-3.23 (m, 1H), 2.27-2.19 (m, 1H), 2.19-2.10 (m, 1H), 1.68 (s, 3H); MS (ESI+) m/z 462 (M+H)$^+$.

Example 90D (3S)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylic acid The product of Example 90C (63.4 mg, 0.137 mmol) and potassium trimethylsilanolate (53.0 mg, 90% purity, 0.372 mmol) were dissolved in tetrahydrofuran (1 mL) and stirred at ambient temperature for 16 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (38.3 mg, 50%) as the trifluoroacetic acid salt. $^1$H NMR (501 MHz, DMSO-$d_6$) δ 9.49 (s, 1H), 7.60 (s, 1H), 7.52 (t, J=8.1 Hz, 1H), 7.17 (d, J=7.8 Hz, 1H), 7.05 (s, 1H), 6.27 (d, J=8.3 Hz, 1H), 5.06 (d, J=9.4 Hz, 1H), 4.43 (d, J=9.4 Hz, 1H), 3.68-3.55 (m, 2H), 3.52-3.36 (m, 2H), 3.23-3.12 (m, 1H), 2.27-2.09 (m, 2H), 1.69 (s, 3H); MS (ESI+) m/z 448 (M+H)$^+$.

Example 91

(7R)-2,2-difluoro-N-{6-[(3R)-3-hydroxypyrrolidin-1-yl]pyridin-2-yl}-7-methyl-6,7-dihydro-2H-furo[2,3-f][1,3]benzodioxole-7-carboxamide The product from Example 85 (28.6 mg, 0.081 mmol) was dissolved in dimethylsulfoxide (1 mL). (R)-3-hydroxypyrrolidine hydrochloride (45.9 mg, 0.371 mmol) and sodium carbonate (52.9 mg, 0.499 mmol) were added. The reaction was stirred at 80° C. for 15 hours. The reaction mixture was diluted with methanol (1 mL), filtered, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (44.0 mg, 80%) as the trifluoroacetic acid salt. $^1$H NMR (501 MHz, DMSO-$d_6$) δ 9.55 (s, 1H), 7.60 (s, 1H), 7.54 (t, J=8.1 Hz, 1H), 7.13 (d, J=7.8 Hz, 1H), 7.06 (s, 1H), 6.28 (d, J=8.3 Hz, 1H), 5.05 (d, J=9.4 Hz, 1H), 4.43 (d, J=9.4 Hz, 1H), 4.41-4.36 (m, 1H), 3.55-3.41 (m, 3H), 3.32 (d, J=11.1 Hz, 1H), 2.07-1.97 (m, 1H), 1.95-1.86 (m, 1H), 1.68 (s, 3H). MS (ESI+) m/z 420 (M+H)$^+$.

Example 92

(7R)—N-(6-{[2R)-2,3-dihydroxypropyl]amino}pyridin-2-yl)-2,2-difluoro-7-methyl-6,7-dihydro-2H-furo[2,3-f][1,3]benzodioxole-7-carboxamide The product from Example 85 (31.2 mg, 0.089 mmol) and (R)-3-amino-1,2-propanediol (46.2 mg, 0.509 mmol) were dissolved in dimethylsulfoxide (1 mL). The reaction was stirred at 100° C. for 18 hours. The reaction mixture was diluted with methanol (1 mL), filtered, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (19.8 mg, 42%) as the trifluoroacetic acid salt. $^1$H NMR (400 MHz, DMSO-$d_6$) δ 9.88 (s, 1H), 7.60-7.53 (m, 2H), 7.07 (s, 1H), 6.95 (d, J=7.8 Hz, 1H), 6.47 (d, J=8.5 Hz, 1H), 5.05 (d, J=9.4 Hz, 1H), 4.43 (d, J=9.4 Hz, 1H), 3.68-3.58 (m, 1H), 3.44-3.29 (m, 3H), 3.18 (dd, J=13.4, 6.6 Hz, 1H), 1.68 (s, 3H). MS (ESI+) m/z 420 (M+H)$^+$.

Example 93

(7R)—N-(6-{[(2S)-2,3-dihydroxypropyl]amino}pyridin-2-yl)-2,2-difluoro-7-methyl-6,7-dihydro-2H-furo[2,3-f][1,3]benzodioxole-7-carboxamide The product from Example 85 (31.2 mg, 0.089 mmol) and (S)-3-amino-1,2-propanediol (44.4 mg, 0.489 mmol) were dissolved in dimethylsulfoxide (1 mL). The reaction was stirred at 100° C. for 18 hours. The reaction mixture was diluted with methanol (1 mL), filtered, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (19.8 mg, 42%) as the trifluoroacetic acid salt. $^1$H NMR (400 MHz, DMSO-$d_6$) δ 9.88 (s, 1H), 7.60-7.52 (m, 2H), 7.07 (s, 1H), 6.96 (d, J=7.8 Hz, 1H), 6.47 (d, J=8.4 Hz, 1H), 5.05 (d, J=9.4 Hz, 1H), 4.43 (d, J=9.4 Hz, 1H), 3.68-3.58 (m, 1H), 3.44-3.29 (m, 3H), 3.19 (dd, J=13.4, 6.7 Hz, 1H), 1.67 (s, 3H). MS (ESI+) m/z 420 (M+H)$^+$.

Example 94

1-(5-{[(7R)-2,2-difluoro-7-methyl-6,7-dihydro-2H-furo[2,3-f][1,3]benzodioxole-7-carbonyl]amino}pyrazin-2-yl)pyrrolidine-3-carboxylic acid

Example 94A (7R)—N-(5-bromopyrazin-2-yl)-2,2-difluoro-7-methyl-6,7-dihydro-2H-furo[2,3-f][1,3]benzodioxole-7-carboxamide Example 3B (0.258 g, 1 mmol) in 2.5 mL CH$_2$Cl$_2$ was treated with DMF (0.13 mL, 1.679 mmol) and then dropwise with oxalyl chloride (0.39 mL, 4.46 mmol). The mixture was stirred at room temperature for 1 hour, and concentrated in vacuo. An additional 2.5 mL CH$_2$Cl$_2$ was added, and the mixture was concentrated again. The procedure was repeated twice more, then the residue taken up in 2.5 mL CH$_2$Cl$_2$ and treated with 5-bromopyrazin-2-amine (0.174 g, 1.000 mmol) and pyridine (2.4 mL, 29.7 mmol). The reaction stirred at 40° C. for 3 hours and at room temperature overnight. The mixture was concentrated in vacuo, and the resulting dark oil was taken up in ethyl acetate (10 mL) and water (5 mL). The phases were separated, and the organic layer was washed with water (2×5 mL) and brine (5 mL) sequentially. The organic layer was dried over Na$_2$SO$_4$, filtered, and concentrated in vacuo. The residue was purified by silica gel chromatography, eluting with 10 to 100% ethyl acetate-heptanes, to afford the title compound. $^1$H NMR (500 MHz, DMSO-$d_6$) δ 10.78 (s, 1H), 9.06 (d, J=1.5 Hz, 1H), 8.66 (d, J=1.4 Hz, 1H), 7.62 (s, 1H), 7.04 (s, 1H), 5.09 (d, J=9.4 Hz, 1H), 4.42 (d, J=9.3 Hz, 1H), 1.71 (s, 3H). MS (APCI$^+$) m/z 414.1 (M+H).

Example 94B 1-(5-{[(7R)-2,2-difluoro-7-methyl-6,7-dihydro-2H-furo[2,3-f][1,3]benzodioxole-7-carbonyl]amino}pyrazin-2-yl)pyrrolidine-3-carboxylic acid The product of Example 94A (0.020 g, 0.048 mmol), methyl pyrrolidine-3-carboxylate hydrochloride (11 mg, 0.066 mmol), sodium 2-methylpropan-2-olate (17 mg, 0.177 mmol), and RuPhos palladacycle (RuPhos precatalyst) (7 mg, 9.61 μmol) were placed in a 2-neck 10 mL round bottom flask. Dioxane (1 mL) was added, and the system was evacuated and purged with nitrogen. The reaction mixture was heated at 85° C. overnight. After this time, the mixture was concentrated in vacuo, then the crude material was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a white solid (2.2 mg, 10%). $^1$H NMR (400 MHz, DMSO-$d_6$) δ 12.48 (br, 1H), 9.89 (s, 1H), 8.55 (d, J=1.7 Hz, 1H), 7.77 (d, J=1.6 Hz, 1H), 7.62 (s, 1H), 6.99 (s, 1H), 5.09 (d, J=9.1 Hz, 1H), 4.38 (d, J=9.4 Hz, 1H), 3.60 (m, 2H), 3.46 (m, 2H), 3.20 (m, 1H), 2.19 (m, 2H), 1.68 (s, 3H). MS (ESI$^+$) m/z 449.1 (M+H).

Example 95

3-(3-chloro-6-{[(7R)-2,2-difluoro-7-methyl-6,7-dihydro-2H-furo[2,3-f][1,3]benzodioxole-7-carbonyl]amino}pyridin-2-yl)benzoic acid

Example 95A tert-butyl 3-(3-chloropyridin-2-yl)benzoate

2-Bromo-3-chloropyridine (0.8 g, 4.16 mmol), (3-(tert-butoxycarbonyl)phenyl)boronic acid (0.923 g, 4.16 mmol), potassium carbonate (1.207 g, 8.73 mmol), and PdCl$_2$dppf (0.152 g, 0.208 mmol) were mixed in dimethoxyethane (9 mL) and water (5 mL), and the mixture was heated overnight at 80° C. After this time, the mixture was diluted with ether (50 mL), then washed with a solution of 0.25 mL CH$_3$SO$_3$H in 12 mL water, followed by washing with brine (20 mL). The organic layer was dried over Na$_2$SO$_4$, filtered, and concentrated in vacuo. The residue was then purified by silica gel chromatography (0 to 30% ethyl acetate-heptanes, eluent) to afford the title compound (0.856 g, 71% yield). $^1$H NMR (500 MHz, DMSO-$d_6$) δ 8.67 (dd, J=4.6, 1.5 Hz, 1H), 8.19 (t, J=1.8 Hz, 1H), 8.09 (dd, J=8.3, 1.5 Hz, 1H), 8.07-7.84 (m, 2H), 7.64 (t, J=7.8 Hz, 1H), 7.49 (dd, J=8.2, 4.6 Hz, 1H), 1.56 (s, 9H).

Example 95B 2-(3-(tert-butoxycarbonyl)phenyl)-3-chloropyridine 1-oxide

The product of Example 95A (0.856 g, 2.95 mmol) in ethyl acetate (25 mL) and water (1.7 mL) was treated in one portion with urea-hydrogen peroxide (0.834 g, 8.86 mmol), then in 4 portions with phthalic anhydride (1.313 g, 8.86 mmol). The reaction then stirred at 45° C. for 5 hours before being cooled to room temperature. It was then treated with a solution of 1.6 g Na$_2$SO$_3$ in 16 mL water, and the mixture was stirred vigorously at room temperature for 1 hour. The phases were separated, and the organic layer was washed with 1M aqueous Na$_2$CO$_3$ (10 mL) and brine (10 mL) sequentially. The organic layer was dried over Na$_2$SO$_4$, filtered, and concentrated in vacuo. The residue was further dried azeotropically with toluene. The crude title compound was obtained as a thick yellow oil (0.796 g, 88%), which was taken into the next reaction without further purification.

Example 95C tert-butyl 3-(6-amino-3-chloropyridin-2-yl)benzoate

The product from Example 95B (0.902 g, 2.95 mmol) was taken up in dry acetonitrile (22 mL) and treated with pyridine (0.954 mL, 11.80 mmol). The mixture was heated to 65° C., followed by the addition of a solution of methanesulfonic anhydride (0.771 g, 4.43 mmol) in dry acetonitrile (6 mL) dropwise via addition funnel over about an hour. After completion of the addition, the mixture was stirred for another 30 minutes at 65° C. and was then cooled to room temperature and treated dropwise with ethanolamine (1.784 mL, 29.5 mmol) from an addition funnel. The orange clear solution became a heterogeneous tan mixture, which was allowed to stir overnight at room temperature. After this time, the mixture was treated with 13 mL water and cooled to 10° C., and stirred for 2 hours at this temperature. The mixture was then concentrated in vacuo to remove volatiles, and the remaining aqueous mixture was extracted with ethyl acetate (3×50 mL). The extracts were washed with water (25 mL) and brine (25 mL), dried over $Na_2SO_4$, filtered, and concentrated in vacuo. The residue was purified by silica gel chromatography, eluting with 0 to 40% ethyl acetate-heptanes, to afford the title compound as an off-white solid (0.428 g, 48% yield). $^1$H NMR (400 MHz, DMSO-$d_6$) δ 8.12 (t, J=1.7 Hz, 1H), 7.93 (dt, J=7.7, 1.4 Hz, 1H), 7.85 (dt, J=7.7, 1.5 Hz, 1H), 7.57 (t, J=7.7 Hz, 1H), 7.54 (d, J=8.7 Hz, 1H), 6.50 (d, J=8.7 Hz, 1H), 6.30 (bs, 2H), 1.56 (s, 9H).

Example 95D tert-butyl 3-(3-chloro-6-{[(7R)-2,2-difluoro-7-methyl-6,7-dihydro-2H-furo[2,3-f][1,3]benzodioxole-7-carbonyl]amino}pyridin-2-yl)benzoate The product from Example 3B (0.181 g, 0.702 mmol), the product from Example 95C (0.214 g, 0.702 mmol), HATU (0.280 g, 0.737 mmol), and DIEA (0.48 mL, 2.75 mmol) were stirred in $CH_2Cl_2$ (14 mL) overnight at room temperature. The mixture was diluted with more $CH_2Cl_2$ (10 mL) and washed with water (3×5 mL). The organics were dried over $Na_2SO_4$, filtered, and concentrated in vacuo. The residue was purified by reverse-phase preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to provide the title compound (0.013 g, 3%). $^1$H NMR (400 MHz, DMSO-$d_6$) δ 10.47 (s, 1H), 8.16 (s, 1H), 8.09-7.96 (m, 3H), 7.92 (dt, J=7.7, 1.3 Hz, 1H), 7.70-7.57 (m, 2H), 7.03 (s, 1H), 5.09 (d, J=9.4 Hz, 1H), 4.42 (d, J=9.4 Hz, 1H), 1.71 (s, 3H), 1.56 (s, 9H). MS (ESI$^+$) m/z 545.0 (M+H).

Example 95E 3-(3-chloro-6-{[(7R)-2,2-difluoro-7-methyl-6,7-dihydro-2H-furo[2,3-f][1,3]benzodioxole-7-carbonyl]amino}pyridin-2-yl)benzoic acid The product from Example 95D (0.013 g, 0.024 mmol) and trifluoroacetic acid (0.15 mL, 1.947 mmol) were stirred together in $CH_2Cl_2$ (0.3 mL) for 2 hours at room temperature. The mixture was then concentrated in vacuo to afford the title compound as a tan residue (0.011 g, 94%). $^1$H NMR (400 MHz, DMSO-$d_6$) δ 10.47 (s, 1H), 8.22 (s, 1H), 8.05 (m, 3H), 7.98-7.81 (m, 1H), 7.70-7.47 (m, 2H), 7.03 (s, 1H), 5.09 (d, J=9.4 Hz, 1H), 4.42 (d, J=9.4 Hz, 1H), 1.71 (s, 3H). MS (ESI$^+$) m/z 489.1 (M+H)$^+$.

Example 96

1-(6-{[(7R)-2,2-difluoro-7-methyl-6,7-dihydro-2H-furo[2,3-f][1,3]benzodioxole-7-carbonyl]amino}pyridin-2-yl)-3-methylazetidine-3-carboxylic acid Example 96A tert-butyl 1-(6-{[(7R)-2,2-difluoro-7-methyl-6,7-dihydro-2H-furo[2,3-f][1,3]benzodioxole-7-carbonyl]amino}pyridin-2-yl)-3-methylazetidine-3-carboxylate The product from Example 85 (26.5 mg, 0.075 mmol) was dissolved in dimethylsulfoxide (1 mL). Tert-Butyl 3-methylazetidine-3-carboxylate (54.2 mg, 0.317 mmol) and sodium carbonate (40.0 mg, 0.377 mmol) were added. The reaction was stirred at 80° C. for 16 hours. The reaction mixture was diluted with methanol (1 mL), filtered, and purified by reverse-phase preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (18.0 mg, 48%). $^1$H NMR (400 MHz, DMSO-$d_6$) δ 9.51 (s, 1H), 7.61 (s, 1H), 7.50 (t, J=8.0 Hz, 1H), 7.29 (d, J=7.9 Hz, 1H), 7.03 (s, 1H), 6.15 (d, J=8.1 Hz, 1H), 5.05 (d, J=9.4 Hz, 1H), 4.41 (d, J=9.4 Hz, 1H), 4.10 (dd, J=8.1, 1.7 Hz, 2H), 3.72 (dd, J=7.9, 1.6 Hz, 2H), 1.68 (s, 3H), 1.49 (s, 3H), 1.42 (s, 9H). MS (ESI+) m/z 504 (M+H)$^+$.

Example 96B 1-(6-{[(7R)-2,2-difluoro-7-methyl-6,7-dihydro-2H-furo[2,3-f][1,3]benzodioxole-7-carbonyl]amino}pyridin-2-yl)-3-methylazetidine-3-carboxylic acid The product from Example 96A (15.0 mg, 0.030 mmol) was dissolved in dichloromethane (1 mL). Trifluoroacetic acid (0.5 mL, 6.49 mmol) was added, and the reaction mixture was stirred at ambient temperature for 3 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (16.4 mg, 98%) as the trifluoroacetate salt. $^1$H NMR (501 MHz, DMSO-$d_6$) δ 9.58 (s, 1H), 7.61 (s, 1H), 7.51 (t, J=8.0 Hz, 1H), 7.28 (d, J=7.8 Hz, 1H), 7.03 (s, 1H), 6.16 (d, J=8.0 Hz, 1H), 5.05 (d, J=9.4 Hz, 1H), 4.41 (d, J=9.4 Hz, 1H), 4.15 (dd, J=8.0, 1.3 Hz, 2H), 3.74 (dd, J=7.9, 1.9 Hz, 2H), 1.68 (s, 3H), 1.51 (s, 3H); MS (ESI+) m/z 448 (M+H)$^+$.

Example 97

4-[5-bromo-3-{[(7R)-2,2-difluoro-7-methyl-6,7-dihydro-2H-furo[2,3-f][1,3]benzodioxole-7-carbonyl]amino}-2-oxopyridin-1(2H)-yl]benzoic acid

Example 97A methyl 4-(3-nitro-2-oxopyridin-1(2H)-yl)benzoate

A mixture of 2-hydroxy-3-nitropyridine (1.168 g, 8.33 mmol), copper (II) acetate (2.271 g, 12.50 mmol), 4-methoxycarbonylphenylboronic acid (3 g, 16.67 mmol) and pyridine (10.11 mL, 125 mmol) was stirred under $N_2$ for 5 minutes, and the atmosphere (balloon) was changed to $O_2$. The mixture was then stirred at 90° C. overnight. The mixture was cooled to room temperature, treated with water (50 mL) and stirred for 5 minutes. The solid was collected by filtration, washed with water, and dried under vacuum. The solid was chromatographed on silica gel eluting with a gradient of 0-100% ethyl acetate in [9:1 $CH_2Cl_2$:ethyl acetate] to provide the title compound (1.57 g, 5.73 mmol, 68.7% yield). $^1$H NMR (400 MHz, DMSO-$d_6$) δ 8.53 (dd, J=7.7, 2.0 Hz, 1H), 8.20 (dd, J=6.7, 2.0 Hz, 1H), 8.12 (d, J=8.5 Hz, 2H), 7.67 (d, J=8.5 Hz, 2H), 6.58-6.53 (m, 1H), 3.90 (s, 3H); MS (ESI+) m/z 275 (M+H)$^+$.

Example 97B methyl 4-(5-bromo-3-nitro-2-oxopyridin-1(2H)-yl)benzoate

A solution of the product from Example 97A (1 g, 3.65 mmol) in N,N-dimethylformamide (20 mL) was treated with N-bromosuccinimide (0.779 g, 4.38 mmol), stirred at ambient temperature for 30 minutes and heated at 70° C. overnight. The mixture was cooled, treated with water (100 mL) and stirred at ambient temperature for 5 minutes. The solid was collected by filtration, washed with water, and dried under vacuum. The solid was purified by chromatography on silica gel eluting with a gradient of 25% to 100% [9:1 $CH_2Cl_2$: ethyl acetate] in $CH_2Cl_2$ to provide the title compound (1 g, 2.83 mmol, 78% yield). $^1$H NMR (500 MHz, DMSO-$d_6$) δ 8.69 (d, J=2.7 Hz, 1H), 8.54 (d, J=2.7 Hz, 1H), 8.12-8.09 (m, 2H), 7.70-7.67 (m, 2H), 3.90 (s, 3H).

Example 97C methyl 4-(3-amino-5-bromo-2-oxopyridin-1(2H)-yl)benzoate

A solution of the product from Example 97B (0.93 g, 2.63 mmol) in acetic acid (10 mL) was treated with zinc (1.722 g, 26.3 mmol) and stirred at ambient temperature for 1 hour. The mixture was treated with more zinc (1.722 g, 26.3 mmol). After stirring for 1 hour, the mixture was filtered to remove the solids. The solids were washed with acetic acid. The combined filtrates were concentrated. The residue was partitioned between saturated $NaHCO_3$ solution and $CH_2Cl_2$. The layers were separated and the aqueous layer was extracted with $CH_2Cl_2$. The combined $CH_2Cl_2$ layers were dried ($MgSO_4$), filtered, concentrated and chromatographed on silica gel, eluting with a gradient of 0% to 50% ethyl acetate in [9:1 $CH_2Cl_2$: ethyl acetate] to provide the title compound (0.65 g, 2.011 mmol, 76% yield). $^1$H NMR (400 MHz, DMSO-$d_6$) δ 8.06 (d, J=8.5 Hz, 2H), 7.60 (d, J=8.5 Hz, 2H), 7.12 (d, J=2.4 Hz, 1H), 6.56 (d, J=2.4 Hz, 1H), 5.67 (s, 2H), 3.89 (s, 3H); MS (ESI+) m/z 323 (M+H)$^+$.

Example 97D methyl 4-[5-bromo-3-{[(7R)-2,2-difluoro-7-methyl-6,7-dihydro-2H-furo[2,3-f][1,3]benzodioxole-7-carbonyl]amino}-2-oxopyridin-1(2H)-yl]benzoate A mixture of the product from Example 3B (182 mg, 0.703 mmol), the product from Example 97C (250 mg, 0.774 mmol) and 1-[bis(dimethylamino)methylene]-1H-1,2,3-triazolo[4,5-b]pyridinium 3-oxid hexafluorophosphate (401 mg, 1.055 mmol) was dissolved in N,N-dimethylformamide (2 mL) under $N_2$, treated with $Et_3N$ (294 μL, 2.110 mmol), and stirred over night at ambient temperature. The mixture was diluted with methyl tert-butyl ether (30 mL), washed with saturated $NaHCO_3$ solution, washed with brine, dried ($MgSO_4$), filtered, concentrated, and chromatographed on silica gel eluting with a gradient of 25% to 100% [1:1 ethyl acetate: $CH_2Cl_2$] in heptanes to provide the title compound (192 mg, 0.341 mmol, 48.5% yield). $^1$H NMR (400 MHz, CDCl$_3$) δ 8.68 (bs, 1H), 8.56 (d, J=2.4 Hz, 1H), 8.17 (d, J=8.5 Hz, 2H), 7.43 (d, J=8.5 Hz, 2H), 7.22 (d, J=2.4 Hz, 1H), 6.96 (s, 1H), 6.65 (s, 1H), 5.01 (d, J=9.3 Hz, 1H), 4.36 (d, J=9.3 Hz, 1H), 3.95 (s, 3H), 1.68 (s, 3H); MS (ESI+) m/z 563 (M+H)$^+$; MS (ESI–) m/z 561 (M–H)$^-$.

Example 97E

4-[5-bromo-3-{[(7R)-2,2-difluoro-7-methyl-6,7-dihydro-2H-furo[2,3-f][1,3]benzodioxole-7-carbonyl]amino}-2-oxopyridin-1(2H)-yl]benzoic acid A solution of the product from Example 97D (23.5 mg, 0.042 mmol), in tetrahydrofuran (1 mL) was diluted with methanol (1 mL), treated with 1 M NaOH (0.5 mL), stirred for 15 minutes at ambient temperature, treated with 1 M HCl (3 mL) and extracted with ethyl acetate (25 mL). The ethyl acetate layer was washed with brine, dried ($MgSO_4$), filtered, concentrated and chromatographed on silica gel eluting with a gradient of 25% to 100% [200:1:1 ethyl acetate: HCOOH:$H_2O$] in heptane to provide the title compound (16 mg, 0.029 mmol, 69.8% yield). $^1$H NMR (400 MHz, CDCl$_3$) δ 8.69 (s, 1H), 8.58 (d, J=2.4 Hz, 1H), 8.23 (d, J=8.6 Hz, 2H), 7.48 (d, J=8.6 Hz, 2H), 7.23 (d, J=2.5 Hz, 1H), 6.97 (s, 1H), 6.65 (s, 1H), 5.01 (d, J=9.3 Hz, 1H), 4.36 (d, J=9.4 Hz, 1H), 1.68 (s, 3H); MS (ESI+) m/z 549 (M+H)$^+$; MS (ESI–) m/z 547 (M–H)$^-$.

Example 98

(7R)—N-{5-bromo-1-[(2R)-2,3-dihydroxypropyl]-2-oxo-1,2-dihydropyridin-3-yl}-2,2-difluoro-7-methyl-6,7-dihydro-2H-furo[2,3-f][1,3]benzodioxole-7-carboxamide

Example 98A

1-{[(4R)-2,2-dimethyl-1,3-dioxolan-4-yl]methyl}-3-nitropyridin-2(1H)-one

A solution of 2-hydroxy-3-nitropyridine (1 g, 7.14 mmol), (R)-(−)-2,2-dimethyl-1,3-dioxolane-4-methanol (1.226 g, 9.28 mmol) and triphenylphosphine (2.81 g, 10.71 mmol) in $CH_2Cl_2$ (70 mL) was cooled to 0° C., treated dropwise with 40 weight % diethyl azodicarboxylate in toluene (4.88 mL, 10.71 mmol) over 15 minutes, stirred at 0° C. for 1 hour and overnight at ambient temperature. Methanol (20 mL) was added and mixture was stirred for 15 minutes. The mixture was treated with water (100 mL) and extracted with $CH_2Cl_2$ (twice). The combined $CH_2Cl_2$ layers were dried ($MgSO_4$), filtered, concentrated, and chromatographed on silica gel eluting with 5% ethyl acetate in heptanes to provide the title compound. $^1$H NMR (400 MHz, $CDCl_3$) δ 8.35 (dd, J=7.7, 2.1 Hz, 1H), 7.81 (dd, J=6.6, 2.1 Hz, 1H), 6.33 (dd, J=7.6, 6.7 Hz, 1H), 4.55-4.45 (m, 2H), 4.16 (dd, J=8.9, 6.5 Hz, 1H), 3.93 (dd, J=13.9, 7.8 Hz, 1H), 3.72 (dd, J=8.9, 5.9 Hz, 1H), 1.41 (s, 3H), 1.33 (s, 3H); MS (ESI+) m/z 255 (M+H)$^+$.

Example 98B 5-bromo-1-{[(4R)-2,2-dimethyl-1,3-dioxolan-4-yl]methyl}-3-nitropyridin-2(1H)-one A mixture of the product from Example 98A (270 mg, 1.062 mmol) in N,N-dimethylformamide (1.5 mL) was treated with N-bromosuccinimide (284 mg, 1.593 mmol) and heated at 70° C. for 1 hour. The mixture was cooled, diluted with methyl tert-butyl ether (30 mL), washed with water (25 mL), washed with brine, dried ($MgSO_4$), filtered, and concentrated. The residue was taken up in $CH_2Cl_2$ (1 mL) and heptanes (2 mL) were added. A yellow solid precipitated. This solid was isolated by filtration to provide the title compound. The filtrate was concentrated and chromatographed on silica gel eluting with a gradient of 25% to 100% ethyl acetate in heptane to provide more of the title compound. Overall yield (205 mg, 0.615 mmol, 57.9% yield). $^1$H NMR (500 MHz, $CDCl_3$) δ 8.40 (d, J=2.8 Hz, 1H), 7.91 (d, J=2.8 Hz, 1H), 4.48 (qd, J=6.8, 2.6 Hz, 1H), 4.41 (dd, J=13.6, 2.5 Hz, 1H), 4.16 (dd, J=9.0, 6.7 Hz, 1H), 3.98 (dd, J=13.6, 7.0 Hz, 1H), 3.71 (dd, J=9.0, 5.9 Hz, 1H), 1.43 (s, 3H), 1.34 (s, 3H); MS (ESI+) m/z 333 (M+H)$^+$; MS (ESI−) m/z 331 (M−H)$^-$.

Example 98C 3-amino-5-bromo-1-{[(4R)-2,2-dimethyl-1,3-dioxolan-4-yl]methyl}pyridin-2(1H)-one A solution of the product from Example 98B (0.16 g, 0.480 mmol) in acetic acid (5 mL) was treated with zinc (0.314 g, 4.80 mmol), stirred at ambient temperature 30 minutes, treated with more zinc (0.031 g, 0.480 mmol), stirred for an additional 30 minutes, diluted with ethyl acetate and filtered to remove the solids. The filtrate was concentrated to dryness and partitioned between ethyl acetate and saturated $NaHCO_3$ solution. The layers were separated and the ethyl acetate layer was washed with brine, dried ($MgSO_4$), filtered, and concentrated to provide the title compound (110 mg, 0.363 mmol, 76% yield). $^1$H NMR (500 MHz, $CDCl_3$) δ 6.94 (d, J=2.4 Hz, 1H), 6.57 (d, J=2.4 Hz, 1H), 4.45 (qd, J=6.4, 3.3 Hz, 1H), 4.36 (bs, 2H), 4.23 (dd, J=13.7, 3.3 Hz, 1H), 4.11 (dd, J=8.8, 6.5 Hz, 1H), 3.92 (dd, J=13.7, 6.5 Hz, 1H), 3.69 (dd, J=8.8, 6.2 Hz, 1H), 1.41 (s, 3H), 1.34 (s, 3H); MS (ESI-1) m/z 303 (M+H)$^+$.

Example 98D (7R)—N-(5-bromo-1-{[(4R)-2,2-dimethyl-1,3-dioxolan-4-yl]methyl}-2-oxo-1,2-dihydropyridin-3-yl)-2,2-difluoro-7-methyl-6,7-dihydro-2H-furo[2,3-f][1,3]benzodioxole-7-carboxamide A mixture of the product from Example 98C (102 mg, 0.396 mmol), the product from Example 3B (109 mg, 0.360 mmol), and 1-[bis(dimethylamino)methylene]-1H-1,2,3-triazolo[4,5-b]pyridinium 3-oxid hexafluorophosphate (205 mg, 0.539 mmol) was dissolved in N,N-dimethylformamide (1 mL) under $N_2$, treated with triethylamine (150 μL, 1.079 mmol) and stirred overnight at ambient temperature. The mixture was diluted with methyl tert-butyl ether (30 mL), washed with saturated $NaHCO_3$ solution, washed with brine, dried ($MgSO_4$), filtered, concentrated and chromatographed on silica gel eluting with a gradient of 15% to 100% ethyl acetate in heptanes to provide the title compound (100 mg, 0.184 mmol, 51.2% yield). $^1$H NMR (400 MHz, $CDCl_3$) δ 8.62 (s, 1H), 8.47 (d, J=2.5 Hz, 1H), 7.25 (d, J=2.5 Hz, 1H), 6.98 (d, J=0.8 Hz, 1H), 6.68 (s, 1H), 5.00 (dd, J=9.3, 1.3 Hz, 1H), 4.44-4.38 (m, 1H), 4.36 (d, J=9.4 Hz, 1H), 4.23 (ddd, J=13.7, 4.0, 3.0 Hz, 1H), 4.09 (dd, J=8.8, 6.7 Hz, 1H), 3.86 (ddd, J=13.7, 6.8, 3.4 Hz, 1H), 3.65 (td, J=6.0, 3.0 Hz, 1H), 1.67 (s, 3H), 1.40 (s, 3H), 1.32 (s, 3H); MS (ESI−) m/z 541 (M−H)$^-$.

Example 98E (7R)— N-{5-bromo-1-[(2R)-2,3-dihydroxypropyl]-2-oxo-1,2-dihydropyridin-3-yl}-2,2-difluoro-7-methyl-6,7-dihydro-2H-furo[2,3-f][1,3]benzodioxole-7-carboxamide A solution of the product from Example 98D (28.4 mg, 0.052 mmol) in methanol (1 mL) was treated with 6 M HCl (1 mL) and stirred for 2 hours. The mixture was partitioned between ethyl acetate (30 mL) and water (15 mL). The ethyl acetate layer was washed with brine, dried ($MgSO_4$), filtered, and concentrated to provide the title compound (25 mg, 0.050 mmol, 95% yield). $^1$H NMR (400 MHz, $CDCl_3$) δ 8.60 (s, 1H), 8.52 (d, J=2.4 Hz, 1H), 7.23 (d, J=2.4 Hz, 1H), 6.98 (s, 1H), 6.69 (s, 1H), 5.00 (d, J=9.3 Hz, 1H), 4.36 (d, J=9.3 Hz, 1H), 4.17-3.97 (m, 3H), 3.61-3.49 (m, 2H), 2.94 (bs, 1H), 2.76 (bs, 1H), 1.68 (s, 3H); MS (ESI-1) m/z 503 (M+H)$^+$; MS (ESI−) m/z 501 (M−H)$^-$.

Example 99

4-[3-{[(7R)-2,2-difluoro-7-methyl-6,7-dihydro-2H-furo[2,3-f][1,3]benzodioxole-7-carbonyl]amino}-2-oxo-5-phenylpyridin-1(2H)-yl]benzoic acid Example 99A methyl 4-[3-{[(7R)-2,2-difluoro-7-methyl-6,7-dihydro-2H-furo[2,3-f][1,3]benzodioxole-7-carbonyl]amino}-2-oxo-5-phenylpyridin-1(2H)-yl]benzoate A mixture of the product from Example 97D (23.9 mg, 0.042 mmol), phenylboronic acid (15.52 mg, 0.127 mmol), palladium(II) acetate (0.476 mg, 2.121 μmol) and 2-dicyclohexylphosphino-2',6'-dimethoxybiphenyl (1.742 mg, 4.24 μmol) was treated with a stream of $N_2$ for 5 seconds, and treated with tetrahydrofuran (1 mL). The mixture was heated at 90° C. under $N_2$ for 6 hours and allowed to stir at ambient temperature overnight. The mixture was partitioned between ethyl acetate (30 mL) and $H_2O$ (5 mL). The ethyl acetate layer was washed with brine, dried ($MgSO_4$), filtered, concentrated and chromatographed on silica gel eluting with a gradient of 10% to 30% ethyl acetate in heptanes to provide the title compound (24 mg, 0.043 mmol, 101% yield). $^1$H NMR (501 MHz, $CDCl_3$) δ 8.84 (d, J=2.4 Hz, 1H), 8.76 (s, 1H), 8.21-8.18 (m, 2H), 7.54-7.45 (m, 4H), 7.41 (t, J=7.5 Hz, 2H), 7.38-7.31 (m, 1H), 7.29 (d, J=2.4 Hz, 1H), 7.00 (s, 1H), 6.66 (s, 1H), 5.05 (d, J=9.3 Hz, 1H), 4.38 (d, J=9.2 Hz, 1H), 3.96 (s, 3H), 1.70 (s, 3H); MS (ESI+) m/z 561 (M+H)⁺; MS (ESI−) m/z 559 (M−H)⁻.

Example 99B

4-[3-{[(7R)-2,2-difluoro-7-methyl-6,7-dihydro-2H-furo[2,3-f][1,3]benzodioxole-7-carbonyl]amino}-2-oxo-5-phenylpyridin-1(2H)-yl]benzoic acid A solution of the product from Example 99A (23.5 mg, 0.042 mmol) in tetrahydrofuran (1 mL) was diluted with methanol (1 mL), treated with 1 M NaOH (0.5 mL), stirred for 15 minutes at ambient temperature, treated with 1 M HCl (about 3 mL) and extracted with ethyl acetate (25 mL). The ethyl acetate layer was washed with brine, dried (MgSO₄), filtered, concentrated and chromatographed on silica gel, eluting with a gradient of 25% to 100% [200:1:1 ethyl acetate:HCOOH:H₂O] in heptane to provide the title compound (15 mg, 0.027 mmol, 65.5% yield). ¹H NMR (400 MHz, CDCl₃) δ 8.85 (d, J=2.4 Hz, 1H), 8.77 (s, 1H), 8.24 (d, J=8.5 Hz, 2H), 7.55 (d, J=8.5 Hz, 2H), 7.51-7.47 (m, 2H), 7.41 (t, J=7.5 Hz, 2H), 7.37-7.32 (m, 1H), 7.30 (d, J=2.4 Hz, 1H), 7.02 (s, 1H), 6.66 (s, 1H), 5.06 (d, J=9.3 Hz, 1H), 4.39 (d, J=9.3 Hz, 1H), 1.71 (s, 3H); MS (ESI+) m/z 547 (M+H)⁺; MS (ESI−) m/z 545 (M−H)⁻.

Example 100

(7R)—N-{1-[(2R)-2,3-dihydroxypropyl]-2-oxo-5-phenyl-1,2-dihydropyridin-3-yl}-2,2-difluoro-7-methyl-6,7-dihydro-2H-furo[2,3-f][1,3]benzodioxole-7-carboxamide Example 100A (7R)—N-(1-{[(4R)-2,2-dimethyl-1,3-dioxolan-4-yl]methyl}-2-oxo-5-phenyl-1,2-dihydropyridin-3-yl)-2,2-difluoro-7-methyl-6,7-dihydro-2H-furo[2,3-f][1,3]benzodioxole-7-carboxamide A mixture of the product from Example 98D (37.6 mg, 0.069 mmol), phenylboronic acid (25.3 mg, 0.208 mmol), potassium phosphate hydrate (47.8 mg, 0.208 mmol) and 2-dicyclohexylphosphino-2',6'-dimethoxybiphenyl (2.84 mg, 6.92 μmol) was treated with a stream of N₂ for 5 seconds, treated with tetrahydrofuran (1 mL) and heated at 90° C. for 6 hours under N₂ and allowed to stand at ambient temperature overnight. The mixture was partitioned between ethyl acetate (30 mL) and H₂O (5 mL). The ethyl acetate layer was washed with brine, dried (MgSO₄), filtered, concentrated and chromatographed on silica gel, eluting with a gradient of 10% to 50% ethyl acetate in heptanes to provide the title compound (34 mg, 0.063 mmol, 91% yield). ¹H NMR (400 MHz, CDCl₃) δ 8.75 (d, J=2.4 Hz, 1H), 8.70 (s, 1H), 7.47-7.38 (m, 4H), 7.33 (dd, J=6.1, 2.2 Hz, 2H), 7.02 (s, 1H), 6.69 (s, 1H), 5.04 (dd, J=9.3, 2.3 Hz, 1H), 4.48 (dt, J=8.8, 4.4 Hz, 1H), 4.41-4.32 (m, 2H), 4.13 (dd, J=8.7, 6.6 Hz, 1H), 3.96 (ddd, J=13.6, 6.8, 3.4 Hz, 1H), 3.71 (ddd, J=8.8, 6.2, 2.6 Hz, 1H), 1.70 (s, 3H), 1.40 (s, 3H), 1.32 (s, 3H); MS (ESI−) m/z 539 (M−H)⁻.

Example 100B (7R)—N-{1-[(2R)-2,3-dihydroxypropyl]-2-oxo-5-phenyl-1,2-dihydropyridin-3-yl}-2,2-difluoro-7-methyl-6,7-dihydro-2H-furo[2,3-f][1,3]benzodioxole-7-carboxamide A solution of the product from Example 100A (33 mg, 0.061 mmol) in methanol (1 mL) was treated with 6 M HCl (1 mL) and stirred for 2 hours. The mixture was partitioned between ethyl acetate (30 mL) and water (15 mL). The ethyl acetate layer was washed with brine, dried (MgSO₄), filtered, concentrated and chromatographed on silica gel, eluting with a gradient of 25% to 100% ethyl acetate in heptanes to provide the title compound (24 mg, 0.048 mmol, 79% yield). ¹H NMR (400 MHz, CDCl₃) δ 8.78 (d, J=2.3 Hz, 1H), 8.68 (s, 1H), 7.47-7.37 (m, 4H), 7.36-7.31 (m, 1H), 7.30 (d, J=2.4 Hz, 1H), 7.01 (s, 1H), 6.69 (s, 1H), 5.04 (d, J=9.3 Hz, 1H), 4.38 (d, J=9.3 Hz, 1H), 4.27-4.14 (m, 2H), 4.06 (q, J=5.1 Hz, 1H), 3.62-3.52 (m, 2H), 3.14-3.11 (m, 1H), 2.96 (t, J=6.4 Hz, 1H), 1.70 (s, 3H); MS (ESI+) m/z 501 (M+H)⁺; MS (ESI−) m/z 499 (M−H)⁻.

Example 101

(7R)—N-[6-(3,3-dimethylpyrrolidin-1-yl)pyridin-2-yl]-2,2-difluoro-7-methyl-6,7-dihydro-2H-furo[2,3-f][1,3]benzodioxole-7-carboxamide The product from Example 85 (30.6 mg, 0.087 mmol) and 3,3-dimethylpyrrolidine (55.6 mg, 0.561 mmol) were dissolved in dimethylsulfoxide (1 mL). The reaction was stirred at 80° C. for 6 hours. The reaction mixture was diluted with methanol (1 mL), filtered, and purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (40.9 mg, 86%) as the trifluoroacetic acid salt. ¹H NMR (400 MHz, DMSO-d₆) δ 9.40 (s, 1H), 7.59 (s, 1H), 7.48 (t, J=8.0 Hz, 1H), 7.12 (d, J=7.7 Hz, 1H), 7.04 (s, 1H), 6.19 (d, J=8.3 Hz, 1H), 5.04 (d, J=9.4 Hz, 1H), 4.41 (d, J=9.4 Hz, 1H), 3.44 (t, J=7.0 Hz, 2H), 3.17 (s, 2H), 1.74 (t, J=7.0 Hz, 2H), 1.67 (s, 3H), 1.08 (s, 6H). MS (ESI+) m/z 432 (M+H)⁺.

Example 102

1-(5-{[(7R)-2,2-difluoro-7-methyl-6,7-dihydro-2H-furo[2,3-f][1,3]benzodioxole-7-carbonyl]amino}pyrazin-2-yl)proline Example 102A tert-butyl 1-(5-{[(7R)-2,2-difluoro-7-methyl-6,7-dihydro-2H-furo[2,3-f][1,3]benzodioxole-7-carbonyl]amino}pyrazin-2-yl)pyrrolidine-2-carboxylate The product from Example 94A (0.060 g, 0.145 mmol), tert-butyl pyrrolidine-2-carboxylate (0.034 g, 0.198 mmol), sodium 2-methylpropan-2-olate (0.051 g, 0.530 mmol), and RuPhos palladacycle (RuPhos precatalyst) (0.021 g, 0.029 mmol) were treated with dioxane (3 mL), then the mixture was heated at 85° C. overnight. The mixture was diluted with ethyl acetate (20 mL) and washed with water (2×5 mL) and with brine (5 mL). The organic layer was dried over Na₂SO₄, filtered, and concentrated in vacuo. The residue was purified by reverse-phase preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (0.018 g, 25%). ¹H NMR (400 MHz, DMSO-d₆) δ 9.92 (s, 1H), 8.56-8.47 (m, 1H), 7.76 (d, J=1.5 Hz, 1H), 7.61 (s, 1H), 7.02 (s, 1H), 5.09 (d, J=9.2 Hz, 1H), 4.37 (m, 2H), 3.51 (t, J=6.5 Hz, 2H), 2.27 (m, 1H), 2.00 (m, 3H), 1.68 (s, 3H), 1.35 (s, 9H). MS (ESI$^+$) m/z 505.0 (M+H).

Example 102B 1-(5-{[(7R)-2,2-difluoro-7-methyl-6,7-dihydro-2H-furo[2,3-f][1,3]benzodioxole-7-carbonyl]amino}pyrazin-2-yl)proline The product from Example 102A (0.018 g, 0.036 mmol) and trifluoroacetic acid (0.25 ml, 3.24 mmol) were stirred together in CH$_2$Cl$_2$ (0.5 mL) overnight at room temperature. After this time, the mixture was concentrated in vacuo, and the residue was dried under vacuum at 75° C. for 1 hour. The title compound was obtained as a beige residue (0.002 g, 13%). $^1$H NMR (500 MHz, DMSO-d$_6$) δ 9.90 (s, 1H), 8.50 (t, J=1.7 Hz, 1H), 7.75 (d, J=1.4 Hz, 1H), 7.61 (d, J=1.8 Hz, 1H), 7.02 (s, 1H), 5.09 (dd, J=9.2, 1.4 Hz, 1H), 4.46-4.34 (m, 2H), 3.57-3.44 (m, 2H), 2.27 (m, 1H), 2.01 (m, 3H), 1.68 (s, 3H). MS (ESI$^+$) m/z 449.1 (M+H).

Example 103

3-(6-{[(7R)-2,2-difluoro-7-methyl-6,7-dihydro-2H-furo[2,3-f][1,3]benzodioxole-7-carbonyl]amino}-4-methylpyridin-2-yl)benzoic acid Example 103A (7R)—N-(6-chloro-4-methylpyridin-2-yl)-2,2-difluoro-7-methyl-6,7-dihydro-2H-furo[2,3-f][1,3]benzodioxole-7-carboxamide The product from Example 3B (0.163 g, 0.631 mmol) was refluxed in thionyl chloride (1.2 mL, 16.44 mmol) for 1 hour, then the mixture was cooled to room temperature and concentrated in vacuo. Excess thionyl chloride was chased with CH$_2$Cl$_2$ (3×1.2 mL), then the remaining syrup was taken up in 1.2 mL CH$_2$Cl$_2$ and treated with a solution of 6-chloro-4-methylpyridin-2-amine (0.090 g, 0.631 mmol) in pyridine (0.6 mL, 7.42 mmol). The reaction mixture stirred overnight at room temperature. After this time, the mixture was diluted with CH$_2$Cl$_2$ (10 mL) and washed with water (3×5 mL), then the organic layer was dried over Na$_2$SO$_4$, filtered, and concentrated in vacuo. The residue was purified by silica gel chromatography, eluting with 5 to 25% ethyl acetate-heptanes to afford the title compound as a colorless oil (0.164 g, 68%). $^1$H NMR (400 MHz, DMSO-d$_6$) δ 10.41 (s, 1H), 7.84 (t, J=1.0 Hz, 1H), 7.63 (s, 1H), 7.12 (d, J=0.9 Hz, 1H), 7.03 (s, 1H), 5.07 (d, J=9.3 Hz, 1H), 4.40 (d, J=9.3 Hz, 1H), 2.31 (s, 3H), 1.69 (s, 3H). MS (APCI$^+$) m/z 383.2 (M+H).

Example 103B tert-butyl 3-(6-{[(7R)-2,2-difluoro-7-methyl-6,7-dihydro-2H-furo[2,3-f][1,3]benzodioxole-7-carbonyl]amino}-4-methylpyridin-2-yl)benzoate The product from Example 103A (0.080 g, 0.209 mmol), (3-(tert-butoxycarbonyl)phenyl)boronic acid (0.046 g, 0.209 mmol), PdCl$_2$dppf (10.71 mg, 0.015 mmol), and potassium carbonate (0.066 g, 0.481 mmol) in dimethoxyethane (0.8 mL) and water (0.4 mL) were heated at 80° C. overnight. The mixture was diluted with ethyl acetate (10 mL) and washed with water (3×5 mL) and with brine (5 mL). The organic layer was dried over Na$_2$SO$_4$, filtered, and concentrated in vacuo. The residue was purified by reverse-phase preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/minute to yield the title compound (0.055 g, 50%). $^1$H NMR (500 MHz, DMSO-d$_6$) δ 10.03 (s, 1H), 8.58 (t, J=1.8 Hz, 1H), 8.28 (dt, J=7.9, 1.3 Hz, 1H), 7.95 (dt, J=7.6, 1.4 Hz, 1H), 7.84 (t, J=1.0 Hz, 1H), 7.71-7.57 (m, 3H), 7.05 (s, 1H), 5.13 (d, J=9.3 Hz, 1H), 4.44 (d, J=9.2 Hz, 1H), 2.39 (s, 3H), 1.74 (s, 3H), 1.59 (s, 9H). MS (ESI$^+$) m/z 525.1 (M+H).

Example 103C 3-(6-{[(7R)-2,2-difluoro-7-methyl-6,7-dihydro-2H-furo[2,3-f][1,3]benzodioxole-7-carbonyl]amino}-4-methylpyridin-2-yl)benzoic acid The product from Example 103B (0.054 g, 0.104 mmol) and trifluoroacetic acid (0.68 mL, 8.83 mmol) were stirred in CH$_2$Cl$_2$ (1.3 mL) overnight at room temperature. After this time, the mixture was concentrated in vacuo, and the resulting material was dried under vacuum at 75° C. to afford the title compound as a tan residue (0.048 g, 98%). $^1$H NMR (400 MHz, DMSO-d$_6$) δ 10.11 (s, 1H), 8.65 (t, J=1.8 Hz, 1H), 8.29 (dt, J=7.8, 1.6 Hz, 1H), 8.01 (dt, J=7.8, 1.4 Hz, 1H), 7.84 (s, 1H), 7.69-7.56 (m, 3H), 7.05 (s, 1H), 5.12 (m, 1H), 4.46 (d, J=9.3 Hz, 1H), 2.39 (s, 3H), 1.74 (s, 3H). MS (ESI$^+$) m/z 469.1 (M+H).

Example 104

(7R)—N-(2-{(2S)-2-[(4R)-2,2-dimethyl-1,3-dioxolan-4-yl]-2-hydroxyethyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide Example 104A 4-amino-6-phenylpyridazin-3(2H)-one A mixture of 6-phenylpyridazin-3(2H)-one (1 g, 5.81 mmol) and hydrazine monohydrate (15 mL, 309 mmol) was heated at 120° C. under N$_2$ for 90 minutes. Mixture was cooled and more hydrazine monohydrate (15 mL, 309 mmol) was added. The mixture was heated at 120° C. over night. The mixture was cooled and the resulting solid was collected by filtration and washed with water. The solid was taken up in acetonitrile (20 mL) and stirred for 5 minutes. The solid was collected by filtration, washed with acetonitrile and dried under vacuum to provide the title compound (0.66 g, 3.53 mmol, 60.7% yield). $^1$H NMR (400 MHz, DMSO-d$_6$) δ ppm 12.66 (bs, 1H), 7.75-7.70 (m, 2H), 7.47-7.36 (m, 3H), 6.74 (s, 1H), 6.43 (bs, 2H); MS (ESI+) m/z 188 (M+H)$^+$.

Example 104B (4R)-2,2-dimethyl-4-[(2S)-oxiran-2-yl]-1,3-dioxolane

Trimethylsulfoxonium iodide (5.07 g, 23.05 mmol) was pulverized using a mortar and pestle. This solid was combined with 60% dispersion of sodium hydride in mineral oil (0.922 g, 23.05 mmol) under N$_2$ and the solid mixture was vigorously mixed with a magnetic stir bar. This mixture was treated dropwise with anhydrous dimethylsulfoxide (40 mL) (slowly at first, and then more rapidly at the end) over 30 minutes. The mixture was stirred at ambient temperature for an additional 30 minutes. A solution of (R)-(+)-2,2-dimethyl-1,3-dioxolane-4-carboxaldehyde (1:1 with $CH_2Cl_2$) (5 g, 19.21 mmol) in dimethylsulfoxide (5 mL) was added via cannula dropwise over 5 minutes. The mixture was stirred overnight. The mixture was partitioned between methyl tert-butyl ether (100 mL) and water (100 mL). The aqueous layer was extracted with methyl tert-butyl ether (2×50 mL). The combined methyl tert-butyl ether layers were washed with brine, dried ($MgSO_4$), filtered, and concentrated. The residue was chromatographed on silica gel eluting with a gradient of 10% to 30% methyl tert-butyl ether in pentane to provide the title compound (0.84 g, 5.83 mmol, 30.3% yield) as the first eluting isomer. $^1H$ NMR (400 MHz, $CDCl_3$) δ ppm 4.13 (dd, J=8.3, 6.3 Hz, 1H), 3.92 (dd, J=8.4, 5.7 Hz, 1H), 3.86 (q, J=6.0 Hz, 1H), 3.02 (ddd, J=6.2, 3.9, 2.6 Hz, 1H), 2.85 (dd, J=4.8, 4.0 Hz, 1H), 2.65 (dd, J=4.9, 2.6 Hz, 1H), 1.46 (s, 3H), 1.37 (s, 3H).

Example 104C (4R)-2,2-dimethyl-4-[(2R)-oxiran-2-yl]-1,3-dioxolane

The title compound (0.19 g, 1.318 mmol, 6.86% yield) was collected as the second eluting isomer from the silica gel chromatography as described in Example 104B. $^1H$ NMR (400 MHz, $CDCl_3$) δ ppm 4.10 (dd, J=8.2, 6.6 Hz, 1H), 3.98 (q, J=6.3 Hz, 1H), 3.85 (dd, J=8.2, 6.4 Hz, 1H), 3.03 (ddd, J=5.3, 4.1, 2.7 Hz, 1H), 2.81-2.78 (m, 1H), 2.67 (dd, J=5.0, 2.6 Hz, 1H), 1.44 (s, 3H), 1.37 (s, 3H).

Example 104D 4-amino-2-{(2S)-2-[(4R)-2,2-dimethyl-1,3-dioxolan-4-yl]-2-hydroxyethyl}-6-phenylpyridazin-3(2H)-one A suspension of the product from Example 104A (97 mg, 0.520 mmol), $K_2CO_3$ (71.9 mg, 0.520 mmol) and the product from Example 104B (90 mg, 0.624 mmol) in N,N-dimethylformamide (2.5 mL) under $N_2$ was heated at 110° C. for 1 hour. The mixture was cooled, diluted with methyl tert-butyl ether (30 mL), washed with water (twice, 15 mL and 15 mL), washed with brine, dried ($MgSO_4$), filtered, and concentrated. The residue was dissolved in $CH_2Cl_2$/methanol, treated with silica gel (1.5 g) and concentrated to dryness. This silica gel suspension of the crude product was purified by chromatography on silica gel eluting with a gradient of 50% to 100% ethyl acetate in heptanes to provide the title compound (105 mg, 0.317 mmol, 60.9%). $^1H$ NMR (400 MHz, DMSO-$d_6$) δ ppm 7.76-7.72 (m, 2H), 7.48-7.37 (m, 3H), 6.74 (s, 1H), 6.49 (bs, 2H), 5.16 (d, J=5.9 Hz, 1H), 4.19 (d, J=5.9 Hz, 2H), 4.05-3.93 (m, 3H), 3.90 (dd, J=7.2, 4.2 Hz, 1H), 1.37 (s, 3H), 1.27 (s, 3H); MS (ESI+) m/z 332 (M+H)$^+$.

Example 104E (7R)—N-(2-{(2S)-2-[(4R)-2,2-dimethyl-1,3-dioxolan-4-yl]-2-hydroxyethyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide A mixture of the product from Example 3B (81 mg, 0.314 mmol), the product from Example 104D (104 mg, 0.314 mmol) and 1-[bis(dimethylamino)methylene]-1H-1,2,3-triazolo[4,5-b]pyridinium 3-oxid hexafluorophosphate (179 mg, 0.471 mmol) was dissolved in N,N-dimethylformamide (1.5 mL) under $N_2$, treated with triethylamine (0.131 mL, 0.942 mmol), and stirred at ambient temperature over the weekend. The mixture was diluted with methyl tert-butyl ether (30 mL), washed with saturated $NaHCO_3$ solution (15 mL), water (15 mL), and brine sequentially, dried ($MgSO_4$), filtered, concentrated, and chromatographed on silica gel, eluting with a gradient of 30% to 100% ethyl acetate in heptanes to provide the title compound (54 mg, 0.094 mmol, 30.1% yield). $^1H$ NMR (501 MHz, $CDCl_3$) δ ppm 7.70-7.66 (m, 2H), 7.44-7.37 (m, 3H), 6.90 (s, 1H), 6.63 (s, 1H), 6.38 (s, 1H), 5.59 (ddd, J=8.8, 5.1, 3.8 Hz, 1H), 4.96-4.91 (m, 3H), 4.53-4.49 (m, 2H), 4.34-4.28 (m, 1H), 4.13 (d, J=9.1 Hz, 1H), 4.05 (dd, J=8.6, 6.7 Hz, 1H), 3.86 (dd, J=8.6, 5.6 Hz, 1H), 1.45 (s, 3H), 1.41 (s, 3H), 1.36 (s, 3H); MS (ESI−) m/z 570 (M−H)$^−$.

Example 105

(7R)-2,2-difluoro-7-methyl-N-{3-oxo-6-phenyl-2-[(2S,3R)-2,3,4-trihydroxybutyl]-2,3-dihydropyridazin-4-yl}-6,7-dihydro-2H-furo[2,3-f][1,3]benzodioxole-7-carboxamide A solution of the product from Example 104E (40 mg, 0.070 mmol) in methanol (2 mL) was treated with 6 M HCl (1 mL) and stirred for 30 minutes. The mixture was diluted with water (15 mL) and extracted with ethyl acetate (30 mL). The ethyl acetate layer was washed with brine, dried ($MgSO_4$), filtered, concentrated, and chromatographed on silica gel, eluting with a gradient of 30% to 100% [9:1 ethyl acetate:ethanol] in heptanes to provide the title compound (30 mg, 0.056 mmol, 81% yield). $^1H$ NMR (501 MHz, $CDCl_3$) δ ppm 7.65 (dd, J=6.6, 2.8 Hz, 2H), 7.40 (dq, J=7.0, 3.4 Hz, 4H), 6.83 (s, 1H), 6.74 (s, 1H), 6.42 (s, 1H), 5.19 (dt, J=8.7, 3.4 Hz, 1H), 5.07 (bs, 2H), 4.90-4.87 (m, 2H), 4.80 (dd, J=14.5, 3.8 Hz, 1H), 4.66 (dd, J=14.5, 3.2 Hz, 1H), 4.07 (d, J=9.2 Hz, 1H), 3.68-3.61 (m, 2H), 3.47 (dt, J=11.8, 5.5 Hz, 1H), 1.40 (s, 3H); MS (ESI−) m/z 530 (M−H)$^−$.

Example 106

(7R)—N-(2-{(2R)-2-[(4R)-2,2-dimethyl-1,3-dioxolan-4-yl]-2-hydroxyethyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide Example 106A 4-amino-2-{(2R)-2-[(4R)-2,2-dimethyl-1,3-dioxolan-4-yl]-2-hydroxyethyl}-6-phenylpyridazin-3(2H)-one A suspension of the product from Example 104A (53.0 mg, 0.283 mmol), $K_2CO_3$ (39.1 mg, 0.283 mmol) and the product from Example 104C (49 mg, 0.340 mmol) in N,N-dimethylformamide (1 mL) under $N_2$ was heated at 110° C. for 1 hour. The mixture was cooled, diluted with methyl tert-butyl ether (30 mL), washed with water (twice, 15 mL and 15 mL) and brine sequentially, dried ($MgSO_4$), filtered, treated with silica gel (1.5 g) and concentrated to dryness. This silica gel suspension of the crude product was purified by chromatography on silica gel eluting with a gradient of 50% to 100% ethyl acetate in heptanes to provide the title compound (52 mg, 0.157 mmol, 55.4% yield). $^1$H NMR (400 MHz, DMSO-$d_6$) δ ppm 7.78-7.71 (m, 2H), 7.49-7.37 (m, 3H), 6.73 (s, 1H), 6.49 (bs, 2H), 4.95 (d, J=5.9 Hz, 1H), 4.32 (dd, J=12.8, 7.9 Hz, 1H), 4.13-4.03 (m, 2H), 4.02-3.94 (m, 2H), 3.77-3.70 (m, 1H), 1.36 (s, 3H), 1.29 (s, 3H); MS (ESI+) m/z 332 (M+H)$^+$.

Example 106B (7R)—N-(2-{(2R)-2-[(4R)-2,2-dimethyl-1,3-dioxolan-4-yl]-2-hydroxyethyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide A mixture of the product from Example 3B (50.6 mg, 0.196 mmol), the product from Example 106A (65 mg, 0.196 mmol) and 1-[bis(dimethylamino) methylene]-1H-1,2,3-triazolo[4,5-b]pyridinium 3-oxid hexafluorophosphate (112 mg, 0.294 mmol) was dissolved in N,N-dimethylformamide (1 mL) under $N_2$, treated with triethylamine (82 µL, 0.588 mmol), and stirred at ambient temperature over the weekend. The mixture was diluted with methyl tert-butyl ether (30 mL), washed with saturated NaHCO$_3$ solution (15 mL), water (15 mL), and brine sequentially, dried (MgSO$_4$), filtered, concentrated, and chromatographed on silica gel, eluting with a gradient of 30% to 100% ethyl acetate in heptanes to provide title compound (20 mg, 0.035 mmol, 17.84% yield). $^1$H NMR (501 MHz, CDCl$_3$) δ ppm 7.63-7.59 (m, 2H), 7.39 (dq, J=7.7, 2.3 Hz, 3H), 6.85 (s, 1H), 6.63 (s, 1H), 6.36 (s, 1H), 5.60 (ddd, J=8.5, 4.4, 2.9 Hz, 1H), 4.96-4.92 (m, 3H), 4.57 (dd, J=13.9, 8.6 Hz, 1H), 4.45 (dd, J=13.9, 2.9 Hz, 1H), 4.39 (td, J=5.9, 4.5 Hz, 1H), 4.11-4.07 (m, 2H), 3.75 (dd, J=8.7, 5.8 Hz, 1H), 1.42 (s, 3H), 1.41 (s, 3H), 1.35 (s, 3H); MS (ESI−) m/z 570 (M−H)$^-$.

Example 107

2,2-difluoro-7-methyl-N-[6-(5-methylhexahydropyrrolo[3,4-c]pyrrol-2(1H)-yl)pyridin-2-yl]-6,7-dihydro-2H-furo[2,3-f][1,3]benzodioxole-7-carboxamide To a 4 mL vial was added the product from Example 85 (18 mg, 1 equivalent) followed by (3aR,6aS)-2-methyloctahydropyrrolo[3,4-c]pyrrole (6 equivalents) and then N,N-diisopropylethylamine (26 µL, 3 equivalents) in a total concentrated volume of 100 µL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 µm 100 Å AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 minutes linear gradient 5-100% A, 8.7-10.7 min 100% A, 10.7-11.0 min linear gradient 100-5% A to afford the title compound as the trifluoroacetic acid salt. $^1$H NMR (400 MHz, Pyridine-$d_5$) δ 7.98 (d, J=7.8 Hz, 1H), 7.56-7.45 (m, 2H), 6.77 (s, 1H), 6.21 (d, J=8.1 Hz, 1H), 5.38 (d, J=9.1 Hz, 2H), 4.5 (d, 1H) 3.24 (s, 2H), 3.18-3.02 (m, 2H), 2.89 (s, 2H), 2.60 (s, 4H), 2.49 (s, 3H), 1.82 (s, 3H). MS (ESI$^+$) m/z 459 (M+H)$^+$.

Example 108

2,2-difluoro-7-methyl-N-{6-[5-(2-methylpropyl) hexahydropyrrolo[3,4-c]pyrrol-2(1H)-yl]pyridin-2-yl}-6,7-dihydro-2H-furo[2,3-f][1,3]benzodioxole-7-carboxamide To a 4 mL vial was added the product from Example 85 (18 mg, 1 equivalent) followed by (3aR,6aS)-2-isobutyloctahydropyrrolo[3,4-c]pyrrole (6 equivalents) and then diisopropylethylamine (26 µL, 3 equivalents) in a total concentrated volume of 100 µL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8 (2) 5 µm 100 Å AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A to afford the title compound as the trifluoroacetic acid salt. $^1$H NMR (400 MHz, Pyridine-$d_5$) δ 7.97 (d, J=7.9 Hz, 1H), 7.54 (t, J=8.0 Hz, 1H), 7.49 (s, 1H), 6.77 (s, 1H), 6.23 (d, J=8.1 Hz, 1H), 5.37 (d, J=9.2 Hz, 1H), 4.54 (d, J=9.1 Hz, 1H), 3.22-3.08 (m, 4H), 2.86 (s, 2H), 2.54-2.43 (m, 4H), 1.82 (s, 3H), 0.90 (d, J=6.6 Hz, 6H). MS (ESI$^+$) m/z 501 (M+H)$^+$.

Example 109

(7R)-2,2-difluoro-N-{6-[3-(methanesulfonyl)pyrrolidin-1-yl]pyridin-2-yl}-7-methyl-6,7-dihydro-2H-furo[2,3-f][1,3]benzodioxole-7-carboxamide To a 4 mL vial was added The product from Example 85 (18 mg, 1 equivalent) followed by 3-(methylsulfonyl)pyrrolidine (6 equivalents) and then diisopropylethylamine (26 µL, 3 equivalents) in a total concentrated volume of 100 µL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 µm 100 Å a AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A to afford the title compound as the trifluoroacetic acid salt. $^1$H NMR (400 MHz, Pyridine-$d_5$) δ 9.94 (s, 1H), 7.97 (d, J=7.8 Hz, 1H), 7.52 (t, J=8.0 Hz, 1H), 7.47 (d, J=1.3 Hz, 1H), 6.72 (s, 1H), 6.15 (d, J=8.2 Hz, 1H), 5.37 (dd, J=9.2, 4.0 Hz, 1H), 4.54 (dd, J=9.1, 3.1 Hz, 1H), 3.98 (p, J=7.1 Hz, 1H), 3.86 (dd, J=11.7, 5.7 Hz, 1H), 3.62 (dd, J=11.6, 8.2 Hz, 1H), 3.51-3.37 (m, 1H), 3.24-3.11 (m, 2H), 3.04 (d, J=1.4 Hz, 3H), 2.49 (d, J=7.3 Hz, 2H), 2.29-2.16 (m, 1H), 1.81 (d, J=1.3 Hz, 3H). MS (ESI$^+$) m/z 482 (M+H)$^+$.

Example 110

(7R)—N-{6-[3-(chloromethyl)-3-(hydroxymethyl) pyrrolidin-1-yl]pyridin-2-yl}-2,2-difluoro-7-methyl-6,7-dihydro-2H-furo[2,3-f][1,3]benzodioxole-7-carboxamide To a 4 mL vial was added the product from Example 85 (18 mg, 1 equivalent) followed by 2-oxa-6-azaspiro[3.4]

octane HCl salt (6 equivalents) and then N,N-diisopropylethylamine (26 μL, 3 equivalents) in a total concentrated volume of 100 μL. This was placed on a heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A to afford the title compound as the trifluoroacetic acid salt. $^1$H NMR (400 MHz, Pyridine-$d_5$) δ 9.84 (s, 1H), 7.94 (d, J=7.8 Hz, 1H), 7.55-7.49 (m, 1H), 7.48 (s, 1H), 6.73 (s, 1H), 6.14 (d, J=8.2 Hz, 1H), 5.38 (d, J=9.2 Hz, 1H), 4.53 (d, J=9.1 Hz, 1H), 3.85 (s, 2H), 3.78 (s, 2H) 3.36 (d, J=11.0 Hz, 1H), 3.29-3.21 (m, 3H), 1.97 (dt, J=13.3, 6.7 Hz, 1H), 1.88-1.77 (m, 4H). MS (ESI$^+$) m/z 482 (M+H)$^+$.

Example 111

(7R)-2,2-difluoro-N-{6-[(3R)-3-(methanesulfonyl)pyrrolidin-1-yl]pyridin-2-yl}-7-methyl-6,7-dihydro-2H-furo[2,3-f][1,3]benzodioxole-7-carboxamide To a 4 mL vial was added the product from Example 85 (18 mg, 1 equivalent) followed by (R)-3-(methylsulfonyl)pyrrolidine (6 equivalents) and then N,N-diisopropylethylamine (26 μL, 3 equivalents) in a total concentrated volume of 100 μL. This was placed on a heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A to afford the title compound as the trifluoroacetic acid salt. $^1$H NMR (400 MHz, Pyridine-$d_5$) δ 9.94 (s, 1H), 7.97 (d, J=7.9 Hz, 1H), 7.52 (t, J=8.0 Hz, 1H), 7.47 (s, 1H), 6.72 (s, 1H), 6.15 (d, J=8.1 Hz, 1H), 5.37 (d, J=9.2 Hz, 1H), 4.54 (d, J=9.1 Hz, 1H), 4.05-3.90 (m, 1H), 3.86 (dd, J=11.6, 5.8 Hz, 1H), 3.62 (dd, J=11.6, 8.2 Hz, 1H), 3.44 (ddd, J=9.9, 8.3, 5.5 Hz, 1H), 3.19 (ddd, J=9.9, 7.9, 6.4 Hz, 1H), 3.05 (s, 3H), 2.62-2.40 (m, 2H), 2.36-2.16 (m, 1H), 1.81 (s, 3H). MS (ESI$^+$) m/z 482 (M+H)$^+$.

Example 112 methyl (3R,4S)-1-(6-{[(7R)-2,2-difluoro-7-methyl-6,7-dihydro-2H-furo[2,3-f][1,3]benzodioxole-7-carbonyl]amino}pyridin-2-yl)-4-phenylpyrrolidine-3-carboxylate To a 4 mL vial was added the product from Example 85 (18 mg, 1 equivalent) followed by (3R,4S)-methyl 4-phenylpyrrolidine-3-carboxylate (CAS [156469-70-4], 6 equivalents) and then N,N-diisopropylethylamine (26 μL, 3 equivalents) in a total concentrated volume of 100 μL. This was placed on a heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å a AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A to afford the title compound as the trifluoroacetic acid salt. $^1$H NMR (400 MHz, Pyridine-$d_5$) δ 8.00 (d, J=8.0 Hz, 1H), 7.52 (t, J=8.0 Hz, 1H), 7.47 (s, 1H, 7.53 (d, J=10.4 Hz, 1H), 7.41-7.36 (m, 2H), 7.36-7.30 (m, 3H), 6.73 (d, J=5.0 Hz, 1H), 6.18 (d, J=8.2 Hz, 1H), 5.43 (d, 1H), 4.56 (dd, J=9.1, 2.1 Hz, 1H), 3.77-3.60 (m, 4H), 3.54 (s, 2H), 3.49 (t, J=9.5 Hz, 2H), 3.43-3.28 (m, 2H), 3.16 (t, J=8.6 Hz, 1H), 1.84 (d, J=5.4 Hz, 4H). MS (ESI$^+$) m/z 538 (M+H)$^+$.

Example 113

(7R)—N-[6-(3-benzylpyrrolidin-1-yl)pyridin-2-yl]-2,2-difluoro-7-methyl-6,7-dihydro-2H-furo[2,3-f][1,3]benzodioxole-7-carboxamide To a 4 mL vial was added the product from Example 85 (18 mg, 1 equivalent) followed by 3-benzylpyrrolidine (6 equivalents) and then N,N-diisopropylethylamine (26 μL, 3 equivalents) in a total concentrated volume of 100 μL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å a AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A to afford the title compound as the trifluoroacetic acid salt. $^1$H NMR (400 MHz, Pyridine-$d_5$) δ 7.94 (d, J=7.9 Hz, 1H), 7.54 (d, J=8.0 Hz, 1H), 7.51 (d, J=1.3 Hz, 1H), 6.74 (d, J=3.3 Hz, 2H), 6.16 (d, J=8.2 Hz, 1H), 5.40 (d, J=9.2 Hz, 1H), 4.63-4.47 (m, 1H), 3.66 (dd, J=8.4, 1.6 Hz, 2H), 3.49 (ddd, J=9.8, 7.3, 2.5 Hz, 1H), 2.83-2.64 (m, 2H), 2.64-2.53 (m, 1H), 1.83 (s, 3H), 1.12 (d, J=6.5 Hz, 3H). MS (ESI$^+$) m/z 462 (M+H)$^+$.

Example 114

(7R)-2,2-difluoro-N-{6-[3-(4-fluorophenyl)pyrrolidin-1-yl]pyridin-2-yl}-7-methyl-6,7-dihydro-2H-furo[2,3-f][1,3]benzodioxole-7-carboxamide To a 4 mL vial was added the product from Example 85 (18 mg, 1 equivalent) followed by 3-(4-fluorophenyl)pyrrolidine (CAS [144620-11-1], 6 equivalents) and then N,N-diisopropylethylamine (26 μL, 3 equivalents) in a total concentrated volume of 100 μL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to afford the title compound as the trifluoroacetic acid salt. $^1$H NMR (400 MHz, Pyridine-$d_5$) δ 7.96 (d, J=7.8 Hz, 1H), 7.55 (d, J=8.0 Hz, 1H), 7.49 (s, 1H), 7.15-7.08 (m, 4H), 6.74 (d, J=3.8 Hz, 1H), 6.17 (d, J=8.2 Hz, 1H), 5.39 (d, J=9.2 Hz, 1H), 4.54 (dd, J=9.2, 1.4 Hz, 1H), 3.53 (dd, J=10.3, 7.5 Hz, 1H), 3.41-3.29 (m, 1H), 3.24-3.08 (m, 2H), 3.00 (t, J=9.5 Hz, 1H), 2.16-1.95 (m, 1H), 1.82 (s, 4H). MS (ESI$^+$) m/z 498 (M+H)$^+$.

Example 115

1-(6-{[(7R)-2,2-difluoro-7-methyl-6,7-dihydro-2H-furo[2,3-f][1,3]benzodioxole-7-carbonyl]amino}pyridin-2-yl)-4,4-dimethylpyrrolidine-3-carboxylic acid To a 4 mL vial was added the product from Example 85 (18 mg, 1 equivalent) followed by 4,4-dimethylpyrrolidine-3-carboxylic acid (6 equivalents) and then N,N-diisopropylethylamine (26 μL, 3 equivalents) in a total concentrated volume of 100 μL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to afford the title compound as the trifluoroacetic acid salt. $^1$H NMR (400 MHz, Pyridine-d$_5$) δ 9.72 (d, J=10.4 Hz, 1H), 7.92 (dd, J=7.6, 1.2 Hz, 1H), 7.52 (t, J=8.0 Hz, 1H), 7.47 (s, 1H), 7.36 (ddd, J=7.5, 6.4, 1.4 Hz, 2H), 7.31-7.25 (m, 1H), 7.20-7.16 (m, 2H), 6.73 (d, J=5.4 Hz, 1H), 6.08 (d, J=8.2 Hz, 1H), 5.35 (dd, J=9.1, 1.1 Hz, 1H), 4.51 (dd, J=9.1, 1.1 Hz, 1H), 3.31-3.17 (m, 2H), 3.03 (ddd, J=10.2, 8.4, 7.0 Hz, 1H), 2.82 (ddd, J=9.8, 7.8, 1.5 Hz, 1H), 2.60-2.47 (m, 2H), 2.37-2.20 (m, 1H), 1.79 (s, 3H), 1.72 (ddq, J=12.6, 6.7, 3.4 Hz, 1H), 1.40 (dq, J=12.2, 8.5 Hz, 1H). MS (ESI$^+$) m/z 494 (M+H)$^+$.

Example 116

1-(6-{[(7R)-2,2-difluoro-7-methyl-6,7-dihydro-2H-furo[2,3-f][1,3]benzodioxole-7-carbonyl]amino}pyridin-2-yl)-4-methylpyrrolidine-3-carboxylic acid To a 4 mL vial was added the product from Example 85 (18 mg, 1 equivalent) followed by 4-methylpyrrolidine-3-carboxylic acid (CAS [885952-85-2], 6 equivalents) and then N,N-diisopropylethylamine (26 μL, 3 equivalents) in a total concentrated volume of 100 μL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to afford the title compound as the trifluoroacetic acid salt. $^1$H NMR (400 MHz, Pyridine-d$_5$) δ 7.94 (d, J=7.9 Hz, 1H), 7.54 (d, J=8.0 Hz, 1H), 7.51 (d, J=1.3 Hz, 1H), 6.74 (d, J=3.3 Hz, 2H), 6.16 (d, J=8.2 Hz, 1H), 5.40 (d, J=9.2 Hz, 1H), 4.63-4.47 (m, 1H), 3.66 (dd, J=8.4, 1.6 Hz, 2H), 3.49 (ddd, J=9.8, 7.3, 2.5 Hz, 1H), 2.83-2.64 (m, 2H), 2.64-2.53 (m, 1H), 1.83 (s, 3H), 1.12 (d, J=6.5 Hz, 3H). MS (ESI$^+$) m/z 462 (M+H)$^+$.

Example 117

2-(6-{[(7R)-2,2-difluoro-7-methyl-6,7-dihydro-2H-furo[2,3-f][1,3]benzodioxole-7-carbonyl]amino}pyridin-2-yl)hexahydrocyclopenta[c]pyrrole-3a(1H)-carboxylic acid To a 4 mL vial was added the product from Example 85 (18 mg, 1 equivalent) followed by octahydrocyclopenta[c]pyrrole-3a-carboxylic acid (6 equivalents) and then N,N-diisopropylethylamine (26 μL, 3 equivalent) in a total concentrated volume of 100 μL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to afford the title compound as the trifluoroacetic acid salt. $^1$H NMR (400 MHz, Pyridine-d$_5$) δ 9.87-9.80 (m, 1H), 7.95 (d, J=7.9 Hz, 1H), 7.54 (t, J=8.0 Hz, 1H), 7.50 (s, 1H), 6.75 (s, 1H), 6.25 (d, J=8.2 Hz, 1H), 5.40 (dd, J=9.1, 3.8 Hz, 1H), 4.54 (dd, J=9.2, 1.2 Hz, 1H), 4.08 (d, J=11.0 Hz, 1H), 3.54 (dd, J=10.1, 7.6 Hz, 1H), 3.29 (d, J=11.0 Hz, 1H), 3.16-3.02 (m, 2H), 2.42 (dt, J=12.4, 7.2 Hz, 1H), 1.98-1.86 (m, 1H), 1.83 (s, 3H), 1.80-1.62 (m, 3H), 1.52-1.33 (m, 1H). MS (ESI$^+$) m/z 488 (M+H)$^+$.

Example 118

(7R)-2,2-difluoro-7-methyl-N-[6-(pyrrolidin-1-yl)pyridin-2-yl]-6,7-dihydro-2H-furo[2,3-f][1,3]benzodioxole-7-carboxamide To a 4 mL vial was added the product from Example 85 (18 mg, 1 equivalent) followed by pyrrolidine (6 equivalents) and then N,N-diisopropylethylamine (26 μL, 3 equivalents) in a total concentrated volume of 100 μL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 μm 100 Å a AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to afford the title compound as the trifluoroacetic acid salt. $^1$H NMR (400 MHz, Pyridine-d$_5$) δ 7.91 (d, J=7.8 Hz, 1H), 7.54-7.41 (m, 2H), 6.75 (s, 1H), 6.10 (d, J=8.2 Hz, 1H), 5.35 (d, J=9.1 Hz, 1H), 4.51 (d, J=9.1 Hz, 1H), 3.17-3.01 (m, 4H), 1.80 (s, 3H), 1.65-1.48 (m, 4H). MS (ESI$^+$) m/z 404 (M+H)$^+$.

Example 119

(7R)-2,2-difluoro-7-methyl-N-[6-(piperidin-1-yl)pyridin-2-yl]-6,7-dihydro-2H-furo[2,3-f][1,3]benzodioxole-7-carboxamide To a 4 mL vial was added the product from Example 85 (18 mg, 1 equivalent) followed by piperidine (6 equivalents) and then N,N-diisopropylethylamine (26 μL, 3 equivalents)

in a total concentrated volume of 100 µL. This was placed on heater shaker and allowed to stir at 120° C. overnight. The residues once dried down, were dissolved in 1:1 DMSO/methanol and purified by reverse phase HPLC (TFA method). Samples were purified by preparative HPLC on a Phenomenex Luna C8(2) 5 µm 100 Å a AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to afford the title compound as the trifluoroacetic acid salt. $^1$H NMR (400 MHz, Pyridine-d$_5$) δ 9.91 (s, 1H), 7.93 (d, J=7.8 Hz, 1H), 7.53 (t, J=8.1 Hz, 1H), 7.46 (s, 1H), 6.44 (d, J=8.3 Hz, 1H), 5.37 (d, J=9.1 Hz, 1H), 4.53 (d, J=9.1 Hz, 1H), 3.25-3.13 (m, 4H), 1.81 (s, 3H), 1.42-1.31 (m, 2H), 1.31-1.22 (m, 4H). MS (ESI$^+$) m/z 418 (M+H)$^+$.

Example 120

4-(6-{[(7R)-2,2-difluoro-7-methyl-6,7-dihydro-2H-furo[2,3-f][1,3]benzodioxole-7-carbonyl]amino}pyridin-2-yl)-3-methylbenzoic acid Example 120A methyl 4-(6-aminopyridin-2-yl)-3-methylbenzoate A mixture of 6-chloropyrid-2-amine (138.8 mg, 1.080 mmol) and methyl 3-methyl-4-(4,4,5,5-tetramethyl-1,3,2-dioxaborolan-2-yl)benzoate (263.4 mg, 0.954 mmol) in dimethoxyethane (2.5 mL) and water (1.25 mL) was degassed under a N$_2$ flow for 15 minutes. Potassium carbonate (352.2 mg, 2.67 mmol) and 1,1'-bis(diphenylphosphino)ferrocene-palladium(II) dichloride (40.2 mg, 0.055 mmol) were added, and the mixture stirred at 80° C. for 17 hours. Water was then added to the reaction mixture (35 mL), and extracted with ethyl acetate (3×35 mL). The combined organic layers were dried (MgSO$_4$), filtered, and concentrated under reduced pressure. The residue was purified by flash chromatography, eluted with 5% ethyl acetate in dichloromethane (R$_f$=0.30), to provide the title compound (44.2 mg, 19%). $^1$H NMR (400 MHz, DMSO-d$_6$) δ 7.85 (d, J=1.8 Hz, 1H), 7.81 (dd, J=8.0, 1.8 Hz, 1H), 7.50-7.42 (m, 2H), 6.61 (d, J=7.2 Hz, 1H), 6.45 (d, J=8.2 Hz, 1H), 6.00 (s, 2H), 3.86 (s, 3H), 2.38 (s, 3H). MS (ESI+) m/z 243 (M+H)$^+$.

Example 120B methyl 4-(6-{[(7R)-2,2-difluoro-7-methyl-6,7-dihydro-2H-furo[2,3-f][1,3]benzodioxole-7-carbonyl]amino}pyridin-2-yl)-3-methylbenzoate The product from Example 3B (52.1, 0.202 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product from Example 120A (20.2 mg, 0.083 mmol) was added, and the reaction mixture was stirred at 60° C. for 16 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (19.9 mg, 50%). $^1$H NMR (400 MHz, DMSO-d$_6$) δ 10.20 (s, 1H), 8.01 (d, J=8.3 Hz, 1H), 7.93-7.85 (m, 3H), 7.65 (s, 1H), 7.52 (d, J=8.0 Hz, 1H), 7.29 (d, J=7.3 Hz, 1H), 7.03 (s, 1H), 5.10 (d, J=9.3 Hz, 1H), 4.42 (d, J=9.3 Hz, 1H), 3.88 (s, 3H), 2.36 (s, 3H), 1.71 (s, 3H); MS (ESI+) m/z 483 (M+H)$^+$.

Example 120C (7R)-2,2-difluoro-7-methyl-N-[6-(piperidin-1-yl)pyridin-2-yl]-6,7-dihydro-2H-furo[2,3-f][1,3]benzodioxole-7-carboxamide The product of Example 120B (16.9 mg, 0.035 mmol) and potassium trimethylsilanolate (13.1 mg, 90% purity, 0.092 mmol) were dissolved in tetrahydrofuran (1 mL) and stirred at ambient temperature for 4 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound (12.1 mg, 74%). $^1$H NMR (501 MHz, DMSO-d$_6$) δ 12.98 (s, 1H), 10.19 (s, 1H), 8.01 (d, J=8.5 Hz, 1H), 7.92-7.87 (m, 2H), 7.85 (dd, J=8.0, 1.7 Hz, 1H), 7.65 (s, 1H), 7.49 (d, J=7.9 Hz, 1H), 7.28 (d, J=7.4 Hz, 1H), 7.04 (s, 1H), 5.11 (d, J=9.3 Hz, 1H), 4.42 (d, J=9.3 Hz, 1H), 2.35 (s, 3H), 1.72 (s, 3H); MS (ESI+) m/z 469 (M+H)$^+$.

Example 121

(7R)—N-[5-(3R,4R)-dihydroxypyrrolidin-1-yl)pyrazin-2-yl]-2,2-difluoro-7-methyl-6,7-dihydro-2H-furo[2,3-f][1,3]benzodioxole-7-carboxamide and (7R)—N-[5-(3S,4S)-dihydroxypyrrolidin-1-yl)pyrazin-2-yl]-2,2-difluoro-7-methyl-6,7-dihydro-2H-furo[2,3-f][1,3]benzodioxole-7-carboxamide Example 121A trans tert-butyl 3,4-dihydroxypyrrolidine-1-carboxylate A solution of tert-butyl 6-oxa-3-azabicyclo[3.1.0]hexane-3-carboxylate (0.473 g, 2.55 mmol) in dioxane (3 mL) was treated with sodium hydroxide (2M aqueous, 9.2 mL, 18.40 mmol), and the reaction mixture was stirred at 95° C. for 24 hours. After this time, the mixture was cooled to room temperature and concentrated in vacuo. The residue was taken up in water (5 mL) and extracted with ethyl acetate (3×10 mL). The organic extracts were washed with brine (5 mL), dried over Na$_2$SO$_4$, filtered, and concentrated in vacuo. Trituration of the crude material with ethyl acetate afforded the title compound as a pale yellow solid, (0.155 g, 30% yield). The crude material was taken on without further purification.

Example 121B trans pyrrolidine-3,4-diol 2,2,2-trifluoroacetate

The product from Example 121A (0.060 g, 0.295 mmol) in CH$_2$Cl$_2$ (4.6 mL) was treated with trifluoroacetic acid (0.46 mL, 5.97 mmol) and the reaction was stirred at room temperature for 1 hour. The reaction mixture was then concentrated in vacuo, and the resulting oil was further dried under vacuum 75° C. for 1 hour. The title compound was obtained as a light brown oil. $^1$H NMR (400 MHz, DMSO-$d_6$) δ 9.51-9.00 (br, 2H), 4.08 (d, J=3.4 Hz, 2H), 3.39-3.14 (m, 2H), 3.04 (dt, J=12.1, 4.7 Hz, 2H). MS (DCI$^+$) m/z 103.9 (M+H).

Example 121C (7R)—N-[5-(3R,4R)-dihydroxypyrrolidin-1-yl) pyrazin-2-yl]-2,2-difluoro-7-methyl-6,7-dihydro-2H-furo[2,3-f][1,3]benzodioxole-7-carboxamide and (7R)—N-[5-(3S,4S)-dihydroxypyrrolidin-1-yl) pyrazin-2-yl]-2,2-difluoro-7-methyl-6,7-dihydro-2H-furo[2,3-f][1,3]benzodioxole-7-carboxamide The product from Example 94A (0.040 g, 0.097 mmol), the product from Example 121B (0.028 g, 0.130 mmol), sodium tert-butoxide (0.046 g, 0.483 mmol), and RuPhos palladacycle (RuPhos precatalyst) (0.014 g, 0.019 mmol) in dioxane (2 ml) were heated in the preheated heating block at 85° C. overnight. The mixture was diluted with ethyl acetate (20 mL) and washed with water (3×5 mL). The organic layer was dried over Na$_2$SO$_4$, filtered, and concentrated in vacuo. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to afford the title compound (0.0021 g, 5%). $^1$H NMR (400 MHz, DMSO-$d_6$) δ 9.84 (s, 1H), 8.51 (s, 1H), 7.72 (s, 1H), 7.62 (s, 1H), 7.02 (s, 1H), 5.09 (d, J=9.2 Hz, 1H), 4.38 (d, J=9.3 Hz, 1H), 4.05 (d, J=3.6 Hz, 2H), 3.55 (m, 4H), 1.68 (s, 3H). MS (ESI$^+$) m/z 437.1 (M+H).

Example 122

3-(6-{[(7R)-2,2-difluoro-7-methyl-6,7-dihydro-2H-furo[2,3-f][1,3]benzodioxole-7-carbonyl] amino}pyridin-2-yl)-2-methylbenzoic acid Example 122A methyl 3-(6-aminopyridin-2-yl)-2-methylbenzoate 6-chloropyridin-2-amine (0.257 g, 2 mmol), methyl 2-methyl-3-(4,4,5,5-tetramethyl-1,3,2-dioxaborolan-2-yl) benzoate (0.607 g, 2.200 mmol), potassium carbonate (0.663 g, 4.80 mmol), and PdCl$_2$dppf (0.073 g, 0.100 mmol) in dimethoxyethane (6 mL) and water (3 ml) were heated at 80° C. overnight. The mixture was diluted with ethyl acetate (20 mL) and washed with water (3×5 mL) and brine (5 mL) sequentially. The organic layer was dried over Na$_2$SO$_4$, filtered, and concentrated in vacuo. The residue was chromatographed on silica gel, eluting with 10 to 60% ethyl acetate-heptanes. The title compound was obtained as a white solid (0.378 g, 78%). $^1$H NMR (400 MHz, DMSO-$d_6$) δ 7.70 (dd, J=7.7, 1.5 Hz, 1H), 7.51-7.26 (m, 3H), 6.57-6.38 (m, 2H), 5.97 (s, 2H), 3.84 (s, 3H), 2.36 (s, 3H). MS (DCI$^+$) m/z 243.0 (M+H).

Example 122B methyl 3-(6-{[(7R)-2,2-difluoro-7-methyl-6,7-dihydro-2H-furo[2,3-f][1,3]benzodioxole-7-carbonyl] amino}pyridin-2-yl)-2-methylbenzoate The product from Example 3B (0.403 g, 1.560 mmol) was refluxed in thionyl chloride (3 ml, 41.1 mmol) for 1 hour, and the mixture was cooled to room temperature and concentrated in vacuo. The remaining syrup was taken up in 3 mL CH$_2$Cl$_2$ and treated with a solution of the product from Example 122B (0.378 g, 1.560 mmol) in pyridine (1.4 mL, 17.31 mmol). The reaction mixture stirred for 3 days at room temperature. The mixture was diluted with CH$_2$Cl$_2$ (20 mL) and washed with water (3×5 mL) and brine (5 mL) sequentially. The organic layer was dried over Na$_2$SO$_4$, filtered, and concentrated in vacuo to afford the crude title compound, which was taken into the next reaction without further purification. MS (APCI$^+$) m/z 483.2 (M+H).

Example 122C 3-(6-{[(7R)-2,2-difluoro-7-methyl-6,7-dihydro-2H-furo[2,3-f][1,3]benzodioxole-7-carbonyl] amino}pyridin-2-yl)-2-methylbenzoic acid The product from Example 122B (0.753 g, 1.56 mmol) and potassium trimethylsilanoate (0.600 g, 4.68 mmol) were stirred in THF (20 mL) overnight at room temperature. After this time, the mixture was diluted with 27 mL CH$_2$Cl$_2$ and 13.5 mL 1N HCl, and the mixture was stirred vigorously at room temperature for 45 minutes. It was then diluted with ethyl acetate (100 mL), and the phases were separated. The organic layer was washed with water (2×20 mL) and brine (20 mL) sequentially, dried over Na$_2$SO$_4$, filtered, and concentrated in vacuo. A portion of the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to afford the title compound as a white solid. $^1$H NMR (400 MHz, DMSO-$d_6$) δ 12.96 (s, 1H), 10.17 (s, 1H), 8.01 (d, J=8.3 Hz, 1H), 7.95-7.73 (m, 2H), 7.65 (s, 1H), 7.53-7.30 (m, 2H), 7.21 (d, J=7.5 Hz, 1H), 7.03 (s, 1H), 5.10 (d, J=9.3 Hz, 1H), 4.41 (d, J=9.3 Hz, 1H), 2.36 (s, 3H), 1.71 (s, 3H). MS (ESI$^+$) m/z 469.1 (M+H).

Example 123

4-(6-{[(7R)-2,2-difluoro-7-methyl-6,7-dihydro-2H-furo[2,3-f][1,3]benzodioxole-7-carbonyl] amino}pyridin-2-yl)-3-fluorobenzoic acid Example 123A methyl 4-(6-aminopyridin-2-yl)-3-fluorobenzoate 6-Chloropyridin-2-amine (0.257 g, 2 mmol), (2-fluoro-4-(methoxycarbonyl)phenyl)boronic acid (0.436 g, 2.200 mmol), potassium carbonate (0.663 g, 4.80 mmol), and PdCl$_2$dppf (0.073 g, 0.100 mmol) in dimethoxyethane (6 mL) and water (3 mL) were heated at 80° C. overnight. The mixture was diluted with ethyl acetate (25 mL) and washed with water (3×10 mL) and brine (10 mL) sequentially. The organic layer was dried over Na$_2$SO$_4$, filtered, and concentrated in vacuo. The residue was purified by silica gel chromatography, eluting with 10 to 50% ethyl acetate-heptanes, to afford the title compound as a white solid (0.181 g, 37% yield). $^1$H NMR (400 MHz, DMSO-d$_6$) δ 8.04 (t, J=8.0 Hz, 1H), 7.92-7.70 (m, 2H), 7.50 (dd, J=8.3, 7.4 Hz, 1H), 7.04-6.93 (m, 1H), 6.51 (dd, J=8.3, 0.8 Hz, 1H), 6.12 (s, 2H), 3.89 (s, 3H). MS (DCI$^+$) m/z 246.9 (M+H).

Example 123B methyl 4-(6-{[(7R)-2,2-difluoro-7-methyl-6,7-di-hydro-2H-furo[2,3-f][1,3]benzodioxole-7-carbonyl] amino}pyridin-2-yl)-3-fluorobenzoate The product from Example 3B (0.190 g, 0.735 mmol) refluxed in thionyl chloride (1.4 mL, 19.18 mmol) for 1 hour, then the mixture was cooled to room temperature and concentrated in vacuo. The remaining syrup was taken up in 1.5 mL CH$_2$Cl$_2$ and treated with a suspension of the product from Example 123A (0.181 g, 0.735 mmol) in pyridine (0.7 mL, 8.65 mmol) and 0.5 mL CH$_2$Cl$_2$. The reaction mixture stirred for 3 days at room temperature, diluted with CH$_2$Cl$_2$ (10 mL) and washed three times with water (3×3 mL) and brine (3 mL) sequentially. The organic layer was dried over Na$_2$SO$_4$, filtered, and concentrated in vacuo to afford the crude title compound, which was taken into the next reaction without further purification. MS (APCI$^+$) m/z 487.0 (M+H).

Example 123C 4-(6-{[(7R)-2,2-difluoro-7-methyl-6,7-dihydro-2H-furo[2,3-f][1,3]benzodioxole-7-carbonyl] amino}pyridin-2-yl)-3-fluorobenzoic acid The crude product from Example 123B (0.358 g, 0.735 mmol) in THF (9.2 ml) was treated with potassium trimethylsilanoate (0.283 g, 2.205 mmol), and the reaction mixture stirred overnight at room temperature. The mixture was then diluted with 12.9 mL CH$_2$Cl$_2$ and 6.5 mL 1N HCl, and stirred vigorously at room temperature for 45 minutes. It was then diluted with ethyl acetate (60 mL), and the phases were separated. The organic layer was washed with water (2×15 mL) and brine (15 mL) sequentially, dried over Na$_2$SO$_4$, filtered, and concentrated in vacuo. The resulting crude product was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to afford the title compound as a white solid (0.186 g, 54%). $^1$H NMR (400 MHz, DMSO-d$_6$) δ 13.34 (br, 1H), 10.26 (s, 1H), 8.14-7.73 (m, 5H), 7.69-7.53 (m, 2H), 7.05 (s, 1H), 5.12 (d, J=9.4 Hz, 1H), 4.45 (d, J=9.4 Hz, 1H), 1.73 (s, 3H). MS (ESI$^+$) m/z 473.1 (M+H).

Example 124

(7R)—N-{6-[3-(cyclopropylsulfamoyl)phenyl]-5-methylpyridin-2-yl}-2,2-difluoro-7-methyl-6,7-di-hydro-2H-furo[2,3-f][1,3]benzodioxole-7-carboxamide Example 124A 3-(6-amino-3-methylpyridin-2-yl)-N-cyclopropyl-benzene-1-sulfonamide (3-(N-cyclopropylsulfamoyl)phenyl)boronic acid (CAS [913835-28-6], 0.250 g, 1.037 mmol), 6-chloro-5-methyl-pyridin-2-amine (0.158 g, 1.110 mmol), PdCl$_2$dppf (0.053 g, 0.073 mmol), and potassium carbonate (0.330 g, 2.385 mmol) in dimethoxyethane (2.8 mL) and water (1.4 mL) were heated at 80° C. overnight. The mixture was then diluted with ethyl acetate (20 mL) and washed with water (3×5 mL) and brine (5 mL). It was dried over Na$_2$SO$_4$, filtered, and concentrated in vacuo. The crude material was purified by silica gel chromatography, eluting with 20 to 100% ethyl acetate-heptanes, to afford the title compound was obtained as a gold residue (0.166 g, 53%). $^1$H NMR (400 MHz, DMSO-d$_6$) δ 7.97-7.85 (m, 2H), 7.85-7.59 (m, 3H), 7.34 (d, J=8.3 Hz, 1H), 6.44 (d, J=8.3 Hz, 1H), 5.83 (s, 2H), 2.13 (s, 3H), 2.08 (m, 1H), 0.55-0.32 (m, 4H). MS (DCI$^+$) m/z 304.0 (M+H).

Example 124B (7R)—N-{6-[3-(cyclopropylsulfamoyl)phenyl]-5-methylpyridin-2-yl}-2,2-difluoro-7-methyl-6,7-di-hydro-2H-furo[2,3-f][1,3]benzodioxole-7-carboxamide The product from Example 3B (0.141 g, 0.547 mmol) was refluxed in thionyl chloride (1 ml, 13.70 mmol) for 1 hour. The mixture was then cooled to room temperature and concentrated in vacuo. The oil was then taken up in 1 mL CH$_2$Cl$_2$ and treated with a solution of the product from Example 124A (0.166 g, 0.547 mmol) in pyridine (0.52 mL, 6.43 mmol). The reaction was then stirred overnight at room temperature. The mixture was diluted with ethyl acetate (20 mL) and washed with water (3×5 mL) and brine (5 mL). The organic layer was dried over Na$_2$SO$_4$, filtered, and concentrated in vacuo. The crude product was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to afford the title compound as a foamy white solid (0.135 g, 45%). $^1$H NMR (400 MHz, DMSO-d$_6$) δ 10.19 (s, 1H), 8.02-7.59 (m, 8H), 7.03 (s, 1H), 5.09 (d, J=9.4 Hz, 1H), 4.41 (d, J=9.4 Hz, 1H), 2.25 (s, 3H), 2.12 (m, 1H), 1.70 (s, 3H), 0.55-0.33 (m, 4H). MS (ESI$^+$) m/z 544.1 (M+H).

Example 125

3-(6-{[(7R)-2,2-difluoro-7-methyl-6,7-dihydro-2H-furo[2,3-f][1,3]benzodioxole-7-carbonyl] amino}pyridin-2-yl)-2-fluorobenzoic acid Example 125A ethyl 3-(6-aminopyridin-2-yl)-2-fluorobenzoate A mixture of 6-chloropyrid-2-amine (259.6 mg, 2.019 mmol) and 2-fluoro-3-(ethoxycarbonyl)phenylboronic acid (438.0 mg, 2.066 mmol) in dimethoxyethane (5 mL) and water (2.5 mL) was degassed under a N$_2$ flow for 15 minutes. Potassium carbonate (589.3 mg, 4.26 mmol) and 1,1'-bis(diphenylphosphino)ferrocene-palladium(II)dichloride (83.9 mg, 0.115 mmol) were added, and the mixture was stirred at 80° C. for 17 hours. Water was then added to the reaction mixture (35 mL), and it was extracted with ethyl acetate (3×35 mL). The combined organic layers were dried (MgSO$_4$), filtered, and concentrated under reduced pressure.

215

The residue was purified by flash chromatography, eluted with 5% ethyl acetate in dichloromethane ($R_f$=0.28), to provide the title compound (246.6 mg, 47%). $^1$H NMR (400 MHz, DMSO-$d_6$) δ 8.02 (td, J=7.4, 1.9 Hz, 1H), 7.85 (ddd, J=8.4, 6.7, 1.9 Hz, 1H), 7.48 (t, J=7.8 Hz, 1H), 7.38 (t, J=7.7 Hz, 1H), 6.89 (dd, J=7.3, 2.5 Hz, 1H), 6.49 (d, J=8.2 Hz, 1H), 6.07 (s, 2H), 4.34 (q, J=7.1 Hz, 2H), 1.33 (t, J=7.1 Hz, 3H). MS (ESI+) m/z 261 (M+H)$^+$.

Example 125B ethyl 3-(6-{[(7R)-2,2-difluoro-7-methyl-6,7-di-hydro-2H-furo[2,3-f][1,3]benzodioxole-7-carbonyl] amino}pyridin-2-yl)-2-fluorobenzoate The product from Example 3B (57.4, 0.222 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product from example 125A (49.7 mg, 0.306 mmol) was added, and the reaction mixture was stirred at 60° C. for 21 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (62.8 mg, 56%). $^1$H NMR (400 MHz, DMSO-$d_6$) δ 10.23 (s, 1H), 8.09 (td, J=7.4, 1.9 Hz, 1H), 8.04 (d, J=8.3 Hz, 1H), 7.98-7.89 (m, 2H), 7.65 (s, 1H), 7.52 (dd, J=7.4, 2.2 Hz, 1H), 7.46 (t, J=7.7 Hz, 1H), 7.04 (s, 1H), 5.12 (d, J=9.4 Hz, 1H), 4.44 (d, J=9.4 Hz, 1H), 4.36 (q, J=7.1 Hz, 2H), 1.73 (s, 3H), 1.34 (t, J=7.1 Hz, 3H); MS (ESI+) m/z 501 (M+H)$^+$.

Example 125C 3-(6-{[(7R)-2,2-difluoro-7-methyl-6,7-dihydro-2H-furo[2,3-f][1,3]benzodioxole-7-carbonyl] amino}pyridin-2-yl)-2-fluorobenzoic acid The product of Example 125B (59.8 mg, 0.119 mmol) and potassium trimethylsilanolate (54.4 mg, 90% purity, 0.375 mmol) were dissolved in tetrahydrofuran (1 mL) and stirred at ambient temperature for 4 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (34.7 mg, 62%). $^1$H NMR (501 MHz, DMSO-$d_6$) δ 13.35 (s, 1H), 10.22 (s, 1H), 8.09-8.01 (m, 2H), 7.95-7.89 (m, 2H), 7.65 (s, 1H), 7.52 (dd, J=7.6, 2.0 Hz, 1H), 7.43 (t, J=7.7 Hz, 1H), 7.04 (s, 1H), 5.12 (d, J=9.4 Hz, 1H), 4.44 (d, J=9.3 Hz, 1H), 1.73 (s, 3H). MS (ESI+) m/z 473 (M+H)$^+$.

Example 126

(7R)—N-{6-[3-(1,2-dihydroxyethyl)phenyl]-5-methylpyridin-2-yl}-2,2-difluoro-7-methyl-6,7-dihydro-2H-furo[2,3-f][1,3]benzodioxole-7-carboxamide Example 126A 6-(3-ethenylphenyl)-5-methylpyridin-2-amine (3-vinylphenyl)boronic acid (0.125 g, 0.845 mmol), 6-chloro-5-methylpyridin-2-amine (0.129 g, 0.904 mmol), PdCl$_2$dppf (0.043 g, 0.059 mmol), and potassium carbonate (0.269 g, 1.943 mmol) in dimethoxyethane (2.3 mL) and water (1.2 mL) were heated at 80° C. overnight. The mixture was diluted with ethyl acetate (20 mL) and washed with water (3×5 mL) and brine (5 mL) sequentially. The organic layer was dried over Na$_2$SO$_4$, filtered, and concentrated in vacuo. The residue was purified by silica gel chromatography, eluting with 0 to 50% ethyl acetate-heptanes to afford the title compound as a colorless oil, (0.107 g, 60%). $^1$H NMR (500 MHz, DMSO-$d_6$) δ 7.55-7.26 (m, 5H), 6.85-6.72 (m, 1H), 6.39 (d, J=8.3 Hz, 1H), 5.91-5.80 (m, 1H), 5.72 (s, 2H), 5.32-5.23 (m, 1H), 2.11 (s, 3H). MS (DCI$^+$) m/z 211.0 (M+H).

Example 126B (7R)—N-[6-(3-ethenylphenyl)-5-methylpyridin-2-yl]-2,2-difluoro-7-methyl-6,7-dihydro-2H-furo[2,3-f][1,3]benzodioxole-7-carboxamide The product from Example 3B (0.131 g, 0.509 mmol) was refluxed in thionyl chloride (1 ml, 13.70 mmol) for 1 hour. The mixture was concentrated in vacuo, then the resulting oil was then taken up in 1 mL CH$_2$Cl$_2$ and treated with a solution of the product from Example 126A (0.107 g, 0.509 mmol) in pyridine (0.5 mL, 6.18 mmol). The reaction was then stirred overnight at room temperature. After this time, the mixture was diluted with ethyl acetate (20 mL) and washed with water (3×5 mL) and brine (5 mL) sequentially. The organic layer was dried over Na$_2$SO$_4$, filtered, and concentrated in vacuo. The crude syrup was chromatographed on silica gel, eluting with 5 to 25% ethyl acetate-heptanes, to yield the title compound (0.068 g, 30%). $^1$H NMR (400 MHz, DMSO-$d_6$) δ 10.10 (s, 1H), 7.90 (d, J=8.3 Hz, 1H), 7.78-7.35 (m, 6H), 6.81 (dd, J=17.7, 11.0 Hz, 1H), 5.89 (dd, J=17.7, 0.9 Hz, 1H), 5.36-5.25 (m, 1H), 5.09 (d, J=9.3 Hz, 1H), 4.40 (d, J=9.4 Hz, 1H), 2.24 (s, 3H), 1.70 (s, 3H). MS (ESI$^+$) m/z 451.1 (M+H).

Example 126C (7R)—N-{6-[3-(1,2-dihydroxyethyl)phenyl]-5-methylpyridin-2-yl}-2,2-difluoro-7-methyl-6,7-dihydro-2H-furo[2,3-f][1,3]benzodioxole-7-carboxamide A solution of the product of Example 126B (0.034 g, 0.075 mmol) in acetonitrile (3 mL) and tert-butanol (0.75 mL) was treated with 4-methylmorpholine N-oxide (50% weight solution in water; 0.028 mL, 0.136 mmol) and then osmium tetroxide (2.5% weight solution in tert-butanol; 0.047 mL, 3.77 µmol), and the reaction mixture was stirred overnight at room temperature. The mixture was then diluted with ethyl acetate (15 mL) and washed with saturated aqueous sodium sulfite solution (3×3 mL), followed by water (3 mL) and brine (3 mL). The organic layer was dried over Na$_2$SO$_4$, filtered, and concentrated in vacuo. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to afford the title compound as a white solid (0.0019 g, 5% yield). $^1$H NMR (400 MHz, DMSO-d$_6$) δ 10.11 (s, 1H), 7.88 (d, J=8.5 Hz, 1H), 7.82-7.60 (m, 2H), 7.48-7.30 (m, 4H), 7.02 (s, 1H), 5.09 (d, J=9.3 Hz, 1H), 4.59 (t, J=6.0 Hz, 1H), 4.40 (d, J=9.3 Hz, 1H), 3.48 (m, 2H), 2.22 (s, 3H), 1.70 (s, 3H). MS (ESI$^+$) m/z 485.1 (M+H).

Example 127

5-(6-{[(7R)-2,2-difluoro-7-methyl-6,7-dihydro-2H-furo[2,3-f][1,3]benzodioxole-7-carbonyl]amino}-3-methylpyridin-2-yl)thiophene-3-carboxylic acid Example 127A methyl 5-(6-amino-3-methylpyridin-2-yl)thiophene-3-carboxylate A mixture of methyl 5-(4,4,5,5-tetramethyl-1,3,2-dioxaborolan-2-yl)thiophene-3-carboxylate (0.250 g, 0.932 mmol), 6-chloro-5-methylpyridin-2-amine (0.142 g, 0.998 mmol), PdCl$_2$dppf (0.048 g, 0.065 mmol), and potassium carbonate (0.296 g, 2.144 mmol) in dimethoxyethane (2.4 mL) and water (1.2 mL) was heated at 80° C. overnight. Water (35 mL) was then added to the reaction mixture. The mixture was extracted with ethyl acetate (3×35 mL). The combined organic layers were dried over Na$_2$SO$_4$, filtered, and concentrated in vacuo, and the crude material was purified by silica gel chromatography (10 to 50% ethyl acetate-heptanes, eluent) to afford the title compound as a yellow solid (0.065 g, 28%). $^1$H NMR (400 MHz, DMSO-d$_6$) δ 8.33 (d, J=1.2 Hz, 1H), 7.68 (d, J=1.3 Hz, 1H), 7.33 (d, J=8.4 Hz, 1H), 6.36 (dd, J=22.4, 8.2 Hz, 1H), 5.86 (s, 2H), 3.81 (s, 3H), 2.36 (s, 3H). MS (DCI$^+$) m/z 248.9 (M+H).

Example 127B methyl 5-(6-{[(7R)-2,2-difluoro-7-methyl-6,7-dihydro-2H-furo[2,3-f][1,3]benzodioxole-7-carbonyl]amino}-3-methylpyridin-2-yl)thiophene-3-carboxylate The product from Example 3B (0.068 g, 0.262 mmol) was refluxed in thionyl chloride (0.5 ml, 6.85 mmol) for 1 hour. After this time, the mixture was cooled to room temperature and concentrated in vacuo. Residual thionyl chloride was chased with CH$_2$Cl$_2$ (3×0.5 mL). The resulting yellow oil was taken up in CH$_2$Cl$_2$ (0.5 mL) and treated with a solution of the product from Example 127A (0.065 g, 0.262 mmol) in pyridine (0.25 mL, 3.09 mmol). The resulting mixture was stirred overnight at room temperature, diluted with 10 mL ethyl acetate, and washed with water (3×5 mL) and brine (5 mL) sequentially. The organic layer was dried over Na$_2$SO$_4$, filtered, and concentrated to afford the crude title compound, which was taken into the next reaction without further purification. MS (APCI$^+$) m/z 489.0 (M+H).

Example 127C 5-(6-{[(7R)-2,2-difluoro-7-methyl-6,7-dihydro-2H-furo[2,3-f][1,3]benzodioxole-7-carbonyl]amino}-3-methylpyridin-2-yl)thiophene-3-carboxylic acid The product from Example 127B (0.120 g, 0.246 mmol) in THF (3 mL) was treated with potassium trimethylsilanolate (0.095 g, 0.737 mmol), and the reaction stirred at room temperature overnight. After this time, it was treated with 4.4 mL CH$_2$Cl$_2$ and 2.6 mL 1N HCl, and the mixture was stirred vigorously at room temperature for 1 hour. It was then diluted with ethyl acetate (20 mL), and the phases were separated. The organic layer was washed with water (2×10 mL), dried over Na$_2$SO$_4$, filtered, and concentrated in vacuo. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to afford the title compound as a tan solid (0.043 g, 37%). $^1$H NMR (400 MHz, DMSO-d$_6$) δ 12.68 (br, 1H), 9.97 (s, 1H), 8.36 (d, J=1.2 Hz, 1H), 7.89-7.69 (m, 3H), 7.64 (s, 1H), 7.04 (s, 1H), 5.10 (d, J=9.3 Hz, 1H), 4.44 (d, J=9.4 Hz, 1H), 2.50 (s, 3H), 1.72 (s, 3H). MS (ESI$^+$) m/z 475.1 (M+H).

Example 128

3-(6-{[(7R)-2,2-difluoro-7-methyl-6,7-dihydro-2H-furo[2,3-f][1,3]benzodioxole-7-carbonyl]amino}pyridin-2-yl)-4-fluorobenzoic acid Example 128A methyl 3-(6-aminopyridin-2-yl)-4-fluorobenzoate A mixture of 6-chloropyrid-2-amine (256.3 mg, 1.994 mmol) and 2-fluoro-5-(methoxycarbonyl)phenylboronic acid (429.8 mg, 2.171 mmol) in dimethoxyethane (5 mL) and water (2.5 mL) was degassed under a N$_2$ flow for 15 minutes. Potassium carbonate (621.0 mg, 4.49 mmol) and 1,1'-bis(diphenylphosphino)ferrocene-palladium(II)dichloride (71.3 mg, 0.097 mmol) were added, and the mixture stirred at 80° C. for 17 hours. Water was then added to the reaction mixture (35 mL), and it was extracted with ethyl acetate (3×35 mL). The combined organic layers were dried (MgSO$_4$), filtered, and concentrated under reduced pressure. The residue was purified by flash chromatography, eluted with 10% ethyl acetate in dichloromethane (R$_f$=0.31), to provide the title compound (246.6 mg, 47%). $^1$H NMR (400 MHz, DMSO-d$_6$) δ 8.54 (dd, J=7.6, 2.4 Hz, 1H), 7.99 (ddd, J=8.6, 4.7, 2.4 Hz, 1H), 7.49 (dd, J=8.3, 7.4 Hz, 1H), 7.43 (dd, J=11.2, 8.6 Hz, 1H), 6.97 (ddd, J=7.5, 2.7, 0.8 Hz, 1H), 6.50 (dd, J=8.3, 0.8 Hz, 1H), 6.16 (s, 2H), 3.88 (s, 3H). MS (ESI+) m/z 247 (M+H)$^+$.

Example 128B methyl 3-(6-{[(7R)-2,2-difluoro-7-methyl-6,7-dihydro-2H-furo[2,3-f][1,3]benzodioxole-7-carbonyl]amino}pyridin-2-yl)-4-fluorobenzoate The product from Example 3B (57.2, 0.222 mmol) was dissolved in dichloromethane (1 mL). Oxalyl chloride (80 μL) and N,N-dimethylformamide (25 μL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product from example 128A (79.5 mg, 0.323 mmol) was added, and the reaction mixture was stirred at 60° C. for 22 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (104.8 mg, 97%). $^1$H NMR (400 MHz, HMSO-$d_6$) δ 10.31 (s, 1H), 8.51 (dd, J=7.5, 2.4 Hz, 1H), 8.08 (ddd, J=8.6, 4.8, 2.4 Hz, 1H), 8.04 (d, J=8.3 Hz, 1H), 7.93 (t, J=8.0 Hz, 1H), 7.65 (s, 1H), 7.56 (dd, J=7.5, 2.4 Hz, 1H), 7.51 (dd, J=10.8, 8.6 Hz, 1H), 7.04 (s, 1H), 5.12 (d, J=9.4 Hz, 1H), 4.46 (d, J=9.4 Hz, 1H), 3.89 (s, 3H), 1.74 (s, 3H); MS (ESI+) m/z 487 (M+H)$^+$.

Example 128C 3-(6-{[(7R)-2,2-difluoro-7-methyl-6,7-dihydro-2H-furo[2,3-f][1,3]benzodioxole-7-carbonyl]amino}pyridin-2-yl)-4-fluorobenzoic acid The product of Example 128B (100.8 mg, 0.207 mmol) and potassium trimethylsilanolate (66.7 mg, 90% purity, 0.468 mmol) were dissolved in tetrahydrofuran (1 mL) and stirred at ambient temperature for 4 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (73.3 mg, 75%). $^1$H NMR (501 MHz, DMSO-$d_6$) δ 13.21 (s, 1H), 10.32 (s, 1H), 8.53 (dd, J=7.7, 2.3 Hz, 1H), 8.09-8.01 (m, 2H), 7.93 (t, J=8.0 Hz, 1H), 7.65 (s, 1H), 7.56 (dd, J=7.6, 2.3 Hz, 1H), 7.48 (dd, J=10.9, 8.6 Hz, 1H), 7.04 (s, 1H), 5.12 (d, J=9.4 Hz, 1H), 4.46 (d, J=9.4 Hz, 1H), 1.74 (s, 3H). MS (ESI+) m/z 473 (M+H)$^+$.

Example 129

3-(6-{[(7R)-2,2-difluoro-7-methyl-6,7-dihydro-2H-furo[2,3-f][1,3]benzodioxole-7-carbonyl]amino}pyridin-2-yl)-4-methylbenzoic acid Example 129A methyl 3-(6-aminopyridin-2-yl)-4-methylbenzoate 6-chloropyridin-2-amine (0.129 g, 1 mmol), methyl 4-methyl-3-(4,4,5,5-tetramethyl-1,3,2-dioxaborolan-2-yl)benzoate (0.304 g, 1.100 mmol), potassium carbonate (0.332 g, 2.400 mmol), and PdCl$_2$dppf (0.037 g, 0.050 mmol) in dimethoxyethane (3.4 mL) and water (1.7 mL) were heated at 80° C. overnight. The mixture was diluted with ethyl acetate (20 mL) and washed with water (3×5 mL) and brine (5 mL) sequentially. The organic layer was dried over Na$_2$SO$_4$, filtered, and concentrated in vacuo. The dark brown crude oil was purified by silica gel chromatography, eluting with 10 to 70% ethyl acetate-heptanes, to afford the title compound as a white solid (0.085 g, 35%). $^1$H NMR (500 MHz, DMSO-$d_6$) δ 7.94-7.79 (m, 2H), 7.51-7.37 (m, 2H), 6.61 (dd, J=7.3, 0.9 Hz, 1H), 6.44 (dd, J=8.3, 0.9 Hz, 1H), 6.01 (s, 2H), 3.84 (s, 3H), 2.39 (s, 3H). MS (DCI$^+$) m/z 243.0 (M+H).

Example 129B methyl 3-(6-{[(7R)-2,2-difluoro-7-methyl-6,7-dihydro-2H-furo[2,3-f][1,3]benzodioxole-7-carbonyl]amino}pyridin-2-yl)-4-methylbenzoate The product from Example 3B (0.092 g, 0.355 mmol) was refluxed in thionyl chloride (0.68 mL, 9.32 mmol) for 1 hour, then the mixture was cooled to room temperature and concentrated in vacuo. Excess thionyl chloride was chased three times with CH$_2$Cl$_2$, then a suspension of the product from Example 129A (0.086 g, 0.355 mmol) in pyridine (0.6 mL, 7.42 mmol) and 1.2 mL CH$_2$Cl$_2$ was added. The reaction mixture was stirred at room temperature overnight, then it was diluted with CH$_2$Cl$_2$ (10 mL) and washed with water (3×5 mL). The organic layer was dried over Na$_2$SO$_4$, filtered, and concentrated in vacuo, to afford the crude title compound, which was taken into the next reaction without further purification. MS (APCI$^+$) m/z 483.3 (M+H).

Example 129C 3-(6-{[(7R)-2,2-difluoro-7-methyl-6,7-dihydro-2H-furo[2,3-f][1,3]benzodioxole-7-carbonyl]amino}pyridin-2-yl)-4-methylbenzoic acid The crude product of Example 129B (0.171 g, 0.355 mmol) in THF (4.5 mL) was treated with potassium trimethylsilanolate (0.137 g, 1.065 mmol), and the reaction stirred overnight at room temperature. The mixture was then diluted with 6.5 mL CH$_2$Cl$_2$ and treated with 3.3 mL 1N HCl, and the mixture was stirred vigorously for 1 hour. The mixture was diluted with ethyl acetate (20 mL), and the phases were separated. The organic layer was washed with water (2×5 mL) and brine (5 mL), dried over Na$_2$SO$_4$, filtered, and concentrated in vacuo. The oil thus obtained was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to afford the title compound as a white solid (0.047 g, 28%). $^1$H NMR (400 MHz, DMSO-$d_6$) δ 12.93 (s, 1H), 10.18 (s, 1H), 8.05-7.83 (m, 4H), 7.65 (s, 1H), 7.44 (d, J=8.0 Hz, 1H), 7.30 (d, J=7.5 Hz, 1H), 7.03 (s, 1H), 5.11 (d, J=9.4 Hz, 1H), 4.42 (d, J=9.4 Hz, 1H), 2.38 (s, 3H), 1.72 (s, 3H). MS (ESI$^+$) m/z 469.1 (M+H).

Example 130

(7R)—N-{1-[(2R)-2,3-dihydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide Example 130A (2R)-1-(benzyloxy)-3-(3-fluoro-4-nitroanilino)propan-2-ol To a solution of 3-fluoro-4-nitroaniline (10 g, 64.1 mmol) in ethyl acetate (125 mL) was added (S)-2-((benzyloxy)

methyl)oxirane (15.8 g, 96 mmol), followed by the addition of iron(III) chloride (0.520 g, 3.20 mmol). An exotherm to 28° C. was observed. The reaction was stirred for 30 minutes before additional iron(III) chloride (0.520 g, 3.20 mmol) was added. After an additional 30 minutes, another portion of iron(III) chloride (0.520 g, 3.20 mmol) was added and the reaction was stirred for 1 hour at room temperature before diluting with ethyl acetate (100 mL) and washing with water (100 mL) and brine (100 mL) sequentially. The organic layer was dried over sodium sulfate, filtered, and concentrated. The resulting dark red oil was purified via flash chromatography on a 330 g silica gel cartridge, eluting with 0-15% ethyl acetate/dichloromethane to afford 10.32 g of the title compound as a yellow oil. (50% yield). $^1$H NMR (501 MHz, CDCl$_3$) δ 7.95 (t, J=8.9 Hz, 1H), 7.43-7.28 (m, 5H), 6.37-6.21 (m, 2H), 5.10 (t, J=5.4 Hz, 1H), 4.57 (s, 2H), 4.09-3.99 (m, 1H), 3.60 (dd, J=9.6, 4.1 Hz, 1H), 3.52 (dd, J=9.5, 5.8 Hz, 1H), 3.34 (ddd, J=13.1, 6.4, 4.2 Hz, 1H), 3.23 (ddd, J=13.1, 7.1, 4.7 Hz, 1H), 2.67-2.56 (m, 1H). MS (ESI$^-$) m/z 319 (M–H)$^-$.

Example 130B (2R)-1-(benzyloxy)-3-(2-bromo-5-fluoro-4-nitroanilino)propan-2-ol

To a solution of Example 130A (9.26 g, 28.9 mmol) in ethyl acetate (60 mL) was added N-bromosuccinimide (5.15 g, 28.9 mmol) in two lots at room temperature. The reaction mixture was stirred at room temperature for 1 hour, washed with saturated aqueous NaHCO$_3$, and partitioned. The organic layer was dried over anhydrous sodium sulfate, filtered, and concentrated in vacuo. The resulting crude product was purified by flash chromatography using a 330 gm silica gel cartridge, eluting with 0-5% ethyl acetate/ dichloromethane to afford 9.36 g of the title product as light yellow solid. (81% yield). $^1$H NMR (501 MHz, CDCl$_3$) δ 2.50 (d, J=5.5 Hz, 1H), 3.26-3.44 (m, 2H), 3.53-3.67 (m, 2H), 4.05-4.15 (m, 1H), 4.59 (s, 2H), 5.62-5.75 (m, 1H), 6.37 (d, J=13.7 Hz, 1H), 7.28-7.42 (m, 5H), 8.27 (d, J=7.8 Hz, 1H). MS (ESI-0: M+H=398.9.

Example 130C (2R)-1-(4-amino-2-bromo-5-fluoroanilino)-3-(benzyloxy)propan-2-ol

To a solution of Example 130B (6.00 g, 15.03 mmol) in isopropyl acetate (60 mL) was added 5% Pt/C sulfided (0.6 g, 0.311 mmol) in a 250 mL stainless steel pressure bottle and stirred for 17.5 hours at 50 psi of hydrogen and at room temperature. The reaction mixture was filtered, and concentrated in vacuo to give a pale yellow oil. (5.55 g, 100%) $^1$H NMR (501 MHz, DMSO-d$_6$) δ 7.35 (d, J=4.4 Hz, 4H), 7.32-7.25 (m, 1H), 6.94 (d, J=9.2 Hz, 1H), 6.52 (d, J=13.5 Hz, 1H), 5.14-5.07 (m, 1H), 4.61 (s, 2H), 4.51 (s, 2H), 4.49-4.42 (m, 1H), 3.83 (t, J=6.2 Hz, 1H), 3.47-3.40 (m, 2H), 3.15 (dd, J=12.7, 4.8 Hz, 1H), 2.93 (dd, J=12.5, 7.0 Hz, 1H). MS (ESI+): M+H=369.0.

Example 130D (2R)-1-{4-amino-2-[4-(benzyloxy)-3,3-dimethylbut-1-yn-1-yl]-5-fluoroanilino}-3-(benzyloxy)propan-2-ol To a suspension of palladium (II) acetate (0.058 g, 0.258 mmol), 1,4-bis(diphenylphosphino)butane (0.165 g, 0.388 mmol), copper(I) iodide (0.074 g, 0.388 mmol), and potassium carbonate (5.36 g, 38.8 mmol) under nitrogen sparge in 10 mL of acetonitrile was added a solution of (((2,2-dimethylbut-3-yn-1-yl)oxy)methyl)benzene (4.86 g, 25.8 mmol) in acetonitrile (10 mL) via cannula. The reaction was sparged with nitrogen and then a solution of the product of Example 130C (4.77 g, 12.92 mmol) in acetonitrile (30 ml) was added via cannula. The reaction was sparged with nitrogen again and then heated at 80° C. for 8 hours, then allowed to cool to room temperature overnight and filtered thorough diatomaceous earth, and washed with acetonitrile. The solvent was removed in vacuo and the crude material chromatographed using a 120 g silica gel cartridge with a gradient of 25-35% ethyl acetate/heptanes over 60 minutes to give the title compound (3.96 g, 8.31 mmol, 64.3% yield) as a tan oil. $^1$H NMR (400 MHz, CDCl$_3$) δ 7.38-7.26 (m, 10H), 6.74 (d, J=9.6 Hz, 1H), 6.34 (d, J=13.1 Hz, 1H), 4.61 (s, 2H), 4.54 (s, 2H), 3.94 (ddd, J=8.4, 7.3, 4.3 Hz, 1H), 3.52 (dd, J=9.6, 4.1 Hz, 1H), 3.50-3.43 (m, 1H), 3.40 (s, 2H), 3.16 (dd, J=12.8, 4.3 Hz, 1H), 3.05 (dd, J=12.8, 7.4 Hz, 1H), 1.32 (s, 6H). MS (ESI+): M+H=477.

Example 130E (2R)-1-{5-amino-2-[1-(benzyloxy)-2-methylpropan-2-yl]-6-fluoro-1H-indol-1-yl}-3-(benzyloxy)propan-2-ol To a degassed suspension of bis(acetonitrile)dichloropalladium(II) (0.216 g, 0.831 mmol) and copper(I) iodide (0.158 g, 0.831 mmol) was added the product of Example 130D (3.96 g, 8.31 mmol) in acetonitrile (20 mL) via cannula. The reaction was sparged with nitrogen and then heated at 80° C. for 3 hours. The reaction was allowed to cool to room temperature, filtered, and washed with acetonitrile. The solvent was removed in vacuo and the resulting black oil dissolved in 200 mL of ethyl acetate. The organics were washed with aqueous ammonium chloride followed by brine, followed by the addition of 25 g of Si-Thiol. The reaction was stirred at room temperature for 1 hour, filtered, and concentrated. The crude material was chromatographed using a 120 g silica gel cartridge, eluting with a gradient of 25-35% ethyl acetate/heptanes over 60 minutes to give the title compound (2.431 g, 5.10 mmol, 61.4% yield) as a yellow solid: 1H NMR (400 MHz, DMSO-d$_6$) δ 7.38-7.32 (m, 4H), 7.32-7.21 (m, 6H), 7.18 (d, J=12.7 Hz, 1H), 6.75 (d, J=9.0 Hz, 1H), 6.04 (s, 1H), 5.09 (d, J=5.1 Hz, 1H), 4.53 (s, 2H), 4.44 (s, 4H), 4.31 (d, J=12.3 Hz, 1H), 4.08-3.97 (m, 2H), 3.61 (d, J=9.2 Hz, 1H), 3.55 (d, J=9.2 Hz, 1H), 3.50-3.38 (m, 2H), 1.38 (s, 6H). MS (ESI+): M+H=477.

Example 130F (7R)—N-{1-[(2R)-3-(benzyloxy)-2-hydroxypropyl]-2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide The product from Example 3B (203.7 mg, 0.789 mmol) was dissolved in dichloromethane (5 mL). Oxalyl chloride (250 µL) and N,N-dimethylformamide (50 µL) were added which resulted in bubbling of the reaction mixture. The reaction was stirred at ambient temperature for 1 hour. The reaction was concentrated, and the residue was dissolved in dichloromethane (2 mL) and concentrated two times. The residue was dissolved in dichloromethane (3 mL) and pyridine (1 mL). The product of Example 130E (337.8 mg, 0.709 mmol) was added, and the reaction mixture was stirred at 60° C. for 19 hours. The reaction mixture was concentrated, and the residue was purified by silica gel chromatography, eluting with 5% ethyl acetate in dichloromethane ($R_f$=0.44) to yield the title compound (415.4 mg, 82%). $^1$H NMR (501 MHz, DMSO-$d_6$) δ 9.21 (s, 1H), 7.56 (s, 1H), 7.39-7.33 (m, 6H), 7.31-7.24 (m, 4H), 7.22-7.19 (m, 2H), 7.04 (s, 1H), 6.27 (s, 1H), 5.15 (d, J=5.4 Hz, 1H), 5.09 (d, J=9.1 Hz, 1H), 4.54 (s, 2H), 4.46-4.36 (m, 4H), 4.13 (dd, J=15.2, 8.6 Hz, 1H), 4.06-3.94 (m, 1H), 3.64 (d, J=9.2 Hz, 1H), 3.56 (d, J=9.3 Hz, 1H), 3.49 (dd, J=9.7, 4.8 Hz, 1H), 3.44 (dd, J=9.6, 6.4 Hz, 1H), 1.67 (s, 3H), 1.41 (d, J=3.9 Hz, 6H); MS (ESI+) m/z 717 (M+H)$^+$.

Example 130G (7R)—N-{1-[(2R)-2,3-dihydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide The product of Example 130F (622 mg, 0.868 mmol) was dissolved in dichloromethane (8.7 mL) and the resulting solution was cooled to <−70° C. in an acetone-dry ice bath. Boron trichloride (4339 μL, 4.34 mmol) was added dropwise, and a slight exotherm was noted (Temperature <−60° C. during the addition). The mixture was stirred at the same temperature for 15 minutes, and then warmed to −30° C. The mixture was cooled to −78° C. before quenching with 0.5 mL of methanol. The mixture was diluted with ethyl acetate, warmed to room temperature, and stirred with saturated sodium bicarbonate for 30 minutes at room temperature before separating the layers. The organic layer was washed with saturated sodium bicarbonate and brine sequentially, dried over sodium sulfate, filtered, and concentrated. The residue was loaded onto a 12 g silica gel column and eluting with 20-100% ethyl acetate/heptanes over 15 minutes to give of the title compound (410 mg, 88%). $^1$H NMR (400 MHz, DMSO-$d_6$) δ 9.22 (s, 1H), 7.56 (s, 1H), 7.42-7.30 (m, 2H), 7.04 (s, 1H), 6.24 (s, 1H), 5.09 (d, J=9.1 Hz, 1H), 4.49-4.36 (m, 2H), 4.13 (dd, J=15.2, 8.7 Hz, 1H), 3.92 (q, J=6.1, 4.2 Hz, 1H), 3.67-3.55 (m, 2H), 3.47 (dd, J=11.0, 4.9 Hz, 2H), 3.40 (dd, J=11.1, 6.5 Hz, 1H), 1.87 (s, 1H), 1.68 (s, 3H), 1.37 (s, 3H), 1.33 (s, 3H); MS (ESI+) m/z 537 (M+H)$^+$.

Example 131

(7R)—N-(2-tert-butyl-1H-indol-5-yl)-2,2-difluoro-7-methyl-6,7-dihydro-2H-furo[2,3-f][1,3]benzodioxole-7-carboxamide The product from Example 3B (52.0, 0.201 mmol) was dissolved in dichloromethane (1 mL). Oxalyl chloride (80 μL) and N,N-dimethylformamide (25 μL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). 2-tert-Butyl-1H-indol-5-amine (52.8 mg, 0.280 mmol) was added, and the reaction mixture was stirred at 60° C. for 21 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (65.5 mg, 76%). $^1$H NMR (501 MHz, DMSO-$d_6$) δ 10.79 (d, J=1.7 Hz, 1H), 9.25 (s, 1H), 7.60-7.57 (m, 2H), 7.20 (d, J=8.5 Hz, 1H), 7.10 (dd, J=8.7, 2.0 Hz, 1H), 7.03 (s, 1H), 6.06 (d, J=1.9 Hz, 1H), 5.12 (d, J=9.1 Hz, 1H), 4.39 (d, J=9.1 Hz, 1H), 1.68 (s, 3H), 1.33 (s, 9H); MS (ESI+) m/z 429 (M+H)$^+$.

Example 132

(7R)—N-{1-[(2R)-3-(benzyloxy)-2-hydroxypropyl]-2-tert-butyl-6-fluoro-1H-indol-5-yl}-2,2-difluoro-7-methyl-6,7-dihydro-2H-furo[2,3-f][1,3]benzodioxole-7-carboxamide Example 132A (2R)-1-[4-amino-2-(3,3-dimethylbut-1-yn-1-yl)-5-fluoroanilino]-3-(benzyloxy)propan-2-ol The product of Example 130C (124.5 mg, 0.337 mmol), Pd(OAc)$_2$ (4.4 mg, 0.020 mmol), 1,4-bis(diphenylphosphino)butane (16.7 mg, 0.039 mmol), copper(I) iodide (17.0 mg, 0.089 mmol) and potassium carbonate (102.2 mg, 0.739) were suspended in acetonitrile (2 mL) and purged with nitrogen for 15 minutes. 3,3-Dimethylbut-1-yne (75.4 mg, 0.918 mmol) was added and the reactions was purged with nitrogen for an additional 15 minutes then heated at 80° C. for 22 hours. The reaction mixture was diluted with acetonitrile (5 mL), filtered through diatomaceous earth, and washed with additional acetonitrile (3×2 mL). The filtrate was concentrated, and azeotroped to dryness with acetonitrile (2×3 mL). The crude product was used without further purification.

Example 132B (2R)-1-(5-amino-2-tert-butyl-6-fluoro-1H-indol-1-yl)-3-(benzyloxy)propan-2-ol The crude product from Example 132A was dissolved in acetonitrile (2 mL) under nitrogen. Bis(acetonitrile)dichloropalladium(II) (10.2 mg, 0.039 mmol) and copper(I) iodide (8.0 mg, 0.042 mmol) were added. The reaction was purged with nitrogen for 1 hour and heated at 80° C. for 20 hours. The reaction was complete based on TLC (10% ethyl acetate in dichloromethane). The reaction mixture was diluted with acetonitrile (5 mL), filtered through diatomaceous earth, and washed with additional acetonitrile (3×2 mL). The filtrate was concentrated and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (54.7 mg, 44%, 2 steps). $^1$H NMR (400 MHz, DMSO-$d_6$) δ 7.40-7.34 (m, 4H), 7.32-7.27 (m, 1H), 7.18 (d, J=12.6 Hz, 1H), 6.74 (d, J=8.9 Hz, 1H), 5.99 (s, 1H), 5.11 (d, J=5.1 Hz, 1H), 4.55 (s, 2H), 4.47-4.27 (m, 3H), 4.09 (dd, J=14.6, 8.2 Hz, 2H), 3.54-3.40 (m, 2H), 1.38 (s, 9H); MS (ESI+) m/z 371 (M+H)$^+$.

Example 132C (7R)-N-{1-[(2R)-3-(benzyloxy)-2-hydroxypropyl]-2-tert-butyl-6-fluoro-1H-indol-5-yl}-2,2-difluoro-7-methyl-6,7-dihydro-2H-furo[2,3-f][1,3]benzodioxole-7-carboxamide The product from Example 3B (49.4, 0.191 mmol) was dissolved in dichloromethane (1 mL). Oxalyl chloride (80 µL) and N,N-dimethylformamide (25 µL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product of Example 132B (50.1 mg, 0.135 mmol) was added, and the reaction mixture was stirred at 60° C. for 21 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (38.6 mg, 47%). $^1$H NMR (501 MHz, DMSO-$d_6$) δ 9.21 (s, 1H), 7.56 (s, 1H), 7.40-7.34 (m, 6H), 7.32-7.27 (m, 1H), 7.04 (s, 1H), 6.22 (s, 1H), 5.09 (d, J=9.1 Hz, 1H), 4.56 (s, 2H), 4.47-4.37 (m, 2H), 4.19 (dd, J=15.2, 8.6 Hz, 1H), 4.05 (dtd, J=8.5, 5.6, 5.1, 3.1 Hz, 1H), 3.55-3.47 (m, 3H), 1.68 (s, 3H), 1.41 (s, 9H)); MS (ESI-) m/z 609 (M-H)$^-$.

Example 133

(7R)-N-{2-tert-butyl-1-[(2R)-2,3-dihydroxypropyl]-6-fluoro-1H-indol-5-yl}-2,2-difluoro-7-methyl-6,7-dihydro-2H-furo[2,3-f][1,3]benzodioxole-7-carboxamide The product of Example 132C (31.0 mg, 0.051 mmol) was dissolved in dichloromethane (1 mL) and the resulting solution was cooled to <-70° C. in an acetone-dry ice bath. Boron trichloride (1M in dichloromethane, 250 µL, 0.25 mmol) was added dropwise. The mixture was stirred at the same temperature for 15 minutes, and then warmed to -30° C. The mixture was then cooled to -78° C. before quenching with 0.5 mL of methanol, and then concentrated. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (22.3 mg, 84%). $^1$H NMR (400 MHz, DMSO-$d_6$) δ 9.21 (s, 1H), 7.55 (s, 1H), 7.43-7.37 (m, 1H), 7.35 (d, J=7.7 Hz, 1H), 7.04 (s, 1H), 6.22 (s, 1H), 5.09 (d, J=9.1 Hz, 1H), 4.49-4.36 (m, 2H), 4.11 (dd, J=15.2, 8.6 Hz, 1H), 3.89 (dtt, J=8.1, 5.0, 2.8 Hz, 1H), 3.46 (d, J=4.8 Hz, 1H), 3.43-3.36 (m, 1H), 1.67 (s, 3H), 1.42 (s, 9H); MS (ESI-) m/z 519 (M-H)$^-$.

Example 134

(7R)-N-{1-[(2R)-2,3-dihydroxypropyl]-6-fluoro-2-[1-(hydroxymethyl)cyclobutyl]-1H-indol-5-yl}-2,2-difluoro-7-methyl-6,7-dihydro-2H-furo[2,3-f][1,3]benzodioxole-7-carboxamide

Example 134A

{1-[(benzyloxy)methyl]cyclobutyl}methanol

A solution of cyclobutane-1,1-diyldimethanol (1.04 g, 8.95 mmol) in 1:1 tetrahydrofuran: N,N-dimethylformamide (10 mL) under $N_2$ was treated with 60% dispersion of sodium hydride in mineral oil (0.358 g, 8.95 mmol), stirred at ambient temperature for 2 hours, treated with benzyl bromide (1.065 ml, 8.95 mmol) and stirred at ambient temperature overnight. The mixture was partitioned between methyl tert-butyl ether (50 mL) and saturated NH$_4$Cl solution. The methyl tert-butyl ether layer was washed with water (25 mL) and brine sequentially, dried (MgSO$_4$), filtered, concentrated, and chromatographed on silica gel, eluting with a gradient of 10% to 30% ethyl acetate in heptanes to provide the title compound (0.7 g, 3.39 mmol, 37.9% yield). $^1$H NMR (500 MHz, CDCl$_3$) δ 7.40-7.30 (m, 5H), 4.56 (s, 2H), 3.72 (d, J=5.6 Hz, 2H), 3.59 (s, 2H), 2.58 (t, J=5.7 Hz, 1H), 2.01-1.78 (m, 6H); MS (DCI) m/z 224 (M+NH$_4$)$^+$.

Example 134B

1-[(benzyloxy)methyl]cyclobutane-1-carbaldehyde

A solution of oxalyl chloride (0.594 mL, 6.79 mmol) in dichloromethane (20 mL) was cooled to -78° C. under $N_2$, treated dropwise with DMSO (0.722 mL, 10.18 mmol), and stirred for 10 minutes at -78° C., and treated with a solution of the product from Example 134A (0.7 g, 3.39 mmol) in CH$_2$Cl$_2$ (5 mL). The reaction mixture was stirred at -78° C. for 15 minutes, treated dropwise with triethylamine (1.892 mL, 13.57 mmol), stirred at -78° C. for 20 minutes and then allowed to warm to 0° C. The mixture was treated with water (30 mL) and the layers were separated. The aqueous layer was extracted with CH$_2$Cl$_2$. The combined CH$_2$Cl$_2$ layers were washed with brine, dried (MgSO$_4$), filtered, and concentrated. The residue was chromatographed on silica gel, eluting with 10% ethyl acetate in heptanes to provide the title compound (0.31 g, 1.518 mmol, 44.7% yield). $^1$H NMR (400 MHz, CDCl$_3$) δ 9.68 (s, 1H), 7.37-7.25 (m, 5H), 4.54 (s, 2H), 3.71 (s, 2H), 2.37-2.25 (m, 2H), 2.04-1.82 (m, 4H); MS (DCI) m/z 222 (M+NH$_4$)$^+$.

Example 134C

{[(1-ethynylcyclobutyl)methoxy]methyl}benzene

A mixture of the product from Example 134B (0.3 g, 1.469 mmol) and K$_2$CO$_3$ (0.406 g, 2.94 mmol) in anhydrous methanol (7.5 mL) was treated with 10% dimethyl (1-diazo-2-oxopropyl)phosphonate in acetonitrile (2.82 g, 1.469 mmol) and stirred at ambient temperature for 2 hours. The mixture was diluted with methyl tert-butyl ether (about 30 mL), washed with saturated NaHCO$_3$ solution and brine sequentially, dried (MgSO$_4$), filtered, and concentrated. The residue was chromatographed on silica gel eluting with 5% ethyl acetate in heptane to provide the title compound (97 mg, 0.484 mmol, 33.0% yield). $^1$H NMR (501 MHz, CDCl$_3$)

δ 7.39-7.33 (m, 4H), 7.30-7.26 (m, 1H), 4.63 (s, 2H), 3.50 (s, 2H), 2.30 (s, 1H), 2.29-2.19 (m, 2H), 2.16 (dddd, J=9.2, 7.1, 5.9, 1.9 Hz, 2H), 2.10-1.97 (m, 1H), 1.95-1.82 (m, 1H); MS (DCI) m/z 218 (M+NH$_4$)$^+$.

Example 134D (2R)-1-[4-amino-2-({1-[(benzyloxy)methyl] cyclobutyl}ethynyl)-5-fluoroanilino]-3-(benzyloxy) propan-2-ol A vial containing palladium(II) acetate (3.04 mg, 0.014 mmol), copper(I) iodide (3.87 mg, 0.020 mmol), 1,4-bis (diphenylphosphino)butane (8.66 mg, 0.020 mmol) and K$_2$CO$_3$ (56.1 mg, 0.406 mmol) was treated with a solution of the product of Example 130C (50 mg, 0.135 mmol), and the product from Example 134C (28.5 mg, 0.142 mmol) in acetonitrile (0.25 mL). Three 0.25 mL portions of acetonitrile were used to wash the reagents into the bottom of the vial. The atmosphere in the vial was treated with stream of N$_2$ for 5 seconds. The vial was capped and stirred overnight at 80° C. The mixture was cooled and partitioned between ethyl acetate and a saturated NaHCO$_3$ solution. The ethyl acetate layer was washed with brine, dried (MgSO$_4$), filtered, concentrated, and chromatographed on silica gel, eluting with a gradient of 10% to 50% ethyl acetate in heptanes to provide the title compound (12.3 mg, 0.025 mmol, 18.59% yield). $^1$H NMR (400 MHz, CDCl$_3$) δ 7.40-7.27 (m, 10H), 6.77 (d, J=9.6 Hz, 1H), 6.35 (d, J=13.1 Hz, 1H), 4.64 (s, 2H), 4.54 (s, 2H), 4.30 (s, 1H), 3.94 (s, 1H), 3.54-3.51 (m, 1H), 3.47 (dd, J=9.6, 6.3 Hz, 1H), 3.15 (d, J=7.0 Hz, 2H), 2.53-2.42 (m, 3H), 2.35-2.19 (m, 4H), 2.14-2.01 (m, 1H), 1.98-1.85 (m, 1H); MS (ESI+) m/z 489 (M+H)$^+$.

Example 134E (2R)-1-(5-amino-2-{1-[(benzyloxy)methyl]cyclobutyl}-6-fluoro-1H-indol-1-yl)-3-(benzyloxy)propan-2-ol A mixture the product from Example 134D (12.3 mg, 0.025 mmol), bis(acetonitrile)dichloropalladium(II) (3.27 mg, 0.013 mmol) and copper(I) iodide (2.397 mg, 0.013 mmol) in acetonitrile (2 mL) was heated at 80° C. for 2 hours. The mixture was concentrated and the residue was taken up in CH$_2$Cl$_2$ and chromatographed on silica gel, eluting with a gradient of 10% to 50% ethyl acetate in heptanes to provide the title compound (7.8 mg, 0.016 mmol, 63.4% yield). $^1$H NMR (501 MHz, CDCl$_3$) δ 7.39-7.29 (m, 5H), 7.24-7.21 (m, 3H), 7.16-7.12 (m, 2H), 7.07 (d, J=11.9 Hz, 1H), 6.89 (d, J=8.7 Hz, 1H), 6.04 (s, 1H), 4.56 (d, J=1.4 Hz, 2H), 4.45 (s, 2H), 4.30 (s, 2H), 4.22 (s, 1H), 4.09-4.05 (m, 1H), 3.96 (dd, J=15.1, 8.6 Hz, 1H), 3.78 (d, J=9.3 Hz, 1H), 3.71 (d, J=9.3 Hz, 1H), 3.45 (d, J=5.1 Hz, 2H), 2.75 (s, 1H), 2.58 (q, J=9.5 Hz, 1H), 2.48-2.41 (m, 1H), 2.34-2.24 (m, 2H), 2.12-2.00 (m, 1H), 1.95-1.86 (m, 1H); MS (ESI+) m/z 489 (M+H)$^+$.

Example 134F (7R)-2,2-difluoro-7-methyl-6,7-dihydro-2H-furo[2, 3-f][1,3]benzodioxole-7-carbonyl chloride A solution of the product from Example 3B (150 mg, 0.581 mmol) in CH$_2$Cl$_2$ (3 mL) was treated with oxalyl chloride (254 μL, 2.91 mmol) and N,N-dimethylformamide (0.01 mL), stirred at ambient temperature for 1 hour and concentrated to provide the title compound (149 mg, 0.539 mmol, 93% yield). $^1$H NMR (400 MHz, CDCl$_3$) δ 7.03 (s, 1H), 6.62 (s, 1H), 5.14 (d, J=9.7 Hz, 1H), 4.32 (d, J=9.7 Hz, 1H), 1.74 (s, 3H).

Example 134G (7R)—N-(1-[(2R)-3-(benzyloxy)-2-hydroxypropyl]-2-{1-[(benzyloxy)methyl]cyclobutyl}-6-fluoro-1H-indol-5-yl)-2,2-difluoro-7-methyl-6,7-dihydro-2H-furo[2,3-f][1,3]benzodioxole-7-carboxamide The product from Example 134E (7.8 mg, 0.016 mmol) and triethylamine (30 μL, 0.215 mmol) in CH$_2$Cl$_2$ (0.3 mL) at 0° C. was treated with the product from Example 134F (23 mg, 0.083 mmol) and stirred at ambient temperature for 1 hour. The mixture was partitioned between ethyl acetate (30 mL) and saturated NaHCO$_3$ solution (5 mL). The ethyl acetate layer was washed with brine, dried (MgSO$_4$), filtered, concentrated, and chromatographed on silica gel, eluting with a gradient of 10% to 100% ethyl acetate in heptane to provide the title compound (11.5 mg). $^1$H NMR (400 MHz, CDCl$_3$) δ 8.19 (d, J=7.7 Hz, 1H), 7.46 (d, J=2.7 Hz, 1H), 7.39-7.28 (m, 5H), 7.22 (dd, J=5.0, 1.7 Hz, 3H), 7.15-7.09 (m, 3H), 7.03 (s, 1H), 6.70 (s, 1H), 6.15 (s, 1H), 5.04 (d, J=9.3 Hz, 1H), 4.54 (s, 2H), 4.43 (s, 2H), 4.40 (d, J=9.3 Hz, 1H), 4.18-4.04 (m, 2H), 3.97 (dd, J=15.0, 8.5 Hz, 1H), 3.78 (d, J=9.3 Hz, 1H), 3.71 (d, J=9.3 Hz, 1H), 3.42 (d, J=5.1 Hz, 2H), 2.71 (d, J=5.0 Hz, 1H), 2.57 (q, J=9.6 Hz, 1H), 2.45 (q, J=9.7 Hz, 1H), 2.35-2.22 (m, 2H), 2.14-2.00 (m, 1H), 1.93 (t, J=10.4 Hz, 1H), 1.71 (s, 3H); MS (ESI+) m/z 729 (M+H)$^+$; MS (ESI−) m/z 727 (M−H)$^-$.

Example 134H (7R)—N-{1-[(2R)-2,3-dihydroxypropyl]-6-fluoro-2-[1-(hydroxymethyl)cyclobutyl]-1H-indol-5-yl}-2,2-difluoro-7-methyl-6,7-dihydro-2H-furo[2,3-f][1,3] benzodioxole-7-carboxamide A solution of the product from Example 134G (10.8 mg, 0.015 mmol) in CH$_2$Cl$_2$ (0.5 mL) under N$_2$ was cooled to −78° C., treated dropwise with 1 M boron trichloride in CH$_2$Cl$_2$ (74.1 μL, 0.074 mmol), stirred at −40° C. for 15 minutes, cooled to −78° C., treated with methanol (0.2 mL) dropwise, allowed to warm to 0° C., treated with saturated NaHCO$_3$ solution (2 mL) and ethyl acetate (10 mL) and stirred for 2 minutes. The mixture was extracted with ethyl acetate (30 mL). The ethyl acetate layer was washed with brine, dried (MgSO$_4$), filtered, concentrated, and chromatographed on silica gel, eluting with a gradient of 0% to 100% [3:1 ethyl acetate:ethanol] in ethyl acetate to provide the title compound (6 mg, 10.94 μmol, 73.8% yield). $^1$H NMR (400 MHz, CDCl$_3$) δ 8.10 (d, J=7.6 Hz, 1H), 7.43 (d, 1H), 7.01 (d, J=12.4 Hz, 2H), 6.71 (s, 1H), 6.17 (s, 1H), 5.02 (d, J=9.3 Hz, 1H), 4.40 (d, J=9.3 Hz, 1H), 4.15-4.07 (m, 1H), 4.03-3.97 (m, 3H), 3.83 (d, J=11.0 Hz, 1H), 3.68 (d, J=11.3 Hz, 1H), 3.57-3.50 (m, 1H), 2.79 (s, 1H), 2.55 (q, J=9.7 Hz, 1H), 2.43-2.07 (m, 6H), 1.96 (q, J=9.5 Hz, 1H), 1.71 (s, 3H); MS (ESI−) m/z 547 (M−H)$^-$.

Example 135

(7R)—N-{1-[(2R)-2,3-dihydroxypropyl]-6-fluoro-2-[3-(hydroxymethyl)oxetan-3-yl]-1H-indol-5-yl}-2,2-difluoro-7-methyl-6,7-dihydro-2H-furo[2,3-f][1,3]benzodioxole-7-carboxamide

Example 135A

{3-[(benzyloxy)methyl]oxetan-3-yl}methanol

A solution of oxetane-3,3-diyldimethanol (0.53 g, 4.49 mmol) in 1:1 tetrahydrofuran:N,N-dimethylformamide (5 mL) under $N_2$ was treated with 60% dispersion of sodium hydride in mineral oil (0.179 g, 4.49 mmol), stirred at ambient temperature for 30 minutes, treated with benzyl bromide (0.534 ml, 4.49 mmol), and stirred over night at room temperature. The reaction was quenched with aqueous ammonium chloride followed by extraction with methyl tert-butyl ether (twice). The combined methyl tert-butyl ether layers were washed with brine, dried ($MgSO_4$), filtered, concentrated, and chromatographed on silica gel, eluting with a gradient of 5% to 100% ethyl acetate in heptane to provide the title compound (0.41 g, 1.969 mmol, 43.9% yield). $^1$H NMR (501 MHz, $CDCl_3$) δ 7.38-7.34 (m, 2H), 7.33-7.29 (m, 3H), 4.56 (s, 2H), 4.49 (d, J=6.2 Hz, 2H), 4.43 (d, J=6.2 Hz, 2H), 3.94 (d, J=5.6 Hz, 2H), 3.80 (s, 2H), 2.32 (t, J=5.6 Hz, 1H).

Example 135B

3-[(benzyloxy)methyl]oxetane-3-carbaldehyde

A solution of oxalyl chloride (0.345 ml, 3.94 mmol) in dichloromethane (10 mL) was cooled to −78° C. under $N_2$, treated dropwise with DMSO (0.419 mL, 5.91 mmol), stirred for 10 minutes at −78° C., treated with a solution of the product from Example 135A (0.41 g, 1.969 mmol) in $CH_2Cl_2$ (5 mL), stirred at −78° C. for 15 minutes, treated dropwise with triethylamine (1.098 mL, 7.88 mmol), stirred at −78° C. for 20 minutes, and then allowed to warm to 0° C. The mixture was treated with water (30 mL) and the layers were separated. The aqueous layer was extracted with $CH_2Cl_2$. The combined $CH_2Cl_2$ layers were washed with brine, dried ($MgSO_4$), filtered, concentrated, and chromatographed on silica gel eluting with a gradient of 15% to 100% ethyl acetate in heptanes to provide the title compound (370 mg, 1.794 mmol, 91% yield). $^1$H NMR (400 MHz, $CDCl_3$) δ 9.88 (s, 1H), 7.40-7.27 (m, 5H), 4.81 (d, J=6.4 Hz, 2H), 4.57 (s, 2H), 4.55 (d, J=6.4 Hz, 2H), 3.93 (s, 2H).

Example 135C

3-[(benzyloxy)methyl]-3-ethynyloxetane

A mixture of the product from Example 135B (0.37 g, 1.794 mmol) and $K_2CO_3$ (0.496 g, 3.59 mmol) in anhydrous methanol (2.5 mL) was treated with 10% dimethyl (1-diazo-2-oxopropyl)phosphonate in acetonitrile (2.8 g, 1.458 mmol) and stirred at ambient temperature over the weekend. The mixture was concentrated on the rotary evaporator without heating. The residue was diluted with methyl tert-butyl ether (30 mL), washed with saturated $NaHCO_3$ solution and brine sequentially, dried ($MgSO_4$), filtered, concentrated, and chromatographed on silica gel, eluting with a gradient of 10% to 100% ethyl acetate in heptanes to provide the title compound (206 mg, 1.019 mmol, 56.8% yield). $^1$H NMR (400 MHz, $CDCl_3$) δ 7.39-7.27 (m, 5H), 4.76 (d, J=5.7 Hz, 2H), 4.66 (s, 2H), 4.56 (d, J=5.7 Hz, 2H), 3.72 (s, 2H), 2.43 (s, 1H).

Example 135D (2R)-1-[4-amino-2-({3-[(benzyloxy)methyl]oxetan-3-yl}ethynyl)-5-fluoroanilino]-3-(benzyloxy)propan-2-ol A mixture of palladium(II) acetate (3.04 mg, 0.014 mmol), copper(I) iodide (3.87 mg, 0.020 mmol), 1,4-bis(diphenylphosphino)butane (8.66 mg, 0.020 mmol), $K_2CO_3$ (56.1 mg, 0.406 mmol) and the product of Example 130C (50 mg, 0.135 mmol) was treated with a solution of the product from Example 135C (54.8 mg, 0.271 mmol) in acetonitrile (0.25 mL). The mixture was stirred over night at 80° C. under $N_2$. The mixture was cooled and partitioned between ethyl acetate (30 mL) and saturated $NaHCO_3$ solution (3 mL). The ethyl acetate layer was washed with brine, dried ($MgSO_4$), filtered, concentrated, and chromatographed on silica gel, eluting with a gradient of 15% to 100% ethyl acetate in heptanes to provide the title compound (28 mg, 0.057 mmol, 42.1% yield). $^1$H NMR (501 MHz, $CDCl_3$) δ 7.39-7.27 (m, 10H), 6.77 (d, J=9.6 Hz, 1H), 6.36 (d, J=13.0 Hz, 1H), 4.83 (d, J=5.6 Hz, 2H), 4.67 (s, 2H), 4.65-4.60 (bs, 1H), 4.63 (d, J=5.6 Hz, 2H), 4.54 (s, 2H), 3.99-3.92 (m, 1H), 3.81 (s, 2H), 3.53 (dd, J=9.6, 4.0 Hz, 1H), 3.47 (dd, J=9.6, 6.3 Hz, 1H), 3.27 (s, 2H), 3.18 (dd, J=12.7, 4.0 Hz, 1H), 3.06 (dd, J=12.8, 7.5 Hz, 1H), 2.39 (d, J=4.4 Hz, 1H); MS (ESI+) m/z 491 (M+H)$^+$.

Example 135E (2R)-1-(5-amino-2-{3-[(benzyloxy)methyl]oxetan-3-yl}-6-fluoro-1H-indol-1-yl)-3-(benzyloxy)propan-2-ol A mixture of the product from Example 135D (27 mg, 0.055 mmol), bis(acetonitrile)dichloropalladium(II) (2.86 mg, 0.011 mmol), and copper(I) iodide (2.096 mg, 0.011 mmol) in acetonitrile (2 mL) was heated at 80° C. for 2 hours. The mixture was cooled and concentrated. The residue was taken up in $CH_2Cl_2$ and chromatographed on silica gel with a gradient of 10% to 50% ethyl acetate in heptanes to provide the title compound (13 mg, 0.027 mmol, 48.1% yield). $^1$H NMR (400 MHz, $CDCl_3$) δ 7.41-7.29 (m, 5H), 7.27-7.22 (m, 3H), 7.15 (dd, J=6.5, 3.0 Hz, 2H), 7.04 (d, J=11.7 Hz, 1H), 6.91 (d, J=8.7 Hz, 1H), 6.01 (s, 1H), 5.15 (d, J=5.6 Hz, 1H), 5.01 (d, J=5.5 Hz, 1H), 4.72-4.67 (m, 2H), 4.56 (s, 2H), 4.50 (s, 2H), 4.23-4.15 (m, 1H), 4.02-3.94 (m, 2H), 3.91 (dd, J=15.1, 3.5 Hz, 1H), 3.62 (dd, J=15.2, 8.9 Hz, 1H), 3.55 (s, 2H), 3.47-3.40 (m, 2H), 2.46 (d, J=4.2 Hz, 1H); MS (ESI+) m/z 491 (M+H)$^+$.

Example 135F (7R)—N-(1-[(2R)-3-(benzyloxy)-2-hydroxypropyl]-2-{3-[(benzyloxy)methyl]oxetan-3-yl}-6-fluoro-1H-indol-5-yl)-2,2-difluoro-7-methyl-6,7-dihydro-2H-furo[2,3-f][1,3]benzodioxole-7-carboxamide A solution of the product from Example 135E (12 mg, 0.024 mmol) and triethylamine (3.41 μL, 0.024 mmol) in $CH_2Cl_2$ (0.25 mL) was treated with the product from Example 134F (13.53 mg, 0.049 mmol) and stirred at 0° C.

231 for 30 minutes, stirred at ambient temperature for 15 minutes, and partitioned between CH$_2$Cl$_2$ (25 mL) and saturated NaHCO$_3$ solution (5 mL). The layers were separated and the aqueous was extracted with CH$_2$Cl$_2$. The combined CH$_2$Cl$_2$ layers were washed with brine, dried (MgSO$_4$), filtered, concentrated, and chromatographed on silica gel, eluting with a gradient of 10% to 50% ethyl acetate in heptanes to provide the title compound. $^1$H NMR (400 MHz, CDCl$_3$) δ 8.24 (d, J=7.7 Hz, 1H), 7.47 (d, J=2.5 Hz, 1H), 7.40-7.28 (m, 6H), 7.25-7.19 (m, 3H), 7.15-7.08 (m, 3H), 7.03 (s, 1H), 6.71 (s, 1H), 6.14 (s, 1H), 5.13 (d, J=5.7 Hz, 1H), 5.06-5.00 (m, 2H), 4.69 (dd, J=10.8, 5.6 Hz, 1H), 4.54 (s, 2H), 4.48 (s, 2H), 4.40 (d, J=9.3 Hz, 1H), 4.14-4.07 (m, 1H), 4.01-3.95 (m, 2H), 3.92 (dd, J=15.3, 3.4 Hz, 1H), 3.72-3.62 (m, 1H), 3.45-3.35 (m, 2H), 2.45 (d, J=4.7 Hz, 1H), 1.71 (s, 3H); MS (ESI+) m/z 731 (M+H)$^+$; MS (ESI−) m/z 729 (M−H)$^-$.

Example 135G (7R)—N-{1-[(2R)-2,3-dihydroxypropyl]-6-fluoro-2-[3-(hydroxymethyl)oxetan-3-yl]-1H-indol-5-yl}-2,2-difluoro-7-methyl-6,7-dihydro-2H-furo[2,3-f][1,3]benzodioxole-7-carboxamide A mixture of the product from Example 135F (13 mg, 0.018 mmol), 10% Pd/C (10 mg), and methanol (1 mL) was stirred under an atmosphere of H$_2$ (balloon) overnight. The atmosphere was exchanged with N$_2$ and the mixture was treated with a gentle stream of N$_2$ until the solvent evaporated. The residue was treated with CH$_2$Cl$_2$ (about 3 mL) and stirred for 5 minutes, mixed with silica gel (0.5 g) and chromatographed on silica gel, eluting with a gradient of 0% to 100% [9:1 ethyl acetate:EtOH] in ethyl acetate to provide the title compound (7 mg, 0.013 mmol, 71.5% yield). $^1$H NMR (501 MHz, CDCl$_3$) δ 8.09 (d, J=7.5 Hz, 1H), 7.44 (d, J=2.1 Hz, 1H), 7.03 (s, 1H), 7.00 (d, J=11.3 Hz, 1H), 6.71 (s, 1H), 6.13 (s, 1H), 5.09 (d, J=5.7 Hz, 1H), 5.01 (d, J=9.3 Hz, 1H), 4.90 (d, J=5.6 Hz, 1H), 4.69 (d, J=5.6 Hz, 1H), 4.63 (d, J=5.7 Hz, 1H), 4.40 (d, J=9.3 Hz, 1H), 4.26 (d, J=11.1 Hz, 1H), 4.10 (bs, 1H), 4.07 (bs, 1H), 3.94 (dd, J=15.0, 3.1 Hz, 1H), 3.65 (d, J=10.8 Hz, 1H), 3.59 (dd, J=14.9, 10.0 Hz, 1H), 3.52-3.47 (m, 1H), 2.95 (bs, 1H), 2.82 (bs, 1H), 2.32 (bs, 1H), 1.70 (s, 3H); MS (ESI−) m/z 549 (M−H).

Example 136

(7R)—N-{1-[(2R)-2,3-dihydroxypropyl]-6-fluoro-2-[1-(hydroxymethyl)cyclopropyl]-1H-indol-5-yl}-2,2-difluoro-7-methyl-6,7-dihydro-2H-furo[2,3-f][1,3]benzodioxole-7-carboxamide Example 136A {1-[(benzyloxy)methyl]cyclopropyl}methanol To a cold (0° C.) solution of 1,1-bis(hydroxymethyl)cyclopropane (5.00 g, 49.0 mmol) in N,N-dimethylformamide (100 ml) was added 60% sodium hydride in mineral oil (1.958 g, 49.0 mmol) in portionwise manner Benzylbromide (5.82 mL, 49.0 mmol) was added to the reaction mixture at room temperature resulting in a slight exotherm. The reaction mixture was stirred at room temperature for 18 hours, and partitioned between 1N HCl solution and methyl tert-butyl ether. The layers were separated and the aqueous layer was washed with CHCl$_3$:isopropyl alcohol (120 mL:40 mL). The combined organic extracts were dried over anhydrous sodium sulfate, filtered, and concentrated in vacuo. The resulting crude product was purified by flash chromatography using a 220 gm cartridge, eluting with 10-70% methyl tert-butyl ether/heptanes to afford 6.58 g of the title product as colorless oil. (70% Yield) $^1$H NMR (400 MHz, CDCl$_3$) δ 0.45-0.51 (m, 2H), 0.51-0.57 (m, 2H), 2.46 (d, J=4.6 Hz, 1H), 3.46 (s, 2H), 3.56 (d, J=3.3 Hz, 2H), 4.54 (s, 2H), 7.27-7.39 (m, 5H). MS (ESI+): M+H=192.8.

Example 136B 1-((benzyloxy)methyl)cyclopropanecarbaldehyde

To a cold (0° C.) solution of Example 136A (3.5 g, 18.21 mmol), DMSO (4.52 ml, 63.7 mmol) and triethylamine (8.88 ml, 63.7 mmol) in dichloromethane (40 ml) was added pyridine sulfur trioxide (7.24 g, 45.5 mmol) in portionwise manner Reaction mixture was stirred at same temp for 3.5 hours. The reaction mixture was washed with saturated ammonium chloride solution and the organic phase was separated, dried over anhydrous sodium sulfate, filtered, and concentrated in vacuo. The resulting crude product was purified by flash chromatography using a 120 gm silica gel cartridge, eluting with 10-60% methyl tert-butyl ether/heptanes to afford 2.66 g of the title compound as colorless oil. (77% yield). $^1$H NMR (400 MHz, CDCl$_3$) δ 1.07-1.15 (m, 2H), 1.24 (p, J=4.4, 3.9 Hz, 2H), 3.70 (s, 2H), 4.55 (s, 2H), 7.26-7.41 (m, 4H), 9.05 (s, 1H). MS (ESI$^+$): M+H=190.8.

Example 136C

{[(1-ethynylcyclopropyl)methoxy]methyl}benzene

To a cold (0° C.) suspension of Example 136B (2.6508 g, 13.93 mmol) and potassium carbonate (3.85 g, 27.9 mmol) in methanol (50 ml) was added dimethyl (1-diazo-2-oxopropyl)phosphonate (2.300 mL, 15.33 mmol) in dropwise manner Reaction mixture was stirred at same temperature for 1 hour and then allowed to warm to room temperature and stirred overnight. The reaction mixture was partitioned between water and methyl tert-butyl ether. The organic phase was dried over anhydrous sodium sulfate, filtered, and concentrated in vacuo. The resulting crude product was purified by flash chromatography using a 120 gm cartridge, eluting with 0-20% methyl tert-butyl ether/heptanes to afford 2.06 g of the title compound as colorless oil. (80% Yield). $^1$H NMR (400 MHz, CDCl$_3$) δ 0.73-0.80 (m, 2H), 0.95-1.02 (m, 2H), 1.93 (s, 1H), 3.39 (s, 2H), 4.62 (s, 2H), 7.24-7.39 (m, 5H). MS (LC/MS): M+H=187.0.

Example 136D (2R)-1-[4-amino-2-({1-[(benzyloxy)methyl]cyclopropyl}ethynyl)-5-fluoroanilino]-3-(benzyloxy)propan-2-ol Palladium(II) acetate (9.6 mg, 0.043 mmol), 1,4-bis(diphenylphosphino)butane (25.7 mg, 0.060 mmol), copper(I) iodide (14.0 mg, 0.064 mmol) and potassium carbonate (485.0 mg, 3.51) were suspended in acetonitrile (10 mL) and purged with nitrogen for 15 minutes. The product of Example 136C (281.4 mg, 1.511 mmol) was added and the reactions was purged with nitrogen for an additional 15 minutes. The product of Example 130C (425.7 mg, 1.153 mmol) was added and the reactions was purged with nitrogen for an additional 15 minutes then heated to 80° C. for 16 hours. The reaction was diluted with acetonitrile (10 mL), filtered through diatomaceous earth, and washed with additional acetonitrile (3×2 mL). The filtrate was concentrated and the residue was purified by silica gel chromatography (10% ethyl acetate in dichloromethane, $R_f$=0.43) to yield the title compound (522.2 mg, 95%). $^1$H NMR (500 MHz, DMSO-$d_6$) δ 7.37-7.32 (m, 8H), 7.31-7.25 (m, 2H), 6.67 (d, J=9.8 Hz, 1H), 6.39 (d, J=13.6 Hz, 1H), 5.10 (d, J=5.1 Hz, 1H), 4.65 (ddd, J=6.7, 5.2, 1.8 Hz, 1H), 4.57 (s, 2H), 4.49 (s, 2H), 4.36 (s, 2H), 3.81 (tdd, J=5.6, 4.2, 1.6 Hz, 1H), 3.44 (s, 2H), 3.41 (dd, J=5.6, 2.3 Hz, 2H), 3.14 (ddd, J=12.6, 6.9, 4.3 Hz, 1H), 2.92 (ddd, J=12.2, 7.0, 5.0 Hz, 1H), 1.00-0.93 (m, 2H), 0.92-0.84 (m, 2H); MS (ESI+) m/z 475 (M+H)$^+$.

Example 136E (2R)-1-(5-amino-2-{1-[(benzyloxy)methyl]cyclopropyl}-6-fluoro-1H-indol-1-yl)-3-(benzyloxy)propan-2-ol The product from Example 136D (522.2 mg, 1.10 mmol) was dissolved in acetonitrile (10 mL) under nitrogen. Bis(acetonitrile)dichloropalladium(II) (28.5 mg, 0.110 mmol) and copper(I) iodide (21.5 mg, 0.103 mmol) were added. The reaction was purged with nitrogen for 1 hour and heated at 80° C. (21 hours). The reaction was diluted with acetonitrile (5 mL), filtered through diatomaceous earth, and washed with additional acetonitrile (3×2 mL). The filtrate was concentrated and the residue was purified by silica gel chromatography (10% ethyl acetate in dichloromethane, $R_f$=0.46) to yield the title compound (326.6 mg, 63%). $^1$H NMR (400 MHz, DMSO-$d_6$) δ 7.38-7.10 (m, 11H), 6.76 (d, J=9.0 Hz, 1H), 6.06 (s, 1H), 5.09 (d, J=4.7 Hz, 1H), 4.53 (s, 2H), 4.45 (s, 2H), 4.38 (s, 2H), 4.31-4.23 (m, 1H), 4.13-3.96 (m, 2H), 3.58-3.37 (m, 4H), 1.04-0.95 (m, 1H), 0.85 (q, J=4.1, 3.5 Hz, 3H); MS (ESI+) m/z 475 (M+H)$^+$.

Example 136F (7R)—N-(1-[(2R)-3-(benzyloxy)-2-hydroxypropyl]-2-{1-[(benzyloxy)methyl]cyclopropyl}-6-fluoro-1H-indol-5-yl)-2,2-difluoro-7-methyl-6,7-dihydro-2H-furo[2,3-f][1,3]benzodioxole-7-carboxamide The product from Example 3B (296.4 mg, 1.148 mmol) was dissolved in dichloromethane (5 mL). Oxalyl chloride (500 μL) and N,N-dimethylformamide (50 μL) were added which resulted in bubbling of the reaction mixture. The reaction was stirred at ambient temperature for 1 hour. The reaction was concentrated, and the residue was dissolved in dichloromethane (2 mL) and concentrated two times. The residue was dissolved in dichloromethane (4 mL) and pyridine (2 mL). The product of Example 136E (323.6 mg, 0.682 mmol) was added, and the reaction mixture was stirred at 60° C. for 21 hours. The reaction mixture was concentrated, and the residue was purified by silica gel chromatography (5% ethyl acetate in dichloromethane, $R_f$=0.44) to yield the title compound (326.6 mg, 63%). $^1$H NMR (400 MHz, DMSO-$d_6$) δ 9.22 (s, 1H), 7.55 (s, 1H), 7.39-7.19 (m, 10H), 7.15 (dd, J=7.4, 2.0 Hz, 2H), 7.03 (s, 1H), 6.31 (s, 1H), 5.15 (d, J=5.3 Hz, 1H), 5.08 (d, J=9.0 Hz, 1H), 4.60-4.48 (m, 2H), 4.44-4.31 (m, 4H), 4.16 (dd, J=14.7, 8.9 Hz, 1H), 4.09-4.00 (m, 1H), 3.59-3.37 (m, 4H), 1.66 (s, 3H), 1.09-0.98 (m, 1H), 0.93-0.81 (m, 3H); MS (ESI+) m/z 715 (M+H)$^+$.

Example 136G (7R)—N-{1-[(2R)-2,3-dihydroxypropyl]-6-fluoro-2-[1-(hydroxymethyl)cyclopropyl]-1H-indol-5-yl}-2,2-difluoro-7-methyl-6,7-dihydro-2H-furo[2,3-f][1,3]benzodioxole-7-carboxamide The product of Example 136F (219.8 mg, 0.308 mmol) was dissolved in methanol (2 mL). 10% Palladium on carbon (55.0 mg) was added and hydrogen was delivered to the reaction via balloon. The reaction was stirred at ambient temperature then heated at 60° C. for 15 hours, and filtered. The filtrate was concentrated, and the residue was purified by silica gel chromatography (50% to 100% ethyl acetate in dichloromethane) to yield the title compound (83.3 mg, 51%). $^1$H NMR (400 MHz, DMSO-$d_6$) δ 9.23 (s, 1H), 7.56 (s, 1H), 7.40-7.30 (m, 2H), 7.04 (s, 1H), 6.24 (s, 1H), 5.09 (d, J=9.1 Hz, 1H), 4.99 (d, J=5.2 Hz, 1H), 4.85 (t, J=5.6 Hz, 1H), 4.75 (t, J=6.0 Hz, 1H), 4.40 (d, J=9.1 Hz, 1H), 4.38-4.29 (m, 1H), 4.19-4.10 (m, 1H), 3.98-3.88 (m, 1H), 3.59-3.43 (m, 3H), 3.42-3.34 (m, 1H), 1.67 (s, 3H), 1.00-0.72 (m, 4H). MS (ESI+) m/z 535 (M+H)$^+$.

Example 137

(7R)—N-{1-[(2R)-2,3-dihydroxypropyl]-6-fluoro-2-(1-hydroxy-2-methylpropan-2-yl)-1H-benzimidazol-5-yl}-2,2-difluoro-7-methyl-6,7-dihydro-2H-furo[2,3-f][1,3]benzodioxole-7-carboxamide Example 137A N-{[(4R)-2,2-dimethyl-1,3-dioxolan-4-yl]methyl}-5-fluoro-2,4-dinitroaniline A solution of 1,5-difluoro-2,4-dinitrobenzene (0.778 g, 3.81 mmol) and N,N-diisopropylethylamine (0.732 mL, 4.19 mmol) in tetrahydrofuran (38 mL) was treated dropwise with a solution of (R)-(2,2-dimethyl-1,3-dioxolan-4-yl)methanamine (0.500 g, 3.81 mmol) in tetrahydrofuran (38 mL). The reaction was stirred at room temperature for 1 hour. Volatiles were then removed in vacuo, and the crude material was then partitioned between ethyl acetate (150 mL) and water (100 mL). The organic layer was washed with water (2×50 mL), dried over Na$_2$SO$_4$, filtered, and concentrated in vacuo. The residue was purified by silica gel chromatography (10 to 70% ethyl acetate-heptanes, eluent) to afford the title compound as a yellow oil (0.989 g, 82%). $^1$H NMR (400 MHz, CDCl$_3$) δ 9.15 (d, J=8.0 Hz, 1H), 8.78 (s, 1H), 6.67 (d, J=13.3 Hz, 1H), 4.48 (qd, J=5.8, 3.7 Hz, 1H), 4.24-4.07 (m, 1H), 3.81 (dd, J=8.7, 5.7 Hz, 1H), 3.58 (ddd, J=13.4, 4.9, 3.8 Hz, 1H), 3.42 (dt, J=13.3, 5.5 Hz, 1H), 1.52 (s, 3H), 1.40 (s, 3H). MS (DCI$^+$) m/z 333.0 (M+H).

Example 137B

N$^1$-{[(4R)-2,2-dimethyl-1,3-dioxolan-4-yl]methyl}-5-fluorobenzene-1,2,4-triamine The product from Example 137A (0.989 g, 3.14 mmol) in methanol (100 mL) was hydrogenated (hydrogen balloon) over a small amount of 10% palladium-C overnight at room temperature. After this time, the mixture was filtered through diatomaceous earth, and the diatomaceous earth pad was washed with ethanol. The filtrate was concentrated in vacuo, and the residue was purified by silica gel chromatography (0 to 5% methanol-ethyl acetate, eluent) to afford the title compound (0.365 g, 46%). $^1$H NMR (400 MHz, DMSO-$d_6$) δ 6.25 (d, J=13.1 Hz, 1H), 6.09 (d, J=9.2 Hz, 1H), 4.30-3.97 (m, 6H), 3.90 (t, J=6.1 Hz, 1H), 3.66 (dd, J=8.2, 6.3 Hz, 1H), 2.99 (t, J=6.0 Hz, 2H), 1.35 (s, 3H), 1.28 (s, 3H).

Example 137C 3-(benzyloxy)-2,2-dimethylpropan-1-ol

A solution of 2,2-dimethylpropane-1,3-diol (2 g, 19.20 mmol) in THF (30 mL) was treated with 60% sodium hydride (0.256 g, 6.40 mmol) at room temperature, and the mixture stirred at room temperature for 5 minutes. Benzyl bromide (0.761 mL, 6.40 mmol) and tetrabutylammonium iodide (0.709 g, 1.920 mmol) were then added, and the reaction stirred overnight at room temperature. After this time, the mixture was diluted with ethyl acetate (150 mL) and water (50 mL), and the phases were separated. The aqueous layer was extracted with ethyl acetate (2×50 mL). The combined organics were washed with water (2×50 mL) and brine (50 mL) sequentially, dried over $Na_2SO_4$, filtered, and concentrated in vacuo. The residue was purified on silica gel chromatography (10 to 50% ethyl acetate-heptanes, eluent) to afford the title compound (0.992 g, 80%). $^1$H NMR (400 MHz, $CDCl_3$) δ 7.41-7.32 (m, 5H), 4.51 (s, 2H), 3.46 (d, J=5.7 Hz, 2H), 3.33 (s, 2H), 2.55 (t, J=5.9 Hz, 1H), 0.93 (s, 6H). MS ($DCI^+$) m/z 195.0 (M+H).

Example 137D 3-(benzyloxy)-2,2-dimethylpropanal

A solution of the product from Example 137C in $CH_2Cl_2$ (20 ml) and DMSO (3.6 mL, 50.7 mmol) was cooled to 0° C., then triethylamine (1.43 mL, 10.26 mmol) was added. Pyridine-sulfur trioxide complex (1.625 g, 10.21 mmol) was added in 5 portions over about 40 minutes. After the final addition, the reaction mixture was continued to stir at 0° C. for 30 minutes. The mixture was then poured into a separatory funnel and washed with water (3×5 mL). The organic layer was dried over $Na_2SO_4$, filtered, and concentrated in vacuo. The crude oil was purified by silica gel chromatography, eluting with 0 to 15% ethyl acetate-heptanes to afford the title compound (0.584 g, 60%). $^1$H NMR (400 MHz, $CDCl_3$) δ 9.57 (s, 1H), 7.47-7.15 (m, 5H), 4.51 (s, 2H), 3.45 (s, 2H), 1.09 (s, 6H). MS ($DCI^+$) m/z 210.0 (M+$NH_4$).

Example 137E

2-[1-(benzyloxy)-2-methylpropan-2-yl]-1-{[(4R)-2,2-dimethyl-1,3-dioxolan-4-yl]methyl}-6-fluoro-1H-benzimidazol-5-amine A mixture of the product from Example 137B (0.100 g, 0.392 mmol), the product from Example 137D (0.075 g, 0.392 mmol), and sodium bisulfite (0.041 g, 0.392 mmol) in DMA (1.6 mL) was heated at 130° C. for 4 hours. The mixture was then cooled to room temperature and concentrated in vacuo. The residue was purified on silica gel chromatography (0 to 10% methanol-ethyl acetate, eluent) to afford the title compound (27 mg, 16%). $^1$H NMR (400 MHz, DMSO-$d_6$) δ 7.37-7.20 (m, 6H), 6.88 (d, J=8.3 Hz, 1H), 4.68 (s, 2H), 4.49 (s, 2H), 4.46-4.26 (m, 3H), 4.15 (m, 1H), 3.78-3.59 (m, 3H), 1.46 (s, 3H), 1.44 (s, 3H), 1.39 (s, 3H), 1.19 (s, 3H). MS ($ESI^+$) m/z 428.2 (M+H).

Example 137F (7R)—N-(2-[1-(benzyloxy)-2-methylpropan-2-yl]-1-{[(4R)-2,2-dimethyl-1,3-dioxolan-4-yl]methyl}-6-fluoro-1H-benzimidazol-5-yl)-2,2-difluoro-7-methyl-6,7-dihydro-2H-furo[2,3-f][1,3]benzodioxole-7-carboxamide The product from Example 3B (0.080 g, 0.309 mmol) was refluxed in thionyl chloride (0.6 mL, 8.22 mmol) for 1 hour. The mixture was then concentrated in vacuo, and excess thionyl chloride was chased three times with $CH_2Cl_2$ (0.6 mL each time). The remaining yellow syrup was treated with a solution of the product from Example 137E (0.132 g, 0.309 mmol) in pyridine (0.6 mL, 7.42 mmol) and 1.2 mL $CH_2Cl_2$, and the reaction stirred at room temperature for 3 days. The mixture was concentrated in vacuo, and the crude oil thus obtained was purified by silica gel chromatography, eluting with 20 to 70% ethyl acetate-heptanes to afford the title compound (0.071 g, 34%). $^1$H NMR (400 MHz, DMSO-$d_6$) δ 9.31 (s, 1H), 7.62-7.46 (m, 3H), 7.45-7.15 (m, 5H), 7.05 (s, 1H), 5.08 (d, J=9.1 Hz, 1H), 4.61-4.33 (m, 6H), 4.13 (m, 1H), 3.80-3.64 (m, 3H), 1.68 (s, 3H), 1.50 (s, 3H), 1.47 (s, 3H), 1.39 (s, 3H), 1.17 (s, 3H). MS ($ESI^+$) m/z 668.3 (M+H).

Example 137G (7R)—N-{1-[(2R)-2,3-dihydroxypropyl]-6-fluoro-2-(1-hydroxy-2-methylpropan-2-yl)-1H-benzimidazol-5-yl}-2,2-difluoro-7-methyl-6,7-dihydro-2H-furo[2,3-f][1,3]benzodioxole-7-carboxamide The product from Example 137F (0.071 g, 0.106 mmol) in $CH_2Cl_2$ (2.2 mL) was cooled to −78° C. and then treated dropwise with boron trichloride (1M solution in $CH_2Cl_2$, 0.53 mL, 0.530 mmol). The mixture was stirred at −78° C. for 30 minutes and then at 0° C. for another 30 minutes. The mixture was then quenched with 2 mL methanol and concentrated in vacuo, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), to provide the title compound as a white solid (0.017 g, 30%). $^1$H NMR (400 MHz, DMSO-$d_6$) δ 9.33 (s, 1H), 7.53 (m, 3H), 7.04 (s, 1H), 5.14-4.88 (m, 3H), 4.59-4.36 (m, 2H), 4.27-4.12 (m, 1H), 3.93 (m, 1H), 3.67 (m, 2H), 3.56-3.38 (m, 3H), 1.67 (s, 3H), 1.42 (s, 3H), 1.41 (s, 3H). MS ($ESI^+$) m/z (M+H).

Example 138

(7S)—N-{1-[(2R)-2,3-dihydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide Example 138A (7S)—N-{1-[(2R)-3-(benzyloxy)-2-hydroxypropyl]-2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide The product from Example 3A (50.3 mg, 0.195 mmol) was dissolved in dichloromethane (1 mL). Oxalyl chloride (80 μL) and N,N-dimethylformamide (25 μL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product of Example 130E (89.8 mg, 0.188 mmol) was added, and the reaction mixture was stirred at 60° C. for 16 hours. The reaction mixture was concentrated, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (85.0 mg, 63%). $^1$H NMR (500 MHz, DMSO-$d_6$) δ 9.24 (s, 1H), 7.57 (s, 1H), 7.42-7.33 (m, 6H), 7.33-7.18 (m, 6H), 7.06 (s, 1H), 6.28 (s, 1H), 5.14 (s, 1H), 5.10 (d, J=9.1 Hz, 1H), 4.55 (s, 2H), 4.49-4.34 (m, 4H), 4.14 (dd, J=15.2, 8.6 Hz, 1H), 4.02 (dtd, J=8.4, 5.6, 5.1, 2.9 Hz, 1H), 3.65 (d, J=9.2 Hz, 1H), 3.57 (d, J=9.2 Hz, 1H), 3.50 (dd, J=9.6, 4.8 Hz, 1H), 3.45 (dd, J=9.7, 6.4 Hz, 1H), 1.68 (s, 3H), 1.42 (s, 3H), 1.41 (s, 3H). MS (ESI+) m/z 717 (M+H)$^+$.

Example 138B (7S)—N-{1-[(2R)-2,3-dihydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide The product of Example 138A (77.0 mg, 0.107 mmol) was dissolved in dichloromethane (2 mL) and the resulting solution was cooled to <−70° C. in an acetone-dry ice bath. Boron trichloride (1M in dichloromethane, 500 µL, 0.5 mmol) was added dropwise, and the mixture was stirred at the same temperature for 30 minutes. The reaction was quenched with 0.5 mL of methanol and concentrated. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (38.5 mg, 67%). $^1$H NMR (501 MHz, DMSO-$d_6$) δ 9.21 (s, 1H), 7.55 (s, 1H), 7.39-7.32 (m, 2H), 7.04 (s, 1H), 6.24 (s, 1H), 5.08 (d, J=9.1 Hz, 1H), 4.46-4.37 (m, 2H), 4.13 (dd, J=15.2, 8.8 Hz, 1H), 3.97-3.88 (m, 1H), 3.63 (d, J=10.9 Hz, 1H), 3.57 (d, J=10.9 Hz, 1H), 3.46 (dd, J=10.9, 4.8 Hz, 1H), 3.39 (dd, J=11.0, 6.5 Hz, 1H), 1.67 (s, 3H), 1.36 (s, 3H), 1.33 (s, 3H). MS (ESI+) m/z 537 (M+H)$^+$.

Example 139

4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid Example 139A methyl 4-[(2R,4R)-4-{[(7R)-2,2-difluoro-7-methyl-6,7-dihydro-2H-furo[2,3-f][1,3]benzodioxole-7-carbonyl]amino}-7-hydroxy-3,4-dihydro-2H-1-benzopyran-2-yl]benzoate The product of Example 19 (68.5 mg, 0.124 mmol) and tetrabutylammonium iodide (51.5 mg, 0.139 mmol) were dissolved in dichloromethane (2 mL) and the resulting solution was cooled to 0° C. in an ice bath. Boron trichloride (1M in dichloromethane, 250 µL, 0.25 mmol) was added dropwise, and stirred at the same temperature for 30 minutes. The reaction was allowed to warm to ambient temperature overnight (17 hours). The reaction was quenched with methanol (1 mL) and concentrated. The residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (32.4 mg, 49%). $^1$H NMR (501 MHz, DMSO-$d_6$) δ 9.39 (s, 1H), 8.03-7.98 (m, 2H), 7.96 (d, J=8.8 Hz, 1H), 7.61-7.57 (m, 2H), 7.45 (s, 1H), 6.99 (s, 1H), 6.91 (dt, J=8.5, 1.8 Hz, 1H), 6.39 (dd, J=8.4, 2.4 Hz, 1H), 6.27 (d, J=2.4 Hz, 1H), 5.39-5.26 (m, 2H), 5.03 (d, J=8.9 Hz, 1H), 4.33 (d, J=8.9 Hz, 1H), 3.87 (s, 3H), 2.14 (ddd, J=13.1, 6.2, 2.0 Hz, 1H), 2.00 (dt, J=12.8, 11.6 Hz, 1H), 1.57 (s, 3H). MS (ESI−) m/z 538 (M−H)$^-$.

Example 139B methyl 4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoate The product of Example 139A (32.4 mg, 0.060 mmol) was dissolved in acetonitrile (1 mL) and water (0.5 mL). The resulting solution was cooled to 0° C. in an ice bath. Diethyl (bromodifluoromethyl)phosphonate (254.0 mg, 0.951 mmol) was added, followed by 1M potassium hydroxide (0.5 mL, 0.5 mmol). The mixture was stirred at the same temperature for 30 minutes. The reaction was allowed to warm to ambient temperature and stirred overnight (16 hours). The reaction was concentrated and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (7.9 mg, 22%). MS (ESI−) m/z 588 (M−H)$^-$.

Example 139C

4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid The product of Example 139B (7.7 mg, 0.013 mmol) and potassium trimethylsilanolate (4.3 mg, 90% purity, 0.030 mmol) were dissolved in tetrahydrofuran (1 mL) and stirred at ambient temperature for 4 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (3.8 mg, 51%). $^1$H NMR (400 MHz, DMSO-$d_6$) δ 12.98 (s, 1H), 8.07 (d, J=8.7 Hz, 1H), 8.02-7.95 (m, 2H), 7.60-7.55 (m, 2H), 7.46 (s, 1H), 7.26 (t, 1H) 7.18 (d, J=8.5 Hz, 1H), 7.00 (s, 1H), 6.77 (dd, J=8.5, 2.5 Hz, 1H), 6.73 (d, J=2.4 Hz, 1H), 5.47 (dd, J=11.5, 1.8 Hz, 1H), 5.40 (ddd, J=11.1, 8.4, 6.0 Hz, 1H), 5.03 (d, J=9.0 Hz, 1H), 4.34 (d, J=9.0 Hz, 1H), 2.20 (ddd, J=13.1, 6.2, 2.1 Hz, 1H), 2.13-1.98 (m, 1H), 1.58 (s, 3H); MS (ESI−) m/z 574 (M−H)⁻.

Example 140

(7R)—N-[(2R)-1-[(2R)-2,3-dihydroxypropyl]-6-fluoro-2-(1-hydroxy-2-methylpropan-2-yl)-2,3-dihydro-1H-indol-5-yl]-2,2-difluoro-7-methyl-6,7-dihydro-2H-furo[2,3-f][1,3]benzodioxole-7-carboxamide The product from Example 130G (176.8 mg, 0.330 mmol) was dissolved in acetic acid (1 mL). Sodium cyanoborohydride (93.1 mg, 1.481 mmol) was added, and the reaction was stirred at ambient temperature for 3 hours. The reaction was diluted with methanol (1 mL) then concentrated. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield a diastereomeric mixture of Example 140 and 141. The mixture of diastereomers was separated by supercritical fluid chromatography on a 21×250 mm, 5 micron CHIRALPAK OD-H column with the sample at a concentration of 25 mg/mL in methanol with co-solvent of methanol to afford the title compound (51.3 mg, 29%) as the first eluting isomer. Retention time=2.05 minutes. Chirality was arbitrarily assigned. ¹H NMR (501 MHz, DMSO-d₆) δ 8.92 (s, 1H), 7.49 (s, 1H), 7.03 (s, 1H), 6.82 (d, J=7.8 Hz, 1H), 6.40 (d, J=11.8 Hz, 1H), 5.03 (d, J=9.1 Hz, 1H), 4.75 (d, J=4.9 Hz, 1H), 4.59-4.52 (m, 2H), 4.36 (d, J=9.0 Hz, 1H), 3.91 (dd, J=10.5, 5.2 Hz, 1H), 3.77-3.68 (m, 1H), 3.45 (dd, J=14.9, 2.7 Hz, 1H), 3.29-3.18 (m, 3H), 3.17 (d, J=5.2 Hz, 1H), 3.02 (ddd, J=15.0, 12.7, 9.7 Hz, 2H), 2.74 (dd, J=16.4, 5.1 Hz, 1H), 1.62 (s, 3H), 0.76 (s, 3H), 0.75 (s, 3H). MS (ESI+) m/z 539 (M+H)⁺.

Example 141

(7R)—N-[(2S)-1-[(2R)-2,3-dihydroxypropyl]-6-fluoro-2-(1-hydroxy-2-methylpropan-2-yl)-2,3-dihydro-1H-indol-5-yl]-2,2-difluoro-7-methyl-6,7-dihydro-2H-furo[2,3-f][1,3]benzodioxole-7-carboxamide The mixture of diastereomers from Example 140 was separated by supercritical fluid chromatography on a 21×250 mm, 5 micron CHIRALPAK OD-H column with the sample at a concentration of 25 mg/mL in methanol with co-solvent of methanol to afford the title compound (51.3 mg, 29%) as the second eluting isomer. Retention time=2.81 minutes. Chirality was arbitrarily assigned. ¹H NMR (501 MHz, DMSO-d₆) δ 8.92 (s, 1H), 7.49 (s, 1H), 7.03 (s, 1H), 6.82 (d, J=7.8 Hz, 1H), 6.40 (d, J=11.8 Hz, 1H), 5.03 (d, J=9.1 Hz, 1H), 4.75 (d, J=4.9 Hz, 1H), 4.59-4.52 (m, 2H), 4.36 (d, J=9.0 Hz, 1H), 3.91 (dd, J=10.5, 5.2 Hz, 1H), 3.77-3.68 (m, 1H), 3.45 (dd, J=14.9, 2.7 Hz, 1H), 3.29-3.18 (m, 3H), 3.17 (d, J=5.2 Hz, 1H), 3.02 (ddd, J=15.0, 12.7, 9.7 Hz, 2H), 2.74 (dd, J=16.4, 5.1 Hz, 1H), 1.62 (s, 3H), 0.76 (s, 3H), 0.75 (s, 3H). MS (ESI+) m/z 539 (M+H)⁺.

Example 142

(7R)-2,2-difluoro-N-(6-{4-[(methanesulfonyl)carbamoyl]phenyl}-5-methylpyridin-2-yl)-7-methyl-6,7-dihydro-2H-furo[2,3-f][1,3]benzodioxole-7-carboxamide A mixture of the product of Example 83 (0.042 g, 0.090 mmol), O-(benzotriazol-1-yl)-N,N,N',N''-tetramethyluronium tetrafluoroborate (TBTU, 0.043 g, 0.134 mmol) and triethylamine (0.04 mL, 0.287 mmol) in THF (0.9 mL) was stirred at room temperature for 90 minutes, at which time a cloudy white mixture was observed. The mixture was treated with lithium chloride (1.2 mg, 0.029 mmol) and methanesulfonamide (10.8 mg, 0.114 mmol), and the reaction was stirred overnight at room temperature. After this time, the reaction mixture was concentrated in vacuo, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield the title compound as a white solid (32 mg, 65%). ¹H NMR (400 MHz, DMSO-d₆) δ 12.20 (s, 1H), 10.16 (s, 1H), 8.09-7.99 (m, 2H), 7.93 (d, J=8.5 Hz, 1H), 7.81-7.60 (m, 4H), 7.03 (s, 1H), 5.09 (d, J=9.4 Hz, 1H), 4.41 (d, J=9.4 Hz, 1H), 3.41 (s, 3H), 2.25 (s, 3H), 1.70 (s, 3H). MS (ESI⁺) m/z 546.0 (M+H).

Example 143

(7R)-2,2-difluoro-N-[6-fluoro-2-(1-hydroxy-2-methylpropan-2-yl)-1H-indol-5-yl]-7-methyl-6,7-dihydro-2H-furo[2,3-f][1,3]benzodioxole-7-carboxamide Example 143A 2-[1-(benzyloxy)-2-methylpropan-2-yl]-6-fluoro-1H-indol-5-amine 2-(1-(Benzyloxy)-2-methylpropan-2-yl)-6-fluoro-5-nitro-1H-indole (CAS [1152311-77-7], 0.297 g, 0.867 mmol) was dissolved in acetic acid (7.4 mL) and treated with zinc dust (1.134 g, 17.35 mmol). The reaction stirred at room temperature for 2.5 hours and was then diluted with 220 mL of ethyl acetate and filtered through a fritted-glass funnel. The filtrate was washed four times with saturated NaHCO₃ solution until pH of the aqueous washes was pH 8-9. The organic layer was then washed with brine, dried over Na₂SO₄, filtered, and concentrated in vacuo to afford the title compound as a brown oil, which was taken into the next step without further purification. ¹H NMR (400 MHz, CDCl₃) δ 8.68 (s, 1H), 7.42-7.27 (m, 7H), 6.92 (m, 2H), 6.05 (d, J=2.4 Hz, 1H), 4.56 (s, 2H), 3.48 (s, 2H), 1.36 (s, 6H). MS (ESI⁺) m/z 313.1 (M+H).

Example 143B (7R)—N-{2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide The product from Example 3B (0.111 g, 0.430 mmol) was refluxed in thionyl chloride (0.82 mL, 11.23 mmol) for 1 hour. The mixture was cooled to room temperature and concentrated in vacuo, then excess thionyl chloride was chased with $CH_2Cl_2$. The resulting yellow oil was treated with a solution of the product from Example 143A (0.134 g, 0.43 mmol) and pyridine (0.41 mL, 5.07 mmol) in 1 mL $CH_2Cl_2$, and the reaction was stirred at room temperature overnight. After this time, the reaction mixture was concentrated in vacuo, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), yielding the title compound as a dark purple semi-solid (0.107 g, 45%). $^1$H NMR (400 MHz, DMSO-$d_6$) δ 10.91 (br, 1H), 9.20 (s, 1H), 7.56 (s, 1H), 7.41-7.19 (m, 5H), 7.12-7.00 (m, 2H), 6.15 (d, J=2.0 Hz, 1H), 5.09 (d, J=9.1 Hz, 1H), 4.50-4.34 (m, 3H), 3.49 (s, 2H), 1.68 (s, 3H), 1.33 (s, 6H). MS (ESI$^+$) m/z 553.0 (M+H).

Example 143C (7R)-2,2-difluoro-N-[6-fluoro-2-(1-hydroxy-2-methylpropan-2-yl)-1H-indol-5-yl]-7-methyl-6,7-dihydro-2H-furo[2,3-f][1,3]benzodioxole-7-carboxamide The product from Example 143B (0.050 g, 0.090 mmol) was dissolved in ethanol (5 mL) and hydrogenated (balloon) over 10% Pd—C overnight at room temperature. After this time, the mixture was filtered, and the filtrate was concentrated in vacuo. The residue thus obtained was further dried under vacuum at 75° C. for 1 hour to afford the title compound as a beige solid (0.033 g, 79%). $^1$H NMR (400 MHz, DMSO-$d_6$) δ 10.82 (s, 1H), 9.18 (s, 1H), 7.57 (s, 1H), 7.34 (m, 1H), 7.07 (m, 2H), 6.11 (s, 1H), 5.08 (m, 1H), 4.82 (m, 1H), 4.39 (m, 1H), 3.46 (m, 2H), 1.67 (s, 3H), 1.26 (s, 6H). MS (ESI$^+$) m/z 463.1 (M+H).

Example 144

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid Example 144A methyl 5-[(1S,3E)-1-hydroxy-3-(2-hydroxy-4-methoxyphenyl)-3-{[(S)-2-methylpropane-2-sulfinyl]imino}propyl]pyrazine-2-carboxylate A solution of diisopropylamine (163 μL, 1.143 mmol) in tetrahydrofuran (2 mL) under $N_2$ at −20° C. was treated with 2.5 M n-butyllithium in hexanes (437 μL, 1.091 mmol) and stirred for 15 minutes. In a separate flask, a solution of the product from Example 89A (140 mg, 0.520 mmol) in tetrahydrofuran (2 mL) under $N_2$ at −20° C. was treated over 1 minute with the lithium diisopropyl amine solution. The mixture was stirred at −20° C. for 1 hour, cooled to −78° C., and treated with a solution of methyl 5-formylpyrazine-2-carboxylate (CAS #710322-57-9) (86 mg, 0.520 mmol) in tetrahydrofuran (1.5 mL). The reaction mixture was warmed to 0° C., cooled to −30° C., treated with a solution of 10% acetic acid in tetrahydrofuran (about 1.5 mL) and allowed to warm to room temperature. The mixture was partitioned between ethyl acetate and saturated $NaHCO_3$ solution. The ethyl acetate layer was washed with brine, dried ($MgSO_4$), filtered, and concentrated. The crude material on chromatographed on silica gel and eluted with a gradient of 25-100% ethyl acetate in heptanes. The collected fractions were concentrated and chromatographed on silica gel and eluting with a gradient of 50% ethyl acetate in $CH_2Cl_2$ to provide the title compound. $^1$H NMR (501 MHz, CDCl$_3$) δ 13.04 (s, 1H), 9.26 (d, J=1.4 Hz, 1H), 8.82-8.81 (m, 1H), 7.14 (d, J=9.2 Hz, 1H), 6.38 (d, J=2.6 Hz, 1H), 6.19 (dd, J=9.1, 2.6 Hz, 1H), 5.43 (q, J=5.0 Hz, 1H), 5.06 (d, J=4.6 Hz, 1H), 4.04 (s, 3H), 3.91 (dd, J=13.6, 6.4 Hz, 1H), 3.85 (dd, J=13.7, 5.2 Hz, 1H), 3.79 (s, 3H), 1.40 (s, 9H). LC/MS (ESI+) m/z 436 (M+H)$^+$.

Example 144B methyl 5-[(2R,4E)-7-methoxy-4-{[(S)-2-methylpropane-2-sulfinyl]imino}-3,4-dihydro-2H-1-benzopyran-2-yl]pyrazine-2-carboxylate A solution of the product from Example 144A (21.3 mg, 0.049 mmol) and triphenylphosphine (15.39 mg, 0.059 mmol) in $CH_2Cl_2$ (1 mL) at 0° C. was treated dropwise with a 40 weight % solution of diethyl azodicarboxylate in toluene (55.7 μL, 0.122 mmol) over 3 minutes, stirred at 0° C. for 10 minutes, stirred at room temperature for 1 hour, and concentrated. The residue was chromatographed on silica gel eluting with a gradient of 20-100% ethyl acetate in $CH_2Cl_2$ to provide the title compound. $^1$H NMR (400 MHz, CDCl$_3$) δ 9.27 (d, J=1.3 Hz, 1H), 9.00 (d, J=1.3 Hz, 1H), 7.96 (d, J=8.9 Hz, 1H), 6.64 (dd, J=8.9, 2.5 Hz, 1H), 6.54 (d, J=2.4 Hz, 1H), 5.49 (dd, J=12.1, 3.2 Hz, 1H), 4.06 (s, 3H), 3.96 (dd, J=17.5, 3.2 Hz, 1H), 3.86 (s, 3H), 3.39 (dd, J=17.5, 12.1 Hz, 1H), 1.30 (s, 9H); LC/MS (ESI+) m/z 418 (M+H)$^+$.

Example 144C

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid Step 1:

A solution of the product from Example 144B (15 mg, 0.036 mmol) in methanol (1 mL) was cooled to 0° C., treated with NaBH$_4$ (4.08 mg, 0.108 mmol), stirred at 0° C. for 30 minutes, treated with 4 M HCl in dioxane (180 μL, 0.719 mmol), stirred at 0° C. 5 minutes and then at room temperature for 45 minutes. Mixture was partitioned between methyl tert-butyl ether (30 mL, discarded) and water (15 mL). The aqueous layer was basified to pH 8 with solid NaHCO$_3$ and extracted with ethyl acetate. The ethyl acetate layer was washed with brine, dried (MgSO$_4$), filtered, and concentrated to provide a 6:4 ratio of methyl 5-[(2R,4R)-4-amino-7-methoxy-3,4-dihydro-2H-1-benzopyran-2-yl]pyrazine-2-carboxylate and {5-[(2R,4R)-4-amino-7-methoxy-3,4-dihydro-2H-1-benzopyran-2-yl]pyrazin-2-yl}methanol.
$^1$H NMR (400 MHz, CDCl$_3$) δ 9.29 (d, J=1.3 Hz, 0.6H), 9.04 (s, 0.6H), 8.86 (s, 0.4H), 8.63 (s, 0.4H), 7.46 (s, 0.5H), 7.44 (s, 0.5H), 6.68-6.59 (m, 1H), 6.55 (d, J=2.5 Hz, 0.6H), 6.52 (d, J=2.6 Hz, 0.4H), 5.42 (dd, J=11.5, 2.0 Hz, 0.6H), 5.36 (dd, J=11.5, 1.5 Hz, 0.4H), 4.90 (s, 0.8H), 4.36-4.27 (m, 1H), 4.09 (s, 1.8H), 3.83 (s, 1.8H), 3.82 (s, 1.2H), 2.75-2.62

(m, 1H), 2.02-1.85 (m, 1H); LC/MS (ESI+) m/z 299 (M−NH₃)⁺ and 271 (M−NH₃)⁺.

Step 2:

A solution of the products from Step 1 (10 mg, 0.032 mmol) in CH₂Cl₂ (0.5 mL) was treated with a solution of Example 134F (17.55 mg, 0.063 mmol) in CH₂Cl₂ (0.5 mL) and the mixture was stirred at 0° C. for 45 minutes. The mixture was partitioned between saturated NaHCO₃ solution (3 mL) and methyl tert-butyl ether (30 mL). The methyl tert-butyl ether layer was washed with brine, dried (MgSO₄), filtered, and concentrated. The residue was chromatographed on silica gel and eluting with a gradient of 10% to 50% ethyl acetate in heptane to provide a mixture of {5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazin-2-yl}methyl (7R)-2,2-difluoro-7-methyl-6,7-dihydro-2H-furo[2,3-f][1,3]benzodioxole-7-carboxylate and methyl 5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylate in a 1:1 ratio.

Step 3:

A solution of the products from Step 2 in tetrahydrofuran (0.5 mL) was diluted with methanol (0.5 mL) and treated with 8 drops of 1 M NaOH. The mixture was stirred at room temperature for 20 minutes, treated with 1 M HCl (2 mL), and extracted with ethyl acetate (30 mL). The ethyl acetate layer was washed with brine, dried (MgSO₄), filtered, and concentrated. The residue was chromatographed on silica gel and eluting with a gradient of 25%-100% ethyl acetate in heptane and then eluted with a gradient of 0%-100% [10:1:1 ethyl acetate:HCOOH:H₂O] in ethyl acetate to provide the title compound as the second eluting product. ¹H NMR (501 MHz, DMSO-d₆) δ 9.15 (s, 1H), 8.91 (s, 1H), 8.06 (d, J=8.7 Hz, 1H), 7.47 (s, 1H), 7.05 (d, J=8.5 Hz, 1H), 6.99 (s, 1H), 6.57 (dd, J=8.5, 2.5 Hz, 1H), 6.52 (d, J=2.2 Hz, 1H), 5.60-5.53 (m, 1H), 5.39-5.32 (m, 1H), 5.04 (d, J=9.0 Hz, 1H), 4.33 (d, J=9.0 Hz, 1H), 3.72 (s, 3H), 2.37-2.31 (m, 1H), 2.18 (q, J=11.8 Hz, 1H), 1.58 (s, 3H); MS (ESI−) m/z 540 (M−H)⁻.

Example 145

6-[(2R,4R)-4-{[(7R)-2,2-difluoro-7-methyl-6,7-dihydro-2H-furo[2,3-f][1,3]benzodioxole-7-carbonyl] amino}-7-(trifluoromethoxy)-3,4-dihydro-2H-1-benzopyran-2-yl]pyridine-3-carboxylic acid Example 145A 1-(2-hydroxy-4-(trifluoromethoxy)phenyl)ethan-1-one A solution of 2'-methoxy-4'-(trifluoromethoxy)acetophenone (5 g, 21.35 mmol) in CH₂Cl₂ (50 mL) under N₂ was cooled to −25° C., treated dropwise with 1 M boron trichloride in CH₂Cl₂ (21.35 ml, 21.35 mmol) over 5 minutes. Mixture was quenched by pouring into ice. The mixture was allowed to warm and was extracted with CH₂Cl₂ (twice). The combined CH₂Cl₂ layers were dried (MgSO₄), filtered, and concentrated to provide the title compound (4.50 g, 20.44 mmol, 96% yield). ¹H NMR (400 MHz, CDCl₃) δ 12.47 (s, 1H), 7.77 (d, J=8.8 Hz, 1H), 6.81 (s, 1H), 6.76-6.66 (m, 1H), 2.63 (s, 3H).

Example 145B (S)—N-{(1E)-1-[2-hydroxy-4-(trifluoromethoxy) phenyl]ethylidene}-2-methylpropane-2-sulfinamide A solution of Example 145A (1.36 g, 6.18 mmol) and (S)-(−)-2-methyl-2-propanesulfinamide (2.99 g, 24.71 mmol) in 2-methyl-tetrahydrofuran (12 mL) was treated with titanium(IV) ethoxide (5.64 g, 24.71 mmol) and heated at 110° C. under N₂ for 12 hours and cooled. The mixture was stirred and diluted with ethyl acetate (about 50 mL) and then with water (100 mL), which resulted in solid immediately precipitating out of the solution. The slurry was stirred for about 10 minutes. The solids were removed by filtration through diatomaceous earth. The layers of the filtrate were separated and the aqueous phase was extracted with ethyl acetate (50 mL). The combined organic layers were washed with brine, dried (MgSO₄), filtered, and concentrated. The residue was chromatographed on silica gel eluting with a gradient of 25% to 100% ethyl acetate in heptanes to provide the title compound (0.83 g, 2.57 mmol, 41.6% yield). ¹H NMR (501 MHz, CDCl₃) δ 13.37 (s, 1H), 7.67 (d, J=9.0 Hz, 1H), 6.81 (dd, J=2.3, 1.1 Hz, 1H), 6.74 (ddd, J=9.0, 2.4, 1.0 Hz, 1H), 2.81 (s, 3H), 1.32 (s, 9H).

Example 145C methyl 6-[(1S,3E)-1-hydroxy-3-[2-hydroxy-4-(trifluoromethoxy)phenyl]-3-{[(S)-2-methylpropane-2-sulfinyl]imino}propyl]pyridine-3-carboxylate A solution of diisopropylamine (1.493 mL, 10.48 mmol) in tetrahydrofuran (14.5 mL) was cooled to −20° C., treated with 2.5 M n-butyllithium in hexanes (4.00 mL, 10 mmol), stirred at 0° C. for 15 minutes to provide 0.5 M lithium diisopropyl amine in tetrahydrofuran. In a separate flask, a solution of Example 145B (416 mg, 1.287 mmol) in tetrahydrofuran (3 mL) under N₂ at −40° C. was treated with 0.5 M lithium diisopropyl amine in tetrahydrofuran (4912 μL, 2.456 mmol), stirred at 0° C. for 1 hour, cooled to −78° C. and treated with a solution of methyl 6-formylnicotinate (193 mg, 1.170 mmol) in tetrahydrofuran (1 mL). The mixture was allowed to slowly warm to 0° C. and stirred for 20 minutes. The mixture was cooled to −40° C. and quenched with the addition of 2 mL of 20% acetic acid in tetrahydrofuran. The mixture was warmed to 0° C., diluted with ethyl acetate (30 mL), washed with saturated NaHCO₃ solution, washed with brine, dried (MgSO₄), filtered, and concentrated. The residue was chromatographed on silica gel and eluting with a gradient of 15% to 100% ethyl acetate in heptanes to provide the title compound (81.2 mg, 0.166 mmol, 14.21% yield). ¹H NMR (400 MHz, CDCl₃) δ 12.93 (s, 1H), 9.17 (s, 1H), 8.22 (dd, J=8.2, 1.8 Hz, 1H), 7.59 (s, 1H), 7.57 (s, 1H), 6.76 (s, 1H), 6.58 (d, J=8.8 Hz, 1H), 5.36-5.31 (m, 1H), 4.94-4.90 (m, 1H), 3.96 (s, 3H), 3.78 (d, J=5.8 Hz, 2H), 1.40 (s, 9H); LC/MS (ESI+) m/z 489 (M+H)⁺.

Example 145D methyl 6-[(2R,4E)-4-{[(S)-2-methylpropane-2-sulfinyl]imino}-7-(trifluoromethoxy)-3,4-dihydro-2H-1-benzopyran-2-yl]pyridine-3-carboxylate A solution of Example 145C (81.2 mg, 0.166 mmol) and triphenylphosphine (52.3 mg, 0.199 mmol) in CH₂Cl₂ (2 mL) at 0° C. under N₂ was treated with a 40 weight % solution of diethyl azodicarboxylate in toluene (189 μL, 0.416 mmol). The mixture was stirred at 0° C. for 5 minutes, and at room temperature for 75 minutes, diluted with heptanes and chromatographed on silica gel eluting with a gradient of 15% to 50% ethyl acetate in heptane to provide the title compound (51.2 mg, 0.109 mmol, 65.5% yield). $^1$H NMR (400 MHz, CDCl$_3$) δ 9.20-9.18 (m, 1H), 8.38 (dd, J=8.2, 2.0 Hz, 1H), 8.06 (d, J=8.7 Hz, 1H), 7.69 (d, J=8.2 Hz, 1H), 6.93-6.91 (m, 1H), 6.91-6.87 (m, 1H), 5.42 (dd, J=12.5, 2.8 Hz, 1H), 4.04 (dd, J=17.6, 3.0 Hz, 1H), 3.97 (s, 3H), 3.33 (dd, J=17.6, 12.5 Hz, 1H), 1.31 (s, 9H); LC/MS (ESI+) m/z 471 (M+H)$^+$.

Example 145E methyl 6-[(2R,4R)-4-amino-7-(trifluoromethoxy)-3,4-dihydro-2H-1-benzopyran-2-yl]pyridine-3-carboxylate A solution of Example 145D (51.2 mg, 0.109 mmol) in methanol (1 mL) was cooled to 0° C., treated with NaBH$_4$ (12.35 mg, 0.326 mmol), stirred at 0° C. for 30 minutes, treated with 4 M HCl in dioxane (336 μL, 1.345 mmol), stirred for 5 minutes at 0° C., and at room temperature for 45 minutes. The mixture was partitioned between methyl tert-butyl ether (30 mL) and water (5 mL). The methyl tert-butyl ether layer was extracted with 0.1 M HCl (5 mL). The methyl tert-butyl ether layer was discarded. The combined aqueous layers were basified with solid NaHCO$_3$ and extracted with ethyl acetate (2×25 mL). The combined ethyl acetate layers were washed with brine, dried (MgSO$_4$), filtered, and concentrated to provide the title compound (29.2 mg, 0.079 mmol, 72.8% yield). $^1$H NMR (400 MHz, CDCl$_3$) δ 9.19-9.18 (m, 1H), 8.38 (dd, J=8.2, 2.0 Hz, 1H), 7.71 (d, J=8.2 Hz, 1H), 7.57 (d, J=8.3 Hz, 1H), 6.86 (d, J=8.7 Hz, 1H), 6.83 (s, 1H), 5.36 (dd, J=11.4, 1.6 Hz, 1H), 4.34-4.28 (m, 1H), 3.97 (s, 3H), 2.73 (ddd, J=13.1, 5.6, 2.0 Hz, 1H), 1.90-1.80 (m, 1H); LC/MS (ESI+) m/z 352 (M–NH$_3$)$^+$.

Example 145F methyl 6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylate A solution of Example 145E (29.2 mg, 0.079 mmol) and triethylamine (22.10 μL, 0.159 mmol) in CH$_2$Cl$_2$ (2 mL) at 0° C. under N$_2$ was treated with a solution of Example 134F (24.12 mg, 0.087 mmol) in CH$_2$Cl$_2$ (1 mL). The mixture was stirred at 0° C. for 15 minutes and at room temperature for 1 hour. More Example 134F solution was added and mixture was stirred for an additional hour. The mixture was partitioned between methyl tert-butyl ether (30 mL) and saturated NaHCO$_3$ solution (3 mL). The methyl tert-butyl ether layer was washed with brine, dried (MgSO$_4$), filtered, and concentrated. The residue was chromatographed on silica gel eluting with a gradient of 50% to 100% ethyl acetate in heptanes to provide the title compound (49 mg, 0.081 mmol, 102% yield). $^1$H NMR (501 MHz, CDCl$_3$) δ 9.11 (dd, J=2.1, 0.7 Hz, 1H), 8.32 (dd, J=8.2, 2.1 Hz, 1H), 7.62 (d, J=8.2 Hz, 1H), 7.02 (dd, J=8.5, 0.9 Hz, 1H), 6.85 (s, 1H), 6.83-6.82 (m, 1H), 6.80-6.77 (m, 1H), 6.60 (s, 1H), 5.82 (d, J=8.9 Hz, 1H), 5.46 (td, J=9.0, 6.6 Hz, 1H), 5.39 (dd, J=10.0, 2.6 Hz, 1H), 4.80 (d, J=9.3 Hz, 1H), 4.32 (d, J=9.3 Hz, 1H), 3.97 (s, 3H), 2.77 (ddd, J=13.6, 6.3, 2.7 Hz, 1H), 2.04-1.98 (m, 1H), 1.64 (s, 3H); LC/MS (ESI+) m/z 609 (M+H)$^+$.

Example 145G

6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylic acid A solution of Example 145F (26.1 mg, 0.043 mmol) in tetrahydrofuran (1 mL) and methanol (1 mL) was treated with 1 M NaOH (0.5 mL) and stirred at room temperature for 20 minutes. The mixture was treated with 1 M HCl (2 mL) and extracted with ethyl acetate (30 mL). The ethyl acetate layer was washed with brine, dried (MgSO$_4$), filtered, and concentrated. The residue was chromatographed on silica gel eluting with a gradient of 50% to 100% [200:1:1 ethyl acetate:HCOOH:H$_2$O] in heptanes to provide the title compound (17 mg, 0.029 mmol, 66.7% yield). $^1$H NMR (400 MHz, CDCl$_3$) δ 9.18 (d, J=1.7 Hz, 1H), 8.38 (dd, J=8.2, 2.1 Hz, 1H), 7.66 (d, J=8.2 Hz, 1H), 7.02 (d, J=8.5 Hz, 1H), 6.86 (s, 1H), 6.85-6.83 (m, 1H), 6.81-6.77 (m, 1H), 6.61 (s, 1H), 5.82 (d, J=8.8 Hz, 1H), 5.48 (td, J=9.1, 6.6 Hz, 1H), 5.42 (dd, J=10.1, 2.5 Hz, 1H), 4.81 (d, J=9.3 Hz, 1H), 4.33 (d, J=9.4 Hz, 1H), 2.79 (ddd, J=13.5, 6.2, 2.6 Hz, 1H), 2.01 (dt, J=13.5, 10.0 Hz, 1H), 1.65 (s, 3H); MS (ESI–) m/z 593 (M–H)$^−$.

Example 146

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-2-carboxylic acid Example 146A methyl 5-[(1S,3E)-1-hydroxy-3-(2-hydroxy-4-methoxyphenyl)-3-{[(S)-2-methylpropane-2-sulfinyl]imino}propyl]pyridine-2-carboxylate A solution of Example 89A (300 mg, 1.114 mmol) in tetrahydrofuran (3 mL) under N$_2$ at –40° C. was treated with 0.5 M lithium diisopropyl amine in tetrahydrofuran (4253 μL, 2.126 mmol), stirred at 0° C. for 1 hour, cooled to –78° C. and treated with a solution of methyl 5-formylpicolinate (167 mg, 1.013 mmol) in tetrahydrofuran (1 mL). The mixture was allowed to slowly warm to 0° C. and then stirred for 15 minutes. The mixture was cooled to –40° C. and quenched with the addition of 2 mL of 20% acetic acid in tetrahydrofuran. The mixture was warmed to 0° C., diluted with ethyl acetate (30 mL), washed with saturated NaHCO$_3$ solution, washed with brine, dried (MgSO$_4$), filtered, and concentrated. The residue was chromatographed on silica gel eluting with a gradient of 50% to 100% ethyl acetate in heptanes to provide the title compound. $^1$H NMR (501 MHz, CDCl$_3$) δ 13.18 (s, 1H), 8.78 (d, J=2.1 Hz, 1H), 8.02 (d, J=8.1 Hz, 1H), 7.89 (dd, J=8.2, 2.1 Hz, 1H), 7.22 (d, J=9.2 Hz, 1H), 6.39 (d, J=2.6 Hz, 1H), 6.26 (dd, J=9.1, 2.6 Hz, 1H), 5.46-5.40 (m, 1H), 4.39 (d, J=3.3 Hz, 1H), 3.99 (s, 3H), 3.80 (s, 3H), 3.71 (dd, J=13.5, 7.4 Hz, 1H), 3.59 (dd, J=13.6, 4.4 Hz, 1H), 1.37 (s, 9H); LC/MS (ESI+) m/z 435 (M+H)$^+$.

Example 146B methyl 5-[(2R,4E)-7-methoxy-4-{[(S)-2-methylpropane-2-sulfinyl]imino}-3,4-dihydro-2H-1-benzopyran-2-yl]pyridine-2-carboxylate A solution of Example 146A (46.2 mg, 0.106 mmol) and triphenylphosphine (33.5 mg, 0.128 mmol) in $CH_2Cl_2$ (2 mL) at 0° C. under $N_2$ was treated with a 40 weight % solution of diethyl azodicarboxylate in toluene (121 μL, 0.266 mmol). The mixture was stirred at 0° C. for 5 minutes and at room temperature for 75 minutes, diluted with heptanes, and chromatographed on silica gel, eluting with a gradient of 50% to 100% ethyl acetate in heptanes to provide the title compound (28 mg, 0.067 mmol, 63.2% yield) which was contaminated with triphenylphosphine oxide. $^1$H NMR (400 MHz, $CDCl_3$) δ 8.84 (d, J=1.9 Hz, 1H), 8.17 (d, J=8.1 Hz, 1H), 7.99 (dd, J=8.2, 2.1 Hz, 1H), 7.93 (d, J=9.0 Hz, 1H), 6.62 (dd, J=8.9, 2.4 Hz, 1H), 6.48 (d, J=2.3 Hz, 1H), 5.38 (dd, J=12.1, 2.9 Hz, 1H), 4.02 (s, 3H), 3.84 (s, 3H), 3.77 (dd, J=17.4, 3.0 Hz, 1H), 3.38 (dd, J=17.4, 12.1 Hz, 1H), 1.30 (s, 9H); LC/MS (ESI+) m/z 417 $(M+H)^+$.

Example 146C methyl 5-[(2R,4R)-4-amino-7-methoxy-3,4-dihydro-2H-1-benzopyran-2-yl]pyridine-2-carboxylate A solution of Example 146B (28 mg, 0.067 mmol) in methanol (1 mL) was cooled to 0° C., treated with $NaBH_4$ (7.63 mg, 0.202 mmol), stirred at 0° C. for 30 minutes, treated with 4 M HCl in dioxane (336 μL, 1.345 mmol), stirred for 5 minutes at 0° C. and at room temperature for 45 minutes. The mixture was partitioned between methyl tert-butyl ether (30 mL) and water (5 mL). The methyl tert-butyl ether layer was extracted with 0.1 M HCl (5 mL). The methyl tert-butyl ether layer was discarded. The combined aqueous layers were basified with solid $NaHCO_3$ and extracted with ethyl acetate (2×25 mL). The combined ethyl acetate layers were washed with brine, dried ($MgSO_4$), filtered, and concentrated to the title compound (18.6 mg, 0.059 mmol, 88% yield). $^1$H NMR (400 MHz, $CDCl_3$) δ 8.79 (d, J=1.8 Hz, 1H), 8.19 (d, J=8.1 Hz, 1H), 7.97 (dd, J=8.1, 2.1 Hz, 1H), 7.41 (d, J=8.6 Hz, 1H), 6.60 (dd, J=8.5, 2.4 Hz, 1H), 6.45 (d, J=2.5 Hz, 1H), 5.28 (d, J=11.5 Hz, 1H), 4.31-4.24 (m, 1H), 4.03 (s, 3H), 3.79 (s, 3H), 2.47-2.40 (m, 1H), 1.90 (q, J=11.8 Hz, 1H); LC/MS (ESI+) m/z 315 $(M+H)^+$.

Example 146D methyl 5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-2-carboxylate A solution of Example 146C (21.4 mg, 0.068 mmol) and triethylamine (18.98 μL, 0.136 mmol) in $CH_2Cl_2$ (2 mL) at 0° C. under $N_2$ was treated with a solution of Example 134F (20.72 mg, 0.075 mmol) in $CH_2Cl_2$ (1 mL). The mixture was stirred at 0° C. for 15 minutes and at room temperature for 1 hour. More of the solution of Example 134F was added and mixture was stirred for an additional hour. The mixture was partitioned between methyl tert-butyl ether (30 mL) and saturated $NaHCO_3$ solution (3 mL). The methyl tert-butyl ether layer was washed with brine, dried ($MgSO_4$), filtered, and concentrated. The residue was chromatographed on silica gel, eluting with a gradient of 50% to 100% ethyl acetate in heptanes to provide the title compound. $^1$H NMR (400 MHz, $CDCl_3$) δ 8.77 (s, 1H), 8.15 (d, J=8.1 Hz, 1H), 7.89 (dd, J=8.0, 2.1 Hz, 1H), 6.90 (s, 1H), 6.83 (d, J=8.6 Hz, 1H), 6.60 (s, 1H), 6.53 (dd, J=8.6, 2.5 Hz, 1H), 6.46 (d, J=2.4 Hz, 1H), 5.62 (d, J=8.6 Hz, 1H), 5.46-5.37 (m, 1H), 5.29 (d, J=10.3 Hz, 1H), 4.80 (d, J=9.3 Hz, 1H), 4.32 (d, J=9.3 Hz, 1H), 4.02 (s, 3H), 3.77 (s, 3H), 2.54 (ddd, J=13.2, 6.1, 1.3 Hz, 1H), 1.89-1.77 (m, 1H), 1.66 (s, 3H); LC/MS (ESI+) m/z 555 $(M+H)^+$.

Example 146E

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-2-carboxylic acid A solution of Example 146D (14.4 mg, 0.026 mmol) in tetrahydrofuran (1 mL) and methanol (1 mL) was treated with 1 M NaOH (0.5 mL) and stirred at room temperature for 20 minutes. The mixture was acidified with 1 M HCl (2 mL) and extracted with ethyl acetate (30 mL). The ethyl acetate layer was washed with brine, dried ($MgSO_4$), filtered, and concentrated. The residue was chromatographed on silica gel, eluting with a gradient of 50% to 100% [200:1:1 ethyl acetate:$HCOOH$:$H_2O$] in heptanes to provide the title compound (13 mg, 0.024 mmol, 93% yield). $^1$H NMR (501 MHz, $CDCl_3$) δ 8.68 (s, 1H), 8.24 (d, J=8.0 Hz, 1H), 8.00 (dd, J=8.1, 1.8 Hz, 1H), 6.90 (s, 1H), 6.85 (d, J=8.7 Hz, 1H), 6.61 (s, 1H), 6.55 (dd, J=8.6, 2.5 Hz, 1H), 6.47 (d, J=2.5 Hz, 1H), 5.61 (d, J=8.4 Hz, 1H), 5.46-5.37 (m, 1H), 5.33 (d, J=10.6 Hz, 1H), 4.80 (d, J=9.3 Hz, 1H), 4.32 (d, J=9.3 Hz, 1H), 3.78 (s, 3H), 2.58 (ddd, J=13.5, 6.1, 1.8 Hz, 1H), 1.89-1.77 (m, 1H), 1.66 (s, 3H); MS (ESI−) m/z 539 $(M-H)^-$.

Example 147 ethyl trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate

Example 147A methyl cis-4-[4-oxo-7-(trifluoromethoxy)-3,4-dihydro-2H-1-benzopyran-2-yl]cyclohexane-1-carboxylate A vial containing a solution of Example 145A (2.39 g, 10.86 mmol) in toluene (4 mL) was treated with trans methyl 4-formylcyclohexanecarboxylate (1.848 g, 10.86 mmol), treated with acetic acid (0.746 mL, 13.03 mmol), treated with pyrrolidine (0.898 ml, 10.86 mmol) and stirred overnight at 70° C. The mixture was cooled to room temperature, diluted with ethyl acetate (100 mL), washed with 1 M HCl (30 mL), washed with saturated $NaHCO_3$ solution (15 mL), washed with brine, dried ($MgSO_4$), filtered, and concentrated. The residue was chromatographed on silica gel eluting with a gradient of 10% to 30% ethyl acetate in heptanes. Mixed fractions of the isomers were collected and concentrated. The residue was rechromatographed on silica gel eluting with a gradient of 10% to 50% ethyl acetate in heptanes. The title compound (0.81 g, 20% yield) was obtained as the first eluting isomer. $^1$H NMR (400 MHz, CDCl₃) δ 7.90 (d, J=8.4 Hz, 1H), 6.86-6.80 (m, 2H), 4.30 (dt, J=9.2, 6.6 Hz, 1H), 3.70 (s, 3H), 2.73-2.62 (m, 3H), 2.21-2.09 (m, 2H), 1.89-1.76 (m, 2H), 1.70-1.53 (m, 3H), 1.53-1.38 (m, 2H); LC/MS (ESI+) m/z 414 (M+CH$_3$CN)⁺.

Example 147B methyl trans-4-[4-oxo-7-(trifluoromethoxy)-3,4-dihydro-2H-1-benzopyran-2-yl]cyclohexane-1-carboxylate The title compound (2.88 g, 71% yield) was obtained as the second eluting isomer from the chromatography separation described in Example 147A. ¹H NMR (501 MHz, CDCl₃) δ 7.90 (dd, J=8.5, 0.5 Hz, 1H), 6.85-6.81 (m, 2H), 4.25 (ddd, J=12.9, 5.9, 3.1 Hz, 1H), 3.68 (s, 3H), 2.74 (dd, J=16.7, 12.9 Hz, 1H), 2.66 (dd, J=16.7, 3.2 Hz, 1H), 2.30 (tt, J=12.3, 3.3 Hz, 1H), 2.13-2.07 (m, 3H), 1.90-1.83 (m, 1H), 1.74 (dddq, J=12.1, 9.1, 6.3, 3.1 Hz, 1H), 1.55-1.42 (m, 2H), 1.31-1.16 (m, 2H); LC/MS (ESI+) m/z 414 (M+CH$_3$CN)⁺.

Example 147C ethyl trans-4-[(2S,4E)-4-{[(S)-2-methylpropane-2-sulfinyl]imino}-7-(trifluoromethoxy)-3,4-dihydro-2H-1-benzopyran-2-yl]cyclohexane-1-carboxylate and ethyl trans-4-[(2R,4E)-4-{[(S)-2-methylpropane-2-sulfinyl]imino}-7-(trifluoromethoxy)-3,4-dihydro-2H-1-benzopyran-2-yl]cyclohexane-1-carboxylate A mixture of Example 147B (0.21 g, 0.564 mmol) and (S)-(−)-2-methyl-2-propanesulfinamide (0.137 g, 1.128 mmol) in toluene (5 mL) was treated with titanium(IV) ethoxide (0.515 g, 2.256 mmol). The mixture was stirred at 90° C. for 6 hours, cooled, diluted with ethyl acetate (50 mL), treated with water (50 mL), stirred for 5 minutes and filtered through diatomaceous earth to remove the solids. The ethyl acetate layer of the filtrate was washed with brine, dried (MgSO₄), filtered and concentrated to provide the title compound. ¹H NMR (500 MHz, CDCl₃) δ 7.98 (d, J=8.8 Hz, 0.5H), 7.95 (d, J=8.8 Hz, 0.5H), 6.79 (d, J=8.8 Hz, 1H), 6.77-6.75 (m, 1H), 4.11 (q, J=7.1 Hz, 2H), 4.06 (ddd, J=12.2, 6.1, 2.6 Hz, 0.5H), 3.99 (ddd, J=12.5, 6.0, 2.5 Hz, 0.5H), 3.88 (dd, J=16.8, 2.6 Hz, 0.5H), 3.55 (dd, J=17.3, 2.6 Hz, 0.5H), 3.00 (dd, J=17.3, 12.6 Hz, 0.5H), 2.71 (dd, J=16.8, 12.2 Hz, 0.5H), 2.32-2.19 (m, 1H), 2.11-2.01 (m, 3H), 1.93-1.82 (m, 1H), 1.72-1.64 (m, 1H), 1.53-1.37 (m, 2H), 1.34-1.14 (m, 14H); LC/MS (ESI+) m/z 490 (M+H)⁺.

Example 147D ethyl trans-4-[(2S,4S)-4-{[(S)-2-methylpropane-2-sulfinyl]amino}-7-(trifluoromethoxy)-3,4-dihydro-2H-1-benzopyran-2-yl]cyclohexane-1-carboxylate A solution of Example 147C (274 mg, 0.56 mmol) in ethanol (5 mL) was cooled to 0° C. and treated with NaBH₄ (42.4 mg, 1.120 mmol). The mixture was stirred at 0° C. for 45 minutes, diluted with CH₂Cl₂, treated with silica gel (approximately 1.5 g) and concentrated. This silica gel suspension was chromatographed on silica gel column, eluting with a gradient of 0% to 100% [1:1 ethyl acetate:CH₂Cl₂] in [9:1 CH₂Cl₂: ethyl acetate] to provide the title compound (59.9 mg, 0.122 mmol, 21.76% yield) as the first eluting isomer. ¹H NMR (501 MHz, CDCl₃) δ 7.67 (dd, J=8.6, 1.0 Hz, 1H), 6.77 (ddd, J=8.6, 2.3, 0.9 Hz, 1H), 6.66 (dd, J=2.3, 1.0 Hz, 1H), 4.64 (dt, J=11.5, 6.7 Hz, 1H), 4.13 (q, J=7.1 Hz, 2H), 3.91 (ddd, J=11.6, 5.6, 1.3 Hz, 1H), 3.50 (d, J=7.9 Hz, 1H), 2.31-2.19 (m, 2H), 2.06 (ddt, J=9.8, 6.1, 3.4 Hz, 3H), 1.89-1.77 (m, 2H), 1.61 (s, 1H), 1.53-1.40 (m, 2H), 1.32-1.12 (m, 14H); LC/MS (ESI+) m/z 492 (M+H)⁺.

Example 147E ethyl trans-4-[(2R,4R)-4-{[(S)-2-methylpropane-2-sulfinyl]amino}-7-(trifluoromethoxy)-3,4-dihydro-2H-1-benzopyran-2-yl]cyclohexane-1-carboxylate The title compound (75.2 mg, 0.153 mmol, 27.3% yield) was obtained as the second eluting isomer from the chromatography separation as described in Example 147D. ¹H NMR (400 MHz, CDCl₃) δ 7.39 (dd, J=8.5, 0.7 Hz, 1H), 6.74 (dd, J=8.6, 1.2 Hz, 1H), 6.67 (d, J=1.1 Hz, 1H), 4.57 (td, J=11.0, 6.0 Hz, 1H), 4.12 (q, J=7.1 Hz, 2H), 3.94 (dd, J=10.7, 5.3 Hz, 1H), 3.27 (d, J=10.8 Hz, 1H), 2.61 (ddd, J=13.4, 5.8, 1.2 Hz, 1H), 2.24 (tt, J=12.2, 3.4 Hz, 1H), 2.10-1.99 (m, 3H), 1.87 (d, J=12.2 Hz, 1H), 1.82-1.72 (m, 1H), 1.66-1.56 (m, 1H), 1.44 (dtt, J=18.1, 8.6, 4.3 Hz, 2H), 1.33-1.13 (m, 14H); LC/MS (ESI+) m/z 492 (M+H)⁺.

Example 147F ethyl trans-4-[(2S,4S)-4-amino-7-(trifluoromethoxy)-3,4-dihydro-2H-1-benzopyran-2-yl]cyclohexane-1-carboxylate A solution of Example 147D (59 mg, 0.120 mmol) in ethanol (3 mL) was treated with 4 M HCl in dioxane (300 μL, 1.200 mmol), stirred at room temperature for 15 minutes, diluted with ethyl acetate (30 mL) and washed with saturated NaHCO₃ solution (15 mL). The ethyl acetate layer was washed with brine, dried (MgSO₄), filtered, and concentrated. The residue was chromatographed on silica gel eluting with a gradient of 0% to 100% [10:1:1 ethyl acetate:HCOOH:H₂O] in [200:1:1 ethyl acetate:HCOOH:H₂O]. Fractions containing the product were combined, washed with NaHCO₃ to remove the formic acid, washed with brine, dried (MgSO₄), filtered, and concentrated to provide the title compound (35.4 mg, 0.091 mmol, 76% yield). ¹H NMR (400 MHz, CDCl₃) δ 7.45 (d, J=8.5 Hz, 1H), 6.75 (d, J=8.5 Hz, 1H), 6.65 (s, 1H), 4.13 (q, J=7.1 Hz, 2H), 4.07 (dd, J=11.0, 5.4 Hz, 1H), 3.94-3.89 (m, 1H), 2.31-2.22 (m, 1H), 2.19 (ddd, J=12.9, 5.8, 1.3 Hz, 1H), 2.11-2.01 (m, 3H), 1.90-1.82 (m, 1H), 1.66-1.56 (m, 2H), 1.54-1.40 (m, 2H), 1.31-1.11 (m, 5H); LC/MS (ESI+) m/z 371 (M−NH₃)⁺.

Example 147G ethyl trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate A solution of Example 147F (35.4 mg, 0.091 mmol) and triethylamine (25.5 μL, 0.183 mmol) in CH₂Cl₂ (1 mL) was cooled to 0° C. under N₂, treated with a solution of Example 134F (30.3 mg, 0.110 mmol) in CH₂Cl₂ (0.5 mL), stirred at 0° C. for 25 minutes and then at room temperature for 15 minutes. The mixture was cooled to 0° C., treated with 37% NH₄OH solution (5 drops) and stirred for 5 minutes. The mixture was diluted with ethyl acetate (30 mL), washed with 1 M HCl (5 mL), washed with saturated NaHCO₃ solution (5 mL), washed with brine, dried (MgSO$_4$), filtered, and concentrated. The residue was chromatographed on silica gel eluting with a gradient of 15% to 50% ethyl acetate in heptanes to provide the title compound (44 mg, 0.070 mmol, 77% yield). $^1$H NMR (501 MHz, CDCl$_3$) δ 6.93 (d, J=8.5 Hz, 1H), 6.87 (s, 1H), 6.71-6.68 (m, 1H), 6.67-6.65 (m, 2H), 5.57 (d, J=8.9 Hz, 1H), 5.28 (ddd, J=10.9, 9.0, 6.3 Hz, 1H), 4.94 (d, J=9.3 Hz, 1H), 4.37 (d, J=9.3 Hz, 1H), 4.13 (q, J=7.1 Hz, 2H), 3.96-3.90 (m, 1H), 2.30-2.20 (m, 2H), 2.11-2.00 (m, 3H), 1.83 (d, J=12.0 Hz, 1H), 1.65 (s, 3H), 1.63-1.39 (m, 5H), 1.25 (t, J=7.1 Hz, 3H), 1.16 (qd, J=13.8, 13.0, 3.8 Hz, 1H); LC/MS (ESI+) m/z 628.6 (M+H)$^+$.

Example 148 ethyl trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate Example 148A ethyl trans-4-[(2R,4R)-4-amino-7-(trifluoromethoxy)-3,4-dihydro-2H-1-benzopyran-2-yl]cyclohexane-1-carboxylate A solution of Example 147E (74 mg, 0.151 mmol) in ethanol (3 mL) was treated with 4 M HCl in dioxane (376 μL, 1.505 mmol), stirred at room temperature for 30 minutes, diluted with ethyl acetate (30 mL) and washed with saturated NaHCO$_3$ solution (15 mL). The ethyl acetate layer was washed with brine, dried (MgSO$_4$), filtered, and concentrated. The residue was chromatographed on silica gel eluting with a gradient of 0% to 100% [10:1:1 ethyl acetate: HCOOH:H$_2$O] in [200:1:1 ethyl acetate:HCOOH:H$_2$O]. Fractions containing the product were combined, washed with saturated NaHCO$_3$ solution to remove the formic acid, washed with brine, dried (MgSO$_4$), filtered, and concentrated to provide the title compound (52.2 mg, 0.135 mmol, 90% yield). $^1$H NMR (400 MHz, CDCl$_3$) δ 7.44 (dd, J=8.6, 0.6 Hz, 1H), 6.78-6.74 (m, 1H), 6.67-6.65 (m, 1H), 4.17-4.06 (m, 3H), 3.91 (ddd, J=11.6, 5.5, 1.1 Hz, 1H), 2.33-2.16 (m, 4H), 2.11-2.02 (m, 3H), 1.90-1.82 (m, 1H), 1.68-1.56 (m, 2H), 1.55-1.39 (m, 2H), 1.32-1.11 (m, 5H); LC/MS (ESI+) m/z 371 (M−NH$_3$)$^+$.

Example 148B ethyl trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate A solution of Example 148A (52.2 mg, 0.135 mmol) and triethylamine (37.6 μL, 0.269 mmol) in CH$_2$Cl$_2$ (1 mL) was cooled to 0° C. under N$_2$, treated with a solution of Example 134F (44.7 mg, 0.162 mmol) in CH$_2$Cl$_2$ (about 0.5 mL), stirred at 0° C. for 25 minutes and then at room temperature for 15 minutes. The mixture was cooled to 0° C., treated with 37% NH$_4$OH solution (5 drops) and stirred for 5 minutes. The mixture was diluted with ethyl acetate (30 mL), washed with 1 M HCl (5 mL), washed with saturated NaHCO$_3$ solution (5 mL), washed with brine, dried (MgSO$_4$), filtered, and concentrated. The residue was chromatographed on silica gel eluting with a gradient of 15% to 50% (over 9 minutes) ethyl acetate in heptanes to provide the title compound (62 mg, 0.099 mmol, 73.3% yield). $^1$H NMR (400 MHz, CDCl$_3$) δ 6.91 (s, 1H), 6.87 (d, J=8.4 Hz, 1H), 6.71-6.65 (m, 2H), 6.64 (s, 1H), 5.64 (d, J=8.9 Hz, 1H), 5.31-5.22 (m, 1H), 4.89 (d, J=9.3 Hz, 1H), 4.35 (d, J=9.3 Hz, 1H), 4.12 (q, J=7.1 Hz, 2H), 3.92 (dd, J=11.3, 5.5 Hz, 1H), 2.29-2.20 (m, 2H), 2.10-1.99 (m, 3H), 1.86-1.78 (m, 1H), 1.67 (s, 3H), 1.63-1.37 (m, 4H), 1.30-1.08 (m, 5H); LC/MS (ESI+) m/z 628.6 (M+H)$^+$.

Example 149 trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid A solution of Example 147G (34.5 mg, 0.055 mmol) in tetrahydrofuran (1.5 mL) and methanol (1.5 mL) was treated with 1 M NaOH (0.5 mL) and stirred at room temperature for 15 minutes, heated at 55° C. for 20 minutes, cooled to room temperature, acidified with 1 M HCl (2 mL), and extracted with ethyl acetate (30 mL). The ethyl acetate layer was washed with brine, dried (MgSO$_4$), filtered, and concentrated to provide the title compound (30 mg, 0.050 mmol, 91% yield). $^1$H NMR (501 MHz, CDCl$_3$) δ 6.93 (dd, J=8.5, 0.9 Hz, 1H), 6.87 (s, 1H), 6.71-6.68 (m, 1H), 6.67-6.66 (m, 1H), 6.66 (s, 1H), 5.58 (d, J=9.0 Hz, 1H), 5.31-5.25 (m, 1H), 4.94 (d, J=9.3 Hz, 1H), 4.37 (d, J=9.3 Hz, 1H), 3.94 (dd, J=10.5, 5.5 Hz, 1H), 2.32 (tt, J=12.1, 3.5 Hz, 1H), 2.24 (ddd, J=12.8, 6.1, 1.2 Hz, 1H), 2.15-2.09 (m, 2H), 2.08-2.02 (m, 1H), 1.89-1.82 (m, 1H), 1.65 (s, 3H), 1.63-1.56 (m, 1H), 1.56-1.42 (m, 3H), 1.32-1.13 (m, 2H); LC/MS (ESI+) m/z 600 (M+H)$^+$.

Example 150 trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid A solution of Example 148B (47.2 mg, 0.075 mmol) in tetrahydrofuran (1.5 mL) and methanol (1.5 mL) was treated with 1 M NaOH (0.5 mL), stirred at room temperature for 15 minutes, heated at 55° C. for 20 minutes, cooled to room temperature, acidified with 1 M HCl (2 mL) and extracted with ethyl acetate (30 mL). The ethyl acetate layer was washed with brine, dried (MgSO$_4$), filtered, and concentrated to provide the title compound (41 mg, 0.068 mmol, 91% yield). $^1$H NMR (400 MHz, CDCl$_3$) δ 6.91 (s, 1H), 6.87 (d, J=8.4 Hz, 1H), 6.71-6.68 (m, 1H), 6.67 (s, 1H), 6.64 (s, 1H), 5.64 (d, J=8.9 Hz, 1H), 5.31-5.23 (m, 1H), 4.89 (d, J=9.3 Hz, 1H), 4.35 (d, J=9.4 Hz, 1H), 3.93 (dd, J=10.9, 5.5 Hz, 1H), 2.35-2.20 (m, 2H), 2.14-2.07 (m, 2H), 2.07-2.01 (m, 1H), 1.87-1.80 (m, 1H), 1.67 (s, 3H), 1.64-1.40 (m, 4H), 1.32-1.11 (m, 2H); LC/MS (ESI+) m/z 600 (M+H)$^+$.

Example 151

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid Example 151A 1-(2-((tert-butyldimethylsilyl)oxy)-4-(difluoromethoxy)phenyl)ethan-1-one A solution of Example 156A (1.51 g, 7.47 mmol) in CH$_2$Cl$_2$ (60 mL) was treated with tert-butyldimethylsilyl chloride (2.53 g, 16.79 mmol), triethylamine (3.12 mL, 22.36 mmol), and 4-dimethylaminopyridine (0.137 g, 1.121 mmol). The mixture was stirred over night at room temperature, and concentrated to remove the $CH_2Cl_2$. The residue was partitioned between methyl tert-butyl ether (100 mL) and water (25 mL). The methyl tert-butyl ether layer was washed with 5% citric acid (25 mL), saturated $NaHCO_3$ solution (15 mL), and brine, dried ($MgSO_4$), filtered, and concentrated. The residue was chromatographed on silica gel, eluting with 5% ethyl acetate in heptanes to provide the title compound (2.37 g, 7.49 mmol, 100% yield). $^1$H NMR (400 MHz, $CDCl_3$) δ 7.67 (d, J=9 Hz, 1H), 6.73 (d, J=9 Hz, 1H), 6.64 (s, 1H), 6.53 (t, J=74 Hz, 1H), 2.58 (s, 3H), 1.00 (s, 9H), 0.29 (s, 6H); LC/MS (ESI+) m/z 317 (M+H)$^+$.

Example 151B (S)—N-{(1E)-1-[2-{[tert-butyl(dimethyl)silyl]oxy}-4-(difluoromethoxy)phenyl]ethylidene}-2-methyl-propane-2-sulfinamide A solution of Example 151A (2.37 g, 7.49 mmol) and (S)-(−)-2-methyl-2-propanesulfinamide (1.816 g, 14.98 mmol) in toluene (15 mL) was treated with titanium(IV) ethoxide (6.21 mL, 30.0 mmol), stirred at 90° C. overnight and cooled. The mixture was diluted with ethyl acetate (100 mL), treated with water (100 mL), stirred vigorously for 5 minutes and filtered through diatomaceous earth. The ethyl acetate layer was washed with brine, dried ($MgSO_4$), filtered, and concentrated. The residue was chromatographed on silica gel, eluting with a gradient of 15% to 50% ethyl acetate in heptanes to provide the title compound (2.084 g, 4.97 mmol, 66.3% yield). $^1$H NMR (501 MHz, $CDCl_3$) δ 7.41 (d, J=8.5 Hz, 1H), 6.72 (dd, J=8.5, 2.0 Hz, 1H), 6.62 (d, J=2.2 Hz, 1H), 6.51 (t, J=73.5 Hz, 1H), 1.58 (s, 3H), 1.29 (s, 9H), 0.98 (s, 9H), 0.25 (s, 3H), 0.23 (s, 3H); LC/MS (ESI+) m/z 420 (M+H)$^+$.

Example 151C methyl 6-[(1S,3E)-3-[4-(difluoromethoxy)-2-hydroxyphenyl]-1-hydroxy-3-{[(S)-2-methylpropane-2-sulfinyl]imino}propyl]pyridine-3-carboxylate A solution of diisopropylamine (280 μL, 1.965 mmol) in tetrahydrofuran (8 mL) was cooled to 0° C., treated dropwise with 2.5 M n-butyllithium in hexanes (720 μL, 1.801 mmol), stirred at 0° C. for 30 minutes, cooled to −78° C., treated dropwise with a solution of Example 151B (687 mg, 1.637 mmol) in tetrahydrofuran (4 mL), stirred at −78° C. for 45 minutes, treated dropwise with a solution of methyl 6-formylnicotinate (270 mg, 1.637 mmol) in tetrahydrofuran (4 mL), stirred at −78° C. for 1 hour, allowed to warm to −10° C. for 1 hour, treated dropwise with a solution of acetic acid (281 μL, 4.91 mmol) in tetrahydrofuran (1 mL) and partitioned between ethyl acetate (30 mL) and saturated $NaHCO_3$ solution (5 mL). The ethyl acetate layer was washed with brine, dried ($MgSO_4$), filtered, and concentrated. The residue was chromatographed on silica gel, eluting with a gradient of 15% 100% ethyl acetate in heptanes to provide products that contained the silyl protecting group (first eluting), followed by the title compound that eluted later. The fractions containing the silyl protecting group were combined, concentrated to dryness, dissolved in tetrahydrofuran (10 mL) under $N_2$, cooled to 0° C., treated with 1 M tetra-n-butylammonium fluoride in tetrahydrofuran (1637 μl, 1.637 mmol) and stirred at 0° C. for 1 hour. The mixture was partitioned between methyl tert-butyl ether (50 mL) and 5% citric acid solution (25 mL). The methyl tert-butyl ether layer was washed with brine, dried ($MgSO_4$), filtered, and concentrated. The residue was chromatographed on silica gel, eluting with a gradient of 15% to 100% ethyl acetate in heptanes to provide more of the title compound. The two portions of title compound were combined to provide 192 mg of title compound. $^1$H NMR (501 MHz, $CDCl_3$) δ 13.00 (s, 1H), 9.18 (d, J=1.6 Hz, 1H), 8.22 (dd, J=8.2, 2.1 Hz, 1H), 7.58 (d, J=8.2 Hz, 1H), 7.54 (d, J=9.1 Hz, 1H), 6.63 (d, J=2.4 Hz, 1H), 6.54 (t, J=73.1 Hz, 1H), 6.47 (dd, J=9.0, 2.5 Hz, 1H), 5.33 (q, J=5.3 Hz, 1H), 4.90 (d, J=5.3 Hz, 1H), 3.96 (s, 3H), 3.80-3.74 (m, 2H), 1.40 (s, 9H); LC/MS (ESI+) m/z 471 (M+H)$^+$.

Example 151D methyl 6-[(2R,4E)-7-(difluoromethoxy)-4-{[(S)-2-methylpropane-2-sulfinyl]imino}-3,4-dihydro-2H-1-benzopyran-2-yl]pyridine-3-carboxylate A solution of Example 151C (192 mg, 0.408 mmol) and triphenylphosphine (128 mg, 0.490 mmol) in $CH_2Cl_2$ (4 mL) at 0° C. under $N_2$ was treated with a 40 weight % solution of diethyl azodicarboxylate in toluene (465 μL, 1.020 mmol), stirred at 0° C. for 5 minutes, stirred at room temperature for 30 minutes, diluted with heptanes and chromatographed on silica gel, eluting with a gradient of 15% to 50% ethyl acetate in heptanes to provide the title compound.

$^1$H NMR (400 MHz, $CDCl_3$) δ 9.18 (d, J=1.5 Hz, 1H), 8.37 (dd, J=8.2, 2.1 Hz, 1H), 8.03 (d, J=9.4 Hz, 1H), 7.68 (d, J=8.2 Hz, 1H), 6.81-6.77 (m, 2H), 6.58 (t, J=73.0 Hz, 1H), 5.41 (dd, J=12.5, 2.9 Hz, 1H), 4.03-3.95 (m, 4H), 3.31 (dd, J=17.6, 12.5 Hz, 1H), 1.30 (s, 9H); LC/MS (ESI+) m/z 453 (M+H)$^+$.

Example 151E methyl 6-[(2R,4R)-4-amino-7-(difluoromethoxy)-3,4-dihydro-2H-1-benzopyran-2-yl]pyridine-3-carboxylate A solution of Example 151D (136 mg, 0.301 mmol) in methanol (5 mL) was cooled to 0° C., treated with $NaBH_4$ (22.74 mg, 0.601 mmol), stirred at 0° C. for 15 minutes, treated with more $NaBH_4$ (22.74 mg, 0.601 mmol), stirred at 0° C. for 15 minutes, treated with 4 M HCl in dioxane (1052 μL, 4.21 mmol), stirred at room temperature for 15 minutes, and partitioned between methyl tert-butyl ether (30 mL) and water (15 mL). The layers were separated and the methyl tert-butyl ether layer was extracted with 1 M HCl (5 mL). The combined aqueous layers were basified with solid $NaHCO_3$ and extracted twice with ethyl acetate (30 mL and 15 mL). These ethyl acetate layers were combined, washed with brine, dried ($MgSO_4$), filtered and concentrated to provide the title compound (98 mg, 0.280 mmol, 93% yield). $^1$H NMR (500 MHz, $CDCl_3$) δ 9.17 (d, J=1.0 Hz, 1H), 8.36 (dd, J=8.2, 2.0 Hz, 1H), 7.69 (d, J=8.2 Hz, 1H), 7.53 (d, J=8.4 Hz, 1H), 6.75 (q, J=8.4, 1.8 Hz, 1H), 6.72 (d, J=1.0 Hz, 1H), 6.50 (t, J=74.0 Hz, 1H), 5.33 (d, J=10.6 Hz, 1H), 4.34-4.28 (m, 1H), 3.96 (s, 3H), 2.72 (dd, J=13.0, 4.0 Hz, 1H), 1.94 (s, 2H), 1.85 (q, J=11.4 Hz, 1H); LC/MS (ESI+) m/z 334 (M−$NH_3$)$^+$.

Example 151F methyl 6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylate A solution of Example 151E (62 mg, 0.177 mmol) and triethylamine (49.3 µL, 0.354 mmol) in $CH_2Cl_2$ (2 mL) at 0° C. under $N_2$ was treated with a solution of Example 134F (58.7 mg, 0.212 mmol) in $CH_2Cl_2$ (0.5 mL). The mixture was stirred at 0° C. for 30 minutes, stirred at room temperature for 30 minutes, treated with 5 drops of 37% $NH_4OH$ solution and stirred at room temperature for 2 min. The mixture was partitioned between ethyl acetate (50 mL) and $NaHCO_3$ (10 mL). The ethyl acetate layer was washed with brine, dried ($MgSO_4$), filtered, and concentrated to provide the title compound.

Example 151G

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid A solution of Example 151F (105 mg, 0.177 mmol) in tetrahydrofuran (1.5 mL) was diluted with methanol (1.5 mL), treated with 1 M NaOH (about 1 mL), stirred at room temperature for 15 minutes, treated with 1 M HCl (2 mL) and extracted with ethyl acetate (30 mL). The ethyl acetate layer was washed with brine, dried ($MgSO_4$), filtered, and concentrated. The residue was chromatographed on silica gel, eluting with a gradient of 50% to 100% [200:1:1 ethyl acetate:HCOOH:$H_2O$] in heptane to provide impure product. The product was chromatographed again on silica gel, eluting with a gradient of 50% to 100% ethyl acetate in $CH_2Cl_2$, followed by eluting with 200:1:1 ethyl acetate:HCOOH:$H_2O$ to provide the title compound. $^1H$ NMR (501 MHz, DMSO-$d_6$) δ 9.06 (dd, J=2.1, 0.8 Hz, 1H), 8.37 (dd, J=8.1, 2.2 Hz, 1H), 8.08 (d, J=8.7 Hz, 1H), 7.72 (d, J=8.1 Hz, 1H), 7.47 (s, 1H), 7.23 (t, J=74.1 Hz, 1H), 7.19 (dd, J=8.4, 0.6 Hz, 1H), 6.99 (s, 1H), 6.78 (dd, J=8.4, 2.5 Hz, 1H), 6.76 (d, J=2.4 Hz, 1H), 5.51 (dd, J=11.8, 1.8 Hz, 1H), 5.40 (ddd, J=11.2, 8.6, 6.3 Hz, 1H), 5.03 (d, J=9.0 Hz, 1H), 4.34 (d, J=9.0 Hz, 1H), 2.38 (ddd, J=13.0, 6.0, 1.9 Hz, 1H), 2.15-2.07 (m, 1H), 1.58 (s, 3H); LC/MS (ESI+) m/z 577 (M+H)$^+$.

Example 152 ethyl trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylate

Example 152A methyl trans-4-(7-methoxy-4-oxo-3,4-dihydro-2H-1-benzopyran-2-yl)cyclohexane-1-carboxylate A solution of 1-(2-hydroxy-4-methoxyphenyl)ethanone (0.703 g, 4.23 mmol) and methyl trans-4-formylcyclohexane-1-carboxylate (0.72 g, 4.23 mmol) in methanol (15 mL) was treated with pyrrolidine (0.700 mL, 8.46 mmol) and the mixture was stirred at 60° C. for 90 minutes. The mixture was concentrated to dryness and the residue was partitioned between ethyl acetate (30 mL) and 1 M HCl (20 mL). The ethyl acetate layer was washed with saturated $NaHCO_3$ solution and brine, dried ($MgSO_4$), filtered, and concentrated. The residue was chromatographed on silica gel, eluting with a gradient of 10% to 30% ethyl acetate in heptanes to provide the title compound as the second eluting isomer. $^1H$ NMR (400 MHz, CDCl$_3$) δ 7.80 (d, J=8.8 Hz, 1H), 6.56 (dd, J=8.8, 2.3 Hz, 1H), 6.40 (d, J=2.3 Hz, 1H), 4.19 (ddd, J=12.7, 6.0, 3.2 Hz, 1H), 3.83 (s, 3H), 3.67 (s, 3H), 2.68 (dd, J=16.6, 12.8 Hz, 1H), 2.58 (dd, J=16.6, 3.2 Hz, 1H), 2.29 (tt, J=12.2, 3.4 Hz, 1H), 2.15-2.05 (m, 3H), 1.90-1.82 (m, 1H), 1.79-1.65 (m, 1H), 1.57-1.39 (m, 2H), 1.31-1.11 (m, 2H); LC/MS (ESI+) m/z 319 (M+H)$^+$.

Example 152B ethyl trans-4-[(2S,4E)-7-methoxy-4-{[(R)-2-methylpropane-2-sulfinyl]imino}-3,4-dihydro-2H-1-benzopyran-2-yl]cyclohexane-1-carboxylate and ethyl trans-4-[(2R,4E)-7-methoxy-4-{[(R)-2-methylpropane-2-sulfinyl]imino}-3,4-dihydro-2H-1-benzopyran-2-yl]cyclohexane-1-carboxylate A mixture of Example 152A (0.78 g, 2.450 mmol) and (R)-(+)-2-methyl-2-propanesulfinamide (0.297 g, 2.450 mmol) in toluene (25 mL) was treated with titanium(IV) ethoxide (2.235 g, 9.80 mmol) and stirred at 90° C. for 5 hours, heated at 110° C. for 4 hours, and cooled to room temperature. The mixture was diluted with ethyl acetate (25 mL), treated with water (25 mL), stirred for 5 minutes, and filtered through diatomaceous earth to remove the solids. The ethyl acetate layer washed with brine, dried ($MgSO_4$), filtered, and concentrated. The residue was chromatographed on silica gel, eluting with a gradient of 10% to 50% ethyl acetate in heptanes. The chromatography only partially separated the isomers, and provided 0.34 g of a product enriched in ethyl trans-4-[(2S,4E)-7-methoxy-4-{[(R)-2-methylpropane-2-sulfinyl]imino}-3,4-dihydro-2H-1-benzopyran-2-yl]cyclohexane-1-carboxylate as the first eluting isomer [$^1H$ NMR (400 MHz, CDCl$_3$) δ 7.88 (d, J=8.9 Hz, 1H), 6.53 (dd, J=8.9, 2.3 Hz, 1H), 6.37 (d, J=2.5 Hz, 1H), 4.12 (q, J=7.1 Hz, 2H), 3.96 (ddd, J=12.5, 6.0, 2.7 Hz, 1H), 3.81 (s, 3H), 3.44 (dd, J=17.2, 2.6 Hz, 1H), 2.97 (dd, J=17.2, 12.6 Hz, 1H), 2.25 (tt, J=12.0, 3.2 Hz, 1H), 2.13-2.02 (m, 3H), 1.95-1.87 (m, 1H), 1.74-1.65 (m, 1H), 1.54-1.38 (m, 2H), 1.34-1.12 (m, 14H); LC/MS (ESI+) m/z 436 (M+H)$^+$], and 0.42 g of a product enriched in ethyl trans-4-[(2R,4E)-7-methoxy-4-{[(R)-2-methylpropane-2-sulfinyl]imino}-3,4-dihydro-2H-1-benzopyran-2-yl]cyclohexane-1-carboxylate as the second eluting isomer [$^1H$ NMR (400 MHz, CDCl$_3$) δ 7.92 (d, J=8.9 Hz, 1H), 6.54 (dd, J=8.9, 2.4 Hz, 1H), 6.37 (d, J=2.4 Hz, 1H), 4.12 (q, J=7.1 Hz, 2H), 4.02 (ddd, J=12.2, 6.1, 2.7 Hz, 1H), 3.81 (s, 3H), 3.76 (dd, J=16.7, 2.7 Hz, 1H), 2.66 (dd, J=16.7, 12.2 Hz, 1H), 2.26 (tt, J=12.1, 3.3 Hz, 1H), 2.12-2.02 (m, 3H), 1.91-1.83 (m, 1H), 1.72-1.65 (m, 1H), 1.53-1.37 (m, 2H), 1.33-1.12 (m, 14H); LC/MS (ESI+) m/z 436 (M+H)$^+$].

Example 152C ethyl trans-4-[(2S,4S)-7-methoxy-4-{[(R)-2-methylpropane-2-sulfinyl]amino}-3,4-dihydro-2H-1-benzopyran-2-yl]cyclohexane-1-carboxylate A solution of the product from Example 152B enriched in ethyl trans-4-[(2S,4E)-7-methoxy-4-{[(R)-2-methylpropane-2-sulfinyl]imino}-3,4-dihydro-2H-1-benzopyran-2-yl]

cyclohexane-1-carboxylate (0.33 g, 0.758 mmol) in ethanol (8 mL) was cooled to 0° C., treated with NaBH$_4$ (0.057 g, 1.515 mmol), stirred at 0° C. for 30 minutes, stirred at room temperature for 45 minutes, treated with more NaBH$_4$ (0.057 g, 1.515 mmol), and stirred overnight. The mixture was partitioned between ethyl acetate (50 mL) and saturated NaHCO$_3$ solution (15 mL). The layers were separated and the aqueous layer was extracted with ethyl acetate (25 mL). The combined ethyl acetate layers were washed with brine, dried (MgSO$_4$), filtered, and concentrated. The residue was chromatographed on silica gel, eluting with a gradient of 0%-50% ethyl acetate in [9:1 CH$_2$Cl$_2$: ethyl acetate] to provide the title compound (157 mg) as the second eluting isomer. $^1$H NMR (501 MHz, CDCl$_3$) δ 7.27 (dd, J=8.4, 0.9 Hz, 1H), 6.47 (dd, J=8.6, 2.6 Hz, 1H), 6.34 (d, J=2.6 Hz, 1H), 4.54 (td, J=10.8, 6.1 Hz, 1H), 4.12 (q, J=7.1 Hz, 2H), 3.91-3.84 (m, 1H), 3.76 (s, 3H), 3.23 (dd, J=37.5, 12.5 Hz, 1H), 2.58 (ddd, J=13.3, 6.0, 1.3 Hz, 1H), 2.24 (tt, J=12.3, 3.5 Hz, 1H), 2.09-2.00 (m, 3H), 1.92-1.84 (m, 1H), 1.74 (dt, J=13.2, 11.5 Hz, 1H), 1.64-1.56 (m, 1H), 1.51-1.39 (m, 2H), 1.31-1.13 (m, 14H); LC/MS (ESI+) m/z 317 (100%) (M−tBuSONH$_2$)$^+$, 438 (30%) (M+H)$^+$.

Example 152D ethyl trans-4-[(2S,4S)-4-amino-7-methoxy-3,4-dihydro-2H-1-benzopyran-2-yl]cyclohexane-1-carboxylate A solution of Example 152C (157 mg, 0.359 mmol) in ethanol (9 mL) was cooled to 0° C., treated with 4 M HCl in dioxane (897 µL, 3.59 mmol), stirred at 0° C. for 20 minutes, diluted with ethyl acetate (30 mL) and washed with saturated NaHCO$_3$ solution (15 mL). The ethyl acetate layer was washed with brine, dried (MgSO$_4$), filtered and concentrated. The residue was dissolved in CH$_2$Cl$_2$ (1.5 mL). After standing over night, the residue contained a solid. The residue was treated with CH$_2$Cl$_2$ (3 mL) and filtered through diatomaceous earth to remove the solid. The filtrate was concentrated to dryness to provide the title compound. $^1$H NMR (400 MHz, CDCl$_3$) δ 7.32 (d, J=8.6 Hz, 1H), 6.49 (dd, J=8.6, 2.6 Hz, 1H), 6.34 (d, J=2.6 Hz, 1H), 4.13 (q, J=7.1 Hz, 2H), 4.07 (dd, J=11.2, 5.9 Hz, 1H), 3.86 (dd, J=11.5, 5.5 Hz, 1H), 3.76 (s, 3H), 2.26 (tt, J=12.2, 3.3 Hz, 1H), 2.21-2.15 (m, 1H), 2.14-2.03 (m, 5H), 1.90-1.84 (m, 1H), 1.66-1.54 (m, 2H), 1.54-1.40 (m, 2H), 1.32-1.11 (m, 5H); LC/MS (ESI+) m/z 317 (M−NH$_3$)$^+$.

Example 152E ethyl trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylate A solution of Example 152D (50.5 mg, 0.151 mmol) and triethylamine (42.2 µL, 0.303 mmol) in CH$_2$Cl$_2$ (1 mL) was cooled to 0° C. under N$_2$, treated with a solution of Example 134F (50.3 mg, 0.182 mmol) in CH$_2$Cl$_2$ (about 0.5 mL), stirred at 0° C. for 5 minutes and then at room temperature for 15 minutes. The mixture was treated with 37% NH$_4$OH solution (5 drops) and stirred for 5 minutes, diluted with ethyl acetate (30 mL), washed with 1 M HCl (5 mL), washed with saturated NaHCO$_3$ solution (5 mL), washed with brine, dried (MgSO$_4$), filtered, and concentrated. The residue was chromatographed on silica gel, eluting with a gradient of 15% to 50% ethyl acetate in heptanes to provide the title compound (72.2 mg, 0.126 mmol, 83% yield). $^1$H NMR (400 MHz, CDCl$_3$) δ 6.86 (s, 1H), 6.82 (d, J=8.6 Hz, 1H), 6.64 (s, 1H), 6.43 (dd, J=8.6, 2.4 Hz, 1H), 6.33 (d, J=2.4 Hz, 1H), 5.56 (d, J=8.7 Hz, 1H), 5.27-5.18 (m, 1H), 4.95 (d, J=9.2 Hz, 1H), 4.36 (d, J=9.2 Hz, 1H), 4.12 (q, J=7.0 Hz, 2H), 3.88 (dd, J=11.2, 5.6 Hz, 1H), 3.73 (s, 3H), 2.30-2.21 (m, 2H), 2.11-1.99 (m, 3H), 1.88-1.79 (m, 1H), 1.67-1.53 (m, 4H), 1.52-1.37 (m, 3H), 1.29-1.08 (m, 5H); MS (ESI−) m/z 572 (M−H)$^-$.

Example 153 ethyl trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylate Example 153A ethyl trans-4-[(2R,4R)-7-methoxy-4-{[(R)-2-methylpropane-2-sulfinyl]amino}-3,4-dihydro-2H-1-benzopyran-2-yl]cyclohexane-1-carboxylate A solution of the product from 152B enriched in ethyl trans-4-[(2R,4E)-7-methoxy-4-{[(R)-2-methylpropane-2-sulfinyl]imino}-3,4-dihydro-2H-1-benzopyran-2-yl]cyclohexane-1-carboxylate (0.42 g, 0.964 mmol) in ethanol (10 mL) was cooled to 0° C., treated with NaBH$_4$ (0.073 g, 1.928 mmol), stirred at 0° C. for 30 minutes, stirred at room temperature for 45 minutes, treated with more NaBH$_4$ (50 mg), and stirred overnight. The mixture was partitioned between ethyl acetate (50 mL) and saturated NaHCO$_3$ solution (15 mL). The layers were separated and the aqueous was extracted with ethyl acetate (25 mL). The combined ethyl acetate layers were washed with brine, dried (MgSO$_4$), filtered, concentrated and chromatographed on silica gel eluting with a gradient of 0%-50% ethyl acetate in [9:1 CH$_2$Cl$_2$: ethyl acetate] the title compound (191 mg, 0.436 mmol, 45.3% yield) as the first eluting isomer. $^1$H NMR (400 MHz, CDCl$_3$) δ 7.50 (d, J=8.7 Hz, 1H), 6.52 (dd, J=8.6, 2.6 Hz, 1H), 6.34 (d, J=2.6 Hz, 1H), 4.61 (dt, J=11.3, 6.7 Hz, 1H), 4.13 (q, J=7.1 Hz, 2H), 3.86 (dd, J=10.5, 5.6 Hz, 1H), 3.76 (s, 3H), 3.47 (d, J=7.3 Hz, 1H), 2.32-2.16 (m, 2H), 2.11-2.04 (m, 3H), 1.90-1.84 (m, 1H), 1.84-1.73 (m, 1H), 1.68-1.55 (m, 1H), 1.54-1.39 (m, 2H), 1.32-1.12 (m, 14H); LC/MS (ESI+) m/z 317 (100%) (M−tBuSONH$_2$)$^+$, 438 (30%) (M+H)$^+$.

Example 153B ethyl trans-4-[(2R,4R)-4-amino-7-methoxy-3,4-dihydro-2H-1-benzopyran-2-yl]cyclohexane-1-carboxylate A solution of Example 153A (191 mg, 0.436 mmol) in ethanol (11 mL) was cooled to 0° C., treated with 4 M HCl in dioxane (1091 µL, 4.36 mmol), stirred at room temperature for 20 minutes, diluted with ethyl acetate (30 mL) and washed with saturated NaHCO$_3$ solution (15 mL). The ethyl acetate layer was washed with brine, dried (MgSO$_4$), filtered, and concentrated. The residue was dissolved in CH$_2$Cl$_2$ (1.5 mL). After standing over night, the residue contained a solid. The residue was treated with CH$_2$Cl$_2$ (3 mL) and filtered through diatomaceous earth to remove the solid. The filtrate was concentrated to dryness to provide the title compound. $^1$H NMR (400 MHz, CDCl$_3$) δ 7.32 (d, J=8.6 Hz, 1H), 6.50 (dd, J=8.6, 2.6 Hz, 1H), 6.34 (d, J=2.6

Hz, 1H), 4.13 (q, J=7.2 Hz, 2H), 4.07 (dd, J=11.3, 6.0 Hz, 1H), 3.86 (dd, J=11.5, 5.5 Hz, 1H), 3.76 (s, 3H), 2.26 (tt, J=12.2, 3.3 Hz, 1H), 2.21-2.15 (m, 1H), 2.12-2.02 (m, 5H), 1.90-1.83 (m, 1H), 1.65-1.55 (m, 1H), 1.54-1.40 (m, 3H), 1.31-1.12 (m, 5H); LC/MS (ESI+) m/z 317 (M−NH$_3$)$^+$.

Example 153C ethyl trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylate A solution of Example 153B (77.4 mg, 0.232 mmol) and triethylamine (64.7 µL, 0.464 mmol) in CH$_2$Cl$_2$ (1 mL) was cooled to 0° C. under N$_2$, treated with a solution of Example 134F (77 mg, 0.279 mmol) in CH$_2$Cl$_2$ (about 0.5 mL), stirred at 0° C. for 25 minutes and then at room temperature for 15 minutes. The mixture was cooled to 0° C., treated with 37% NH$_4$OH solution (5 drops) and stirred for 5 minutes. The mixture was diluted with ethyl acetate (30 mL), washed with 1 M HCl (5 mL), washed with saturated NaHCO$_3$ solution (5 mL), washed with brine, dried (MgSO$_4$), filtered, and concentrated. The residue was chromatographed on silica gel eluting with a gradient of 15% to 50% ethyl acetate in heptanes to provide the title compound (104 mg, 0.181 mmol, 78% yield). $^1$H NMR (400 MHz, CDCl$_3$) δ 6.91 (s, 1H), 6.76 (d, J=8.6 Hz, 1H), 6.62 (s, 1H), 6.43 (dd, J=8.6, 2.5 Hz, 1H), 6.33 (d, J=2.5 Hz, 1H), 5.60 (d, J=8.7 Hz, 1H), 5.26-5.15 (m, 1H), 4.88 (d, J=9.3 Hz, 1H), 4.34 (d, J=9.3 Hz, 1H), 4.12 (q, J=7.1 Hz, 2H), 3.87 (dd, J=11.2, 5.4 Hz, 1H), 3.74 (s, 3H), 2.28-2.20 (m, 2H), 2.09-1.98 (m, 3H), 1.86-1.79 (m, 1H), 1.66 (s, 3H), 1.62-1.53 (m, 1H), 1.52-1.38 (m, 3H), 1.25 (t, J=7.1 Hz, 3H), 1.25-1.07 (m, 2H); MS (ESI−) m/z 572 (M−H)$^-$.

Example 154 trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid A solution of Example 152E (53.3 mg, 0.093 mmol) in tetrahydrofuran (1.5 mL) was diluted with methanol (1.5 mL), treated with 1 M NaOH (about 0.5 mL), stirred at 55° C. for 30 minutes, cooled, treated with 1 M HCl (3 mL), and extracted with ethyl acetate (30 mL). The ethyl acetate layer was washed with brine, dried (MgSO$_4$), filtered, and concentrated to provide the title compound (48.8 mg, 0.089 mmol, 96% yield). $^1$H NMR (400 MHz, CDCl$_3$) δ 6.86 (s, 1H), 6.82 (d, J=8.6 Hz, 1H), 6.64 (s, 1H), 6.43 (dd, J=8.6, 2.5 Hz, 1H), 6.33 (d, J=2.5 Hz, 1H), 5.56 (d, J=8.8 Hz, 1H), 5.27-5.19 (m, 1H), 4.95 (d, J=9.2 Hz, 1H), 4.36 (d, J=9.2 Hz, 1H), 3.89 (dd, J=10.9, 5.4 Hz, 1H), 3.74 (s, 3H), 2.37-2.22 (m, 2H), 2.16-2.06 (m, 3H), 1.89-1.82 (m, 1H), 1.63 (s, 3H), 1.62-1.55 (m, 1H), 1.54-1.40 (m, 3H), 1.32-1.12 (m, 2H); MS (ESI−) m/z 544 (M−H)$^-$.

Example 155 trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid A solution of Example 153C (97.7 mg, 0.170 mmol) in tetrahydrofuran (1.5 mL) was diluted with methanol (1.5 mL), added 1 M NaOH (about 0.5 mL), stirred at 55° C. for 30 minutes, cooled, treated with 1 M HCl (3 mL), and extracted with ethyl acetate (30 mL). The ethyl acetate layer was washed with brine, dried (MgSO$_4$), filtered, and concentrated. The residue was chromatographed on silica gel, eluting with a gradient of 15% to 100% [200:1:1 ethyl acetate:HCOOH:H$_2$O] in heptanes to provide the title compound (83.3 mg, 0.153 mmol, 90% yield). $^1$H NMR (400 MHz, CDCl$_3$) δ 6.91 (s, 1H), 6.77 (d, J=8.6 Hz, 1H), 6.62 (s, 1H), 6.43 (dd, J=8.6, 2.4 Hz, 1H), 6.33 (d, J=2.4 Hz, 1H), 5.61 (d, J=8.7 Hz, 1H), 5.26-5.17 (m, 1H), 4.88 (d, J=9.3 Hz, 1H), 4.34 (d, J=9.3 Hz, 1H), 3.88 (dd, J=11.2, 5.4 Hz, 1H), 3.75 (s, 3H), 2.35-2.21 (m, 2H), 2.14-2.01 (m, 3H), 1.88-1.81 (m, 1H), 1.67 (s, 3H), 1.62-1.53 (m, 1H), 1.53-1.40 (m, 3H), 1.32-1.10 (m, 2H); MS (ESI−) m/z 544 (M−H)$^-$.

Example 156 ethyl trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate Example 156A 1-(4-(difluoromethoxy)-2-hydroxyphenyl)ethan-1-one A suspension of 2',4'-dihydroxyacetophenone (4.57 g, 30.0 mmol) and powdered potassium carbonate (6.22 g, 45.0 mmol) were stirred under nitrogen in N,N-dimethylformamide (10 mL) and water (3.0 mL [deoxygenated by bubbling nitrogen through the water overnight]) for about ten minutes to give a suspension that was heated to 90° C. Then a solution of sodium chlorodifluoroacetate (5.03 g, 33.0 mmol) in N,N-dimethylformamide (20 mL) was added slowly to the hot mixture over 30 minutes. The suspension became very thick and was occasionally hand swirled. The mixture was heated at 90° C. for 4 hours, cooled to room temperature, slowly quenched with 1 M aqueous citric acid (30 mL) and extracted thrice with methyl tert-butyl ether. The combined organic phases were washed with 0.1 M aqueous citric acid (20 mL) then with brine, dried (Na$_2$SO$_4$), filtered, and concentrated. The residue was chromatographed on silica gel (eluted with 10 to 15% methyl tert-butyl ether/heptanes) to give 3.14 g of a clear oil (52%). $^1$H NMR (400 MHz, CDCl$_3$) δ 12.53 (s, 1H), 7.74 (d, J=8.8 Hz, 1H), 6.67 (d, J=2.5 Hz, 1H), 6.63 (t, J=8.8, 2.5 Hz, 1H), 6.59 (t, J=72.9 Hz, 1H), 2.61 (s, 3H); MS (DCI) m/z 203 (M+H)$^+$.

Example 156B methyl trans-4-[7-(difluoromethoxy)-4-oxo-3,4-dihydro-2H-1-benzopyran-2-yl]cyclohexane-1-carboxylate Example 156A (607 mg, 3.00 mmol) and trans-methyl 4-formylcyclohexanecarboxylate (562 mg, 3.3 mmol) were stirred together, mixed with 15% tetra-n-butylammonium fluoride on alumina (3.0 g), placed under nitrogen, wet with (trifluoromethyl)benzene (300 µL) and stirred at 65° C. for one hour, then cooled to room temperature. The flask was flushed with nitrogen overnight to evaporate water droplets which had formed. More (trifluoromethyl)benzene (300 µL) was added and the reaction mixture was heated at 65° C. for forty minutes. The syrupy slurry was mixed with neutral alumina and filtered with a CH$_2$Cl$_2$ rinse followed by dilute acetic acid in CH$_2$Cl$_2$. The filtrate was concentrated and chromatographed on silica (eluted with 20 to 30% methyl tert-butyl ether/heptanes) to give 428 mg of a pale yellow crystalline solid (40%). $^1$H NMR (501 MHz, CDCl$_3$) δ 7.88 (d, J=8.7 Hz, 1H), 6.74 (dd, J=8.7, 2.3 Hz, 1H), 6.69 (d, J=2.3 Hz, 1H), 6.58 (t, J=72.9 Hz, 1H), 4.24 (ddd, J=12.9, 6.0, 3.2 Hz, 1H), 3.68 (s, 3H), 2.72 (dd, J=16.6, 12.9 Hz, 1H), 2.64 (dd, J=16.6, 3.2 Hz, 1H), 2.30 (II, J=12.4, 3.4 Hz, 1H), 2.14-2.07 (m, 3H), 1.90-1.84 (m, 1H), 1.78-1.70 (m, 1H), 1.55-1.43 (m, 2H), 1.31-1.15 (m, 2H); MS (DCI) m/z 372 (M+NH$_4$)$^+$.

Example 156C ethyl trans-4-[(2S,4E)-7-(difluoromethoxy)-4-{[(R)-2-methylpropane-2-sulfinyl]imino}-3,4-dihydro-2H-1-benzopyran-2-yl]cyclohexane-1-carboxylate Example 156B (422 mg, 1.19 mmol) and (R)-tert-butylsulfinamide (202 mg, 1.67 mmol) were placed under nitrogen, dissolved into anhydrous 2-methyltetrahydrofuran (2.5 mL). The mixture was treated with titanium(IV) ethoxide (technical grade, 750 4<3.6 mmol) and heated at 75° C. for four hours. The reaction mixture was brought to room temperature, diluted with ethyl acetate and brine, and swirled well. The solids were removed by filtration through diatomaceous earth with a thorough ethyl acetate rinse. The filtrate was concentrated and chromatographed on silica (eluted with 15 to 25% ethyl acetate/heptane) to provide the title compound (233 mg) as the first eluting isomer. $^1$H NMR (501 MHz, CDCl$_3$) δ 7.95 (d, J=8.8 Hz, 1H), 6.71 (dd, J=8.8, 2.3 Hz, 1H), 6.65 (d, J=2.3 Hz, 1H), 6.52 (t, J=73.2 Hz, 1H), 4.13 (q, J=7.1 Hz, 2H), 3.99 (ddd, J=12.6, 6.0, 2.7 Hz, 1H), 3.54 (dd, J=17.3, 2.7 Hz, 1H), 3.00 (dd, J=17.3, 12.6 Hz, 1H), 2.26 (tt, J=12.3, 3.4 Hz, 1H), 2.11-2.05 (m, 3H), 1.94-1.88 (m, 1H), 1.73-1.65 (m, 1H), 1.51-1.39 (m, 2H), 1.31 (s, 9H), 1.29-1.16 (m, 5H); MS (DCI) m/z 489 (M+NH$_4$)$^+$.

Example 156D ethyl trans-4-[(2R,4E)-7-(difluoromethoxy)-4-{[(R)-2-methylpropane-2-sulfinyl]imino}-3,4-dihydro-2H-1-benzopyran-2-yl]cyclohexane-1-carboxylate The title compound (190 mg) was obtained as the second eluting isomer from the chromatography separation described in Example 156C. $^1$H NMR (501 MHz, CDCl$_3$) δ 7.98 (d, J=8.8 Hz, 1H), 6.71 (dd, J=8.8, 2.4 Hz, 1H), 6.65 (d, J=2.4 Hz, 1H), 6.48 (t, J=73.2 Hz, 1H), 4.13 (q, J=7.1 Hz, 2H), 4.05 (ddd, J=12.2, 6.1, 2.7 Hz, 1H), 3.86 (dd, J=16.8, 2.7 Hz, 1H), 2.71 (dd, J=16.8, 12.2 Hz, 1H), 2.26 (tt, J=12.4, 3.4 Hz, 1H), 2.11-2.05 (m, 3H), 1.89-1.83 (m, 1H), 1.72-1.64 (m, 1H), 1.52-1.39 (m, 2H), 1.31 (s, 9H), 1.28-1.17 (m, 5H); MS (DCI) m/z 489 (M+NH$_4$)$^+$.

Example 156E ethyl trans-4-[(2R,4R)-4-amino-7-(difluoromethoxy)-3,4-dihydro-2H-1-benzopyran-2-yl]cyclohexane-1-carboxylate A solution of the product from Example 156D (188 mg, 0.40 mmol) in ethanol (4 mL) was cooled with a 0° C. bath and treated with NaBH$_4$ (45 mg, 1.2 mmol). The reaction mixture was stirred for 40 minutes in the bath and then at room temperature for one hour and 45 minutes. 4 M HCl in diethyl ether (800 µL, 3 mmol) was added. The mixture was stirred at room temperature for more than four hours and then concentrated. The residue was partitioned between methyl tert-butyl ether and 1 M aqueous Na$_2$CO$_3$. The organic phase was separated, dried (Na$_2$SO$_4$), filtered, and concentrated to provide the title compound (138 mg (94%)). $^1$H NMR (501 MHz, CDCl$_3$) δ 7.41 (d, J=8.5 Hz, 1H), 6.67 (dd, J=8.5, 2.4 Hz, 1H), 6.55 (d, J=2.4 Hz, 1H), 6.47 (t, J=74.2 Hz, 1H), 4.13 (q, J=7.1 Hz, 2H), 4.08-3.97 (m, 1H), 3.90 (dd, J=11.5, 5.4 Hz, 1H), 2.26 (tt, J=12.3, 3.6 Hz, 1H), 2.17 (dd, J=13.0, 5.7 Hz, 1H), 2.11-2.02 (m, 3H), 1.90-1.82 (m, 1H), 1.66-1.12 (m, 9H); MS (ESI+) m/z 353 (M−NH$_3$)$^+$.

Example 156F ethyl trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate A solution of the product from Example 156E (137 mg, 0.37 mmol) and triethylamine (103 µL, 0.74 mmol) in anhydrous dichloromethane (3.0 mL) was cooled in a water-ice bath, followed by dropwise addition of a solution of Example 134F (123 mg, 0.44 mmol) in dichloromethane (1.0 mL). The solution was stirred in the bath for 20 minutes. The bath was then removed and the mixture was stirred for another 20 minutes, then quenched with concentrated aqueous NH$_4$OH (100 µL). The aqueous phase was separated and extracted with CH$_2$Cl$_2$. The combined organic phases were concentrated and the residue was chromatographed on silica gel (eluted with 30 to 45% methyl tert-butyl ether/heptane) to give 178 mg of a white foam (79%). $^1$H NMR (400 MHz, CDCl$_3$) δ 6.91 (s, 1H), 6.84 (d, J=8.5 Hz, 1H), 6.64 (s, 1H), 6.60 (dd, J=8.5, 2.4 Hz, 1H), 6.57 (d, J=2.4 Hz, 1H), 6.45 (t, J=73.8 Hz, 1H), 5.62 (d, J=8.8 Hz, 1H), 5.29-5.20 (m, 1H), 4.89 (d, J=9.3 Hz, 1H), 4.35 (d, J=9.3 Hz, 1H), 4.12 (q, J=7.1 Hz, 2H), 3.94-3.87 (m, 1H), 2.28-2.20 (m, 2H), 2.09-1.98 (m, 3H), 1.86-1.77 (m, 1H), 1.67 (s, 3H), 1.62-1.37 (m, 4H), 1.3-1.08 (m, 5H); MS (ESI+) m/z 610 (M+H)$^+$.

Example 157 ethyl cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate Example 157A ethyl cis-4-[(2S,4E)-4-{[(S)-2-methylpropane-2-sulfinyl]imino}-7-(trifluoromethoxy)-3,4-dihydro-2H-1-benzopyran-2-yl]cyclohexane-1-carboxylate and ethyl cis-4-[(2R,4E)-4-{[(S)-2-methylpropane-2-sulfinyl]imino}-7-(trifluoromethoxy)-3,4-dihydro-2H-1-benzopyran-2-yl]cyclohexane-1-carboxylate A mixture of Example 147A (0.81 g, 2.175 mmol) and (S)-(−)-2-methyl-2-propanesulfinamide (0.527 g, 4.35 mmol) in toluene (20 mL) was treated with titanium(IV) ethoxide (1.985 g, 8.70 mmol), stirred at 100° C. for 3 hours, cooled, diluted with ethyl acetate (100 mL), treated with water (100 mL), stirred for 5 minutes and filtered through diatomaceous earth to remove the solids. The ethyl acetate layer was washed with brine, dried (MgSO$_4$), filtered, and concentrated to provide the title compounds. $^1$H NMR (501 MHz, CDCl$_3$) 7.98 (d, J=8.4 Hz, 0.5H), 7.96 (d, J=8.5 Hz, 0.5H), 6.81-6.77 (m, 1H), 6.77-6.75 (m, 1H), 4.15 (q, J=7.1 Hz, 1H), 4.15 (q, J=7.1 Hz, 1H), 4.13-4.09 (m, 0.5H), 4.04 (ddd, J=12.1, 7.1, 2.7 Hz, 0.5H), 3.85 (dd, J=16.8, 2.8 Hz, 0.5H), 3.54 (dd, J=17.3, 2.7 Hz, 0.5H), 2.99 (dd, J=17.3, 12.2 Hz, 0.5H), 2.73 (dd, J=16.9, 11.8 Hz, 0.5H), 2.63-2.58 (m, 1H), 2.17-2.07 (m, 2H), 1.86-1.78 (m, 1H), 1.76-1.61 (m, 3H), 1.60-1.43 (m, 3H), 1.31 (s, 4.5H), 1.30 (s, 4.5H), 1.26 (t, J=7.1 Hz, 1.5H), 1.26 (t, J=7.1 Hz, 1.5H); LC/MS (ESI+) m/z 490 (M+H)$^+$.

Example 157B ethyl cis-4-[(2S,4S)-4-{[(S)-2-methylpropane-2-sulfinyl]amino}-7-(trifluoromethoxy)-3,4-dihydro-2H-1-benzopyran-2-yl]cyclohexane-1-carboxylate A solution of Example 157A (1065 mg, 2.175 mmol) in ethanol (20 mL) was cooled to 0° C., treated with NaBH$_4$ (165 mg, 4.35 mmol), stirred at 0° C. for 2 hours and then stirred at room temperature overnight. The mixture was concentrated on the rotary evaporator without heating to about 10 mL volume. The residue was diluted with ethyl acetate (100 mL) and washed with saturated NaHCO$_3$ solution (20 mL). The layers were separated and the aqueous layer was extracted with ethyl acetate (25 mL). The combined ethyl acetate layers were washed with brine, dried (MgSO$_4$), filtered, and concentrated. The residue was chromatographed on silica gel eluting with a gradient of 0% to 100% [1:1 ethyl acetate: CH$_2$Cl$_2$] in [9:1 CH$_2$Cl$_2$: ethyl acetate] to provide the title compound (407 mg, 0.828 mmol, 38.1% yield) as the first eluting isomer. $^1$H NMR (400 MHz, CDCl$_3$) δ 7.67 (d, J=8.6 Hz, 1H), 6.75 (d, J=8.6 Hz, 1H), 6.63 (s, 1H), 4.60 (dt, J=11.4, 7.0 Hz, 1H), 4.14 (q, J=7.1 Hz, 2H), 3.94 (dd, J=11.2, 6.2 Hz, 1H), 3.53 (d, J=8.0 Hz, 1H), 2.63-2.58 (m, 1H), 2.22 (dd, J=13.1, 6.1 Hz, 1H), 2.19-2.07 (m, 2H), 1.83-1.69 (m, 2H), 1.69-1.60 (m, 2H), 1.60-1.50 (m, 2H), 1.50-1.35 (m, 2H), 1.27-1.22 (m, 12H); LC/MS (ESI+) m/z 492 (M+H)$^+$.

Example 157C ethyl cis-4-[(2R,4R)-4-{[(S)-2-methylpropane-2-sulfinyl]amino}-7-(trifluoromethoxy)-3,4-dihydro-2H-1-benzopyran-2-yl]cyclohexane-1-carboxylate The title compound (444 mg, 0.903 mmol, 41.5% yield) was obtained as the second eluting isomer from the chromatography separation as described in Example 157B. $^1$H NMR (400 MHz, CDCl$_3$) δ 7.39 (dd, J=8.6, 0.8 Hz, 1H), 6.77-6.70 (m, 1H), 6.69-6.64 (m, 1H), 4.56 (td, J=11.0, 6.0 Hz, 1H), 4.16 (q, J=7.1 Hz, 2H), 3.97 (dd, J=10.4, 6.1 Hz, 1H), 3.27 (d, J=10.7 Hz, 1H), 2.68-2.55 (m, 2H), 2.19-2.07 (m, 2H), 1.83-1.42 (m, 8H), 1.31 (s, 9H), 1.27 (t, J=7.1 Hz, 3H); LC/MS (ESI+) m/z 492 (M+H)$^+$.

Example 157D ethyl cis-4-[(2R,4R)-4-amino-7-(trifluoromethoxy)-3,4-dihydro-2H-1-benzopyran-2-yl]cyclohexane-1-carboxylate A solution of Example 157C (444 mg, 0.903 mmol) in ethanol (10 mL) was treated with 4 M HCl in dioxane (2258 μL, 9.03 mmol), stirred for 30 minutes at room temperature, diluted with ethyl acetate (30 mL) and washed with saturated NaHCO$_3$ solution (15 mL). The ethyl acetate layer was washed with brine, dried (MgSO$_4$), filtered, and concentrated to provide the title compound. $^1$H NMR (400 MHz, CDCl$_3$) δ 7.48-7.41 (m, 1H), 6.78-6.71 (m, 1H), 6.67-6.61 (m, 1H), 4.15 (q, J=7.1 Hz, 1H), 4.06 (dd, J=11.8, 5.2 Hz, 1H), 4.00-3.90 (m, 1H), 2.62 (p, J=4.4 Hz, 1H), 2.23 (ddd, J=13.0, 5.8, 1.5 Hz, 1H), 2.18-2.08 (m, 2H), 2.04 (bs, 2H), 1.83-1.75 (m, 1H), 1.71-1.38 (m, 8H), 1.26 (t, J=7.1 Hz, 3H); LC/MS (ESI+) m/z 371 (M−NH$_3$)$^+$.

Example 157E ethyl cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate A solution of Example 157D (101 mg, 0.261 mmol) and triethylamine (72.7 μL, 0.521 mmol) in CH$_2$Cl$_2$ (1 mL) was cooled to 0° C. under N$_2$, treated with a solution of Example 134F (108 mg, 0.391 mmol) in CH$_2$Cl$_2$ (0.5 mL), stirred at 0° C. for 15 minutes, and then stirred at room temperature for 30 minutes. The mixture was cooled to 0° C., treated with 37% NH$_4$OH solution (5 drops) and stirred for 5 minutes. The mixture was diluted with ethyl acetate (30 mL), washed with 1 M HCl (5 mL), washed with saturated NaHCO$_3$ solution (5 mL), washed with brine, dried (MgSO$_4$), filtered, and concentrated. The residue was chromatographed on silica gel eluting with a gradient of 10% to 30% ethyl acetate in heptanes to provide the title compound (123 mg, 0.196 mmol, 75% yield). $^1$H NMR (400 MHz, CDCl$_3$) δ 6.90 (s, 1H), 6.86 (d, J=8.4 Hz, 1H), 6.70-6.65 (m, 2H), 6.64 (s, 1H), 5.62 (d, J=8.9 Hz, 1H), 5.30-5.21 (m, 1H), 4.90 (d, J=9.3 Hz, 1H), 4.35 (d, J=9.3 Hz, 1H), 4.15 (q, J=7.1 Hz, 2H), 3.96 (dd, J=11.1, 5.9 Hz, 1H), 2.64-2.58 (m, 1H), 2.24 (dd, J=12.5, 6.2 Hz, 1H), 2.18-2.07 (m, 2H), 1.77-1.70 (m, 1H), 1.67 (s, 3H), 1.66-1.34 (m, 7H), 1.26 (t, J=7.2 Hz, 3H); LC/MS (ESI+) m/z 628.6 (M+H)$^+$.

Example 158 ethyl cis-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate Example 158A ethyl cis-4-[(2S,4S)-4-amino-7-(trifluoromethoxy)-3,4-dihydro-2H-1-benzopyran-2-yl]cyclohexane-1-carboxylate A solution of Example 157B (407 mg, 0.828 mmol) in ethanol (10 mL) was treated with 4 M HCl in dioxane (2070 μL, 8.28 mmol), stirred at room temperature for 30 minutes, diluted with ethyl acetate (40 mL) and washed with saturated NaHCO$_3$ solution (15 mL). The ethyl acetate layer was washed with brine, dried (MgSO$_4$), filtered, and concentrated to provide the title compound (0.39 g, 1.007 mmol, 122% yield). $^1$H NMR (400 MHz, CDCl$_3$) δ 7.45 (d, J=8.5 Hz, 1H), 6.78-6.71 (m, 1H), 6.67-6.61 (m, 1H), 4.15 (q, J=7.1 Hz, 2H), 4.06 (dd, J=11.3, 5.9 Hz, 1H), 4.00-3.90 (m, 1H), 2.62 (p, J=4.4 Hz, 1H), 2.22 (ddd, J=13.0, 5.8, 1.5 Hz, 1H), 2.19-2.07 (m, 2H), 1.99 (bs, 2H), 1.85-1.74 (m, 2H), 1.72-1.37 (m, 6H), 1.26 (t, J=7.1 Hz, 3H); LC/MS (ESI+) m/z 371 (M−NH$_3$)$^+$.

Example 158B ethyl cis-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate A solution of Example 158A (82.3 mg, 0.212 mmol) and triethylamine (59.2 μL, 0.425 mmol) in $CH_2Cl_2$ (1 mL) was cooled to 0° C. under $N_2$ and treated with a solution of Example 134F (88 mg, 0.319 mmol) in $CH_2Cl_2$ (0.5 mL). The mixture was stirred at 0° C. for 5 minutes, and then at room temperature for 30 minutes. The mixture was cooled to 0° C., treated with 37% $NH_4OH$ solution (5 drops) and stirred for 5 minutes. The mixture was diluted with ethyl acetate (30 mL), washed with 1 M HCl (5 mL), washed with saturated $NaHCO_3$ solution (5 mL), washed with brine, dried ($MgSO_4$), filtered, and concentrated. The residue was chromatographed on silica gel, eluting with a gradient of 10% to 30% ethyl acetate in heptanes to provide the title compound (98 mg, 0.156 mmol, 73.5% yield). $^1$H NMR (400 MHz, $CDCl_3$) δ 6.92 (dd, J=8.5, 0.8 Hz, 1H), 6.88 (s, 2H), 6.71-6.67 (m, 1H), 6.65-6.64 (m, 2H), 5.56 (d, J=9.0 Hz, 1H), 5.31-5.21 (m, 1H), 4.94 (d, J=9.3 Hz, 1H), 4.37 (d, J=9.3 Hz, 1H), 4.16 (q, J=7.1 Hz, 1H), 3.97 (dd, J=10.5, 6.0 Hz, 1H), 2.62 (p, J=4.2 Hz, 1H), 2.25 (ddd, J=12.8, 6.1, 1.2 Hz, 1H), 2.18-2.09 (m, 2H), 1.80-1.71 (m, 1H), 1.65 (s, 3H), 1.69-1.50 (m, 4H), 1.50-1.37 (m, 3H), 1.27 (t, J=7.1 Hz, 3H); LC/MS (ESI+) m/z 628.6 $(M+H)^+$.

Example 159 ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate

Example 159A ethyl trans-4-[(2S,4S)-4-amino-7-(difluoromethoxy)-3,4-dihydro-2H-1-benzopyran-2-yl]cyclohexane-1-carboxylate A solution of the product of Example 156C (230 mg, 0.49 mmol) in ethanol (5 mL) was cooled with a 0° C. bath and treated with $NaBH_4$ (57 mg, 1.5 mmol). The reaction mixture was stirred in the cold bath for 40 minutes and then at room temperature for 80 minutes. 4 M HCl in diethyl ether (1.0 mL, 4 mmol) was added to the mixture which was then stirred at room temperature for five hours and concentrated. The residue was partitioned between methyl tert-butyl ether and 1 M aqueous $Na_2CO_3$. The organic phase was dried ($Na_2SO_4$), filtered, and concentrated to provide the title compound (166 mg (92%)). $^1$H NMR (400 MHz, $CDCl_3$) δ 7.41 (d, J=8.4 Hz, 1H), 6.69-6.64 (m, 1H), 6.55 (d, J=2.4 Hz, 1H), 6.47 (t, J=74.2 Hz, 1H), 4.13 (q, J=7.1 Hz, 2H), 4.07-4.00 (m, 1H), 3.91 (dd, J=11.7, 5.5 Hz, 1H), 2.26 (tt, J=12.1, 3.4 Hz, 1H), 2.17 (dd, J=13.0, 5.8 Hz, 1H), 2.12-2.01 (m, 3H), 1.90-1.81 (m, 1H), 1.66-1.11 (m, 9H); MS (ESI+) m/z 353 $(M-NH_3)^+$.

Example 159B ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate A solution of Example 159A (164 mg, 0.44 mmol) and triethylamine (125 μL, 0.90 mmol) in anhydrous dichloromethane (4.0 mL) was cooled in a water ice bath, followed by dropwise addition of a solution of Example 134F (147 mg, 0.53 mmol) in dichloromethane (1.0 mL). The solution was stirred in the bath for 20 minute, and stirred for another 20 minutes after removal of the bath. The mixture was then quenched with concentrated aqueous $NH_4OH$ (100 μL). The aqueous phase was separated and extracted with $CH_2Cl_2$. The combined organic phases were concentrated and the residue chromatographed on silica (eluted with 25 to 40% methyl tert-butyl ether/heptane) to provide the title compound (184 mg, 68%) as a white foam. $^1$H NMR (400 MHz, $CDCl_3$) δ 6.90 (d, J=8.5 Hz, 1H), 6.87 (s, 1H), 6.65 (s, 1H), 6.61 (dd, J=8.5, 2.4 Hz, 1H), 6.56 (d, J=2.4 Hz, 1H), 6.44 (t, J=73.8 Hz, 1H), 5.56 (d, J=8.9 Hz, 1H), 5.30-5.22 (m, 1H), 4.94 (d, J=9.3 Hz, 1H), 4.36 (d, J=9.3 Hz, 1H), 4.12 (q, J=7.1 Hz, 2H), 3.94-3.88 (m, 1H), 2.30-2.20 (m, 2H), 2.10-1.99 (m, 3H), 1.87-1.79 (m, 1H), 1.64 (s, 3H), 1.63-1.38 (m, 4H), 1.30-1.09 (m, 5H); MS (ESI+) m/z 610 $(M+H)^+$.

Example 160 trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid A solution of Example 156F (164 mg, 0.27 mmol) in tetrahydrofuran (2.0 mL) and methanol (800 μL) was treated with 1 M aqueous NaOH (800 μL, 0.8 mmol). The mixture was heated at 50° C. for about 35 minutes and then cooled to room temperature, quenched with 3 M aqueous citric acid (130 μL, 0.39 mmol) and partitioned with brine and heptane. The aqueous phase was separated and extracted with methyl tert-butyl ether. The combined organic phases were washed with brine, dried ($Na_2SO_4$), filtered, and concentrated to provide the title compound (172 mg, 100%) as a white foam. $^1$H NMR (501 MHz, $CDCl_3$) δ 6.91 (s, 1H), 6.85 (dd, J=8.5, 1.1 Hz, 1H), 6.64 (s, 1H), 6.62-6.59 (m, 1H), 6.57 (d, J=2.4 Hz, 1H), 6.46 (t, J=73.8 Hz, 1H), 5.62 (d, J=8.9 Hz, 1H), 5.28-5.22 (m, 1H), 4.89 (d, J=9.3 Hz, 1H), 4.35 (d, J=9.3 Hz, 1H), 3.92 (ddd, J=11.6, 5.5, 1.5 Hz, 1H), 2.30 (tt, J=12.2, 3.5 Hz, 1H), 2.24 (ddd, J=12.9, 6.2, 1.5 Hz, 1H), 2.14-2.08 (m, 2H), 2.06-2.00 (m, 1H), 1.87-1.81 (m, 1H), 1.67 (s, 3H), 1.62-1.40 (m, 4H), 1.32-1.12 (m, 2H); MS (ESI-) m/z 580 $(M-H)^-$.

Example 161 cis-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid A solution of Example 158B (85.3 mg, 0.136 mmol) in tetrahydrofuran (1 mL) was diluted with methanol (1 mL), treated with 1 M NaOH (0.5 mL), heated at 60° C. for 30 minutes, cooled, treated with 1 M HCl (2 mL) and extracted with ethyl acetate (30 mL). The ethyl acetate layer was washed with brine, dried (MgSO$_4$), filtered, and concentrated. The residue was chromatographed on silica gel, eluting with a gradient of 15% to 100% [200:1:1 ethyl acetate:HCOOH:H$_2$O] in heptanes to provide the title compound (44 mg, 0.073 mmol, 54.0% yield). $^1$H NMR (501 MHz, CDCl$_3$) δ 6.92 (dd, J=8.5, 0.9 Hz, 1H), 6.88 (s, 1H), 6.70-6.67 (m, 1H), 6.65-6.64 (m, 2H), 5.60 (d, J=9.0 Hz, 1H), 5.30-5.24 (m, 1H), 4.94 (d, J=9.3 Hz, 1H), 4.36 (d, J=9.3 Hz, 1H), 3.97 (dd, J=10.5, 6.1 Hz, 1H), 2.71 (p, J=4.1 Hz, 1H), 2.27 (ddd, J=12.8, 6.2, 1.2 Hz, 1H), 2.21-2.12 (m, 2H), 1.83-1.78 (m, 1H), 1.64 (s, 3H), 1.69-1.55 (m, 4H), 1.51-1.39 (m, 3H); MS (ESI-) m/z 598 (M-H)$^-$.

Example 162 cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid A solution of Example 157E (101.2 mg, 0.161 mmol) in tetrahydrofuran (1 mL) was diluted with methanol (1 mL), treated with 1 M NaOH (0.5 mL), heated at 60° C. for 30 minutes, cooled, treated with 1 M HCl (2 mL) and extracted with ethyl acetate (30 mL). The ethyl acetate layer was washed with brine, dried (MgSO$_4$), filtered, and concentrated. The residue was chromatographed on silica gel, eluting with a gradient of 15% to 100% [200:1:1 ethyl acetate:HCOOH:H$_2$O] in heptanes to provide the title compound (61 mg, 0.102 mmol, 63.1% yield). $^1$H NMR (501 MHz, CDCl$_3$) δ 6.91 (s, 1H), 6.85 (dt, J=8.4, 0.7 Hz, 1H), 6.68-6.64 (m, 2H), 6.64 (s, 1H), 5.65 (d, J=8.9 Hz, 1H), 5.26 (ddd, J=10.8, 9.2, 6.4 Hz, 1H), 4.89 (d, J=9.3 Hz, 1H), 4.35 (d, J=9.3 Hz, 1H), 3.96 (dd, J=10.5, 6.0 Hz, 1H), 2.70 (p, J=4.2 Hz, 1H), 2.28-2.23 (m, 1H), 2.22-2.12 (m, 2H), 1.82-1.76 (m, 1H), 1.69-1.52 (m, 4H), 1.67 (s, 3H), 1.52-1.38 (m, 3H); MS (ESI-) m/z 598 (M-H)$^-$.

Example 163 trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid A solution of Example 159B (164 mg, 0.27 mmol) in tetrahydrofuran (2.0 mL) and methanol (800 μL) was treated with 1 M aqueous NaOH (800 μL, 0.8 mmol). The mixture was heated at 50° C. for 35 minutes, cooled to room temperature, quenched with 1 M aqueous citric acid (130 μL), and partitioned with brine and heptane. The aqueous phase was separated and extracted with methyl tert-butyl ether. The combined organic phases were acidified with 3 M aqueous citric acid (50 μL). The organic phase was separated and concentrated to provide the title compound (160 mg) as a white foam. $^1$H NMR (400 MHz, CDCl$_3$) δ 6.90 (dd, J=8.5, 1.1 Hz, 1H), 6.87 (s, 1H), 6.65 (s, 1H), 6.61 (dd, J=8.5, 2.4 Hz, 1H), 6.56 (d, J=2.4 Hz, 1H), 6.45 (t, J=73.8 Hz, 1H), 5.57 (d, J=8.9 Hz, 1H), 5.31-5.22 (m, 1H), 4.94 (d, J=9.3 Hz, 1H), 4.37 (d, J=9.3 Hz, 1H), 3.92 (ddd, J=11.5, 5.4, 1.5 Hz, 1H), 2.36-2.27 (m, 1H), 2.25 (ddd, J=12.9, 6.3, 1.5 Hz, 1H), 2.16-2.08 (m, 2H), 2.08-2.01 (m, 1H), 1.89-1.82 (m, 1H), 1.64 (s, 3H), 1.62-1.41 (m, 4H), 1.32-1.12 (m, 2H); MS (ESI-) m/z 580 (M-H)$^-$.

Example 164 ethyl 1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylate Example 164A methyl 1-(hydroxymethyl)cyclopropane-1-carboxylate A solution of 1-(methoxycarbonyl)cyclopropanecarboxylic acid (10 g, 69.4 mmol) and triethylamine (10.83 ml, 78 mmol) in tetrahydrofuran (200 mL) under N$_2$ was cooled to -10° C., treated with isobutyl chloroformate (10.21 mL, 78 mmol) dropwise and stirred at -10° C. for 1 hour. The mixture was warmed to 0° C. and the solid was removed by filtration. In a separate flask, NaBH$_4$ (7.87 g, 208 mmol) was dissolved in a mixture of tetrahydrofuran (100 mL) and water (25 mL). This mixture was then cooled to 0° C. and added dropwise to the filtrate over 90 minutes. Stirring was continued for 1 hour at 0° C. and the mixture was poured into a 0° C. solution of 20% citric acid in water. The mixture was swirled for 5 minutes and then concentrated on the rotary evaporator with minimal heating to remove the majority of the tetrahydrofuran. The residue was extracted with ethyl acetate (4×150 mL). The combined ethyl acetate layers were washed with brine, dried (MgSO$_4$), filtered, and concentrated to provide the title compound (9 g, 69.2 mmol, 100% yield). $^1$H NMR (500 MHz, CDCl$_3$) δ 4.44 (bs, 1H), 3.68 (s, 3H), 3.62 (s, 2H), 1.27-1.25 (m, 2H), 0.88-0.86 (m, 2H).

Example 164B methyl 1-formylcyclopropane-1-carboxylate

A solution of Example 164A (9.03 g, 69.4 mmol) in CH$_2$Cl$_2$ (180 mL) under N$_2$ was cooled to -5° C. and treated portion wise over 20 minutes with trichloroisocyanuric acid (16.45 g, 70.8 mmol), treated all at once with 2,2,6,6-tetramethyl-1-piperidinyloxy (TEMPO, CAS #2564-83-2, 1.084 g, 6.94 mmol), stirred at -5° C. for 5 minutes, allowed to warm to room temperature and stirred for 20 minutes. Mixture was diluted with CH$_2$Cl$_2$ (100 mL) and filtered through diatomaceous earth to remove solids. The CH$_2$Cl$_2$ layer was washed with saturated Na$_2$CO$_3$ (180 mL), washed with 1 N HCl (180 mL), washed with brine (180 mL), washed with saturated ammonium chloride (3×180 mL), dried (MgSO$_4$), filtered, and concentrated on the rotary evaporator without heating to provide the title compound (8.77 g, 68.4 mmol, 99% yield). $^1$H NMR (501 MHz, CDCL$_3$) δ 10.37 (s, 1H), 3.81 (s, 3H), 1.69-1.58 (m, 4H).

Example 164C methyl 1-[4-oxo-7-(trifluoromethoxy)-3,4-dihydro-2H-1-benzopyran-2-yl]cyclopropane-1-carboxylate A mixture of Example 145A (3.44 g, 15.61 mmol) and Example 164B (2 g, 15.61 mmol) in toluene (6.5 mL) was treated with acetic acid (1.072 ml, 18.73 mmol), and pyrrolidine (1.291 mL, 15.61 mmol). The mixture was stirred at 70° C. overnight, and then cooled to room temperature. The mixture was dissolved in ethyl acetate (100 mL) and washed with 1 M HCl (30 mL). An emulsion was present, so the mixture was diluted with methyl tert-butyl ether (30 mL) and then with heptanes (20 mL). The layers were separated and the organic layer was washed with saturated NaHCO$_3$ solution (25 mL), washed with brine, dried (MgSO$_4$), filtered, and concentrated. The residue was chromatographed on silica gel, eluting with a gradient of 5% to 30% ethyl acetate in heptanes to provide the title compound (2.6 g). $^1$H NMR (500 MHz, CDCl$_3$) δ 7.92 (d, J=8.7 Hz, 1H), 6.87-6.84 (m, 1H), 6.83-6.81 (m, 1H), 4.66 (dd, J=13.8, 2.6 Hz, 1H), 3.71 (s, 3H), 3.01 (dd, J=16.8, 13.9 Hz, 1H), 2.83 (dd, J=16.8, 2.7 Hz, 1H), 1.46 (ddd, J=9.8, 7.0, 4.2 Hz, 1H), 1.37 (ddd, J=9.7, 7.1, 4.2 Hz, 1H), 1.27 (ddd, J=9.7, 7.0, 4.2 Hz, 1H), 1.09 (ddd, J=9.6, 7.1, 4.2 Hz, 1H); LC/MS (ESI+) m/z 331 (M+H)$^+$.

Example 164D ethyl 1-[(2R,4E)-4-{[(R)-2-methylpropane-2-sulfinyl]imino}-7-(trifluoromethoxy)-3,4-dihydro-2H-1-benzopyran-2-yl]cyclopropane-1-carboxylate and ethyl 1-[(2S,4E)-4-{[(R)-2-methylpropane-2-sulfinyl]imino}-7-(trifluoromethoxy)-3,4-dihydro-2H-1-benzopyran-2-yl]cyclopropane-1-carboxylate A mixture of Example 164C (1.145 g, 3.47 mmol) and (R)-(+)-2-methyl-2-propanesulfinamide (0.840 g, 6.93 mmol) in toluene (35 mL) was treated with titanium(IV) ethoxide (3.16 g, 13.87 mmol), stirred at 100° C. for 3 hours, cooled, diluted with ethyl acetate (100 mL), treated with water (100 mL), stirred for 5 minutes and filtered through diatomaceous earth to remove the solids. The ethyl acetate layer washed with brine, dried (MgSO$_4$), filtered and concentrated to provide the title compounds (1.68 g). $^1$H NMR (501 MHz, CDCl$_3$) δ 8.02 (d, J=8.8 Hz, 0.5H), 8.00 (d, J=8.8 Hz, 0.5H), 6.86-6.74 (m, 2H), 4.55 (dd, J=13.5, 2.4 Hz, 0.5H), 4.37 (dd, J=13.3, 2.5 Hz, 0.5H), 4.20-4.10 (m, 2.5H), 3.86 (dd, J=17.4, 2.4 Hz, 0.5H), 3.01 (dd, J=17.5, 13.6 Hz, 0.5H), 2.95 (dd, J=17.1, 13.5 Hz, 0.5H), 1.45-1.36 (m, 1H), 1.35-1.17 (m, 2H), 1.32 (s, 4.5H), 1.31 (s, 4.5H), 1.26 (t, J=7.1 Hz, 1.5H), 1.25 (t, J=7.1 Hz, 1.5H), 1.05 (m, 1H); LC/MS (ESI+) m/z 448 (M+H)$^+$.

Example 164E ethyl 1-[(2R,4R)-4-{[(R)-2-methylpropane-2-sulfinyl]amino}-7-(trifluoromethoxy)-3,4-dihydro-2H-1-benzopyran-2-yl]cyclopropane-1-carboxylate A solution of Example 164D (1.553 g, 3.47 mmol) in ethanol (35 mL) was cooled to 0° C., treated with NaBH$_4$ (0.263 g, 6.94 mmol), and stirred at 0° C. for 2 hours. The mixture was diluted with ethyl acetate (150 mL) and washed with saturated NaHCO$_3$ solution (30 mL). The layers were separated and the aqueous layer was extracted with ethyl acetate (50 mL). The combined ethyl acetate layers were washed with brine, dried (MgSO$_4$), filtered, and concentrated. The residue was chromatographed on silica gel, eluting with a gradient of 15% to 100% ethyl acetate in heptanes to provide the title compound (0.54 g) as the first eluting isomer. $^1$H NMR (500 MHz, CDCl$_3$) δ 7.71 (dd, J=8.6, 1.0 Hz, 1H), 6.78 (dd, J=8.6, 2.2, 0.9 Hz, 1H), 6.62 (dd, J=2.2, 0.9 Hz, 1H), 4.72-4.66 (m, 1H), 4.46 (dd, J=11.5, 1.5 Hz, 1H), 4.13 (qd, J=7.1, 2.8 Hz, 2H), 3.56 (d, J=8.3 Hz, 1H), 2.44 (ddd, J=13.2, 6.1, 1.6 Hz, 1H), 1.94 (dt, J=13.1, 11.6 Hz, 1H), 1.37-1.31 (m, 1H), 1.29-1.19 (m, 5H), 1.24 (s, 9H), 0.97 (ddd, J=9.4, 7.1, 3.9 Hz, 1H); LC/MS (ESI+) m/z 450 (M+H)$^+$.

Example 164F ethyl 1-[(2S,4S)-4-{[(R)-2-methylpropane-2-sulfinyl]amino}-7-(trifluoromethoxy)-3,4-dihydro-2H-1-benzopyran-2-yl]cyclopropane-1-carboxylate The chromatography separation described in Example 164E provided the title compound as the second eluting isomer. This second eluting isomer was impure and was chromatographed again on silica gel, eluting with a gradient of 15% to 100% methyl tert-butyl ether in heptanes to provide the pure title compound (0.57 g). $^1$H NMR (501 MHz, CDCl$_3$) δ 7.40 (dd, J=8.6, 1.0 Hz, 1H), 6.74 (ddd, J=8.6, 2.3, 0.9 Hz, 1H), 6.65 (dd, J=2.2, 1.0 Hz, 1H), 4.64-4.58 (m, 1H), 4.44 (dd, J=11.6, 1.6 Hz, 1H), 4.19-4.08 (m, 2H), 3.27 (d, J=10.8 Hz, 1H), 2.78 (ddd, J=13.3, 6.1, 1.7 Hz, 1H), 1.94 (dt, J=13.3, 11.6 Hz, 1H), 1.36-1.16 (m, 3H), 1.29 (s, 9H), 1.23 (t, J=7.1 Hz, 3H), 0.97 (ddd, J=9.5, 7.2, 4.1 Hz, 1H); LC/MS (ESI+) m/z 450 (M+H)$^+$.

Example 164G ethyl 1-[(2R,4R)-4-amino-7-(trifluoromethoxy)-3,4-dihydro-2H-1-benzopyran-2-yl]cyclopropane-1-carboxylate hydrochloride A solution of Example 164E (487 mg, 1.08 mmol) in ethanol (11 mL) was treated with 2 M HCl in diethyl ether (5.4 mL, 10.8 mmol) at room temperature, stirred for 45 minutes, and slowly concentrated to a solid. The solids were treated with methyl tert-butyl ether, collected by filtration and rinsed with more methyl tert-butyl ether to give 400 mg of a white solid (97%). $^1$H NMR (500 MHz, CD$_3$OD) δ 7.51 (d, J=8.6 Hz, 1H), 6.97-6.93 (m, 1H), 6.82-6.79 (m, 1H), 4.75 (dd, J=11.5, 6.4 Hz, 1H), 4.32 (d, J=11.1 Hz, 1H), 4.16 (q, J=7.1 Hz, 2H), 2.62 (dd, J=12.3, 6.0 Hz, 1H), 2.26 (q, J=11.8 Hz, 1H), 1.43-1.36 (m, 1H), 1.31-1.20 (m, 5H), 1.11-1.05 (m, 1H); MS (ESI+) m/z 346 (M+H)$^+$.

Example 164H ethyl 1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylate A solution of Example 134F (252 mg, 0.91 mmol) in CH$_2$Cl$_2$ (2 mL) was added over six minutes to a solution of Example 164G (268 mg, 0.70 mmol) and triethylamine (350 μL, 2.5 mmol) in CH$_2$Cl$_2$ (5 mL) which was cooled with a water ice bath. The reaction mixture was stirred for 20 minutes. The bath was removed and the mixture was stirred for another 20 minutes at room temperature. The mixture was quenched and thoroughly stirred with concentrated aqueous NH$_4$OH (200 μL), filtered through a pad of sodium sulfate, and washed with CH$_2$Cl$_2$. The combined filtrates were concentrated and the residue chromatographed on silica (eluted with 1:2 methyl tert-butyl ether/heptane) to provide the title compound (399 mg, 97%) as a white foam. $^1$H NMR (400 MHz, CDCl$_3$) δ 6.91-6.87 (m, 2H), 6.73-6.68 (m, 1H), 6.67-6.64 (m, 1H), 6.64 (s, 1H), 5.65 (d, J=8.9 Hz, 1H), 5.37-5.28 (m, 1H), 4.89 (d, J=9.3 Hz, 1H), 4.37-4.32 (m, 2H), 4.13 (q, J=7.1 Hz, 2H), 2.41 (ddd, J=12.9, 6.2, 1.8 Hz, 1H), 1.79 (q, J=11.6 Hz, 1H), 1.67 (s, 3H), 1.38-1.32 (m, 1H), 1.27-1.16 (m, 5H), 0.98-0.92 (m, 1H); MS (ESI−) m/z 584 (M−H)$^-$.

Example 165 ethyl 1-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylate

Example 165A ethyl 1-[(2S,4S)-4-amino-7-(trifluoromethoxy)-3,4-dihydro-2H-1-benzopyran-2-yl]cyclopropane-1-carboxylate hydrochloride A solution of Example 164F (533 mg, 1.18 mmol) in ethanol (12 mL) was treated with 2 M HCl in diethyl ether (5.9 mL, 11.8 mmol) at room temperature, stirred for 70 minutes and slowly concentrated to a solid. The solids were treated with methyl tert-butyl ether, collected by filtration and rinsed with more methyl tert-butyl ether to provide the title compound (414 mg, 91%) as a white solid. $^1$H NMR (400 MHz, CD$_3$OD) δ 7.50 (d, J=8.6 Hz, 1H), 6.97-6.92 (m, 1H), 6.82-6.79 (m, 1H), 4.75 (dd, J=11.5, 6.4 Hz, 1H), 4.32 (d, J=11.4 Hz, 1H), 4.16 (q, J=7.1 Hz, 2H), 2.62 (dd, J=12.5, 6.2 Hz, 1H), 2.26 (q, J=12.0 Hz, 1H), 1.43-1.36 (m, 1H), 1.31-1.21 (m, 5H), 1.12-1.05 (m, 1H); MS (ESI+) m/z 346 (M+H)$^+$.

Example 165B ethyl 1-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylate A solution of Example 134F (252 mg, 0.91 mmol) in CH$_2$Cl$_2$ (2 mL) was added over six minutes to a solution of Example 165A (268 mg, 0.70 mmol) and triethylamine (350 μL, 2.5 mmol) in CH$_2$Cl$_2$ (5 mL) which was cooled with a water ice bath, and stirred for 20 minutes. The mixture was stirred for another 20 minutes at room temperature after removal of the bath, followed by quenching and thoroughly stirring with concentrated aqueous NH$_4$OH (200 μL). The mixture was then filtered through a pad of sodium sulfate and washed with CH$_2$Cl$_2$. The combined filtrates were concentrated and the residue chromatographed on silica gel (eluted with 1:2 methyl tert-butyl ether/heptane) to provide the title compound (395 mg, 96%) as a white powder. $^1$H NMR (501 MHz, CDCl$_3$) δ 6.95 (dd, J=8.6, 1.1 Hz, 1H), 6.87 (s, 1H), 6.73-6.69 (m, 1H), 6.66-6.64 (m, 2H), 5.60 (d, J=9.0 Hz, 1H), 5.37-5.30 (m, 1H), 4.94 (d, J=9.3 Hz, 1H), 4.38-4.34 (m, 2H), 4.15 (qd, J=7.1, 0.8 Hz, 2H), 2.42 (ddd, J=12.8, 6.2, 1.8 Hz, 1H), 1.81-1.73 (m, 1H), 1.64 (s, 3H), 1.36 (ddd, J=9.6, 7.1, 4.1 Hz, 1H), 1.26-1.18 (m, 5H), 0.96 (ddd, J=9.5, 7.2, 4.1 Hz, 1H); MS (ESI−) m/z 584 (M−H)$^-$.

Example 166

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid A solution of Example 164H (381 mg, 0.65 mmol) in tetrahydrofuran (5 mL) and methanol (2 mL) was treated with 1 M aqueous NaOH (2 mL) and heated at 50° C. for 90 minutes. The reaction mixture was cooled to room temperature, quenched with 3 M aqueous citric acid (1 mL) and partitioned with heptane (2 mL) and brine (1 mL). The separated aqueous phase was extracted twice with methyl tert-butyl ether. The combined organic phases were washed with brine, dried (Na$_2$SO$_4$), filtered, and concentrated to provide the title compound (368 mg, 100%) as an off-white foam. $^1$H NMR (501 MHz, CDCl$_3$) δ 6.91 (s, 1H), 6.87 (dd, J=8.5, 1.1 Hz, 1H), 6.72-6.69 (m, 1H), 6.66-6.65 (m, 1H), 6.64 (s, 1H), 5.68 (d, J=9.0 Hz, 1H), 5.35-5.28 (m, 1H), 4.88 (d, J=9.3 Hz, 1H), 4.35 (d, J=9.3 Hz, 1H), 4.27 (dd, J=11.6, 1.7 Hz, 1H), 2.43 (ddd, J=12.9, 6.1, 1.7 Hz, 1H), 1.87-1.78 (m, 1H), 1.67 (s, 3H), 1.42 (ddd, J=9.7, 7.2, 4.1 Hz, 1H), 1.33 (ddd, J=9.7, 7.3, 4.1 Hz, 1H), 1.29-1.24 (m, 1H), 1.04 (ddd, J=9.4, 7.3, 4.1 Hz, 1H); MS (ESI−) m/z 556 (M−H)$^-$.

Example 167 trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid

Example 167A 2,2-difluoro-5-methyl-6,7-dihydro-2H,5H-indeno[5,6-d][1,3]dioxole-5-carbonyl chloride A solution of Example 35F (3 g, 11.71 mmol) in CH$_2$Cl$_2$ (25 mL) at 0° C. was treated with oxalyl chloride (5.12 mL, 58.5 mmol), and a small amount of N,N-dimethylformamide (1 drop), stirred at room temperature for 2 hours, and concentrated to provide the title compound. $^1$H NMR (501 MHz, CDCl$_3$) δ 7.04-7.00 (m, 1H), 6.94-6.93 (m, 1H), 3.14-3.07 (m, 1H), 2.96 (ddd, J=16.0, 8.8, 4.1 Hz, 1H), 2.85 (ddd, J=13.3, 8.4, 4.0 Hz, 1H), 2.12 (ddd, J=13.4, 8.7, 7.8 Hz, 1H), 1.66 (s, 3H).

Example 167B (5R)-2,2-difluoro-N-[(1S)-2-hydroxy-1-phenylethyl]-5-methyl-6,7-dihydro-2H,5H-indeno[5,6-d][1,3]dioxole-5-carboxamide A solution of (S)-(+)-2-phenylglycinol (0.749 g, 5.46 mmol) and triethylamine (1.015 ml, 7.28 mmol) in CH$_2$Cl$_2$ (15 mL) at 0° C. was treated with a solution of Example 167A (1 g, 3.64 mmol) in CH$_2$Cl$_2$ (2 mL) over 1 minutes, stirred at 0° C. for 10 minutes, stirred at room temperature for 30 minutes, and concentrated to remove the CH$_2$Cl$_2$. The residue was partitioned between ethyl acetate (100 mL) and 1 M HCl (25 mL). The layers were separated and the aqueous layer was extracted with ethyl acetate (25 mL). The combined ethyl acetate layers were washed with brine, dried (MgSO$_4$), filtered, and concentrated. The residue was chromatographed on silica gel eluting with a gradient of 25%-65% methyl tert-butyl ether in heptanes to provide the title compound (0.49 g) as the first eluting isomer. $^1$H NMR (501 MHz, CDCl$_3$) δ 7.34-7.25 (m, 3H), 7.16-7.13 (m, 2H), 7.01 (s, 1H), 6.95 (s, 1H), 6.09 (d, J=6.8 Hz, 1H), 5.04-4.99 (m, 1H), 3.85-3.77 (m, 2H), 2.98-2.86 (m, 2H), 2.58 (ddd, J=12.9, 7.7, 5.2 Hz, 1H), 2.11-2.05 (m, 1H), 1.55 (s, 3H); LC/MS (ESI+) m/z 412.0 (M+H)$^+$).

Example 167C (5S)-2,2-difluoro-N-[(1S)-2-hydroxy-1-phenylethyl]-5-methyl-6,7-dihydro-2H,5H-indeno[5,6-d][1,3]dioxole-5-carboxamide The title compound (0.31 g) was isolated as the second eluting isomer from the chromatography separation described in Example 167B. ¹H NMR (400 MHz, CDCl₃) δ 7.39-7.25 (m, 3H), 7.18-7.11 (m, 2H), 7.00-6.94 (m, 2H), 6.10 (d, J=6.6 Hz, 1H), 5.03 (q, J=5.4 Hz, 1H), 3.85-3.73 (m, 2H), 3.08-2.90 (m, 2H), 2.65 (ddd, J=12.8, 8.0, 4.7 Hz, 1H), 2.40 (s, 1H), 2.11 (dt, J=13.0, 8.1 Hz, 1H), 1.54 (s, 3H); LC/MS (ESI+) m/z 412.0 (M+H)⁺.

Example 167D (5S)-2,2-difluoro-5-methyl-6,7-dihydro-2H,5H-indeno[5,6-d][1,3]dioxole-5-carboxylic acid A solution of Example 167C (310 mg, 0.826 mmol) in ethylene glycol (8 mL) was treated with 4.6 mL of a 10% weight/volume potassium hydroxide (4634 mg, 8.26 mmol) solution in water. The mixture was heated at 130° C. for 2.5 hours and then at room temperature overnight. The mixture was partitioned between methyl tert-butyl ether (100 mL) and 1 M HCl (50 mL). The layers were separated and the methyl tert-butyl ether layer was washed with 0.1 M HCl (50 mL), washed with brine, dried (MgSO₄), filtered, and concentrated to provide the title compound (195 mg, 0.761 mmol, 92% yield). ¹H NMR (501 MHz, CDCl₃) δ 7.03 (s, 1H), 6.89 (s, 1H), 3.04 (dt, J=15.8, 7.9 Hz, 1H), 2.90 (ddd, J=15.8, 8.6, 4.5 Hz, 1H), 2.75 (ddd, J=12.9, 8.4, 4.5 Hz, 1H), 2.00 (ddd, J=13.0, 8.6, 7.6 Hz, 1H), 1.55 (s, 3H).

Example 167E (5S)-2,2-difluoro-5-methyl-6,7-dihydro-2H,5H-indeno[5,6-d][1,3]dioxole-5-carbonyl chloride A solution of Example 167D (0.213 g, 0.83 mmol) in CH₂Cl₂ (3 mL) at 0° C. was treated all at once with oxalyl chloride (0.363 ml, 4.15 mmol), and one drop of N,N-dimethylformamide. The mixture was stirred at room temperature for 2 hours, and concentrated to dryness to provide the title compound. ¹H NMR (400 MHz, CDCl₃) δ 7.05 (s, 1H), 6.96 (s, 1H), 3.13 (dt, J=16.1, 8.1 Hz, 1H), 2.98 (ddd, J=16.0, 8.7, 3.9 Hz, 1H), 2.88 (ddd, J=12.5, 8.4, 4.0 Hz, 1H), 2.15 (dt, J=13.4, 8.2 Hz, 1H), 1.69 (s, 3H).

Example 167F ethyl trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylate A mixture of Example 148A (28 mg, 0.071 mmol) and triethylamine (19.73 µL, 0.142 mmol) in CH₂Cl₂ (0.2 mL) was cooled to 0° C. under N₂, treated with a solution of Example 167E (29.2 mg, 0.106 mmol) in CH₂Cl₂ (~0.2 mL), stirred at 0° C. for 5 minutes, stirred at room temperature for 30 minutes, treated with 37% NH₄OH solution (5 mL) and stirred for 5 minutes. The mixture was diluted with ethyl acetate (30 mL), washed with 1 M HCl (10 mL), washed with saturated NaHCO₃ solution (10 mL), washed with brine, dried (MgSO₄), filtered, and concentrated. The residue was chromatographed on silica gel, eluting with a gradient of 10% to 50% ethyl acetate in heptanes to provide the title compound. LC/MS (ESI+) m/z 626 (M+H)⁺.

Example 167G trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid A solution of Example 167F (41.5 mg, 0.066 mmol) in tetrahydrofuran (1.5 mL) and methanol (1.5 mL) was treated with 1 M NaOH (1 mL) and stirred at 55° C. for 30 minutes. The mixture was treated with 1 M HCl (3 mL) and extracted with ethyl acetate (30 mL). The ethyl acetate layer was washed with brine, dried (MgSO₄), filtered, and concentrated to provide the title compound (36.4 mg, 0.061 mmol, 92% yield). ¹H NMR (501 MHz, CDCl₃) δ 6.98 (s, 1H), 6.98 (dd, J=8.5, 1.0 Hz, 1H), 6.95-6.95 (m, 1H), 6.73-6.70 (m, 1H), 6.66 (dd, J=2.2, 1.0 Hz, 1H), 5.41 (d, J=8.9 Hz, 1H), 5.27 (ddd, J=10.6, 8.9, 6.4 Hz, 1H), 3.95-3.91 (m, 1H), 2.95-2.92 (m, 1H), 2.62 (ddd, J=12.7, 6.7, 5.8 Hz, 1H), 2.31 (tt, J=12.3, 3.4 Hz, 1H), 2.23 (ddd, J=12.8, 6.1, 1.2 Hz, 1H), 2.16-2.07 (m, 3H), 2.07-2.00 (m, 1H), 1.87-1.81 (m, 1H), 1.62-1.54 (m, 1H), 1.60 (s, 3H), 1.52-1.41 (m, 4H), 1.29-1.12 (m, 2H); MS (ESI−) m/z 596 (M−H)⁻.

Example 168 trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid Example 168A ethyl trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylate A solution of Example 153B (21 mg, 0.063 mmol) and triethylamine (17.56 µL, 0.126 mmol) in CH₂Cl₂ (0.5 mL) at 0° C. under N₂ was treated with a solution of Example 167E (17.30 mg, 0.063 mmol) in CH₂Cl₂ (0.5 mL). The mixture was stirred for 1 hour at room temperature, treated with saturated NH₄OH solution (5 drops) and stirred for 5 minutes. The mixture was partitioned between ethyl acetate (30 mL) and 1 M HCl (10 mL). The ethyl acetate layer was washed with saturated NaHCO₃ solution (10 mL), washed with brine, dried (MgSO₄), filtered, and concentrated. The residue was chromatographed on silica gel, eluting with a gradient of 15% to 50% ethyl acetate in heptanes to provide the title compound. ¹H NMR (400 MHz, CDCl₃) δ 6.98 (s, 1H), 6.93 (s, 1H), 6.86 (d, J=8.6 Hz, 1H), 6.45 (dd, J=8.6, 2.5 Hz, 1H), 6.33 (d, J=2.5 Hz, 1H), 5.37 (d, J=8.6 Hz, 1H), 5.25-5.17 (m, 1H), 4.12 (q, J=7.1 Hz, 2H), 3.87 (dd, J=11.1, 5.7 Hz, 1H), 3.74 (s, 3H), 2.95-2.90 (m, 2H), 2.61 (ddd, J=12.6, 6.9, 5.5 Hz, 1H), 2.30-2.19 (m, 2H), 2.15-1.97 (m, 4H), 1.86-1.78 (m, 1H), 1.59 (s, 3H), 1.52-1.34 (m, 3H), 1.25 (t, J=7.1 Hz, 3H), 1.21-1.06 (m, 2H); LC/MS (ESI+) m/z 317 (100%) (M-C₁₂H₁₁F₂NO₃)⁺, 572 (5%) (M+H)⁺.

Example 168B trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid A solution of Example 168A (22 mg, 0.039 mmol) in tetrahydrofuran (1.5 mL) and methanol (1.5 mL) was treated with 1 M NaOH (1 mL) and stirred at 55° C. for 30 minutes. The mixture was treated with 1 M HCl (3 mL) and extracted with ethyl acetate (30 mL). The ethyl acetate layer was washed with brine, dried (MgSO$_4$), filtered, and concentrated. The residue was chromatographed on silica gel, eluting with a gradient of 15% to 100% [200:1:1 ethyl acetate:HCOOH:H$_2$O] in heptane to provide the title compound (19 mg). $^1$H NMR (501 MHz, CDCl$_3$) δ 6.98 (s, 1H), 6.93 (s, 1H), 6.86 (dd, J=8.6, 0.9 Hz, 1H), 6.45 (dd, J=8.6, 2.6 Hz, 1H), 6.33 (d, J=2.6 Hz, 1H), 5.38 (d, J=8.7 Hz, 1H), 5.24-5.18 (m, 1H), 3.92-3.84 (m, 1H), 3.74 (s, 3H), 2.94-2.91 (m, 2H), 2.61 (ddd, J=12.7, 7.0, 5.5 Hz, 1H), 2.30 (ddd, J=15.6, 7.8, 3.4 Hz, 1H), 2.25 (ddd, J=12.7, 6.2, 1.2 Hz, 1H), 2.15-2.01 (m, 4H), 1.87-1.81 (m, 1H), 1.59 (s, 3H), 1.58-1.53 (m, 1H), 1.51-1.36 (m, 3H), 1.29-1.12 (m, 2H); MS (ESI-) m/z 542 (M-H)$^-$.

Example 169 trans-4-[(2R,4R)-4-{[(5R)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid Example 169A (5R)-2,2-difluoro-5-methyl-6,7-dihydro-2H,5H-indeno[5,6-d][1,3]dioxole-5-carboxylic acid A solution of Example 167B (295 mg, 0.786 mmol) in ethylene glycol (10 mL) was treated with of a 10% weight/volume potassium hydroxide (5291 mg, 9.43 mmol) solution in water (5.3 mL). The mixture was heated at 130° C. for 3 hours and then stirred at room temperature overnight. The mixture was partitioned between methyl tert-butyl ether (100 mL) and 1 M HCl (50 mL). The layers were separated and the methyl tert-butyl ether layer was washed with 0.1 M HCl (50 mL), washed with brine, dried (MgSO$_4$), filtered, and concentrated to provide the title compound (226 mg, 0.882 mmol, 112% yield). $^1$H NMR (400 MHz, CDCl$_3$) δ 7.03 (s, 1H), 6.89 (s, 1H), 3.04 (dt, J=15.9, 7.9 Hz, 1H), 2.90 (ddd, J=15.8, 8.6, 4.5 Hz, 1H), 2.75 (ddd, J=12.9, 8.4, 4.5 Hz, 1H), 2.00 (ddd, J=13.0, 8.5, 7.6 Hz, 1H), 1.55 (s, 3H).

Example 169B (5R)-2,2-difluoro-5-methyl-6,7-dihydro-2H,5H-indeno[5,6-d][1,3]dioxole-5-carbonyl chloride A solution of Example 169A (0.205 g, 0.8 mmol) in CH$_2$Cl$_2$ (3 mL) at 0° C. was treated all at once with oxalyl chloride (0.350 ml, 4.00 mmol) and one drop of N,N-dimethylformamide. The mixture was stirred at room temperature for 2 hours, and concentrated to dryness to provide the title compound. $^1$H NMR (501 MHz, CDCl$_3$) δ 7.02 (s, 1H), 6.94 (s, 1H), 3.10 (dt, J=16.1, 8.1 Hz, 1H), 2.96 (ddd, J=16.0, 8.7, 4.0 Hz, 1H), 2.85 (ddd, J=13.3, 8.4, 4.0 Hz, 1H), 2.12 (ddd, J=13.4, 8.7, 7.8 Hz, 1H), 1.66 (s, 3H).

Example 169C ethyl trans-4-[(2R,4R)-4-{[(5R)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylate A mixture of Example 148A (28 mg, 0.071 mmol) and triethylamine (19.73 µL, 0.142 mmol) in CH$_2$Cl$_2$ (0.2 mL) was cooled to 0° C. under N$_2$, and treated with a solution of Example 169B (29.2 mg, 0.106 mmol) in CH$_2$Cl$_2$ (0.2 mL). The mixture was stirred at 0° C. for 5 minutes, stirred at room temperature for 30 minutes, treated with 37% NH$_4$OH solution (5 mL), and stirred for 5 minutes. The mixture was diluted with ethyl acetate (30 mL), washed with 1 M HCl (10 mL), washed with saturated NaHCO$_3$ solution (10 mL), washed with brine, dried (MgSO$_4$), filtered, and concentrated. The residue was chromatographed on silica gel, eluting with a gradient of 10% to 50% ethyl acetate in heptanes to provide the title compound. $^1$H NMR (501 MHz, CDCl$_3$) δ 6.96 (s, 1H), 6.94-6.92 (m, 2H), 6.70-6.67 (m, 1H), 6.66-6.65 (m, 1H), 5.36 (d, J=9.0 Hz, 1H), 5.32-5.26 (m, 1H), 4.13 (q, J=7.1 Hz, 2H), 3.92 (dd, J=11.5, 5.6 Hz, 1H), 3.02-2.91 (m, 2H), 2.66 (ddd, J=12.6, 7.3, 5.1 Hz, 1H), 2.30-2.19 (m, 2H), 2.16 (dt, J=13.0, 8.3 Hz, 1H), 2.10-2.00 (m, 3H), 1.87-1.80 (m, 1H), 1.62-1.54 (m, 2H), 1.58 (s, 3H), 1.52-1.39 (m, 3H), 1.25 (t, J=7.1 Hz, 3H), 1.20-1.10 (m, 1H); LC/MS (ESI+) m/z 626 (M+H)$^+$.

Example 169D trans-4-[(2R,4R)-4-{[(5R)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid A solution of Example 169C (40 mg, 0.064 mmol) in tetrahydrofuran (1.5 mL) and methanol (1.5 mL) was treated with 1 M NaOH (1 mL) and stirred at 55° C. for 30 minutes. The mixture was treated with 1 M HCl (3 mL) and extracted with ethyl acetate (30 mL). The ethyl acetate layer was washed with brine, dried (MgSO$_4$), filtered, and concentrated to provide the title compound (36.4 mg, 0.061 mmol, 95% yield). $^1$H NMR (500 MHz, CDCl$_3$) δ 6.96 (s, 1H), 6.95-6.92 (m, 2H), 6.70-6.67 (m, 1H), 6.66-6.65 (m, 1H), 5.37 (d, J=9.0 Hz, 1H), 5.33-5.27 (m, 1H), 3.93 (dd, J=10.7, 5.5 Hz, 1H), 3.03-2.91 (m, 2H), 2.67 (ddd, J=12.7, 7.3, 5.2 Hz, 1H), 2.32 (tt, J=12.1, 3.4 Hz, 1H), 2.25 (ddd, J=12.9, 6.0, 0.9 Hz, 1H), 2.20-2.09 (m, 3H), 2.08-2.03 (m, 1H), 1.88-1.83 (m, 1H), 1.65-1.55 (m, 1H), 1.53-1.42 (m, 3H), 1.58 (s, 3H), 1.30-1.12 (m, 2H); MS (ESI-) m/z 596 (M-H)$^-$.

Example 170

(7R)—N-{1-[(2R)-2,3-dihydroxypropyl]-6-fluoro-2-[4-(hydroxymethyl)oxan-4-yl]-1H-indol-5-yl}-2,2-difluoro-7-methyl-6,7-dihydro-2H-furo[2,3-f][1,3]benzodioxole-7-carboxamide Example 170A {4-[(benzyloxy)methyl]oxan-4-yl}methanol A solution of [4-(hydroxymethyl)oxan-4-yl]methanol (2.5 g, 17.10 mmol) in N,N-dimethylformamide (35 mL) under N$_2$ was treated with 60% dispersion of sodium hydride in mineral oil (0.684 g, 17.10 mmol), stirred at room temperature for 30 minutes, treated with benzyl bromide (2.034 ml, 17.10 mmol), and stirred over night at room temperature. The reaction was quenched with saturated aqueous ammonium chloride followed by extraction with methyl tert-butyl ether (twice). The combined methyl tert-butyl ether layers were washed with brine, dried (MgSO$_4$), filtered, concentrated and chromatographed on silica gel eluting with a gradient of 5 to 100% ethyl acetate in heptanes to provide the titled compound (2.4 g, 10.16 mmol, 59.4% yield). $^1$H NMR (400 MHz, CDCl$_3$) δ 7.40-7.27 (m, 5H), 4.53 (s, 2H), 3.70-3.58 (m, 6H), 3.48 (s, 2H), 2.68 (t, J=6.0 Hz, 1H), 1.61-1.44 (m, 4H); MS (DCI) m/z 254 (M+NH$_4$)$^+$.

Example 170B

4-[(benzyloxy)methyl]oxane-4-carbaldehyde

A solution of oxalyl chloride (0.837 ml, 9.56 mmol) in dichloromethane (10 mL) was cooled to −78° C. under N$_2$, treated dropwise with dimethyl sulfoxide (1.018 mL, 14.35 mmol), stirred for 10 minutes at −78° C., treated with a solution of Example 170A (1.13 g, 4.78 mmol) in dichloromethane (5 mL), stirred at −78° C. for 15 minutes, treated dropwise with triethylamine (2.67 mL, 19.13 mmol), stirred at −78° C. for 20 minutes and then allowed to warm to 0° C. The mixture was treated with water (30 mL) and the layers were separated. The aqueous layer was extracted with CH$_2$Cl$_2$. The combined CH$_2$Cl$_2$ layers were washed with brine, dried (MgSO$_4$), filtered, and concentrated. The residue was chromatographed on silica gel eluting with a gradient of 15 to 50% ethyl acetate in heptanes to provide the title compound (1.12 g, 4.78 mmol, 100% yield). $^1$H NMR (400 MHz, CDCl$_3$) δ 9.63 (s, 1H), 7.38-7.24 (m, 5H), 4.48 (s, 2H), 3.77 (dt, J=11.9, 4.3 Hz, 2H), 3.53-3.45 (m, 4H), 2.03-1.96 (m, 2H), 1.64-1.56 (m, 2H); MS (DCI) m/z 252 (M+NH$_4$)$^+$.

Example 170C

4-[(benzyloxy)methyl]-4-ethynyloxane

A mixture of Example 170B (1.12 g, 4.78 mmol) and K$_2$CO$_3$ (1.321 g, 9.56 mmol) in anhydrous methanol (5 mL) was treated with dimethyl (1-diazo-2-oxopropyl)phosphonate (0.918 g, 4.78 mmol) and stirred at over the weekend. The mixture was concentrated using a rotary evaporator without heating. The residue was diluted with methyl tert-butyl ether (30 mL), washed with saturated aqueous-NaHCO$_3$ solution, washed with brine, dried (MgSO$_4$), filtered, and concentrated. The residue was chromatographed on silica gel eluting with a gradient of 10 to 30% ethyl acetate in heptanes to provide the title compound (1 g, 4.34 mmol, 91% yield). $^1$H NMR (400 MHz, CDCl$_3$) δ 7.37-7.27 (m, 5H), 4.61 (s, 2H), 3.89-3.74 (m, 4H), 3.40 (s, 2H), 2.27 (s, 1H), 1.76-1.59 (m, 4H); MS (DCI) m/z 248 (M+NH$_4$)$^+$.

Example 170D (2R)-1-(benzyloxy)-3-[2-({4-[(benzyloxy)methyl] oxan-4-yl}ethynyl)-5-fluoro-4-nitroanilino]propan-2-ol To a suspension of palladium (II) acetate (0.0087 g, 0.039 mmol), 1,4-bis(diphenylphosphino)butane (0.0262 g, 0.061 mmol), copper(I) iodide (0.0127 g, 0.067 mmol), and potassium carbonate (0.5042 g, 3.65 mmol) under nitrogen sparge in acetonitrile (10 mL) was added a solution of Example 170C (0.3126 g, 1.357 mmol) in acetonitrile (10 mL) via cannula. The reaction mixture was sparged with nitrogen and then a solution of the product of Example 130B (0.4027 g, 1.009 mmol) in acetonitrile (30 mL) was added via cannula. The reaction mixture was sparged with nitrogen again and then heated at 80° C. for 8 hours. The mixture was allowed to cool to room temperature overnight, filtered thorough diatomaceous earth, and washed with acetonitrile. The solvent was removed in vacuo and the crude material was chromatographed using a 40 g silica gel cartridge, and eluting with 25% ethyl acetate/dichloromethane to give the title compound (0.379 g, 69% yield). $^1$H NMR (400 MHz, DMSO-d$_6$) δ δ 8.00 (d, J=8.6 Hz, 1H), 7.39-7.19 (m, 10H), 6.75 (d, J=14.9 Hz, 1H), 6.33-6.24 (m, 1H), 5.32 (d, J=5.0 Hz, 1H), 4.59 (s, 2H), 4.49 (s, 2H), 3.91-3.83 (m, 1H), 3.83-3.72 (m, 2H), 3.65 (td, J=11.0, 4.6 Hz, 2H), 3.50 (s, 2H), 3.48-3.34 (m, 3H), 3.29-3.19 (m, 1H), 1.75-1.53 (m, 4H). MS (ESI+): M+H=549.

Example 170E (2R)-1-(benzyloxy)-3-(2-{4-[(benzyloxy)methyl] oxan-4-yl}-6-fluoro-5-nitro-1H-indol-1-yl)propan-2-ol To a degassed suspension of bis(acetonitrile)dichloropalladium(II) (18.7 mg, 0.072 mmol) and copper(I) iodide (13.4 mg, 0.070 mmol) was added the product of Example 170D (375 mg, 0.684 mmol) in acetonitrile (10 mL) via cannula. The reaction mixture was sparged with nitrogen and then heated at 80° C. for 3 hours. The reaction was allowed to cool to room temperature, filtered, and washed with acetonitrile. The crude material was chromatographed, eluting with a gradient of 10% ethyl acetate/dichloromethane to give the title compound (85.5 mg, 23% yield) as a yellow solid: 1H NMR (500 MHz, DMSO-d$_6$) δ 8.36 (d, J=7.5 Hz, 1H), 7.63 (d, J=13.3 Hz, 1H), 7.40-7.26 (m, 5H), 7.24-7.19 (m, 3H), 7.12-7.06 (m, 2H), 6.67 (s, 1H), 5.22 (d, J=5.5 Hz, 1H), 4.53 (s, 2H), 4.37 (s, 2H), 4.20 (dd, J=15.5, 9.4 Hz, 1H), 3.98-3.90 (m, 1H), 3.69-3.36 (m, 9H), 2.22 (dd, J=27.8, 14.3 Hz, 2H), 2.02-1.85 (m, 2H). M+H=549.

Example 170F (2R)-1-(5-amino-2-{4-[(benzyloxy)methyl]oxan-4-yl}-6-fluoro-1H-indol-1-yl)-3-(benzyloxy)propan-2-ol To a solution of Example 170E (84.6 mg, 0.154 mmol) in methanol (1 mL) was added 10% Pd/C (36.4 mg, 0.034 mmol). Hydrogen was delivered via a balloon and the reaction was stirred at ambient temperature for 17 hours. The reaction mixture was filtered, and concentrated in vacuo to give a pale yellow oil. (66 mg, 83%)$^1$H NMR (501 MHz, DMSO-d$_6$) δ 7.38-7.21 (m, 8H), 7.17 (d, J=12.6 Hz, 1H), 7.13-7.08 (m, 2H), 6.78 (d, J=9.0 Hz, 1H), 6.13 (d, J=0.8 Hz, 1H), 5.09 (d, J=5.4 Hz, 1H), 4.51 (s, 2H), 4.46 (s, 2H), 4.35 (s, 2H), 4.26 (dd, J=15.5, 2.6 Hz, 1H), 4.10-3.98 (m, 1H), 3.93 (d, J=7.7 Hz, 1H), 3.68-3.49 (m, 6H), 3.46 (dd, J=9.6, 4.7 Hz, 1H), 3.42-3.33 (m, 1H), 2.30-2.20 (m, 1H), 2.20-2.06 (m, 1H), 1.98-1.82 (m, 2H). M+H=517.

Example 170G (7R)—N-(1-[(2R)-3-(benzyloxy)-2-hydroxypropyl]-2-{4-[(benzyloxy)methyl]oxan-4-yl}-6-fluoro-1H-indol-5-yl)-2,2-difluoro-7-methyl-6,7-dihydro-2H-furo[2,3-f][1,3]benzodioxole-7-carboxamide The product from Example 3B (37.9 mg, 0.147 mmol) was dissolved in dichloromethane (1 mL). Oxalyl chloride (50 μL) and N,N-dimethylformamide (25 μL) were added which resulted in bubbling of the reaction mixture. The reaction was stirred at ambient temperature for 1 hour. The reaction was concentrated, and the residue was dissolved in dichloromethane (1 mL) and concentrated two times. The residue was dissolved in dichloromethane (1 mL) and pyridine (0.5 mL). The product of Example 170E (64.8 mg, 0.125 mmol) was added, and the reaction mixture was stirred at 60° C. for 18 hours. The reaction mixture was concentrated, and the residue was purified by silica gel chromatography (eluted with 5% ethyl acetate in dichloromethane, $R_f$=0.46) to yield the title compound (35.5 mg, 37%). $^1$H NMR (400 MHz, DMSO-$d_6$) δ 9.22 (s, 1H), 7.54 (s, 1H), 7.41-7.25 (m, 8H), 7.22-7.17 (m, 2H), 7.10-7.04 (m, 2H), 7.03 (s, 1H), 6.35 (s, 1H), 5.07 (d, J=9.1 Hz, 1H), 4.50 (s, 2H), 4.48 (d, J=7.3 Hz, 1H), 4.39 (d, J=9.1 Hz, 1H), 4.37-4.28 (m, 3H), 4.09 (dd, J=15.3, 8.9 Hz, 1H), 3.93 (d, J=7.3 Hz, 1H), 3.59 (s, 2H), 3.57-3.33 (m, 6H), 2.31-2.21 (m, 1H), 2.17 (d, J=14.1 Hz, 1H), 1.91 (tdd, J=12.8, 8.7, 3.8 Hz, 2H), 1.66 (s, 3H); MS (ESI+) m/z 759 (M+H)$^+$.

Example 170H (7R)—N-{1-[(2R)-2,3-dihydroxypropyl]-6-fluoro-2-[4-(hydroxymethyl)oxan-4-yl]-1H-indol-5-yl}-2,2-difluoro-7-methyl-6,7-dihydro-2H-furo[2,3-f][1,3]benzodioxole-7-carboxamide The product of Example 170G (33.0 mg, 0.043 mmol) was dissolved in dichloromethane (1 mL) and the resulting solution was cooled to <−70° C. in an acetone-dry ice bath. Boron trichloride (1M in dichloromethane, 200 μL, 0.20 mmol) was added dropwise. The mixture was stirred at the same temperature for 15 minutes, and then warmed to −30° C. The mixture was then cooled to −78° C. before quenching with 0.5 mL of methanol, and then concentrated. The residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (18.9 mg, 75%). $^1$H NMR (500 MHz, DMSO-$d_6$) δ 9.23 (s, 1H), 7.55 (s, 1H), 7.41-7.32 (m, 2H), 7.04 (s, 1H), 6.31 (s, 1H), 5.08 (d, J=9.1 Hz, 1H), 4.46-4.38 (m, 2H), 4.15 (dd, J=15.4, 9.0 Hz, 1H), 3.83 (d, J=7.0 Hz, 1H), 3.75-3.28 (m, 11H), 2.25 (d, J=13.8 Hz, 1H), 2.15-2.08 (m, 1H), 1.87 (tdd, J=13.3, 9.5, 3.8 Hz, 2H), 1.67 (s, 3H); MS (ESI+) m/z 579 (M+H)$^+$.

Example 171

(7R)—N-{1-[(2R)-2,3-dihydroxypropyl]-6-fluoro-2-(3-methyloxetan-3-yl)-1H-indol-5-yl}-2,2-difluoro-7-methyl-6,7-dihydro-2H-furo[2,3-f][1,3]benzodioxole-7-carboxamide Example 171A 3-(2,2-dibromoethenyl)-3-methyloxetane A solution of triphenylphosphine (12.41 g, 47.3 mmol) in dichloromethane (59 mL) was cooled in an ice bath for 10 minutes, then treated in one portion with carbon tetrabromide (7.84 g, 23.65 mmol). The mixture was stirred in the ice bath for 30 minutes and was then treated dropwise with a solution of 3-methyloxetane-3-carbaldehyde (1.184 g, 11.83 mmol) in dichloromethane (3 mL). The mixture was stirred in the ice bath for 30 minutes and then at room temperature for another 30 minutes. 190 mL of hexane was then added, and the suspension stirred vigorously at room temperature for 10 minutes. It was then filtered through a pad of silica gel. 10% ethyl acetate-hexane was added to the reaction flask (3×100 mL), and these rinses were also filtered through the silica gel pad. The combined filtrates were concentrated in vacuo to afford the title compound as a colorless oil (2.10 g, 69% yield). $^1$H NMR (500 MHz, CDCl$_3$) δ 6.69 (s, 1H), 4.81 (d, J=5.7 Hz, 2H), 4.38 (d, J=5.9 Hz, 2H), 1.60 (s, 3H).

Example 171B trimethyl((3-methyloxetan-3-yl)ethynyl)silane

The product of Example 171A (2.10 g, 8.21 mmol) in tetrahydrofuran (80 mL) was cooled to −78° C., then treated dropwise over about 5 minutes with n-butyllithium (1.6 M in hexanes, 11.8 mL, 18.88 mmol). The reaction mixture was stirred at −78° for 45 minutes, then chlorotrimethylsilane (3.7 mL, 28.9 mmol) was added dropwise. The reaction flask was removed from the cold bath, and the reaction mixture was stirred at room temperature for 45 minutes. The mixture was diluted with 50 mL ether and 50 mL water, then the mixture was transferred to a separatory funnel, and the phases were separated. The aqueous layer was extracted with 25 mL ether, and the combined organics were dried over Na$_2$SO$_4$ and concentrated in vacuo. The crude oil was taken up in 10 mL ether and filtered through a pad of silica gel on a sintered glass funnel, eluting with 50 mL of additional ether. The filtrate was concentrated in vacuo to afford the title compound as a pale yellow oil (1.05 g, 76%), which was taken into the next reaction without further purification. $^1$H NMR (500 MHz, DMSO-$d_6$) δ 4.59 (d, J=5.5 Hz, 2H), 4.29 (d, J=5.6 Hz, 2H), 1.51 (s, 3H), 0.13 (s, 9H). MS (DCI+) m/z 186.1 (M+NH$_4$)$^+$.

Example 171C (2R)-1-(benzyloxy)-3-[6-fluoro-2-(3-methyloxetan-3-yl)-5-nitro-1H-indol-1-yl]propan-2-ol Palladium acetate (1.069 mg, 4.76 μmol), 1,4-bis(diphenylphosphino)butane (3.26 mg, 7.64 μmol), copper(I) iodide (1.574 mg, 8.27 μmol), and potassium carbonate (0.062 g, 0.451 mmol) were suspended in acetonitrile (1.2 mL). The system was evacuated and back-filled with nitrogen several times, then a mixture of the product of Example 171B (0.032 g, 0.188 mmol) in 0.2 mL acetonitrile was added. The system was again evacuated and back-filled with nitrogen several times, then the product of Example 130 B (0.050 g, 0.125 mmol) and tetrabutylammonium fluoride trihydrate (0.059 g, 0.188 mmol) were added. The system was evacuated and back-filled with nitrogen several times, then the mixture was heated at 75° C. overnight. After this time, the mixture was cooled to room temperature and concentrated in vacuo. Silica gel chromatography (5 to 70% ethyl acetate-heptanes, eluent) afforded the title compound as a bright yellow-orange solid. (0.009 g, 17% yield). $^1$H NMR (500 MHz, DMSO-$d_6$) δ 8.37 (d, J=7.6 Hz, 1H), 7.64 (d, J=12.9 Hz, 1H), 7.47-7.12 (m, 5H), 6.49 (s, 1H), 5.30 (d, J=5.2 Hz, 1H), 5.10 (d, J=5.8 Hz, 1H), 4.99 (d, J=5.6 Hz, 1H), 4.57 (d, J=3.8 Hz, 2H), 4.50 (m, 2H), 4.06 (m, 1H), 3.80 (m, 1H), 3.50 (m, 2H), 1.76 (s, 3H). MS (ESI$^+$) m/z 415.1 (M+H)$^+$.

Example 171D (2R)-1-[5-amino-6-fluoro-2-(3-methyloxetan-3-yl)-1H-indol-1-yl]-3-(benzyloxy)propan-2-ol The product from Example 171C (0.034 g, 0.082 mmol) in methanol (2 mL) was hydrogenated (hydrogen balloon)

over 10% Pd—C at room temperature overnight. After this time, the mixture was diluted with methanol (3 mL) and filtered through a syringe filter. The filtrate was concentrated in vacuo to afford the title compound as a brown oil (21 mg, 66%). $^1$H NMR (400 MHz, DMSO-d$_6$) δ 7.40-7.21 (m, 5H), 7.19-7.01 (m, 1H), 6.76 (d, J=8.9 Hz, 1H), 5.90 (s, 1H), 5.15 (d, J=5.3 Hz, 1H), 5.08-4.99 (m, 1H), 4.93 (dd, J=14.7, 5.1 Hz, 1H), 4.82 (m, 1H), 4.60-4.32 (m, 5H), 4.01-3.76 (m, 2H), 3.63-3.34 (m, 3H), 1.70 (s, 3H). MS (ESI$^+$) m/z 385.1 (M+H)$^+$.

Example 171E (7R)—N-{1-[(2R)-2,3-dihydroxypropyl]-6-fluoro-2-(3-methyloxetan-3-yl)-1H-indol-5-yl}-2,2-difluoro-7-methyl-6,7-dihydro-2H-furo[2,3-f][1,3]benzodioxole-7-carboxamide The product from Example 3B (0.014 g, 0.055 mmol) was refluxed in thionyl chloride (0.11 mL, 1.426 mmol) for 1 hour. The mixture was cooled to room temperature and concentrated in vacuo, then excess thionyl chloride was chased three times with CH$_2$Cl$_2$ (1 mL each). The resulting yellow oil was treated with a solution of the product of Example 171D (0.021 g, 0.055 mmol) and pyridine (0.052 mL, 0.645 mmol) in 0.2 mL CH$_2$Cl$_2$. The reaction mixture was stirred at room temperature for 3 days. The reaction mixture was concentrated in vacuo, and excess pyridine was chased with acetonitrile (3×1 mL).

The resulting crude product and 10% palladium on carbon was hydrogenated (hydrogen balloon) in 2 mL methanol overnight at room temperature. The mixture was then diluted with additional methanol (5 mL) and filtered through a syringe filter, and the filtrate was concentrated in vacuo. Silica gel chromatography (40% ethyl acetate-heptanes to 100% ethyl acetate, gradient eluent) afforded the title compound as a white solid (0.0097 g, 33%). $^1$H NMR (400 MHz, DMSO-d$_6$) δ 9.21 (s, 1H), 7.52 (s, 1H), 7.40-7.30 (m, 2H), 7.01 (s, 1H), 6.14 (s, 1H), 5.10-4.99 (m, 3H), 4.95 (d, J=5.5 Hz, 1H), 4.87 (t, J=5.5 Hz, 1H), 4.50-4.36 (m, 3H), 4.06-3.94 (m, 1H), 3.86 (m, 1H), 3.55 (dd, J=14.9, 9.1 Hz, 2H), 3.46-3.38 (m, 1H), 1.73 (s, 3H), 1.64 (s, 3H). MS (ESI$^+$) m/z 535.1 (M+H)$^+$.

Example 172

(7R)-2,2-difluoro-N-{6-fluoro-2-[1-(hydroxymethyl)cyclobutyl]-1H-indol-5-yl}-7-methyl-6,7-dihydro-2H-furo[2,3-f][1,3]benzodioxole-7-carboxamide Example 172A 2-({1-[(benzyloxy)methyl]cyclobutyl}ethynyl)-5-fluoro-4-nitroaniline A mixture of 2-bromo-5-fluoro-4-nitroaniline (CAS #952664-69-6, 100 mg, 0.424 mmol), the product from Example 134C (170 mg, 0.849 mmol), copper(I) iodide (8.08 mg, 0.042 mmol), bis(triphenylphosphine)palladium (II) chloride (29.8 mg, 0.042 mmol) and triethylamine (160 μL, 1.146 mmol) in tetrahydrofuran (2 mL) was heated at 60° C. for 90 minutes. The mixture was cooled, concentrated and chromatographed on silica gel eluting with a gradient of 10 to 50% ethyl acetate in heptanes to provide the title compound (51 mg, 0.144 mmol, 33.9% yield). $^1$H NMR (400 MHz, CDCl$_3$) δ 8.06 (d, J=8.3 Hz, 1H), 7.41-7.28 (m, 5H), 6.32 (d, J=12.9 Hz, 1H), 4.96 (bs, 2H), 4.62 (s, 2H), 3.65 (s, 2H), 2.42-2.33 (m, 2H), 2.26-2.17 (m, 2H), 2.15-2.05 (m, 1H), 2.03-1.91 (m, 1H); LC/MS (ESI+) m/z 355 (M+H)$^+$.

Example 172B

2-{1-[(benzyloxy)methyl]cyclobutyl}-6-fluoro-5-nitro-1H-indole

A vial containing copper(I) iodide (5.37 mg, 0.028 mmol) and palladium(II) chloride (5.00 mg, 0.028 mmol) under N$_2$ was treated with a solution of Example 172A (50 mg, 0.141 mmol) in acetonitrile (about 1.5 mL). The mixture was heated at 80° C. for 1 hour, cooled, concentrated, and chromatographed on silica gel (eluting with a gradient of 10 to 30% ethyl acetate in heptanes) to provide the title compound (40 mg, 0.113 mmol, 80% yield). $^1$H NMR (400 MHz, CDCl$_3$) δ 9.18 (bs, 1H), 8.35 (d, J=7.2 Hz, 1H), 7.45-7.35 (m, 5H), 7.06 (d, J=11.7 Hz, 1H), 6.45-6.44 (m, 1H), 4.66 (s, 2H), 3.82 (s, 2H), 2.42-2.33 (m, 2H), 2.29-2.20 (m, 2H), 2.16-2.04 (m, 2H); LC/MS (ESI+) m/z 355 (M+H)$^+$.

Example 172C

[1-(5-amino-6-fluoro-1H-indol-2-yl)cyclobutyl]methanol

A mixture of Example 172B (40 mg, 0.113 mmol) and 10% Pd/C (about 10 mg) in acetic acid (1 mL) was stirred under 112 (balloon) for 1 hour, treated with more Pd/C (about 10 mg), stirred for 1 hour under H$_2$, diluted with acetic acid, filtered through diatomaceous earth, and the filtrate was concentrated to dryness. The residue was partitioned between ethyl acetate (30 mL) and saturated aqueous NaHCO$_3$ solution (about 10 mL). The ethyl acetate layer was washed with brine, dried (MgSO$_4$), filtered, and concentrated. The residue was chromatographed on silica gel eluting with a gradient of 25 to 100% ethyl acetate in heptanes to provide the title compound (18 mg, 0.077 mmol, 68.1% yield). $^1$H NMR (400 MHz, DMSO-d$_6$) δ 10.28 (s, 1H), 6.92 (d, J=11.8 Hz, 1H), 6.76 (d, J=9.0 Hz, 1H), 5.95 (d, J=1.6 Hz, 1H), 4.84 (t, J=5.5 Hz, 1H), 4.35 (s, 2H), 3.60 (d, J=5.5 Hz, 2H), 2.25-2.09 (m, 4H), 1.96-1.78 (m, 2H); LC/MS (ESI+) m/z 235 (M+H)$^+$.

Example 172D (7R)-2,2-difluoro-N-{6-fluoro-2-[1-(hydroxymethyl)cyclobutyl]-1H-indol-5-yl}-7-methyl-6,7-dihydro-2H-furo[2,3-f][1,3]benzodioxole-7-carboxamide A suspension of Example 172C (17.3 mg, 0.074 mmol) in CH$_2$Cl$_2$ (1 mL) at 0° C. was treated with triethylamine (13.38 μL, 0.096 mmol), and a solution of Example 134F (40.9 mg, 0.148 mmol) in CH$_2$Cl$_2$ (0.5 mL). The mixture was stirred over night at room temperature, concentrated to about 0.5 mL volume with a stream of N$_2$, treated with more triethylamine (about 0.02 mL) and stirred overnight. The mixture was concentrated with a steam of N$_2$ and then dissovled in methanol (about 1 mL) and tetrahydrofuran (about 1 mL), treated with 1 M NaOH (0.5 mL), stirred for 15 minutes, acidified with 1 M HCl (2 mL) and extracted with ethyl acetate (30 mL). The ethyl acetate layer was washed with brine, dried (MgSO$_4$), filtered, and concentrated. The residue was chromatographed on silica gel (eluting with a gradient of 15 to 50% ethyl acetate in heptanes). The fractions collected were concentrated to provide a residue which was then partitioned between methyl tert-butyl ether (30 mL) and 1 M NaOH (5 mL). The methyl tert-butyl ether layer was washed with brine, dried (MgSO$_4$), filtered, and concentrated to provide the title compound (23 mg, 0.048 mmol, 65.6% yield). $^1$H NMR (501 MHz, CDCl$_3$) δ 8.60 (bs, 1H), 8.21 (d, J=7.6 Hz, 1H), 7.46-7.45 (m, 1H), 7.03 (s, 1H), 6.98 (d, J=11.1 Hz, 1H), 6.70 (s, 1H), 6.26 (dd, J=2.1, 0.7 Hz, 1H), 5.04 (d, J=9.3 Hz, 1H), 4.40 (d, J=9.3 Hz, 1H), 3.90 (d, J=2.3 Hz, 2H), 2.37-2.31 (m, 2H), 2.20-2.14 (m, 2H), 2.10-2.01 (m, 2H), 1.85 (bs, 1H), 1.71 (s, 3H); LC/MS (ESI+) m/z 475 (M+H)$^+$.

Example 173

(7R)-2,2-difluoro-N-{(2R,4R)-2-[5-(hydroxymethyl) pyrazin-2-yl]-7-methoxy-3,4-dihydro-2H-1-benzopyran-4-yl}-7-methyl-6,7-dihydro-2H-furo[2,3-f][1,3]benzodioxole-7-carboxamide The title compound was obtained from step 3 of Example 144C as the first eluting product. $^1$H NMR (501 MHz, CDCl$_3$) δ 8.75 (s, 1H), 8.55 (s, 1H), 6.89-6.86 (m, 2H), 6.60 (s, 1H), 6.52 (dd, J=8.6, 2.6 Hz, 1H), 6.48 (d, J=2.5 Hz, 1H), 5.70 (d, J=8.7 Hz, 1H), 5.45-5.38 (m, 1H), 5.35 (dd, J=10.5, 2.4 Hz, 1H), 4.85 (d, J=3.7 Hz, 2H), 4.80 (d, J=9.3 Hz, 1H), 4.31 (d, J=9.3 Hz, 1H), 3.78 (s, 3H), 3.00 (bt, J=4.8 Hz, 1H), 2.73 (ddd, J=13.4, 6.3, 2.5 Hz, 1H), 1.98 (dt, J=13.4, 10.2 Hz, 1H), 1.65 (s, 3H); MS (ESI+) m/z 528 (M+H)$^+$.

Example 174

(7R)-2,2-difluoro-N-{(2R,4R)-2-[5-(hydroxymethyl) pyridin-2-yl]-7-methoxy-3,4-dihydro-2H-1-benzopyran-4-yl}-7-methyl-6,7-dihydro-2H-furo[2,3-f][1,3] benzodioxole-7-carboxamide A solution of Example 89E (52.3 mg, 0.094 mmol) in tetrahydrofuran (1 mL) at 0° C. under N$_2$ was treated dropwise with 1 M lithium aluminum hydride in tetrahydrofuran (94 μL, 0.094 mmol), stirred at room temperature for 30 minutes, cooled to 0° C., treated with 1 M HCl (1 mL) and partitioned between ethyl acetate (about 30 mL) and water (about 3 mL). The ethyl acetate layer was washed with brine, dried (MgSO$_4$), filtered, and concentrated. The residue was chromatographed on silica gel eluting with a gradient of 50 to 100% ethyl acetate in heptanes, then eluting with 9:1 ethyl acetate:ethanol to provide the title compound (42.5 mg, 0.081 mmol, 86% yield). $^1$H NMR (501 MHz, CDCl$_3$) δ 8.51 (d, J=1.6 Hz, 1H), 7.72 (dd, J=8.0, 2.2 Hz, 1H), 7.48 (d, J=8.0 Hz, 1H), 6.90 (dd, J=8.5, 0.8 Hz, 1H), 6.84 (s, 1H), 6.58 (s, 1H), 6.50 (dd, J=8.5, 2.6 Hz, 1H), 6.47 (d, J=2.5 Hz, 1H), 5.78 (d, J=8.7 Hz, 1H), 5.37 (td, J=8.3, 6.6 Hz, 1H), 5.31 (dd, J=9.3, 2.9 Hz, 1H), 4.74-4.71 (m, 3H), 4.29 (d, J=9.2 Hz, 1H), 3.77 (s, 3H), 2.68 (ddd, J=13.6, 6.3, 2.9 Hz, 1H), 2.06 (dt, J=13.6, 9.1 Hz, 1H), 1.96 (t, J=5.7 Hz, 1H), 1.61 (s, 3H); MS (ESI+) m/z 527 (M+H)$^+$; MS (ESI−) m/z 525 (M−H)$^-$.

Example 175

(7R)—N-{(2R,4R)-2-[5-(1,2-dihydroxyethyl) pyrazin-2-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide Example 175A methyl 5-ethenylpyrazine-2-carboxylate A solution of methyl 5-chloropyrazine-2-carboxylate (1 g, 5.79 mmol), potassium vinyltrifluoroborate (1.708 g, 12.75 mmol) and 1,1'-bis(diphenylphosphino)ferrocenedichloro palladium(II) dichloromethane complex (0.424 g, 0.579 mmol) in isopropyl alcohol (18 mL) was treated with triethylamine (1.615 mL, 11.59 mmol) and the atmosphere was vacuum purged with N$_2$ a few times. The mixture was heated at 80° C. under N$_2$ for 3.5 hours. The mixture was cooled, diluted with ethyl acetate (about 100 mL) and washed with 1 M HCl (about 50 mL). The layers were separated and the aqueous layer was extracted twice with methyl tert-butyl ether (25 mL×2). The combined organic layers were washed with brine, dried (MgSO$_4$), filtered, and concentrated. 100 mL of ethyl acetate was added, and significant amount of solid did not dissolve. The solid was removed by filtration and discarded. The filtrate was concentrated to dryness and chromatographed on silica gel eluting with a gradient of 30 to 100% ethyl acetate in heptanes to provide the title compound (0.3 g, 1.827 mmol, 31.5% yield). $^1$H NMR (400 MHz, CDCl$_3$) δ 9.23 (d, J=1.3 Hz, 1H), 8.67 (d, J=1.3 Hz, 1H), 6.90 (dd, J=17.4, 10.9 Hz, 1H), 6.52 (dd, J=17.4, 0.8 Hz, 1H), 5.78 (dd, J=10.9, 0.8 Hz, 1H), 4.03 (s, 3H).

Example 175B methyl 5-(1,2-dihydroxyethyl)pyrazine-2-carboxylate

A solution of N-methylmorpholine N-oxide (0.246 g, 2.102 mmol) in 4.5 mL water and 1.5 mL tetrahydrofuran was treated with 2.5% osmium tetroxide in tert-butanol (0.459 mL, 0.037 mmol), treated with a solution of Example 175A (0.3 g, 1.827 mmol) in tetrahydrofuran (2 mL) and stirred at room temperature overnight. The mixture was diluted with tetrahydrofuran, treated with silica gel (3 g) and concentrated to dryness. The silica gel suspension was chromatographed on silica gel eluting with a gradient of 20 to 100% ethyl acetate in heptanes, then eluted with 10% ethanol in ethyl acetate to provide the title compound (195 mg, 0.984 mmol, 53.8% yield). $^1$H NMR (501 MHz, CDCl$_3$) δ 9.21 (d, J=1.4 Hz, 1H), 8.88 (d, J=1.0 Hz, 1H), 5.01 (q, J=5.4 Hz, 1H), 4.06-3.99 (m, 4H), 3.94-3.86 (m, 2H), 2.69 (t, J=6.0 Hz, 1H); MS (ESI+) m/z 199 (M+H)$^+$.

Example 175C methyl 5-(2,2-dimethyl-1,3-dioxolan-4-yl)pyrazine-2-carboxylate

A solution of Example 175B (192 mg, 0.969 mmol) and 2,2-dimethoxypropane (238 μL, 1.938 mmol) tetrahydrofuran (2 mL) was treated with p-toluenesulfonic acid monohydrate (18.43 mg, 0.097 mmol), stirred at room temperature for 1 hour, diluted with ethyl acetate (30 mL), washed with saturated aqueous NaHCO$_3$ solution (3 mL), washed with brine, dried (MgSO$_4$), filtered, concentrated, and chromatographed on silica gel eluting with a gradient of 15-100% ethyl acetate in heptanes to provide the title compound (199 mg, 0.835 mmol, 86% yield). $^1$H NMR (501 MHz, CDCl$_3$) δ 9.24 (d, J=1.4 Hz, 1H), 8.95 (dd, J=1.4, 0.6 Hz, 1H), 5.32 (t, J=6.5 Hz, 1H), 4.53 (dd, J=8.6, 7.0 Hz, 1H), 4.09 (dd, J=8.6, 5.9 Hz, 1H), 4.07 (s, 3H), 1.56 (d, J=0.5 Hz, 3H), 1.53 (d, J=0.5 Hz, 3H); LC/MS (ESI+) m/z 239 (M+H)$^+$.

Example 175D 5-(2,2-dimethyl-1,3-dioxolan-4-yl)pyrazine-2-carbaldehyde

A solution of Example 175C (24 mg, 0.101 mmol) in tetrahydrofuran (1 mL) at −78° C. under N$_2$ was treated dropwise with 1 M lithium aluminum hydride in tetrahydrofuran (50.4 µL, 0.050 mmol), stirred an additional 20 minutes at −78° C., quenched with the dropwise addition of acetic acid (about 0.2 mL) and allowed to warm to room temperature. The mixture was partitioned between ethyl acetate (30 mL) and saturated aqueous NaHCO$_3$ solution (about 5 mL). The ethyl acetate layer was washed with brine, dried (MgSO$_4$), filtered, and concentrated. The residue was chromatographed on silica gel eluting with a gradient of 15 to 100% ethyl acetate in heptanes to provide the title compound. $^1$H NMR (400 MHz, CDCl$_3$) δ 10.16 (s, 1H), 9.08 (d, J=1.2 Hz, 1H), 8.98 (s, 1H), 5.31 (t, J=6.5 Hz, 1H), 4.52 (dd, J=8.6, 7.1 Hz, 1H), 4.06 (dd, J=8.6, 5.9 Hz, 1H), 1.56 (s, 3H), 1.52 (s, 3H); LC/MS (ESI+) m/z 209 (M+11)$^+$.

Example 175E

A solution of N,N-diisopropylamine (70.8 µL, 0.497 mmol) in tetrahydrofuran (1 mL) under N$_2$ at −20° C. was treated with 2.5 M n-butyl lithium in hexanes (190 µL, 0.474 mmol), stirred for 15 minutes, cooled to −40° C., treated with a solution of Example 89A (66.9 mg, 0.248 mmol) in tetrahydrofuran (1 mL), stirred at 0° C. for 1 hour, cooled to −78° C., treated with a solution of Example 175D (47 mg, 0.226 mmol) in tetrahydrofuran (1 mL), allowed to warm to 0° C., quenched with saturated NH$_4$Cl solution (5 mL), stirred for 1 minute, and extracted with ethyl acetate. The organic layer was washed with brine, dried (MgSO$_4$), filtered, concentrated and chromatographed on silica gel eluting with a gradient of 15 to 100% ethyl acetate in heptanes to provide the title compound (31 mg, 0.065 mmol, 28.8% yield). LC/MS (ESI+) m/z 478 (M+H)$^+$.

Example 175F

A solution of Example 175E (30 mg, 0.063 mmol) and triphenylphosphine (19.77 mg, 0.075 mmol) in CH$_2$Cl$_2$ (2 mL) at 0° C. under N$_2$ was treated with diethyl azodicarboxylate, 40 wt. % solution in toluene (71.5 µL, 0.157 mmol), stirred at 0° C. for 5 minutes, stirred at room temperature for 75 minutes, diluted with heptanes, stirred for 5 minutes, and filtered to remove the solids. The filtrate was chromatographed on silica gel eluting with a gradient of 25 to 50% ethyl acetate in heptanes to provide the title compound (21 mg, 0.046 mmol, 72.7% yield). LC/MS (ESI+) m/z 460 (M+H)$^+$.

Example 175G

1-{5-[(2R,4R)-4-amino-7-methoxy-3,4-dihydro-2H-1-benzopyran-2-yl]pyrazin-2-yl}ethane-1,2-diol A solution of Example 175F (19.4 mg, 0.042 mmol) in methanol (1 mL) was cooled to 0° C., treated with NaBH$_4$ (4.79 mg, 0.127 mmol), stirred at 0° C. for 1 hour, treated with more NaBH$_4$ (4 mg), stirred at 0° C. for 45 minutes, treated with 4 M HCl in dioxane (317 µL, 1.266 mmol), stirred for 5 minutes at 0° C., and stirred at room temperature for 1 hour. The mixture was partitioned between methyl tert-butyl ether (20 mL) and water (3 mL). The methyl tert-butyl ether layer was extracted with 0.5 M HCl (2×3 mL). These aqueous layers were combined, concentrated, and dried under vacuum to provide the HCl salt of the title compound. $^1$H NMR (400 MHz, DMSO-d$_6$) δ 8.90 (bs, 3H), 8.77 (s, 1H), 8.76 (s, 2H), 7.65 (d, J=8.6 Hz, 1H), 6.65 (dd, J=8.7, 2.4 Hz, 1H), 6.53 (t, J=2.2 Hz, 1H), 5.43 (d, J=11.6 Hz, 1H), 4.80-4.74 (m, 1H), 4.71 (t, J=5.3 Hz, 1H), 3.76- 3.69 (m, 4H), 3.63 (dd, J=11.0, 5.8 Hz, 1H), 2.74 (dd, J=12.9, 5.7 Hz, 1H), 2.20 (q, J=12.0 Hz, 1H); LC/MS (ESI+) m/z 301 (M−NH$_3$)$^+$.

Example 175H (7R)—N-{(2R,4R)-2-[5-(1,2-dihydroxyethyl)pyrazin-2-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide A suspension of Example 175G (25 mg, 0.071 mmol) in CH$_2$Cl$_2$ (1 mL) was cooled to 0° C., treated with a solution of Example 134F (21.50 mg, 0.078 mmol) in CH$_2$Cl$_2$, stirred at room temperature for 30 minutes, treated with more Example 134F (about 30 mg) in CH$_2$Cl$_2$ (about 1 mL), stirred for 30 more minutes and concentrated with a stream of N$_2$. The residue was suspended in tetrahydrofuran (1.5 mL), brought into solution with the addition of methanol (1.5 mL), and then treated with 1 M NaOH (about 2 mL). The mixture was stirred at room temperature for 15 minutes, diluted with 1 M NaOH (2 mL), and extracted with methyl tert-butyl ether (twice, 2×30 mL). The combined methyl tert-butyl ether layers were washed with brine, dried (MgSO$_4$), filtered, concentrated and chromatographed on silica gel eluting with a gradient of 50 to 100% [9:1 ethyl acetate:ethanol] in heptanes to provide the title compound. $^1$H NMR (501 MHz, CDCl$_3$) δ 8.74 (dd, J=4.2, 1.2 Hz, 1H), 8.66 (s, 1H), 6.89 (dd, J=2.6, 0.3 Hz, 2H), 6.87 (d, J=8.6 Hz, 1H), 6.60 (s, 1H), 6.52 (dd, J=8.6, 2.5 Hz, 1H), 6.47 (d, J=2.5 Hz, 1H), 5.72-5.67 (m, 1H), 5.45-5.38 (m, 1H), 5.35 (dd, J=10.7, 2.3 Hz, 1H), 4.95-4.92 (m, 1H), 4.80 (dd, J=9.3, 4.9 Hz, 1H), 4.31 (dd, J=9.3, 1.7 Hz, 1H), 3.99 (dd, J=11.4, 4.0 Hz, 1H), 3.87 (ddd, J=11.5, 5.5, 2.5 Hz, 1H), 3.77 (s, 3H), 2.74 (ddd, J=13.4, 6.3, 2.5 Hz, 1H), 1.95 (dq, J=13.3, 10.6 Hz, 1H), 1.65 (d, J=1.0 Hz, 3H); MS (ESI+) m/z 558 (M+H)$^+$; MS (ESI−) m/z 556 (M−H)$^−$.

Example 176

(7R)—N-[(2R,4R)-2-(6-bromopyridin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide Example 176A (S)—N-[(1E,3S)-3-(6-bromopyridin-3-yl)-3-hydroxy-1-(2-hydroxy-4-methoxyphenyl)propylidene]-2-methylpropane-2-sulfinamide A solution of Example 89A (100 mg, 0.371 mmol) in tetrahydrofuran (3 mL) under N$_2$ at −40° C. was treated with 0.5 M lithium diisopropyamine in tetrahydrofuran (1418 µL, 0.709 mmol), stirred at 0° C. for 1 hour, cooled to −78° C., and treated with a solution of 6-bromonicotinaldehyde (CAS #149806-06-4, 62.8 mg, 0.338 mmol) in tetrahydrofuran (1 mL). The mixture was allowed to slowly warm to 0° C. and stirred for 15 minutes. The mixture was cooled to −40° C. and quenched with the addition of 2 mL of 20% acetic acid in tetrahydrofuran. The mixture was warmed to near 0° C., diluted with ethyl acetate (about 30 mL), washed with saturated aqueous NaHCO$_3$ solution, washed with brine, dried (MgSO$_4$), filtered, concentrated and chromatographed on silica gel eluting with a gradient of 15 to 100% ethyl acetate in heptanes to provide title compound as the second eluting isomer (44 mg, 0.097 mmol, 28.6% yield). LC/MS (ESI+) m/z 455, 457 (M+H)+.

Example 176B (S)—N-[(2R,E)-2-(6-bromopyridin-3-yl)-7-methoxy-2,3-dihydro-4H-1-benzopyran-4-ylidene]-2-methylpropane-2-sulfinamide A solution of Example 176A (44 mg, 0.097 mmol) and triphenylphosphine (30.4 mg, 0.116 mmol) in $CH_2Cl_2$ (2 mL) at 0° C. under $N_2$ was treated with diethyl azodicarboxylate, 40 wt. % solution in toluene (110 μL, 0.242 mmol), stirred at 0° C. for 5 minutes, stirred at room temperature for 75 minutes, diluted with heptanes and chromatographed on silica gel eluting with a gradient of 15 to 50% ethyl acetate in heptanes to provide the title compound (28.5 mg, 0.065 mmol, 67.4% yield). $^1$H NMR (400 MHz, $CDCl_3$) δ 8.49 (d, J=2.5 Hz, 1H), 7.92 (d, J=8.9 Hz, 1H), 7.69 (dd, J=8.3, 2.5 Hz, 1H), 7.53 (d, J=8.2 Hz, 1H), 6.61 (dd, J=8.9, 2.5 Hz, 1H), 6.46 (d, J=2.4 Hz, 1H), 5.27 (dd, J=12.2, 2.9 Hz, 1H), 3.83 (s, 3H), 3.73 (dd, J=17.4, 3.0 Hz, 1H), 3.35 (dd, J=17.4, 12.1 Hz, 1H), 1.30 (s, 9H); LC/MS (ESI+) m/z 437,439 (M+H)+.

Example 176C (2R,4R)-2-(6-bromopyridin-3-yl)-7-methoxy-3,4-dihydro-2H-1-benzopyran-4-amine A solution of Example 176B (28.5 mg, 0.065 mmol) in methanol (1 mL) was cooled to 0° C., treated with $NaBH_4$ (7.40 mg, 0.195 mmol), stirred at 0° C. for 30 minutes, treated with 4 M HCl in dioxane (326 μL, 1.303 mmol), stirred for 5 minutes at 0° C., stirred at room temperature for 45 minutes, and partitioned between methyl tert-butyl ether (30 mL) and water (5 mL). The methyl tert-butyl ether layer was extracted with 0.1 M HCl (5 mL). The methyl tert-butyl ether layer was discarded. The combined aqueous layers were basified with solid $NaHCO_3$ and extracted with ethyl acetate (2×25 mL). The combined ethyl acetate layers were washed with brine, dried ($MgSO_4$), filtered, and concentrated to provide the title compound (19.6 mg, 0.058 mmol, 90% yield). $^1$H NMR (400 MHz, $CDCl_3$) δ 8.44 (d, J=2.3 Hz, 1H), 7.66 (dd, J=8.2, 2.5 Hz, 1H), 7.53 (d, J=8.2 Hz, 1H), 7.40 (d, J=8.6 Hz, 1H), 6.59 (dd, J=8.6, 2.5 Hz, 1H), 6.42 (d, J=2.5 Hz, 1H), 5.16 (d, J=11.2 Hz, 1H), 4.25 (bs, 1H), 3.78 (s, 3H), 2.39 (dd, J=13.0, 4.7 Hz, 1H), 1.89 (q, J=11.6 Hz, 1H); LC/MS (ESI+) m/z 318,320 (M−$NH_3$)+, 336,338 (M+H)+.

Example 176D (7R)—N-[(2R,4R)-2-(6-bromopyridin-3-yl)-7-methoxy-3,4-dihydro-2H-1-benzopyran-4-yl]-2,2-difluoro-7-methyl-6,7-dihydro-2H-furo[2,3-f][1,3] benzodioxole-7-carboxamide A solution of Example 176C (19.6 mg, 0.058 mmol) and triethylamine (16.30 μL, 0.117 mmol) in $CH_2Cl_2$ (2 mL) at 0° C. under $N_2$ was treated with a solution of Example 134F (17.79 mg, 0.064 mmol) in $CH_2Cl_2$ (1 mL). The mixture was stirred at 0° C. for 15 minutes and at room temperature for 1 hour. The mixture was partitioned between methyl tert-butyl ether (about 30 mL) and saturated aqueous $NaHCO_3$ solution (about 3 mL). The methyl tert-butyl ether layer was washed with brine, dried ($MgSO_4$), filtered, concentrated and chromatographed on silica gel eluting with a gradient of 15 to 100% ethyl acetate in heptanes to provide the title compound (27 mg, 0.047 mmol, 80% yield). $^1$H NMR (501 MHz, $CDCl_3$) δ 8.42 (d, J=2.5 Hz, 1H), 7.60 (dd, J=8.2, 2.5 Hz, 1H), 7.50 (d, J=8.2 Hz, 1H), 6.91 (s, 1H), 6.83 (dd, J=8.6, 0.9 Hz, 1H), 6.62 (s, 1H), 6.52 (dd, J=8.6, 2.6 Hz, 1H), 6.43 (d, J=2.5 Hz, 1H), 5.62 (d, J=8.6 Hz, 1H), 5.43-5.36 (m, 1H), 5.17 (dd, J=11.5, 1.7 Hz, 1H), 4.82 (d, J=9.3 Hz, 1H), 4.32 (d, J=9.3 Hz, 1H), 3.77 (s, 3H), 2.50 (ddd, J=13.2, 6.2, 1.9 Hz, 1H), 1.79 (dt, J=13.2, 11.3 Hz, 1H), 1.66 (s, 3H); MS (ESI+) m/z 575,577 (M+H)+; MS (ESI−) m/z 573,575 (M−H)−.

Example 177

(7R)-2,2-difluoro-N-[(2R,4R)-2-[5-(hydroxymethyl) pyridin-2-yl]-7-(trifluoromethoxy)-3,4-dihydro-2H-1-benzopyran-4-yl]-7-methyl-6,7-dihydro-2H-furo [2,3-f][1,3]benzodioxole-7-carboxamide A solution of Example 145F (22.7 mg, 0.037 mmol) in tetrahydrofuran (1 mL) at 0° C. under $N_2$ was treated dropwise with 1 M lithium aluminum hydride in tetrahydrofuran (37.3 μL, 0.037 mmol), stirred at room temperature for 1 hour, cooled to 0° C., treated dropwise with more 1 M lithium aluminum hydride in tetrahydrofuran (50 μL, 0.050 mmol), stirred at 0° C. for 1 hour, treated with 1 M HCl (1 mL) and extracted with ethyl acetate (about 30 mL). The ethyl acetate layer was washed with brine, dried ($MgSO_4$), filtered, and concentrated. The residue was chromatographed on silica gel eluting with a gradient of 20 to 100% [9:1 ethyl acetate:ethanol] in heptanes to provide the title compound (13.9 mg, 0.024 mmol, 64.2% yield). $^1$H NMR (400 MHz, $CDCl_3$) δ 8.50 (d, J=1.3 Hz, 1H), 7.76 (dd, J=8.1, 2.0 Hz, 1H), 7.50 (d, J=8.0 Hz, 1H), 7.03 (d, J=8.5 Hz, 1H), 6.86 (s, 1H), 6.81-6.75 (m, 2H), 6.61 (s, 1H), 5.99 (d, J=8.8 Hz, 1H), 5.48-5.41 (m, 1H), 5.35 (dd, J=9.3, 2.8 Hz, 1H), 4.79 (d, J=9.3 Hz, 1H), 4.75 (s, 2H), 4.31 (d, J=9.3 Hz, 1H), 2.71 (ddd, J=13.7, 6.2, 2.9 Hz, 1H), 2.09 (td, J=13.7, 9.4 Hz, 1H), 1.63 (s, 3H); MS (ESI+) m/z 581 (M+H)+; MS (ESI−) m/z 579 (M−H)−.

Example 178

(7R)-2,2-difluoro-N-{(2R,4R)-2-[6-(hydroxymethyl) pyridin-3-yl]-7-methoxy-3,4-dihydro-2H-1-benzopyran-4-yl}-7-methyl-6,7-dihydro-2H-furo[2,3-f][1,3] benzodioxole-7-carboxamide A solution of Example 146D (13.6 mg, 0.025 mmol) in tetrahydrofuran (1 mL) at 0° C. under $N_2$ was treated dropwise with 1 M lithium aluminum hydride in tetrahydrofuran (24.53 μL, 0.025 mmol), stirred at room temperature for 1 hour, cooled to 0° C., treated dropwise with 1 M lithium aluminum hydride in tetrahydrofuran (50 μL, 0.050 mmol), stirred at 0° C. for 1 hour, treated with 1 M HCl (1 mL) and extracted with ethyl acetate (about 30 mL). The ethyl acetate layer was washed with brine, dried ($MgSO_4$), filtered, and concentrated. The residue was chromatographed on silica gel eluting with a gradient of 20 to 100% [9:1 ethyl acetate:ethanol] in heptanes to provide the title compound (3.7 mg, 7.03 μmol, 28.7% yield). $^1$H NMR (400 MHz, $CDCl_3$) δ 8.60 (d, J=1.2 Hz, 1H), 7.73 (dd, J=8.1, 2.0 Hz, 1H), 7.27 (d, J=8.7 Hz, 1H), 6.91 (s, 1H), 6.84 (d, J=8.6 Hz, 1H), 6.61 (s, 1H), 6.52 (dd, J=8.6, 2.5 Hz, 1H), 6.44 (d, J=8.7 Hz, 1H), 5.63 (d, J=8.8 Hz, 1H), 5.45-5.37 (m, 1H), 5.22 (d, J=10.6 Hz, 1H), 4.81 (d, J=9.3 Hz, 1H), 4.78 (s, 2H), 4.32 (d, J=9.3 Hz, 1H), 3.77 (s, 3H), 2.51 (ddd, J=13.0, 6.0, 1.5 Hz, 1H), 1.85 (td, J=13.0, 11.1 Hz, 1H), 1.66 (s, 3H); MS (ESI+) m/z 527 (M+H)⁺; MS (ESI−) m/z 525 (M−H)⁻.

Example 179

(7R)—N-{1-[(2S)-3-cyano-2-hydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide Example 179A (2R)-3-[5-{[(7R)-2,2-difluoro-7-methyl-6,7-dihydro-2H-furo[2,3-f][1,3]benzodioxole-7-carbonyl]amino}-6-fluoro-2-(1-hydroxy-2-methylpropan-2-yl)-1H-indol-1-yl]-2-hydroxypropyl 4-methylbenzene-1-sulfonate The product from Example 130G (0.100 g, 0.186 mmol) in dichloromethane (2 mL) was treated with p-toluenesulfonyl chloride (0.036 g, 0.186 mmol) and then dropwise with pyridine (0.033 ml, 0.410 mmol). The mixture was stirred overnight at room temperature, diluted with 10 mL dichloromethane, and washed three times with water (2 mL each) and once with brine (2 mL). The organic layer was dried over Na₂SO₄, filtered, and concentrated in vacuo. The residue was purified by silica gel chromatography, eluting with 0 to 70% ethyl acetate-heptanes, to afford the title compound (0.037 g, 29%). ¹H NMR (400 MHz, DMSO-d₆) δ 9.18 (s, 1H), 7.73 (d, J=8.3 Hz, 2H), 7.60-7.42 (m, 3H), 7.40-7.23 (m, 2H), 7.01 (s, 1H), 6.20 (s, 1H), 5.49 (d, J=5.0 Hz, 1H), 5.05 (d, J=9.1 Hz, 1H), 4.72 (m 1H), 4.37 (d, J=9.0 Hz, 1H), 4.26-4.01 (m, 5H), 3.49 (m, 2H), 2.37 (s, 3H), 1.64 (s, 3H), 1.26 (s, 3H), 1.23 (s, 3H). MS (ESI⁺) m/z 691.0 (M+H)⁺.

Example 179B (7R)—N-{1-[(2S)-3-cyano-2-hydroxypropyl]-6-fluoro-2-(1-hydroxy-2-methylpropan-2-yl)-1H-indol-5-yl}-2,2-difluoro-7-methyl-6,7-dihydro-2H-furo[2,3-f][1,3]benzodioxole-7-carboxamide The product of Example 179A (0.039 g, 0.056 mmol) and sodium cyanide (8.30 mg, 0.169 mmol) were stirred in N,N-dimethylformamide (1 mL) at 80° C. for 2 hours. After cooling to room temperature, the reaction mixture was concentrated in vacuo, and the crude product was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The title compound was obtained as a white solid (8.6 mg, 28%). ¹H NMR (501 MHz, CDCl₃) δ 8.11 (d, J=7.6 Hz, 1H), 7.46 (d, J=2.7 Hz, 1H), 7.08-6.91 (m, 2H), 6.73 (s, 1H), 6.36 (d, J=0.8 Hz, 1H), 5.04 (d, J=9.3 Hz, 1H), 4.48-4.35 (m, 3H), 4.32 (d, J=12.4 Hz, 1H), 3.94 (dd, J=11.4, 5.2 Hz, 1H), 3.78 (d, J=3.8 Hz, 1H), 3.61 (dd, J=11.4, 5.9 Hz, 1H), 2.65 (dd, J=5.3, 4.0 Hz, 2H), 2.48 (t, J=6.1 Hz, 1H), 1.73 (s, 3H), 1.49 (s, 3H), 1.38 (s, 3H). MS (ESI⁺) m/z 546.1 (M+H)⁺.

Example 180

(7R)—N-[(2R,4R)-2-(5-acetylpyridin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 89E (27 mg, 0.049 mmol) in tetrahydrofuran (about 1 mL) under N₂ was cooled to 0° C., treated with 3 M methylmagnesium bromide in diethyl ether (97 µL, 0.292 mmol), stirred at 0° C. for 1 hour, quenched with 1 M HCl (2 mL), and extracted with ethyl acetate (30 mL). The ethyl acetate layer was washed with brine, dried (MgSO₄), filtered, and concentrated. The residue was chromatographed on silica gel eluting with a gradient of 30 to 90% ethyl acetate in heptanes to provide the title compound as the first eluting product (4.6 mg, 8.54 µmol, 17.54% yield). ¹H NMR (501 MHz, CDCl₃) δ 9.08 (dd, J=2.2, 0.7 Hz, 1H), 8.23 (dd, J=8.2, 2.2 Hz, 1H), 7.63 (d, J=8.2 Hz, 1H), 6.89 (dd, J=8.6, 0.7 Hz, 1H), 6.84 (s, 1H), 6.56 (s, 1H), 6.52 (dd, J=8.5, 2.6 Hz, 1H), 6.50 (d, J=2.5 Hz, 1H), 5.62 (d, J=8.6 Hz, 1H), 5.39 (td, J=9.1, 6.9 Hz, 1H), 5.34 (dd, J=9.9, 2.6 Hz, 1H), 4.75 (d, J=9.3 Hz, 1H), 4.30 (d, J=9.3 Hz, 1H), 3.78 (s, 3H), 2.75 (ddd, J=13.5, 6.2, 2.7 Hz, 1H), 2.64 (s, 3H), 1.98 (dt, J=13.5, 9.7 Hz, 1H), 1.63 (s, 3H); LC/MS (ESI+) m/z 539 (M+H)⁺.

Example 181

(7R)-2,2-difluoro-N-{(2R,4R)-2-[5-(2-hydroxypropan-2-yl)pyridin-2-yl]-7-methoxy-3,4-dihydro-2H-1-benzopyran-4-yl}-7-methyl-6,7-dihydro-2H-furo[2,3-f][1,3]benzodioxole-7-carboxamide A solution of Example 89E (27 mg, 0.049 mmol) in tetrahydrofuran (about 1 mL) under N₂ was cooled to 0° C., treated with 3 M methylmagnesium bromide in diethyl ether (97 µL, 0.292 mmol), stirred at 0° C. for 1 hour, quenched with 1 M HCl (2 mL) and extracted with ethyl acetate (30 mL). The ethyl acetate layer was washed with brine, dried (MgSO₄), filtered, concentrated, and chromatographed on silica gel eluting with a gradient of 30 to 90% ethyl acetate in heptanes to provide the title compound as the second eluting product (5.6 mg, 10.10 µmol, 20.74% yield). ¹H NMR (501 MHz, CDCl₃) δ 8.67 (dd, J=2.4, 0.7 Hz, 1H), 7.85 (dd, J=8.2, 2.4 Hz, 1H), 7.47 (d, J=8.2 Hz, 1H), 6.90 (dd, J=8.6, 0.7 Hz, 1H), 6.87 (s, 1H), 6.58 (d, J=0.3 Hz, 1H), 6.50 (dd, J=8.6, 2.6 Hz, 1H), 6.47 (d, J=2.6 Hz, 1H), 5.85 (d, J=8.8 Hz, 1H), 5.40 (td, J=8.8, 6.2 Hz, 1H), 5.30 (dd, J=9.8, 2.6 Hz, 1H), 4.77 (d, J=9.2 Hz, 1H), 4.29 (d, J=9.2 Hz, 1H), 3.76 (s, 3H), 2.69 (ddd, J=13.5, 6.4, 2.8 Hz, 1H), 2.02 (dt, J=13.5, 9.6 Hz, 1H), 1.61 (s, 3H), 1.56 (s, 6H); LC/MS (ESI+) m/z 555 (M+H)⁺.

Example 182

(7R)-2,2-difluoro-7-methyl-N-[(2R,4R)-2-(piperidin-4-yl)-7-(trifluoromethoxy)-3,4-dihydro-2H-1-benzopyran-4-yl]-6,7-dihydro-2H-furo[2,3-f][1,3]benzodioxole-7-carboxamide A mixture of Example 224C (0.380 g, 0.550 mmol) and 10% Pd/C (0.059 g, 0.055 mmol) in methanol (2 mL) was stirred under an atmosphere of H₂ (balloon) for 1 hour. The atmosphere was exchanged with N₂. The mixture was diluted with methanol (30 mL), stirred for 5 minutes and filtered through diatomaceous earth to remove the solids.

The filtrate was concentrated and dried under vacuum (50° C., 30 minutes) to provide the title compound (297 mg, 0.534 mmol, 97% yield). $^1$H NMR (400 MHz, CDCl$_3$) δ 6.91 (s, 1H), 6.87 (d, J=8.5 Hz, 1H), 6.71-6.67 (m, 1H), 6.66 (s, 1H), 6.64 (s, 1H), 5.64 (d, J=8.9 Hz, 1H), 5.30-5.22 (m, 1H), 4.89 (d, J=9.3 Hz, 1H), 4.34 (d, J=9.3 Hz, 1H), 3.93 (dd, J=11.3, 5.5 Hz, 1H), 3.15 (d, J=12.0 Hz, 2H), 2.61 (t, J=12.1 Hz, 2H), 2.24 (dd, J=12.8, 6.2 Hz, 1H), 2.05-1.94 (m, 2H), 1.87 (d, J=12.8 Hz, 1H), 1.76-1.62 (m, 1H), 1.67 (s, 3H), 1.50 (q, J=11.9 Hz, 1H), 1.44-1.26 (m, 2H); LC/MS (ESI+) m/z 557 (M+H)$^+$.

Example 183 tert-butyl {4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetate A solution of Example 185 (35 mg, 0.063 mmol) and triethylamine (17.53 μL, 0.126 mmol) was treated with tert-butyl bromoacetate (13.94 μL, 0.094 mmol), stirred at room temperature for 45 minutes and then partitioned between ethyl acetate (about 30 mL) and saturated aqueous NaHCO$_3$ solution (about 5 mL). The ethyl acetate layer was washed with brine, dried (MgSO$_4$), filtered, and concentrated. The residue was chromatographed on silica gel eluting with a gradient of 25-100% ethyl acetate in heptanes to provide the title compound (37 mg, 0.055 mmol, 88% yield). $^1$H NMR (501 MHz, CDCl$_3$) δ 6.93 (dd, J=8.5, 1.0 Hz, 1H), 6.86 (s, 1H), 6.69 (ddd, J=8.5, 2.3, 0.9 Hz, 1H), 6.65 (s, 1H), 6.64 (dd, J=2.2, 0.9 Hz, 1H), 5.57 (d, J=9.1 Hz, 1H), 5.31-5.25 (m, 1H), 4.93 (d, J=9.3 Hz, 1H), 4.37 (d, J=9.3 Hz, 1H), 3.96 (dd, J=11.7, 3.4 Hz, 1H), 3.12 (s, 2H), 3.02 (d, J=11.0 Hz, 2H), 2.26 (ddd, J=12.9, 6.2, 1.4 Hz, 1H), 2.20-2.14 (m, 2H), 1.87 (dd, J=10.0, 2.2 Hz, 1H), 1.69-1.65 (m, 1H), 1.64 (s, 3H), 1.61-1.54 (m, 3H), 1.53-1.45 (m, 1H), 1.47 (s, 9H); LC/MS (ESI+) m/z 671 (M+H)$^+$.

Example 184

{4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetic acid A solution of Example 183 (29.8 mg, 0.044 mmol) in trifluoroacetic acid (1 mL) was stirred at room temperature for 15 minutes, heated at 55° C. for 30 minutes, cooled, concentrated and dried under vacuum with heating to 50° C. to provide the title compound (33.5 mg, 0.046 mmol, 103% yield). $^1$H NMR (400 MHz, DMSO-d$_6$) δ 8.04 (d, J=8.7 Hz, 1H), 7.41 (s, 1H), 7.04 (s, 1H), 6.93 (d, J=8.5 Hz, 1H), 6.82-6.79 (m, 1H), 6.74 (s, 1H), 5.26-5.17 (m, 1H), 5.00 (d, J=9.1 Hz, 1H), 4.35 (d, J=9.1 Hz, 1H), 4.20-4.14 (m, 1H), 4.10 (s, 2H), 3.43 (s, 2H), 3.13-3.01 (m, 2H), 2.12-2.03 (m, 2H), 1.91-1.62 (m, 5H), 1.58 (s, 3H); LC/MS (ESI+) m/z 615 (M+H)$^+$.

Example 185

(7R)-2,2-difluoro-7-methyl-N-[(2S,4S)-2-(piperidin-4-yl)-7-(trifluoromethoxy)-3,4-dihydro-2H-1-benzopyran-4-yl]-6,7-dihydro-2H-furo[2,3-f][1,3]benzodioxole-7-carboxamide A mixture of Example 225E (0.339 g, 0.491 mmol) and 10% Pd/C (0.052 g, 0.049 mmol) in methanol (2 mL) was stirred under an atmosphere of H$_2$ (balloon) for 1 hour. The atmosphere was exchanged with N$_2$. The mixture was diluted with methanol (30 mL), stirred for 5 minutes and filtered through diatomaceous earth to remove the solids. The filtrate was concentrated and dried under vacuum (50° C., 30 minutes) to provide the title compound (218 mg, 0.392 mmol, 80% yield). $^1$H NMR (400 MHz, CDCl$_3$) δ 6.93 (d, J=8.5 Hz, 1H), 6.86 (s, 1H), 6.69 (d, J=8.6 Hz, 1H), 6.67-6.64 (m, 2H), 5.58 (d, J=8.9 Hz, 1H), 5.33-5.24 (m, 1H), 4.94 (d, J=9.3 Hz, 1H), 4.37 (d, J=9.3 Hz, 1H), 3.94 (dd, J=11.3, 5.7 Hz, 11), 3.15 (d, J=12.1 Hz, 2H), 2.62 (tt, J=12.2, 2.7 Hz, 2H), 2.25 (ddd, J=12.8, 6.1, 1.1 Hz, 1H), 1.98-1.66 (m, 4H), 1.64 (s, 3H), 1.50 (q, J=11.7 Hz, 1H), 1.44-1.27 (m, 1H); LC/MS (ESI+) m/z 557 (M+H)$^+$.

Example 186 tert-butyl {4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetate A solution of Example 182 (35 mg, 0.063 mmol) and triethylamine (17.53 μL, 0.126 mmol) was treated with tert-butyl bromoacetate (13.94 μL, 0.094 mmol) and stirred at room temperature for 40 minutes. The mixture was treated with more triethylamine (0.1 mL) and more tert-butyl bromoacetate (43 mg), stirred at room temperature for 30 minutes, and partitioned between ethyl acetate (about 30 mL) and saturated aqueous NaHCO$_3$ solution (about 5 mL). The ethyl acetate layer was washed with brine, dried (MgSO$_4$), filtered, concentrated and chromatographed on silica gel eluting with a gradient of 25-100% ethyl acetate in heptanes to provide the title compound (37 mg, 0.055 mmol, 88% yield). $^1$H NMR (501 MHz, CDCl$_3$) δ 6.90 (d, J=0.3 Hz, 1H), 6.87 (dd, J=8.5, 0.9 Hz, 1H), 6.69 (ddd, J=8.5, 2.2, 0.9 Hz, 1H), 6.65 (dd, J=2.2, 1.0 Hz, 1H), 6.64 (d, J=0.3 Hz, 1H), 5.61 (d, J=8.9 Hz, 1H), 5.26 (ddd, J=10.6, 8.8, 6.4 Hz, 1H), 4.88 (d, J=9.3 Hz, 1H), 4.34 (d, J=9.3 Hz, 1H), 3.95 (dd, J=11.7, 3.4 Hz, 1H), 3.11 (s, 2H), 3.01 (d, J=11.2 Hz, 2H), 2.25 (ddd, J=12.9, 6.2, 1.4 Hz, 1H), 2.19-2.13 (m, 2H), 1.86 (dd, J=10.1, 1.6 Hz, 1H), 1.67 (s, 3H), 1.64 (d, J=2.5 Hz, 1H), 1.58 (s, 3H), 1.49 (d, J=12.9 Hz, 1H), 1.46 (s, 9H); LC/MS (ESI+) m/z 671 (M+H)$^+$.

Example 187

{4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetic acid A solution of Example 186 (25 mg, 0.037 mmol) in trifluoroacetic acid (1 mL) was stirred at room temperature for 15 minutes, heated at 55° C. for 30 minutes, cooled, concentrated and dried under vacuum with heating to 50° C. to provide the title compound (24.5 mg, 0.034 mmol, 90% yield). $^1$H NMR (501 MHz, CDCl$_3$) δ 6.92 (s, 1H), 6.85 (d, J=8.6 Hz, 1H), 6.71 (d, J=9.0 Hz, 1H), 6.65 (s, 1H), 6.63 (s, 1H), 5.93 (d, J=8.7 Hz, 1H), 5.42 (bs, 3H), 5.29-5.23 (m, 1H), 4.87 (d, J=9.4 Hz, 1H), 4.34 (d, J=9.5 Hz, 1H), 3.98 (dd, J=10.6, 4.3 Hz, 1H), 3.93-3.74 (m, 4H), 2.97-2.87 (m, 2H), 2.29 (dd, J=12.3, 5.8 Hz, 1H), 2.19 (d, J=12.6 Hz, 1H), 2.05-1.81 (m, 4H), 1.66 (s, 3H), 1.53 (dd, J=23.2, 11.5 Hz, 1H); LC/MS (ESI+) m/z 615 (M+H)±.

Example 188

(7R)—N-[(2S,4S)-2-{1-[(2S)-2,3-dihydroxypropyl]piperidin-4-yl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide A solution of Example 226 (14.6 mg, 0.022 mmol) in methanol (1 mL) was treated with 3 M HCl (1 mL) and stirred at room temperature for 90 minutes. The mixture was partitioned between $CH_2Cl_2$ (30 mL) and 1 M NaOH (10 mL). The layers were separated and the aqueous was extracted with $CH_2Cl_2$. The combined $CH_2Cl_2$ layers were dried ($MgSO_4$), filtered and concentrated to provide the title compound (8.7 mg, 0.014 mmol, 63.4% yield). $^1$H NMR (501 MHz, $CDCl_3$) δ 6.94 (dd, J=8.5, 0.9 Hz, 1H), 6.87 (s, 1H), 6.72-6.69 (m, 1H), 6.68-6.66 (m, 1H), 6.66 (s, 1H), 5.57 (d, J=9.0 Hz, 1H), 5.32-5.26 (m, 1H), 4.94 (d, J=9.3 Hz, 1H), 4.37 (d, J=9.3 Hz, 1H), 3.96 (ddd, J=11.4, 6.0, 1.1 Hz, 1H), 3.84-3.80 (m, 1H), 3.76 (dd, J=11.3, 3.9 Hz, 1H), 3.51 (dd, J=11.3, 4.2 Hz, 1H), 3.09 (d, J=11.3 Hz, 1H), 2.93 (d, J=11.7 Hz, 1H), 2.57 (dd, J=12.4, 9.6 Hz, 1H), 2.35 (dd, J=12.4, 4.0 Hz, 1H), 2.29 (dd, J=11.8, 1.9 Hz, 1H), 2.27-2.23 (m, 1H), 2.00 (td, J=11.7, 2.3 Hz, 1H), 1.92-1.88 (m, 1H), 1.74-1.67 (m, 2H), 1.65 (s, 3H), 1.64-1.57 (m, 1H), 1.54-1.45 (m, 2H); LC/MS (ESI+) m/z 631.5 (M+H)$^+$.

Example 189

(7R)—N-[(2R,4R)-2-{1-[(2S)-2,3-dihydroxypropyl]piperidin-4-yl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide A solution of Example 247 (42 mg, 0.063 mmol) in methanol (1 mL) was treated with 3 M HCl (1 mL) and stirred at room temperature for 90 minutes. The mixture was partitioned between $CH_2Cl_2$ (30 mL) and 1 M NaOH (10 mL). The layers were separated and the aqueous was extracted with $CH_2Cl_2$ (2×25 mL). The combined $CH_2Cl_2$ layers were dried ($MgSO_4$), filtered and concentrated to provide the title compound (29 mg, 0.046 mmol, 73.4% yield). $^1$H NMR (400 MHz, $CDCl_3$) δ 6.91 (s, 1H), 6.87 (d, J=8.4 Hz, 1H), 6.72-6.66 (m, 2H), 6.64 (s, 1H), 5.64 (d, J=8.8 Hz, 1H), 5.31-5.23 (m, 1H), 4.89 (d, J=9.3 Hz, 1H), 4.35 (d, J=9.3 Hz, 1H), 3.95 (dd, J=11.3, 5.4 Hz, 1H), 3.82 (dq, J=8.2, 4.0 Hz, 1H), 3.74 (dd, J=11.3, 3.8 Hz, 1H), 3.50 (dd, J=11.3, 4.2 Hz, 1H), 3.09 (d, J=11.4 Hz, 1H), 2.91 (d, J=11.4 Hz, 1H), 2.56 (dd, J=12.4, 9.6 Hz, 1H), 2.34 (dd, J=12.4, 4.0 Hz, 1H), 2.31-2.22 (m, 2H), 1.98 (td, J=11.9, 2.1 Hz, 1H), 1.92-1.86 (m, 1H), 1.72-1.66 (m, 1H), 1.67 (s, 3H), 1.65-1.37 (m, 4H); LC/MS (ESI+) m/z 631.5 (M+H)$^+$.

Example 190

(7R)—N-[(2R,4R)-2-(5-ethenylpyrazin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide

Example 190A 1-(2-((tert-butyldimethylsilyl)oxy)-4-methoxyphenyl)ethan-1-one A solution of 2'-hydroxy-4'-methoxyacetophenone (20 g, 120 mmol) and tert-butyldimethylsilyl chloride (27.2 g, 181 mmol) in $CH_2Cl_2$ (600 mL) was treated with triethylamine (33.6 mL, 241 mmol), treated with 4-(dimethylamino)pyridine (1.470 g, 12.04 mmol) and stirred over night at room temperature. More 4-(dimethylamino)pyridine (1.5 g) was added and the mixture was stirred at room temperature over night. The mixture was washed with water (200 mL), washed with 5% citric acid (twice, 200 mL and 100 mL), washed with 1 M NaOH (100 mL), dried ($MgSO_4$), filtered, and concentrated to provide the title compound (39.25 g). $^1$H NMR (501 MHz, $CDCl_3$) δ 7.70 (d, J=8.8 Hz, 1H), 6.53 (dd, J=8.8, 2.4 Hz, 1H), 6.36 (d, J=2.4 Hz, 1H), 3.80 (s, 3H), 2.56 (s, 3H), 1.00 (s, 9H), 0.29 (s, 6H); LC/MS (ESI+) m/z 281 (M+H)$^+$.

Example 190B (S)—N-[(1E)-1-(2-{[tert-butyl(dimethyl)silyl]oxy}-4-methoxyphenyl)ethylidene]-2-methylpropane-2-sulfinamide A solution of Example 190A (1.46 g, 5.21 mmol) and (S)-(−)-2-methyl-2-propanesulfinamide (CAS #343338-28-3, 1.262 g, 10.41 mmol) in 2-methyl-tetrahydrofuran (10 mL) under $N_2$ was treated with titanium(IV) ethoxide (4.32 mL, 20.82 mmol), heated at 70° C. for 1 hour, heated at 80° C. for 1 hour, and heated at 95° C. over night. The mixture was cooled, diluted with ethyl acetate (about 60 mL) and poured into a stirred mixture of ethyl acetate (about 100 mL) and water (100 mL). The mixture was stirred for 5 minutes and filtered through diatomaceous earth to remove the solids. The ethyl acetate layer was isolated, washed with brine, dried ($MgSO_4$), filtered, and concentrated. The residue was chromatographed on silica gel eluting with a gradient of 10 to 30% ethyl acetate in heptanes to provide the title compound (1.19 g, 3.10 mmol, 59.6% yield). $^1$H NMR (501 MHz, $CDCl_3$) δ 7.44 (d, J=8.6 Hz, 1H), 6.52 (dd, J=8.6, 2.4 Hz, 1H), 6.37 (d, J=2.1 Hz, 1H), 3.79 (s, 3H), 2.70 (s, 3H), 1.28 (s, 9H), 0.97 (s, 9H), 0.24 (s, 3H), 0.22 (s, 3H).

Example 190C methyl 5-ethenylpyrazine-2-carboxylate

A solution of methyl 5-chloropyrazine-2-carboxylate (3 g, 17.38 mmol), potassium vinyltrifluoroborate (5.12 g, 38.2 mmol) and 1,1'-bis(diphenylphosphino)ferrocenedichloro palladium(II) dichloromethane complex (1.272 g, 1.738 mmol) in isopropyl alcohol (45 mL, anhydrous) was treated with triethylamine (4.85 mL, 34.8 mmol) and the atmosphere was vacuum purged with $N_2$ a few times. The mixture was heated at 80° C. under $N_2$ for 2 hours and cooled. The mixture was partitoned between saturated aqueous $NaHCO_3$ solution (50 mL) and ethyl acetate (150 mL). The layers were separated and the aqueous layer was extracted with ethyl acetate (2×50 mL). The combined ethyl acetate layers were washed with brine, dried ($MgSO_4$), filtered, and concentrated. The residue was chromatographed on silica gel eluting with a gradient of 25 to 100% ethyl acetate in heptanes to provide the title compound (2.28 g, 13.89 mmol, 80% yield) $^1$H NMR (400 MHz, $CDCl_3$) δ 9.23 (d, J=1.0 Hz, 1H), 8.67 (d, J=1.1 Hz, 1H), 6.89 (dd, J=17.4, 10.8 Hz, 1H), 6.51 (d, J=17.4 Hz, 1H), 5.78 (d, J=10.9 Hz, 1H), 4.03 (s, 3H); LC/MS (ESI+) m/z 165 (M+H)$^+$.

Example 190D 5-ethenylpyrazine-2-carbaldehyde

A solution of Example 190C (1 g, 6.09 mmol) in tetrahydrofuran (60 mL) was cooled to −78° C., treated dropwise with 1 M lithium aluminum hydride in tetrahydrofuran (1.523 mL, 1.523 mmol) over 8 minutes, stirred at −78° C. for 20 minutes, treated dropwise with acetic acid (1 mL), warmed to room temperature and partitioned between ethyl acetate (about 50 mL) and saturated aqueous NaHCO$_3$ solution (about 25 mL). The layers were separated and the aqueous layer was extracted with ethyl acetate (about 25 mL). An emulsion was present, so the mixture was filtered through diatomaceous earth. The ethyl acetate layers were combined, washed with brine, dried (MgSO$_4$), filtered, and concentrated. The residue was chromatographed on silica gel eluting with a gradient of 15 to 100% ethyl acetate in heptanes to provide the title compound (105 mg, 0.783 mmol, 12.85% yield). $^1$H NMR (400 MHz, CDCl$_3$) δ 10.12 (s, 1H), 9.09 (s, 1H), 8.71 (s, 1H), 6.90 (dd, J=17.4, 10.8 Hz, 1H), 6.55 (d, J=17.4 Hz, 1H), 5.81 (d, J=10.8 Hz, 1H); LC/MS (ESI+) m/z 176 (M+CH$_3$CN)$^+$.

Example 190E (S)—N-[(1E,3S)-3-(5-ethenylpyrazin-2-yl)-3-hydroxy-1-(2-hydroxy-4-methoxyphenyl)propylidene]-2-methylpropane-2-sulfinamide A solution of N,N-diisopropylamine (145 μL, 1.018 mmol) in tetrahydrofuran (5 mL) under N$_2$ at −78° C. was treated with 2.5 M n-butyl lithium in hexanes (376 μL, 0.939 mmol), warmed to 0° C., stirred for 15 minutes at 0° C., cooled to −78° C., treated with a solution of Example 190B (450 mg, 1.174 mmol) in tetrahydrofuran (2 mL), stirred at −78° C. for 45 minutes, treated with a solution of Example 190D (105 mg, 0.783 mmol), stirred at −78° C. for 45 minutes, treated with a solution of acetic acid (90 μL, 1.566 mmol) in tetrahydrofuran (1 mL) and warmed to 0° C. The mixture was partitioned between ethyl acetate (about 30 mL) and saturated aqueous NaHCO$_3$ solution (about 5 mL). The ethyl acetate layer was washed with brine, dried (MgSO$_4$), filtered and concentrated. The mixture was taken up in tetrahydrofuran (5 mL), cooled to 0° C., treated with 1 M tetrabutylammonium fluoride in tetrahydrofuran (1174 μL, 1.174 mmol), stirred at 0° C. for 1 hour, and partitioned between ethyl acetate (50 mL) and 5% citric acid solution (15 mL). The ethyl acetate layer was washed with brine, dried (MgSO$_4$), filtered, and concentrated. The residue was chromatographed on silica gel eluting with a gradient of 15 to 100% ethyl acetate in heptanes to provide the title compound (140 mg, 0.347 mmol, 44.3% yield) as the second eluting isomer. $^1$H NMR (400 MHz, CDCl$_3$) δ 13.21 (s, 1H), 8.65 (s, 1H), 8.55 (s, 1H), 7.28 (d, J=9.2 Hz, 1H), 6.82 (dd, J=17.5, 10.9 Hz, 1H), 6.40 (d, J=2.6 Hz, 1H), 6.32 (d, J=17.5 Hz, 1H), 6.26 (dd, J=9.1, 2.6 Hz, 1H), 5.60 (d, J=10.9 Hz, 1H), 5.38-5.32 (m, 1H), 4.68 (d, J=5.2 Hz, 1H), 3.85 (dd, J=13.6, 7.2 Hz, 1H), 3.80 (s, 3H), 3.75 (dd, J=13.6, 4.6 Hz, 1H), 1.38 (s, 9H); LC/MS (ESI+) m/z 404 (M+H)$^+$.

Example 190F (S)—N-[(2R,E)-2-(5-ethenylpyrazin-2-yl)-7-methoxy-2,3-dihydro-4H-1-benzopyran-4-ylidene]-2-methylpropane-2-sulfinamide A solution of Example 190E (0.14 g, 0.347 mmol) and triphenylphosphine (0.109 g, 0.416 mmol) in CH$_2$Cl$_2$ (3.5 mL) was cooled to 0° C., treated dropwise with diethyl azodicarboxylate, 40 wt. % solution in toluene (0.395 ml, 0.867 mmol), stirred at 0° C. for 5 minutes, stirred at room temperature for 75 minutes, diluted with heptanes and filtered to remove the solids. The filtrate was chromatographed on silica gel eluting with a gradient of 15 to 100% ethyl acetate in heptanes to provide the title compound (57.7 mg, 0.150 mmol, 43.1% yield). $^1$H NMR (400 MHz, CDCl$_3$) δ 8.78 (d, J=1.3 Hz, 1H), 8.57 (d, J=1.4 Hz, 1H), 7.96 (d, J=8.9 Hz, 1H), 6.85 (dd, J=17.5, 10.9 Hz, 1H), 6.62 (dd, J=8.9, 2.5 Hz, 1H), 6.51 (d, J=2.4 Hz, 1H), 6.37 (dd, J=17.5, 1.0 Hz, 1H), 5.65 (dd, J=10.9, 1.0 Hz, 1H), 5.41 (dd, J=12.1, 3.1 Hz, 1H), 3.88 (dd, J=17.5, 3.2 Hz, 1H), 3.84 (s, 3H), 3.43 (dd, J=17.5, 12.1 Hz, 1H), 1.30 (s, 9H); LC/MS (ESI+) m/z 386 (M+H)$^+$.

Example 190G (2R,4R)-2-(5-ethenylpyrazin-2-yl)-7-methoxy-3,4-dihydro-2H-1-benzopyran-4-amine A solution of Example 190F (58 mg, 0.150 mmol) in methanol (2 mL) was cooled to 0° C., treated with NaBH$_4$ (11.38 mg, 0.301 mmol), stirred at 0° C. for 30 minutes, treated with more NaBH$_4$ (6 mg) and stirred for 1 hour at 0° C. The mixture was treated with 1 M HCl (about 1 mL) and stirred at room temperature for 3 hours. Concentrated HCl (about 0.5 mL) was added and mixture was stirred at room temperature for 15 minutes, treated with more concentrated HCl (0.5 mL) stirred for 30 minutes, and concentrated using a stream of N$_2$. After the mixture had been concentrated to approximately 0.5 mL volume, the mixture was partitioned between ethyl acetate and saturated aqueous NaHCO$_3$ solution. The layers were separated and the aqueous layer was extracted with ethyl acetate. The combined ethyl acetate layers were washed with brine, dried (MgSO$_4$), filtered, and concentrated. The residue was chromatographed on silica gel eluting with a gradient of 15 to 100% [2% (37% NH$_4$OH solution) in 3:1 ethyl acetate:ethanol] in heptanes to provide the title compound (37 mg, 0.131 mmol, 87% yield). $^1$H NMR (400 MHz, CDCl$_3$) δ 8.81 (s, 1H), 8.55 (s, 1H), 7.44 (d, J=8.6 Hz, 1H), 6.85 (dd, J=17.5, 10.9 Hz, 1H), 6.59 (dd, J=8.6, 2.4 Hz, 1H), 6.48 (d, J=2.5 Hz, 1H), 6.37 (d, J=17.5 Hz, 1H), 5.63 (d, J=10.9 Hz, 1H), 5.31 (dd, J=11.1, 1.8 Hz, 1H), 4.31 (dd, J=10.4, 5.8 Hz, 1H), 3.79 (s, 3H), 2.64 (ddd, J=13.1, 5.8, 2.0 Hz, 1H), 2.04-1.94 (m, 1H); LC/MS (ESI+) m/z 267 (M−NH$_3$)$^+$.

Example 190H (7R)—N-[(2R,4R)-2-(5-ethenylpyrazin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 190G (37 mg, 0.131 mmol) and triethylamine (36.4 μL, 0.261 mmol) in CH$_2$Cl$_2$ (2 mL) at 0° C. under N$_2$ was treated with a solution of Example 134F (39.7 mg, 0.144 mmol) in CH$_2$Cl$_2$ (1 mL). The mixture was stirred at 0° C. for 15 minutes and at room temperature for 1 hour. The mixture was treated with 37% NH$_4$OH solution (5 drops), stirred for 5 minutes and partitioned between ethyl acetate (30 mL) and 1 M HCl (5 mL). The ethyl acetate layer was washed with saturated aqueous NaHCO$_3$ solution (5 mL), washed with brine, dried (MgSO$_4$), filtered, and concentrated. The residue was chromatographed on silica gel and eluted with 15 to 50% ethyl acetate in heptanes to provide the title compound (48 mg, 0.092 mmol, 70.2% yield). $^1$H NMR (400 MHz, CDCl$_3$) δ 8.72 (d, J=1.2 Hz, 1H), 8.49 (d, J=1.4 Hz, 1H), 6.90-6.79 (m, 3H), 6.59 (s, 1H), 6.52 (dd, J=8.6, 2.6 Hz, 1H), 6.47 (d, J=2.5 Hz, 1H), 6.36

(dd, J=17.5, 1.0 Hz, 1H), 5.73 (d, J=8.7 Hz, 1H), 5.64 (dd, J=10.9, 1.0 Hz, 1H), 5.41 (td, J=9.1, 6.7 Hz, 1H), 5.33 (dd, J=10.3, 2.4 Hz, 1H), 4.81 (d, J=9.3 Hz, 1H), 4.32 (d, J=9.3 Hz, 1H), 3.77 (s, 3H), 2.71 (ddd, J=13.5, 6.3, 2.6 Hz, 1H), 2.00 (dt, J=13.5, 10.1 Hz, 1H), 1.64 (s, 3H); LC/MS (ESI+) m/z 524 (M+H)+.

Example 191

(7R)—N-[(2R,4R)-2-{5-[(1R)-1,2-dihydroxyethyl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 190H (22 mg, 0.042 mmol) in tert-butyl alcohol (0.5 mL) and H$_2$O (0.5 mL) was cooled to 0° C., treated with AD-mix-alpha (Sigma-Aldrich Catalogue Number: 392758-50G, 200 mg) and stirred over night in the ice bath allowing the mixture to slowly warm to room temperature. More AD mix alpha (200 mg) was added, and the mixture was stirred over the weekend. The mixture was diluted with water and ethanol. The mixture was treated with silica gel (about 3 g) and concentrated to dryness. This silica gel suspension was transferred to a Poppy-12 cartridge and chromatographed on silica gel eluting with a gradient of 15 to 100% [9:1 ethyl acetate:ethanol] in heptanes to provide the title compound (7 mg, 0.013 mmol, 29.9% yield). The stereochemistry of the diol was assigned arbitrarily. Chiral Analytical Supercritical Fluid chromatographic analysis indicated 69% diastereomeric excess. $^1$H NMR (400 MHz, CDCl$_3$) δ 8.74 (s, 1H), 8.66 (s, 1H), 6.91-6.84 (m, 2H), 6.60 (s, 1H), 6.52 (dd, J=8.6, 2.5 Hz, 1H), 6.47 (d, J=2.4 Hz, 1H), 5.69 (d, J=8.3 Hz, 1H), 5.45-5.38 (m, 1H), 5.35 (dd, J=10.5, 1.8 Hz, 1H), 4.93 (q, J=5.5 Hz, 1H), 4.79 (d, J=9.3 Hz, 1H), 4.31 (d, J=9.3 Hz, 1H), 4.02-3.96 (m, 1H), 3.91-3.84 (m, 1H), 3.77 (s, 3H), 3.67 (d, J=5.3 Hz, 1H), 2.74 (ddd, J=13.1, 6.2, 2.3 Hz, 1H), 2.35 (bs, 1H), 1.97 (dt, J=13.3, 10.3 Hz, 1H), 1.65 (s, 3H); LC/MS (ESI+) m/z 301 (100%), 558 (M+H)+ (10%).

Example 192

(7R)—N-[(2R,4R)-2-{5-[(1S)-1,2-dihydroxyethyl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 190H (20 mg, 0.038 mmol) in tert-butyl alcohol (0.5 mL) and H$_2$O (0.5 mL) was cooled to 0° C., treated with AD-mix-beta (Sigma-Aldrich Catalogue Number: 392766-50G, 400 mg) and stirred over the weekend at room temperature. The mixture was diluted with water and ethanol. The mixture was treated with silica gel (about 3 g) and concentrated to dryness. This silica gel suspension was transferred to a Poppy-12 cartridge and chromatographed on silica gel eluting with a gradient of 15 to 100% [9:1 ethyl acetate:ethanol] in heptanes provided the title compound (11.5 mg, 0.021 mmol, 54.0% yield). The stereochemistry of the diol was arbitrarily assigned. Chiral Analytical Supercritical Fluid chromatographic analysis indicated 70% diastereomeric excess. $^1$H NMR (400 MHz, CDCl$_3$) δ 8.74 (d, J=1.1 Hz, 1H), 8.66 (d, J=1.1 Hz, 1H), 6.89 (s, 1H), 6.87 (d, J=8.8 Hz, 1H), 6.60 (s, 1H), 6.52 (dd, J=8.6, 2.5 Hz, 1H), 6.47 (d, J=2.5 Hz, 1H), 5.70 (d, J=8.7 Hz, 1H), 5.45-5.38 (m, 1H), 5.35 (dd, J=10.6, 2.2 Hz, 1H), 4.93 (q, J=4.9 Hz, 1H), 4.80 (d, J=9.3 Hz, 1H), 4.32 (d, J=9.3 Hz, 1H), 4.03-3.95 (m, 1H), 3.90-3.83 (m, 1H), 3.77 (s, 3H), 3.67 (d, J=5.6 Hz, 1H), 2.74 (ddd, J=13.4, 6.3, 2.4 Hz, 1H), 2.33 (t, J=5.9 Hz, 1H), 1.94 (dt, J=13.4, 10.4 Hz, 1H), 1.65 (s, 3H); LC/MS (ESI+) m/z 301 (100%), 558 (M+H)+ (10%).

Example 193

(7R)—N-[(2R,4R)-2-(5-chloropyrazin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide Example 193A (S)—N-[(1E,3S)-3-(5-chloropyrazin-2-yl)-3-hydroxy-1-(2-hydroxy-4-methoxyphenyl)propylidene]-2-methylpropane-2-sulfinamide A solution of N,N-diisopropylamine (136 μL, 0.958 mmol) in tetrahydrofuran (5 mL) under N$_2$ at −78° C. was treated with 2.5 M n-butyl lithium in hexanes (354 μL, 0.884 mmol), warmed to 0° C., stirred for 15 minutes at 0° C., cooled to −78° C., treated with a solution of Example 190B (394 mg, 1.027 mmol) in tetrahydrofuran (2 mL), stirred at −78° C. for 45 minutes, treated with a solution of 5-chloropyrazine-2-carbaldehyde (CAS #88625-24-5, 105 mg, 0.737 mmol), stirred at −78° C. for 75 minutes, treated with a solution of acetic acid (84 μL, 1.473 mmol) in tetrahydrofuran (1 mL), warmed to 0° C., treated with 1 m tetrabutylammonium fluoride in tetrahydrofuran (1105 μL, 1.105 mmol), stirred at 0° C. for 90 minutes, diluted with ethyl acetate (75 mL) and washed with saturated aqueous NaHCO$_3$ solution. The ethyl acetate layer was washed with brine, dried (MgSO$_4$), filtered, and concentrated. The residue was chromatographed on silica gel eluting with a gradient of 0 to 100% (over 10 minutes) [1:1 CH$_2$Cl$_2$: ethyl acetate] in [9:1 CH$_2$Cl$_2$: ethyl acetate] to provide the title compound (0.13 g, 0.316 mmol, 42.8% yield) as the second eluting isomer. $^1$H NMR (500 MHz, CDCl$_3$) δ 13.07 (s, 1H), 8.55 (d, J=1.4 Hz, 1H), 8.45 (dd, J=1.3, 0.6 Hz, 1H), 7.13 (d, J=9.2 Hz, 1H), 6.39 (d, J=2.6 Hz, 1H), 6.23 (dd, J=9.1, 2.6 Hz, 1H), 5.36 (q, J=4.9 Hz, 1H), 4.93 (d, J=4.6 Hz, 1H), 3.86 (dd, J=13.6, 6.4 Hz, 0H), 3.81 (s, 3H), 3.79 (dd, J=13.6, 5.0 Hz, 1H), 1.39 (s, 9H); LC/MS (ESI+) m/z 412 (M+H)+.

Example 193B (S)—N-[(2R,E)-2-(5-chloropyrazin-2-yl)-7-methoxy-2,3-dihydro-4H-1-benzopyran-4-ylidene]-2-methylpropane-2-sulfinamide A solution of Example 193A (0.14 g, 0.340 mmol) and triphenylphosphine (0.107 g, 0.408 mmol) in CH$_2$Cl$_2$ (4 mL) was cooled to 0° C., treated dropwise with diethyl azodicarboxylate, 40 wt. % solution in toluene (0.387 mL, 0.850 mmol), stirred at 0° C. for 5 minutes, stirred at room temperature over night, diluted with heptanes, stirred for 5 minutes, and filtered to remove the solids. The filtrate was chromatographed on silica gel eluting with a gradient of 5 to 50% ethyl acetate in heptanes to provide the title compound (66.5 mg, 0.169 mmol, 49.7% yield). $^1$H NMR (501 MHz, CDCl$_3$) δ 8.65 (dd, J=1.4, 0.6 Hz, 1H), 8.58 (d, J=1.4 Hz, 1H), 7.96 (d, J=8.9 Hz, 1H), 6.63 (dd, J=8.9, 2.5 Hz, 1H), 6.51 (d, J=2.5 Hz, 1H), 5.41 (dd, J=12.1, 3.1 Hz, 1H), 3.90 (dd, J=17.5, 3.2 Hz, 1H), 3.85 (s, 3H), 3.38 (dd, J=17.5, 12.2 Hz, 1H), 1.30 (s, 9H); LC/MS (ESI+) m/z 394 (M+H)+.

Example 193C (2R,4R)-2-(5-chloropyrazin-2-yl)-7-methoxy-3,4-dihydro-2H-1-benzopyran-4-amine A solution of Example 193B (66 mg, 0.168 mmol) in methanol (3 mL) was cooled to 0° C., treated with NaBH$_4$ (12.68 mg, 0.335 mmol), stirred at 0° C. for 20 minutes, treated with more NaBH$_4$ (30 mg in three 10 mg additions over 30 minutes) and stirred for 75 minutes. The mixture was treated with 4 M HCl in dioxane (419 µL, 1.676 mmol) and stirred at room temperature for 70 minutes. The mixture was partitioned between methyl tert-butyl ether (30 mL) and water (15 mL). The layers were separated and the methyl tert-butyl ether layer was extracted with 0.2 M HCl (10 mL). The methyl tert-butyl ether layer was discarded. The combined aqueous layers were basified with solid NaHCO$_3$ and extracted with ethyl acetate (2×, 30 mL and 15 mL). The combined ethyl acetate layers were washed with brine, dried (MgSO$_4$), filtered and concentrated to provide the title compound (37.5 mg, 0.129 mmol, 77% yield). $^1$H NMR (501 MHz, CDCl$_3$) δ 8.67 (s, 1H), 8.56 (s, 1H), 7.42 (d, J=8.6 Hz, 1H), 6.59 (dd, J=8.5, 2.0 Hz, 1H), 6.48 (d, J=2.2 Hz, 1H), 5.30 (d, J=11.3 Hz, 1H), 4.28 (dd, J=9.7, 5.6 Hz, 1H), 3.79 (s, 3H), 2.64 (dd, J=12.3, 4.8 Hz, 1H), 1.89 (q, J=11.7 Hz, 1H); LC/MS (ESI+) m/z 275 (M+NH$_3$)$^+$.

Example 193D (7R)—N-[(2R,4R)-2-(5-chloropyrazin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 193C (36.8 mg, 0.126 mmol) and triethylamine (35.2 µL, 0.252 mmol) in CH$_2$Cl$_2$ (2 mL) at 0° C. under N$_2$ was treated with a solution of Example 134F (38.4 mg, 0.139 mmol) in CH$_2$Cl$_2$ (1 mL). The mixture was stirred at 0° C. for 15 minutes and at room temperature for 1 hour. The mixture was treated with 37% NH$_4$OH solution (5 drops), stirred for 5 minutes and partitioned between ethyl acetate (30 mL) and 1 M HCl (5 mL). The ethyl acetate layer was washed with saturated aqueous NaHCO$_3$ solution (5 mL), washed with brine, dried (MgSO$_4$), filtered, and concentrated. The residue was chromatographed on silica gel eluting with a gradient of 15 to 30% ethyl acetate in heptanes to provide the title compound (64 mg, 0.120 mmol, 95% yield). $^1$H NMR (501 MHz, CDCl$_3$) δ 8.59 (dd, J=1.4, 0.6 Hz, 1H), 8.52 (d, J=1.4 Hz, 1H), 6.88 (s, 1H), 6.86 (dd, J=8.6, 0.9 Hz, 1H), 6.61 (d, J=0.3 Hz, 1H), 6.53 (dd, J=8.6, 2.6 Hz, 1H), 6.48 (d, J=2.5 Hz, 1H), 5.63 (d, J=8.6 Hz, 1H), 5.43-5.38 (m, 1H), 5.32 (dd, J=10.8, 2.2 Hz, 1H), 4.81 (d, J=9.3 Hz, 1H), 4.32 (d, J=9.3 Hz, 1H), 3.78 (s, 3H), 2.73 (ddd, J=13.3, 6.3, 2.4 Hz, 1H), 1.90 (dt, J=13.3, 10.6 Hz, 1H), 1.65 (s, 3H); MS (ESI−) m/z 530 (M−H)$^-$.

Example 194 propan-2-yl trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate The title compound was obtained as the first eluting product from the procedure as described in Example 148B. $^1$H NMR (400 MHz, CDCl$_3$) δ 6.91 (s, 1H), 6.87 (d, J=8.4 Hz, 1H), 6.71-6.66 (m, 2H), 6.64 (s, 1H), 5.62 (d, J=8.9 Hz, 1H), 5.31-5.22 (m, 1H), 4.99 (hept, J=6.0 Hz, 1H), 4.89 (d, J=9.3 Hz, 1H), 4.35 (d, J=9.3 Hz, 1H), 3.92 (dd, J=11.5, 5.5 Hz, 1H), 2.26-2.16 (m, 2H), 2.08-1.98 (m, 2H), 1.82 (d, J=12.4 Hz, 1H), 1.68 (s, 3H), 1.62-1.52 (m, 2H), 1.50-1.37 (m, 3H), 1.22 (d, J=6.3 Hz, 6H), 1.29-1.06 (m, 2H); LC/MS (ESI+) m/z 643 (M+H)$^+$.

Example 195

(7R)—N-[(2R,4R)-2-(6-chloropyridazin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide

Example 195A (S)—N-[(1E,3S)-3-(6-chloropyridazin-3-yl)-3-hydroxy-1-(2-hydroxy-4-methoxyphenyl)propylidene]-2-methylpropane-2-sulfinamide A solution of N,N-diisopropylamine (0.605 mL, 4.25 mmol) in tetrahydrofuran (20 mL) under N$_2$ at −78° C. was treated with 2.5 M n-butyl lithium in hexanes (1.568 mL, 3.92 mmol), warmed to 0° C., stirred for 15 minutes at 0° C., cooled to −78° C., treated with a solution of Example 190B (1.88 g, 4.90 mmol) in tetrahydrofuran (5 mL), stirred at −78° C. for 45 minutes, treated with a solution of 6-chloropyridazine-3-carbaldehyde (CAS #303085-53-2, 0.466 g, 3.27 mmol) in tetrahydrofuran (10 mL), stirred at −78° C. for 45 minutes, treated dropwise with a solution of acetic acid (0.374 ml, 6.53 mmol) in tetrahydrofuran (0.5 mL), warmed to 0° C., treated over 1 minute with 1 M tetrabutylammonium fluoride in tetrahydrofuran (4.90 mL, 4.90 mmol), stirred at 0° C. for 1 hour, concentrated on the rotary evaporator with minimal heating to approximately 15 mL total volume and partitioned between ethyl acetate (about 75 mL) and 5% citric acid (10 mL). The layers were separated and the aqueous phase was extracted with ethyl acetate (about 20 mL). The combined ethyl acetate layers were washed with saturated aqueous NaHCO$_3$ solution (about 25 mL), washed with brine, dried (MgSO$_4$), filtered, and concentrated. The residue was chromatographed on silica gel eluting with a gradient of 15 to 100% ethyl acetate in heptanes to provide the title compound (0.67 g, 1.627 mmol, 49.8% yield) as the second eluting isomer. $^1$H NMR (400 MHz, CDCl$_3$) δ 12.94 (s, 1H), 7.56 (d, J=8.9 Hz, 1H), 7.31 (d, J=8.8 Hz, 1H), 7.12 (d, J=9.2 Hz, 1H), 6.35 (d, J=2.5 Hz, 1H), 6.19 (dd, J=9.1, 2.5 Hz, 1H), 5.55 (bt, J=4.8 Hz, 1H), 5.44-5.41 (m, 1H), 3.91 (d, J=5.4 Hz, 2H), 3.79 (s, 3H), 1.38 (s, 9H); LC/MS (ESI+) m/z 412 (M+H)$^+$.

Example 195B (S)—N-[(2R,E)-2-(6-chloropyridazin-3-yl)-7-methoxy-2,3-dihydro-4H-1-benzopyran-4-ylidene]-2-methylpropane-2-sulfinamide A solution of Example 195A (0.58 g, 1.408 mmol) and triphenylphosphine (0.443 g, 1.690 mmol) in CH$_2$Cl$_2$ (14 mL) was cooled to 0° C., treated dropwise with diethyl azodicarboxylate, 40 wt. % solution in toluene (1.603 mL, 3.52 mmol), stirred at 0° C. for 5 minutes, stirred at room temperature for 45 minutes, diluted with heptanes, stirred for 5 minutes, and filtered to remove the solids. The filtrate was chromatographed on silica gel eluting with a gradient of 15 to 100% ethyl acetate in heptanes to provide the title compound (338 mg, 0.858 mmol, 60.9% yield). $^1$H NMR (400 MHz, CDCl$_3$) δ 8.00 (d, J=8.9 Hz, 1H), 7.79 (d, J=8.8 Hz, 1H), 7.61 (d, J=8.9 Hz, 1H), 6.64 (d, J=9.0 Hz, 1H), 6.48 (s, 1H), 5.62 (dd, J=12.9, 2.6 Hz, 1H), 3.94 (dd, J=17.4, 2.7 Hz, 1H), 3.84 (s, 3H), 3.26 (dd, J=17.5, 13.0 Hz, 1H), 1.30 (s, 9H); LC/MS (ESI+) m/z 394 (M+H)$^+$.

Example 195C (2R,4R)-2-(6-chloropyridazin-3-yl)-7-methoxy-3,4-dihydro-2H-1-benzopyran-4-amine A solution of Example 195B (340 mg, 0.863 mmol) in methanol (8 mL) was cooled to 0° C., treated with NaBH$_4$ (65.3 mg, 1.726 mmol), stirred at 0° C. for 45 minutes, treated with 4 M HCl in dioxane (2158 μL, 8.63 mmol) and stirred at room temperature for 1 hour. The mixture was partitioned between ethyl acetate (about 75 mL) and saturated aqueous NaHCO$_3$ solution (about 20 mL). The layers were separated and the aqueous was extracted with ethyl acetate (about 25 mL). The combined ethyl acetate layers were washed with brine, dried (MgSO$_4$), filtered, and concentrated. The residue was chromatographed on silica gel eluting with a gradient of 0 to 100% [10:1:1 ethyl acetate: HCOOH:H$_2$O] in [200:1:1 ethyl acetate:HCOOH:H$_2$O]. Fractions containing the product were combined and concentrated to near dryness. This solution was partitioned between ethyl acetate (100 mL) and saturated aqueous NaHCO$_3$ solution (30 mL). The layers were separated and the aqueous was extracted with ethyl acetate (2×20 mL). The combined ethyl acetate layers were washed with brine, dried (MgSO$_4$), filtered and concentrated to provide the title compound (180 mg, 0.617 mmol, 71.5% yield). $^1$H NMR (500 MHz, CDCl$_3$) δ 7.80 (dd, J=8.9, 0.4 Hz, 1H), 7.58 (d, J=8.9 Hz, 1H), 7.43 (dd, J=8.6, 0.9 Hz, 1H), 6.60 (dd, J=8.6, 2.6 Hz, 1H), 6.45 (d, J=2.6 Hz, 1H), 5.54 (dd, J=11.5, 2.2 Hz, 1H), 4.30 (ddd, J=10.7, 5.8, 0.6 Hz, 1H), 3.79 (s, 3H), 2.74 (ddd, J=13.2, 5.7, 2.2 Hz, 1H), 1.86 (ddd, J=13.2, 11.5, 10.8 Hz, 1H); LC/MS (ESI+) m/z 275 (M−NH$_3$)$^+$.

Example 195D (7R)—N-[(2R,4R)-2-(6-chloropyridazin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 195C (172 μl, 1.234 mmol) in CH$_2$Cl$_2$ (5 mL) at 0° C. under N$_2$ was treated with a solution of Example 134F (188 mg, 0.679 mmol) in CH$_2$Cl$_2$ (1 mL). The mixture became thick and was diluted with more CH$_2$Cl$_2$ (5 mL) and was stirred for 1 hour at room temperature. The mixture was partitioned between ethyl acetate (50 mL) and 0.2 M HCl (15 mL). The ethyl acetate layer was washed with saturated aqueous NaHCO$_3$ solution (10 mL), washed with brine, dried (MgSO$_4$), filtered, and concentrated. The residue was chromatographed on silica gel eluting with a gradient of 10 to 40% [1:1 ethyl acetate:CH$_2$Cl$_2$] in CH$_2$Cl$_2$ to provide the title compound (290 mg, 0.545 mmol, 88% yield). $^1$H NMR (400 MHz, DMSO-d$_6$) δ 8.06 (d, J=8.7 Hz, 1H), 8.02 (d, J=8.9 Hz, 1H), 7.93 (d, J=8.9 Hz, 1H), 7.48 (s, 1H), 7.06 (d, J=8.6 Hz, 1H), 6.99 (s, 1H), 6.57 (dd, J=8.6, 2.5 Hz, 1H), 6.49 (d, J=2.5 Hz, 1H), 5.64 (d, J=10.5 Hz, 1H), 5.42-5.34 (m, 1H), 5.04 (d, J=9.0 Hz, 1H), 4.34 (d, J=9.0 Hz, 1H), 3.72 (s, 3H), 2.38 (ddd, J=13.1, 6.0, 1.7 Hz, 1H), 2.20 (q, J=11.9 Hz, 1H), 1.58 (s, 3H); LC/MS (ESI+) m/z 275 (100%), 532 (M+H)$^+$ (10%).

Example 196

(7R)—N-[(4R)-2-{1-[(2R)-2,3-dihydroxypropyl]-6-oxo-1,6-dihydropyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide Example 196A (7R)-2,2-difluoro-N-[(2S,4R)-7-methoxy-2-(6-oxo-1,6-dihydropyridazin-3-yl)-3,4-dihydro-2H-1-benzopyran-4-yl]-7-methyl-6,7-dihydro-2H-furo[2,3-f][1,3]benzodioxole-7-carboxamide and (7R)-2,2-difluoro-N-[(2R,4R)-7-methoxy-2-(6-oxo-1,6-dihydropyridazin-3-yl)-3,4-dihydro-2H-1-benzopyran-4-yl]-7-methyl-6,7-dihydro-2H-furo[2,3-f][1,3]benzodioxole-7-carboxamide A mixture of Example 195D (10 mg, 0.019 mmol) and sodium acetate (1.619 mg, 0.020 mmol) in acetic acid (19.37 μL, 0.338 mmol) and water (4.74 μL, 0.263 mmol) was heated at 100° C. More acetic acid (about 0.02 mL) was added. The mixture was heated at 100° C. for 6 hours and allowed to stir at room temperature overnight. The mixture was partitioned between ethyl acetate and saturated aqueous NaHCO$_3$ solution. The ethyl acetate layer was washed with brine, dried (MgSO$_4$), filtered, and concentrated. The residue was chromatographed on silica gel eluting with a gradient of 0 to 100% [9:1 ethyl acetate:ethanol] in ethyl acetate to provide the title compound which by NMR is a 1:3 mixture of trans:cis isomer: $^1$H NMR (400 MHz, CDCl$_3$) δ 11.36 (bs, 1H), 7.48 (d, J=9.8 Hz, 1H), 6.98 (d, J=9.8 Hz, 1H), 6.91 (s, 1H), 6.84 (d, J=8.6 Hz, 1H), 6.63 (s, 1H), 6.51 (dd, J=8.6, 2.5 Hz, 1H), 6.40 (d, J=2.5 Hz, 1H), 5.76 (d, J=8.6 Hz, 1H), 5.39-5.31 (m, 1H), 5.09 (dd, J=10.8, 2.2 Hz, 1H), 4.87 (d, J=9.3 Hz, 1H), 4.34 (d, J=9.3 Hz, 1H), 3.75 (s, 3H), 2.61 (ddd, J=13.4, 6.3, 2.3 Hz, 1H), 1.89 (dt, J=13.4, 10.5 Hz, 1H), 1.67 (s, 3H). $^1$H NMR for cis isomer: $^1$H NMR (400 MHz, CDCl$_3$) δ 11.36 (bs, 1H), 7.49 (d, J=9.8 Hz, 1H), 6.99 (d, J=9.9 Hz, 1H), 6.96 (d, J=8.7 Hz, 1H), 6.87 (s, 1H), 6.60 (s, 1H), 6.54 (dd, J=8.6, 2.5 Hz, 1H), 6.42 (d, J=2.5 Hz, 1H), 5.88 (d, J=6.6 Hz, 1H), 5.06-5.01 (m, 1H), 4.87-4.82 (m, 2H), 4.34 (d, J=9.3 Hz, 1H), 3.76 (s, 3H), 2.34 (dt, J=14.0, 2.8 Hz, 1H), 2.18 (ddd, J=14.4, 11.2, 4.8 Hz, 1H), 1.62 (s, 3H); LC/MS (ESI+) m/z 514 (M+H)$^+$.

Example 196B (7R)—N-[(4R)-2-{1-[(2R)-2,3-dihydroxypropyl]-6-oxo-1,6-dihydropyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 196A (about 5 mg of 3:1 ratio), (R)-(−)-2,2-dimethyl-1,3-dioxolane-4-methanol (1.9 mg, 0.015 mmol), and triphenylphosphine (3.83 mg, 0.015 mmol) in tetrahydrofuran (about 0.3 mL) was cooled to 0° C. and treated over 1 minute with 40% w/w diethyl azodicarboxylate in toluene (8.87 μl, 0.019 mmol). The mixture was stirred over night, in the ice bath, allowing reaction to slowly warm to room temperature. The mixture was concentrated using a stream of nitrogen. The residue was dissolved in methanol (1 mL), treated with 3 M HCl (0.5 mL), stirred at room temperature for 45 minutes, and partitioned between 1 M NaOH (about 10 mL) and CH$_2$Cl$_2$ (25 mL). The layers were separated and the aqueous layer was extracted with CH$_2$Cl$_2$ (15 mL). The combined CH$_2$Cl$_2$ layers were dried (MgSO$_4$), filtered, and concentrated. The residue was chromatographed on silica gel eluting with a gradient of 15 to 100% [3:1 ethyl acetate:ethanol] in heptanes to provide the title compound. 1H NMR indicates about 4:1 ratio of cis:trans. $^1$H NMR (501 MHz, CDCl$_3$) δ 7.51 (d, J=9.6 Hz, 0.8H), 7.50 (d, J=9.6 Hz, 0.2H), 7.06 (d, J=9.6 Hz, 1H), 7.02 (d, J=10.1 Hz, 0.2H), 6.95 (s, 0.8H), 6.92 (d, J=8.7 Hz, 0.2H), 6.90 (s, 0.2H), 6.85 (d, J=8.8 Hz, 0.8H), 6.66 (s, 1H), 6.57-6.54 (m, 1H), 6.45 (d, J=2.2 Hz, 0.2H), 6.43 (d, J=2.3 Hz, 0.8H), 5.83 (d, J=6.9 Hz, 0.2H), 5.68 (d, J=7.7 Hz, 0.8H), 5.43-5.36 (m, 0.8H), 5.12 (d, J=10.3 Hz, 0.2H), 4.97 (dd, J=9.0, 2.9 Hz, 0.8H), 4.90 (d, J=9.3 Hz, 0.2H), 4.89 (d, J=9.3 Hz, 0.8H), 4.51-4.28 (m, 3H), 4.20-4.15 (m, 0.2H), 4.14-4.09 (m, 0.8H), 3.79 (s, 3H), 3.72-3.48 (m, 2H), 2.63 (dd, J=11.9, 6.4 Hz, 0.8H), 2.45-2.37 (m, 0.2H), 2.30-2.24 (m, 0.2H), 1.88-1.80 (m, 0.8H), 1.70 (s, 2.4H), 1.66 (s, 0.6H); LC/MS (ESI+) m/z 588.6 (M+H)$^+$.

Example 197

(7R)-2,2-difluoro-N-[(2R,4R)-7-methoxy-2-(6-oxo-1,6-dihydropyridazin-3-yl)-3,4-dihydro-2H-1-benzopyran-4-yl]-7-methyl-6,7-dihydro-2H-furo[2,3-f][1,3]benzodioxole-7-carboxamide A mixture of Example 273 (2.7 mg, 4.47 μmol) and 10% Pd/C (about 1 mg) was treated with tetrahydrofuran (about 0.5 mL), stirred under an H$_2$ atmosphere (balloon) for 30 minutes, treated with a stream of N$_2$ for 2 minutes and directly chromatographed on silica gel eluting with a gradient of 15 to 100% [3:1 ethyl acetate:ethanol] in heptanes to provide the title compound. $^1$H NMR (500 MHz, CDCl$_3$) δ 11.26 (bs, 1H), 7.48 (d, J=9.8 Hz, 1H), 6.99 (d, J=9.8 Hz, 1H), 6.91 (s, 1H), 6.84 (d, J=8.6 Hz, 1H), 6.63 (s, 1H), 6.51 (dd, J=8.6, 2.5 Hz, 1H), 6.40 (d, J=2.5 Hz, 1H), 5.75 (d, J=8.6 Hz, 1H), 5.38-5.32 (m, 1H), 5.09 (dd, J=10.8, 2.1 Hz, 1H), 4.87 (d, J=9.3 Hz, 1H), 4.35 (d, J=9.3 Hz, 1H), 3.76 (s, 3H), 2.61 (ddd, J=13.1, 6.2, 2.0 Hz, 1H), 1.89 (dt, J=13.2, 10.6 Hz, 1H), 1.67 (s, 3H); LC/MS (ESI+) m/z 514 (M+H)$^+$.

Example 198 tert-butyl {trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexyl}carbamate The Example 163 (41 mg, 0.07 mmol) and triethylamine (12 μL, 0.086 mmol) in anhydrous tert-butanol (100 μL) were treated with diphenyl phosphorazidate (17 μL, 0.079 mmol) and heated at 80° C. for four hours. The reaction mixture was brought to room temperature and chromatographed on silica gel (5 to 15% methyl tert-butyl ether in 1:1 CH$_2$Cl$_2$/heptane) to give 12 mg of the title compound (26%). $^1$H NMR (500 MHz, DMSO-d$_6$) δ 8.08 (d, J=8.7 Hz, 1H), 7.49 (s, 1H), 7.24 (t, J=73.9 Hz, 1H), 7.09 (s, 1H), 6.88 (d, J=8.2 Hz, 1H), 6.80-6.76 (m, 1H), 6.67-6.63 (m, 2H), 5.24-5.17 (m, 1H), 5.07 (d, J=9.0 Hz, 1H), 4.39 (d, J=9.0 Hz, 1H), 4.11-4.05 (m, 1H), 3.29-3.19 (m, 1H), 2.12-2.06 (m, 1H), 2.00-1.76 (m, 4H), 1.64 (s, 3H), 1.59-1.51 (m, 1H), 1.44 (s, 9H), 1.33-1.15 (m, 5H); MS (ESI) m/z=651 (M−H)$^−$.

Example 199 tert-butyl {trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexyl}carbamate A solution of Example 160 (86 mg, 0.15 mmol) and triethylamine (21 μL, 0.15 mmol) in anhydrous toluene (200 μL) was treated with 1,8-diazabicyclo[5.4.0]undec-7-ene (18 μL, 0.12 mmol) and then dropwise with diphenyl phosphorazidate (35 μL, 0.16 mmol). The reaction mixture was briefly sonicated, stirred for 15 minutes, diluted with tert-butanol (200 μL) and heated at 80° C. for four hours. 1 M potassium tert-butoxide in tert-butanol (50 μL, 0.05 mmol) was added and the mixture was stirred overnight at room temperature. Additional 1 M potassium tert-butoxide in tert-butanol (50 μL, 0.05 mmol) was added and the mixture was stirred for about 100 minutes, diluted with methyl tert-butyl ether and washed with water. The aqueous phase was separated and extracted with methyl tert-butyl ether and the combined organic phases were dried (Na$_2$SO$_4$), concentrated, and chromatographed on silica (10% ethyl acetate/CH$_2$Cl$_2$) to give 29 mg of the title compound (30%). $^1$H NMR (501 MHz, CDCl$_3$) δ 6.90 (s, 1H), 6.85-6.82 (m, 1H), 6.64 (s, 1H), 6.62-6.30 (m, 3H), 5.61 (d, J=8.8 Hz, 1H), 5.27-5.20 (m, 1H), 4.89 (d, J=9.3 Hz, 1H), 4.41-4.33 (m, 2H), 3.93-3.88 (m, 1H), 3.44-3.35 (m, 1H), 2.25-2.20 (m, 1H), 2.11-2.05 (m, 2H), 2.01-1.95 (m, 1H), 1.82-1.74 (m, 1H), 1.67 (s, 3H), 1.44 (s, 9H), 1.55-1.05 (m, 6H); MS (ESI) m/z=651 (M−H)$^−$.

Example 200

(7R)-2,2-difluoro-N-[(2S,4R)-7-methoxy-2-(6-oxo-1,6-dihydropyridazin-3-yl)-3,4-dihydro-2H-1-benzopyran-4-yl]-7-methyl-6,7-dihydro-2H-furo[2,3-f][1,3]benzodioxole-7-carboxamide A mixture of Example 272 (40 mg, 0.066 mmol) and 10% Pd/C (1 mg) was treated with tetrahydrofuran (about 0.5 mL), stirred under an H$_2$ atmosphere (balloon) for 30 minutes, treated with a stream of N$_2$ for 2 minutes and directly chromatographed on silica gel eluting with a gradient of 15 to 100% [3:1 ethyl acetate:ethanol] in heptanes to provide the title compound (23.5 mg, 0.046 mmol, 69.1% yield). $^1$H NMR (501 MHz, CDCl$_3$) δ 10.93 (bs, 1H), 7.48 (d, J=9.8 Hz, 1H), 7.00-6.95 (m, 2H), 6.86 (d, J=0.3 Hz, 1H), 6.61 (d, J=0.3 Hz, 1H), 6.54 (dd, J=8.6, 2.6 Hz, 1H), 6.43 (d, J=2.5 Hz, 1H), 5.84 (d, J=6.6 Hz, 1H), 5.05-5.02 (m, 1H), 4.86-4.81 (m, 2H), 4.35 (d, J=9.3 Hz, 1H), 3.77 (s, 3H), 2.34 (dt, J=14.3, 2.8 Hz, 1H), 2.19 (ddd, J=14.3, 11.2, 4.7 Hz, 1H), 1.62 (s, 3H); LC/MS (ESI+) m/z 514 (M+H)$^+$.

Example 201

1-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid Example 165 (381 mg, 0.65 mmol) was dissolved into tetrahydrofuran (5 mL) and methanol (2 mL), treated with 1

M aqueous NaOH (2 mL) and heated at 50° C. for 90 minutes. The reaction mixture was brought to room temperature, quenched with 3 M aqueous citric acid (1 mL) and partitioned with heptane (2 mL) and brine (1 mL). The separated aqueous phase was extracted twice with methyl tert-butyl ether, and the combined organic phases were washed with brine, dried ($Na_2SO_4$) and concentrated to 390 mg of an off-white solid (100%). $^1$H NMR (501 MHz, $CDCl_3$) δ 6.93 (dd, J=8.5, 1.1 Hz, 1H), 6.87 (s, 1H), 6.73-6.69 (m, 1H), 6.66-6.64 (m, 2H), 5.62 (d, J=9.0 Hz, 1H), 5.36-5.30 (m, 1H), 4.95 (d, J=9.3 Hz, 1H), 4.36 (d, J=9.3 Hz, 1H), 4.31 (dd, J=11.6, 1.7 Hz, 1H), 2.45 (ddd, J=12.8, 6.2, 1.7 Hz, 1H), 1.84-1.76 (m, 1H), 1.64 (s, 3H), 1.44 (q, J=9.7, 7.3, 4.1 Hz, 1H), 1.37-1.26 (m, 2H), 1.05 (ddd, J=9.4, 7.3, 4.1 Hz, 1H); MS (ESI) m/z=556 (M−H)$^-$.

Example 202

(7R)-2,2-difluoro-N-[(2R,4R)-7-methoxy-2-(1H-tetrazol-5-yl)-3,4-dihydro-2H-1-benzopyran-4-yl]-7-methyl-6,7-dihydro-2H-furo[2,3-f][1,3]benzodioxole-7-carboxamide A solution of Example 283G (12.5 mg, 0.022 mmol) in methanol (0.5 mL) was treated with 10% Pd/C (5 mg) and was stirred under a $H_2$ atmosphere (balloon) for 6 hours. The atmosphere was replaced with $N_2$. The mixture was diluted with $CH_2Cl_2$ and was filtered through diatomaceous earth to remove the solids. The solids were washed with $CH_2Cl_2$/methanol (2×2 mL). The combined filtrates were concentrated and chromatographed on silica gel eluting with a gradient of 50 to 100% [200:1:1 ethyl acetate:HCOOH:$H_2O$] in heptanes to provide the title compound (4.5 mg, 9.23 µmol, 42.7% yield). $^1$H NMR (400 MHz, DMSO-$d_6$) δ 8.16 (d, J=8.6 Hz, 1H), 7.49 (s, 1H), 7.05 (d, J=8.8 Hz, 1H), 7.01 (s, 1H), 6.58 (dd, J=8.6, 2.5 Hz, 1H), 6.43 (d, J=2.5 Hz, 1H), 5.80 (dd, J=10.9, 2.6 Hz, 1H), 5.39-5.32 (m, 1H), 5.05 (d, J=9.0 Hz, 1H), 4.35 (d, J=9.0 Hz, 1H), 3.71 (s, 3H), 2.43-2.27 (m, 2H), 1.59 (s, 3H); MS (ESI−) m/z 486 (M−H)$^-$.

Example 203

(7R)—N-(2-{1-[(benzyloxy)methyl]cyclopropyl}-1-[(2R)-2,3-dihydroxypropyl]-6-fluoro-1H-indol-5-yl)-2,2-difluoro-7-methyl-6,7-dihydro-2H-furo[2,3-f][1,3]benzodioxole-7-carboxamide The product of Example 136F (219.8 mg, 0.308 mmol) was dissolved in methanol (2 mL). 10% Palladium on carbon (55.0 mg) was added and hydrogen was delivered to the reaction via balloon. The reaction was stirred at ambient temperature then heated at 60° C. for 15 hours, and filtered. The filtrate was concentrated, and the residue was purified by silica gel chromatography (50% to 100% ethyl acetate in dichloromethane) to yield the title compound as the first eluting compound (77.3 mg, 40%). $^1$H NMR (400 MHz, DMSO-$d_6$) δ 9.22 (s, 1H), 7.56 (s, 1H), 7.41-7.16 (m, 7H), 7.04 (s, 1H), 6.25 (s, 1H), 5.18 (d, J=5.3 Hz, 1H), 5.09 (d, J=9.1 Hz, 1H), 4.76 (t, J=5.8 Hz, 1H), 4.57 (d, J=1.4 Hz, 1H), 4.46-4.28 (m, 2H), 4.20 (dd, J=14.6, 8.9 Hz, 1H), 4.11 (s, 1H), 3.60-3.40 (m, 3H), 1.67 (s, 3H), 0.97-0.73 (m, 4H). MS (ESI+) m/z 623 (M+H)$^+$.

Example 204

(7R)—N-{2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide The product from Example 143A (0.111 g, 0.430 mmol) was refluxed in thionyl chloride (0.82 ml, 11.23 mmol) for 1 h. The mixture was cooled to room temperature and concentrated in vacuo, then excess thionyl chloride was chased three times with $CH_2Cl_2$ (5 mL each). The resulting yellow oil was treated with a solution of the product of Example 3B (0.134 g, 0.43 mmol) and pyridine (0.410 mL, 5.07 mmol) in 1 mL $CH_2Cl_2$, and the reaction was stirred at room temperature overnight. After this time, the mixture was concentrated in vacuo and purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The title compound was obtained as a dark red residue (0.107 g, 45%). %). $^1$H NMR (400 MHz, DMSO-$d_6$) δ 10.91 (br, 1H), 9.20 (s, 1H), 7.56 (s, 1H), 7.41-7.19 (m, 5H), 7.12-7.00 (m, 2H), 6.15 (d, J=2.0 Hz, 1H), 5.09 (d, J=9.1 Hz, 1H), 4.50-4.34 (m, 3H), 3.49 (s, 2H), 1.68 (s, 3H), 1.33 (s, 6H). MS (ESI$^+$) m/z 553.0 (M+H)$^+$.

Example 205

(7S)—N-{1-[(2R)-3-(benzyloxy)-2-hydroxypropyl]-2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide The product from Example 3A (50.3 mg, 0.195 mmol) was dissolved in dichloromethane (1 mL). Oxalyl chloride (80 µL) and N,N-dimethylformamide (25 µL) were added which resulted in bubbling of the reaction mixture. The reaction mixture was stirred at ambient temperature for 1 hour. The reaction mixture was concentrated, and the residue was dissolved in dichloromethane (1 mL) and concentrated two times. The residue was dissolved in dichloromethane (1 mL) and pyridine (0.5 mL). The product of Example 130E (89.8 mg, 0.188 mmol) was added, and the reaction mixture was stirred at 60° C. for 16 hours. The reaction mixture was concentrated, and the residue was purified by reverse-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A to yield the title compound (85.0 mg, 63%). $^1$H NMR (500 MHz, DMSO-$d_6$) δ 9.24 (s, 1H), 7.57 (s, 1H), 7.42-7.33 (m, 6H), 7.33-7.18 (m, 6H), 7.06 (s, 1H), 6.28 (s, 1H), 5.14 (s, 1H), 5.10 (d, J=9.1 Hz, 1H), 4.55 (s, 2H), 4.49-4.34 (m, 4H), 4.14 (dd, J=15.2, 8.6 Hz, 1H), 4.02 (dtd, J=8.4, 5.6, 5.1, 2.9 Hz, 1H), 3.65 (d, J=9.2 Hz, 1H), 3.57 (d, J=9.2 Hz, 1H), 3.50 (dd, J=9.6, 4.8 Hz, 1H), 3.45 (dd, J=9.7, 6.4 Hz, 1H), 1.68 (s, 3H), 1.42 (s, 3H), 1.41 (s, 3H). MS (ESI+) m/z 717 (M+H)$^+$.

Example 206

(7R)—N-{5-[(2R)-2,3-dihydroxypropyl]-7-fluoro-1,1,4,4-tetramethyl-1,3,4,5-tetrahydropyrano[4,3-b]indol-8-yl}-2,2-difluoro-7-methyl-6,7-dihydro-2H-furo[2,3-f][1,3]benzodioxole-7-carboxamide The product of Example 130G (2.57 g, 4.79 mmol) in acetone (50 ml) was treated with p-toluenesulfonic acid (50 mg, 0.263 mmol) and 2,2-dimethoxypropane (0.7 ml, 5.69 mmol), and the reaction mixture was stirred overnight at room temperature. The mixture was then concentrated in vacuo. The residue was chromatographed on silica gel, eluting with 0 to 50% ethyl acetate-heptanes to afford the title compound (minor product of the reaction) as a white solid (0.298 g, 11%). $^1$H NMR (500 MHz, DMSO-d$_6$) δ 9.21 (s, 1H), 7.54 (s, 1H), 7.43-7.33 (m, 2H), 7.03 (s, 1H), 5.10-4.99 (m, 2H), 4.94 (t, J=5.5 Hz, 1H), 4.43-4.30 (m, 2H), 4.06-3.92 (m, 2H), 3.86 (s, 1H), 3.53-3.37 (m, 3H), 1.66 (s, 3H), 1.49 (s, 3H), 1.48 (s, 3H), 1.34 (s, 3H), 1.30 (s, 3H). MS m/z 577.1 (M+H)$^+$.

Example 207

(7R)—N-(5-{[(4R)-2,2-dimethyl-1,3-dioxolan-4-yl]methyl}-7-fluoro-1,1,4,4-tetramethyl-1,3,4,5-tetrahydropyrano[4,3-b]indol-8-yl)-2,2-difluoro-7-methyl-6,7-dihydro-2H-furo[2,3-f][1,3]benzodioxole-7-carboxamide The title compound was obtained as the main product from the chromatography of the reaction described in Example 206: white solid, 2.38 g (81%). $^1$H NMR (500 MHz, DMSO-d$_6$) δ 9.22 (s, 1H), 7.54 (s, 1H), 7.42-7.36 (m, 2H), 7.03 (s, 1H), 5.08 (d, J=9.1 Hz, 1H), 4.45-4.33 (m, 3H), 4.25 (dd, J=15.5, 8.4 Hz, 1H), 4.15 (dd, J=8.4, 6.4 Hz, 1H), 3.70 (dd, J=8.4, 7.2 Hz, 1H), 3.52 (d, J=11.3 Hz, 1H), 3.45 (d, J=11.3 Hz, 1H), 1.66 (s, 3H), 1.49 (s, 3H), 1.48 (s, 3H), 1.41 (s, 3H), 1.33 (s, 3H), 1.28 (s, 3H), 1.20 (s, 3H). MS (ESI$^+$) m/z 617.0 (M+H)$^+$.

Example 208

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyphenyl)pyridine-3-carboxamide A stock solution containing Example 89F (300 μL, 0.15 M, 0.046 mmol, 1.0 equivalent) and diisopropylethylamine (300 μL, 0.45 M, 0.14 mmol, 3.0 equivalents) in N,N-dimethylacetamide was mixed with a stock solution of HATU (300 μL, 0.19 M, 0.056 mmol, 1.2 equivalents) in N,N-dimethylacetamide at room temperature. The resultant solution was added to neat 2-aminophenol (7.57 mg, 0.069 mmol, 1.5 equivalents) and the reaction mixture was stirred at room temperature for 30 minutes at which point the reaction was deemed complete by LC. The reaction mixture was loaded directly into an injection loop and purified using Prep LC/MS Method TFA6 to provide the title compound (5.1 mg, 14.8% yield). $^1$H NMR (400 MHz, 90° C., DMSO-d$_6$:D$_2$O=9:1 (v/v)) δ 9.07 (d, J=2.3 Hz, 1H), 8.36 (dd, J=8.2, 2.3 Hz, 1H), 8.20 (d, J=8.2 Hz, 1H), 7.67 (dd, J=7.9, 1.8 Hz, 2H), 7.35 (s, 1H), 7.11-7.05 (m, 1H), 7.03-6.98 (m, 1H), 6.98-6.93 (m, 1H), 6.91-6.83 (m, 2H), 6.54 (dd, J=8.5, 2.6 Hz, 1H), 6.48 (d, J=2.6 Hz, 1H), 5.43-5.24 (m, 2H), 4.99 (d, J=9.1 Hz, 1H), 4.34 (d, J=9.1 Hz, 1H), 3.74 (s, 3H), 2.47-2.39 (m, 1H), 2.25-2.12 (m, 1H), 1.58 (s, 3H). MS (APCI+) m/z 631.9 (M+H)$^+$.

Example 209

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)-N-propylpyridine-3-carboxamide Example 209 was prepared according to the procedure used for the preparation of Example 208, substituting 2-propylaminoethanol for 2-aminophenol and purified using Prep LC/MS Method TFA7, to provide the title compound (25.9 mg, 75.6% yield). $^1$H NMR (400 MHz, 90° C., DMSO-d$_6$:D$_2$O=9:1 (v/v)) δ 8.55 (dd, J=2.2, 0.8 Hz, 1H), 7.87 (m, J=8.0, 2.2 Hz, 1H), 7.64 (d, J=8.0 Hz, 1H), 7.36 (s, 1H), 6.99 (dd, J=8.5, 1.0 Hz, 1H), 6.86 (s, 1H), 6.53 (dd, J=8.6, 2.6 Hz, 1H), 6.46 (d, J=2.6 Hz, 1H), 5.35-5.27 (m, 2H), 4.99 (d, J=9.1 Hz, 1H), 4.34 (d, J=9.1 Hz, 1H), 3.73 (s, 3H), 3.56 (d, J=6.2 Hz, 2H), 3.48-3.33 (m, 4H), 2.46-2.36 (m, 1H), 2.25-2.12 (m, 1H), 1.65-1.51 (m, 5H), 0.92-0.72 (m, 3H). MS (APCI+) m/z 625.8 (M+H)$^+$.

Example 210

N-benzyl-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)pyridine-3-carboxamide Example 210 was prepared according to the procedure used for the preparation of Example 208, substituting 2-benzylaminoethanol for 2-aminophenol and purified using Prep LC/MS Method TFA7, to provide the title compound (21.8 mg, 59.8% yield). $^1$H NMR (400 MHz, 90° C., DMSO-d$_6$:D$_2$O=9:1 (v/v)) δ 8.60 (d, J=2.1 Hz, 1H), 7.92 (dd, J=8.0, 2.2 Hz, 1H), 7.68 (d, J=8.5 Hz, 1H), 7.63 (d, J=8.0 Hz, 1H), 7.40-7.32 (m, 3H), 7.32-7.21 (m, 3H), 6.99 (dd, J=8.6, 1.0 Hz, 1H), 6.52 (dd, J=8.6, 2.6 Hz, 1H), 6.45 (d, J=2.6 Hz, 1H), 5.36-5.23 (m, 2H), 4.99 (d, J=9.1 Hz, 1H), 4.68 (s, 2H), 4.33 (d, J=9.1 Hz, 1H), 3.72 (s, 3H), 3.64-3.53 (m, 2H), 3.45-3.34 (m, 2H), 2.45-2.32 (m, 1H), 2.22-2.07 (m, 1H), 1.57 (s, 3H). MS (APCI+) m/z 673.8 (M+H)+.

Example 211

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-2-phenylethyl)-N-methylpyridine-3-carboxamide Example 211 was prepared according to the procedure used for the preparation of Example 208, substituting 2-methylamino-1-phenylethanol for 2-aminophenol and purified using Prep LC/MS Method TFA7, to provide the title compound (30.1 mg, 82.5% yield). $^1$H NMR (400 MHz, 90° C., DMSO-d$_6$:D$_2$O=9:1 (v/v)) δ 8.44 (s, 1H), 7.73 (dd, J=25.2, 8.2 Hz, 2H), 7.60 (d, J=8.0 Hz, 1H), 7.41-7.14 (m, 5H), 7.00 (d, J=8.5 Hz, 1H), 6.86 (s, 1H), 6.53 (dd, J=8.5, 2.6 Hz, 1H), 6.46 (d, J=2.6 Hz, 1H), 5.39-5.25 (m, 2H), 5.00 (d, J=9.1 Hz, 1H), 4.86 (s, 1H), 4.34 (d, J=9.1 Hz, 1H), 3.73

(s, 3H), 3.63-3.47 (m, 2H), 3.00 (s, 3H), 2.43-2.33 (m, 1H), 2.23-2.09 (m, 1H), 1.58 (s, 3H). MS (APCI+) m/z 673.8 (M+H)+.

Example 212

(7R)-2,2-difluoro-N-{(2R,4R)-2-[5-(4-hydroxypiperidine-1-carbonyl)pyridin-2-yl]-7-methoxy-3,4-dihydro-2H-1-benzopyran-4-yl}-7-methyl-6,7-dihydro-2H-furo[2,3-f][1,3]benzodioxole-7-carboxamide Example 212 was prepared according to the procedure used for the preparation of Example 208, substituting piperidin-4-ol for 2-aminophenol and purified using Prep LC/MS Method TFA7, to provide the title compound (23.4 mg, 68.5% yield). $^1$H NMR (400 MHz, 90° C., DMSO-d$_6$:D$_2$O=9:1 (v/v)) δ 8.55 (d, J=2.2 Hz, 1H), 7.88 (dd, J=8.0, 2.2 Hz, 1H), 7.65 (d, J=8.0 Hz, 1H), 7.35 (s, 1H), 6.99 (d, J=8.6 Hz, 1H), 6.86 (s, 1H), 6.53 (dd, J=8.6, 2.6 Hz, 1H), 6.45 (d, J=2.5 Hz, 1H), 5.36-5.25 (m, 2H), 4.99 (d, J=9.2 Hz, 1H), 4.33 (d, J=9.1 Hz, 1H), 3.84-3.69 (m, 6H), 3.28-3.16 (m, 2H), 2.47-2.33 (m, 1H), 2.25-2.10 (m, 1H), 1.80 (dd, J=13.8, 5.3 Hz, 2H), 1.58 (s, 3H), 1.52-1.36 (m, 2H). MS (APCI+) m/z 624.0 (M+H)+.

Example 213

(7R)-2,2-difluoro-N-[(2R,4R)-2-{5-[4-(2-hydroxyethyl)piperazine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide Example 213 was prepared according to the procedure used for the preparation of Example 208, substituting 2-piperazin-1-yl-ethanol for 2-aminophenol and purified using Prep LC/MS Method TFA7, to provide the title compound (36.2 mg, 88.8% yield). $^1$H NMR (400 MHz, 90° C., DMSO-d$_6$:D$_2$O=9:1 (v/v)) δ 8.65 (dd, J=2.3, 0.8 Hz, 1H), 7.96 (dd, J=8.1, 2.2 Hz, 1H), 7.69 (d, J=8.1 Hz, 1H), 7.36 (s, 1H), 7.01 (dd, J=8.6, 1.0 Hz, 1H), 6.86 (s, 1H), 6.54 (dd, J=8.6, 2.5 Hz, 1H), 6.45 (d, J=2.5 Hz, 1H), 5.36-5.24 (m, 2H), 5.00 (d, J=9.1 Hz, 1H), 4.34 (d, J=9.1 Hz, 1H), 3.86-3.77 (m, 4H), 3.73 (s, 3H), 3.37 (t, J=5.0 Hz, 4H), 3.28-3.20 (m, 4H), 2.46-2.37 (m, 1H), 2.24-2.10 (m, 1H), 1.58 (s, 3H). MS (APCI+) m/z 653.0 (M+H)+.

Example 214

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-2-methylpropyl)pyridine-3-carboxamide Example 214 was prepared according to the procedure used for the preparation of Example 208, substituting 1-amino-2-methyl-propan-2-ol for 2-aminophenol and purified using Prep LC/MS Method TFA7, to provide the title compound (26.2 mg, 78.0% yield). $^1$H NMR (400 MHz, 90° C., DMSO-d$_6$:D$_2$O=9:1 (v/v)) δ 8.97 (d, J=2.2 Hz, 1H), 8.26 (dd, J=8.2, 2.3 Hz, 1H), 7.67 (d, J=8.2 Hz, 1H), 7.35 (s, 1H), 6.99 (dd, J=8.5, 0.9 Hz, 1H), 6.85 (s, 1H), 6.53 (dd, J=8.6, 2.6 Hz, 1H), 6.46 (d, J=2.5 Hz, 1H), 5.37-5.26 (m, 2H), 4.98 (d, J=9.2 Hz, 1H), 4.33 (d, J=9.1 Hz, 1H), 3.73 (s, 3H), 3.32 (s, 2H), 2.44-2.37 (m, 1H), 2.25-2.10 (m, 1H), 1.57 (s, 3H), 1.16 (s, 6H). MS (APCI+) m/z 612.0 (M+H)+.

Example 215

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1-hydroxy-2-methylpropan-2-yl)pyridine-3-carboxamide Example 215 was prepared according to the procedure used for the preparation of Example 208, substituting 2-amino-2-methyl-propan-1-ol for 2-aminophenol and purified using Prep LC/MS Method TFA7, to provide the title compound (8.4 mg, 25.0% yield). $^1$H NMR (400 MHz, 90° C., DMSO-d$_6$:D$_2$O=9:1 (v/v)) δ 8.89 (d, J=2.3 Hz, 1H), 8.18 (dd, J=8.2, 2.3 Hz, 1H), 7.63 (d, J=8.1 Hz, 1H), 7.35 (s, 1H), 6.99 (dd, J=8.5, 1.0 Hz, 1H), 6.86 (s, 1H), 6.53 (dd, J=8.6, 2.6 Hz, 1H), 6.46 (d, J=2.6 Hz, 1H), 5.37-5.26 (m, 2H), 4.99 (d, J=9.1 Hz, 1H), 4.33 (d, J=9.1 Hz, 1H), 3.73 (s, 3H), 3.55 (s, 2H), 2.43-2.33 (m, 1H), 2.22-2.08 (m, 1H), 1.57 (s, 3H), 1.35 (s, 6H). MS (APCI+) m/z 612.0 (M+H)+.

Example 216

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-1-phenylethyl)pyridine-3-carboxamide Example 216 was prepared according to the procedure used for the preparation of Example 208, substituting 2-amino-2-phenyl-ethanol for 2-aminophenol and purified using Prep LC/MS Method TFA7, to provide the title compound (28.7 mg, 80.1% yield). $^1$H NMR (400 MHz, 90° C., DMSO-d$_6$:D$_2$O=9:1 (v/v)) δ 9.01 (d, J=2.2 Hz, 1H), 8.29 (dd, J=8.1, 2.3 Hz, 1H), 7.67 (d, J=8.2 Hz, 1H), 7.44-7.37 (m, 2H), 7.37-7.28 (m, 3H), 7.28-7.20 (m, 1H), 6.99 (d, J=8.5 Hz, 1H), 6.85 (s, 1H), 6.53 (dd, J=8.6, 2.6 Hz, 1H), 6.46 (d, J=2.5 Hz, 1H), 5.38-5.26 (m, 2H), 5.16-5.07 (m, 1H), 4.99 (d, J=9.1 Hz, 1H), 4.33 (d, J=9.1 Hz, 1H), 3.83-3.73 (m, 2H), 3.73 (s, 3H), 2.45-2.34 (m, 1H), 2.23-2.09 (m, 1H), 1.57 (s, 3H). MS (APCI+) m/z 659.9 (M+H)+.

Example 217

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1,1-dioxo-1lambda$^6$-thian-4-yl)pyridine-3-carboxamide Example 217 was prepared according to the procedure used for the preparation of Example 208, substituting 1,1-dioxothian-4-amine for 2-aminophenol and purified using Prep LC/MS Method TFA7, to provide the title compound (7.6 mg, 20.9% yield). $^1$H NMR (400 MHz, 90° C., DMSO-d$_6$:D$_2$O=9:1 (v/v)) δ 8.96 (d, J=2.2 Hz, 1H), 8.25 (dd, J=8.2, 2.3 Hz, 1H), 7.70-7.63 (m, 2H), 7.35 (s, 1H), 6.99 (d, J=8.6 Hz, 1H), 6.53 (dd, J=8.6, 2.6 Hz, 1H), 6.46 (d, J=2.6 Hz, 1H), 5.37-5.25 (m, 2H), 4.99 (d, J=9.1 Hz, 1H), 4.33 (d, J=9.2 Hz, 1H), 4.24-4.15 (m, 1H), 3.73 (s, 3H), 3.26-3.18 (m, 1H), 3.14 (t, J=9.1 Hz, 3H), 2.44-2.34 (m, 1H), 2.28-2.08 (m, 5H), 1.58 (s, 3H). MS (APCI+) m/z 671.9 (M+H)+.

Example 218

(7R)—N-{(2R,4R)-2-[5-(4,4-difluoropiperidine-1-carbonyl)pyridin-2-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide Example 218 was prepared according to the procedure used for the preparation of Example 208, substituting 4,4-difluoropiperidine hydrochloride for 2-aminophenol and purified using Prep LC/MS Method TFA7, to provide the title compound (28.3 mg, 80.7% yield). $^1$H NMR (400 MHz, 90° C., DMSO-d$_6$:D$_2$O=9:1 (v/v)) δ 8.62 (d, J=2.1 Hz, 1H), 7.94 (dd, J=8.1, 2.2 Hz, 1H), 7.66 (d, 1H), 7.35 (s, 1H), 7.00 (dd, J=8.7, 1.0 Hz, 1H), 6.86 (s, 1H), 6.53 (dd, J=8.6, 2.6 Hz, 1H), 6.45 (d, J=2.5 Hz, 1H), 5.37-5.26 (m, 2H), 4.99 (d, J=9.1 Hz, 1H), 4.34 (d, J=9.1 Hz, 1H), 3.73 (s, 3H), 3.62 (t, J=5.8 Hz, 4H), 2.46-2.35 (m, 1H), 2.24-2.10 (m, 1H), 2.13-1.98 (m, 4H), 1.58 (s, 3H). MS (APCI+) m/z 643.9 (M+H)$^+$.

Example 219

(7R)-2,2-difluoro-N-{(2R,4R)-7-methoxy-2-[5-(1,4-oxazepane-4-carbonyl)pyridin-2-yl]-3,4-dihydro-2H-1-benzopyran-4-yl}-7-methyl-6,7-dihydro-2H-furo[2,3-f][1,3]benzodioxole-7-carboxamide Example 219 was prepared according to the procedure used for the preparation of Example 208, substituting 1,4-oxazepane hydrochloride for 2-aminophenol and purified using Prep LC/MS Method TFA7, to provide the title compound (25.0 mg, 73.2% yield). $^1$H NMR (400 MHz, 90° C., DMSO-d$_6$:D$_2$O=9:1 (v/v)) δ 8.57 (d, J=2.2 Hz, 1H), 7.90 (dd, J=8.0, 2.2 Hz, 1H), 7.65 (d, J=8.0 Hz, 1H), 7.35 (s, 1H), 6.99 (d, J=8.5 Hz, 1H), 6.86 (s, 1H), 6.53 (dd, J=8.5, 2.6 Hz, 1H), 6.45 (d, J=2.5 Hz, 1H), 5.35-5.26 (m, 2H), 4.99 (d, J=9.1 Hz, 1H), 4.34 (d, J=9.0 Hz, 1H), 3.76-3.45 (m, 11H), 2.45-2.35 (m, 1H), 2.24-2.10 (m, 1H), 1.83 (s, 2H), 1.58 (s, 3H). MS (APCI+) m/z 624.0 (M+H)$^+$.

Example 220

(7R)-2,2-difluoro-N-{(2R,4R)-7-methoxy-2-[5-(morpholine-4-carbonyl)pyridin-2-yl]-3,4-dihydro-2H-1-benzopyran-4-yl}-7-methyl-6,7-dihydro-2H-furo[2,3-f][1,3]benzodioxole-7-carboxamide Example 220 was prepared according to the procedure used for the preparation of Example 208, substituting morpholine for 2-aminophenol and purified using Prep LC/MS Method TFA7, to provide the title compound (24.7 mg, 73.7% yield). $^1$H NMR (400 MHz, 90° C., DMSO-d$_6$:D$_2$O=9:1 (v/v)) δ 8.59 (d, J=2.2 Hz, 1H), 7.91 (dd, J=8.0, 2.2 Hz, 1H), 7.66 (d, J=8.1 Hz, 1H), 7.35 (s, 1H), 6.99 (d, J=8.4 Hz, 1H), 6.86 (s, 1H), 6.53 (dd, J=8.5, 2.0 Hz, 1H), 6.46 (d, J=8.6 Hz, 1H), 5.42-5.25 (m, 2H), 4.98 (d, J=9.1 Hz, 1H), 4.33 (d, J=9.2 Hz, 1H), 3.73 (s, 3H), 3.68-3.61 (m, 4H), 3.58-3.45 (m, 4H), 2.43-2.36 (m, 1H), 2.23-2.10 (m, 1H), 1.57 (s, 3H). MS (APCI+) m/z 609.8 (M+H)$^+$.

Example 221

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-2,3-dihydro-1H-inden-1-yl)pyridine-3-carboxamide Example 221 was prepared according to the procedure used for the preparation of Example 208, substituting 1-amino-indan-2-ol for 2-aminophenol and purified using Prep LC/MS Method TFA7, to provide the title compound (27.8 mg, 76.4% yield). $^1$H NMR (400 MHz, 90° C., DMSO-d$_6$:D$_2$O=9:1 (v/v)) δ 9.05 (d, J=2.3 Hz, 1H), 8.33 (dd, J=8.1, 2.3 Hz, 1H), 7.68 (d, J=8.1 Hz, 1H), 7.35 (s, 1H), 7.31-7.15 (m, 4H), 7.00 (dd, J=8.5, 1.0 Hz, 1H), 6.86 (s, 1H), 6.53 (dd, J=8.5, 2.5 Hz, 1H), 6.47 (d, J=2.5 Hz, 1H), 5.46 (d, J=5.3 Hz, 1H), 5.33 (td, J=10.2, 8.9, 3.9 Hz, 2H), 4.99 (d, J=9.1 Hz, 1H), 4.62-4.54 (m, 1H), 4.33 (d, J=9.1 Hz, 1H), 3.73 (s, 3H), 3.14 (dd, J=16.3, 5.4 Hz, 1H), 2.93 (dd, J=16.3, 2.5 Hz, 1H), 2.46-2.35 (m, 1H), 2.24-2.10 (m, 1H), 1.58 (s, 3H). MS (APCI+) m/z 672.0 (M+H)$^+$.

Example 222

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[2-hydroxy-1-(2-methoxyphenyl)ethyl]pyridine-3-carboxamide Example 222 was prepared according to the procedure used for the preparation of Example 208, substituting 2-amino-2-(2-methoxy-phenyl)-ethanol for 2-aminophenol and purified using Prep LC/MS Method TFA7, to provide the title compound (17.5 mg, 47.0% yield). $^1$H NMR (400 MHz, 90° C., DMSO-d$_6$:D$_2$O=9:1 (v/v)) δ 9.00 (s, 1H), 8.28 (d, J=8.2 Hz, 1H), 7.67 (d, J=8.2 Hz, 1H), 7.39-7.31 (m, 2H), 7.28-7.19 (m, 1H), 7.00 (d, J=8.5 Hz, 2H), 6.91 (t, J=7.4 Hz, 1H), 6.85 (d, J=2.0 Hz, 1H), 6.53 (d, J=8.6, 2.6 Hz, 1H), 6.46 (d, J=2.6 Hz, 1H), 5.50-5.42 (m, 1H), 5.38-5.26 (m, 2H), 4.99 (d, J=9.2 Hz, 1H), 4.33 (d, J=9.1 Hz, 1H), 3.85 (s, 3H), 3.73 (s, 3H), 3.73-3.64 (m, 2H), 2.45-2.35 (m, 1H), 2.23-2.09 (m, 1H), 1.58 (s, 3H). MS (APCI+) m/z 689.8 (M+H)$^+$.

Example 223

(7R)—N-{(2R,4R)-2-[4-(4,4-difluoropiperidine-1-carbonyl)phenyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide The product from Example 50 (0.014 g, 0.026 mmol), 4,4-difluoropiperidine hydrochloride (4.91 mg, 0.031 mmol), and N$^1$-((ethylimino)methylene)-N$^3$,N$^3$-dimethylpropane-1,3-diamine hydrochloride (9.45 mg, 0.049 mmol) were stirred in N,N-dimethylformamide (0.2 mL) and pyridine (0.200 mL) for 3 days at room temperature. After this time, the mixture was concentrated in vacuo, and the crude product was purified by silica gel chromatography, eluting with 30 to 70% ethyl acetate-heptanes. The title compound was obtained as a white solid (0.0144 g, 86%). $^1$H NMR (400 MHz, DMSO-d$_6$) δ 7.97 (d, J=8.7 Hz, 1H), 7.58-7.42 (m, 5H), 7.08-6.95 (m, 2H), 6.60-6.40 (m, 2H), 5.31 (m, 2H), 5.00 (d, J=9.0 Hz, 1H), 4.30 (d, J=9.0 Hz, 1H), 3.67 (s, 3H), 3.65 (m, 2H), 3.26 (m, 1H), 3.14 (m, 1H), 2.12-1.95 (m, 6H), 1.54 (s, 3H). MS (ESI$^+$) m/z 642.9 (M+H)$^+$.

Example 224 benzyl 4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidine-1-carboxylate

Example 224A benzyl 4-[(2R,4R)-4-{[(S)-2-methylpropane-2-sulfinyl]amino}-7-(trifluoromethoxy)-3,4-dihydro-2H-1-benzopyran-2-yl]piperidine-1-carboxylate A solution of Example 225B (0.967 g, 1.75 mmol) in methanol (25 mL) was cooled to 0° C., treated with NaBH$_4$ (0.132 g, 3.50 mmol), and stirred for 45 minutes. The mixture was diluted with CH$_2$Cl$_2$ (15 mL), treated with about 3 g of silica gel and concentrated to dryness. This silica gel suspension was transferred to a Poppy-65 cartridge and chromatographed on silica gel eluting with a gradient of 0 to 50% ethyl acetate in [9:1 CH$_2$Cl$_2$:ethyl acetate] to provide the title compound as the second eluting isomer. $^1$H NMR (400 MHz, CDCl$_3$) δ 7.40 (d, J=8.6 Hz, 1H), 7.38-7.35 (m, 4H), 7.35-7.29 (m, 1H), 6.75 (d, J=8.7 Hz, 1H), 6.67 (s, 1H), 5.14 (s, 2H), 4.58 (td, J=11.1, 5.9 Hz, 1H), 4.28 (bs, 2H), 3.96 (dd, J=11.3, 5.3 Hz, 1H), 3.28 (d, J=10.8 Hz, 1H), 2.82-2.73 (m, 2H), 2.63 (dd, J=13.2, 5.9 Hz, 1H), 1.94-1.86 (m, 1H), 1.83-1.68 (m, 3H), 1.52-1.33 (m, 2H), 1.30 (s, 9H); LC/MS (ESI+) m/z 555 (M+H)$^+$.

Example 224B benzyl 4-[(2R,4R)-4-amino-7-(trifluoromethoxy)-3,4-dihydro-2H-1-benzopyran-2-yl]piperidine-1-carboxylate A solution of Example 224A (0.36 g, 0.649 mmol) in ethanol (3.5 mL) was treated with 4 M HCl in dioxane (1.623 mL, 6.49 mmol) and stirred at room temperature for 15 minutes. The mixture was partitioned between ethyl acetate and saturated aqueous NaHCO$_3$ solution. The ethyl acetate layer was washed with brine, dried (MgSO$_4$), filtered, and concentrated. The residue was chromatographed on silica gel eluting with a gradient of 0 to 100% [10:1:1 ethyl acetate:HCOOH:H$_2$O] in [200:1:1 ethyl acetate:HCOOH:H$_2$O]. The fractions containing product were combined and basifed with saturated aqueous NaHCO$_3$ solution, adding more solid NaHCO$_3$ to the mixture until the pH was 8. This ethyl acetate layer was washed with brine, dried (MgSO$_4$), filtered and concentrated to provide the title compound (0.276 g, 0.613 mmol, 94% yield). $^1$H NMR (400 MHz, CDCl$_3$) δ 7.47 (d, J=8.5 Hz, 1H), 7.43-7.32 (m, 5H), 6.80 (dd, J=8.5, 1.2 Hz, 1H), 6.67 (d, J=1.2 Hz, 1H), 5.17 (s, 2H), 4.31 (bs, 2H), 4.08 (dd, J=11.2, 5.8 Hz, 1H), 3.97 (dd, J=11.0, 5.5 Hz, 1H), 2.83 (t, J=10.9 Hz, 2H), 2.21 (dd, J=13.0, 5.4 Hz, 1H), 1.96 (d, J=13.2 Hz, 1H), 1.85-1.69 (m, 2H), 1.66-1.53 (m, 1H), 1.50-1.33 (m, 2H); LC/MS (ESI+) m/z 390 (100%), 451 (M+H)$^+$ (10%).

Example 224C benzyl 4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidine-1-carboxylate A solution of Example 224B (0.276 g, 0.613 mmol) and triethylamine (0.171 mL, 1.225 mmol) in CH$_2$Cl$_2$ (3 mL) at 0° C. under N$_2$ was treated with a solution of Example 134F (0.203 g, 0.735 mmol) in CH$_2$Cl$_2$ (1 mL). The mixture was stirred at 0° C. for 45 minutes and at room temperature for 15 minutes. The reaction mixture was treated with 10 drops of 37% NH$_4$OH solution and stirred at room temperature for 2 minutes. The mixture was partitioned between ethyl acetate (about 50 mL) and 1 M HCl (15 mL). The layers were separated and the ethyl acetate layer was washed with saturated aqueous NaHCO$_3$ solution (about 10 mL), washed with brine, dried (MgSO$_4$), filtered, and concentrated. The residue was chromatographed on silica gel eluting with a gradient of 25 to 100% ethyl acetate in heptanes to provide the title compound (0.394 g, 0.571 mmol, 93% yield). $^1$H NMR (501 MHz, CDCl$_3$) δ 7.38-7.34 (m, 4H), 7.34-7.29 (m, 1H), 6.91 (s, 1H), 6.87 (dd, J=8.5, 0.9 Hz, 1H), 6.72-6.69 (m, 1H), 6.67-6.65 (m, 1H), 6.64 (s, 1H), 5.64 (d, J=8.9 Hz, 1H), 5.30-5.24 (m, 1H), 5.13 (s, 2H), 4.89 (d, J=9.3 Hz, 1H), 4.35 (d, J=9.3 Hz, 1H), 4.27 (bs, 2H), 3.96 (dd, J=10.8, 5.5 Hz, 1H), 2.77 (bs, 2H), 2.23 (dd, J=12.1, 6.1 Hz, 1H), 1.87 (d, J=11.8 Hz, 1H), 1.81-1.69 (m, 1H), 1.67 (s, 3H), 1.65-1.56 (m, 1H), 1.51 (q, J=11.7 Hz, 1H), 1.45-1.27 (m, 2H); LC/MS (ESI+) m/z 691 (M+H)$^+$.

Example 225 benzyl 4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidine-1-carboxylate

Example 225A benzyl 4-[4-oxo-7-(trifluoromethoxy)-3,4-dihydro-2H-1-benzopyran-2-yl]piperidine-1-carboxylate A solution of Example 145A (0.72 g, 3.27 mmol) and benzyl 4-formylpiperidine-1-carboxylate (CAS #138163-08-3, 0.809 g, 3.27 mmol) in methanol (15 mL) was treated with pyrrolidine (0.541 ml, 6.54 mmol) and the mixture was stirred at 60° C. for 90 minutes. The mixture was concentrated to dryness and the residue was partitioned between ethyl acetate (30 mL) and 1 M HCl (20 mL). The ethyl acetate layer was washed with saturated aqueous NaHCO$_3$ solution, washed with brine, dried (MgSO$_4$), filtered, and concentrated. The residue was chromatographed on silica gel eluting with a gradient of 15 to 100% ethyl acetate in heptanes to provide the title compound (0.79 g, 1.758 mmol, 53.7% yield). $^1$H NMR (400 MHz, CDCl$_3$) δ 7.91 (d, J=8.6 Hz, 1H), 7.39-7.29 (m, 5H), 6.85 (d, J=8.8 Hz, 1H), 6.82 (s, 1H), 5.14 (s, 2H), 4.37-4.25 (m, 3H), 2.88-2.62 (m, 4H), 2.00-1.87 (m, 2H), 1.72 (d, J=11.5 Hz, 1H), 1.47-1.21 (m, 2H); LC/MS (ESI+) m/z 450 (M+H)$^+$.

Example 225B benzyl 4-[(4E)-4-{[(S)-2-methylpropane-2-sulfinyl]imino}-7-(trifluoromethoxy)-3,4-dihydro-2H-1-benzopyran-2-yl]piperidine-1-carboxylate A mixture of Example 225A (0.79 g, 1.758 mmol) and (S)-(−)-2-methyl-2-propanesulfinamide (CAS #343338-28-3, 0.426 g, 3.52 mmol) in toluene (5 mL) was treated with titanium(IV) ethoxide (1.458 ml, 7.03 mmol), stirred at 90° C. for 7 hours, cooled, diluted with ethyl acetate (50 mL), treated with water (50 mL), stirred for 5 minutes, and filtered through diatomaceous earth to remove the solids. The ethyl acetate layer washed with brine, dried (MgSO$_4$), filtered and concentrated to provide the title compound. LC/MS (ESI+) m/z 553 (M+H)$^+$.

Example 225C benzyl 4-[(2S,4S)-4-{[(S)-2-methylpropane-2-sulfinyl]amino}-7-(trifluoromethoxy)-3,4-dihydro-2H-1-benzopyran-2-yl]piperidine-1-carboxylate A solution of Example 225B (0.967 g, 1.75 mmol) in methanol (25 mL) was cooled to 0° C., treated with NaBH$_4$ (0.132 g, 3.50 mmol), and stirred for 45 minutes. The mixture was diluted with CH$_2$Cl$_2$ (15 mL), treated with about 3 g of silica gel and concentrated to dryness. This silica gel suspension was transferred to an Poppy-65 cartridge and chromatographed on silica gel, eluting with a gradient of 0 to 50% ethyl acetate in [9:1 CH$_2$Cl$_2$:ethyl acetate] to provide the title compound as the first eluting isomer. $^1$H NMR (400 MHz, CDCl$_3$) δ 7.68 (d, J=8.6 Hz, 1H), 7.39-7.29 (m, 5H), 6.78 (d, J=8.6 Hz, 1H), 6.66 (s, 1H), 5.14 (s, 2H), 4.64 (dt, J=13.4, 6.8 Hz, 1H), 4.29 (bs, 2H), 3.95 (dd, J=11.2, 5.5 Hz, 1H), 3.52 (d, J=7.9 Hz, 1H), 2.79 (t, J=10.8 Hz, 2H), 2.22 (dd, J=13.1, 6.0 Hz, 1H), 1.91 (d, J=13.0 Hz, 1H), 1.87-1.68 (m, 3H), 1.48-1.32 (m, 2H), 1.26 (s, 9H); LC/MS (ESI+) m/z 555 (M+H)$^+$.

Example 225D benzyl 4-[(2S,4S)-4-amino-7-(trifluoromethoxy)-3,4-dihydro-2H-1-benzopyran-2-yl]piperidine-1-carboxylate A solution of Example 225C (0.283 g, 0.51 mmol) in ethanol (2.5 mL) was treated with 4 M HCl in dioxane (1.275 mL, 5.10 mmol) and stirred at room temperature for 15 minutes. The mixture was partitioned between methyl tert-butyl ether (about 30 mL) and water (15 mL). The layers were separated and the methyl tert-butyl ether layer was extracted with 1 M HCl (10 mL). The combined acidic layers were basified with solid NaHCO$_3$ and extracted with ethyl acetate. This ethyl acetate layer was washed with brine, dried (MgSO$_4$), filtered and concentrated. The methyl tert-butyl ether layer was separately washed with brine, dried (MgSO$_4$), filtered, and concentrated. The residues from the two layers was combined and chromatographed on silica gel eluting with a gradient of 0 to 100% [10:1:1 ethyl acetate:HCOOH:H$_2$O] in [200:1:1 ethyl acetate:HCOOH:H$_2$O]. The fractions containing product were combined and basifed with a saturated aqueous NaHCO$_3$ solution, adding more solid NaHCO$_3$ to the mixture until the pH was 8. This ethyl acetate layer was washed with brine, dried (MgSO$_4$), filtered, and concentrated to provide the title compound (0.217 g, 0.482 mmol, 94% yield). $^1$H NMR (400 MHz, CDCl$_3$) δ 7.45 (d, J=8.5 Hz, 1H), 7.39-7.28 (m, 5H), 6.77 (d, J=8.5 Hz, 1H), 6.65 (s, 1H), 5.14 (s, 2H), 4.28 (bs, 2H), 4.07 (dd, J=11.1, 5.5 Hz, 1H), 3.94 (dd, J=11.0, 5.6 Hz, 1H), 2.84-2.75 (m, 2H), 2.19 (dd, J=12.5, 5.2 Hz, 1H), 1.93 (d, J=13.1 Hz, 1H), 1.87-1.67 (m, 2H), 1.59 (q, J=11.7 Hz, 1H), 1.48-1.29 (m, 2H); LC/MS (ESI+) m/z 390 (100%), 451 (M+H)$^+$ (10%).

Example 225E benzyl 4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidine-1-carboxylate A solution of Example 225D (0.217 g, 0.482 mmol) and triethylamine (0.134 ml, 0.963 mmol) in CH$_2$Cl$_2$ (3 mL) at 0° C. under N$_2$ was treated with a solution of Example 134F (0.160 g, 0.578 mmol) in CH$_2$Cl$_2$ (1 mL). The mixture was stirred at 0° C. for 45 minutes and at room temperature for 30 minutes. The mixture was treated with 10 drops of 37% NH$_4$OH solution and stirred at room temperature for 2 minutes. The mixture was partitioned between ethyl acetate (about 50 mL) and 1 M HCl (15 mL). The layers were separated and the ethyl acetate layer was washed with saturated aqueous NaHCO$_3$ solution (about 10 mL), washed with brine, dried (MgSO$_4$), filtered, and concentrated. The residue was chromatographed on silica gel eluting with a gradient of 25 to 100% ethyl acetate in heptanes to provide the title compound (0.339 g, 0.491 mmol, 102% yield). $^1$H NMR (501 MHz, CDCl$_3$) δ 7.38-7.35 (m, 4H), 7.34-7.29 (m, 1H), 6.93 (dd, J=8.5, 0.8 Hz, 1H), 6.86 (s, 1H), 6.72-6.69 (m, 1H), 6.66-6.64 (m, 2H), 5.60 (d, J=8.9 Hz, 1H), 5.28 (ddd, J=10.9, 9.2, 6.5 Hz, 1H), 5.13 (s, 2H), 4.94 (d, J=9.3 Hz, 1H), 4.37 (d, J=9.3 Hz, 1H), 4.28 (bs, 2H), 3.96 (dd, J=11.0, 5.5 Hz, 1H), 2.78 (bs, 2H), 2.24 (dd, J=12.5, 6.1 Hz, 1H), 1.88 (d, J=12.9 Hz, 1H), 1.80-1.66 (m, 2H), 1.64 (s, 3H), 1.51 (q, J=11.9 Hz, 1H), 1.45-1.25 (m, 2H); LC/MS (ESI+) m/z 691 (M+H)$^+$.

Example 226

(7R)—N-[(2S,4S)-2-(1-{[(4S)-2,2-dimethyl-1,3-dioxolan-4-yl]methyl}piperidin-4-yl)-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide A solution of Example 185 (33 mg, 0.059 mmol) and (R)-(−)-2,2-dimethyl-1,3-dioxolan-4-ylmethyl p-toluenesulfonate (CAS #23788-74-1, 16.98 mg, 0.059 mmol) in N,N-dimethylformamide (0.3 mL) was treated with triethylamine (24.80 μL, 0.178 mmol). The mixture was heated at 80° C. over night, heated at 100° C. for 90 minutes, and heated at 120° C. for 90 minutes, cooled, and partitioned between methyl tert-butyl ether (about 25 mL) and water. An emulsion was present which settled after several minutes. The layers were separated and the organic layer was washed with brine (more emulsion), diluted with heptanes (about 20 mL) (emulsion mostly settled), dried (MgSO$_4$), filtered, and concentrated. The residue was chromatographed on silica gel eluting with a gradient of 0 to 100% [22:1:1 ethyl acetate:HCOOH:H$_2$O] in [200:1:1 ethyl acetate:HCOOH:H$_2$O]. The fractions containing the product were combined, treated with saturated aqueous NaHCO$_3$ solution (about 40 mL) and treated with solid NaHCO$_3$ so that the aqueous layer was pH 8. The organic layer was dried (MgSO$_4$), filtered, concentrated to provide the title compound (23.6 mg, 0.035 mmol, 59.3% yield). $^1$H NMR (400 MHz, CDCl$_3$) δ 6.93 (dd, J=8.5, 0.6 Hz, 1H), 6.86 (s, 1H), 6.72-6.68 (m, 1H), 6.65 (s, 1H), 6.65-6.63 (m, 1H), 5.58 (d, J=9.0 Hz, 1H), 5.31-5.23 (m, 1H), 4.93 (d, J=9.3 Hz, 1H), 4.37 (d, J=9.3 Hz, 1H), 4.36-4.30 (m, 1H), 4.09 (dd, J=8.1, 6.3 Hz, 1H), 3.96 (dd, J=11.4, 3.5 Hz, 1H), 3.58 (dd, J=7.9, 7.5 Hz, 1H), 3.19 (d, J=10.1 Hz, 1H), 3.06 (d, J=10.5 Hz, 1H), 2.58 (d, J=5.5 Hz, 2H), 2.26 (ddd, J=12.6, 6.0, 1.0 Hz, 1H), 2.20-2.08 (m, 1H), 1.94-1.85 (m, 2H), 1.72-1.56 (m, 4H), 1.64 (s, 3H), 1.55-1.44 (m, 1H), 1.41 (s, 3H), 1.36 (s, 3H); LC/MS (ESI+) m/z 671.6 (M+H)$^+$.

Example 227

N-(2-amino-2-oxoethyl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide A stock solution of compound core and diisopropylethyl amine (0.11 M and 0.32 M in dimethylacetamide, respectively, 352 µL, 0.037 mmol Example 89F (1.0 equivalent) and 0.11 mmol diisopropylethyl amine (3.0 equivalents)), HATU (0.13 M in dimethylacetamide, 352 µL, 0.044 mmol, 1.2 equivalents), and 2-amino-acetamide hydrochloride (0.40 M in dimethylacetamide, 140.8 µL, 0.056 mmol, 1.5 equivalents) were aspirated from their respective source vials, mixed through a perfluoroalkoxy (PFA) mixing tube (0.2 mm inner diameter), and loaded into an injection loop. The reaction segment was injected into the flow reactor (Hastelloy coil, 0.75 mm inner diameter, 1.8 mL internal volume) set at 75° C., and passed through the reactor at 180 µL, min$^{-1}$ (10 minute residence time). Upon exiting the reactor, the reaction mixture was loaded directly into an injection loop and purified using Prep LC/MS Method TFA7 to provide the title compound (9.4 mg, 35.8% yield). $^1$H NMR (400 MHz, 90° C., DMSO-d$_6$:D$_2$O=9:1 (v/v)) δ 9.00 (d, J=2.2 Hz, 1H), 8.29 (dd, J=8.2, 2.3 Hz, 1H), 7.69 (d, J=8.1 Hz, 1H), 7.36 (s, 1H), 7.00 (d, J=8.6 Hz, 1H), 6.87 (s, 1H), 6.54 (dd, J=8.6, 2.6 Hz, 1H), 6.48 (d, J=2.6 Hz, 1H), 5.39-5.27 (m, 2H), 4.99 (d, J=9.1 Hz, 1H), 4.34 (d, J=9.1 Hz, 1H), 3.92 (s, 2H), 3.74 (s, 3H), 2.46-2.36 (m, 1H), 2.24-2.10 (m, 1H), 1.58 (s, 3H). MS (APCI+) m/z 596.6 (M+H)$^+$.

Example 228

N-(4-amino-4-oxobutyl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide Example 228 was prepared according to the procedure used for the preparation of Example 227, substituting 4-amino-butyramide hydrochloride for 2-amino-acetamide hydrochloride, to provide the title compound (10.6 mg, 38.8% yield). $^1$H NMR (400 MHz, 90° C., DMSO-d$_6$: D$_2$O=9:1 (v/v)) δ 8.96 (d, J=2.2 Hz, 1H), 8.24 (dd, J=8.1, 2.3 Hz, 1H), 7.67 (d, J=8.2 Hz, 1H), 7.35 (s, 1H), 7.04-6.96 (m, 1H), 6.87 (s, 1H), 6.54 (dd, J=8.6, 2.6 Hz, 1H), 6.47 (d, J=2.5 Hz, 1H), 5.38-5.27 (m, 2H), 4.99 (d, J=9.1 Hz, 1H), 4.34 (d, J=9.1 Hz, 1H), 3.74 (s, 3H), 3.33 (t, J=6.9 Hz, 2H), 2.40 (ddd, J=13.1, 6.2, 2.3 Hz, 1H), 2.23-2.10 (m, 3H), 1.88-1.76 (m, 2H), 1.58 (s, 3H). MS (APCI+) m/z 624.8 (M+H)$^+$.

Example 229

N-(4-amino-4-oxobutan-2-yl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide Example 229 was prepared according to the procedure used for the preparation of Example 227, substituting 3-amino-butyramide hydrochloride for 2-amino-acetamide hydrochloride, to provide the title compound (7.0 mg, 25.6% yield). $^1$H NMR (400 MHz, 90° C., DMSO-d$_6$:D$_2$O=9:1 (v/v)) δ 8.93 (d, J=2.2 Hz, 1H), 8.22 (dd, J=8.1, 2.3 Hz, 1H), 7.66 (d, J=8.2 Hz, 1H), 7.35 (s, 1H), 7.00 (d, J=8.6 Hz, 1H), 6.86 (s, 1H), 6.54 (dd, J=8.5, 2.6 Hz, 1H), 6.47 (d, J=2.5 Hz, 1H), 5.39-5.28 (m, 2H), 4.99 (d, J=9.2 Hz, 1H), 4.44-4.24 (m, 2H), 3.74 (s, 3H), 2.49-2.29 (m, 3H), 2.25-2.10 (m, 1H), 1.58 (s, 3H), 1.24 (d, J=6.6 Hz, 3H). MS (APCI+) m/z 624.8 (M+H)$^+$.

Example 230

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[2-(methanesulfonyl)ethyl]pyridine-3-carboxamide Example 230 was prepared according to the procedure used for the preparation of Example 227, substituting 2-methylsulfonylethanamine hydrochloride for 2-amino-acetamide hydrochloride, to provide the title compound (17.0 mg, 60.5% yield). $^1$H NMR (400 MHz, 90° C., DMSO-d$_6$: D$_2$O=9:1 (v/v)) δ 8.96 (d, J=2.2 Hz, 1H), 8.24 (dd, J=8.2, 2.3 Hz, 1H), 7.69 (d, J=8.1 Hz, 1H), 7.36 (s, 1H), 7.00 (d, J=8.6 Hz, 1H), 6.87 (s, 1H), 6.54 (dd, J=8.6, 2.6 Hz, 1H), 6.47 (d, J=2.5 Hz, 1H), 5.39-5.27 (m, 2H), 4.99 (d, J=9.1 Hz, 1H), 4.34 (d, J=9.1 Hz, 1H), 3.80-3.71 (m, 5H), 3.41 (t, J=6.8 Hz, 2H), 3.02 (s, 3H), 2.46-2.35 (m, 1H), 2.23-2.10 (m, 1H), 1.58 (s, 3H). MS (APCI+) m/z 646.1 (M+H)$^+$.

Example 231

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[(5-oxopyrrolidin-3-yl)methyl]pyridine-3-carboxamide Example 231 was prepared according to the procedure used for the preparation of Example 227, substituting 4-(aminomethyl)pyrrolidin-2-one for 2-amino-acetamide hydrochloride, to provide the title compound (11.8 mg, 42.5% yield). $^1$H NMR (400 MHz, 90° C., DMSO-d$_6$: D$_2$O=9:1 (v/v)) δ 8.96 (d, J=2.2 Hz, 1H), 8.24 (dd, J=8.2, 2.3 Hz, 1H), 7.68 (d, J=8.1 Hz, 1H), 7.35 (s, 1H), 7.00 (dd, J=8.6, 1.0 Hz, 1H), 6.86 (s, 1H), 6.54 (dd, J=8.6, 2.6 Hz, 1H), 6.47 (d, J=2.5 Hz, 1H), 5.38-5.27 (m, 2H), 4.99 (d, J=9.1 Hz, 1H), 4.34 (d, J=9.1 Hz, 1H), 3.74 (s, 3H), 3.46-3.31 (m, 3H), 3.08 (dd, J=9.9, 5.4 Hz, 1H), 2.78-2.64 (m, 1H), 2.45-2.36 (m, 1H), 2.32 (dd, J=16.8, 8.9 Hz, 1H), 2.24-2.10 (m, 1H), 2.03 (dd, J=16.8, 6.5 Hz, 1H), 1.58 (s, 3H). MS (APCI+) m/z 636.9 (M+H)$^+$.

Example 232

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-oxopiperidin-4-yl)pyridine-3-carboxamide Example 232 was prepared according to the procedure used for the preparation of Example 227, substituting 4-aminopiperidin-2-one trifluoroacetate for 2-amino-acetamide hydrochloride, to provide the title compound (24.9 mg, 90.0% yield). $^1$H NMR (400 MHz, 90° C., DMSO-d$_6$: D$_2$O=9:1 (v/v)) δ 8.96 (d, J=2.2 Hz, 1H), 8.25 (dd, J=8.1, 2.3 Hz, 1H), 7.67 (d, J=8.1 Hz, 1H), 7.35 (s, 1H), 7.00 (dd, J=8.6, 1.0 Hz, 1H), 6.86 (s, 1H), 6.54 (dd, J=8.5, 2.5 Hz, 1H), 6.47 (d, J=2.6 Hz, 1H), 5.38-5.27 (m, 2H), 4.99 (d, J=9.1 Hz, 1H), 4.34 (d, J=9.2 Hz, 1H), 4.32-4.19 (m, 1H), 3.74 (s, 3H), 3.29-3.17 (m, 2H), 2.62-2.53 (m, 1H), 2.45-2.37 (m, 1H), 2.33 (dd, J=17.3, 9.0 Hz, 1H), 2.23-2.09 (m, 1H), 2.09-1.97 (m, 1H), 1.88-1.74 (m, 1H), 1.58 (s, 3H). MS (APCI+) m/z 637.0 (M+H)$^+$.

Example 233

(7R)-2,2-difluoro-N-{(2R,4R)-7-methoxy-2-[5-(4-sulfamoylpiperazine-1-carbonyl)pyridin-2-yl]-3,4-dihydro-2H-1-benzopyran-4-yl}-7-methyl-6,7-dihydro-2H-furo[2,3-f][1,3]benzodioxole-7-carboxamide Example 233 was prepared according to the procedure used for the preparation of Example 227, substituting piperazine-1-sulfonic acid amide for 2-amino-acetamide hydrochloride, to provide the title compound (19.1 mg, 64.4% yield). $^1$H NMR (400 MHz, 90° C., DMSO-d$_6$:D$_2$O=9:1 (v/v)) δ 8.61 (dd, J=2.3, 0.8 Hz, 1H), 7.92 (dd, J=8.1, 2.2 Hz, 1H), 7.68 (d, J=7.7 Hz, 1H), 7.36 (s, 1H), 7.01 (dd, J=8.5, 1.0 Hz, 1H), 6.87 (s, 1H), 6.54 (dd, J=8.6, 2.6 Hz, 1H), 6.46 (d, J=2.5 Hz, 1H), 5.37-5.27 (m, 2H), 5.00 (d, J=9.1 Hz, 1H), 4.34 (d, J=9.1 Hz, 1H), 3.74 (s, 3H), 3.62 (t, J=5.0 Hz, 4H), 3.10 (t, J=5.2 Hz, 4H), 2.46-2.36 (m, 1H), 2.25-2.11 (m, 1H), 1.59 (s, 3H). MS (APCI+) m/z 688.0 (M+H)$^+$.

Example 234

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)-N-methylpyridine-3-carboxamide Example 234 was prepared according to the procedure used for the preparation of Example 227, substituting 2-methylaminoethanol for 2-amino-acetamide hydrochloride, to provide the title compound (14.7 mg, 55.8% yield). $^1$H NMR (400 MHz, 90° C., DMSO-d$_6$:D$_2$O=9:1 (v/v)) δ 8.59 (d, J=2.1 Hz, 1H), 7.91 (dd, J=8.0, 2.2 Hz, 1H), 7.65 (d, J=8.1 Hz, 1H), 7.36 (s, 1H), 7.05-6.97 (m, 1H), 6.87 (s, 1H), 6.53 (dd, J=8.6, 2.5 Hz, 1H), 6.46 (d, J=2.5 Hz, 1H), 5.36-5.27 (m, 2H), 5.00 (d, J=9.0 Hz, 1H), 4.35 (d, J=8.9 Hz, 1H), 3.73 (s, 3H), 3.63-3.58 (m, 2H), 3.49-3.40 (m, 2H), 3.02 (s, 3H), 2.46-2.36 (m, 1H), 2.29-2.12 (m, 1H), 1.59 (s, 3H). MS (APCI+) m/z 597.9 (M+H)$^+$.

Example 235

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-ethyl-N-(2-hydroxyethyl)pyridine-3-carboxamide Example 235 was prepared according to the procedure used for the preparation of Example 227, substituting 2-ethylaminoethanol for 2-amino-acetamide hydrochloride, to provide the title compound (15.2 mg, 56.6% yield). $^1$H NMR (400 MHz, 90° C., DMSO-d$_6$:D$_2$O=9:1 (v/v)) δ 8.57 (d, J=2.1 Hz, 1H), 7.89 (dd, J=8.0, 2.2 Hz, 1H), 7.65 (d, J=8.0 Hz, 1H), 7.36 (s, 1H), 7.00 (dd, J=8.6, 1.0 Hz, 1H), 6.87 (s, 1H), 6.53 (dd, J=8.6, 2.6 Hz, 1H), 6.46 (d, J=2.6 Hz, 1H), 5.36-5.27 (m, 2H), 5.00 (d, J=9.1 Hz, 1H), 4.35 (d, J=9.1 Hz, 1H), 3.73 (s, 3H), 3.62-3.55 (m, 2H), 3.49-3.36 (m, 4H), 2.46-2.35 (m, 1H), 2.25-2.11 (m, 1H), 1.59 (s, 3H), 1.14 (t, J=7.1 Hz, 3H). MS (APCI+) m/z 611.9 (M+H)$^+$.

Example 236

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N,N-bis(2-hydroxyethyl)pyridine-3-carboxamide Example 236 was prepared according to the procedure used for the preparation of Example 227, substituting 2-(2-hydroxy-ethylamino)-ethanol for 2-amino-acetamide hydrochloride, to provide the title compound (21.0 mg, 76.5% yield). $^1$H NMR (400 MHz, 90° C., DMSO-d$_6$:D$_2$O=9:1 (v/v)) δ 8.59 (d, J=2.1 Hz, 1H), 7.91 (dd, J=8.0, 2.2 Hz, 1H), 7.64 (d, J=8.0 Hz, 1H), 7.37 (s, 1H), 7.00 (dd, J=8.6, 1.0 Hz, 1H), 6.87 (s, 1H), 6.53 (dd, J=8.6, 2.6 Hz, 1H), 6.46 (d, J=2.6 Hz, 1H), 5.36-5.27 (m, 2H), 5.00 (d, J=9.1 Hz, 1H), 4.35 (d, J=9.1 Hz, 1H), 3.73 (s, 3H), 3.63-3.58 (m, 4H), 3.54-3.45 (m, 4H), 2.46-2.35 (m, 1H), 2.25-2.11 (m, 1H), 1.59 (s, 3H). MS (APCI+) m/z 628.0 (M+H)$^+$.

Example 237

(7R)-2,2-difluoro-N-[(2R,4R)-2-{5-[2-(hydroxymethyl)morpholine-4-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide Example 237 was prepared according to the procedure used for the preparation of Example 227, substituting morpholin-2-yl-methanol hydrochloride for 2-amino-acetamide hydrochloride, to provide the title compound (3.8 mg, 13.6% yield). $^1$H NMR (400 MHz, 90° C., DMSO-d$_6$:D$_2$O=9:1 (v/v)) δ 8.60 (d, J=2.1 Hz, 1H), 7.92 (dd, J=8.0, 2.2 Hz, 1H), 7.67 (d, J=8.1 Hz, 1H), 7.36 (s, 1H), 7.00 (d, J=8.5 Hz, 1H), 6.87 (s, 1H), 6.54 (dd, J=8.6, 2.7 Hz, 1H), 6.46 (d, J=2.6 Hz, 1H), 5.40-5.24 (m, 2H), 5.00 (d, J=9.1 Hz, 1H), 4.34 (d, J=9.1 Hz, 1H), 3.88 (d, J=11.6 Hz, 3H), 3.73 (s, 4H), 3.54-3.37 (m, 3H), 3.23-2.91 (m, 2H), 2.45-2.33 (m, 1H), 2.26-2.10 (m, 1H), 1.58 (s, 3H). MS (APCI+) m/z 640.1 (M+H)$^+$.

Example 238

(7R)-2,2-difluoro-N-[(2R,4R)-2-{5-[3-hydroxy-3-(2-hydroxyethyl)pyrrolidine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide Example 238 was prepared according to the procedure used for the preparation of Example 227, substituting 3-(2-hydroxyethyl)pyrrolidin-3-ol trifluoroacetate for 2-amino-acetamide hydrochloride, to provide the title compound (7.4 mg, 26.1% yield). $^1$H NMR (400 MHz, 90° C., DMSO-d$_6$:D$_2$O=9:1 (v/v)) δ 8.67 (d, J=2.2 Hz, 1H), 7.99 (d, J=8.5 Hz, 1H), 7.66 (d, J=8.1 Hz, 1H), 7.36 (s, 1H), 7.00 (dd, J=8.6, 1.0 Hz, 1H), 6.87 (s, 1H), 6.54 (dd, J=8.6, 2.5 Hz, 1H), 6.46 (d, J=2.6 Hz, 1H), 5.36-5.27 (m, 2H), 5.00 (d, J=9.0 Hz, 1H), 4.34 (d, J=9.1 Hz, 1H), 3.74 (s, 3H), 3.70-3.41 (m, 6H), 2.46-2.36 (m, 1H), 2.25-2.11 (m, 1H), 1.91 (t, J=7.5 Hz, 2H), 1.82-1.77 (m, 2H), 1.58 (s, 3H). MS (APCI+) m/z 654.0 (M+H)$^+$.

Example 239

(7R)-2,2-difluoro-N-[(2R,4R)-2-{5-[3-hydroxy-3-(2-hydroxyethyl)azetidine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide Example 239 was prepared according to the procedure used for the preparation of Example 227, substituting 3-(2-hydroxyethyl)azetidin-3-ol trifluoroacetate for 2-amino-acetamide hydrochloride, to provide the title compound (1.6 mg, 5.7% yield). $^1$H NMR (400 MHz, 90° C., DMSO-$d_6$:D$_2$O=9:1 (v/v)) δ 8.77 (s, 1H), 8.19-7.97 (m, 1H), 7.67 (d, J=8.1 Hz, 1H), 7.36 (s, 1H), 7.00 (d, J=8.6 Hz, 1H), 6.87 (s, 1H), 6.54 (dd, J=8.6, 2.6 Hz, 1H), 6.46 (d, J=2.6 Hz, 1H), 5.33 (d, J=11.2 Hz, 2H), 4.99 (d, J=9.2 Hz, 1H), 4.34 (d, J=9.0 Hz, 1H), 4.27-3.91 (m, 4H), 3.74 (d, J=0.9 Hz, 3H), 3.62 (t, J=6.4 Hz, 2H), 2.47-2.32 (m, 1H), 2.27-2.10 (m, 1H), 1.91 (t, J=6.4 Hz, 2H), 1.58 (s, 3H). MS (APCI+) m/z 640.1 (M+H)$^+$.

Example 240

(7R)-2,2-difluoro-N-[(2R,4R)-2-{5-[3-(hydroxymethyl)morpholine-4-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide Example 240 was prepared according to the procedure used for the preparation of Example 227, substituting morpholin-3-ylmethanol for 2-amino-acetamide hydrochloride and purified using Prep LC/MS Method AA7, to provide the title compound (17 mg, 71.8% yield). $^1$H NMR (400 MHz, 90° C., DMSO-$d_6$:D$_2$O=9:1 (v/v)) δ 8.61 (d, J=2.0 Hz, 1H), 7.92 (dd, J=8.1, 2.2 Hz, 1H), 7.65 (d, J=8.0 Hz, 1H), 7.36 (s, 1H), 7.00 (d, J=8.5 Hz, 1H), 6.87 (s, 1H), 6.53 (dd, J=8.6, 2.6 Hz, 1H), 6.46 (d, J=2.5 Hz, 1H), 5.36-5.27 (m, 2H), 5.00 (d, J=9.1 Hz, 1H), 4.34 (d, J=9.1 Hz, 1H), 3.77-3.61 (m, 9H), 3.56 (dd, J=11.9, 3.3 Hz, 1H), 3.52-3.41 (m, 1H), 3.24-3.19 (m, 1H), 2.46-2.35 (m, 1H), 2.25-2.11 (m, 1H), 1.58 (s, 3H). MS (APCI+) m/z 640.1 (M+H)$^+$.

Example 241

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxypropyl)pyridine-3-carboxamide Example 241 was prepared according to the procedure used for the preparation of Example 227, substituting 1-aminopropan-2-ol for 2-amino-acetamide hydrochloride and purified using Prep LC/MS Method AA7, to provide the title compound (16.2 mg, 73.3% yield). $^1$H NMR (400 MHz, 90° C., DMSO-$d_6$:D$_2$O=9:1 (v/v)) δ 8.97 (d, J=2.2 Hz, 1H), 8.25 (dd, J=8.2, 2.4 Hz, 1H), 7.67 (d, J=8.2 Hz, 1H), 7.35 (s, 1H), 7.00 (d, J=8.6 Hz, 1H), 6.86 (s, 1H), 6.53 (dd, J=8.5, 2.6 Hz, 1H), 6.47 (d, J=2.5 Hz, 1H), 5.38-5.27 (m, 2H), 4.99 (d, J=9.1 Hz, 1H), 4.34 (d, J=9.1 Hz, 1H), 3.86 (h, J=6.3 Hz, 1H), 3.74 (s, 3H), 3.37-3.21 (m, 2H), 2.46-2.35 (m, 1H), 2.24-2.10 (m, 1H), 1.58 (s, 3H), 1.12 (d, J=6.3 Hz, 3H). MS (APCI+) m/z 597.9 (M+H)$^+$.

Example 242

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1-hydroxypropan-2-yl)pyridine-3-carboxamide Example 242 was prepared according to the procedure used for the preparation of Example 227, substituting 2-aminopropan-1-ol for 2-amino-acetamide hydrochloride and purified using Prep LC/MS Method AA7, to provide the title compound (17.1 mg, 77.3% yield). $^1$H NMR (400 MHz, 90° C., DMSO-$d_6$:D$_2$O=9:1 (v/v)) δ 8.96 (d, J=2.2 Hz, 1H), 8.25 (dd, J=8.2, 2.3 Hz, 1H), 7.66 (d, J=8.2 Hz, 1H), 7.36 (s, 1H), 7.00 (dd, J=8.6, 1.1 Hz, 1H), 6.87 (s, 1H), 6.54 (dd, J=8.5, 2.6 Hz, 1H), 6.47 (d, J=2.5 Hz, 1H), 5.38-5.27 (m, 2H), 4.99 (d, J=9.1 Hz, 1H), 4.34 (d, J=9.0 Hz, 1H), 4.11-4.00 (m, 1H), 3.74 (s, 3H), 3.57-3.40 (m, 2H), 2.45-2.35 (m, 1H), 2.23-2.09 (m, 1H), 1.58 (s, 3H), 1.19 (d, J=6.9 Hz, 3H). MS (APCI+) m/z 597.9 (M+H)$^+$.

Example 243

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2,3-dihydroxypropyl)pyridine-3-carboxamide Example 243 was prepared according to the procedure used for the preparation of Example 227, substituting 3-aminopropane-1,2-diol for 2-amino-acetamide hydrochloride and purified using Prep LC/MS Method AA7, to provide the title compound (19.3 mg, 85.0% yield). $^1$H NMR (400 MHz, 90° C., DMSO-$d_6$:D$_2$O=9:1 (v/v)) δ 8.97 (d, J=2.2 Hz, 1H), 8.25 (dd, J=8.2, 2.3 Hz, 1H), 7.67 (d, J=8.1 Hz, 1H), 7.36 (s, 1H), 7.00 (d, J=8.6 Hz, 1H), 6.87 (s, 1H), 6.54 (dd, J=8.5, 2.6 Hz, 1H), 6.47 (d, J=2.6 Hz, 1H), 5.39-5.25 (m, 2H), 4.99 (d, J=9.1 Hz, 1H), 4.34 (d, J=9.0 Hz, 1H), 3.79-3.66 (m, 4H), 3.54-3.38 (m, 3H), 3.34-3.24 (m, 1H), 2.45-2.32 (m, 1H), 2.24-2.07 (m, 1H), 1.58 (s, 3H). MS (APCI+) m/z 613.9 (M+H)$^+$.

Example 244

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)pyridine-3-carboxamide Example 244 was prepared according to the procedure used for the preparation of Example 227, substituting 2-aminoethanol for 2-amino-acetamide hydrochloride and purified using Prep LC/MS Method AA7, to provide the title compound (15.6 mg, 72.3% yield). $^1$H NMR (400 MHz, 90° C., DMSO-$d_6$:D$_2$O=9:1 (v/v)) δ 8.97 (d, J=2.2 Hz, 1H), 8.25 (dd, J=8.2, 2.3 Hz, 1H), 7.67 (d, J=8.2 Hz, 1H), 7.35 (s, 1H), 7.00 (d, J=8.6 Hz, 1H), 6.86 (s, 1H), 6.53 (dd, J=8.5, 2.6 Hz, 1H), 6.47 (d, J=2.5 Hz, 1H), 5.38-5.27 (m, 2H), 4.99 (d, J=9.1 Hz, 1H), 4.34 (d, J=9.1 Hz, 1H), 3.74 (s, 3H), 3.59 (t, J=6.0 Hz, 2H), 3.41 (t, J=6.0 Hz, 2H), 2.46-2.35 (m, 1H), 2.24-2.10 (m, 1H), 1.58 (s, 3H). MS (APCI+) m/z 583.9 (M+H)$^+$.

Example 245

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[(trans-3-hydroxycyclobutyl)methyl]pyridine-3-carboxamide Example 245 was prepared according to the procedure used for the preparation of Example 227, substituting trans-3-(aminomethyl)cyclobutanol for 2-amino-acetamide hydrochloride and purified using Prep LC/MS Method AA7, to provide the title compound (18.7 mg, 81.1% yield). $^1$H NMR (400 MHz, 90° C., DMSO-$d_6$:$D_2O$=9:1 (v/v)) δ 8.95 (d, J=2.1 Hz, 1H), 8.23 (dd, J=8.1, 2.3 Hz, 1H), 7.66 (d, J=8.2 Hz, 1H), 7.35 (s, 1H), 7.00 (d, J=8.5 Hz, 1H), 6.86 (s, 1H), 6.53 (dd, J=8.6, 2.5 Hz, 1H), 6.47 (d, J=2.5 Hz, 1H), 5.38-5.26 (m, 2H), 4.99 (d, J=9.2 Hz, 1H), 4.34 (d, J=9.1 Hz, 1H), 4.25 (p, J=6.7 Hz, 1H), 3.74 (s, 3H), 3.36 (d, J=7.6 Hz, 2H), 2.48-2.35 (m, 2H), 2.24-2.11 (m, 1H), 2.11-2.02 (m, 2H), 2.02-1.89 (m, 2H), 1.58 (s, 3H). MS (APCI+) m/z 624.0 $(M+H)^+$.

Example 246

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1-hydroxy-3-methoxypropan-2-yl)pyridine-3-carboxamide Example 246 was prepared according to the procedure used for the preparation of Example 227, substituting 2-amino-3-methoxy-propan-1-ol for 2-amino-acetamide hydrochloride and purified using Prep LC/MS Method AA7, to provide the title compound (13.3 mg, 57.3% yield). $^1$H NMR (400 MHz, 90° C., DMSO-$d_6$:$D_2O$=9:1 (v/v)) δ 8.97 (d, J=2.2 Hz, 1H), 8.25 (dd, J=8.2, 2.3 Hz, 1H), 7.67 (d, J=8.1 Hz, 1H), 7.36 (s, 1H), 7.00 (dd, J=8.5, 1.0 Hz, 1H), 6.87 (s, 1H), 6.54 (dd, J=8.6, 2.5 Hz, 1H), 6.47 (d, J=2.5 Hz, 1H), 5.38-5.27 (m, 2H), 4.99 (d, J=9.1 Hz, 1H), 4.34 (d, J=9.1 Hz, 1H), 4.18 (p, J=5.9 Hz, 1H), 3.74 (s, 3H), 3.58 (d, J=5.7 Hz, 2H), 3.53 (d, J=6.0 Hz, 2H), 3.31 (s, 3H), 2.45-2.35 (m, 1H), 2.23-2.09 (m, 1H), 1.58 (s, 3H). MS (APCI+) m/z 628.0 $(M+H)^+$.

Example 247

(7R)—N-[(2R,4R)-2-(1-{[(4S)-2,2-dimethyl-1,3-dioxolan-4-yl]methyl}piperidin-4-yl)-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide A solution of Example 182 (60.4 mg, 0.109 mmol) and (R)-(−)-2,2-dimethyl-1,3-dioxolan-4-ylmethyl p-toluenesulfonate (CAS #23788-74-1, 62.2 mg, 0.217 mmol) in N,N-dimethylformamide (0.3 mL) was treated with triethylamine (45.4 μL, 0.326 mmol), heated at 120° C. for 90 minutes, cooled, and partitioned between methyl tert-butyl ether (about 25 mL) and water. An emulsion was present which settled after several minutes. The layers were separated and the organic layer was washed with brine (another emulsion), diluted with heptanes (about 20 mL) (emulsion mostly settled), dried (MgSO$_4$), filtered, and concentrated. The residue was chromatographed on silica gel eluting with a gradient of 0 to 100% [22:1:1 ethyl acetate:HCOOH:$H_2O$] in [200:1:1 ethyl acetate:HCOOH:$H_2O$]. The fractions containing the product were combined, and washed with a mixture of saturated aqueous NaHCO$_3$ solution (about 40 mL) and 5 g of solid NaOH. The organic layer was dried (MgSO$_4$), filtered, and concentrated to provide the title compound (51 mg, 0.076 mmol, 70.1% yield). $^1$H NMR (400 MHz, CDCl$_3$) δ 6.91 (s, 1H), 6.86 (d, J=8.6 Hz, 1H), 6.73-6.69 (m, 1H), 6.67-6.65 (m, 1H), 6.65 (s, 1H), 5.64 (d, J=8.8 Hz, 1H), 5.31-5.22 (m, 1H), 4.90 (d, J=9.4 Hz, 1H), 4.59 (bs, 1H), 4.35 (d, J=9.4 Hz, 1H), 4.18-4.13 (m, 1H), 4.01 (dd, J=11.8, 6.3 Hz, 1H), 3.64-3.54 (m, 1H), 3.28 (bs, 1H), 2.90 (bs, 1H), 2.72 (bs, 1H), 2.44 (bs, 2H), 2.27 (dd, J=12.3, 5.8 Hz, 1H), 2.04-1.70 (m, 4H), 1.67 (s, 3H), 1.51 (q, J=11.8 Hz, 1H), 1.41 (s, 3H), 1.36 (s, 3H); LC/MS (ESI+) m/z 671.5 $(M+H)^+$.

Example 248

(7R)—N-[(2R,4R)-2-{5-[(3R,4R)-3,4-dihydroxypyrrolidine-1-carbonyl]pyridin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide Example 248 was prepared according to the procedure used for the preparation of Example 227, substituting (3R,4R)-pyrrolidine-3,4-diol for 2-amino-acetamide hydrochloride, to provide the title compound (29.6 mg, >99% yield). $^1$H NMR (400 MHz, 120° C., DMSO-$d_6$:$D_2O$=9:1 (v/v)) δ 8.64 (d, J=2.2 Hz, 1H), 7.95 (dd, J=8.1, 2.2 Hz, 1H), 7.63 (d, J=8.1 Hz, 1H), 7.30 (s, 1H), 6.97 (dd, J=8.6, 1.0 Hz, 1H), 6.80 (s, 1H), 6.50 (dd, J=8.5, 2.6 Hz, 1H), 6.44 (d, J=2.5 Hz, 1H), 5.33-5.24 (m, 2H), 4.96 (d, J=9.1 Hz, 1H), 4.31 (d, J=9.1 Hz, 1H), 4.03-3.97 (m, 2H), 3.74-3.69 (m, 5H), 3.45-3.22 (m, 2H), 2.47-2.37 (m, 1H), 2.24-2.10 (m, 1H), 1.56 (s, 3H). MS (APCI+) m/z 625.7 $(M+H)^+$.

Example 249

(7R)—N-[(2R,4R)-2-{5-[(3S,4S)-3,4-dihydroxypyrrolidine-1-carbonyl]pyridin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide Example 249 was prepared according to the procedure used for the preparation of Example 227, substituting (3S,4S)-pyrrolidine-3,4-diol for 2-amino-acetamide hydrochloride, to provide the title compound (14.8 mg, 54.1% yield). $^1$H NMR (400 MHz, 120° C., DMSO-$d_6$:$D_2O$=9:1 (v/v)) δ 8.64 (d, J=2.2 Hz, 1H), 7.95 (dd, J=8.0, 2.2 Hz, 1H), 7.63 (d, J=8.0 Hz, 1H), 7.30 (s, 1H), 6.97 (dd, J=8.5, 1.1 Hz, 1H), 6.81 (s, 1H), 6.50 (dd, J=8.5, 2.6 Hz, 1H), 6.44 (d, J=2.6 Hz, 1H), 5.33-5.24 (m, 2H), 4.96 (d, J=9.2 Hz, 1H), 4.31 (d, J=9.1 Hz, 1H), 4.02-3.97 (m, 2H), 3.76-3.67 (m, 5H), 3.33 (s, 2H), 2.47-2.37 (m, 1H), 2.24-2.10 (m, 1H), 1.56 (s, 3H). MS (APCI+) m/z 625.8 $(M+H)^+$.

Example 250

(7R)—N-[(2R,4R)-2-{5-[(3R,4R)-3,4-dihydroxypyrrolidin-1-yl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide A mixture of Example 193D (26 mg, 0.049 mmol) and (3R,4R)-pyrrolidine-3,4-diol (CAS #186393-31-7, 15.12 mg, 0.147 mmol) was treated with 1,8-diazabicyclo[5.4.0]undec-7-ene (6 drops), heated under $N_2$ at 80° C. for 1 hour and partitioned between ethyl acetate (25 mL) and water (10 mL). The layers were separated and the ethyl acetate layer was washed with 0.2 M HCl (5 mL), washed with brine, dried ($MgSO_4$), filtered, and concentrated. The residue was chromatographed on silica gel eluting with a gradient of 0 to 100% [3:1 ethyl acetate:ethanol] in ethyl acetate to provide the title compound (23 mg, 0.038 mmol, 79% yield). $^1$H NMR (501 MHz, $CDCl_3$) δ 8.15 (d, J=1.2 Hz, 1H), 7.78 (d, J=1.3 Hz, 1H), 6.87 (s, 1H), 6.62 (s, 1H), 6.49 (dd, J=8.6, 2.6 Hz, 1H), 6.41 (d, J=2.5 Hz, 1H), 5.86 (d, J=8.7 Hz, 1H), 5.36 (td, J=9.1, 7.1 Hz, 1H), 5.20 (dd, J=9.8, 2.5 Hz, 1H), 4.81 (d, J=9.3 Hz, 1H), 4.38 (bs, 2H), 4.31 (d, J=9.3 Hz, 1H), 3.82 (dd, J=11.6, 4.0 Hz, 2H), 3.74 (s, 3H), 3.54 (d, J=12.0 Hz, 2H), 2.54 (bd, J=2.3 Hz, 1H), 2.17 (s, 2H), 2.11 (dt, J=13.5, 9.7 Hz, 1H), 1.63 (s, 3H); LC/MS (ESI+) m/z 599.6 $(M+H)^+$.

Example 251

(7R)—N-[(2R,4R)-2-{6-[(3R,4R)-3,4-dihydroxypyrrolidin-1-yl]pyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide A mixture of Example 195D (21.3 mg, 0.040 mmol) and (3R,4R)-pyrrolidine-3,4-diol (CAS #186393-31-7, 12.39 mg, 0.120 mmol) was treated with 1,8-diazabicyclo[5.4.0]undec-7-ene (6 drops), heated under $N_2$ at 80° C. for 1 hour, and partitioned between ethyl acetate (25 mL) and water (10 mL). The layers were separated and the ethyl acetate layer was washed with brine, dried ($MgSO_4$), filtered, and concentrated. The material was treated with $CH_2Cl_2$ (about 1 mL) and a solid started to precipitate. More $CH_2Cl_2$ and some heptanes were added. The solid was collected by filtration, washed with 1:1 $CH_2Cl_2$:heptanes and dried under vacuum while heated at 50° C. for 30 minutes to provide the title compound as a 9:1 mixture of cis:trans isomers. $^1$H NMR (400 MHz, DMSO-$d_6$) δ 8.08 (d, J=8.7 Hz, 1H), 7.49 (s, 1H), 7.45 (d, J=9.3 Hz, 1H), 7.03 (d, J=8.6 Hz, 1H), 7.00 (s, 1H), 6.92 (d, J=9.4 Hz, 1H), 6.53 (dd, J=8.6, 2.6 Hz, 1H), 6.41 (d, J=2.5 Hz, 1H), 5.40-5.29 (m, 2H), 5.17 (d, J=2.9 Hz, 2H), 5.05 (d, J=9.0 Hz, 1H), 4.34 (d, J=9.0 Hz, 1H), 4.08 (bs, 2H), 3.70 (s, 3H), 3.61 (dd, J=11.2, 3.6 Hz, 2H), 3.40 (d, J=10.7 Hz, 2H), 2.28-2.21 (m, 2H), 1.59 (s, 3H); LC/MS (ESI+) m/z 600 $(M+H)^+$.

Example 252

(7R)—N-[(4R)-2-{6-[(2S)-2,3-dihydroxypropoxy]pyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide

Example 252A (7R)—N-[(2S,4R)-2-(6-{[(4R)-2,2-dimethyl-1,3-dioxolan-4-yl]methoxy}pyridazin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide and (7R)—N-[(2R,4R)-2-(6-{[(4R)-2,2-dimethyl-1,3-dioxolan-4-yl]methoxy}pyridazin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide A mixture of Example 195D (22.4 mg, 0.042 mmol) and (R)-(−)-2,2-dimethyl-1,3-dioxolane-4-methanol (CAS #14347-78-5, 11.13 mg, 0.084 mmol) in N,N-dimethylformamide (0.3 mL) under $N_2$ was treated with a 60% dispersion of sodium hydride in mineral oil (2.53 mg, 0.063 mmol) and stirred at room temperature for 3 hours. The mixture was partitioned between ethyl acetate and saturated aqueous $NaHCO_3$ solution. The ethyl acetate layer was washed with brine, dried ($MgSO_4$), filtered, concentrated and chromatographed on silica gel eluting with a gradient of 15 to 100% ethyl acetate in heptanes to provide the title compound (2:3 ratio of the trans isomer to cis isomer). $^1$H NMR (500 MHz, $CDCl_3$) δ 7.63 (d, J=9.1 Hz, 0.4H), 7.62 (d, J=9.1 Hz, 0.6H), 7.10 (d, J=9.1 Hz, 0.4H), 7.06 (d, J=9.1 Hz, 0.6H), 6.98 (d, J=8.6 Hz, 0.4H), 6.98 (s, 0.6H), 6.94 (dd, J=8.6, 0.8 Hz, 0.6H), 6.86 (s, 0.4H), 6.61 (s, 0.6H), 6.61 (s, 0.4H), 6.54 (dd, J=8.6, 2.6 Hz, 0.4H), 6.51 (dd, J=8.6, 2.6 Hz, 0.6H), 6.46 (d, J=2.5 Hz, 0.4H), 6.42 (d, J=2.5 Hz, 0.6H), 6.07 (d, J=8.7 Hz, 0.6H), 5.88 (d, J=6.7 Hz, 0.4H), 5.46 (dd, J=9.4, 2.8 Hz, 0.6H), 5.43-5.37 (m, 0.6H), 5.20 (dd, J=11.3, 2.3 Hz, 0.4H), 5.05-5.01 (m, 0.4H), 4.88 (d, J=9.2 Hz, 0.6H), 4.85 (d, J=9.3 Hz, 0.4H), 4.66 (dd, J=4.0, 1.4 Hz, 0.4H), 4.64 (dd, J=4.0, 1.2 Hz, 0.6H), 4.61-4.49 (m, 20H), 4.35 (d, J=9.3 Hz, 0.4H), 4.31 (d, J=9.2 Hz, 0.6H), 4.20-4.16 (m, 1H), 3.87-3.83 (m, 1H), 3.77 (s, 1.2H), 3.76 (s, 1.8H), 2.79 (ddd, J=13.7, 6.5, 2.9 Hz, 0.6H), 2.51 (dt, J=14.2, 2.7 Hz, 0.4H), 2.20 (ddd, J=14.2, 11.4, 4.7 Hz, 0.4H), 2.12 (dt, J=13.7, 9.2 Hz, 0.6H), 1.64 (s, 1.8H), 1.61 (s, 1.2H), 1.48 (s, 1.2H), 1.47 (s, 1.8H), 1.41 (s, 1.2H), 1.41-1.40 (m, 1.8H); LC/MS (ESI+) m/z 628.6 $(M+H)^+$.

Example 252B (7R)—N-[(4R)-2-{6-[(2S)-2,3-dihydroxypropoxy]pyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 252A (16 mg) in methanol (1 mL) was treated with 3 M HCl (0.5 mL), stirred at room temperature for 45 minutes and partitioned between 1 M NaOH (about 10 mL) and $CH_2Cl_2$ (25 mL). The layers were separated and the aqueous layer was extracted with $CH_2Cl_2$ (15 mL). The combined $CH_2Cl_2$ layers were dried ($MgSO_4$), filtered, and concentrated. The residue was chromatographed on silica gel eluting with a gradient of 15 to 100% [3:1 ethyl acetate:ethanol] in heptanes to provide the title compound. $^1$H NMR indicates a 2:3 ratio of trans:cis. $^1$H NMR (500 MHz, $CDCl_3$) δ 7.66 (d, J=9.1 Hz, 0.4H), 7.65 (d, J=9.1 Hz, 0.6H), 7.10 (d, J=9.1 Hz, 0.4H), 7.07 (d, J=9.1 Hz, 0.6H), 6.98 (d, J=8.7 Hz, 0.4H), 6.95 (s, 0.6H), 6.92 (dd, J=8.6, 0.8 Hz, 0.6H), 6.87 (s, 0.4H), 6.61 (s, 0.4H), 6.60 (s, 0.6H), 6.54 (dd, J=8.6, 2.6 Hz, 0.4H), 6.51 (dd, J=8.6, 2.6 Hz, 0.6H), 6.45 (d, J=2.5 Hz, 0.4H), 6.42 (d, J=2.5 Hz, 0.6H), 5.99 (d, J=8.7 Hz, 0.6H), 5.92 (d, J=6.8 Hz, 0.4H), 5.44 (dd, J=9.7, 2.6 Hz, 0.6H), 5.43-5.38 (m, 0.6H), 5.20 (dd, J=11.3, 2.3 Hz, 0.4H), 5.06-5.01 (m, 0.4H), 4.86 (dd, J=9.3, 2.3 Hz, 1H), 4.71-4.58 (m, 20H), 4.36 (d, J=9.3 Hz, 0.4H), 4.32 (d, J=9.3 Hz, 0.6H), 4.15 (bs, 1H), 3.77 (s, 1.2H), 3.76 (s, 1.8H), 3.81-3.74 (m, 1H), 3.74-3.67 (m, 1H), 3.38 (s, 0.4H), 3.32 (s, 0.6H), 2.79 (ddd, J=13.6, 6.4, 2.8 Hz, 6H), 2.50 (dt, J=14.2, 2.7 Hz, 0.4H), 2.46-2.42 (m, 1H), 2.21 (ddd, J=14.3, 11.4, 4.8 Hz, 0.4H), 2.11-2.05 (m, 0.6H), 1.64 (s, 1.8H), 1.62 (s, 1.2H); LC/MS (ESI+) m/z 588.6 $(M+H)^+$.

Example 253

(7R)—N-[(2R,4R)-2-{trans-4-[ethyl(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide In a 4 mL vial was added Example 150 (22 mg, 0.036 mmol), followed by 2-(1H-7-azabenzotriazol-1-yl)-1,1,3,3-tetramethyl uronium hexafluorophosphate methanaminium (16 mg, 0.044 mmol), diisopropylethyl amine (20 µL, 0.11 mmol) and 2-(ethylamino)ethanol (5 mg, 0.06 mmol) in 1 mL of dimethyl acetamide. This mixture was stirred at room temperature for 1 hour, and concentrated in vacuo. The residue was dissolved in DMSO, and purified by reverse phase HPLC (TFA method). Samples were purified by preparative HPLC on a Phenomenex Luna C8(2) 5 µm 100 Å a AXIA column (30 mm×150 mm). A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to provide the title compound. $^1$H NMR (400 MHz, DMSO-$d_6$) δ 7.33 (s, 1H), 7.08 (dd, J=8.6, 1.1 Hz, 1H), 6.82 (d, J=1.1 Hz, 1H), 6.78-6.70 (m, 1H), 6.65 (dd, J=2.4, 1.2 Hz, 1H), 5.18-5.08 (m, 1H), 4.98 (d, J=9.2 Hz, 1H), 4.33 (d, J=9.2 Hz, 1H), 4.00 (ddd, J=11.4, 5.4, 1.8 Hz, 1H), 3.51 (t, J=6.1 Hz, 2H), 3.35 (t, J=6.3 Hz, 4H), 2.07-1.76 (m, 7H), 1.76-1.68 (m, 8H), 1.58 (s, 4H), 1.45 (d, J=12.4 Hz, 2H), 1.25 (s, 2H), 1.17 (td, J=12.8, 3.5 Hz, 1H), 1.06 (t, J=6.9 Hz, 3H). MS (APCI$^+$) m/z 670.8 (M+H)$^+$.

Example 254

(7R)—N-[(2R,4R)-2-{trans-4-[bis(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide Example 254 was prepared according to the procedure used for the preparation of Example 253, substituting 2,2'-azanediyldiethanol for 2-(ethylamino)ethanol. $^1$H NMR (400 MHz, DMSO-$d_6$) δ 7.33 (s, 1H), 7.08 (dd, J=8.5, 1.1 Hz, 1H), 6.82 (s, 1H), 6.74 (ddd, J=8.5, 2.4, 1.2 Hz, 1H), 6.65 (dq, J=2.1, 1.1 Hz, 1H), 5.13 (ddd, J=11.5, 6.2, 1.1 Hz, 1H), 4.98 (d, J=9.2 Hz, 1H), 4.33 (d, J=9.2 Hz, 1H), 4.00 (ddd, J=11.5, 5.3, 1.9 Hz, 1H), 3.53 (t, J=6.0 Hz, 4H), 3.40 (t, J=6.0 Hz, 4H), 2.59 (ddd, J=11.6, 8.3, 3.4 Hz, 1H), 2.07-1.84 (m, 3H), 1.84-1.68 (m, 7H), 1.58 (s, 4H), 1.52-1.36 (m, 2H), 1.34-1.11 (m, 2H). MS (APCI$^+$) m/z 686.8 (M+H)$^+$.

Example 255

(7R)—N-[(2R,4R)-2-{trans-4-[(3R,4R)-3,4-dihydroxypyrrolidine-1-carbonyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide Example 255 was prepared according to the procedure used for the preparation of Example 253, substituting (3R,4R)-pyrrolidine-3,4-diol for 2-(ethylamino)ethanol. $^1$H NMR (400 MHz, DMSO-$d_6$) δ 7.33 (s, 1H), 7.08 (dd, J=8.5, 1.1 Hz, 1H), 6.82 (s, 1H), 6.78-6.70 (m, 1H), 6.65 (dd, J=2.4, 1.2 Hz, 1H), 5.13 (dd, J=11.5, 6.0 Hz, 1H), 4.98 (d, J=9.1 Hz, 1H), 4.33 (d, J=9.1 Hz, 1H), 4.05-3.96 (m, 2H), 3.56 (d, J=59.4 Hz, 2H), 3.30 (s, 2H), 3.06 (d, J=5.4 Hz, 19H), 2.39-2.28 (m, 1H), 2.07-1.70 (m, 8H), 1.58 (s, 4H), 1.42 (t, J=12.2 Hz, 2H), 1.33-1.10 (m, 2H). MS (APCI$^+$) m/z 684.7 (M+H)$^+$.

Example 256

(7R)—N-[(2R,4R)-2-{trans-4-[(3S,4S)-3,4-dihydroxypyrrolidine-1-carbonyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide Example 256 was prepared according to the procedure used for the preparation of Example 253, substituting (3S,4S)-pyrrolidine-3,4-diol for 2-(ethylamino)ethanol. $^1$H NMR (400 MHz, DMSO-$d_6$) δ 7.33 (s, 1H), 7.07 (dd, J=8.5, 1.1 Hz, 1H), 6.82 (s, 1H), 6.74 (dd, J=8.8, 2.0 Hz, 1H), 6.67-6.62 (m, 1H), 5.13 (dd, J=11.4, 6.1 Hz, 1H), 4.98 (d, J=9.2 Hz, 1H), 4.33 (d, J=9.2 Hz, 1H), 4.05-3.97 (m, 2H), 3.96 (s, 1H), 3.61 (s, 2H), 3.30 (s, 1H), 2.02 (ddd, J=13.0, 6.1, 1.9 Hz, 2H), 1.97-1.82 (m, 2H), 1.82-1.72 (m, 5H), 1.58 (s, 4H), 1.42 (qd, J=13.0, 3.5 Hz, 2H), 1.34-1.11 (m, 2H). MS (APCI$^+$) m/z 684.7 (M+H)$^+$.

Example 257

(7R)-2,2-difluoro-N-[(2R,4R)-2-{trans-4-[3-(hydroxymethyl)morpholine-4-carbonyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 257 was prepared according to the procedure used for the preparation of Example 253, substituting morpholin-3-ylmethanol for 2-(ethylamino)ethanol. $^1$H NMR (400 MHz, DMSO-$d_6$) δ 7.33 (s, 1H), 7.08 (dd, J=8.5, 1.2 Hz, 1H), 6.82 (s, 1H), 6.74 (ddt, J=8.5, 2.4, 1.1 Hz, 1H), 6.64 (dt, J=2.4, 1.2 Hz, 1H), 5.18-5.08 (m, 1H), 4.98 (d, J=9.1 Hz, 1H), 4.33 (d, J=9.2 Hz, 1H), 4.00 (ddd, J=11.5, 5.4, 1.9 Hz, 2H), 3.89 (d, J=11.7 Hz, 2H), 3.79 (dd, J=11.4, 3.8 Hz, 1H), 3.67 (dd, J=10.7, 7.8 Hz, 1H), 3.56-3.47 (m, 1H), 3.45-3.25 (m, 2H), 2.50 (d, J=1.9 Hz, 6H), 2.07-1.85 (m, 3H), 1.85-1.71 (m, 4H), 1.58 (s, 5H), 1.55-1.12 (m, 5H). MS (APCI$^+$) m/z 698.8 (M+H)$^+$.

Example 258

(7R)-2,2-difluoro-N-[(2R,4R)-2-{trans-4-[(2-hydroxypropyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 258 was prepared according to the procedure used for the preparation of Example 253, substituting 1-aminopropan-2-ol for 2-(ethylamino)ethanol. $^1$H NMR (400 MHz, DMSO-$d_6$) δ 7.32 (s, 1H), 7.07 (dd, J=8.6, 1.1 Hz, 1H), 6.82 (s, 1H), 6.78-6.70 (m, 1H), 6.64 (dd, J=2.3, 1.1 Hz, 1H), 5.13 (dd, J=11.2, 6.1 Hz, 1H), 4.98 (d, J=9.2 Hz, 1H), 4.33 (d, J=9.2 Hz, 1H), 3.99 (ddd, J=11.5, 5.5, 1.9 Hz, 1H), 3.75-3.62 (m, 1H), 3.01 (dd, J=13.3, 6.3 Hz, 10H), 2.11 (ddt, J=11.9, 7.2, 3.6 Hz, 1H), 2.05-1.87 (m, 2H), 1.87-1.79

(m, 3H), 1.79-1.71 (m, 1H), 1.58 (s, 4H), 1.39 (qt, J=13.0, 4.1 Hz, 2H), 1.29-1.07 (m, 2H), 1.03 (d, J=6.3 Hz, 3H). MS (APCI$^+$) m/z 656.9 (M+H)$^+$.

Example 259

(7R)-2,2-difluoro-N-[(2R,4R)-2-{trans-4-[(1-hydroxypropan-2-yl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 259 was prepared according to the procedure used for the preparation of Example 253, substituting 2-aminopropan-1-ol for 2-(ethylamino)ethanol. $^1$H NMR (400 MHz, DMSO-d$_6$) δ 7.33 (s, 1H), 7.07 (dd, J=8.6, 1.1 Hz, 1H), 6.82 (s, 1H), 6.74 (ddd, J=8.5, 2.5, 1.2 Hz, 1H), 6.64 (dd, J=2.4, 1.2 Hz, 1H), 5.18-5.08 (m, 1H), 4.98 (d, J=9.2 Hz, 1H), 4.33 (d, J=9.2 Hz, 1H), 3.99 (ddd, J=11.7, 5.5, 1.8 Hz, 1H), 3.76 (h, J=6.2 Hz, 1H), 3.41-3.25 (m, 2H), 2.13-1.92 (m, 3H), 1.92-1.71 (m, 4H), 1.58 (s, 4H), 1.46-1.31 (m, 2H), 1.27-1.10 (m, 2H), 1.03 (d, J=6.7 Hz, 3H). MS (APCI$^+$) m/z 656.9 (M+H)$^+$.

Example 260

(7R)—N-[(2R,4R)-2-{trans-4-[(2,3-dihydroxypropyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide Example 260 was prepared according to the procedure used for the preparation of Example 253, substituting 3-aminopropane-1,2-diol for 2-(ethylamino)ethanol. $^1$H NMR (400 MHz, DMSO-d$_6$) δ 7.32 (s, 1H), 7.07 (dd, J=8.6, 1.1 Hz, 1H), 6.82 (s, 1H), 6.74 (dd, J=8.6, 2.2 Hz, 1H), 6.64 (dd, J=2.4, 1.1 Hz, 1H), 5.13 (dd, J=11.5, 6.2 Hz, 1H), 4.98 (d, J=9.2 Hz, 1H), 4.33 (d, J=9.2 Hz, 1H), 3.99 (ddd, J=11.6, 5.6, 1.9 Hz, 1H), 3.54 (p, J=5.7 Hz, 1H), 3.34 (dd, J=5.5, 1.1 Hz, 2H), 3.21 (dd, J=13.5, 5.0 Hz, 1H), 2.17-2.03 (m, 1H), 2.03-1.97 (m, 1H), 1.97-1.83 (m, 3H), 1.82 (s, 2H), 1.78-1.71 (m, 1H), 1.58 (s, 4H), 1.39 (qt, J=12.7, 4.0 Hz, 2H), 1.29-1.07 (m, 2H). MS (APCI$^+$) m/z 672.8 (M+H)$^+$.

Example 261

(7R)-2,2-difluoro-N-[(2R,4R)-2-{trans-4-[(2-hydroxyethyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 261 was prepared according to the procedure used for the preparation of Example 253, substituting 2-aminoethanol for 2-(ethylamino)ethanol. $^1$H NMR (400 MHz, DMSO-d$_6$) δ 7.32 (s, 1H), 7.07 (dd, J=8.6, 1.1 Hz, 1H), 6.82 (s, 1H), 6.78-6.70 (m, 1H), 6.64 (dd, J=2.4, 1.1 Hz, 1H), 5.13 (dd, J=11.4, 6.1 Hz, 1H), 4.98 (d, J=9.2 Hz, 1H), 4.33 (d, J=9.1 Hz, 1H), 3.99 (ddd, J=11.7, 5.6, 1.8 Hz, 1H), 3.47-3.39 (m, 2H), 3.15 (t, J=6.0 Hz, 2H), 2.15-1.71 (m, 7H), 1.58 (s, 4H), 1.38 (dddd, J=16.8, 12.8, 8.6, 4.2 Hz, 2H), 1.18 (dtd, J=31.9, 12.5, 3.4 Hz, 2H). MS (APCI$^+$) m/z 642.9 (M+H)$^+$.

Example 262

(7R)-2,2-difluoro-N-[(2R,4R)-2-{trans-4-[(2-hydroxyphenyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 262 was prepared according to the procedure used for the preparation of Example 253, substituting 2-aminophenol for 2-(ethylamino)ethanol. $^1$H NMR (400 MHz, DMSO-d$_6$) δ 7.58 (dd, J=7.9, 1.6 Hz, 1H), 7.33 (d, J=1.2 Hz, 1H), 7.08 (d, J=8.6 Hz, 1H), 6.98-6.89 (m, 1H), 6.87-6.79 (m, 2H), 6.79-6.70 (m, 2H), 6.65 (d, J=2.3 Hz, 1H), 5.14 (dd, J=11.4, 6.1 Hz, 1H), 4.99 (d, J=9.1 Hz, 1H), 4.33 (d, J=9.0 Hz, 1H), 4.07-3.97 (m, 1H), 2.47-2.36 (m, 1H), 2.09-1.94 (m, 4H), 1.86 (dt, J=24.9, 12.4 Hz, 2H), 1.63 (d, J=36.7 Hz, 5H), 1.48 (td, J=12.6, 4.0 Hz, 2H), 1.36-1.14 (m, 2H). MS (APCI$^+$) m/z 690.2 (M+H)$^+$.

Example 263

(7R)-2,2-difluoro-N-[(2R,4R)-2-{trans-4-[(2-hydroxyethyl)(propyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 263 was prepared according to the procedure used for the preparation of Example 253, substituting 2-(propylamino)ethanol for 2-(ethylamino)ethanol. $^1$H NMR (400 MHz, DMSO-d$_6$) δ 7.33 (s, 1H), 7.08 (dd, J=8.5, 1.2 Hz, 1H), 6.82 (d, J=1.0 Hz, 1H), 6.74 (ddd, J=8.5, 2.5, 1.1 Hz, 1H), 6.65 (dd, J=2.5, 1.2 Hz, 1H), 5.18-5.08 (m, 1H), 4.98 (d, J=9.1 Hz, 1H), 4.33 (d, J=9.1 Hz, 1H), 4.00 (ddd, J=11.6, 5.4, 1.9 Hz, 1H), 3.51 (t, J=6.1 Hz, 2H), 3.35 (t, J=6.2 Hz, 2H), 3.26 (t, J=7.4 Hz, 2H), 2.07-1.94 (m, 2H), 1.94-1.83 (m, 2H), 1.83-1.68 (m, 4H), 1.58 (s, 4H), 1.54-1.38 (m, 4H), 1.34-1.11 (m, 2H), 0.83 (t, J=7.4 Hz, 3H). MS (APCI$^+$) m/z 684.7 (M+H)$^+$.

Example 264

(7R)—N-[(2R,4R)-2-{trans-4-[benzyl(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide Example 264 was prepared according to the procedure used for the preparation of Example 253, substituting 2-(benzylamino)ethanol for 2-(ethylamino)ethanol. $^1$H NMR (400 MHz, DMSO-d$_6$) δ 7.35-7.14 (m, 5H), 7.07 (dd, J=8.5, 1.1 Hz, 1H), 6.82 (s, 1H), 6.74 (ddd, J=8.5, 2.4, 1.2 Hz, 1H), 6.64 (dd, J=2.4, 1.1 Hz, 1H), 5.12 (dd, J=11.3, 6.1 Hz, 1H), 4.98 (d, J=9.2 Hz, 1H), 4.58 (s, 1H), 4.32 (d, J=9.2 Hz, 1H), 3.99 (dd, J=10.7, 5.2 Hz, 1H), 3.51 (t, J=6.0 Hz, 2H), 3.36 (t, J=6.1 Hz, 2H), 2.62 (s, 1H), 2.05-1.94 (m, 2H), 1.87 (dd, J=23.0, 11.3 Hz, 2H), 1.75 (d, J=12.0 Hz, 3H), 1.57 (s, 3H), 1.49 (d, J=12.7 Hz, 3H), 1.21 (s, 1H). MS (APCI$^+$) m/z 733.6 (M+H)$^+$.

Example 265

(7R)-2,2-difluoro-N-[(2R,4R)-2-[trans-4-(4-hydroxypiperidine-1-carbonyl)cyclohexyl]-7-(trifluoromethoxy)-3,4-dihydro-2H-1-benzopyran-4-yl]-7-methyl-6,7-dihydro-2H-furo[2,3-f][1,3]benzodioxole-7-carboxamide Example 265 was prepared according to the procedure used for the preparation of Example 253, substituting piperidin-4-ol for 2-(ethylamino)ethanol. $^1$H NMR (400 MHz, DMSO-d$_6$) δ 7.33 (s, 1H), 7.08 (dd, J=8.5, 1.1 Hz, 1H), 6.82 (s, 1H), 6.78-6.70 (m, 1H), 6.64 (dd, J=2.5, 1.2 Hz, 1H), 5.13 (dd, J=11.4, 6.0 Hz, 1H), 4.98 (d, J=9.1 Hz, 1H), 4.33 (d, J=9.1 Hz, 1H), 4.00 (ddd, J=11.6, 5.4, 1.9 Hz, 1H), 3.84-3.71 (m, 3H), 3.16-3.09 (m, 2H), 2.07-1.81 (m, 3H), 1.81-1.68 (m, 5H), 1.58 (s, 5H), 1.44 (t, J=12.5 Hz, 2H), 1.33 (ddt, J=12.9, 8.7, 3.9 Hz, 3H), 1.28-1.13 (m, 2H). MS (APCI$^+$) m/z 682.9 (M+H)$^+$.

Example 266

(7R)-2,2-difluoro-N-[(2R,4R)-2-{trans-4-[4-(2-hydroxyethyl)piperazine-1-carbonyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 266 was prepared according to the procedure used for the preparation of Example 253, substituting 2-(piperazin-1-yl)ethanol for 2-(ethylamino)ethanol. $^1$H NMR (400 MHz, DMSO-d$_6$) δ 7.32 (d, J=1.1 Hz, 1H), 7.07 (d, J=8.5 Hz, 1H), 6.81 (d, J=1.2 Hz, 1H), 6.78-6.70 (m, 1H), 6.64 (d, J=2.3 Hz, 1H), 5.13 (dd, J=11.4, 6.1 Hz, 1H), 4.98 (d, J=9.2 Hz, 1H), 4.33 (d, J=9.1 Hz, 1H), 4.00 (dt, J=10.0, 3.3 Hz, 1H), 3.49 (dt, J=29.1, 5.6 Hz, 6H), 2.45-2.37 (m, 6H), 2.07-1.86 (m, 3H), 1.85 (s, 2H), 1.83-1.74 (m, 2H), 1.74-1.69 (m, 2H), 1.58 (s, 4H), 1.51-1.12 (m, 4H). MS (APCI) m/z 711.9 (M+H)$^+$.

Example 267

(7R)-2,2-difluoro-N-[(2R,4R)-2-{trans-4-[(2-hydroxy-2-methylpropyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 267 was prepared according to the procedure used for the preparation of Example 253, substituting 1-amino-2-methylpropan-2-ol for 2-(ethylamino)ethanol. $^1$H NMR (400 MHz, DMSO-d$_6$) δ 7.32 (s, 1H), 7.07 (dd, J=8.6, 1.1 Hz, 1H), 6.82 (s, 1H), 6.74 (ddd, J=8.6, 2.5, 1.2 Hz, 1H), 6.64 (dd, J=2.4, 1.2 Hz, 1H), 5.13 (dd, J=11.4, 6.2 Hz, 1H), 4.98 (d, J=9.1 Hz, 1H), 4.33 (d, J=9.2 Hz, 1H), 3.99 (ddd, J=11.5, 5.4, 1.8 Hz, 1H), 2.21-2.09 (m, 1H), 2.07-1.91 (m, 2H), 1.91-1.78 (m, 3H), 1.76 (d, J=13.1 Hz, 1H), 1.58 (s, 4H), 1.41 (qt, J=13.2, 4.1 Hz, 2H), 1.30-1.08 (m, 2H), 1.06 (d, J=0.9 Hz, 6H). MS (APCI$^+$) m/z 670.8 (M+H)$^+$.

Example 268

(7R)-2,2-difluoro-N-[(2R,4R)-2-{trans-4-[(1-hydroxy-2-methylpropan-2-yl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 268 was prepared according to the procedure used for the preparation of Example 253, substituting 2-amino-2-methylpropan-1-ol for 2-(ethylamino)ethanol. $^1$H NMR (400 MHz, DMSO-d$_6$) δ 7.32 (s, 1H), 7.07 (dd, J=8.6, 1.1 Hz, 1H), 6.82 (s, 1H), 6.78-6.70 (m, 1H), 6.63 (dd, J=2.4, 1.2 Hz, 1H), 5.13 (dd, J=11.4, 6.0 Hz, 1H), 4.98 (d, J=9.1 Hz, 1H), 4.33 (d, J=9.2 Hz, 1H), 3.98 (ddd, J=11.5, 5.6, 1.8 Hz, 1H), 3.37 (s, 2H), 2.13-1.91 (m, 3H), 1.91-1.78 (m, 3H), 1.58 (s, 4H), 1.36 (d, J=12.8 Hz, 2H), 1.19 (d, J=0.9 Hz, 8H). MS (APCI$^+$) m/z 670.8 (M+H)$^+$.

Example 269

(7R)-2,2-difluoro-N-[(2R,4R)-2-{trans-4-[(2-hydroxy-1-phenylethyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide Example 269 was prepared according to the procedure used for the preparation of Example 253, substituting 2-amino-2-phenylethanol for 2-(ethylamino)ethanol. $^1$H NMR (400 MHz, DMSO-d$_6$) δ 7.35-7.25 (m, 5H), 7.25-7.14 (m, 1H), 7.07 (dd, J=8.5, 1.1 Hz, 1H), 6.82 (s, 1H), 6.74 (d, J=7.9 Hz, 1H), 6.64 (dd, J=2.4, 1.1 Hz, 1H), 5.13 (dd, J=11.4, 6.1 Hz, 1H), 4.98 (d, J=9.2 Hz, 1H), 4.84 (t, J=6.1 Hz, 1H), 4.33 (d, J=9.2 Hz, 1H), 3.99 (ddd, J=11.6, 5.5, 1.8 Hz, 1H), 3.62 (dt, J=6.6, 1.3 Hz, 2H), 2.20 (tt, J=12.0, 3.7 Hz, 1H), 2.01 (dtd, J=15.8, 9.0, 7.6, 2.7 Hz, 2H), 1.96-1.79 (m, 4H), 1.75 (s, 2H), 1.58 (s, 4H), 1.51-1.07 (m, 5H). MS (APCI$^+$) m/z 718.8 (M+H)$^+$.

Example 270

(7R)—N-[(2R,4R)-2-[trans-4-(4,4-difluoropiperidine-1-carbonyl)cyclohexyl]-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide Example 270 was prepared according to the procedure used for the preparation of Example 253, substituting 4,4-difluoropiperidine for 2-(ethylamino)ethanol. $^1$H NMR (400 MHz, DMSO-d$_6$) δ 7.32 (s, 1H), 7.08 (d, J=8.5 Hz, 1H), 6.81 (s, 1H), 6.78-6.70 (m, 1H), 6.64 (d, J=2.3 Hz, 1H), 5.13 (dd, J=11.4, 6.2 Hz, 1H), 4.98 (d, J=9.1 Hz, 1H), 4.33 (d, J=9.2 Hz, 1H), 4.00 (m, 1H) 3.62-3.54 (m, 4H), 2.59 (ddd, J=11.7, 8.4, 3.5 Hz, 1H), 2.07-1.99 (m, 1H), 1.99-1.92 (m, 3H), 1.92-1.86 (m, 2H), 1.86-1.72 (m, 4H), 1.58 (s, 4H), 1.50-1.26 (m, 3H), 1.21 (dt, J=15.9, 11.0 Hz, 1H). MS (APCI$^+$) m/z 702.8 (M+H)$^+$.

Example 271

(7R)-2,2-difluoro-7-methyl-N-[(2R,4R)-2-[trans-4-(morpholine-4-carbonyl)cyclohexyl]-7-(trifluoromethoxy)-3,4-dihydro-2H-1-benzopyran-4-yl]-6,7-dihydro-2H-furo[2,3-f][1,3]benzodioxole-7-carboxamide Example 271 was prepared according to the procedure used for the preparation of Example 253, substituting morpholine for 2-(ethylamino)ethanol. $^1$H NMR (400 MHz, DMSO-d$_6$) δ 7.32 (d, J=1.1 Hz, 1H), 7.07 (d, J=8.6 Hz, 1H), 6.81 (s, 1H), 6.78-6.70 (m, 1H), 6.64 (d, J=2.3 Hz, 1H), 5.13 (dd, J=11.4, 6.1 Hz, 1H), 4.98 (d, J=9.1 Hz, 1H), 4.33 (d, J=9.2 Hz, 1H), 4.00 (ddd, J=11.2, 5.5, 1.8 Hz, 1H), 3.56 (d, J=4.5 Hz, 3H), 3.55-3.42 (m, 6H), 2.07-1.69 (m, 7H), 1.58 (s, 4H), 1.51-1.12 (m, 5H). MS (APCI$^+$) m/z 668.7 (M+H)$^+$.

Example 272

(7R)—N-{(2S,4R)-2-[6-(benzyloxy)pyridazin-3-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide A solution of benzyl alcohol (15.64 µL, 0.150 mmol) in tetrahydrofuran (about 1.3 mL) under N$_2$ was treated with 1

M potassium tert-butoxide in tetrahydrofuran (60.2 μL, 0.060 mmol), stirred at room temperature for 10 minutes, treated with a solution of Example 195D (16 mg, 0.030 mmol) in tetrahydrofuran (about 0.3 mL), and stirred at room temperature for 2 hours. The mixture was diluted with ethyl acetate, washed with brine, dried (MgSO$_4$), filtered, and concentrated. The residue was chromatographed on silica gel eluting with a gradient of 15 to 40% ethyl acetate in heptanes to provide the title compound as the first eluting isomer. $^1$H NMR (501 MHz, CDCl$_3$) δ 7.63 (d, J=9.1 Hz, 1H), 7.51-7.48 (m, 2H), 7.42-7.38 (m, 2H), 7.37-7.33 (m, 1H), 7.07 (d, J=9.1 Hz, 1H), 6.99 (d, J=8.8 Hz, 1H), 6.87 (s, 1H), 6.61 (s, 1H), 6.54 (dd, J=8.6, 2.6 Hz, 1H), 6.46 (d, J=2.5 Hz, 1H), 5.90 (d, J=6.9 Hz, 1H), 5.60-5.54 (m, 2H), 5.22 (dd, J=11.4, 2.3 Hz, 1H), 5.05 (ddd, J=7.3, 4.7, 3.1 Hz, 1H), 4.86 (d, J=9.3 Hz, 1H), 4.36 (d, J=9.3 Hz, 1H), 3.77 (s, 3H), 2.53 (dt, J=14.3, 2.6 Hz, 1H), 2.22 (ddd, J=14.3, 11.4, 4.7 Hz, 1H), 1.62 (s, 3H); LC/MS (ESI+) m/z 604.6 (M+H)$^+$.

Example 273

(7R)—N-{(2R,4R)-2-[6-(benzyloxy)pyridazin-3-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide A solution of benzyl alcohol (15.64 μL, 0.150 mmol) in tetrahydrofuran (about 1.3 mL) under N$_2$ was treated with 1 M potassium tert-butoxide in tetrahydrofuran (60.2 μL, 0.060 mmol), stirred at room temperature for 10 minutes, treated with a solution of Example 195D (16 mg, 0.030 mmol) in tetrahydrofuran (about 0.3 mL), and stirred at room temperature for 2 hours. The mixture was diluted with ethyl acetate, washed with brine, dried (MgSO$_4$), filtered, concentrated. The residue was chromatographed on silica gel eluting with a gradient of 15 to 40% ethyl acetate in heptanes to provide the title compound as the second eluting isomer. $^1$H NMR (400 MHz, CDCl$_3$) δ 7.62 (d, J=9.2 Hz, 1H), 7.51-7.47 (m, 2H), 7.42-7.32 (m, 3H), 7.04 (d, J=9.1 Hz, 1H), 7.00 (s, 1H), 6.96 (d, J=8.5 Hz, 1H), 6.59 (s, 1H), 6.51 (dd, J=8.6, 2.5 Hz, 1H), 6.42 (d, J=2.5 Hz, 1H), 6.19 (d, J=8.5 Hz, 1H), 5.62-5.53 (m, 2H), 5.48 (dd, J=9.1, 2.7 Hz, 1H), 5.41 (q, J=8.4 Hz, 1H), 4.90 (d, J=9.2 Hz, 1H), 4.31 (d, J=9.2 Hz, 1H), 3.76 (s, 3H), 2.81 (ddd, J=13.7, 6.5, 2.7 Hz, 1H), 2.16 (dt, J=13.7, 9.0 Hz, 1H), 1.63 (s, 3H); LC/MS (ESI+) m/z 604.6 (M+H)$^+$.

Example 274

(7R)—N-[(2R,4R)-2-{[(2R)-2,3-dihydroxypropoxy]methyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide Example 274A (4R)-2,2-dimethyl-4-{[(prop-2-en-1-yl)oxy]methyl}-1,3-dioxolane A solution of (R)-(−)-2,2-dimethyl-1,3-dioxolane-4-methanol (CAS #14347-78-5, 2 g, 15.13 mmol) and allyl bromide (1.441 mL, 16.65 mmol) in N,N-dimethylformamide (30 mL) was cooled to 0° C., treated portionwise with 60% dispersion of sodium hydride in mineral oil (0.726 g, 18.16 mmol) over 15 minutes, stirred at 0° C. for 30 minutes and then stirred at room temperature until the reaction was complete. The mixture was partitioned between methyl tert-butyl ether (150 mL) and water (150 mL). The layers were separated and the aqueous was extracted with methyl tert-butyl ether (100 mL). The combined methyl tert-butyl ether layers were washed with brine, dried (MgSO$_4$), filtered, and concentrated. The residue was chromatographed on silica gel eluting with a gradient of 5 to 30% ethyl acetate in heptanes to provide the title compound (1.07 g, 6.21 mmol, 41.1% yield). $^1$H NMR (501 MHz, CDCl$_3$) δ 5.89 (ddt, J=17.2, 10.4, 5.7 Hz, 1H), 5.26 (dq, J=17.2, 1.6 Hz, 1H), 5.19-5.16 (m, 1H), 4.30-4.24 (m, 1H), 4.07-4.00 (m, 3H), 3.72 (dd, J=8.3, 6.4 Hz, 1H), 3.52 (dd, J=9.9, 5.8 Hz, 1H), 3.44 (dd, J=9.9, 5.5 Hz, 1H), 1.41 (d, J=0.5 Hz, 3H), 1.35 (d, J=0.5 Hz, 3H).

Example 274B

{[(4R)-2,2-dimethyl-1,3-dioxolan-4-yl]methoxy}acetaldehyde

A solution of Example 274A (1.07 g, 6.21 mmol) in 1:1 tetrahydrofuran:H$_2$O (30 mL) was treated with a 4 weight % solution of osmium tetroxide in water (0.395 mL, 0.062 mmol), treated with sodium periodate (6.64 g, 31.1 mmol), stirred at room temperature for about 30 minutes and partitioned between CH$_2$Cl$_2$ and water. The solid which was present between the layers was removed by filtration. The layers were separated and the aqueous layer was extracted with CH$_2$Cl$_2$. The combined CH$_2$Cl$_2$ layers were dried (MgSO$_4$), filtered and concentrated to provide the title compound (0.9 g, 5.17 mmol, 83% yield). $^1$H NMR (400 MHz, CDCl$_3$) δ 9.75 (s, 1H), 4.36 (p, J=5.9 Hz, 1H), 4.19 (d, J=2.4 Hz, 1H), 4.11 (dd, J=8.1, 6.7 Hz, 1H), 3.80 (dd, J=8.3, 6.4 Hz, 1H), 3.64 (d, J=5.3 Hz, 2H), 3.62-3.49 (m, 1H), 1.45 (s, 3H), 1.39 (s, 3H).

Example 274C (S)—N-[(1E,3S)-4-{[(4S)-2,2-dimethyl-1,3-dioxolan-4-yl]methoxy}-3-hydroxy-1-(2-hydroxy-4-methoxyphenyl)butylidene]-2-methylpropane-2-sulfinamide A solution of N,N-diisopropylamine (0.628 mL, 4.40 mmol) in tetrahydrofuran (20 mL) under N$_2$ at −78° C. was treated with 2.5 M n-butyl lithium in hexanes (1.626 mL, 4.06 mmol), warmed to 0° C., stirred for 15 minutes at 0° C., cooled to −78° C., treated with a solution of Example 190B (1.949 g, 5.08 mmol) in tetrahydrofuran (5 mL), stirred at −78° C. for 45 minutes, treated with a solution of Example 274B (0.59 g, 3.39 mmol) in tetrahydrofuran (10 mL), stirred at −78° C. for 45 minutes, treated dropwise with a solution of acetic acid (0.388 mL, 6.77 mmol) in tetrahydrofuran (0.5 mL), warmed to 0° C., treated over 1 minute with 1 M tetrabutylammonium fluoride in tetrahydrofuran (5.08 mL, 5.08 mmol), stirred at 0° C. for 1 hour, concentrated on the rotary evaporator with minimal heating to approximately 15 mL of the total volume and partitioned between ethyl acetate (about 75 mL) and 5% citric acid (10 mL). The layers were separated and the aqueous layer was extracted with ethyl acetate (about 20 mL). The combined ethyl acetate layers were washed with saturated aqueous NaHCO$_3$ solution (about 25 mL), washed with brine, dried (MgSO$_4$), filtered, concentrated and chromatographed on silica gel eluting with a gradient of 15 to 100% ethyl acetate in heptanes to provide the title compound as the second eluting isomer (0.25 g, 16.6% yield). $^1$H NMR (501 MHz, CDCl$_3$) δ 13.51 (s, 1H), 7.67 (d, J=9.1 Hz, 1H), 6.46 (dd, J=9.0, 2.6 Hz, 1H), 6.43 (d, J=2.6 Hz, 1H), 4.33-4.28 (m, 1H), 4.27-4.20 (m, 1H), 4.06 (dd, J=8.3, 6.5 Hz, 1H), 3.83 (s, 3H), 3.72 (dd, J=8.3, 6.5 Hz, 1H), 3.60-3.52 (m, 4H), 3.34-3.29 (m, 2H), 1.74 (bs, 1H), 1.42 (s, 3H), 1.36 (s, 3H), 1.33 (s, 9H); LC/MS (ESI+) m/z 444 (M+H)+.

Example 274D (S)—N-[(2R,E)-2-({[(4S)-2,2-dimethyl-1,3-dioxolan-4-yl]methoxy}methyl)-7-methoxy-2,3-dihydro-4H-1-benzopyran-4-ylidene]-2-methylpropane-2-sulfinamide A solution of Example 274C (203 mg, 0.458 mmol) and triphenylphosphine (144 mg, 0.549 mmol) in toluene (5 mL) was cooled to 0° C., treated dropwise with diethyl azodicarboxylate, 40 wt. % solution in toluene (521 µL, 1.144 mmol), stirred at 0° C. for 1 hour, diluted with heptanes (about 5 mL), stirred for 5 minutes and filtered to remove the solids. The filtrate was chromatographed on silica gel eluting with a gradient of 20 to 100% ethyl acetate in heptanes to provide the title compound (175 mg, 0.411 mmol, 90% yield). $^1$H NMR (500 MHz, CDCl$_3$) δ 7.90 (d, J=8.9 Hz, 1H), 6.55 (dd, J=8.9, 2.5 Hz, 1H), 6.42 (d, J=2.4 Hz, 1H), 4.38 (ddt, J=12.5, 6.3, 3.4 Hz, 1H), 4.30 (p, J=6.0 Hz, 1H), 4.06 (dd, J=8.3, 6.5 Hz, 1H), 3.84-3.79 (m, 4H), 3.77-3.72 (m, 2H), 3.65 (dd, J=10.1, 5.7 Hz, 1H), 3.57 (dd, J=10.1, 5.4 Hz, 1H), 3.49 (dd, J=17.4, 2.9 Hz, 1H), 3.02 (dd, J=17.4, 12.8 Hz, 1H), 1.42 (s, 3H), 1.36 (s, 3H), 1.30 (s, 9H). LC/MS (ESI+) m/z 426 (M+H)+.

Example 274E (S)—N-[(2R,4R)-2-({[(4S)-2,2-dimethyl-1,3-dioxolan-4-yl]methoxy}methyl)-7-methoxy-3,4-dihydro-2H-1-benzopyran-4-yl]-2-methylpropane-2-sulfinamide A solution of Example 274D (175 mg, 0.411 mmol) in methanol (3 mL) was cooled to 0° C., treated with NaBH$_4$ (31.1 mg, 0.822 mmol), stirred at 0° C. for 20 minutes, stored over night at 0° C., and partitioned between ethyl acetate (50 mL) and saturated aqueous NaHCO$_3$ solution (15 mL). The layers were separated and the aqueous layer was extracted with ethyl acetate (15 mL). The combined ethyl acetate layers were washed with brine, dried (MgSO$_4$), filtered, and concentrated. The residue was chromatographed on silica gel eluting with a gradient of 15 to 100% ethyl acetate in heptanes to provide the title compound (146 mg, 0.341 mmol, 83% yield). $^1$H NMR (500 MHz, CDCl$_3$) δ 7.28 (dd, J=8.6, 0.9 Hz, 1H), 6.49 (dd, J=8.6, 2.6 Hz, 1H), 6.39 (d, J=2.6 Hz, 1H), 4.57 (td, J=10.7, 5.9 Hz, 1H), 4.32-4.26 (m, 2H), 4.05 (dd, J=8.3, 6.4 Hz, 1H), 3.77-3.72 (m, 5H), 3.69-3.62 (m, 2H), 3.55 (dd, J=10.0, 5.5 Hz, 1H), 3.28 (d, J=10.8 Hz, 1H), 2.63 (ddd, J=13.4, 6.1, 1.8 Hz, 1H), 1.83 (dt, J=13.4, 11.3 Hz, 1H), 1.42 (s, 3H), 1.36 (s, 3H), 1.29 (s, 9H); LC/MS (ESI+) m/z 307 (100%), 428 (M+H)+ (2%).

Example 274F (2R)-3-{[(2R,4R)-4-amino-7-methoxy-3,4-dihydro-2H-1-benzopyran-2-yl]methoxy}propane-1,2-diol hydrogen chloride A solution of Example 274E (146 mg, 0.341 mmol) in methanol (5 mL) was treated with 4 M HCl in dioxane (854 µL, 3.41 mmol), stirred at room temperature for 30 minutes and then concentrated with a stream of N$_2$ with gentle heating. The residue was treated with methyl tert-butyl ether (about 2 mL) and the oil solidified-after about 5 minutes of scraping with a spatula. Heptanes was added and after 2 minutes, the solvent was decanted off. The solid was treated again with methyl tert-butyl ether (about 2 mL) and heptanes (about 2 mL). The solvent was decanted and the solid was dried with a gentle stream of N$_2$ for 5 minutes, and then dried under vacuum with heating at 50° C. for 30 minutes to provide the title compound (105 mg, 0.328 mmol, 96% yield). $^1$H NMR (501 MHz, DMSO-d$_6$) δ 8.73 (d, J=2.2 Hz, 3H), 7.55 (d, J=8.7 Hz, 1H), 6.57 (dd, J=8.7, 2.6 Hz, 1H), 6.41 (d, J=2.6 Hz, 1H), 4.59-4.52 (m, 1H), 4.30-4.25 (m, 1H), 3.71 (s, 3H), 3.65 (dd, J=4.3, 3.0 Hz, 2H), 3.61-3.57 (m, 1H), 3.50 (dd, J=10.1, 4.7 Hz, 1H), 3.41-3.30 (m, 3H), 2.39-2.35 (m, 1H), 1.81 (q, J=11.6 Hz, 1H); LC/MS (ESI+) m/z 267 (M−NH$_3$)+.

Example 274G (7R)—N-[(2R,4R)-2-{[(2R)-2,3-dihydroxypropoxy]methyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 274F (39 mg, 0.122 mmol) and triethylamine (51.0 µL, 0.366 mmol) in CH$_2$Cl$_2$ (5 mL) was cooled to 0° C. under N$_2$, treated with a solution of Example 134F (50.6 mg, 0.183 mmol) in CH$_2$Cl$_2$ (about 1 mL) and stirred at room temperature for 30 minutes. The mixture was concentrated. The residue was dissolved in methanol (1.5 mL), diluted with tetrahydrofuran (1.5 mL), treated with 1 M NaOH (about 1 mL), stirred at room temperature for 30 minutes and partitioned between 1 M NaOH (5 mL) and methyl tert-butyl ether (30 mL). The layers were separated and the aqueous layer was extracted with methyl tert-butyl ether (15 mL). The combined methyl tert-butyl ether layers were washed with brine, dried (MgSO$_4$), filtered, and concentrated. The residue was chromatographed on silica gel eluting with a gradient of 15% to 100% [3:1 ethyl acetate:ethanol] in heptanes to provide the title compound (54 mg, 0.103 mmol, 85% yield). $^1$H NMR (500 MHz, CDCl$_3$) δ 6.91 (s, 1H), 6.78 (dd, J=8.6, 0.7 Hz, 1H), 6.62 (s, 1H), 6.45 (dd, J=8.6, 2.6 Hz, 1H), 6.36 (d, J=2.5 Hz, 1H), 5.69 (d, J=8.6 Hz, 1H), 5.24 (ddd, J=10.5, 8.9, 6.7 Hz, 1H), 4.88 (d, J=9.3 Hz, 1H), 4.34 (d, J=9.3 Hz, 1H), 4.31-4.25 (m, 1H), 3.90-3.85 (m, 1H), 3.74 (s, 3H), 3.72-3.57 (m, 5H), 2.75 (bd, J=3.2 Hz, 1H), 2.28 (ddd, J=13.0, 6.3, 1.7 Hz, 1H), 2.22-2.19 (m, 1H), 1.68 (bs, 1H), 1.66 (s, 3H), 1.60 (dt, J=12.9, 11.4 Hz, 1H); MS (ESI−) m/z 522 (M−H)−.

Example 275

(7R)—N-[(2S,4S)-2-{[(2R)-2,3-dihydroxypropoxy]methyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide Example 275A (S)—N-[(1E,3R)-4-{[(4S)-2,2-dimethyl-1,3-dioxolan-4-yl]methoxy}-3-hydroxy-1-(2-hydroxy-4-methoxyphenyl)butylidene]-2-methylpropane-2-sulfinamide The procedure for the preparation of Example 274C provided the title compound (0.23 g, 15.3%) as the first eluting isomer. ¹H NMR (501 MHz, CDCl₃) δ 13.24 (s, 1H), 7.64 (d, J=9.1 Hz, 1H), 6.50 (dd, J=9.0, 2.6 Hz, 1H), 6.46 (d, J=2.6 Hz, 1H), 4.68 (d, J=8.0 Hz, 1H), 4.38-4.33 (m, 1H), 4.11 (dd, J=8.2, 6.5 Hz, 1H), 3.86 (s, 3H), 3.81 (dd, J=8.2, 6.5 Hz, 1H), 3.76 (dd, J=9.5, 4.8 Hz, 1H), 3.68 (dd, J=10.2, 5.6 Hz, 1H), 3.62 (dd, J=10.2, 5.0 Hz, 1H), 3.58 (dd, J=13.5, 3.4 Hz, 1H), 3.51 (dd, J=9.5, 7.4 Hz, 1H), 3.34 (dd, J=13.6, 10.1 Hz, 1H), 1.68 (bs, 1H), 1.47 (s, 3H), 1.41 (s, 3H), 1.39 (s, 9H); LC/MS (ESI+) m/z 444 (M+H)⁺.

Example 275B (S)—N-[(2S,E)-2-({[(4S)-2,2-dimethyl-1,3-dioxolan-4-yl]methoxy}methyl)-7-methoxy-2,3-dihydro-4H-1-benzopyran-4-ylidene]-2-methylpropane-2-sulfinamide A solution of Example 275A (219 mg, 0.494 mmol) and triphenylphosphine (155 mg, 0.592 mmol) in toluene (5 mL) was cooled to 0° C., treated dropwise with diethyl azodicarboxylate, 40 wt. % solution in toluene (562 µL, 1.234 mmol), stirred at 0° C. for 1 hour, diluted with heptanes (about 5 mL), stirred for 5 minutes and filtered to remove the solids. The filtrate was chromatographed on silica gel eluting with a gradient of 20 to 100% ethyl acetate in heptanes to provide the title compound. ¹H NMR (500 MHz, CDCl₃) δ 7.95 (d, J=8.9 Hz, 1H), 6.56 (dd, J=8.9, 2.5 Hz, 1H), 6.42 (d, J=2.4 Hz, 1H), 4.47-4.41 (m, 1H), 4.34-4.28 (m, 2H), 4.07 (dd, J=8.3, 6.5 Hz, 1H), 3.85-3.73 (m, 6H), 3.68-3.63 (m, 1H), 3.57 (dd, J=10.1, 5.5 Hz, 1H), 2.81 (dd, J=17.0, 12.3 Hz, 1H), 1.43 (s, 3H), 1.36 (s, 3H), 1.29 (s, 9H); LC/MS (ESI+) m/z 426 (M+H)⁺.

Example 275C (S)—N-[(2S,4S)-2-({[(4S)-2,2-dimethyl-1,3-dioxolan-4-yl]methoxy}methyl)-7-methoxy-3,4-dihydro-2H-1-benzopyran-4-yl]-2-methylpropane-2-sulfinamide A solution of Example 275B (175 mg, 0.411 mmol) in methanol (3 mL) was cooled to 0° C., treated with NaBH₄ (31.1 mg, 0.822 mmol), stirred at 0° C. for 1 hour, treated with more NaBH₄ (31.1 mg, 0.822 mmol), stirred at 0° C. for 1 hour and stirred overnight at room temperature. The mixture was partitioned between ethyl acetate (50 mL) and saturated aqueous NaHCO₃ solution (15 mL). The layers were separated and the aqueous layer was extracted with ethyl acetate (15 mL). The combined ethyl acetate layers were washed with brine, dried (MgSO₄), filtered, and concentrated. The residue was chromatographed on silica gel eluting with a gradient of 15% to 100% ethyl acetate in heptanes to provide the title compound (54 mg, 0.126 mmol, 30.7% yield). ¹H NMR (500 MHz, CDCl₃) δ 7.54 (dd, J=8.7, 0.8 Hz, 1H), 6.56 (dd, J=8.7, 2.6 Hz, 1H), 6.40 (d, J=2.6 Hz, 1H), 4.67 (dt, J=11.0, 6.6 Hz, 1H), 4.36-4.29 (m, 2H), 4.09 (dd, J=8.3, 6.4 Hz, 1H), 3.82-3.71 (m, 6H), 3.67 (dd, J=10.1, 5.6 Hz, 1H), 3.61 (dd, J=10.1, 5.4 Hz, 1H), 3.48 (d, J=7.2 Hz, 1H), 2.29 (ddd, J=13.4, 6.2, 1.9 Hz, 1H), 1.90 (dt, J=13.4, 11.1 Hz, 1H), 1.45 (s, 3H), 1.39 (s, 3H), 1.27 (s, 9H); LC/MS (ESI+) m/z 307 (100%), 428 (M+H)⁺ (5%).

Example 275D (2R)-3-{[(2S,4S)-4-amino-7-methoxy-3,4-dihydro-2H-1-benzopyran-2-yl]methoxy}propane-1,2-diol hydrogen chloride A solution of Example 275C (53.5 mg, 0.125 mmol) in methanol (3 mL) was treated with 4 M HCl in dioxane (313 µL, 1.251 mmol), stirred at room temperature for 30 minutes, and then concentrated with a stream of N₂ with gentle heating. The residue was treated with methyl tert-butyl ether (about 2 mL) and the oil solidified after about 5 minutes of scraping with a spatula. Heptanes were added and after 2 minutes, the solvent was decanted off. The solid was treated again with methyl tert-butyl ether (about 2 mL) and heptanes (about 2 mL). The solvent was decanted and the solid was dried with a gentle stream of N₂ for 5 minutes, and then dried under vacuum with heating at 50° C. for 30 minutes to provide the title compound (32 mg, 0.100 mmol, 80% yield). ¹H NMR (501 MHz, DMSO-d₆) δ 8.71 (bs, 3H), 7.54 (d, J=8.7 Hz, 1H), 6.57 (dd, J=8.7, 2.6 Hz, 1H), 6.41 (d, J=2.6 Hz, 1H), 4.59-4.52 (m, 1H), 4.31-4.25 (m, 1H), 3.71 (s, 3H), 3.65 (d, J=4.4 Hz, 2H), 3.60 (p, J=5.6 Hz, 1H), 3.49 (dd, J=10.1, 4.7 Hz, 1H), 3.42-3.30 (m, 4H), 2.37 (ddd, J=13.0, 6.3, 1.3 Hz, 1H), 1.81 (q, J=11.6 Hz, 1H); LC/MS (ESI+) m/z 267 (M−NH₃)⁺.

Example 275E (7R)—N-[(2S,4S)-2-{[(2R)-2,3-dihydroxypropoxy]methyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 275D (30 mg, 0.094 mmol) and triethylamine (39.2 µL, 0.281 mmol) in CH₂Cl₂ (5 mL) was cooled to 0° C. under N₂, treated with a solution of Example 134F (38.9 mg, 0.141 mmol) in CH₂Cl₂ (about 1 mL), and stirred at room temperature for 30 minutes. The mixture was concentrated. The residue was dissolved in methanol (1.5 mL), diluted with tetrahydrofuran (1.5 mL), treated with 1 M NaOH (about 1 mL), stirred at room temperature for 30 minutes and partitioned between 1 M NaOH (5 mL) and methyl tert-butyl ether (30 mL). The layers were separated and the aqueous layer was extracted with methyl tert-butyl ether (15 mL). The combined methyl tert-butyl ether layers were washed with brine, dried (MgSO₄), filtered, and concentrated. The residue was chromatographed on silica gel eluting with a gradient of 15 to 100% [3:1 ethyl acetate: ethanol] in heptanes to provide the title compound (46 mg, 0.088 mmol, 94% yield). ¹H NMR (500 MHz, CDCl₃) δ 6.87 (s, 1H), 6.84 (dd, J=8.6, 0.9 Hz, 1H), 6.64 (s, 1H), 6.46 (dd, J=8.6, 2.6 Hz, 1H), 6.36 (d, J=2.5 Hz, 1H), 5.67 (d, J=8.7 Hz, 1H), 5.28-5.22 (m, 1H), 4.94 (d, J=9.2 Hz, 1H), 4.36 (d, J=9.2 Hz, 1H), 4.29 (dtd, J=9.3, 4.6, 2.6 Hz, 1H), 3.88 (ddt, J=6.3, 5.3, 3.9 Hz, 1H), 3.75-3.58 (m, 10H), 2.29 (ddd, J=13.0, 6.3, 1.8 Hz, 1H), 1.63 (s, 3H), 1.64-1.56 (m, 1H); MS (ESI−) m/z 522 (M−H)⁻.

Example 276

(7R)—N-{(2R,4R)-2-[(benzyloxy)methyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide Example 276A (S)—N-[(1E,3S)-4-(benzyloxy)-3-hydroxy-1-(2-hydroxy-4-methoxyphenyl)butylidene]-2-methylpropane-2-sulfinamide A solution of N,N-diisopropylamine (1.035 mL, 7.26 mmol) in tetrahydrofuran (24 mL) under N₂ at −78° C. was treated with 2.5 M n-butyl lithium in hexanes (2.66 mL, 6.66 mmol), warmed to 0° C., stirred for 15 minutes at 0° C., cooled to −78° C., treated with a solution of Example 190B (2.322 g, 6.05 mmol) in tetrahydrofuran (5 mL), stirred at −78° C. for 45 minutes, treated with a solution of benzyloxyacetaldehyde (CAS #60656-87-3, 1 g, 6.66 mmol) in tetrahydrofuran (5 mL), stirred at −78° C. for 45 minutes, treated dropwise with a solution of acetic acid (0.520 mL, 9.08 mmol) in tetrahydrofuran (0.5 mL), warmed to 0° C., treated over 1 minute with 1 M tetrabutylammonium fluoride in tetrahydrofuran (7.26 mL, 7.26 mmol), stirred at 0° C. for 1 hour, diluted with methyl tert-butyl ether (about 100 mL) and washed with 10% citric acid (20 mL). The layers were separated and the aqueous was extracted with methyl tert-butyl ether (25 mL). The combined organic layers were washed with saturated aqueous $NaHCO_3$ solution (about 25 mL), washed with brine, dried ($MgSO_4$), filtered, and concentrated. The residue was chromatographed on silica gel eluting with a gradient of 20% to 100% methyl tert-butyl ether in heptanes to provide the title compound (1 g, 2.384 mmol, 39.4% yield) as the second eluting isomer. $^1$H NMR (501 MHz, $CDCl_3$) δ 13.53 (s, 1H), 7.66 (d, J=9.0 Hz, 1H), 7.38-7.28 (m, 5H), 6.44-6.40 (m, 2H), 4.57 (s, 2H), 4.29-4.23 (m, 1H), 3.82 (s, 3H), 3.60 (dd, J=13.6, 7.7 Hz, 1H), 3.58-3.52 (m, 2H), 3.34 (dd, J=13.6, 4.5 Hz, 1H), 3.23 (d, J=5.0 Hz, 1H), 1.33 (s, 9H); LC/MS (ESI+) m/z 420 $(M+H)^+$.

Example 276B (S)—N-{(2R,E)-2-[(benzyloxy)methyl]-7-methoxy-2,3-dihydro-4H-1-benzopyran-4-ylidene}-2-methylpropane-2-sulfinamide A solution of Example 276A (0.99 g, 2.360 mmol) and triphenylphosphine (0.743 g, 2.83 mmol) in toluene (23 mL) was cooled to 0° C., treated dropwise with diethyl azodicarboxylate, 40 wt. % solution in toluene (2.69 mL, 5.90 mmol), stirred at 0° C. for 10 minutes, stirred at room temperature for 1 hour, diluted with heptanes (about 50 mL), stirred for 15 minutes and filtered to remove solids. The filtrate was chromatographed on silica gel eluting with a gradient of 15 to 50% ethyl acetate in heptanes to provide the title compound (0.79 g, 1.968 mmol, 83% yield). $^1$H NMR (501 MHz, $CDCL_3$) δ 7.93 (d, J=8.9 Hz, 1H), 7.43-7.30 (m, 5H), 6.58 (dd, J=8.9, 2.5 Hz, 1H), 6.47 (d, J=2.5 Hz, 1H), 4.69-4.63 (m, 2H), 4.43 (dddd, J=12.6, 5.4, 3.9, 2.9 Hz, 1H), 3.83 (s, 3H), 3.78-3.71 (m, 2H), 3.52 (dd, J=17.4, 2.8 Hz, 1H), 3.08 (dd, J=17.4, 12.9 Hz, 1H), 1.33 (s, 9H); LC/MS (ESI+) m/z 402 $(M+H)^+$.

Example 276C (S)—N-{(2R,4R)-2-[(benzyloxy)methyl]-7-methoxy-3,4-dihydro-2H-1-benzopyran-4-yl}-2-methylpropane-2-sulfinamide A solution of Example 276B (0.79 g, 1.968 mmol) in methanol (20 mL) was cooled to 0° C., treated with $NaBH_4$ (0.149 g, 3.94 mmol), stirred at 0° C. for 30 minutes, concentrated to about 10 mL volume and partitioned between ethyl acetate (100 mL) and saturated aqueous $NaHCO_3$ solution (20 mL). The layers were separated and the aqueous layer was extracted with ethyl acetate (25 mL). The combined ethyl acetate layers were washed with brine, dried ($MgSO_4$), filtered, and concentrated. The residue was chromatographed on silica gel eluting with a gradient of 15 to 50% ethyl acetate in heptanes to provide the title compound (0.554 g, 1.373 mmol, 69.8% yield). $^1$H NMR (500 MHz, $CDCl_3$) δ 7.37-7.26 (m, 6H), 6.50 (dd, J=8.6, 2.6 Hz, 1H), 6.42 (d, J=2.5 Hz, 1H), 4.64-4.54 (m, 3H), 4.35-4.30 (m, 1H), 3.76 (s, 3H), 3.68 (qd, J=10.5, 4.8 Hz, 2H), 3.34 (d, J=10.7 Hz, 1H), 2.63 (ddd, J=13.4, 6.0, 1.8 Hz, 1H), 1.89 (dt, J=13.4, 11.1 Hz, 1H), 1.28 (s, 9H).

Example 276D (2R,4R)-2-[(benzyloxy)methyl]-7-methoxy-3,4-dihydro-2H-1-benzopyran-4-amine hydrogen chloride A solution of Example 276C (0.55 g, 1.363 mmol) in methanol (15 mL) was treated with 4 M HCl in dioxane (3.41 mL, 13.63 mmol), stirred at room temperature for 30 minutes and then concentrated on the rotary evaporator with minimal heating to provide a solid. The solid was treated with methyl tert-butyl ether and heptanes and the solid was collected by filtration and washed with a mixture of methyl tert-butyl ether and heptanes. The solid was dried under vacuum with heating (50° C. for 1 hour) to provide the title compound (425 mg, 1.266 mmol, 93% yield). $^1$H NMR (500 MHz, DMSO-$d_6$) δ 8.76 (bs, 3H), 7.57 (d, J=8.7 Hz, 1H), 7.40-7.28 (m, 5H), 6.58 (dd, J=8.7, 2.6 Hz, 1H), 6.42 (d, J=2.5 Hz, 1H), 4.59-4.54 (m, 3H), 4.37-4.31 (m, 1H), 3.71 (s, 3H), 3.70 (d, J=4.4 Hz, 2H), 2.43-2.37 (m, 1H), 1.86 (q, J=11.8 Hz, 1H); LC/MS (ESI+) m/z 283 $(M-NH_3)^+$.

Example 276E (7R)—N-{(2R,4R)-2-[(benzyloxy)methyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide A mixture of Example 276D (322 mg, 0.959 mmol) and triethylamine (401 µL, 2.88 mmol) in $CH_2Cl_2$ (3 mL) was cooled to 0° C. under $N_2$, treated with a solution of Example 134F (398 mg, 1.438 mmol) in $CH_2Cl_2$ (about 1 mL), stirred at room temperature for 30 minutes, treated with 37% $NH_4OH$ solution (about 1 mL), stirred for 5 minutes and partitioned between ethyl acetate (about 75 mL) and 1 M HCl (about 15 mL). The ethyl acetate layer was washed with saturated aqueous $NaHCO_3$ solution (about 15 mL), washed with brine, dried ($MgSO_4$), filtered, and concentrated. The residue was chromatographed on silica gel eluting with a gradient of 15 to 50% ethyl acetate in heptanes to provide the title compound (425 mg, 0.788 mmol, 82% yield). $^1$H NMR (501 MHz, $CDCl_3$) δ 7.36-7.27 (m, 5H), 6.89 (s, 1H), 6.80 (dd, J=8.6, 0.9 Hz, 1H), 6.61 (s, 1H), 6.46 (dd, J=8.6, 2.6 Hz, 1H), 6.40 (d, J=2.5 Hz, 1H), 5.71 (d, J=8.7 Hz, 1H), 5.29-5.22 (m, 1H), 4.87 (d, J=9.2 Hz, 1H), 4.59 (s, 2H), 4.32 (d, J=9.3 Hz, 1H), 4.32-4.27 (m, 1H), 3.75 (s, 3H), 3.69-3.62 (m, 2H), 2.31 (ddd, J=13.2, 6.3, 2.0 Hz, 1H), 1.63 (s, 3H), 1.67-1.60 (m, 1H); MS (ESI−) m/z 538 $(M-H)^-$.

Example 277

(7R)-2,2-difluoro-N-[(2R,4R)-2-(hydroxymethyl)-7-methoxy-3,4-dihydro-2H-1-benzopyran-4-yl]-7-methyl-6,7-dihydro-2H-furo[2,3-f][1,3]benzodioxole-7-carboxamide A mixture of Example 276E (400 mg, 0.741 mmol) and 10% Pd/C (40 mg) in tetrahydrofuran under an atmosphere of $H_2$ (balloon) was stirred at room temperature for 1 hour.

The atmosphere was exchanged with $N_2$. The mixture was diluted with ethyl acetate and filtered through diatomaceous earth. The residue was concentrated and chromatographed on silica gel eluting with a gradient of 15 to 100% ethyl acetate in heptanes to provide the title compound. $^1$H NMR (501 MHz, $CDCl_3$) δ 6.91 (s, 1H), 6.81 (dd, J=8.6, 0.9 Hz, 1H), 6.62 (s, 1H), 6.46 (dd, J=8.6, 2.6 Hz, 1H), 6.37 (d, J=2.5 Hz, 1H), 5.72 (d, J=8.7 Hz, 1H), 5.29-5.23 (m, 1H), 4.88 (d, J=9.3 Hz, 1H), 4.33 (d, J=9.3 Hz, 1H), 4.22 (dddd, J=11.0, 5.2, 3.2, 2.0 Hz, 1H), 3.85 (bd, J=11.9 Hz, 1H), 3.75 (s, 3H), 3.69 (bd, J=10.9 Hz, 1H), 2.24 (ddd, J=13.1, 6.3, 1.9 Hz, 1H), 1.98 (s, 1H), 1.69-1.61 (m, 4H); MS (ESI−) m/z 448 (M−H)−.

Example 278

(7R)—N-{(2S,4S)-2-[(benzyloxy)methyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide

Example 278A (S)—N-[(1E,3R)-4-(benzyloxy)-3-hydroxy-1-(2-hydroxy-4-methoxyphenyl)butylidene]-2-methylpropane-2-sulfinamide The procedure for the preparation of Example 276A provided the title compound as the first eluting isomer. $^1$H NMR (501 MHz, $CDCl_3$) δ 13.24 (s, 1H), 7.61 (d, J=9.0 Hz, 1H), 7.39-7.28 (m, 5H), 6.44 (d, J=2.5 Hz, 1H), 6.42 (dd, J=8.9, 2.6 Hz, 1H), 4.66 (d, J=7.8 Hz, 1H), 4.62 (s, 2H), 4.09 (tdd, J=8.8, 5.4, 2.2 Hz, 1H), 3.83 (s, 3H), 3.72 (dd, J=9.3, 4.6 Hz, 1H), 3.60 (dd, J=13.5, 3.3 Hz, 1H), 3.49 (dd, J=9.3, 7.6 Hz, 1H), 3.33 (dd, J=13.6, 10.0 Hz, 1H), 1.36 (s, 9H); LC/MS (ESI+) m/z 420 (M+H)+.

Example 278B (S)—N-{(2S,E)-2-[(benzyloxy)methyl]-7-methoxy-2,3-dihydro-4H-1-benzopyran-4-ylidene}-2-methylpropane-2-sulfinamide A solution of Example 278A (670 mg, 1.597 mmol) and triphenylphosphine (503 mg, 1.916 mmol) in toluene (15 mL) was cooled to 0° C., treated dropwise with diethyl azodicarboxylate, 40 wt. % solution in toluene (1818 μL, 3.99 mmol), stirred at 0° C. for 1 hour, diluted with heptanes (about 30 mL), stirred for 15 minutes and filtered to remove the solids. The filrate was chromatographed on silica gel eluting with a gradient of 15 to 50% ethyl acetate in heptanes to provide the title compound. LC/MS (ESI+) m/z 402 (M+H)+.

Example 278C (S)—N-{(2S,4S)-2-[(benzyloxy)methyl]-7-methoxy-3,4-dihydro-2H-1-benzopyran-4-yl}-2-methylpropane-2-sulfinamide A solution of Example 278B (0.55 g, 1.370 mmol) in methanol (14 mL) was cooled to 0° C., treated with $NaBH_4$ (0.104 g, 2.74 mmol), stirred at 0° C. for 30 minutes, and stirred for 4 days at room temperature. The mixture was partitioned between ethyl acetate (100 mL) and saturated aqueous $NaHCO_3$ solution (20 mL). The layers were separated and the aqueous layer was extracted with ethyl acetate (25 mL). The combined ethyl acetate layers were washed with brine, dried ($MgSO_4$), filtered, and concentrated. The residue was chromatographed on silica gel eluting with a gradient of 15 to 100% ethyl acetate in heptanes to provide the title compound (170 mg, 31% yield). $^1$H NMR (501 MHz, $CDCl_3$) δ 7.54 (dd, J=8.7, 0.9 Hz, 1H), 7.40-7.30 (m, 5H), 6.57 (dd, J=8.6, 2.6 Hz, 1H), 6.43 (d, J=2.6 Hz, 1H), 4.70-4.63 (m, 3H), 4.37-4.32 (m, 1H), 3.78 (s, 3H), 3.75 (dd, J=10.4, 5.6 Hz, 1H), 3.67 (dd, J=10.4, 4.4 Hz, 1H), 3.49 (d, J=7.3 Hz, 1H), 2.30 (ddd, J=13.4, 6.2, 1.9 Hz, 1H), 1.92 (dt, J=13.4, 11.0 Hz, 1H), 1.26 (s, 9H).

Example 278D (2S,4S)-2-[(benzyloxy)methyl]-7-methoxy-3,4-dihydro-2H-1-benzopyran-4-amine hydrogen chloride A solution of Example 278C (0.17 g, 0.421 mmol) in methanol (5 mL) was treated with 4 M HCl in dioxane (1.053 mL, 4.21 mmol), stirred at room temperature for 30 minutes and then concentrated on the rotary evaporator with minimal heating to provide a solid. The solid was treated with methyl tert-butyl ether and heptanes and the solid was collected by filtration and washed with methyl tert-butyl ether/heptanes. The solid was dried under vacuum with heating (50° C. for 1 hour) to provide the title compound (121.3 mg, 0.361 mmol, 86% yield). $^1$H NMR (500 MHz, DMSO-$d_6$) δ 8.73 (bs, 3H), 7.55 (d, J=8.7 Hz, 1H), 7.41-7.27 (m, 5H), 6.58 (dd, J=8.7, 2.6 Hz, 1H), 6.42 (d, J=2.6 Hz, 1H), 4.57 (d, J=6.9 Hz, 3H), 4.37-4.31 (m, 1H), 3.71 (s, 3H), 3.70 (d, J=4.4 Hz, 2H), 2.41-2.36 (m, 1H), 1.85 (q, J=11.8 Hz, 1H); LC/MS (ESI+) m/z 283 (M−$NH_3$)+.

Example 278E (7R)—N-{(2S,4S)-2-[(benzyloxy)methyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide A mixture of Example 278D (16 mg, 0.048 mmol) and triethylamine (19.92 μL, 0.143 mmol) in $CH_2Cl_2$ (3 mL) was cooled to 0° C. under $N_2$, treated with a solution of Example 134F (19.77 mg, 0.071 mmol) in $CH_2Cl_2$ (about 1 mL) and stirred at room temperature for 1 hour, treated with 37% $NH_4OH$ solution (about 0.2 mL), stirred for 5 minutes and partitioned between ethyl acetate (about 30 mL) and 1 M HCl (about 10 mL). The ethyl acetate layer was washed with saturated aqueous $NaHCO_3$ solution (about 10 mL), washed with brine, dried ($MgSO_4$), filtered, and concentrated. The residue was chromatographed on silica gel eluting with a gradient of 15 to 50% (over 5 minutes) ethyl acetate in heptanes to provide the title compound (24 mg, 0.044 mmol, 93% yield). $^1$H NMR (500 MHz, $CDCl_3$) δ 7.37-7.28 (m, 5H), 6.86 (d, J=8.6 Hz, 1H), 6.82 (s, 1H), 6.61 (s, 1H), 6.46 (dd, J=8.6, 2.6 Hz, 1H), 6.39 (d, J=2.6 Hz, 1H), 5.71 (d, J=8.7 Hz, 1H), 5.26 (td, J=9.8, 6.6 Hz, 1H), 4.92 (d, J=9.2 Hz, 1H), 4.63-4.56 (m, 2H), 4.35-4.28 (m, 2H), 3.74 (s, 3H), 3.70-3.62 (m, 2H), 2.32 (ddd, J=13.2, 6.3, 2.1 Hz, 1H), 1.68-1.60 (m, 1H), 1.60 (s, 3H); MS (ESI−) m/z 538 (M−H)−.

Example 279

(7R)—N-[(2R,4R)-2-{1-[bis(2-hydroxyethyl)carbamoyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide To a solution of Example 166 (45 mg, 81 μmol) and HATU (38 mg, 100 μmol) in anhydrous N,N-dimethylformamide (400 µL) was added diisopropylethylamine (42 µL, 0.24 mmol) followed by a solution of diethanolamine (21 mg, 0.20 mmol) in N,N-dimethylformamide (200 µL) and the resulting solution was stirred at room temperature overnight. 3:1 Water/brine (2 mL) was added and the mixture was extracted with ethyl acetate/heptane. The combined organic phases were applied directly on silica gel for chromatography (eluted with 20 to 50% acetonitrile/CH$_2$Cl$_2$ then 2% methanol in 1:1 acetonitrile/CH$_2$Cl$_2$) to give 30 mg of a light amber foam. $^1$H NMR (500 MHz, CDCl$_3$) δ 6.97-6.92 (m, 2H), 6.74-6.70 (m, 1H), 6.63 (s, 2H), 6.11 (d, J=8.1 Hz, 1H), 5.26-5.19 (m, 1H), 4.90 (d, J=9.2 Hz, 1H), 4.34 (d, J=9.2 Hz, 1H), 4.31-4.15 (m, 2H), 3.97-3.26 (m, 7H), 2.48-2.40 (m, 1H), 1.78-1.66 (m, 1H), 1.65 (s, 3H), 1.21-1.13 (m, 1H), 1.06-0.94 (m, 3H); MS (ESI) m/z 645 (M+H)$^+$.

Example 280

(7R)—N-[(2S,4S)-2-{1-[bis(2-hydroxyethyl)carbamoyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide To a solution of the Example 201 (45 mg, 81 µmol) and HATU (38 mg, 100 µmol) in anhydrous N,N-dimethylformamide (400 µL) was added diisopropylethylamine (42 µL, 0.24 mmol) followed by half of a solution of diethanolamine (21 mg, 0.20 mmol) in N,N-dimethylformamide (200 µL) and the resulting solution was stirred at room temperature overnight. 3:1 Water/brine (2 mL) was added and the mixture was extracted with ethyl acetate/heptane. The combined organic phases were applied directly on silica gel for chromatography (eluted with 20 to 50% acetonitrile/CH$_2$Cl$_2$ then 2% methanol in 1:1 acetonitrile/CH$_2$Cl$_2$) to give 29 mg of a light amber syrup. $^1$H NMR (400 MHz, CDCl$_3$) δ 6.94 (d, J=8.5 Hz, 1H), 6.92 (s, 1H), 6.74-6.69 (m, 1H), 6.64 (s, 1H), 6.64-6.62 (m, 1H), 5.94 (d, J=8.6 Hz, 1H), 5.27-5.19 (m, 1H), 4.95 (d, J=9.2 Hz, 1H), 4.34 (d, J=9.2 Hz, 1H), 4.31-4.15 (m, 2H), 4.00-3.63 (m, 5H), 3.55-3.43 (m, 1H), 3.39-3.26 (m, 1H), 2.50-2.43 (m, 1H), 1.75-1.65 (m, 1H), 1.62 (s, 3H), 1.22-1.15 (m, 1H), 1.07-0.95 (m, 3H); MS (ESI) m/z=645 (M+H)$^+$.

Example 281

(7R)—N-[(2R,4R)-2-{trans-4-[(3S,4S)-3,4-dihydroxypyrrolidine-1-carbonyl]cyclohexyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide To a solution of Example 155 (25 mg, 45 µmol) and HATU (22 mg, 58 µmol) in anhydrous N,N-dimethylformamide (200 µL) was added diisopropylethylamine (23.5 µL, 0.135 mmol) followed by (3S,4S)-pyrrolidine-3,4-diol (7.1 mg, 69 µmol) and the resulting solution was stirred at room temperature overnight. 3:1 Water/brine (0.8 mL) was added and the mixture was extracted with methyl tert-butyl ether. The combined organic phases were washed with 1:1 water/brine, the separated aqueous phase was extracted with more methyl tert-butyl ether, and the combined organic phases were applied directly to silica for chromatography (eluted with 50% acetonitrile/CH$_2$Cl$_2$ then 2 to 5% methanol in 1:1 acetonitrile/CH$_2$Cl$_2$) to give 12 mg of a white powder (41%). $^1$H NMR (400 MHz, CDCl$_3$) δ 6.93 (s, 1H), 6.78- 6.74 (m, 1H), 6.62 (s, 1H), 6.42 (dd, J=8.5, 2.6 Hz, 1H), 6.32 (d, J=2.6 Hz, 1H), 5.72 (d, J=8.7 Hz, 1H), 5.23-5.15 (m, 1H), 4.89 (d, J=9.2 Hz, 1H), 4.34 (d, J=9.2 Hz, 1H), 4.27-4.24 (m, 1H), 4.19-4.15 (m, 1H), 3.89-3.79 (m, 2H), 3.73 (s, 3H), 3.71-3.65 (m, 1H), 3.54-3.45 (m, 2H), 2.36-2.26 (m, 1H), 2.26-2.20 (m, 1H), 2.07-1.99 (m, 1H), 1.90-1.78 (m, 3H), 1.66 (s, 3H), 1.63-1.42 (m, 3H), 1.29-1.09 (m, 3H); MS (ESI) m/z=629 (M−H)$^-$.

Example 282

(7R)—N-[(2R,4R)-2-{1-[(3S,4S)-3,4-dihydroxypyrrolidine-1-carbonyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide To a solution of the acid Example 166 (45 mg, 81 µmol) and HATU (38 mg, 100 µmol) in anhydrous N,N-dimethylformamide (400 µL) was added diisopropylethylamine (42 µL, 0.24 mmol) followed by (3S,4S)-pyrrolidine-3,4-diol (12.5 mg, 120 µmol) and the resulting solution was stirred at room temperature overnight. 3:1 Water/brine was added and the mixture was extracted with methyl tert-butyl ether. The combined organic phases were washed with 1:1 water/brine, the separated aqueous phase was extracted with more methyl tert-butyl ether, and the combined organic phases were applied directly to silica for chromatography (eluted with 50% acetonitrile/CH$_2$Cl$_2$ then 2 to 5% methanol in 1:1 acetonitrile/CH$_2$Cl$_2$) to give 37 mg of a white powder (71%). $^1$H NMR (400 MHz, CDCl$_3$) δ 7.09 (s, 1H), 6.97-6.92 (m, 1H), 6.74-6.69 (m, 1H), 6.65-6.59 (m, 3H), 5.34-5.26 (m, 1H), 4.99 (d, J=9.3 Hz, 1H), 4.32 (d, J=9.3 Hz, 1H), 4.17-3.94 (m, 3H), 3.86-3.81 (m, 1H), 3.82-3.73 (m, 1H), 3.47-3.38 (m, 1H), 3.15-3.06 (m, 1H), 2.46-2.39 (m, 1H), 1.94-1.83 (m, 1H), 1.64 (s, 3H), 1.06-0.93 (m, 3H), 0.86-0.79 (m, 1H); MS (ESI) m/z=643 (M+H)$^+$.

Example 283

(7R)—N-[(2R,4R)-2-(1-benzyl-1H-tetrazol-5-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide Example 283A 1-benzyl-1H-tetrazole A solution of benzylamine (4.08 mL, 37.3 mmol) in acetic acid (13 mL) was treated with triethyl orthoformate (9.32 mL, 56.0 mmol) and then treated with sodium azide (3.15 g, 48.5 mmol). The mixture was heated at 80° C. for 17 hours and cooled. The mixture was partitioned between methyl tert-butyl ether (500 mL) and 1 M NaOH (250 mL). The methyl tert-butyl ether layer was washed with brine, dried (MgSO$_4$), filtered, and concentrated. The residue was chromatographed on silica gel eluting with a gradient of 25 to 100% (over 14 minutes) ethyl acetate in heptanes to provide the title compound. $^1$H NMR (501 MHz, CDCl$_3$) δ 8.55 (s, 1H), 7.45-7.39 (m, 3H), 7.35-7.30 (m, 2H), 5.62 (s, 2H); LC/MS (ESI+) m/z 161 (M+H)$^+$.

Example 283B 1-benzyl-1H-tetrazole-5-carbaldehyde

A solution of Example 283A (801 mg, 5 mmol) and N,N,N',N'-tetramethylethylenediamine (5 mL, 33.1 mmol)

in tetrahydrofuran (50 mL) under $N_2$ was cooled to −98° C. (methanol/liquid $N_2$ bath), treated dropwise with 2.5 M n-butyl lithium in hexanes (2.200 mL, 5.5 mmol) over 5 minutes, stirred for 5 minutes at −98° C., treated with ethyl formate (5 mL, 61.4 mmol) over 1 minute, stirred at −98° C. for 30 minutes, and allowed to warm to room temperature. The mixture was treated with saturated $NH_4Cl$ solution (30 mL) and extracted with ethyl acetate (250 mL). The organic layer was washed with brine, dried ($MgSO_4$), filtered, and concentrated. The residue was chromatographed on silica gel eluting with a gradient of 25 to 100% ethyl acetate in heptanes to provide the title compound (0.52 g). $^1$H NMR (501 MHz, $CDCl_3$) δ 10.24 (s, 1H), 7.42-7.27 (m, 5H), 5.87 (s, 2H).

Example 283C (S)—N-[(1E,3S)-3-(1-benzyl-1H-tetrazol-5-yl)-3-hydroxy-1-(2-hydroxy-4-methoxyphenyl)propylidene]-2-methylpropane-2-sulfinamide A solution of N,N-diisopropylamine (473 µL, 3.32 mmol) in tetrahydrofuran (11 mL) under $N_2$ at −78° C. was treated with 2.5 M n-butyl lithium in hexanes (1218 µL, 3.05 mmol), warmed to 0° C., stirred for 15 minutes at 0° C., cooled to −78° C., treated with a solution of Example 190B (1062 mg, 2.77 mmol) in tetrahydrofuran (1 mL), stirred at −78° C. for 45 minutes, treated with a solution of Example 283B (521 mg, 2.77 mmol) in tetrahydrofuran (5 mL), stirred at −78° C. for 45 minutes, treated dropwise with a solution of acetic acid (238 µL, 4.15 mmol) in tetrahydrofuran (0.5 mL), warmed to 0° C., treated over 1 minute with 1 M tetrabutylammonium fluoride in tetrahydrofuran (3322 µL, 3.32 mmol), stirred at 0° C. for 1 hour, diluted with methyl tert-butyl ether (about 100 mL) and washed with 10% citric acid (20 mL). The layers were separated and the aqueous layer was extracted with methyl tert-butyl ether (25 mL). The combined organic layers were washed with saturated aqueous $NaHCO_3$ solution (about 25 mL), washed with brine, dried ($MgSO_4$), filtered, and concentrated. The residue was chromatographed on silica gel eluting with a gradient of 0 to 100% ethyl acetate in [9:1 $CH_2Cl_2$:ethyl acetate] to provide the title compound (0.51 g) as the second eluting isomer. $^1$H NMR (400 MHz, $CDCl_3$) δ 13.01 (s, 1H), 7.30-7.22 (m, 5H), 7.16 (d, J=9.2 Hz, 1H), 6.39 (d, J=2.6 Hz, 1H), 6.28 (dd, J=9.2, 2.6 Hz, 1H), 5.68-5.61 (m, 2H), 5.46-5.39 (m, 2H), 4.11 (dd, J=14.0, 6.4 Hz, 1H), 3.86 (dd, J=14.1, 5.1 Hz, 1H), 3.82 (s, 3H), 1.38 (s, 9H); LC/MS (ESI+) m/z 458 (M+H)$^+$.

Example 283D (S)—N-[(2R,E)-2-(1-benzyl-1H-tetrazol-5-yl)-7-methoxy-2,3-dihydro-4H-1-benzopyran-4-ylidene]-2-methylpropane-2-sulfinamide A solution of Example 283C (0.51 g, 1.115 mmol) and triphenylphosphine (0.351 g, 1.338 mmol) in about 1:1 toluene:$CH_2Cl_2$ (12 mL) was cooled to 0° C., treated dropwise with diethyl azodicarboxylate, 40 wt. % solution in toluene (1.269 mL, 2.79 mmol), stirred at 0° C. for 10 minutes, stirred at room temperature for 30 minutes, diluted with heptanes (about 15 mL), stirred for 15 minutes and filtered to remove the solids. The filtrate was chromatographed on silica gel eluting with a gradient of 0 to 50% ethyl acetate in [9:1 $CH_2Cl_2$:ethyl acetate] to provide the title compound. LC/MS (ESI+) m/z 440 (M+H)$^+$.

Example 283E (S)—N-[(2R,4R)-2-(1-benzyl-1H-tetrazol-5-yl)-7-methoxy-3,4-dihydro-2H-1-benzopyran-4-yl]-2-methylpropane-2-sulfinamide A solution of Example 283D (200 mg, 0.455 mmol) in methanol (2 mL) at 0° C. was treated all at once with $NaBH_4$ (39.6 mg, 1.047 mmol), stirred at 0° C. for 90 minutes and partitioned between ethyl acetate (30 mL) and saturated aqueous $NaHCO_3$ solution (5 mL). The ethyl acetate layer was washed with brine, dried ($MgSO_4$), filtered, and concentrated. The residue was chromatographed on silica gel eluting with a gradient of 50 to 100% ethyl acetate in heptanes to provide the title compound. $^1$H NMR (400 MHz, $CDCl_3$) δ 7.40-7.35 (m, 3H), 7.30-7.24 (m, 3H), 6.57 (dd, J=8.7, 2.5 Hz, 1H), 6.19 (d, J=2.5 Hz, 1H), 5.77 (d, J=15.1 Hz, 1H), 5.69 (d, J=15.1 Hz, 1H), 5.40 (dd, J=6.6, 4.0 Hz, 1H), 5.00 (d, J=10.3 Hz, 1H), 4.57 (dt, J=10.3, 6.3 Hz, 1H), 3.73 (s, 3H), 2.93 (ddd, J=14.7, 6.7, 4.1 Hz, 1H), 2.66 (dt, J=14.6, 6.3 Hz, 1H), 1.30 (s, 9H). LC/MS (ESI+) m/z 442 (M+H)$^+$.

Example 283F (2R,4R)-2-(1-benzyl-1H-tetrazol-5-yl)-7-methoxy-3,4-dihydro-2H-1-benzopyran-4-amine hydrogen chloride A solution of Example 283E (20 mg, 0.045 mmol) in methanol (2 mL) at 0° C. was treated all at once with 4 M HCl in dioxane (113 µL, 0.453 mmol), stirred at room temperature for 30 minutes and concentrated. The residue was treated with methyl tert-butyl ether (5 mL) and heptanes (5 mL). The mixture was stirred for 5 minutes and the solvent was decanted off. The flask containing the semi-solid was dried under vacuum with heating (55° C.) for 15 minutes to provide the title compound. $^1$H NMR (400 MHz, DMSO-$d_6$) δ 8.78 (bs, 3H), 7.60 (d, J=8.7 Hz, 1H), 7.45-7.33 (m, 5H), 6.69 (dd, J=8.7, 2.5 Hz, 1H), 6.22 (d, J=2.5 Hz, 1H), 5.89-5.82 (m, 3H), 4.78-4.69 (m, 1H), 3.71 (s, 3H), 2.91-2.82 (m, 1H), 2.51-2.40 (m, 1H); LC/MS (ESI+) m/z 321 (M−$NH_3$)$^+$.

Example 283G (7R)—N-[(2R,4R)-2-(1-benzyl-1H-tetrazol-5-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide A solution of Example 283F (0.017 g, 0.045 mmol) and triethylamine (0.013 mL, 0.090 mmol) in $CH_2Cl_2$ (1 mL) was cooled to 0° C. under $N_2$, treated with a solution of Example 134F (0.019 g, 0.068 mmol) in $CH_2Cl_2$ (about 0.5 mL), stirred at 0° C. for 25 minutes and then at room temperature for 30 minutes. The mixture was treated with 37% $NH_4OH$ solution (5 drops) and stirred for 5 minutes. The mixture was diluted with ethyl acetate (30 mL), washed with 1 M HCl (5 mL), washed with saturated aqueous $NaHCO_3$ solution (5 mL), washed with brine, dried ($MgSO_4$), filtered, and concentrated. The residue was chromatographed on silica gel eluting with a gradient of 50 to 100% [9:1 $CH_2Cl_2$:ethyl acetate] in heptanes to provide the title compound. ¹H NMR (400 MHz, CDCl₃) δ 7.81 (d, J=9.1 Hz, 1H), 7.40-7.35 (m, 3H), 7.31-7.27 (m, 2H), 7.07 (d, J=8.6 Hz, 1H), 6.96 (s, 1H), 6.63 (s, 1H), 6.52 (dd, J=8.7, 2.5 Hz, 1H), 6.17 (d, J=2.4 Hz, 1H), 5.78 (d, J=15.1 Hz, 1H), 5.64 (d, J=15.0 Hz, 1H), 5.38 (td, J=8.2, 4.1 Hz, 1H), 5.32-5.29 (m, 1H), 5.02 (d, J=9.1 Hz, 1H), 4.33 (d, J=9.1 Hz, 1H), 3.72 (s, 3H), 2.79 (ddd, J=14.8, 7.6, 4.6 Hz, 2H), 2.30 (dt, J=14.9, 4.6 Hz, 1H), 1.67 (s, 2H); MS (ESI+) m/z 578 (M+H)⁺; MS (ESI−) m/z 576 (M−H)⁻.

Example 284

(7R)-2,2-difluoro-N-{(2S,4S)-7-methoxy-2-[(6-oxopyridazin-1(6H)-yl)methyl]-3,4-dihydro-2H-1-benzopyran-4-yl}-7-methyl-6,7-dihydro-2H-furo[2,3-f][1,3]benzodioxole-7-carboxamide Example 284A 2-(2,2-diethoxyethyl)pyridazin-3(2H)-one A mixture of 3(2H)-pyridazinone (0.5 g, 5.20 mmol), bromoacetaldehyde diethyl acetal (1.025 g, 5.20 mmol) and K₂CO₃ (0.719 g, 5.20 mmol) in N,N-dimethylformamide (5 mL) was heated at 50° C. until the reaction was complete. Mixture was cooled and partitioned between methyl tert-butyl ether and water. The methyl tert-butyl ether layer was washed with water, washed with brine, dried (MgSO₄), filtered, and concentrated. The residue was chromatographed on silica gel eluting with a gradient of 15 to 100% ethyl acetate in heptanes to provide the title compound (0.28 g, 1.319 mmol, 25.4% yield). ¹H NMR (400 MHz, CDCl₃) δ 7.74 (dd, J=3.8, 1.7 Hz, 1H), 7.15 (dd, J=9.4, 3.8 Hz, 1H), 6.90 (dd, J=9.4, 1.7 Hz, 1H), 5.00 (t, J=5.8 Hz, 1H), 4.28 (d, J=5.8 Hz, 2H), 3.72 (dq, J=9.5, 7.1 Hz, 2H), 3.52 (dq, J=9.5, 7.0 Hz, 2H), 1.14 (t, J=7.0 Hz, 6H).

Example 284B (6-oxopyridazin-1(6H)-yl)acetaldehyde

A solution of Example 284A (260 mg, 1.225 mmol) in tetrahydrofuran (3 mL) was treated with 6 M HCl (3 mL) and stirred at room temperature over night. The mixture was concentrated to an oil and dried under vacuum for 30 minutes at 55° C. The residue was dissolved in CH₂Cl₂ (30 mL), dried (MgSO₄), filtered and concentrated to provide the title compound (159 mg, 1.151 mmol, 94% yield). ¹H NMR (500 MHz, CDCl₃) δ 9.67 (s, 1H), 7.80 (dd, J=3.8, 1.5 Hz, 1H), 7.24 (dd, J=9.5, 3.8 Hz, 1H), 6.98 (dd, J=9.5, 1.6 Hz, 1H), 4.94 (s, 2H).

Example 284C (S)—N-[(1E,3R)-3-hydroxy-1-(2-hydroxy-4-methoxyphenyl)-4-(6-oxopyridazin-1(6H)-yl)butylidene]-2-methylpropane-2-sulfinamide A solution of N,N-diisopropylamine (197 µL, 1.381 mmol) in tetrahydrofuran (5 mL) under N₂ at −78° C. was treated with 2.5 M n-butyl lithium in hexanes (507 µL, 1.266 mmol), warmed to 0° C., stirred for 15 minutes at 0° C., cooled to −78° C., treated with a solution of Example 190B (442 mg, 1.151 mmol) in tetrahydrofuran (1 mL), stirred at −78° C. for 45 minutes, treated with a solution of Example 284B (159 mg, 1.151 mmol) in tetrahydrofuran (5 mL), stirred at −78° C. for 45 minutes, treated dropwise with a solution of acetic acid (99 µL, 1.727 mmol) in tetrahydrofuran (0.5 mL), warmed to 0° C., treated over 1 minute with 1 M tetrabutylammonium fluoride in tetrahydrofuran (1381 µL, 1.381 mmol), stirred at 0° C. for 1 hour, diluted with methyl tert-butyl ether (about 100 mL) and washed with 10% citric acid (20 mL). The layers were separated and the aqueous layer was extracted with methyl tert-butyl ether (25 mL). The combined organic layers were washed with saturated aqueous NaHCO₃ solution (about 25 mL), washed with brine, dried (MgSO₄), filtered, and concentrated. The residue was chromatographed on silica gel eluting with a gradient of 0 to 50% ethyl acetate in methyl tert-butyl ether, then further eluting with a gradient of 0 to 100% [3:1 ethyl acetate:ethanol] in methyl tert-butyl ether to provide the title compound as the first eluting isomer. ¹H NMR (400 MHz, CDCl₃) δ 13.08 (s, 1H), 7.81 (dd, J=3.8, 1.6 Hz, 1H), 7.50 (d, J=9.1 Hz, 1H), 7.20 (dd, J=9.4, 3.8 Hz, 1H), 6.96 (dd, J=9.4, 1.6 Hz, 1H), 6.47 (dd, J=9.0, 2.6 Hz, 1H), 6.42 (d, J=2.6 Hz, 1H), 4.80 (d, J=8.2 Hz, 1H), 4.50-4.42 (m, 2H), 4.36-4.28 (m, 1H), 3.82 (s, 3H), 3.51-3.37 (m, 2H), 1.35 (s, 9H); LC/MS (ESI+) m/z 408 (M+H)⁺.

Example 284D (S)—N-{(2S,E)-7-methoxy-2-[(6-oxopyridazin-1(6H)-yl)methyl]-2,3-dihydro-4H-1-benzopyran-4-ylidene}-2-methylpropane-2-sulfinamide A solution of Example 284C (80 mg, 0.196 mmol) and triphenylphosphine (61.8 mg, 0.236 mmol) in CH₂Cl₂ (2 mL) was cooled to 0° C., treated dropwise with diethyl azodicarboxylate, 40 wt. % solution in toluene (224 µL, 0.491 mmol), stirred at 0° C. for 10 minutes, stirred at room temperature for 30 minutes, diluted with heptanes (about 5 mL), stirred for 15 minutes and filtered to remove solids. The filtrate was chromatographed on silica gel eluting with a gradient of 15 to 100% [10% ethanol in ethyl acetate] in heptanes to provide the title compound (22 mg). ¹H NMR (400 MHz, CDCl₃) δ 7.93 (d, J=8.9 Hz, 1H), 7.80 (dd, J=3.8, 1.7 Hz, 1H), 7.20 (dd, J=9.5, 3.8 Hz, 1H), 6.96 (dd, J=9.5, 1.6 Hz, 1H), 6.56 (dd, J=8.9, 2.5 Hz, 1H), 6.34 (d, J=2.5 Hz, 1H), 4.83 (dddd, J=10.8, 7.5, 5.2, 3.4 Hz, 1H), 4.62 (dd, J=13.3, 7.4 Hz, 1H), 4.33 (dd, J=13.3, 5.3 Hz, 1H), 3.83-3.76 (m, 4H), 2.87 (dd, J=17.1, 10.8 Hz, 1H), 1.29 (d, J=2.6 Hz, 9H); LC/MS (ESI+) m/z 390 (M+H)⁺.

Example 284E (S)—N-{(2S,4S)-7-methoxy-2-[(6-oxopyridazin-1(6H)-yl)methyl]-3,4-dihydro-2H-1-benzopyran-4-yl}-2-methylpropane-2-sulfinamide A solution of Example 284D (22 mg, 0.056 mmol) in methanol (2 mL) at 0° C. was treated all at once with NaBH₄ (4.92 mg, 0.130 mmol), and stirred at 0° C. for 2 hours. The reaction mixture was partitioned between ethyl acetate (30 mL) and saturated aqueous NaHCO₃ solution (5 mL). The ethyl acetate layer was washed with brine, dried (MgSO₄), filtered and concentrated. The residue was chromatographed on silica gel eluting with a gradient of 50 to 100% [10% ethanol in ethyl acetate] in heptanes, then eluting with [25% ethanol in ethyl acetate] to provide the title compound. ¹H NMR (501 MHz, CDCl₃) δ 7.80 (dd, J=3.8, 1.7 Hz, 1H), 7.49 (d, J=8.7, 0.8 Hz, 1H), 7.21 (dd, J=9.5, 3.8 Hz, 1H), 6.96 (dd, J=9.5, 1.7 Hz, 1H), 6.53 (dd, J=8.7, 2.6 Hz, 1H), 6.31 (d, J=2.6 Hz, 1H), 4.68-4.62 (m, 2H), 4.51 (dd, J=13.3, 7.8 Hz, 1H), 4.37 (dd, J=13.3, 4.4 Hz, 1H), 3.73 (s, 3H), 3.47

(d, J=6.9 Hz, 1H), 2.33 (ddd, J=13.4, 6.2, 2.1 Hz, 1H), 1.93 (dt, J=13.4, 10.5 Hz, 1H), 1.24 (s, 9H).

Example 284F

2-{[(2S,4S)-4-amino-7-methoxy-3,4-dihydro-2H-1-benzopyran-2-yl]methyl}pyridazin-3(2H)-one hydrogen chloride A solution of Example 284E (42 mg, 0.107 mmol) in methanol (2 mL) at room temperature was treated all at once with 4 M HCl in dioxane (268 µL, 1.073 mmol), stirred at room temperature for 30 minutes, and concentrated. The residue was treated with methyl tert-butyl ether (5 mL) and heptanes (5 mL). The mixture was stirred for 5 minutes and the solid was collected by filtration. The solid was dried under vacuum with heating (55° C.) for 15 minutes to provide the title compound. $^1$H NMR (400 MHz, DMSO-$d_6$) δ 8.77 (bs, 3H), 7.98 (dd, J=3.8, 1.6 Hz, 1H), 7.56 (d, J=8.7 Hz, 1H), 7.46 (dd, J=9.5, 3.9 Hz, 1H), 7.00 (dd, J=9.5, 1.6 Hz, 1H), 6.58 (dd, J=8.7, 2.5 Hz, 1H), 6.31 (d, J=2.5 Hz, 1H), 4.61-4.46 (m, 3H), 4.27 (dd, J=12.9, 4.8 Hz, 1H), 3.70 (s, 3H), 2.44 (dd, J=12.2, 6.3 Hz, 1H), 1.78 (q, J=11.5 Hz, 1H); LC/MS (ESI+) m/z 271 (M–NH$_3$)$^+$.

Example 284G (7R)-2,2-difluoro-N-{(2S,4S)-7-methoxy-2-[(6-oxopyridazin-1(6H)-yl)methyl]-3,4-dihydro-2H-1-benzopyran-4-yl}-7-methyl-6,7-dihydro-2H-furo[2,3-f][1,3]benzodioxole-7-carboxamide A solution of Example 284F (0.036 g, 0.11 mmol) and triethylamine (0.031 mL, 0.220 mmol) in CH$_2$Cl$_2$ (1 mL) was cooled to 0° C. under N$_2$, treated with a solution of Example 134F (0.046 g, 0.165 mmol) in CH$_2$Cl$_2$ (about 0.5 mL), stirred at 0° C. for 25 minutes and then at room temperature for 15 minutes. The mixture was cooled to 0° C., treated with 37% NH$_4$OH solution (5 drops) and stirred for 5 minutes. The mixture was diluted with ethyl acetate (30 mL), washed with 1 M HCl (5 mL), washed with saturated aqueous NaHCO$_3$ solution (5 mL), washed with brine, dried (MgSO$_4$), filtered, and concentrated. The residue was chromatographed on silica gel eluting with a gradient of 50-100% ethyl acetate in heptanes to provide the title compound. $^1$H NMR (400 MHz, CDCl$_3$) δ 7.79 (dd, J=3.8, 1.7 Hz, 1H), 7.20 (dd, J=9.5, 3.8 Hz, 1H), 6.95 (dd, J=9.5, 1.7 Hz, 1H), 6.88 (s, 1H), 6.82 (d, J=8.6 Hz, 1H), 6.63 (s, 1H), 6.45 (dd, J=8.6, 2.5 Hz, 1H), 6.32 (d, J=2.5 Hz, 1H), 5.61 (d, J=8.6 Hz, 1H), 5.28-5.20 (m, 1H), 4.94 (d, J=9.2 Hz, 1H), 4.66-4.55 (m, 1H), 4.47 (dd, J=13.1, 6.5 Hz, 1H), 4.37-4.30 (m, 2H), 3.72 (s, 3H), 2.39-2.32 (m, 1H), 1.69-1.53 (m, 4H); MS (ESI–) m/z 526 (M–H)$^-$.

Example 285

(7R)-2,2-difluoro-N-{(2R,4R)-7-methoxy-2-[(6-oxopyridazin-1(6H)-yl)methyl]-3,4-dihydro-2H-1-benzopyran-4-yl}-7-methyl-6,7-dihydro-2H-furo[2,3-f][1,3]benzodioxole-7-carboxamide Example 285A (S)—N-[(1E,3S)-3-hydroxy-1-(2-hydroxy-4-methoxyphenyl)-4-(6-oxopyridazin-1(6H)-yl)butylidene]-2-methylpropane-2-sulfinamide The procedure used for the preparation of Example 284C provided the title compound as the second eluting isomer. $^1$H NMR (400 MHz, CDCl$_3$) δ 13.51 (s, 1H), 7.82 (dd, J=3.8, 1.5 Hz, 1H), 7.59 (d, J=9.0 Hz, 1H), 7.24 (dd, J=9.5, 3.9 Hz, 1H), 7.00 (dd, J=9.4, 1.5 Hz, 1H), 6.46 (dd, J=9.0, 2.6 Hz, 1H), 6.43 (d, J=2.5 Hz, 1H), 4.54 (bs, 1H), 4.50-4.41 (m, 2H), 4.16-4.10 (m, 1H), 3.83 (s, 3H), 3.63 (dd, J=13.6, 9.0 Hz, 1H), 3.34 (dd, J=13.5, 3.5 Hz, 1H), 1.33 (s, 9H); LC/MS (ESI+) m/z 408 (M+H)$^+$.

Example 285B (S)—N-{(2R,E)-7-methoxy-2-[(6-oxopyridazin-1(6H)-yl)methyl]-2,3-dihydro-4H-1-benzopyran-4-ylidene}-2-methylpropane-2-sulfinamide A solution of Example 285A (25 mg, 0.061 mmol) and triphenylphosphine (19.31 mg, 0.074 mmol) in CH$_2$Cl$_2$ (5 mL) was cooled to 0° C., treated dropwise with diethyl azodicarboxylate, 40 wt. % solution in toluene (69.9 µL, 0.153 mmol), stirred at 0° C. for 10 minutes, stirred at room temperature for 30 minutes, diluted with heptanes (about 50 mL), stirred for 15 minutes and filtered to remove the solids. The filtrate was chromatographed on silica gel eluting with a gradient of 15 to 100% [10% ethanol in ethyl acetate] in heptanes to provide the title compound (21 mg, 0.054 mmol, 88% yield). $^1$H NMR (501 MHz, CDCl$_3$) δ 7.90 (d, J=8.9 Hz, 1H), 7.82 (dd, J=3.8, 1.7 Hz, 1H), 7.21 (dd, J=9.5, 3.8 Hz, 1H), 6.96 (dd, J=9.5, 1.7 Hz, 1H), 6.55 (dd, J=8.9, 2.5 Hz, 1H), 6.32 (d, J=2.5 Hz, 1H), 4.81-4.75 (m, 1H), 4.60 (dd, J=13.5, 8.2 Hz, 1H), 4.38 (dd, J=13.5, 4.0 Hz, 1H), 3.79 (s, 3H), 3.58 (dd, J=17.3, 2.9 Hz, 1H), 3.06 (dd, J=17.3, 12.2 Hz, 1H), 1.30 (s, 9H); LC/MS (ESI+) m/z 390 (M+H)$^+$.

Example 285C (S)—N-{(2R,4R)-7-methoxy-2-[(6-oxopyridazin-1(6H)-yl)methyl]-3,4-dihydro-2H-1-benzopyran-4-yl}-2-methylpropane-2-sulfinamide A solution of Example 285B (22 mg, 0.056 mmol) in methanol (2 mL) at 0° C. was treated all at once with NaBH$_4$ (4.92 mg, 0.130 mmol), stirred at 0° C. for 2 hours and partitioned between ethyl acetate (30 mL) and saturated aqueous NaHCO$_3$ solution (5 mL). The ethyl acetate layer was washed with brine, dried (MgSO$_4$), filtered, and concentrated to provide the title compound (22.8 mg, 0.058 mmol, 103% yield). $^1$H NMR (400 MHz, CDCl$_3$) δ 7.80 (dd, J=3.8, 1.6 Hz, 1H), 7.29-7.26 (m, 1H), 7.20 (dd, J=9.4, 3.8 Hz, 1H), 6.96 (dd, J=9.5, 1.6 Hz, 1H), 6.49 (dd, J=8.6, 2.5 Hz, 1H), 6.31 (d, J=2.5 Hz, 1H), 4.71-4.63 (m, 1H), 4.62-4.49 (m, 2H), 4.33 (dd, J=13.2, 5.0 Hz, 1H), 3.73 (s, 3H), 3.32 (d, J=10.6 Hz, 1H), 2.69 (ddd, J=13.3, 6.0, 1.5 Hz, 1H), 1.85 (dt, J=13.3, 11.2 Hz, 1H), 1.29 (s, 9H).

Example 285D

2-{[(2R,4R)-4-amino-7-methoxy-3,4-dihydro-2H-1-benzopyran-2-yl]methyl}pyridazin-3(2H)-one hydrogen chloride A solution of Example 285C (22.8 mg, 0.058 mmol) in methanol (2 mL) was treated with 4 M HCl in dioxane (146 µL, 0.582 mmol), stirred at room temperature for 30 minutes and concentrated. The residue was treated with methyl tert-butyl ether (5 mL) and heptanes (5 mL). The mixture was stirred for 5 minutes and the solid was collected by filtration. The solid was dried under vacuum with heating (55° C.) for 15 minutes to provide the title compound. $^1$H NMR (400 MHz, DMSO-d$_6$) δ 8.70 (bs, 3H), 7.98 (dd, J=3.8, 1.6 Hz, 1H), 7.53 (d, J=8.7 Hz, 1H), 7.46 (dd, J=9.5, 3.8 Hz, 1H), 7.01 (dd, J=9.5, 1.6 Hz, 1H), 6.58 (dd, J=8.7, 2.6 Hz, 1H), 6.32 (d, J=2.5 Hz, 1H), 4.62-4.45 (m, 3H), 4.27 (dd, J=12.8, 4.8 Hz, 1H), 3.70 (s, 3H), 2.43 (dd, J=12.1, 6.2 Hz, 1H), 1.78 (q, J=11.5 Hz, 1H); LC/MS (ESI+) m/z 271 (M−NH$_3$)$^+$.

Example 285E (7R)-2,2-difluoro-N-{(2R,4R)-7-methoxy-2-[(6-oxopyridazin-1(614)-yl)methyl]-3,4-dihydro-2H-1-benzopyran-4-yl}-7-methyl-6,7-dihydro-2H-furo[2,3-f][1,3]benzodioxole-7-carboxamide A solution of Example 285D (0.017 mL, 0.120 mmol) in CH$_2$Cl$_2$ (1 mL) was cooled to 0° C. under N$_2$, treated with a solution of Example 134F (0.025 g, 0.090 mmol) in CH$_2$Cl$_2$ (about 0.5 mL), stirred at 0° C. for 25 minutes and then at room temperature for 25 minutes. The mixture was treated with 37% NH$_4$OH solution (5 drops) and stirred for 5 minutes. The mixture was diluted with ethyl acetate (30 mL), washed with 1 M HCl (5 mL), washed with saturated aqueous NaHCO$_3$ solution (5 mL), washed with brine, dried (MgSO$_4$), filtered, and concentrated. The residue was chromatographed on silica gel eluting with a gradient of 15 to 50% ethyl acetate in heptanes to provide the title compound. $^1$H NMR (501 MHz, CDCl$_3$) δ 7.79 (dd, J=3.8, 1.7 Hz, 1H), 7.20 (dd, J=9.5, 3.8 Hz, 1H), 6.95 (dd, J=9.5, 1.7 Hz, 1H), 6.91 (s, 1H), 6.75 (dd, J=8.6, 0.9 Hz, 1H), 6.62 (s, 1H), 6.44 (dd, J=8.6, 2.6 Hz, 1H), 6.33 (d, J=2.6 Hz, 1H), 5.67 (d, J=8.6 Hz, 1H), 5.26-5.20 (m, 1H), 4.88 (d, J=9.3 Hz, 1H), 4.63-4.57 (m, 1H), 4.47 (dd, J=13.1, 6.5 Hz, 1H), 4.36-4.31 (m, 2H), 3.73 (s, 3H), 2.35 (ddd, J=13.1, 6.3, 1.7 Hz, 1H), 1.66 (s, 3H), 1.59 (dt, J=13.1, 11.2 Hz, 1H); MS (ESI−) m/z 526 (M−H)$^-$.

Example 286

(7R)—N-(1-[(2R)-3-(benzyloxy)-2-hydroxypropyl]-2-{1-[(benzyloxy)methyl]cyclopropyl}-6-fluoro-1H-indol-5-yl)-2,2-difluoro-7-methyl-6,7-dihydro-2H-furo[2,3-f][1,3]benzodioxole-7-carboxamide The product from Example 3B (296.4 mg, 1.148 mmol) was dissolved in dichloromethane (5 mL). Oxalyl chloride (500 μL) and N,N-dimethylformamide (50 μL) were added which resulted in bubbling of the reaction mixture. The reaction was stirred at ambient temperature for 1 hour. The reaction was concentrated, and the residue was dissolved in dichloromethane (2 mL) and concentrated two times. The residue was dissolved in dichloromethane (4 mL) and pyridine (2 mL). The product of Example 136E (323.6 mg, 0.682 mmol) was added, and the reaction mixture was stirred at 60° C. for 21 hours. The reaction mixture was concentrated, and the residue was purified by silica gel chromatography (5% ethyl acetate in dichloromethane, R$_f$=0.44) to yield the title compound (326.6 mg, 63%). $^1$H NMR (400 MHz, DMSO-d$_6$) δ 9.22 (s, 1H), 7.55 (s, 1H), 7.39-7.19 (m, 10H), 7.15 (dd, J=7.4, 2.0 Hz, 2H), 7.03 (s, 1H), 6.31 (s, 1H), 5.15 (d, J=5.3 Hz, 1H), 5.08 (d, J=9.0 Hz, 1H), 4.60-4.48 (m, 2H), 4.44-4.31 (m, 4H), 4.16 (dd, J=14.7, 8.9 Hz, 1H), 4.09-4.00 (m, 1H), 3.59-3.37 (m, 4H), 1.66 (s, 3H), 1.09-0.98 (m, 1H), 0.93-0.81 (m, 3H); MS (ESI+) m/z 715 (M+H)$^+$.

Example 287 ethyl 1-(aminomethyl)-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate A solution of the product of Example 148B (283 mg, 0.45 mmol) in anhydrous tetrahydrofuran (2.5 mL) under nitrogen was cooled with a −70° C. bath and treated dropwise with 1 M potassium bis(trimethylsilyl)amide in tetrahydrofuran (990 μL, 0.99 mmol) over 7 minutes. Dry ice was removed from the bath and the bath was warmed to −20° C. over 80 minutes. It was kept near this temperature for 20 minutes, then cooled back to −50° C. A suspension of paraformaldehyde (54 mg, 1.8 mmol) in tetrahydrofuran (1.0 mL) was added slowly while the bath was kept at or below −45° C. After the addition, the bath was permitted to warm to 0° C., where it was kept 20 minutes before the reaction was quenched with saturated aqueous NH$_4$Cl (500 μL). After a couple minutes the bath was removed and concentrated aqueous NH$_4$OH (500 μL) was also added and thoroughly mixed in. The aqueous phase was removed and extracted twice with ethyl acetate, and the combined organic phases were washed twice with 1:1 concentrated aqueous NH$_4$OH/1 M aqueous Na$_2$CO$_3$ (600 μL) with each wash in turn back-extracted with more ethyl acetate. The combined organic phases were washed with brine, dried (Na$_2$SO$_4$) and placed directly on silica for chromatography (eluted with 0 to 5% concentrated aqueous NH$_4$OH/acetonitrile). The combined fractions were concentrated, washed with dilute brine, dried (Na$_2$SO$_4$), filtered, and concentrated to 156 mg of a white foam (52%). $^1$H NMR (400 MHz, CD$_2$Cl$_2$) δ 6.96-6.91 (m, 2H), 6.72-6.68 (m, 1H), 6.65 (s, 1H), 6.65-6.63 (m, 1H), 5.68 (d, J=9.0 Hz, 1H), 5.28-5.20 (m, 1H), 4.90 (d, J=9.3 Hz, 1H), 4.35 (d, J=9.3 Hz, 1H), 4.15 (q, J=7.1 Hz, 2H), 3.95-3.89 (m, 1H), 2.28-2.16 (m, 3H), 1.92-1.85 (m, 1H), 1.72-1.46 (m, 7H?), 1.31-1.04 (m, 8H); MS (ESI) m/z=657 (M+H)$^+$.

Example 288

4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]-1-(hydroxymethyl)cyclohexane-1-carboxylic acid Example 288A ethyl 4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]-1-(hydroxymethyl)cyclohexane-1-carboxylate A solution of the product from example 148B (63 mg, 100 μmol) in anhydrous tetrahydrofuran (700 μL) under nitrogen was cooled with a −40° C. bath. 1 M lithium bis(trimethylsilyl)amide in tetrahydrofuran (240 μL, 0.24 mmol) was added dropwise and the reaction mixture was stirred near −40° C. for 30 minutes. A suspension of paraformaldehyde (9 mg, 0.3 mmol) in tetrahydrofuran (200 μL) was added and the mixture was stirred near −35° C. for another 30 minutes, then allowed to warm to 15° C. over two hours. The reaction was quenched with saturated aqueous NH₄Cl (100 μL) and concentrated aqueous NH₄OH (200 μL). The aqueous phase was separated and extracted with ethyl acetate and the combined organic phases were washed with 1:1 concentrated aqueous NH₄OH/brine. The separated aqueous phase was again extracted with ethyl acetate and the combined organic phases were dried (Na₂SO₄), filtered, and concentrated. The residue was chromatographed on silica (eluted with 1:9 ethyl acetate/CH₂Cl₂ then 1% acetic acid in 1:9 ethyl acetate/CH₂Cl₂) to give 17 mg of a clear gum (25%). MS (ESI) m/z=656 (M−H)⁻.

Example 288B

4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]-1-(hydroxymethyl)cyclohexane-1-carboxylic acid The product of example 288A (17 mg, 26 μmol) was dissolved in dioxane (250 μL), treated with 2 M aqueous NaOH (150 μL), heated at 75° C. for four hours, and then stirred at room temperature for three weeks. The reaction mixture was quenched with 3 M aqueous citric acid (80 μL) and extracted with methyl tert-butyl ether. The combined extracts were washed with brine, dried (Na₂SO₄), concentrated, taken up into dichloromethane, filtered, and reconcentrated to 16 mg of an amber syrup (98%). $^1$H NMR (501 MHz, CDCl₃) δ 7.33-7.20 (m, 2H), 6.92-6.90 (m, 1H), 6.88-6.83 (m, 1H), 6.72-6.62 (m, 3H), 5.69-5.64 (m, 1H), 5.29-5.21 (m, 1H), 4.91-4.87 (m, 1H), 4.37-4.32 (m, 1H), 3.99-3.89 (m, 1H), 3.64-3.58 (m, 1H), 2.33-2.20 (m, 2H), 2.01-1.88 (m, 1H), 1.85-1.12 (m, 11H); MS (ESI) m/z=628 (M−H)⁻.

Example 289

1-(aminomethyl)-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid The product of Example 287 (115 mg, 0.17 mmol) was dissolved in dioxane (1.5 mL), treated with 2 M aqueous NaOH (1.0 mL) and heated at 75° C. for over four hours, stirred at room temperature for three weeks and then heated again at 75° C. for 41 hours. The reaction mixture was quenched with 3 M aqueous citric acid (250 μL) and filtered through diatomaceous earth with a thorough ethyl acetate rinse. The aqueous phase of the filtrate was separated and extracted with ethyl acetate. The combined organic phases were dried (Na₂SO₄), filtered, concentrated and passed through an Alltech ExtractClean C18 column (eluted with 20 to 100% methanol/H₂O) to give 71 mg of an off-white powder (64%). $^1$H NMR (400 MHz, CD₃OD) δ 7.20 (s, 1H), 7.10-7.06 (m, 1H), 6.78-6.71 (m, 2H), 6.64-6.61 (m, 1H), 5.28-5.22 (m, 1H), 5.01-4.97 (m, 1H), 4.38-4.34 (m, 1H), 4.04-3.98 (m, 1H), 3.20 (s, 2H), 2.84-2.79 (m, 1H), 2.28-2.03 (m, 3H), 1.89-1.75 (m, 2H), 1.74-1.49 (m, 7H?), 1.35-1.27 (m, 1H), 1.2-1.11 (m, 1H); MS (ESI) m/z=627 (M−H)⁻.

Example 290 trans-4-[(2R,4R)-6-bromo-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid $^1$H NMR (400 MHz, CDCl₃) δ 6.96 (s, 1H), 6.85 (d, J=1.0 Hz, 1H), 6.65 (s, 1H), 6.35 (s, 1H), 5.63 (d, J=8.9 Hz, 1H), 5.26-5.13 (m, 1H), 4.88 (d, J=9.4 Hz, 1H), 4.36 (d, J=9.4 Hz, 1H), 3.90 (ddd, J=11.4, 5.5, 1.4 Hz, 1H), 3.82 (s, 3H), 2.38-2.18 (m, 2H), 2.18-1.99 (m, 3H), 1.68 (s, 3H), 1.65-1.38 (m, 5H), 1.30-1.10 (m, 3H). LC/MS (ESI−) m/z 624.1 (M−H)⁻.

Example 291 trans-4-[(2R,4R)-4-{[(7R)-2,2-difluoro-4-iodo-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid 1H NMR (400 MHz, CDCl₃) δ 6.89 (s, 1H), 6.82 (d, J=8.6 Hz, 1H), 6.48 (dd, J=8.6, 2.6 Hz, 1H), 6.37 (d, J=2.6 Hz, 1H), 5.65 (d, J=8.7 Hz, 1H), 5.34-5.13 (m, 1H), 5.00 (d, J=9.4 Hz, 1H), 4.45 (d, J=9.4 Hz, 1H), 3.91 (dd, J=11.3, 5.5 Hz, 1H), 3.83-3.69 (s, 3H), 2.39-2.21 (m, 3H), 2.17-1.98 (m, 3H), 1.88 (td, J=6.1, 5.6, 2.8 Hz, 1H), 1.70 (s, 3H), 1.65-1.39 (m, 4H), 1.26 (dtd, J=30.1, 12.8, 3.3 Hz, 2H); LC/MS (ESI−) m/z 670.1 (M−H)⁻.

Example 292

4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid $^1$H NMR (700 MHz, CDCl₃) δ 6.86 (s, 1H), 6.82 (d, J=8.5 Hz, 1H), 6.64 (s, 1H), 6.44 (dd, J=8.5, 2.6 Hz, 1H), 6.33 (d, J=2.6 Hz, 1H), 5.56 (d, J=8.8 Hz, 1H), 5.23 (m, 1H), 4.92 (d, J=9.2 Hz, 1H), 4.36 (d, J=9.2 Hz, 1H), 3.89 (m, 1H), 3.74 (s, 3H), 2.33 (tt, J=12.3, 3.5 Hz, 1H), 2.26 (dd, J=12.8, 6.2 Hz, 1H), 2.11 (m, 2H), 2.07 (m, 1H), 1.86 (m, 1H), 1.64 (s, 3H), 1.59 (m, 1H), 1.47 (m, 2H), 1.22 (m, 2H); MS(ESI−) m/z 544 (M−H)⁻.

Example 293

4-[(2S,4S)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid $^1$H NMR (700 MHz, CDCl₃) δ 6.91 (s, 1H), 6.77 (d, J=8.6 Hz, 1H), 6.63 (s, 1H), 6.44 (dd, J=8.6, 2.6 Hz, 1H), 6.34 (d, J=2.6 Hz, 1H), 5.60 (d, J=8.7 hz, 1H), 5.21 (m, 1H), 4.89 (d, J=9.3 Hz, 1H), 4.34 (d, J=9.3 Hz, 1H), 3.89 (m, 1H), 3.75 (s, 3H), 2.31 (tt, J=12.3, 3.7 Hz, 1H), 2.25 (dd, J=12.8, 6.2 Hz, 1H), 2.10 (m, 2H), 2.04 (m, 1H), 1.85 (m, 1H), 1.67 (s, 3H), 1.57 (m, 1H), 1.46 (m, 2H), 1.24 (m, 2H); MS(ESI−) m/z 544 (M−H)⁻.

Determination of Biological Activity

Cellular Assays
Cell Surface Expression-Horse Radish Peroxidase (CSE-HRP) Assay:

A cellular assay for measuring the F508delCFTR cell surface expression after correction with test compounds was developed in human lung derived epithelial cell line (CFBE41o-) (Veit G et al, (2012) Mol Biol Cell. 23(21): 4188-4202). This was achieved by expressing the F508delCFTR mutation along with a horseradish peroxidase (HRP) in the fourth exofacial loop and then measuring the HRP activity using luminescence readout from these cells, CFBE41o-F508delCFTR-HRP, that were incubated overnight with the test corrector compounds. Briefly, for this primary assay, the CFBE41o-F508delCFTR-HRP cells were plated in 384-well plates (Greiner Bio-one; Cat 781080) at 4,000 cells/well along with 0.5 µg/mL doxycycline to induce the F508delCFTR-HRP expression and further incubated at 37° C., 5% $CO_2$ for 72 hours. The test compounds were then added at the required concentrations and further incubated for 18-24 hours at 33° C. The highest concentration tested was 20 µM with an 8-point concentration response curve using a 3-fold dilution. Three replicate plates were run to determine one $EC_{50}$. All plates contained negative controls (dimethyl sulfoxide, DMSO) and positive controls (3 µM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) as well as on-plate concentration response of the positive control. Post incubation, the plates were washed 5× times with Dulbecco's phosphate buffered saline (DPBS), followed by the addition of the HRP substrate, luminol (50 µL), and measuring the HRP activity using luminescence readout on EnVision® Multilabel Plate Reader (Perkin Elmer; product number 2104-0010). The raw counts from the experiment are analyzed using Accelrys® Assay Explorer v3.3.

Z' greater than 0.5 was used as passing quality control criteria for the plates.

The Z' is defined as:

$$1-[3*SD_{Positive\ Control}+3*SD_{Negative\ Control}/Absolute\ (Mean_{Positive\ Control}-Mean_{Negative\ Control})]$$

wherein "SD" is standard deviation.

The % activity measured at each of the 8 test concentrations of the test compound was normalized to the on-plate positive control using the following formula:

% activity=[(test compound response DMSO response)/(positive control response DMSO response)]*100

The maximum % activity achieved for the test compound at any tested concentration is presented in Table 1 along with the $EC_{50}$ calculated using the following general sigmoidal curve with variable Hill slope equation (described as Model 42 in the Accelrys® Assay Explorer v3.3 software):

$$y=(a-d)/(1+(x/c)^b)+d$$

General sigmoidal curve with concentration, response, top, bottom, $EC_{50}$ and Hill slope.

This model describes a sigmoidal curve with an adjustable baseline, a. The equation can be used to fit curves where response is either increasing or decreasing with respect to the independent variable, "x".
"x" is a concentration of drug under test.
"y" is the response.
"a" is the maximum response, and "d" is the minimum response
"c" is the inflection point ($EC_{50}$) for the curve. That is, "y" is halfway between the lower and upper asymptotes when x=c.
"b" is the slope-factor or Hill coefficient. The sign of b is positive when the response increases with increasing dose and is negative when the response decreases with increasing dose (inhibition).

TABLE 1

CSE-HRP data

| Example | $EC_{50}$ (µM) | Maximum % activity (%) |
|---|---|---|
| 1 | 2.05 | 100 |
| 2 | 0.30 | 159 |
| 3 | >20 | 3 |
| 4 | >20 | 12 |
| 5 | 3.21 | 137 |
| 6 | 0.29 | 157 |
| 7 | 3.77 | 124 |
| 8 | 1.47 | 126 |
| 9 | 1.03 | 135 |
| 10 | 0.41 | 121 |
| 11 | 0.51 | 166 |
| 12 | >20 | 14 |
| 13 | 8.81 | 72 |
| 14 | 0.38 | 187 |
| 15 | 0.15 | 143 |
| 16 | 0.06 | 150 |
| 17 | 8.77 | 31 |
| 18 | 5.75 | 91 |
| 19 | 0.08 | 130 |
| 20 | 0.03 | 150 |
| 21 | 1.26 | 162 |
| 22 | 0.64 | 156 |
| 23 | 0.18 | 127 |
| 24 | 1.18 | 70 |
| 25 | 1.16 | 82 |
| 26 | 0.98 | 85 |
| 27 | 0.81 | 82 |
| 28 | 1.42 | 112 |
| 29 | 1.07 | 155 |
| 30 | 0.98 | 122 |
| 31 | >20 | 7 |
| 32 | 0.88 | 144 |
| 33 | 1.18 | 131 |
| 34 | 0.48 | 109 |
| 35 | 0.94 | 76 |
| 36 | 1.24 | 79 |
| 37 | 0.73 | 83 |
| 38 | 4.56 | 22 |
| 39 | 1.26 | 106 |
| 40 | 0.21 | 132 |
| 41 | >20 | 3 |
| 42 | 1.06 | 61 |
| 43 | 2.51 | 93 |
| 44 | 0.93 | 114 |
| 45 | 0.92 | 111 |
| 46 | 0.43 | 142 |
| 47 | 0.12 | 120 |
| 48 | 2.77 | 27 |
| 49 | 0.21 | 116 |
| 50 | 1.67 | 75 |
| 51 | 0.93 | 153 |
| 52 | 0.96 | 77 |
| 53 | >20 | 1 |
| 54 | 6.45 | 151 |
| 55 | 6.62 | 159 |
| 56 | 0.88 | 107 |
| 57 | 1.77 | 99 |
| 58 | 0.42 | 104 |
| 59 | 2.75 | 50 |
| 60 | 0.63 | 152 |
| 61 | >20 | 8 |
| 62 | >20 | 12 |
| 63 | 8.64 | 41 |
| 64 | 7.29 | 46 |

TABLE 1-continued

| Example | EC$_{50}$ (μM) | Maximum % activity (%) |
|---|---|---|
| 65 | >20 | 1 |
| 66 | 4.11 | 160 |
| 67 | 8.39 | 70 |
| 68 | 4.47 | 44 |
| 69 | 1.39 | 183 |
| 70 | 1.30 | 116 |
| 71 | 1.23 | 128 |
| 72 | 9.20 | 28 |
| 73 | 2.65 | 117 |
| 74 | 0.70 | 105 |
| 75 | 1.73 | 94 |
| 76 | 0.72 | 111 |
| 77 | 6.63 | 116 |
| 78 | 0.57 | 95 |
| 79 | 1.18 | 151 |
| 80 | 4.75 | 147 |
| 81 | 1.40 | 200 |
| 82 | 3.16 | 116 |
| 83 | 0.24 | 172 |
| 84 | 7.51 | 46 |
| 85 | 6.69 | 90 |
| 86 | 2.84 | 112 |
| 87 | 1.86 | 100 |
| 88 | 0.73 | 113 |
| 89 | 0.01 | 112 |
| 90 | 0.62 | 127 |
| 91 | 0.21 | 116 |
| 92 | 1.72 | 98 |
| 93 | 1.53 | 89 |
| 94 | >20 | 8 |
| 95 | 0.59 | 167 |
| 96 | 1.31 | 139 |
| 97 | 0.48 | 148 |
| 98 | 1.14 | 143 |
| 99 | 0.23 | 71 |
| 100 | 0.45 | 85 |
| 101 | 0.87 | 116 |
| 102 | 8.29 | 61 |
| 103 | 1.72 | 170 |
| 104 | >20 | 16 |
| 105 | >20 | 5 |
| 106 | 14.14 | 18 |
| 107 | 3.04 | 136 |
| 108 | 1.99 | 89 |
| 109 | 0.58 | 89 |
| 110 | 3.02 | 120 |
| 111 | 0.54 | 91 |
| 112 | 0.99 | 131 |
| 113 | 1.11 | 83 |
| 114 | 0.75 | 98 |
| 115 | 1.00 | 147 |
| 116 | 1.10 | 136 |
| 117 | 1.39 | 147 |
| 118 | 1.22 | 123 |
| 119 | 1.18 | 136 |
| 120 | 1.44 | 253 |
| 121 | 11.07 | 23 |
| 122 | 1.94 | 173 |
| 123 | 1.53 | 189 |
| 124 | 0.74 | 124 |
| 125 | 1.39 | 136 |
| 126 | 0.62 | 140 |
| 127 | 0.46 | 140 |
| 128 | 4.96 | 172 |
| 129 | 2.26 | 129 |
| 130 | 0.39 | 105 |
| 131 | 1.31 | 173 |
| 132 | 0.33 | 138 |
| 133 | 0.30 | 132 |
| 134 | 0.48 | 109 |
| 135 | 2.56 | 58 |
| 136 | 0.91 | 99 |
| 137 | 2.06 | 72 |
| 138 | 7.65 | 23 |
| 139 | 0.02 | 158 |
| 140 | 1.30 | 49 |
| 141 | 0.96 | 39 |
| 142 | 2.50 | 180 |
| 143 | 0.49 | 129 |
| 89E | 0.018 | 116 |
| 144 | 1.330 | 157 |
| 145 | 0.003 | 118 |
| 146 | 0.335 | 153 |
| 147 | 2.240 | 79 |
| 148 | 0.041 | 145 |
| 149 | 2.200 | 44 |
| 150 | 0.026 | 145 |
| 151 | 0.012 | 132 |
| 152 | 0.806 | 102 |
| 153 | 0.304 | 135 |
| 154 | 0.915 | 103 |
| 155 | 0.092 | 137 |
| 156 | 0.090 | 142 |
| 157 | 0.168 | 117 |
| 158 | 3.670 | 111 |
| 159 | 1.020 | 82 |
| 160 | 0.044 | 136 |
| 161 | 5.090 | 101 |
| 162 | 0.712 | 120 |
| 163 | 0.810 | 75 |
| 164 | 0.106 | 122 |
| 165 | 2.640 | 85 |
| 166 | 0.030 | 129 |
| 167 | 0.053 | 135 |
| 168 | 0.161 | 127 |
| 169 | 1.26 | 107 |
| 170 | 1.26 | 65 |
| 171 | 0.66 | 92 |
| 172 | 0.95 | 210 |
| 173 | 0.09 | 132 |
| 174 | 0.12 | 118 |
| 175 | 0.22 | 139 |
| 176 | 0.27 | 118 |
| 177 | 0.09 | 127 |
| 178 | 0.29 | 158 |
| 179 | 0.28 | 108 |
| 180 | 0.02 | 124 |
| 181 | 0.03 | 129 |
| 182 | 1.68 | 195 |
| 183 | 2.22 | 60 |
| 184 | >20 | 12 |
| 185 | 3.35 | 31 |
| 186 | 0.67 | 189 |
| 187 | 2.54 | 129 |
| 188 | >20 | 20 |
| 189 | 2.03 | 186 |
| 190 | 0.09 | 115 |
| 191 | 0.07 | 123 |
| 192 | 0.09 | 126 |
| 193 | 0.18 | 118 |
| 194 | 0.06 | 143 |
| 195 | 0.34 | 101 |
| 196 | 0.40 | 105 |
| 197 | 0.04 | 130 |
| 198 | 1.07 | 106 |
| 199 | 0.21 | 149 |
| 200 | 0.07 | 132 |
| 201 | 1.61 | 71 |
| 202 | >20 | 8 |
| 203 | 0.66 | 125 |
| 204 | 0.31 | 134 |
| 205 | >20 | 18 |
| 206 | 1.95 | 84 |
| 207 | 0.35 | 69 |
| 208 | 0.01 | 103 |
| 209 | 0.03 | 122 |
| 210 | 0.03 | 147 |
| 211 | 0.03 | 124 |
| 212 | 0.03 | 119 |
| 213 | 0.08 | 117 |
| 214 | 0.06 | 114 |
| 215 | 0.03 | 113 |

TABLE 1-continued

CSE-HRP data

| Example | EC$_{50}$ (µM) | Maximum % activity (%) |
|---|---|---|
| 216 | 0.03 | 130 |
| 217 | 0.12 | 104 |
| 218 | 0.01 | 116 |
| 219 | 0.03 | 105 |
| 220 | 0.01 | 112 |
| 221 | 0.08 | 125 |
| 222 | 0.02 | 116 |
| 223 | 0.07 | 157 |
| 224 | 0.31 | 199 |
| 225 | 4.02 | 54 |
| 226 | >20 | 18 |
| 227 | 0.07 | 113 |
| 228 | 0.09 | 108 |
| 229 | 0.11 | 118 |
| 230 | 0.06 | 115 |
| 231 | 0.25 | 103 |
| 232 | 0.26 | 117 |
| 233 | 0.05 | 112 |
| 234 | 0.04 | 112 |
| 235 | 0.05 | 114 |
| 236 | 0.07 | 131 |
| 237 | 0.05 | 121 |
| 238 | 0.08 | 113 |
| 239 | 0.04 | 111 |
| 240 | 0.06 | 132 |
| 241 | 0.04 | 110 |
| 242 | 0.04 | 116 |
| 243 | 0.07 | 112 |
| 244 | 0.03 | 114 |
| 245 | 0.05 | 107 |
| 246 | 0.08 | 125 |
| 247 | 1.18 | 181 |
| 248 | 0.09 | 116 |
| 249 | 0.10 | 110 |
| 250 | 0.02 | 135 |
| 251 | 0.03 | 128 |
| 252 | 0.09 | 110 |
| 253 | 0.06 | 150 |
| 254 | 0.08 | 136 |
| 255 | 0.09 | 158 |
| 256 | 0.06 | 168 |
| 257 | 0.07 | 170 |
| 258 | 0.11 | 174 |
| 259 | 0.08 | 163 |
| 260 | 0.13 | 174 |
| 261 | 0.06 | 157 |
| 262 | 0.09 | 184 |
| 263 | 0.07 | 167 |
| 264 | 0.06 | 186 |
| 265 | 0.08 | 173 |
| 266 | 0.11 | 160 |
| 267 | 0.09 | 166 |
| 268 | 0.12 | 186 |
| 269 | 0.05 | 192 |
| 270 | 0.18 | 229 |
| 271 | 0.06 | 172 |
| 272 | 0.26 | 108 |
| 273 | 0.12 | 92 |
| 274 | 0.85 | 99 |
| 275 | >20 | 7 |
| 276 | 0.70 | 117 |
| 277 | 0.66 | 110 |
| 278 | 1.54 | 86 |
| 279 | 0.56 | 119 |
| 280 | >20 | 10 |
| 281 | 0.47 | 154 |
| 282 | 1.86 | 135 |
| 283 | 1.76 | 95 |
| 284 | 3.96 | 40 |
| 285 | 1.13 | 54 |
| 286 | 0.21 | 120 |
| 287 | 0.64 | 199 |
| 288 | 0.29 | 138 |
| 289 | 0.64 | 140 |
| 290 | 0.53 | 189 |
| 291 | 0.67 | 117 |
| 292 | 7.54 | 99 |
| 293 | 1.63 | 115 |

Transepithelial Clamp Circuit on Human Bronchial Epithelial Cells Conductance Assay:

A cell based assay using the primary human bronchial epithelial cells (hBE) was used as a secondary assay to test novel F508delCFTR correctors for their activity on primary hBE cells with F508del/F508del CFTR mutation. The assay used a TECC-24 (Transepithelial Clamp Circuit for 24 wells) instrument that measures the functionality of the mutated channel by measuring the equivalent short circuit current (Ieq) generated by the polarized epithelial cells. The instrument works by measuring the transepithelial potential difference (Vt) and transepithelial resistance (Rt) in an open circuit format, and the Ieq is calculated by using Ohms law (Ieq=Vt/Rt). The assay was run in a 24-well format and all 24-wells were measured at the same time point giving a higher throughput for this assay.

Primary human bronchial epithelial (hBE) cells from F508del/F508delCFTR patients were expanded from $1 \times 10^6$ to $250 \times 10^6$ cells (Neuberger T, Burton B, Clark H and VanGoor F; Cystic Fibrosis, Methods in Mole Biol 741; eds. Amaral M D and Kunzelmann K, 2011). For this purpose, cells isolated from CF patients with the homozygous mutation were seeded onto 24 well Corning (Cat #3378) filter plates that were coated with 3T3 conditioned media and grown at an air-liquid interface for 35 days using an Ultroser® G supplemented differentiation media. Apical surface mucus was removed 72 hours before the experiment using 3 mM dithiothreitol (DTT) in phosphate buffered saline (PBS). The apical surface was washed again 24 hours before the experiment using PBS. The cells were incubated with the desired dose response of the corrector compounds 18-24 hours at 37° C., 5% $CO_2$. The corrector compounds are only added on the basolateral side of the epithelial cells.

On the day of measuring the corrector activity on the TECC, the cells were switched into a bicarbonate and serum free F-12 Coon's medium and allowed to equilibrate for 90 minutes in a $CO_2$ free incubator. At the time of measurement, the apical and basolateral sides of the filter were bathed with the F-12 Coon's modification media (with 20 mM 4-(2-hydroxyethyl)-1-piperazineethanesulfonic acid (HEPES), pH 7.4 (using 1 M tris(hydroxymethyl)aminomethane (Tris)), and the measurements were made at 36.5° C. Transepithelial voltage (Vt) and transepithelial resistance (Rt) were measured using a 24 channel transepithelial current clamp (TECC-24). Current responses to the sequential addition of benzamil (apical 6 µM addition; for inhibiting epithelial ENaC channel), forskolin (apical and basolateral 10 µM addition; for activating the CFTR channel), control potentiator (N-(3-carbamoyl-5,5,7,7-tetramethyl-4,7-dihydro-5H-thieno[2,3-c]pyran-2-yl)-1H-pyrazole-5-carboxamide; apical and basolateral 1 KM addition; for potentiating the CFTR channel) and bumetanide (basolateral 20 µM addition; for inhibiting the Na:2Cl:K co-transporter, an indirect measure of inhibiting the Cl-secretion driven by CFTR channel) were measured.

All plates contained negative controls (dimethyl sulfoxide, DMSO) which coupled with the control potentiator (N-(3-carbamoyl-5,5,7,7-tetramethyl-4,7-dihydro-5H- thieno[2,3-c]pyran-2-yl)-1H-pyrazole-5-carboxamide) sets the null response and positive controls (3 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) coupled with the control potentiator sets the 100% response to measure the correction of the mutated CFTR channel. The maximum percent activity is reported relative to the positive control value.

The % activity measured at each of the 6 test concentrations of the test compound was normalized to the on-plate positive control using the following formula:

% activity=[(test compound response DMSO response)/(positive control response DMSO response)]*100

The following log(agonist) vs response using a four parameters variable slope was used to calculate $EC_{50}$ (4 PL in Prism v 5 software):

$$F(x)=D+(A-D)/(1+(x/C)^B)$$

Where:
"x" is a concentration of drug under test.
"F(x)" is the response.
"A" is the maximum response, and "D" is the minimum response
"C" is the inflection point ($EC_{50}$) for the curve. That is, "F(x)" is halfway between the lower and upper asymptotes when x=C.
"B" is the slope-factor or Hill coefficient. The sign of B is positive when the response increases with increasing dose and is negative when the response decreases with increasing dose (inhibition).

The maximum percent activity and $EC_{50}$ values for tested corrector compounds are presented in Table 2.

TABLE 2

| hBE-TECC data | | |
|---|---|---|
| Example | $EC_{50}$ (μM) | Maximum % activity (%) |
| 2 | 0.242 | 99 |
| 6 | 0.199 | 103 |
| 20 | 0.011 | 98 |
| 21 | 0.468 | 94 |
| 37 | 0.564 | 70 |
| 44 | 0.246 | 83 |
| 46 | 0.22 | 105 |
| 47 | 0.032 | 100 |
| 130 | 0.067 | 72 |
| 134 | 0.197 | 79 |
| 135 | 2.7 | 62 |
| 136 | 0.745 | 48 |
| 137 | 2.58 | 67 |
| 144 | 0.55 | 78 |
| 145 | 0.000831 | 91 |
| 146 | 0.16 | 89 |
| 149 | 0.83 | 24 |
| 150 | 0.010 | 94 |
| 151 | 0.0076 | 93 |
| 155 | 0.020 | 102 |
| 160 | 0.005 | 85 |
| 162 | 0.020 | 86 |
| 166 | 0.011 | 84 |
| 167 | 0.087 | 112 |
| 168 | 0.043 | 101 |
| 171 | 0.352 | 45 |
| 172 | 0.098 | 50 |
| 174 | 0.015 | 94 |
| 175 | 0.043 | 107 |
| 177 | 0.013 | 99 |
| 178 | 0.066 | 108 |
| 179 | 0.147 | 70 |
| 192 | 0.006 | 103 |

TABLE 2-continued

| hBE-TECC data | | |
|---|---|---|
| Example | $EC_{50}$ (μM) | Maximum % activity (%) |
| 197 | 0.006 | 105 |
| 206 | 1.028 | 79 |
| 213 | 0.041 | 82 |
| 214 | 0.016 | 88 |
| 220 | 0.010 | 94 |
| 243 | 0.021 | 87 |
| 248 | 0.032 | 105 |
| 250 | 0.001 | 95 |
| 251 | 0.005 | 86 |
| 252 | 0.032 | 106 |
| 256 | 0.010 | 106 |
| 260 | 0.069 | 129 |
| 261 | 0.021 | 104 |
| 263 | 0.004 | 118 |
| 281 | 0.117 | 134 |
| 282 | 0.282 | 100 |

The maximum % activities achieved for test compounds at the specified tested concentration are presented in Table 3

TABLE 3

| Example | testing concentration (μM) | Maximum % activity (%) |
|---|---|---|
| 11 | 1 | 91 |
| 25 | 10 | 61 |
| 27 | 3 | 54 |
| 30 | 10 | 47 |
| 32 | 3 | 51 |
| 35 | 3 | 80 |
| 36 | 10 | 77 |
| 39 | 3 | 47 |
| 83 | 10 | 100 |
| 89 | 1 | 84 |
| 90 | 1 | 65 |
| 95 | 1 | 50 |

It is understood that the foregoing detailed description and accompanying examples are merely illustrative and are not to be taken as limitations upon the scope of the invention, which is defined solely by the appended claims and their equivalents. Various changes and modifications to the described embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

We claim:

1. A compound of formula (I) or a pharmaceutically acceptable salt thereof,

(I)

wherein

R$^1$ is H or C$_1$-C$_3$ alkyl;

X is formula (a) or formula (b)

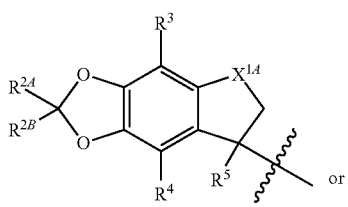
(a)

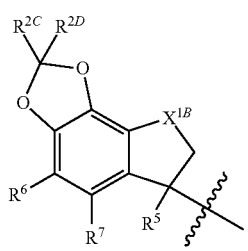
(b)

wherein

R$^{2A}$, R$^{2B}$, R$^{2C}$, and R$^{2D}$, are each independently hydrogen or halogen;

R$^3$, R$^4$, R$^6$, and R$^7$, are each independently hydrogen, C$_1$-C$_3$ alkyl, or halogen;

R$^5$, at each occurrence, is independently hydrogen, C$_1$-C$_3$ alkyl, C$_2$-C$_4$ alkenyl, or C$_1$-C$_3$ haloalkyl;

X$^{1A}$ is O or CH$_2$;

X$^{1B}$ is O or CH$_2$;

Y is -G$^1$, or Y is formula (c), (d), (e), (f), or (g);

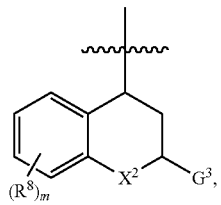
(c)

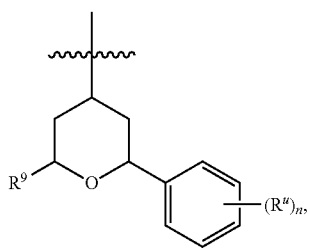
(d)

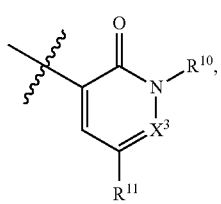
(e)

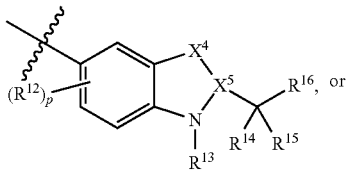
(f)

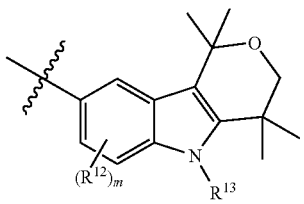
(g)

wherein

G$^1$ is phenyl or monocyclic heteroaryl, each of which is optionally substituted with 1, 2, or 3 independently selected R$^p$ groups; wherein each R$^p$ is independently C$_1$-C$_6$ alkyl, halogen, C$_1$-C$_6$ haloalkyl, G$^2$, C$_1$-C$_3$ alkoxy, C$_1$-C$_3$ haloalkoxy, —C(O)-G$^A$, —C(O)NR$^A$R$^B$, or —NR$^A$R$^B$; wherein R$^A$, at each occurrence, is independently hydrogen, C$_1$-C$_6$ alkyl, or C$_1$-C$_6$ haloalkyl;

R$^B$, at each occurrence, is independently hydrogen, C$_1$-C$_6$ haloalkyl, or C$_1$-C$_6$ alkyl which is optionally substituted with 1 or 2 —OH;

G$^A$ is a C$_3$-C$_6$ cycloalkyl or a 4-6 membered monocyclic heterocycle; each of which is optionally substituted with 1, 2, or 3 substituents independently selected from the group consisting of halogen, C$_1$-C$_6$ alkyl, C$_1$-C$_6$ haloalkyl, —OH, C$_1$-C$_3$ alkoxy, and C$_1$-C$_3$ haloalkoxy; and G$^2$ is phenyl, heterocycle, or monocyclic heteroaryl; each of which is optionally substituted with 1, 2, or 3 independently selected R$^q$ groups;

X$^2$ is O or N(R$^{2x}$) wherein R$^{2x}$ is hydrogen, C$_1$-C$_3$ alkyl, or C$_1$-C$_3$ haloalkyl;

X$^3$ is N or CH;

X$^4$-X$^5$ is N═C, C(R$^{4x}$)═C, or C(R$^{4x}$)$_2$—C(R$^{5x}$), wherein R$^{4x}$ and R$^{5x}$, at each occurrence, are each independently hydrogen, halogen, C$_1$-C$_3$ alkyl, or C$_1$-C$_3$ haloalkyl;

R$^8$ groups are optional substituents on the benzo ring, and are each independently halogen, C$_1$-C$_3$ alkyl, C$_1$-C$_3$ haloalkyl, C$_1$-C$_3$ alkoxy, or C$_1$-C$_3$ haloalkoxy;

m is 0, 1, 2, 3, or 4;

G$^3$ is —(C$_1$-C$_3$ alkylenyl)-OR$^g$, —(C$_1$-C$_3$ alkylenyl)-G$^B$, phenyl, cycloalkyl, 4-6 membered monocyclic heterocycle, or monocyclic heteroaryl; wherein the phenyl, the cycloalkyl, the 4-6 membered monocyclic heterocycle, and the monocyclic heteroaryl are each optionally substituted with 1, 2, or 3 independently selected R$^s$ groups;

G$^B$ is phenyl, cycloalkyl, 4-6 membered monocyclic heterocycle, or monocyclic heteroaryl; each of which is optionally substituted with 1, 2, or 3 independently selected R$^s$ groups;

R$^9$ is C$_1$-C$_3$ alkyl, C$_3$-C$_6$ cycloalkyl, or phenyl; wherein the C$_3$-C$_6$ cycloalkyl and the phenyl are each optionally substituted with 1, 2, or 3 substituents independently selected from the group consisting of halogen, —OH, C$_1$-C$_3$ alkyl, C$_1$-C$_3$ haloalkyl, C$_1$-C$_3$ alkoxy, and C$_1$-C$_3$ haloalkoxy;

n is 0, 1, 2, or 3;

$R^{10}$ is $C_1$-$C_6$ alkyl substituted with 1, 2, or 3 substituents independently selected from the group consisting of halogen, OH, $C_1$-$C_3$ alkoxy, $C_1$-$C_3$ haloalkoxy, and 2,2-dimethyl-1,3-dioxolan-4-yl; or $R^{10}$ is phenyl, $C_3$-$C_6$ cycloalkyl, or monocyclic heteroaryl, wherein the phenyl, $C_3$-$C_6$ cycloalkyl, and monocyclic heteroaryl are each optionally substituted with 1, 2, or 3 independently selected $R^v$ groups;

$R^{11}$ is halogen, $C_1$-$C_3$ alkyl, or $G^4$ wherein $G^4$ is $C_3$-$C_6$ cycloalkyl, 4-6 membered monocyclic heterocycle, monocyclic heteroaryl, or phenyl; each $G^4$ is optionally substituted with 1, 2, or 3 independently selected $R^w$ groups;

$R^{12}$ are optional substituents of the benzo ring, and are each independently halogen, $C_1$-$C_3$ alkyl, or $C_1$-$C_3$ haloalkyl;

p is 0, 1, 2, or 3;

$R^{13}$ is hydrogen or $C_1$-$C_6$ alkyl which is substituted with 1, 2, or 3 substituents independently selected from the group consisting of —CN, 2,2-dimethyl-1,3-dioxolan-4-yl, —OR$^{13a}$, —O-benzyl, —N(R$^{13a}$)$_2$, —N(R$^{13a}$)S(O)$_2$R$^{13b}$, and —N(R$^{13a}$)C(O)R$^{13b}$, wherein $R^{13a}$, at each occurrence, is independently hydrogen, $C_1$-$C_6$ alkyl, or $C_1$-$C_6$ haloalkyl, and $R^{13b}$, at each occurrence, is independently $C_1$-$C_6$ alkyl or $C_1$-$C_6$ haloalkyl;

$R^{14}$ and $R^{15}$ are each independently $C_1$-$C_3$ alkyl, or $R^{14}$ and $R^{15}$, together with the carbon atom to which they are attached, form a $C_3$-$C_6$ cycloalkyl or a 4-6 membered monocyclic heterocycle containing one heteroatom selected from the group consisting of oxygen and nitrogen; wherein the $C_3$-$C_6$ cycloalkyl and the 4-6 membered monocyclic heterocycle are each optionally substituted with 1 or 2 substituents independently selected from the group consisting of $C_1$-$C_3$ alkyl, halogen, $C_1$-$C_3$ haloalkyl, —OH, $C_1$-$C_3$ alkoxy, and $C_1$-$C_3$ haloalkoxy;

$R^{16}$ is —OH or $C_1$-$C_6$ alkyl optionally substituted with 1 or 2 substituents independently selected from the group consisting of —CN, —OR$^j$, —O-benzyl, —OC(O)R$^k$, —OC(O)N(R$^j$)$_2$, —SR$^j$, —S(O)$_2$R$^j$, —S(O)$_2$N(R$^j$)$_2$, —C(O)R$^j$, —C(O)OR$^j$, —C(O)N(R$^j$)$_2$, —C(O)N(R$^j$)S(O)$_2$R$^k$, —N(R$^j$)$_2$, —N(R$^j$)C(O)R$^k$, —N(R$^j$)S(O)$_2$R$^k$, —N(R$^j$)C(O)O(R$^k$), and —N(R$^j$)C(O)N(R$^j$)$_2$;

$R^q$ is $C_2$-$C_6$ alkenyl, $C_2$-$C_6$ alkynyl, halogen, $C_1$-$C_6$ haloalkyl, —CN, oxo, NO$_2$, —OR$^x$, —OC(O)R$^y$, —OC(O)N(R$^x$)$_2$, —SR$^x$, —S(O)$_2$R$^x$, —S(O)$_2$N(R$^x$)$_2$, —C(O)R$^x$, —C(O)OR$^x$, —C(O)N(R$^x$)$_2$, —C(O)N(R$^x$)S(O)$_2$R$^y$, —N(R$^x$)$_2$, —N(R$^x$)C(O)R$^y$, —N(R$^x$)S(O)$_2$R$^y$, —N(R$^x$)C(O)O(R$^y$), —N(R$^x$)C(O)N(R$^x$)$_2$, $G^{2A}$, or $C_1$-$C_6$ alkyl which is optionally substituted with 1 or 2 substituents independently selected from the group consisting of —CN, NO$_2$, —OR$^x$, —OC(O)R$^y$, —OC(O)N(R$^x$)$_2$, —SR$^x$, —S(O)$_2$R$^x$, —S(O)$_2$N(R$^x$)$_2$, —C(O)R$^x$, —C(O)OR$^x$, —C(O)N(R$^x$)$_2$, —C(O)N(R$^x$)S(O)$_2$R$^y$, —N(R$^x$)$_2$, —N(R$^x$)C(O)R$^y$, —N(R$^x$)S(O)$_2$R$^y$, —N(R$^x$)C(O)O(R$^y$), —N(R$^x$)C(O)N(R$^x$)$_2$, and $G^{2A}$;

$R^x$, at each occurrence, is independently hydrogen, $C_1$-$C_6$ alkyl, $G^{2A}$, $C_1$-$C_6$ haloalkyl, or —(C$_1$-$C_6$ alkylenyl)-$G^{2A}$;

$R^y$, at each occurrence, is independently $C_1$-$C_6$ alkyl, $G^{2A}$, $C_1$-$C_6$ haloalkyl, or —(C$_1$-$C_6$ alkylenyl)-$G^{2A}$;

$G^{2A}$, at each occurrence, is independently phenyl or $C_3$-$C_6$ cycloalkyl; each of which is optionally substituted with 1, 2, or 3 $R^z$ groups;

$R^s$, at each occurrence, is independently $C_2$-$C_6$ alkenyl, $C_2$-$C_6$ alkynyl, halogen, $C_1$-$C_6$ haloalkyl, —CN, oxo, NO$_2$, —OR$^j$, —OR$^h$, —OC(O)R$^k$, —OC(O)N(R$^j$)$_2$, —SR, —S(O)$_2$R$^j$, —S(O)$_2$N(R$^j$)$_2$, —C(O)R$^j$, —C(O)OR$^j$, —C(O)O(benzyl), —C(O)N(R$^j$)$_2$, —C(O)N(R$^m$)(R$^n$), —C(O)N(R$^j$)S(O)$_2$R$^k$, —N(R$^j$)$_2$, —N(R$^j$)C(O)R$^k$, —N(R$^j$)S(O)$_2$R$^k$, —N(R$^j$)C(O)O(R$^k$), $G^{3A}$, —N(R$^j$)C(O)N(R$^j$)$_2$, or $C_1$-$C_6$ alkyl which is optionally substituted with 1 or 2 substituents independently selected from the group consisting of —CN, NO$_2$, —OR$^j$, —O-benzyl, —OC(O)R$^k$, —OC(O)N(R$^j$)$_2$, —SR, —S(O)$_2$R$^j$, —S(O)$_2$N(R$^j$)$_2$, —C(O)R$^j$, —C(O)OR$^j$, —C(O)N(R$^j$)$_2$, —C(O)N(R$^j$)S(O)$_2$R$^k$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, and $G^{3A}$;

$G^{3A}$, at each occurrence, is independently phenyl or 4-6 membered monocyclic heterocycle; each $G^{3A}$ is optionally substituted with 1, 2, 3, or 4 $R^c$ groups;

$R^g$ is hydrogen or benzyl, or $R^g$ is $C_2$-$C_6$ alkyl which is substituted with 1 or 2 —OR$^j$;

$R^h$ is benzyl or $R^h$ is $C_2$-$C_6$ alkyl which is substituted with 1 or 2 —OR$^j$;

$R^m$ is $G^{3B}$ or $C_1$-$C_6$ alkyl which is substituted with 1 or 2 substituents independently selected from the group consisting of —OR$^j$, —S(O)$_2$R$^j$, —C(O)N(R$^j$)$_2$, and $G^{3B}$;

$R^n$ is hydrogen, $C_1$-$C_6$ alkyl, $C_1$-$C_6$ haloalkyl, benzyl, or —(C$_2$-$C_6$ alkylenyl)-OR$^j$; or $R^m$ and $R^n$, together with the nitrogen atom to which they are attached, form a 4-7 membered monocyclic heterocycle, wherein the 4-7 membered monocyclic heterocycle is optionally substituted with 1, 2, 3, or 4 independently selected $R^c$ groups;

$G^{3B}$, at each occurrence, is independently a phenyl, a 4-7 membered monocyclic heterocycle, or a 3-10 membered cycloalkyl, each of which is optionally substituted with 1, 2, 3, or 4 independently selected $R^c$ groups;

$R^c$, $R^u$, $R^v$, $R^w$, and $R^z$, at each occurrence, are each independently $C_2$-$C_6$ alkenyl, $C_2$-$C_6$ alkynyl, halogen, $C_1$-$C_6$ haloalkyl, —CN, oxo, NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^j$, —C(O)OR$^j$, —C(O)N(R$^j$)$_2$, —C(O)N(R$^j$)S(O)$_2$R$^k$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, or $C_1$-$C_6$ alkyl which is optionally substituted with 1 or 2 substituents independently selected from the group consisting of —CN, NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^j$, —C(O)OR$^j$, —C(O)N(R$^j$)$_2$, —C(O)N(R$^j$)S(O)$_2$R$^k$, —N(R$^j$)$_2$, —N(R$^j$)C(O)R$^k$, —N(R$^j$)S(O)$_2$R$^k$, —N(R$^j$)C(O)O(R$^k$), and —N(R$^j$)C(O)N(R$^j$)$_2$;

$R^j$, at each occurrence, is independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl.

2. The compound of claim 1 or a pharmaceutically acceptable salt thereof, wherein $R^{2A}$, $R^{2B}$, $R^{2C}$ and $R^{2D}$ are hydrogen or $R^{2A}$, $R^{2B}$, $R^{2C}$ and $R^{2D}$ are halogen.

3. The compound of claim 1 or a pharmaceutically acceptable salt thereof, wherein $R^{2A}$, $R^{2B}$, $R^{2C}$ and $R^{2D}$ are hydrogen or $R^{2A}$, $R^{2B}$, $R^{2C}$ and $R^{2D}$ are halogen;

$R^1$, $R^3$, $R^4$, $R^6$, and $R^7$ are hydrogen; and $R^5$ is $C_1$-$C_3$ alkyl.

4. The compound of claim 1 or a pharmaceutically acceptable salt thereof, wherein Y is -$G^1$; and $G^1$ is phenyl, pyridinyl, pyrazinyl, 1, 3-thiazolyl, or 1,3,4-thiadiazolyl; each of which is optionally substituted with 1, 2, or 3 independently selected $R^p$ groups, wherein each $R^p$ is independently $C_1$-$C_6$ alkyl, halogen, $G^2$, —C(O)N$R^AR^B$, or —N$R^AR^B$.

5. The compound of claim 1 or a pharmaceutically acceptable salt thereof, wherein Y is formula (c);

$X^2$ is O or N($R^{2x}$) wherein $R^{2x}$ is hydrogen;

m is 0 or 1; and $G^3$ is phenyl or monocyclic heteroaryl; each of which is optionally substituted with 1, 2, or 3 independently selected $R^s$ groups.

6. The compound of claim 1 or a pharmaceutically acceptable salt thereof, wherein Y is formula (d);

$R^9$ is $C_1$-$C_3$ alkyl or optionally substituted phenyl; and each $R^u$ is independently $C_1$-$C_3$ alkyl, halogen, $C_1$-$C_3$ haloalkyl, —C(O)O$R^j$, or —O$R^j$.

7. The compound of claim 1 or a pharmaceutically acceptable salt thereof, wherein Y is formula (e);

$R^{11}$ is halogen or $G^4$ wherein $G^4$ is $C_3$-$C_6$ cycloalkyl or phenyl, each of which is optionally substituted with 1, 2, or 3 independently selected $R^w$ groups; and $R^{10}$ is $C_1$-$C_6$ alkyl substituted with 1, 2, or 3 substituents independently selected from the group consisting of OH and 2,2-dimethyl-1,3-dioxolan-4-yl; or $R^{10}$ is phenyl optionally substituted with 1, 2, or 3 independently selected $R^v$ groups.

8. The compound of claim 1 or a pharmaceutically acceptable salt thereof, wherein Y is formula (f);

p is 0 or 1; and $R^{13}$ is hydrogen or $C_1$-$C_6$ alkyl substituted with 1, 2, or 3 substituents independently selected from the group consisting of 2,2-dimethyl-1,3-dioxolan-4-yl, —O$R^{13a}$, and —O-benzyl.

9. The compound of claim 1 or a pharmaceutically acceptable salt thereof, wherein $R^{2A}$, $R^{2B}$, $R^{2C}$, and $R^{2D}$ are hydrogen or $R^{2A}$, $R^{2B}$, $R^{2C}$, and $R^{2D}$ are F;

$R^1$, $R^3$, $R^4$, $R^6$, and $R^7$ are hydrogen;

$R^5$ is $C_1$-$C_3$ alkyl;

Y is -$G^1$; and $G^1$ is phenyl, pyridinyl, pyrazinyl, 1, 3-thiazolyl, or 1,3,4-thiadiazolyl; each of which is optionally substituted with 1, 2, or 3 independently selected $R^p$ groups, wherein each $R^p$ is independently $C_1$-$C_6$ alkyl, halogen, $G^2$, —C(O)N$R^AR^B$, or —N$R^AR^B$.

10. The compound of claim 1 or a pharmaceutically acceptable salt thereof, wherein $R^{2A}$ and $R^{2B}$ are F;

$R^{2C}$ and $R^{2D}$ are hydrogen or $R^{2C}$ and $R^{2D}$ are F;

$R^1$, $R^3$, $R^4$, $R^6$, and $R^7$ are hydrogen;

Y is -$G^1$;

$R^5$ is methyl; and $G^1$ is phenyl, pyridinyl, pyrazinyl, 1, 3-thiazolyl, or 1,3,4-thiadiazolyl; each $G^1$ is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl.

11. The compound of claim 10 or a pharmaceutically acceptable salt thereof, wherein $G^2$ is phenyl, azetidinyl, pyrrolidinyl, piperidinyl, morpholinyl, hexahydropyrrolo[3,4-c]pyrrol-2(1H)-yl, hexahydrocyclopenta[c]pyrrol-3a(1H)-yl, 2-oxa-6-azaspiro[3.4]octan-6-yl, imidazolyl, or thienyl, each of which is optionally substituted with 1, 2, or 3 independently selected $R^q$ groups; and $R^q$ is —CN, halogen, $C_1$-$C_3$ haloalkyl, —O$R^x$, —S(O)$_2$$R^x$, —S(O)$_2$N($R^x$)$_2$, —C(O)O$R^x$, —C(O)N($R^x$)$_2$, —C(O)N($R^x$)S(O)$_2$$R^y$, $G^{2A}$, or $C_1$-$C_6$ alkyl which is optionally substituted with 1 or 2 substituents independently selected from the group consisting of —O$R^x$ and $G^{2A}$.

12. The compound of claim 10 or a pharmaceutically acceptable salt thereof, wherein X is formula (a);

$G^1$ is phenyl or pyridinyl; each of which is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl; and $G^2$ is phenyl, pyrrolidinyl, or thienyl, each of which is substituted with 1, 2, or 3 independently selected $R^q$ groups; wherein one $R^q$ group is —C(O)O$R^x$ or —O$R^x$, and the 1 or 2 optional $R^q$ groups are independently $C_1$-$C_6$ alkyl, halogen, or $C_1$-$C_3$ haloalkyl.

13. The compound of claim 12 or a pharmaceutically acceptable salt thereof, wherein $X^{1A}$ is O;

$G^2$ is phenyl, pyrrolidinyl, or thienyl, each of which is substituted with 1, 2, or 3 independently selected $R^q$ groups; wherein one $R^q$ group is —C(O)O$R^x$, and the 1 or 2 optional $R^q$ groups are independently $C_1$-$C_6$ alkyl, halogen, or $C_1$-$C_3$ haloalkyl, and $R^x$ is hydrogen or $C_1$-$C_6$ alkyl.

14. A compound of formula (I) or a pharmaceutically acceptable salt thereof,

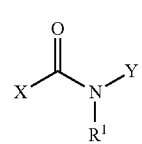

(I)

wherein
R¹ is H;
X is formula (a-i)

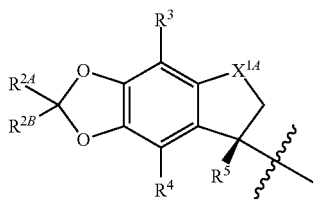
(a-i)

wherein
$R^{2A}$ and $R^{2B}$ are F;
$R^3$ and $R^4$ are hydrogen;
$R^5$ is $C_1$-$C_3$ alkyl;
$X^{1A}$ is O;
Y is -$G^1$; wherein $G^1$ is phenyl or pyridinyl; each of which is substituted with 1, 2, or 3 independently selected $R^p$ groups wherein one $R^p$ group is $G^2$, and the 1 or 2 optional $R^p$ groups are independently $C_1$-$C_6$ alkyl, halogen, or $C_1$-$C_6$ haloalkyl;
$G^2$ is phenyl, pyrrolidinyl, or thienyl, each of which is substituted with one —C(O)O$R^x$; and
$R^x$ is hydrogen or $C_1$-$C_6$ alkyl.

15. The compound of claim 1 or a pharmaceutically acceptable salt thereof, wherein
$R^{2A}$, $R^{2B}$, $R^{2C}$, and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (c);
$X^2$ is O or N($R^{2x}$) wherein $R^{2x}$ is hydrogen;
m is 0 or 1; and
$G^3$ is phenyl or monocyclic heteroaryl; each of which is optionally substituted with 1, 2, or 3 independently selected $R^s$ groups.

16. The compound of claim 1 or a pharmaceutically acceptable salt thereof, wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is formula (c);
$X^2$ is O or N($R^{2x}$) wherein $R^{2x}$ is hydrogen;
m is 0 or 1;
$G^3$ is phenyl or monocyclic heteroaryl; each of which is substituted with 1, 2, or 3 independently selected $R^s$ groups; and
each $R^s$ is independently $C_1$-$C_6$ alkyl, halogen, $C_1$-$C_6$ haloalkyl, —O$R^j$, —C(O)O$R^j$, or —SO$_2R^j$.

17. The compound of claim 16 or a pharmaceutically acceptable salt thereof, wherein
$G^3$ is phenyl or monocyclic heteroaryl; each of which is substituted with 1, 2, or 3 independently selected $R^s$ groups wherein one $R^s$ group is —C(O)O$R^j$ wherein $R^j$ is hydrogen or $C_1$-$C_6$ alkyl; and the optional $R^s$ groups are independently $C_1$-$C_3$ alkyl, halogen, or $C_1$-$C_3$ haloalkyl.

18. The compound of claim 16 or a pharmaceutically acceptable salt thereof, wherein
$G^3$ is phenyl or pyridinyl; each of which is substituted with one $R^s$ group, and
$R^s$ is —C(O)O$R^j$ wherein $R^j$ is hydrogen or $C_1$-$C_6$ alkyl.

19. The compound of claim 18 or a pharmaceutically acceptable salt thereof, wherein
X is formula (a); and
$X^{1A}$ is O.

20. The compound of claim 18 or a pharmaceutically acceptable salt thereof, wherein
X is formula (a); and
$X^{1A}$ is CH$_2$.

21. A compound of formula (I) or a pharmaceutically acceptable salt thereof,

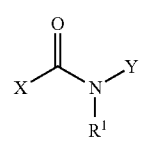
(I)

wherein
R¹ is H;
X is formula (a-i)

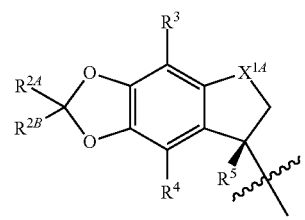
(a-i)

wherein
$R^{2A}$ and $R^{2B}$ are F;
$R^3$ and $R^4$ are hydrogen;
$R^5$ is $C_1$-$C_3$ alkyl;
$X^{1A}$ is O;
Y is formula (c);

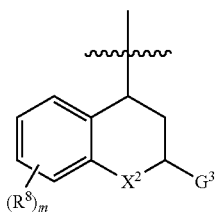
(c)

$X^2$ is O or N($R^{2x}$) wherein $R^{2x}$ is hydrogen;
m is 0 or 1;
$R^8$ is an optional substituent on the benzo ring, and is halogen, $C_1$-$C_3$ alkyl, $C_1$-$C_3$ haloalkyl, $C_1$-$C_3$ alkoxy, or $C_1$-$C_3$ haloalkoxy;
$G^3$ is phenyl or monocyclic heteroaryl; each of which is substituted with one $R^s$ group, and
$R^s$ is —C(O)O$R^j$ wherein $R^j$ is hydrogen or $C_1$-$C_6$ alkyl.

22. A compound of formula (I-a-i) or a pharmaceutically acceptable salt thereof,

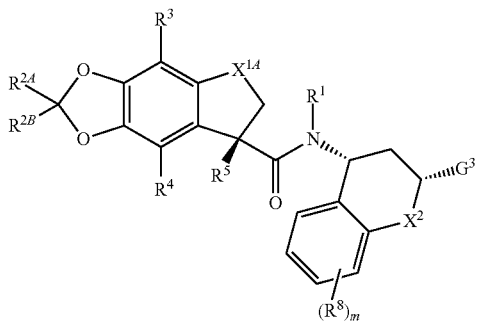
(I-a-i)

wherein
$R^{2A}$ and $R^{2B}$ are F;
$R^1$, $R^3$, and $R^4$ are hydrogen;
$R^5$ is $C_1$-$C_3$ alkyl;
$X^{1A}$ is O;
$X^2$ is O or $N(R^{2x})$ wherein $R^{2x}$ is hydrogen;
m is 0 or 1;
$R^8$ is an optional substituent on the benzo ring, and is halogen, $C_1$-$C_3$ alkyl, $C_1$-$C_3$ haloalkyl, $C_1$-$C_3$ alkoxy, or $C_1$-$C_3$ haloalkoxy;
$G^3$ is phenyl or monocyclic heteroaryl; each of which is substituted with one $R^s$ group, and
$R^s$ is —C(O)$OR^j$ wherein $R^j$ is hydrogen or $C_1$-$C_6$ alkyl.

23. The compound of claim 22 or a pharmaceutically acceptable salt thereof, wherein
$R^5$ is methyl;
$R^8$ is an optional substituent on the benzo ring, and is $C_1$-$C_3$ alkoxy or $C_1$-$C_3$ haloalkoxy; and
$G^3$ is phenyl or pyridinyl; each of which is substituted with one $R^s$ group; and
$R^s$ is —C(O)OR wherein $R^j$ is hydrogen or $C_1$-$C_6$ alkyl.

24. The compound of claim 23 or a pharmaceutically acceptable salt thereof, wherein
$X^2$ is O; and
$G^3$ is

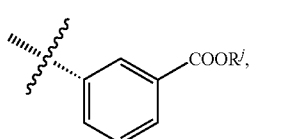

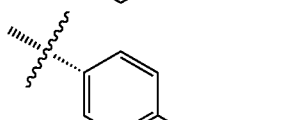

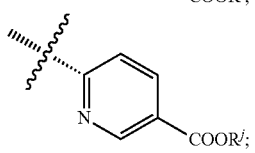

wherein each $R^j$ is independently hydrogen or $C_1$-$C_6$ alkyl.

25. The compound of claim 1 or a pharmaceutically acceptable salt thereof, wherein
$R^{2A}$, $R^{2B}$, $R^{2C}$, and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (d);
n is 1, 2, or 3;
$R^9$ is $C_1$-$C_3$ alkyl or optionally substituted phenyl; and
each $R^u$ is independently $C_1$-$C_3$ alkyl, halogen, $C_1$-$C_3$ haloalkyl, —C(O)$OR^j$, or —$OR^j$.

26. The compound of claim 1 or a pharmaceutically acceptable salt thereof, wherein
$R^{2A}$, $R^{2B}$, $R^{2C}$, and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (e);
$R^{10}$ is $C_1$-$C_6$ alkyl substituted with 1, 2, or 3 substituents independently selected from the group consisting of OH and 2,2-dimethyl-1,3-dioxolan-4-yl; or $R^{10}$ is phenyl optionally substituted with 1, 2, or 3 independently selected $R^v$ groups; and
$R^{11}$ is halogen or $G^4$ wherein $G^4$ is $C_3$-$C_6$ cycloalkyl or phenyl; each of which is optionally substituted with 1, 2, or 3 independently selected $R^w$ groups.

27. The compound of claim 1 or a pharmaceutically acceptable salt thereof, wherein
$R^{2A}$, $R^{2B}$, $R^{2C}$, and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (f); and
$R^{13}$ is hydrogen or $C_1$-$C_6$ alkyl substituted with 1, 2, or 3 substituents independently selected from the group consisting of 2,2-dimethyl-1,3-dioxolan-4-yl, —$OR^{13a}$, and —O-benzyl.

28. The compound of claim 27 or a pharmaceutically acceptable salt thereof, wherein
$R^{13}$ is $C_2$-$C_6$ alkyl substituted with 1, 2, or 3 substituents independently selected from the group consisting of —$OR^{13}$a and —O-benzyl; and
$R^{16}$ is $C_1$-$C_6$ alkyl optionally substituted with one —OH group.

29. The compound of claim 1 or a pharmaceutically acceptable salt thereof, wherein
X is formula (a);
$R^{2A}$ and $R^{2B}$ are F;
$R^1$, $R^3$, and $R^4$ are hydrogen;
$R^5$ is $C_1$-$C_3$ alkyl;
Y is formula (f);
$R^{13}$ is $C_2$-$C_6$ alkyl substituted with 1, 2, or 3 —$OR^{13a}$; and
$R^{16}$ is $C_1$-$C_6$ alkyl optionally substituted with one —OH group.

30. The compound of claim 29 or a pharmaceutically acceptable salt thereof, wherein
$R^{14}$ and $R^{15}$ are each independently $C_1$-$C_3$ alkyl;
p is 0 or 1; and
$R^{12}$ is halogen.

31. The compound of claim 29 or a pharmaceutically acceptable salt thereof, wherein
$R^{14}$ and $R^{15}$, together with the carbon atom to which they are attached, is $C_3$-$C_6$ cycloalkyl, or a 4-6 membered monocyclic heterocycle containing one oxygen atom; each of which is optionally substituted;
p is 0 or 1; and
$R^{12}$ is halogen.

32. The compound of claim 31 or a pharmaceutically acceptable salt thereof, wherein
$X^4$—$X^5$ is —$C(R^{4x})$=C; wherein $R^{4x}$ is hydrogen; and
$R^{14}$ and $R^{15}$, together with the carbon atom to which they are attached, is unsubstituted cyclopropyl, unsubstituted cyclobutyl, or unsubstituted oxetanyl.

33. A compound of formula (I) or a pharmaceutically acceptable salt thereof,

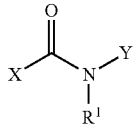

(I)

wherein
$R^1$ is H;
X is formula (a-i)

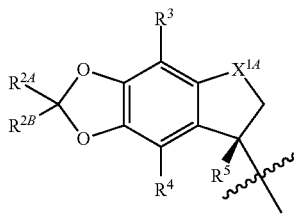

(a-i)

wherein
$R^{2A}$ and $R^{2B}$ are F;
$R^3$ and $R^4$ are hydrogen;
$R^5$ is $C_1$-$C_3$ alkyl;
$X^{1A}$ is O;
Y is formula (f);

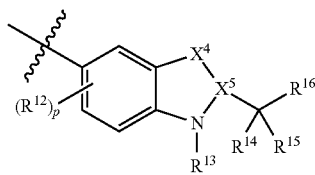

(f)

wherein
$X^4$-$X^5$ is N=C, $C(R^{4x})$=C, or $C(R^{4x})_2$—$C(R^x)$; wherein $R^{4x}$ and $R^{5x}$ are hydrogen;
p is 0 or 1;
$R^{12}$ is halogen;
$R^{14}$ and $R^{15}$ are each independently $C_1$-$C_3$ alkyl; or $R^{14}$ and $R^{15}$, together with the carbon atom to which they are attached, is cyclopropyl, cyclobutyl, or oxetanyl; each of which is optionally substituted with 1 or 2 substituents independently selected from the group consisting of $C_1$-$C_3$ alkyl, halogen, $C_1$-$C_3$ haloalkyl, —OH, $C_1$-$C_3$ alkoxy, and $C_1$-$C_3$ haloalkoxy;
$R^{13}$ is $C_2$-$C_6$ alkyl substituted with 1, 2, or 3 —$OR^{13a}$;
$R^{13a}$ is hydrogen; and
$R^{16}$ is $CH_3$ or —$CH_2OH$.

34. The compound of claim 33 or a pharmaceutically acceptable salt thereof, wherein
$R^{13}$ is n-propyl substituted with 2 —OH groups.

35. The compound of claim 33 or a pharmaceutically acceptable salt thereof, wherein
$R^{13}$ is

36. The compound of claim 33 or a pharmaceutically acceptable salt thereof, wherein
$R^{13}$ is

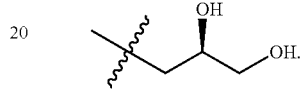

37. The compound of claim 1 or a pharmaceutically acceptable salt thereof, wherein
Y is formula (c);
$X^2$ is O or $N(R^{2x})$ wherein $R^{2x}$ is hydrogen;
m is 0, 1, or 2; and
$G^3$ is $C_3$-$C_6$ cycloalkyl which is optionally substituted with 1, 2, or 3 independently selected $R^s$ groups.

38. The compound of claim 1 or a pharmaceutically acceptable salt thereof, wherein
$R^{2A}$, $R^{2B}$, $R^{2C}$, and $R^{2D}$ are hydrogen or $R^{2A}$, $R^{2B}$, $R^{2C}$, and $R^{2D}$ are F;
$R^1$, $R^3$, $R^4$, $R^6$, and $R^7$ are hydrogen;
$R^5$ is $C_1$-$C_3$ alkyl;
Y is formula (c);
$X^2$ is O or $N(R^{2x})$ wherein $R^{2x}$ is hydrogen;
m is 0 or 1; and
$G^3$ is $C_3$-$C_6$ cycloalkyl which is optionally substituted with 1, 2, or 3 independently selected $R^s$ groups.

39. The compound of claim 1 or a pharmaceutically acceptable salt thereof, wherein
$R^{2A}$ and $R^{2B}$ are F;
$R^{2C}$ and $R^{2D}$ are hydrogen or $R^{2C}$ and $R^{2D}$ are F;
$R^1$, $R^3$, $R^4$, $R^6$, and $R^7$ are hydrogen;
$R^5$ is methyl;
Y is formula (c);
$X^2$ is O or $N(R^{2x})$ wherein $R^{2x}$ is hydrogen;
m is 0 or 1;
$G^3$ is $C_3$-$C_6$ cycloalkyl which is substituted with 1, 2, or 3 independently selected $R^s$ groups; and
each $R^s$ is independently $C_1$-$C_6$ alkyl, halogen, $C_1$-$C_6$ haloalkyl, —$OR^j$, —$C(O)OR^j$, or —$SO_2R^j$.

40. The compound of claim 39 or a pharmaceutically acceptable salt thereof, wherein
$G^3$ is $C_3$-$C_6$ cycloalkyl which is substituted with 1, 2, or 3 independently selected $R^s$ groups wherein one $R^s$ group is —$C(O)OR^j$ wherein $R^j$ is hydrogen or $C_1$-$C_6$ alkyl; and the optional $R^s$ groups are independently $C_1$-$C_3$ alkyl, halogen, or $C_1$-$C_3$ haloalkyl.

41. The compound of claim 39 or a pharmaceutically acceptable salt thereof, wherein
$G^3$ is $C_3$-$C_6$ cycloalkyl which is substituted with one $R^s$ group, and
$R^s$ is —$C(O)OR^j$ wherein $R^j$ is hydrogen or $C_1$-$C_6$ alkyl.

42. The compound of claim 41 or a pharmaceutically acceptable salt thereof, wherein X is formula (a); and $X^{1A}$ is O.

43. The compound of claim 41 or a pharmaceutically acceptable salt thereof, wherein X is formula (a); and $X^{1A}$ is $CH_2$.

44. A compound of formula (I) or a pharmaceutically acceptable salt thereof,

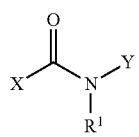
(I)

wherein $R^1$ is H;

X is formula (a-i)

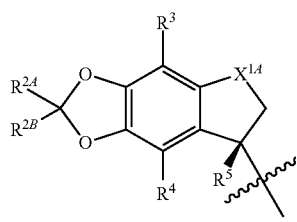
(a-i)

wherein $R^{2A}$ and $R^{2B}$ are F;

$R^3$ and $R^4$ are hydrogen;

$R^5$ is $C_1$-$C_3$ alkyl;

$X^{1A}$ is O or $CH_2$;

Y is formula (c);

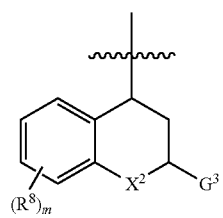
(c)

$X^2$ is O or $N(R^{2x})$ wherein $R^{2x}$ is hydrogen;

m is 0 or 1;

$R^8$ is an optional substituent on the benzo ring, and is halogen, $C_1$-$C_3$ alkyl, $C_1$-$C_3$ haloalkyl, $C_1$-$C_3$ alkoxy, or $C_1$-$C_3$ haloalkoxy; and $G^3$ is $C_3$-$C_6$ cycloalkyl which is substituted with 1, 2, or 3 $R^s$ group, wherein one $R^s$ group is —C(O)O$R^j$ wherein $R^R$ is hydrogen or $C_1$-$C_6$ alkyl; and the optional $R^s$ groups are independently $C_1$-$C_3$ alkyl, halogen, or $C_1$-$C_3$ haloalkyl.

45. A compound of formula (I-a-i) or a pharmaceutically acceptable salt thereof,

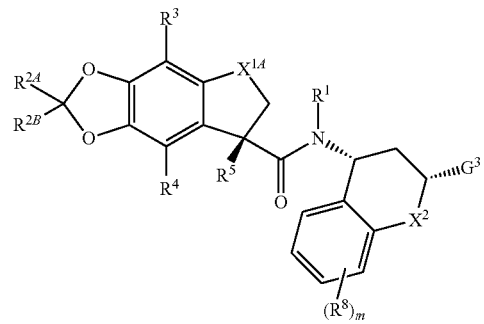
(I-a-i)

wherein $R^{2A}$ and $R^{2B}$ are F;

$R^1$, $R^3$, and $R^4$ are hydrogen;

$R^5$ is $C_1$-$C_3$ alkyl;

$X^{1A}$ is O or $CH_2$;

$X^2$ is O or $N(R^{2x})$ wherein $R^{2x}$ is hydrogen;

m is 0 or 1;

$R^8$ is an optional substituent on the benzo ring, and is halogen, $C_1$-$C_3$ alkyl, $C_1$-$C_3$ haloalkyl, $C_1$-$C_3$ alkoxy, or $C_1$-$C_3$ haloalkoxy;

$G^3$ is $C_3$-$C_6$ cycloalkyl which is substituted with one $R^s$ group, and $R^s$ is —C(O)O$R^j$ wherein $R^j$ is hydrogen or $C_1$-$C_6$ alkyl.

46. The compound of claim 45 or a pharmaceutically acceptable salt thereof, wherein $X^{1A}$ is O;

$R^5$ is methyl;

$R^8$ is an optional substituent on the benzo ring, and is $C_1$-$C_3$ alkoxy or $C_1$-$C_3$ haloalkoxy;

$G^3$ is cyclopropyl or cyclohexyl; each of which is substituted with one $R^s$ group; and $R^s$ is —C(O)O$R^j$ wherein $R^j$ is hydrogen or $C_1$-$C_6$ alkyl.

47. The compound of claim 46 or a pharmaceutically acceptable salt thereof, wherein $X^2$ is O;

$G^3$ is cyclohexyl which is substituted with one $R^s$ group; and $R^s$ is —C(O)O$R^j$ wherein $R^j$ is hydrogen or $C_1$-$C_6$ alkyl.

48. The compound of claim 47 or a pharmaceutically acceptable salt thereof, wherein $G^3$ is

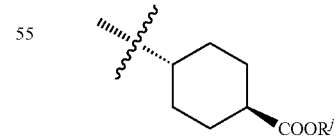

wherein $R^j$ is hydrogen or $C_1$-$C_6$ alkyl.

49. The compound of claim 1 or a pharmaceutically acceptable salt thereof, wherein the compound is selected from the group consisting of:

tert-butyl 3-{6-[(2,2-difluoro-7-methyl-6,7-dihydro-2H-furo[2,3-f][1,3]benzodioxole-7-carbonyl)amino]-3-methylpyridin-2-yl}benzoate;

3-{6-[(2,2-difluoro-7-methyl-6,7-dihydro-2H-furo[2,3-f][1,3]benzodioxole-7-carbonyl)amino]-3-methylpyridin-2-yl}benzoic acid;

tert-butyl 3-(6-{[(7S)-2,2-difluoro-7-methyl-6,7-dihydro-2H-furo[2,3-f][1,3]benzodioxole-7-carbonyl]amino}-3-methylpyridin-2-yl)benzoate;

3-(6-{[(7S)-2,2-difluoro-7-methyl-6,7-dihydro-2H-furo[2,3-f][1,3]benzodioxole-7-carbonyl]amino}-3-methylpyridin-2-yl)benzoic acid;

tert-butyl 3-(6-{[(7R)-2,2-difluoro-7-methyl-6,7-dihydro-2H-furo[2,3-f][1,3]benzodioxole-7-carbonyl]amino}-3-methylpyridin-2-yl)benzoate;

3-(6-{[(7R)-2,2-difluoro-7-methyl-6,7-dihydro-2H-furo[2,3-f][1,3]benzodioxole-7-carbonyl]amino}-3-methylpyridin-2-yl)benzoic acid;

methyl (3R)-1-{6-[(2,2-difluoro-7-methyl-6,7-dihydro-2H-furo[2,3-f][1,3]benzodioxole-7-carbonyl)amino]pyridin-2-yl}pyrrolidine-3-carboxylate;

(3R)-1-{6-[(2,2-difluoro-7-methyl-6,7-dihydro-2H-furo[2,3-f][1,3]benzodioxole-7-carbonyl)amino]pyridin-2-yl}pyrrolidine-3-carboxylic acid;

(3R)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylic acid;

methyl 3-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoate;

3-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoic acid;

methyl 3-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate;

3-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid;

3-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid;

methyl 4-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoate;

4-{(2R,4R)-4-[(2,2-difluoro-7-methyl-6,7-dihydro-2H-furo[2,3-f][1,3]benzodioxole-7-carbonyl)amino]-7-methoxy-3,4-dihydro-2H-1-benzopyran-2-yl}benzoic acid;

methyl 4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate;

4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid;

methyl 4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoate;

4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]benzoic acid;

3-{(2R,4R)-4-[(2,2-difluoro-7-methyl-6,7-dihydro-2H-furo[2,3-f][1,3]benzodioxole-7-carbonyl)amino]-3,4-dihydro-2H-1-benzopyran-2-yl}benzoic acid;

3-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid;

4-[(2R,4R)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid;

N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

N-{2-[(2R)-2,3-dihydroxypropyl]-3-oxo-6-phenyl-2,3-dihydropyridazin-4-yl}-2,2-difluoro-7-methyl-6,7-dihydro-2H-furo[2,3-f][1,3]benzodioxole-7-carboxamide;

(7R)—N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

(7R)—N-{2-[(2R)-2,3-dihydroxypropyl]-3-oxo-6-phenyl-2,3-dihydropyridazin-4-yl}-2,2-difluoro-7-methyl-6,7-dihydro-2H-furo[2,3-f][1,3]benzodioxole-7-carboxamide;

methyl 3-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoate;

3-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoic acid;

4-{3-cyclopropyl-5-[(2,2-difluoro-7-methyl-6,7-dihydro-2H-furo[2,3-f][1,3]benzodioxole-7-carbonyl)amino]-6-oxopyridazin-1(6H)-yl}benzoic acid;

4-[3-cyclopropyl-5-{[(7S)-2,2-difluoro-7-methyl-6,7-dihydro-2H-furo[2,3-f][1,3]benzodioxole-7-carbonyl]amino}-6-oxopyridazin-1(6H)-yl]benzoic acid;

4-[3-cyclopropyl-5-{[(7R)-2,2-difluoro-7-methyl-6,7-dihydro-2H-furo[2,3-f][1,3]benzodioxole-7-carbonyl]amino}-6-oxopyridazin-1(6H)-yl]benzoic acid;

methyl 4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoate and methyl 4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoate;

4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid and 4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid;

3-{(2R,4R)-4-[(2,2-difluoro-5-methyl-6,7-dihydro-2H,5H-indeno[5,6-d][1,3]dioxole-5-carbonyl)amino]-3,4-dihydro-2H-1-benzopyran-2-yl}benzoic acid;

2'-methyl-5'-[(6-methyl-7,8-dihydro-2H,6H-indeno[4,5-d][1,3]dioxole-6-carbonyl)amino][1,1'-biphenyl]-3-carboxylic acid;

2'-methyl-5'-{[(6R)-6-methyl-7,8-dihydro-2H,6H-indeno[4,5-d][1,3]dioxole-6-carbonyl]amino}[1,1'-biphenyl]-3-carboxylic acid;

2'-methyl-5'-{[(6S)-6-methyl-7,8-dihydro-2H,6H-indeno [4,5-d][1,3]dioxole-6-carbonyl]amino}[1,1'-biphenyl]-3-carboxylic acid;

4-{(2R,4R)-4-[(2,2-difluoro-6-methyl-6,7-dihydro-2H-furo[2,3-e][1,3]benzodioxole-6-carbonyl)amino]-7-methoxy-3,4-dihydro-2H-1-benzopyran-2-yl}benzoic acid;

methyl 3-{3-cyclopropyl-5-[(2,2-difluoro-7-methyl-6,7-dihydro-2H-furo[2,3-f][1,3]benzodioxole-7-carbonyl)amino]-6-oxopyridazin-1 (6H)-yl}benzoate;

(7S)—N-(2-{[(4R)-2,2-dimethyl-1,3-dioxolan-4-yl]methyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

4-[(2R,4R)-7-methoxy-4-{[(6S)-6-methyl-7, 8-dihydro-2H,6H-indeno[4,5-d][1,3]dioxole-6-carbonyl]amino}-3,4-dihydro-2H-1-benzopyran-2-yl]benzoic acid;

4-[(2R,4S,6R)-4-{[(7R)-2,2-difluoro-7-methyl-6,7-dihydro-2H-furo[2,3-f][1,3]benzodioxole-7-carbonyl]amino}-6-methyloxan-2-yl]benzoic acid and 4-[(2S,4R,6S)-4-{[(7R)-2,2-difluoro-7-methyl-6,7-dihydro-2H-furo[2,3-f][1,3]benzodioxole-7-carbonyl]amino}-6-methyloxan-2-yl]benzoic acid;

4-[(2R,4S,6S)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid;

4-[(2S,4R,6R)-4-{[(7R)-2,2-difluoro-7-methyl-6,7-dihydro-2H-furo[2,3-f][1,3]benzodioxole-7-carbonyl]amino}-6-phenyloxan-2-yl]benzoic acid;

4-[(2R,4R)-7-methoxy-4-{[(6R)-6-methyl-7,8-dihydro-2H,6H-indeno[4,5-d][1,3]dioxole-6-carbonyl]amino}-3,4-dihydro-2H-1-benzopyran-2-yl]benzoic acid;

4-[(2R,4R)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoic acid;

4-[(2S,4S)-4-{[(7R)-2,2-difluoro-7-methyl-6,7-dihydro-2H-furo[2,3-f][1,3]benzodioxole-7-carbonyl]amino}-1,2,3,4-tetrahydroquinolin-2-yl]benzoic acid;

4-[(2R,4R)-4-{[(5R)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid;

4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid;

3-{6-[(2,2-difluoro-5-methyl-6,7-dihydro-2H,5H-indeno[5,6-d][1,3]dioxole-5-carbonyl)amino]-3-methylpyridin-2-yl}benzoic acid;

methyl 3-{(2R,4R)-4-[(2,2-difluoro-5-methyl-6,7-dihydro-2H,5H-indeno[5,6-d][1,3]dioxole-5-carbonyl)amino]-7-methoxy-3,4-dihydro-2H-1-benzopyran-2-yl}benzoate;

4-{5-[(2,2-difluoro-7-methyl-6,7-dihydro-2H-furo[2,3-f][1,3]benzodioxole-7-carbonyl)amino]-1,3,4-thiadiazol-2-yl}benzoic acid;

N-([1,1'-biphenyl]-3-yl)-2,2-difluoro-7-methyl-6,7-dihydro-2H-furo[2,3-f][1,3]benzodioxole-7-carboxamide;

2,2-difluoro-7-methyl-N-(6-phenylpyridin-2-yl)-6,7-dihydro-2H-furo[2,3-f][1,3]benzodioxole-7-carboxamide;

3-[(2R,4R)-4-{[(5R)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid;

3-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]benzoic acid;

4-[(2R,4R)-4-{[(5R)-2,2-difluoro-5-methyl-6,7-dihydro-2H,5H-indeno[5,6-d][1,3]dioxole-5-carbonyl]amino}-3,4-dihydro-2H-1-benzopyran-2-yl]benzoic acid;

4-[(2R,4R)-4-{[(5S)-2,2-difluoro-5-methyl-6,7-dihydro-2H,5H-indeno[5,6-d][1,3]dioxole-5-carbonyl]amino}-3,4-dihydro-2H-1-benzopyran-2-yl]benzoic acid;

5'-[(2,2-difluoro-7-methyl-6,7-dihydro-2H-furo[2,3-f][1,3]benzodioxole-7-carbonyl)amino]-2'-methyl[1,1'-biphenyl]-3-carboxylic acid;

1-{4-[(2,2-difluoro-7-methyl-6,7-dihydro-2H-furo[2,3-f][1,3]benzodioxole-7-carbonyl)amino]phenyl}azetidine-3-carboxylic acid;

1-{2-[(2,2-difluoro-7-methyl-6,7-dihydro-2H-furo[2,3-f][1,3]benzodioxole-7-carbonyl)amino]-4-(trifluoromethyl)phenyl}-5-methyl-1H-imidazole-4-carboxylic acid;

N-[4-(4-cyanophenyl)-1,3-thiazol-2-yl]-2,2-difluoro-7-methyl-6,7-dihydro-2H-furo[2,3-f][1,3]benzodioxole-7-carboxamide;

methyl 4-{2-[(2,2-difluoro-7-methyl-6,7-dihydro-2H-furo[2,3-f][1,3]benzodioxole-7-carbonyl)amino]-1,3-thiazol-4-yl}benzoate;

6-[(2,2-difluoro-7-methyl-6,7-dihydro-2H-furo[2,3-][1,3]benzodioxole-7-carbonyl)amino]-N-[(2R)-2,3-dihydroxypropyl]pyridine-2-carboxamide;

methyl 3'-[(2,2-difluoro-7-methyl-6,7-dihydro-2H-furo[2,3-][1,3]benzodioxole-7-carbonyl)amino][1,1'-biphenyl]-4-carboxylate;

2,2-difluoro-N-(6-fluoropyridin-2-yl)-7-methyl-6,7-dihydro-2H-furo[2,3-f][1,3]benzodioxole-7-carboxamide;

4-{2-[(2,2-difluoro-7-methyl-6,7-dihydro-2H-furo[2,3-f][1,3]benzodioxole-7-carbonyl)amino]-1,3-thiazol-4-yl}benzoic acid;

3'-[(2,2-difluoro-7-methyl-6,7-dihydro-2H-furo[2,3-f][1,3]benzodioxole-7-carbonyl)amino][1,1'-biphenyl]-4-carboxylic acid;

methyl 1-{6-[(2,2-difluoro-7-methyl-6,7-dihydro-2H-furo[2,3-f][1,3]benzodioxole-7-carbonyl)amino]pyridin-2-yl}piperidine-4-carboxylate;

1-{6-[(2,2-difluoro-7-methyl-6,7-dihydro-2H-furo[2,3-f][1,3]benzodioxole-7-carbonyl)amino]pyridin-2-yl}piperidine-4-carboxylic acid;

(7R)-2,2-difluoro-N-[6-(3-hydroxypyrrolidin-1-yl)pyridin-3-yl]-7-methyl-6,7-dihydro-2H-furo[2,3-f][1,3]benzodioxole-7-carboxamide;

3-(6-{[(7R)-2,2-difluoro-7-methyl-6,7-dihydro-2H-furo[2,3-f][1,3]benzodioxole-7-carbonyl]amino}pyridin-2-yl)benzoic acid;

N-[6-(3-carbamoylphenyl)-5-methylpyridin-2-yl]-2,2-difluoro-7-methyl-6,7-dihydro-2H-furo[2,3-f][1,3]benzodioxole-7-carboxamide;

N-{6-[3-(dimethylcarbamoyl)phenyl]-5-methylpyridin-2-yl}-2,2-difluoro-7-methyl-6,7-dihydro-2H-furo[2,3-f][1,3]benzodioxole-7-carboxamide;

2,2-difluoro-7-methyl-N-{5-methyl-6-[3-(methylcarbamoyl)phenyl]pyridin-2-yl}-6,7-dihydro-2H-furo[2,3-f][1,3]benzodioxole-7-carboxamide;

(7R)—N-(6-chloro-5-methylpyridin-2-yl)-2,2-difluoro-7-methyl-6,7-dihydro-2H-furo[2,3-f][1,3]benzodioxole-7-carboxamide;

(7R)—N-[6-(3-cyanophenyl)-5-methylpyridin-2-yl]-2,2-difluoro-7-methyl-6,7-dihydro-2H-furo[2,3-f][1,3]benzodioxole-7-carboxamide;

methyl 4-(6-{[(7R)-2,2-difluoro-7-methyl-6,7-dihydro-2H-furo[2,3-f][1,3]benzodioxole-7-carbonyl]amino}pyridin-2-yl)benzoate;

(7R)-2,2-difluoro-7-methyl-N-[5-(pyrrolidin-1-yl)pyridin-2-yl]-6,7-dihydro-2H-furo[2,3-f][1,3]benzodioxole-7-carboxamide;

4-(6-{[(7R)-2,2-difluoro-7-methyl-6,7-dihydro-2H-furo[2,3-f][1,3]benzodioxole-7-carbonyl]amino}pyridin-2-yl)benzoic acid;

ethyl 5-(6-{[(7R)-2,2-difluoro-7-methyl-6,7-dihydro-2H-furo[2,3-f][1,3]benzodioxole-7-carbonyl]amino}pyridin-2-yl)thiophene-3-carboxylate;

4-(6-{[(7R)-2,2-difluoro-7-methyl-6,7-dihydro-2H-furo[2,3-f][1,3]benzodioxole-7-carbonyl]amino}-3-methylpyridin-2-yl)benzoic acid;

3-(6-{[(7R)-2,2-difluoro-7-methyl-6,7-dihydro-2H-furo[2,3-f][1,3]benzodioxole-7-carbonyl]amino}-5-methylpyridin-2-yl)benzoic acid;

(7R)-2,2-difluoro-N-(6-fluoropyridin-2-yl)-7-methyl-6,7-dihydro-2H-furo[2,3-f][1,3]benzodioxole-7-carboxamide;

5-(6-{[(7R)-2,2-difluoro-7-methyl-6,7-dihydro-2H-furo[2,3-f][1,3]benzodioxole-7-carbonyl]amino}pyridin-2-yl)thiophene-3-carboxylic acid;

(7R)-2,2-difluoro-N-{6-[2-(hydroxymethyl)morpholin-4-yl]pyridin-2-yl}-7-methyl-6,7-dihydro-2H-furo[2,3-f][1,3]benzodioxole-7-carboxamide;

(7R)-2,2-difluoro-N-{6-[(3S)-3-hydroxypyrrolidin-1-yl]pyridin-2-yl}-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxylic acid;

(3S)-1-(6-{[(7R)-2,2-difluoro-7-methyl-6,7-dihydro-2H-furo[2,3-f][1,3]benzodioxole-7-carbonyl]amino}pyridin-2-yl)pyrrolidine-3-carboxylic acid;

(7R)-2,2-difluoro-N-{6-[(3R)-3-hydroxypyrrolidin-1-yl]pyridin-2-yl}-7-methyl-6,7-dihydro-2H-furo[2,3-f][1,3]benzodioxole-7-carboxamide;

(7R)—N-(6-{[(2R)-2,3-dihydroxypropyl]amino}pyridin-2-yl)-2,2-difluoro-7-methyl-6,7-dihydro-2H-furo[2,3-f][1,3]benzodioxole-7-carboxamide;

(7R)—N-(6-{[(2S)-2,3-dihydroxypropyl]amino}pyridin-2-yl)-2,2-difluoro-7-methyl-6,7-dihydro-2H-furo[2,3-f][1,3]benzodioxole-7-carboxamide;

1-(5-{[(7R)-2,2-difluoro-7-methyl-6,7-dihydro-2H-furo[2,3-f][1,3]benzodioxole-7-carbonyl]amino}pyrazin-2-yl)pyrrolidine-3-carboxylic acid;

3-(3-chloro-6-{[(7R)-2,2-difluoro-7-methyl-6,7-dihydro-2H-furo[2,3-f][1,3]benzodioxole-7-carbonyl]amino}pyridin-2-yl)benzoic acid;

1-(6-{[(7R)-2,2-difluoro-7-methyl-6,7-dihydro-2H-furo[2,3-f][1,3]benzodioxole-7-carbonyl]amino}pyridin-2-yl)-3-methylazetidine-3-carboxylic acid;

4-[5-bromo-3-{[(7R)-2,2-difluoro-7-methyl-6,7-dihydro-2H-furo[2,3-f][1,3]benzodioxole-7-carbonyl]amino}-2-oxopyridin-1(2H)-yl]benzoic acid;

(7R)—N-{f 5-bromo-1-[(2R)-2,3-dihydroxypropyl]-2-oxo-1,2-dihydropyridin-3-yl}-2,2-difluoro-7-methyl-6,7-dihydro-2H-furo[2,3-f][1,3]benzodioxole-7-carboxamide;

4-[3-{[(7R)-2,2-difluoro-7-methyl-6,7-dihydro-2H-furo[2,3-f][1,3]benzodioxole-7-carbonyl]amino}-2-oxo-5-phenylpyridin-1(2)-yl]benzoic acid;

(7R)—N-{1-[(2R)-2,3-dihydroxypropyl]-2-oxo-5-phenyl-1,2-dihydropyridin-3-yl}-2,2-difluoro-7-methyl-6,7-dihydro-2H-furo[2,3-f][1,3]benzodioxole-7-carboxamide;

(7R)—N-[6-(3,3-dimethylpyrrolidin-1-yl)pyridin-2-yl]-2,2-difluoro-7-methyl-6,7-dihydro-2H-furo[2,3-f][1,3]benzodioxole-7-carboxamide;

1-(5-{[(7R)-2,2-difluoro-7-methyl-6,7-dihydro-2H-furo[2,3-][1,3]benzodioxole-7-carbonyl]amino}pyrazin-2-yl)proline;

3-(6-{[(7R)-2,2-difluoro-7-methyl-6,7-dihydro-2H-furo[2,3-f][1,3]benzodioxole-7-carbonyl]amino}-4-methylpyridin-2-yl)benzoic acid;

(7R)—N-(2-{(2S)-2-[(4R)-2,2-dimethyl-1,3-dioxolan-4-yl]-2-hydroxyethyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

(7R)-2,2-difluoro-7-methyl-N-{3-oxo-6-phenyl-2-[(2S,3R)-2,3,4-trihydroxybutyl]-2,3-dihydropyridazin-4-yl}-6,7-dihydro-2H-furo[2,3-f][1,3]benzodioxole-7-carboxamide;

(7R)—N-(2-{(2R)-2-[(4R)-2,2-dimethyl-1,3-dioxolan-4-yl]-2-hydroxyethyl}-3-oxo-6-phenyl-2,3-dihydropyridazin-4-yl)-2,2-difluoro-7-methyl-6,7-dihydro-2H-furo[2,3-f][1,3]benzodioxole-7-carboxamide;

2,2-difluoro-7-methyl-N-[6-(5-methylhexahydropyrrolo[3,4-c]pyrrol-2(1H)-yl)pyridin-2-yl]-6,7-dihydro-2H-furo[2,3-f][1,3]benzodioxole-7-carboxamide;

2,2-difluoro-7-methyl-N-{6-[5-(2-methylpropyl)hexahydropyrrolo[3,4-c]pyrrol-2(1H)-yl]pyridin-2-yl}-6,7-dihydro-2H-furo[2,3-f][1,3]benzodioxole-7-carboxamide;

(7R)-2,2-difluoro-N-{6-[3-(methanesulfonyl)pyrrolidin-1-yl]pyridin-2-yl}-7-methyl-6,7-dihydro-2H-furo[2,3-f][1,3]benzodioxole-7-carboxamide;

(7R)—N-{6-[3-(chloromethyl)-3-(hydroxymethyl)pyrrolidin-1-yl]pyridin-2-yl}-2,2-difluoro-7-methyl-6,7-dihydro-2H-furo[2,3-f][1,3]benzodioxole-7-carboxamide;

(7R)-2,2-difluoro-N-{6-[(3R)-3-(methanesulfonyl)pyrrolidin-1-yl]pyridin-2-yl}-7-methyl-6,7-dihydro-2H-furo[2,3-f][1,3]benzodioxole-7-carboxamide;

methyl (3R,4S)-1-(6-{[(7R)-2,2-difluoro-7-methyl-6,7-dihydro-2H-furo[2,3-f][1,3]benzodioxole-7-carbonyl]amino}pyridin-2-yl)-4-phenylpyrrolidine-3-carboxylate;

(7R)—N-[6-(3-benzylpyrrolidin-1-yl)pyridin-2-yl]-2,2-difluoro-7-methyl-6,7-dihydro-2H-furo[2,3-f][1,3]benzodioxole-7-carboxamide;

(7R)-2,2-difluoro-N-{6-[3-(4-fluorophenyl)pyrrolidin-1-yl]pyridin-2-yl}-7-methyl-6,7-dihydro-2H-furo[2,3-f][1,3]benzodioxole-7-carboxamide;

1-(6-{[(7R)-2,2-difluoro-7-methyl-6,7-dihydro-2H-furo[2,3-f][1,3]benzodioxole-7-carbonyl]amino}pyridin-2-yl)-4,4-dimethylpyrrolidine-3-carboxylic acid;

1-(6-{[(7R)-2,2-difluoro-7-methyl-6,7-dihydro-2H-furo[2,3-f][1,3]benzodioxole-7-carbonyl]amino}pyridin-2-yl)-4-methylpyrrolidine-3-carboxylic acid;

2-(6-{[(7R)-2,2-difluoro-7-methyl-6,7-dihydro-2H-furo[2,3-f][1,3]benzodioxole-7-carbonyl]amino}pyridin-2-yl)hexahydrocyclopenta[c]pyrrole-3a(1H)-carboxylic acid;

(7R)-2,2-difluoro-7-methyl-N-[6-(pyrrolidin-1-yl)pyridin-2-yl]-6,7-dihydro-2H-furo[2,3-f][1,3]benzodioxole-7-carboxamide;

(7R)-2,2-difluoro-7-methyl-N-[6-(piperidin-1-yl)pyridin-2-yl]-6,7-dihydro-2H-furo[2,3-f][1,3]benzodioxole-7-carboxamide;

4-(6-{[(7R)-2,2-difluoro-7-methyl-6,7-dihydro-2H-furo[2,3-f][1,3]benzodioxole-7-carbonyl]amino}pyridin-2-yl)-3-methylbenzoic acid;

(7R)—N-[5-(3R,4R)-dihydroxypyrrolidin-1-yl)pyrazin-2-yl]-2,2-difluoro-7-methyl-6,7-dihydro-2H-furo[2,3-f][1,3]benzodioxole-7-carboxamide and (7R)—N-[5-(3 S,4S)-dihydroxypyrrolidin-1-yl)pyrazin-2-yl]-2,2-difluoro-7-methyl-6,7-dihydro-2H-furo[2,3-f][1,3]benzodioxole-7-carboxamide;

3-(6-{[(7R)-2,2-difluoro-7-methyl-6,7-dihydro-2H-furo[2,3-f][1,3]benzodioxole-7-carbonyl]amino}pyridin-2-yl)-2-methylbenzoic acid;

4-(6-{[(7R)-2,2-difluoro-7-methyl-6,7-dihydro-2H-furo[2,3-f][1,3]benzodioxole-7-carbonyl]amino}pyridin-2-yl)-3-fluorobenzoic acid;

(7R)—N-{6-[3-(cyclopropylsulfamoyl)phenyl]-5-methylpyridin-2-yl}-2,2-difluoro-7-methyl-6,7-dihydro-2H-furo[2,3-f][1,3]benzodioxole-7-carboxamide;

3-(6-{[(7R)-2,2-difluoro-7-methyl-6,7-dihydro-2H-furo[2,3-]][1,3]benzodioxole-7-carbonyl]amino}pyridin-2-yl)-2-fluorobenzoic acid;

(7R)—N-{6-[3-(1,2-dihydroxyethyl)phenyl]-5-methylpyridin-2-yl}-2,2-difluoro-7-methyl-6,7-dihydro-2H-furo[2,3-f][1,3]benzodioxole-7-carboxamide;

5-(6-{[(7R)-2,2-difluoro-7-methyl-6,7-dihydro-2H-furo[2,3-f][1,3]benzodioxole-7-carbonyl]amino}-3-methylpyridin-2-yl)thiophene-3-carboxylic acid;

3-(6-{[(7R)-2,2-difluoro-7-methyl-6,7-dihydro-2H-furo[2,3-f][1,3]benzodioxole-7-carbonyl]amino}pyridin-2-yl)-4-fluorobenzoic acid;

3-(6-{[(7R)-2,2-difluoro-7-methyl-6,7-dihydro-2H-furo[2,3-]][1,3]benzodioxole-7-carbonyl]amino}pyridin-2-yl)-4-methylbenzoic acid;

(7R)—N-{1-[(2R)-2,3-dihydroxypropyl]-6-fluoro-2-(1-hydroxy-2-methylpropan-2-yl)-1H-indol-5-yl}-2,2-difluoro-7-methyl-6,7-dihydro-2H-furo[2,3-]][1,3]benzodioxole-7-carboxamide;

(7R)—N-(2-tert-butyl-1H-indol-5-yl)-2,2-difluoro-7-methyl-6,7-dihydro-2H-furo[2,3-f][1,3]benzodioxole-7-carboxamide;

(7R)—N-{1-[(2R)-3-(benzyloxy)-2-hydroxypropyl]-2-tert-butyl-6-fluoro-1H-indol-5-yl}-2,2-difluoro-7-methyl-6,7-dihydro-2H-furo[2,3-f][1,3]benzodioxole-7-carboxamide;

(7R)—N-{2-tert-butyl-1-[(2R)-2,3-dihydroxypropyl]-6-fluoro-1H-indol-5-yl}-2,2-difluoro-7-methyl-6,7-dihydro-2H-furo[2,3-]][1,3]benzodioxole-7-carboxamide;

(7R)—N-{1-[(2R)-2,3-dihydroxypropyl]-6-fluoro-2-[1-(hydroxymethyl)cyclobutyl]-1H-indol-5-yl}-2,2-difluoro-7-methyl-6,7-dihydro-2H-furo[2,3-f][1,3]benzodioxole-7-carboxamide;

(7R)—N-{1-[(2R)-2,3-dihydroxypropyl]-6-fluoro-2-[3-(hydroxymethyl)oxetan-3-yl]-1H-indol-5-yl}-2,2-difluoro-7-methyl-6,7-dihydro-2H-furo[2,3-]][1,3]benzodioxole-7-carboxamide;

(7R)—N-{1-[(2R)-2,3-dihydroxypropyl]-6-fluoro-2-[1-(hydroxymethyl)cyclopropyl]-1H-indol-5-yl}-2,2-difluoro-7-methyl-6,7-dihydro-2H-furo[2,3-f][1,3]benzodioxole-7-carboxamide;

(7R)—N-{1-[(2R)-2,3-dihydroxypropyl]-6-fluoro-2-(1-hydroxy-2-methylpropan-2-yl)-1H-benzimidazol-5-yl}-2,2-difluoro-7-methyl-6,7-dihydro-2H-furo[2,3-f][1,3]benzodioxole-7-carboxamide;

(7S)—N-{1-[(2R)-2,3-dihydroxypropyl]-6-fluoro-2-(1-hydroxy-2-methylpropan-2-yl)-1H-indol-5-yl}-2,2-difluoro-7-methyl-6,7-dihydro-2H-furo[2,3-]][1,3]benzodioxole-7-carboxamide;

4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]benzoic acid;

(7R)—N-[(2R)-1-[(2R)-2,3-dihydroxypropyl]-6-fluoro-2-(1-hydroxy-2-methylpropan-2-yl)-2,3-dihydro-1H-indol-5-yl]-2,2-difluoro-7-methyl-6,7-dihydro-2H-furo[2,3-f][1,3]benzodioxole-7-carboxamide;

(7R)—N-[(2S)-1-[(2R)-2,3-dihydroxypropyl]-6-fluoro-2-(1-hydroxy-2-methylpropan-2-yl)-2,3-dihydro-1H-indol-5-yl]-2,2-difluoro-7-methyl-6,7-dihydro-2H-furo[2,3-f][1,3]benzodioxole-7-carboxamide;

(7R)-2,2-difluoro-N-(6-{4-[(methanesulfonyl)carbamoyl]phenyl}-5-methylpyridin-2-yl)-7-methyl-6,7-dihydro-2H-furo[2,3-]][1,3]benzodioxole-7-carboxamide;

(7R)-2,2-difluoro-N-[6-fluoro-2-(1-hydroxy-2-methylpropan-2-yl)-1H-indol-5-yl]-7-methyl-6,7-dihydro-2H-furo[2,3-f][1,3]benzodioxole-7-carboxamide;

methyl 6-[(2R,4R)-4-{[(7R)-2,2-difluoro-7-methyl-6,7-dihydro-2H-furo[2, 3-f][1,3]benzodioxole-7-carbonyl]amino}-7-methoxy-3,4-dihydro-2H-1-benzopyran-2-yl]pyridine-3-carboxylate;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylic acid;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-2-carboxylic acid;

ethyl trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;

ethyl trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;

trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid;

ethyl trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylate;

ethyl trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylate;

trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

ethyl trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

ethyl cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;

ethyl cis-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

cis-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

ethyl 1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylate;

ethyl 1-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylate;

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid;

trans-4-[(2R,4R)-4-{[(5R)-2,2-difluoro-5-methyl-6,7-dihydro-2H,5H-indeno[5, 6-d][1,3]dioxole-5-carbonyl]amino}-7-(trifluoromethoxy)-3,4-dihydro-2H-1-benzopyran-2-yl]cyclohexane-1-carboxylic acid;

(7R)—N-{1-[(2R)-2,3-dihydroxypropyl]-6-fluoro-2-[4-(hydroxymethyl)oxan-4-yl]-1H-indol-5-yl}-2,2-difluoro-7-methyl-6,7-dihydro-2H-furo[2,3-f][1,3]benzodioxole-7-carboxamide;

(7R)—N-{1-[(2R)-2,3-dihydroxypropyl]-6-fluoro-2-(3-methyloxetan-3-yl)-1H-indol-5-yl}-2,2-difluoro-7-methyl-6,7-dihydro-2H-furo[2,3-f][1,3]benzodioxole-7-carboxamide;

(7R)-2,2-difluoro-N-{6-fluoro-2-[1-(hydroxymethyl)cyclobutyl]-1H-indol-5-yl})-7-methyl-6,7-dihydro-2H-furo[2,3-f][1,3]benzodioxole-7-carboxamide;

(7R)-2,2-difluoro-N-{(2R,4R)-2-[5-(hydroxymethyl)pyrazin-2-yl]-7-methoxy-3,4-dihydro-2H-1-benzopyran-4-yl}-7-methyl-6,7-dihydro-2H-furo[2,3-][1,3]benzodioxole-7-carboxamide;

(7R)-2,2-difluoro-N-{(2R,4R)-2-[5-(hydroxymethyl)pyridin-2-yl]-7-methoxy-3,4-dihydro-2H-1-benzopyran-4-yl}-7-methyl-6,7-dihydro-2H-furo[2,3-][1,3]benzodioxole-7-carboxamide;

(7R)—N-{(2R,4R)-2-[5-(1,2-dihydroxyethyl)pyrazin-2-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)—N-[(2R,4R)-2-(6-bromopyridin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-2-[5-(hydroxymethyl)pyridin-2-yl]-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-{(2R,4R)-2-[6-(hydroxymethyl)pyridin-3-yl]-7-methoxy-3,4-dihydro-2H-1-benzopyran-4-yl}-7-methyl-6,7-dihydro-2H-furo[2,3-]][1,3]benzodioxole-7-carboxamide;

(7R)—N-{1-[(2S)-3-cyano-2-hydroxypropyl]-6-fluoro-2-(1-hydroxy-2-methylpropan-2-yl)-1H-indol-1-yl}-2,2-difluoro-7-methyl-6,7-dihydro-2H-furo[2,3-f][1,3]benzodioxole-7-carboxamide;

(7R)—N-[(2R,4R)-2-(5-acetylpyridin-2-yl)-7-methoxy-3,4-dihydro-2H-1-benzopyran-4-yl]-2,2-difluoro-7-methyl-6,7-dihydro-2H-furo[2,3-J[1,3]benzodioxole-7-carboxamide;

(7R)-2,2-difluoro-N-{(2R,4R)-2-[5-(2-hydroxypropan-2-yl)pyridin-2-yl]-7-methoxy-3,4-dihydro-2H-1-benzopyran-4-yl}-7-methyl-6,7-dihydro-2H-furo[2,3-f][1,3]benzodioxole-7-carboxamide;

(7R)-2,2-difluoro-7-methyl-N-[(2R,4R)-2-(piperidin-4-yl)-7-(trifluoromethoxy)-3,4-dihydro-2H-1-benzopyran-4-yl]-6,7-dihydro-2H-furo[2,3-f][1,3]benzodioxole-7-carboxamide;

tert-butyl {4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetate;

{4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}) acetic acid;

(7R)-2,2-difluoro-7-methyl-N-[(2S,4S)-2-(piperidin-4-yl)-7-(trifluoromethoxy)-3,4-dihydro-2H-1-benzopyran-4-yl]-6,7-dihydro-2H-furo[2,3-f][1,3]benzodioxole-7-carboxamide;

tert-butyl {4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl}acetate;

{4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidin-1-yl]}) acetic acid;

(7R)—N-[(2S,4S)-2-{1-[(2S)-2,3-dihydroxypropyl]piperidin-4-yl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{1-[(2S)-2,3-dihydroxypropyl]piperidin-4-yl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-(5-ethenylpyrazin-2-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(1R)-1,2-dihydroxyethyl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(1S)-1,2-dihydroxyethyl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-(5-chloropyrazin-2-yl)-7-methoxy-3,4-dihydro-2H-1-benzopyran-4-yl]-2,2-difluoro-7-methyl-6,7-dihydro-2H-furo[2,3-][1,3]benzodioxole-7-carboxamide;

propan-2-yl trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;

(7R)—N-[(2R,4R)-2-(6-chloropyridazin-3-yl)-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(4R)-2-{1-[(2R)-2,3-dihydroxypropyl]-6-oxo-1,6-dihydropyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-7-methoxy-2-(6-oxo-1,6-dihydropyridazin-3-yl)-3,4-dihydro-2H-1-benzopyran-4-yl]-7-methyl-6,7-dihydro-2H-furo[2,3-f][1,3]benzodioxole-7-carboxamide;

tert-butyl {trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexyl}carbamate;

tert-butyl {trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexyl}carbamate;

(7R)-2,2-difluoro-N-[(2S,4R)-7-methoxy-2-(6-oxo-1,6-dihydropyridazin-3-yl)-3,4-dihydro-2H-1-benzopyran-4-yl]-7-methyl-6,7-dihydro-2H-furo[2,3-f][1,3]benzodioxole-7-carboxamide;

1-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

(7R)-2,2-difluoro-N-[(2R,4R)-7-methoxy-2-(1H-tetrazol-5-yl)-3,4-dihydro-2H-1-benzopyran-4-yl]-7-methyl-6,7-dihydro-2H-furo[2,3-f][1,3]benzodioxole-7-carboxamide;

(7R)—N-(2-{1-[(benzyloxy)methyl]cyclopropyl}-1-[(2R)-2,3-dihydroxypropyl]-6-fluoro-1H-indol-5-yl)-2,2-difluoro-7-methyl-6,7-dihydro-2H-furo[2,3-f][1,3]benzodioxole-7-carboxamide;

(7R)—N-{2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide;

(7S)—N-{1-[(2R)-3-(benzyloxy)-2-hydroxypropyl]-2-[1-(benzyloxy)-2-methylpropan-2-yl]-6-fluoro-1H-indol-5-yl}-2,2-difluoro-7-methyl-6,7-dihydro-2H-furo[2,3-f][1,3]benzodioxole-7-carboxamide;

(7R)—N-{5-[(2R)-2,3-dihydroxypropyl]-7-fluoro-1,1,4,4-tetramethyl-1,3,4,5-tetrahydropyrano[4,3-b]indol-8-yl}-2,2-difluoro-7-methyl-6,7-dihydro-2H-furo[2,3-f][1,3]benzodioxole-7-carboxamide;

(7R)—N-(5-{[(4R)-2,2-dimethyl-1,3-dioxolan-4-yl]methyl}-7-fluoro-1,1,4,4-tetramethyl-1,3,4,5-tetrahydropyrano[4,3-b]indol-8-yl)-2,2-difluoro-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyphenyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)-N-propylpyridine-3-carboxamide;

N-benzyl-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxy-2-phenylethyl)-N-methylpyridine-3-carboxamide;

(7R)-2,2-difluoro-N-{(2R,4R)-2-[5-(4-hydroxypiperidine-1-carbonyl)pyridin-2-yl]-7-methoxy-3,4-dihydro-2H-1-benzopyran-4-yl}-7-methyl-6,7-dihydro-2H-furo[2,3-f][1,3]benzodioxole-7-carboxamide;

(7R)-2,2-difluoro-N-[(2R,4R)-2-{5-[4-(2-hydroxyethyl)piperazine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][[1,3]benzodioxole-7-carbonyl]amino}-7-methoxy-3,4-dihydro-2H-1-benzopyran-2-yl]-N-(2-hydroxy-2-methylpropyl)pyridine-3-carboxamide;

6-[(2R,4R)-4-{[(7R)-2,2-difluoro-7-methyl-6,7-dihydro-2H-furo[2,3-f][[1,3]benzodioxole-7-carbonyl]amino}-7-methoxy-3,4-dihydro-2H-1-benzopyran-2-yl]-N-(1-hydroxy-2-methylpropan-2-yl)pyridine-3-carboxamide;

6-[(2R,4R)-4-{[(7R)-2,2-difluoro-7-methyl-6,7-dihydro-2H-furo[2,3-f][[1,3]benzodioxole-7-carbonyl]amino}-7-methoxy-3,4-dihydro-2H-1-benzopyran-2-yl]-N-(2-hydroxy-1-phenylethyl)pyridine-3-carboxamide;

6-[(2R,4R)-4-{[(7R)-2,2-difluoro-7-methyl-6,7-dihydro-2H-furo[2,3-f][[1,3]benzodioxole-7-carbonyl]amino}-7-methoxy-3,4-dihydro-2H-1-benzopyran-2-yl]-N-(1,1-dioxo-1lambda~6~-thian-4-yl)pyridine-3-carboxamide;

(7R)—N-{(2R,4R)-2-[5-(4,4-difluoropiperidine-1-carbonyl)pyridin-2-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)-2,2-difluoro-N-{(2R,4R)-7-methoxy-2-[5-(1,4-oxazepane-4-carbonyl)pyridin-2-yl]-3,4-dihydro-2H-1-benzopyran-4-yl}-7-methyl-6,7-dihydro-2H-furo[2,3-f][1,3]benzodioxole-7-carboxamide;

(7R)-2,2-difluoro-N-{(2R,4R)-7-methoxy-2-[5-(morpholine-4-carbonyl)pyridin-2-yl]-3,4-dihydro-2H-1-benzopyran-4-yl}-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][[1,3]benzodioxole-7-carbonyl]amino}-7-methoxy-3,4-dihydro-2H-1-benzopyran-2-yl]-N-(2-hydroxy-2,3-dihydro-1H-inden-1-yl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[2-hydroxy-1-(2-methoxyphenyl)ethyl]pyridine-3-carboxamide;

(7R)—N-{(2R,4R)-2-[4-(4,4-difluoropiperidine-1-carbonyl)phenyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

benzyl 4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidine-1-carboxylate;

benzyl 4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]piperidine-1-carboxylate;

(7R)—N-[(2S,4S)-2-(1-{[(4S)-2,2-dimethyl-1,3-dioxolan-4-yl]methyl}piperidin-4-yl)-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

N-(2-amino-2-oxoethyl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide;

N-(4-amino-4-oxobutyl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide;

N-(4-amino-4-oxobutan-2-yl)-6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[2-(methanesulfonyl)ethyl]pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[(5-oxopyrrolidin-3-yl)methyl]pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-oxopiperidin-4-yl)pyridine-3-carboxamide;

(7R)-2,2-difluoro-N-{(2R,4R)-7-methoxy-2-[5-(4-sulfamoylpiperazine-1-carbonyl)pyridin-2-yl]-3,4-dihydro-2H-1-benzopyran-4-yl}-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)-N-methylpyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-ethyl-N-(2-hydroxyethyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N,N-bis(2-hydroxyethyl)pyridine-3-carboxamide;

(7R)-2,2-difluoro-N-[(2R,4R)-2-{5-[2-(hydroxymethyl)morpholine-4-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{5-[3-hydroxy-3-(2-hydroxyethyl)pyrrolidine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{5-[3-hydroxy-3-(2-hydroxyethyl)azetidine-1-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{5-[3-(hydroxymethyl)morpholine-4-carbonyl]pyridin-2-yl}-7-methoxy-3,4-dihydro-2H-1-benzopyran-4-yl]-7-methyl-6,7-dihydro-2H-furo[2,3-f][1,3]benzodioxole-7-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxypropyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1-hydroxypropan-2-yl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2,3-dihydroxypropyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(2-hydroxyethyl)pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-[(trans-3-hydroxycyclobutyl)methyl]pyridine-3-carboxamide;

6-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]-N-(1-hydroxy-3-methoxypropan-2-yl)pyridine-3-carboxamide;

(7R)—N-[(2R,4R)-2-(1-{[(4S)-2,2-dimethyl-1,3-dioxolan-4-yl]methyl}piperidin-4-yl)-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(3R,4R)-3,4-dihydroxypyrrolidine-1-carbonyl]pyridin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(3S,4S)-3,4-dihydroxypyrrolidine-1-carbonyl]pyridin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{5-[(3R,4R)-3, 4-dihydroxypyrrolidin-1-yl]pyrazin-2-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{6-[(3R,4R)-3,4-dihydroxypyrrolidin-1-yl]pyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(4R)-2-{6-[(2S)-2,3-dihydroxypropoxy]pyridazin-3-yl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[ethyl(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[bis(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[(3R,4R)-3,4-dihydroxypyrrolidine-1-carbonyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[(3S,4S)-3,4-dihydroxypyrrolidine-1-carbonyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-2-{trans-4-[3-(hydroxymethyl)morpholine-4-carbonyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(2-hydroxypropyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(1-hydroxypropan-2-yl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)—N-[(2R,4R)-2-{trans-4-[(2,3-dihydroxypropyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-2-{trans-4-[(2-hydroxyethyl)carbamoyl]cyclohexyl}-7-(trifluoromethoxy)-3,4-dihydro-2H-1-benzopyran-4-yl]-7-methyl-6,7-dihydro-2H-furo[2,3-]][1,3]benzodioxole-7-carboxamide;

(7R)-2,2-difluoro-N-[(2R,4R)-2-{trans-4-[(2-hydroxyphenyl)carbamoyl]cyclohexyl}-7-(trifluoromethoxy)-3,4-dihydro-2H-1-benzopyran-4-yl]-7-methyl-6,7-dihydro-2H-furo[2,3-][1,3]benzodioxole-7-carboxamide;

(7R)-2,2-difluoro-N-[(2R,4R)-2-{trans-4-[(2-hydroxyethyl)(propyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)—N-[(2R,4R)-2-{trans-4-[benzyl(2-hydroxyethyl)carbamoyl]cyclohexyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-N-[(2R,4R)-2-[trans-4-(4-hydroxypiperidine-1-carbonyl)cyclohexyl]-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[4-(2-hydroxyethyl)piperazine-1-carbonyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(2-hydroxy-2-methylpropyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(1-hydroxy-2-methylpropan-2-yl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)-2,2-difluoro-N-[(2R,4R)-2-{trans-4-[(2-hydroxy-1-phenylethyl)carbamoyl]cyclohexyl}-7-(trifluoromethoxy)-3,4-dihydro-2H-1-benzopyran-4-yl]-7-methyl-6,7-dihydro-2H-furo[2,3-f][1,3]benzodioxole-7-carboxamide;

(7R)—N-[(2R,4R)-2-[trans-4-(4,4-difluoropiperidine-1-carbonyl)cyclohexyl]-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)-2,2-difluoro-7-methyl-N-[(2R,4R)-2-[trans-4-(morpholine-4-carbonyl)cyclohexyl]-7-(trifluoromethoxy)-3,4-dihydro-2H-1-benzopyran-4-yl]-6,7-dihydro-2H-furo[2,3-f][1,3]benzodioxole-7-carboxamide;

(7R)—N-{(2S,4R)-2-[6-(benzyloxy)pyridazin-3-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)—N-{(2R,4R)-2-[6-(benzyloxy)pyridazin-3-yl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)—N-[(2R,4R)-2-{[(2R)-2,3-dihydroxypropoxy]methyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2S,4S)-2-{[(2R)-2,3-dihydroxypropoxy]methyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-{(2R,4R)-2-[(benzyloxy)methyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)-2,2-difluoro-N-[(2R,4R)-2-(hydroxymethyl)-7-methoxy-3,4-dihydro-2H-1-benzopyran-4-yl]-7-methyl-6,7-dihydro-2H-furo[2,3-f][1,3]benzodioxole-7-carboxamide;

(7R)—N-{(2S,4S)-2-[(benzyloxy)methyl]-7-methoxy-3,4-dihydro-2H-1-benzopyran-4-yl}-2,2-difluoro-7-methyl-6,7-dihydro-2H-furo[2,3-f][1,3]benzodioxole-7-carboxamide;

(7R)—N-[(2R,4R)-2-{1-[bis(2-hydroxyethyl)carbamoyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2S,4S)-2-{1-[bis(2-hydroxyethyl)carbamoyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{trans-4-[(3S,4S)-3,4-dihydroxypyrrolidine-1-carbonyl]cyclohexyl}-7-methoxy-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-{1-[(3S,4S)-3,4-dihydroxypyrrolidine-1-carbonyl]cyclopropyl}-7-(trifluoromethoxy)-3,4-dihydro-2H-1-benzopyran-4-yl]-2,2-difluoro-7-methyl-6,7-dihydro-2H-furo[2,3-f][1,3]benzodioxole-7-carboxamide;

(7R)—N-[(2R,4R)-2-(1-benzyl-1H-tetrazol-5-yl)-7-methoxy-3,4-dihydro-2H-1-benzopyran-4-yl]-2,2-difluoro-7-methyl-6,7-dihydro-2H-furo[2,3-][1,3]benzodioxole-7-carboxamide;

(7R)-2,2-difluoro-N-{(2S,4S)-7-methoxy-2-[(6-oxopyridazin-1 (6H)-yl)methyl]-3,4-dihydro-2H-1-benzopyran-4-yl}-7-methyl-6,7-dihydro-2H-furo[2,3-f][1,3]benzodioxole-7-carboxamide;

(7R)-2,2-difluoro-N-{(2R,4R)-7-methoxy-2-[(6-oxopyridazin-1 (6H)-yl)methyl]-3,4-dihydro-2H-1-benzopyran-4-yl}-7-methyl-6,7-dihydro-2H-furo[2,3-f][1,3]benzodioxole-7-carboxamide;

(7R)—N-(1-[(2R)-3-(benzyloxy)-2-hydroxypropyl]-2-{1-[(benzyloxy)methyl]cyclopropyl}-6-fluoro-1H-indol-5-yl)-2,2-difluoro-7-methyl-6,7-dihydro-2H-furo[2,3-f][1,3]benzodioxole-7-carboxamide;

ethyl 1-(aminomethyl)-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate;

4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]-1-(hydroxymethyl)cyclohexane-1-carboxylic acid;

1-(aminomethyl)-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2R,4R)-6-bromo-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-4-iodo-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

4-[(2R,4R)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid; and 4-[(2S,4S)-4-{[(7S)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid.

50. A pharmaceutical composition comprising a therapeutically effective amount of a compound of claim 1, or a pharmaceutically acceptable salt thereof, in combination with a pharmaceutically acceptable carrier.

51. A method for treating cystic fibrosis in a subject comprising administering a therapeutically effective amount of a compound of claim 1 or a pharmaceutically acceptable salt thereof, to a subject in need thereof.

52. A pharmaceutical composition comprising a compound of claim 1 or a pharmaceutically acceptable salt thereof, one potentiator, and one or more additional correctors.

53. A method for treating cystic fibrosis in a subject comprising administering a compound of claim 1 or a pharmaceutically acceptable salt thereof, one CFTR potentiator, and one or more additional CFTR correctors, to a subject in need thereof.

54. A pharmaceutical composition comprising a compound of claim 1 or a pharmaceutically acceptable salt thereof, and one or more additional therapeutic agents.

55. The pharmaceutical composition of claim 54 wherein the additional therapeutic agents are selected from the group consisting of CFTR modulators and CFTR amplifiers.

56. The pharmaceutical composition of claim 54 wherein the additional therapeutic agents are CFTR modulators.

57. A method for treating cystic fibrosis in a subject comprising administering a compound of claim 1 or a pharmaceutically acceptable salt thereof, and one or more additional therapeutic agents.

58. The method of claim 57 wherein the additional therapeutic agents are selected from the group consisting of CFTR modulators and CFTR amplifiers.

59. The method of claim 57 the wherein the additional therapeutic agents are CFTR modulators.

60. ethyl trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylate, or a pharmaceutically acceptable salt thereof.

61. trans-4-[(2R,4R)-4-{[(7R)-2,2-difluoro-7-methyl-6,7-dihydro-2H-furo[2,3-f][1,3]benzodioxole-7-carbonyl[amino}-7-(trifluoromethoxy)-3,4-dihydro-2H-1-benzopyran-2-yl ]cyclohexane-1-carboxylic acid, or a pharmaceutically acceptable salt thereof.

62. 6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihyrdo-2H-1-benzopyran-2-yl]pyridine-3-carboxylic acid, or a pharmaceutically acceptable salt thereof.

63. trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid, or a pharmaceutically acceptable salt thereof.

64. ethyl trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl[amino}-3,4-dihydro-2H-1-benzopyran-2-yl]cyclohexane-1-carboxylate, or a pharmaceutically acceptable salt thereof.

65. trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino{-3,4-dihydro-2H-1-benzopyran-2-yl]cyclohexane-1-carboxylic acid, or a pharmaceutically acceptable salt thereof.

66. 1-[(2R,4R)-4-{[(7R)-2,2-difluoro-7-methyl-6,7-dihydro-2H-furo[2,3-f][benzodioxole-7-carbonyl]amino}-7-(trifluoromethoxy)-3,4-dihydro-2H-1-benzopyran-2-yl]cyclopropane-1-carboxylic acid, or a pharmaceutically acceptable salt thereof.

67. trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid or a pharmaceutically acceptable salt thereof.

68. trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid, or a pharmaceutically acceptable salt thereof.

\* \* \* \* \*

UNITED STATES PATENT AND TRADEMARK OFFICE
CERTIFICATE OF CORRECTION

PATENT NO. : 9,840,513 B2
APPLICATION NO. : 15/205512
DATED : December 12, 2017
INVENTOR(S) : Robert J Altenbach et al.

It is certified that error appears in the above-identified patent and that said Letters Patent is hereby corrected as shown below:

Column 6, Line 41, "$R^w$" should be --$R^v$--.

Column 6, Line 53, "—$N(R^{13})_2$" should be -- —$N(R^{13a})_2$--.

Column 6, Line 54, "—$N(R^{13b})C(O)R^{13b}$" should be -- —$N(R^{13a})C(O)R^{13b}$--.

Column 7, Line 43, "$R^e$" should be --$R^c$--.

Column 7, Line 57, "$R^e$" should be --$R^c$--.

Column 8, Line 5, "$R^3$" should be --$R^j$--.

Column 22, Line 60, "$R^j$" should be --$R^n$--.

Column 22, Line 66, "-$O^j$" should be --OR--.

Column 22, Line 66, "$R^e$" should be --$R^n$--.

Column 23, Line 10, "$R^e$" should be --$R^c$--.

Column 23, Line 32, "$R^e$" should be --$R^u$--.

Column 25, Line 30, "embodiments, when" should be --embodiments, $R^w$, when--.

Column 26, Lines 45-46, "$X^4, X^5$" should be --$X^4, X^4, X^5$--.

Column 26, Line 47, "$R^1$" should be --$R^{11}$--.

Column 26, Line 57, "an $R^{2D}$" should be --and $R^{2D}$--.

Signed and Sealed this
Thirteenth Day of March, 2018

Andrei Iancu
*Director of the United States Patent and Trademark Office*

Column 32, Line 34, "haloalkyl, -C(O)OR$^j$" should be --haloalkyl, -OR$^j$, -C(O)OR$^j$--.

Column 32, Line 67, "R$^k$" should be --R$^j$--.

Column 36, Line 14, "—C(O)O$^j$" should be -- —C(O)OR$^j$--.

Column 37, Line 4, "—C(O)O$^j$" should be -- —C(O)OR$^j$--.

Column 37, Line 23, "—C(O)O$^j$" should be -- —C(O)OR$^j$--.

Column 38, Line 49, "—O$^j$" should be -- —OR$^j$--.

Column 38, Line 66, "—O$^j$" should be -- —OR$^j$--.

Column 40, Line 46, "(0" should be --(f)--.

Column 40, Line 59, "(0" should be --(f)--.

Column 46, Line 18, "C(R$^{4c}$)$_2$" should be --C(R$^{4x}$)$_2$--.

Column 46, Line 52, "—CON" should be -- —CN--.

Column 46, Line 53, "—N(R$^{13}$)$_2$" should be -- —N(R$^{13a}$)$_2$--.

Column 46, Line 54, "—N(R$^{13b}$)C(O)R$^{13b}$" should be -- —N(R$^{13a}$)C(O)R$^{13b}$--.

Column 47, Line 12, "—N(R$^x$)C(O)R$^{3x}$" should be -- —N(R$^x$)C(O)R$^y$--.

Column 47, Line 12, "—N(R$^x$)C(O)$_2$R$^{3x}$" should be -- —N(R$^x$)C(O)$_2$R$^y$--.

Column 47, Line 16, "—OC(O)R$^{3x}$" should be -- —OC(O)R$^y$--.

Column 47, Line 20, "—N(R$^x$)C(O)O(R$^3$)" should be -- —N(R$^x$)C(O)O(R$^y$)--.

Column 64, Line 59, ":$^{36}$O" should be --$^{36}$Cl--.

Column 66, Line 49, "BF$_3$.OEt$_2$" should be --BF$_3$•OEt$_2$--.

Column 66, Line 60, "*N,N,N'*" should be --*N,N,N',N'*--.

Column 67, Line 53, "(TBTU)" should be --(HBTU)--.

Column 80, Line 61, "LG$^4$" should be --LG$^1$--.

Column 93, Line 65, "()" should be --f)--.

CERTIFICATE OF CORRECTION (continued)
U.S. Pat. No. 9,840,513 B2

Column 104, Line 11, "Å a AXIA" should be --Å AXIA--.

Column 104, Line 67, "fun" should be --µm--.

Column 112, Line 32, "frilled" should be --fritted--.

Column 117, Line 15, "fitted" should be --fritted--.

Column 117, Line 44, "111" should be --1H--.

Column 118, Line 41, "311" should be --3H--.

Column 119, Line 33, "(s, 31)" should be --(s, 3H)--.

Column 121, Line 64, "fitted" should be --fritted--.

Column 122, Line 4, "fitted" should be --fritted--.

Column 125, Line 12, "(s, 31)" should be --(s, 3H)--.

Column 130, Line 32, "(s, 911)" should be --(s, 9H)--.

Column 130, Line 41, "(614)" should be --(6H)--.

Column 132, Line 51, "(614)" should be --(6H)--.

Column 137, Line 67, "Raneye®" should be --Raney®--.

Column 155, Line 15, "112" should be --H2--.

Column 163, Line 7, "211,51" should be --2H, 5H--.

Column 164, Line 5, "HMSO" should be --DMSO--.

Column 168, Line 44, "(s, 31)" should be --(s, 3H)--.

Column 282, Line 31, "112" should be --H2--.

Column 351, Line 13, "(614)" should be --(6H)--.

Column 366, Line 7, "—SR" should be -- —SR$^j$--.

Column 366, Line 15, "—SR" should be -- —SR$^j$--.

Column 375, Line 65, "R$^R$" should be --R$^j$--.

Column 394, Claim 61, Line 48, "[amino}" should be --]amino}--.

Column 394, Claim 64, Line 63, "[amino}" should be --]amino}--.

Column 395, Claim 66, Line 5, "[2,3-f][benzodioxole" should be --[2,3-f][1,3]benzodioxole--.